United States Patent
Vinocur et al.

(10) Patent No.: US 10,208,316 B2
(45) Date of Patent: Feb. 19, 2019

(54) USE OF UMP-CMP KINASES FOR INCREASING NITROGEN USE EFFICIENCY AND LOW NITROGEN TOLERANCE IN PLANTS

(71) Applicant: Evogene Ltd., Rehovot (IL)

(72) Inventors: Basia Judith Vinocur, Rechovot (IL); Sharon Ayal, Kiryat-Ekron (IL); Alex Diber, Rishon-LeZion (IL); Eyal Emmanuel, Rechovot (IL); Gil Ronen, Emek Hefer (IL); Michael Gang, Jerusalem (IL); Dotan Dimet, Kibbutz Beir Nir (IL); Hagai Karchi, Moshav Sitriya (IL); Yoav Herschkovitz, Givataim (IL)

(73) Assignee: Evogene Ltd., Rehovot (IL)

( * ) Notice: Subject to any disclaimer, the term of this patent is extended or adjusted under 35 U.S.C. 154(b) by 0 days.

(21) Appl. No.: 15/673,608

(22) Filed: Aug. 10, 2017

(65) Prior Publication Data

US 2017/0342435 A1    Nov. 30, 2017

Related U.S. Application Data

(62) Division of application No. 14/636,275, filed on Mar. 3, 2015, now Pat. No. 9,783,818, which is a division of application No. 13/059,231, filed as application No. PCT/IB2009/053633 on Aug. 18, 2009, now Pat. No. 9,018,445.

(60) Provisional application No. 61/136,189, filed on Aug. 18, 2008.

(51) Int. Cl.
C12N 15/82 (2006.01)
C07K 14/415 (2006.01)

(52) U.S. Cl.
CPC ........ *C12N 15/8261* (2013.01); *C07K 14/415* (2013.01); *C12N 15/8247* (2013.01); *C12N 15/8269* (2013.01); *C12N 15/8271* (2013.01); *C12N 15/8273* (2013.01); *Y02A 40/146* (2018.01)

(58) Field of Classification Search
None
See application file for complete search history.

(56) References Cited

U.S. PATENT DOCUMENTS

| 6,084,153 A | 7/2000 | Good et al. |
|---|---|---|
| 2002/0046419 A1 | 4/2002 | Choo et al. |
| 2004/0034888 A1* | 2/2004 | Liu ........................ C07H 21/04 |
| | | 800/289 |
| 2004/0123343 A1 | 6/2004 | La Rosa et al. |
| 2005/0108791 A1 | 5/2005 | Edgerton |
| 2006/0123505 A1 | 6/2006 | Kikuchi et al. |
| 2006/0137043 A1 | 6/2006 | Puzio et al. |
| 2006/0179511 A1 | 8/2006 | Chomet et al. |
| 2015/0176021 A1 | 6/2015 | Vinocur et al. |

FOREIGN PATENT DOCUMENTS

| WO | WO 03/000906 | 1/2003 |
|---|---|---|
| WO | WO 2004/081173 | 9/2004 |
| WO | WO 2004/104162 | 12/2004 |
| WO | WO 2004/111183 | 12/2004 |
| WO | WO 2005/121364 | 12/2005 |
| WO | WO 2007/020638 | 2/2007 |
| WO | WO 2007/049275 | 5/2007 |
| WO | WO 2008/075364 | 6/2008 |
| WO | WO 2008/122980 | 10/2008 |
| WO | WO 2009/013750 | 1/2009 |
| WO | WO 2009/083958 | 7/2009 |
| WO | WO 2009/141824 | 11/2009 |
| WO | WO 2010/020941 | 2/2010 |
| WO | WO 2010/049897 | 5/2010 |
| WO | WO 2010/076756 | 7/2010 |
| WO | WO 2010/100595 | 9/2010 |
| WO | WO 2010/143138 | 12/2010 |
| WO | WO 2011/015985 | 2/2011 |
| WO | WO 2011/080674 | 7/2011 |
| WO | WO 2011/135527 | 11/2011 |
| WO | WO 2012/028993 | 3/2012 |
| WO | WO 2012/085862 | 6/2012 |
| WO | WO 2012/150598 | 11/2012 |

(Continued)

OTHER PUBLICATIONS

Examination Report dated Dec. 6, 2017 From the Instituto Mexicano de la Propiedad Industrial, IMPI, Direccion Divisional de Patentes Re. Application No. MX/a/2013/009706 and Its Translation Into English. (8 Pages).

Communication Pursuant to Article 94(3) EPC dated Mar. 6, 2018 From the European Patent Office Re. Application No. 16161064.7. (4 Pages).

Requisition by the Examiner dated Apr. 24, 2018 From the Innovation, Science and Economic Development Canada, Canadian Intellectual Property Office Re. Application No. 2,732,773. (4 Pages).

Communication Pursuant to Article 94(3) EPC dated Aug. 2, 2017 From the European Patent Office Re. Application No. 16161064.7. (5 Pages).

(Continued)

*Primary Examiner* — Matthew R Keogh

(57) ABSTRACT

Provided are methods of increasing nitrogen use efficiency, fertilizer use efficiency, yield, growth rate, vigor, biomass, oil content and/or abiotic stress tolerance of a plant by expressing within the plant an exogenous polynucleotide comprising a nucleic acid sequence encoding a polypeptide at least 80% identical to SEQ ID NO: 2560, 2557, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2562 or 2563. Also provided are isolated polynucleotides and polypeptides which can be used to increase nitrogen use efficiency, fertilizer use efficiency, yield, growth rate, vigor, biomass, oil content and/or abiotic stress tolerance of a plant of a plant.

18 Claims, 3 Drawing Sheets

Specification includes a Sequence Listing.

(56) References Cited

FOREIGN PATENT DOCUMENTS

| WO | WO 2013/027223 | 2/2013 |
|---|---|---|
| WO | WO 2013/078153 | 5/2013 |
| WO | WO 2013/080203 | 6/2013 |
| WO | WO 2013/098819 | 7/2013 |
| WO | WO 2013/128448 | 9/2013 |
| WO | WO 2013/179211 | 12/2013 |
| WO | WO 2014/033714 | 3/2014 |
| WO | WO 2014/102773 | 7/2014 |
| WO | WO 2014/102774 | 7/2014 |
| WO | WO 2014/188428 | 11/2014 |
| WO | WO 2015/029031 | 3/2015 |
| WO | WO 2015/181823 | 12/2015 |
| WO | WO 2016/030885 | 3/2016 |

OTHER PUBLICATIONS

Communication Pursuant to Article 94(3) EPC dated Jan. 3, 2013 From the European Patent Office Re. Application No. 09807983.3.
Communication Pursuant to Article 94(3) EPC dated May 19, 2014 From the European Patent Office Re. Application No. 09807983.3.
European Search Report and the European Search Opinion dated Nov. 8, 2016 From the European Patent Office Re. Application No. 16161064.7. (10 Pages).
Examination Report dated Dec. 2, 2013 From the Instituto Mexicano de la Propiedad Industrial Re. Application No. MX/a/2011/001741 and Its Translation Into English.
Examination Report dated Apr. 3, 2017 From the Instituto Mexicano de la Propiedad Industrial, IMPI, Direccion Divisional de Patentes Re. Application No. MX/a/2013/009706 and Its Translation Into English. (13 Pages).
Examination Report dated Mar. 11, 2016 From the Government of India, Patent Office, Intellectual Property Building Re. Application No. 508/MUMNP/2011.
Examination Report dated Aug. 15, 2014 From the Instituto Mexicano de la Propiedad Industrial Re. Application No. MX/a/2011/001741 and Its Translation Into English.
Examination Report dated Dec. 16, 2016 From the Australian Government, IP Australia Re. Application No. 2016202091. (3 Pages).
Examination Report dated May 23, 2013 From the Instituto Mexicano de la Propiedad Industrial Re. Application No. MX/a/2011/001741 and Its Translation Into English.
Examination Report dated Sep. 29, 2016 From the Instituto Mexicano de la Propiedad Industrial, IMPI Re. Application No. MX/a/2013/009706 and Its Translation Into English. (4 Pages).
Examination Report dated Mar. 30, 2017 From the Australian Government, IP Australia Re. Application No. 2016202091. (3 Pages).
Hearing Notice dated Jul. 7, 2017 From the Government of India, Patent Office, Intellectual Property Building Re. Application No. 508/MUMNP/2011. (1 Page).
Hearing Notice dated Nov. 7, 2016 From the Government of India, Patent Office, Intellectual Property Building Re. Application No. 508/MUMNP/2011. (2 Pages).
International Preliminary Report on Patentability dated Mar. 3, 2011 From the International Bureau of WIPO Re.: Application No. PCT/IB2009/053633.
International Search Report and the Written Opinion dated Jun. 2, 2010 From the International Searching Authority Re. Application No. PCT/IB09/53633.
Invitation to Pay Additional Fees dated Mar. 2, 2010 From the International Searching Authority Re. Application No. PCT/IB09/53633.
Official Action dated Feb. 12, 2016 From the US Patent and Trademark Office Re. U.S. Appl. No. 14/636,275.
Official Action dated May 15, 2014 From the US Patent and Trademark Office Re. U.S. Appl. No. 13/059,231.
Official Action dated May 20, 2013 From the US Patent and Trademark Office Re. U.S. Appl. No. 13/059,231.
Official Action dated Oct. 23, 2014 From the US Patent and Trademark Office Re. U.S. Appl. No. 13/059,231.
Official Action dated Jan. 25, 2017 From the US Patent and Trademark Office Re. U.S. Appl. No. 14/636,275. (30 Pages).
Official Action dated Oct. 29, 2013 From the US Patent and Trademark Office Re. U.S. Appl. No. 13/059,231.
Official Action dated Jul. 31, 2015 From the US Patent and Trademark Office Re. U.S. Appl. No. 14/636,275.
Patent Examination Report dated Sep. 16, 2015 From the Australian Government, IP Australia Re. Application No. 2009283785.
Patent Examination Report dated Mar. 17, 2015 From the Australian Government, IP Australia Re. Application No. 2009283785.
Requisition by the Examiner dated Jun. 9, 2016 From the Canadian Intellectual Property Office Re. Application No. 2,732,773.
Requisition by the Examiner dated May 12, 2017 From the Canadian Intellectual Property Office Re. Application No. 2,732,773. (10 Pages).
Requisition by the Examiner dated Sep. 23, 2015 From the Canadian Intellectual Property Office Re. Application No. 2,732,773.
Supplementary European Search Report and the European Search Opinion dated Aug. 2, 2016 From the European Patent Office Re. Application No. 16161064.7.
Supplementary European Search Report and the European Search Opinion dated Jan. 2, 2012 From the European Patent Office Re. Application No. 09807983.3.
Adachi et al. "*Oryza sativa* Japonica Group cDNA Clone:J023021L06, Full Insert Sequence", Database EMBASE [Online], XP002665608, Retrieved From EBI, Database Accession No. AK099270, Jul. 19, 2003.
Boyes et al. "Growth Stage-Based Phenotypic Analysis of *Arabidopsis*: A Model for High Throughput Functional Genomics in Plants", The Plant Cell, 13(7): 1499-1510, Jul. 2001.
Feng et al. "Probable Cinnamyl Alcohol Dehydrogenase 6", Darabase UniProt [Online], XP002665609, Retrieved From EBI, Database Accession No. Q7XWU3, Mar. 1, 2004.
Flexas et al. "Drought-Inhibition of Photosynthesis in C3 Plants: Stomatal and Non-Stomatal Limitations Revisited", Annals of Bontany, 89: 183-189, 2002.
Hirner et al. "*Arabidopsis* LHT1 Is a High-Affinity Transporter for Cellular Amino Acid Uptake in Both Root Epidermis and Leaf Mesophyll", The Plant Cell, 18: 1931-1946, Aug. 2006.
Plant Energy Biology "Protein_Coding: Cationic Amino Acid Transporter 2 (TAIR10)", Plant Energy Biology: SUBA3 Flatfile for AT1G58030.1, Database, 1 P., 2007.
Rolletschek et al. "Ectopic Expression of an Amino Acid Transporter (VfAAP1) in Seeds of Vica Narbonensis and Pea Increases Storage Proteins", Plant Physiology, 137: 1236-1249, Apr. 2005.
Seki et al. "Monitoring the Expression Profiles of 7000 *Arabidopsis* Genes Under Drought, Cold and High-Salinity Stresses Using a Full-Length cDNA Microarray", The Plant Journal, 31(3): 279-292, 2002.
Soderlund et al. "*Zea mays* Full-Length cDNA Clone ZM_BFb0168A22 mRNA, Complete CDS", GenBank Database [Online], GenBank: BT037402.1, Database Accession No. BT037402, Jul. 20, 2008.
Su et al. "Molecular and Functional Characterization of a Family of Amino Acid Transporter From *Arabidopsis*", Plant Physiology, 136: 3104-3113, Oct. 2004.
TAIR "Encodes a Member of the Cationic Amino Acid Transporter (CAT) Subfamily of Amino Acid Polyamine Choline Transporters. Localized to the Tonoplast", TAIR, Locus: AT1G58030, TAIR Accession No. Locus:2196245, 4 P., 2013.
TAIR "Protein Kinase Superfamily Protein. Functions in: Protein Serine/Threonine Kinase Activity, Protein Kinase Activity, Kinase Activity, ATP Binding ff.", TAIR, Locus: AT5G15080, TAIR Accession No. Locus:2147805, 4 P., 2013.
Tobias et al. "Structure of the Cinnamyl-Alcohol Dehydrogenase Gene Family in Rice and Promoter Activity of a Member Associated With Lignification", Planta, 220: 678-688, 2005.
Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.

(56) References Cited

OTHER PUBLICATIONS

Examination Report dates May 10, 2018 from the Instituto Mexicano de la Propiedad Industrial, IMPI Re. Application No. MX/a/2013/009706 and Its Translation Into English. (7 Pages).
Clarifications Prior to Substantive Examination dated Jul. 2, 2018 from the Argentinean Patent Office Re. Application No. P090103167 and its Summary in English. (7 Pages).
Examination Report dated Dec. 13, 2018 from IP Australia, Australian Government Re. Application No. 2017251729. (3 pages).

* cited by examiner

USE OF UMP-CMP KINASES FOR INCREASING NITROGEN USE EFFICIENCY AND LOW NITROGEN TOLERANCE IN PLANTS

RELATED APPLICATIONS

This application is a division of U.S. patent application Ser. No. 14/636,275, filed Mar. 3, 2015, which is a division of U.S. patent application Ser. No. 13/059,231 filed Feb. 16, 2011, now U.S. Pat. No. 9,018,445, which is a National Phase of PCT Patent Application No. PCT/IB2009/053633 having International Filing Date of Aug. 18, 2009, which claims the benefit of priority of U.S. Provisional Patent Application No. 61/136,189 filed on Aug. 18, 2008. The contents of the above applications are all incorporated by reference as if fully set forth herein in their entirety.

SEQUENCE LISTING STATEMENT

The ASCII file, entitled 70820SequenceListing.txt, created on Aug. 10, 2017, comprising 5,350,431 bytes, submitted concurrently with the filing of this application is incorporated herein by reference.

FIELD AND BACKGROUND OF THE INVENTION

The present invention, in some embodiments thereof, relates to isolated polypeptides and polynucleotides, nucleic acid constructs comprising same, transgenic plants expressing same and methods of using same for increasing nitrogen use efficiency, yield, biomass, vigor, growth rate, oil content, fertilizer use efficiency, water use efficiency and abiotic stress tolerance of a plant.

A common approach to promote plant growth has been, and continues to be, the use of natural as well as synthetic nutrients (fertilizers). Thus, fertilizers are the fuel behind the "green revolution", directly responsible for the exceptional increase in crop yields during the last 40 years, and are considered the number one overhead expense in agriculture. Of the three macronutrients provided as main fertilizers [Nitrogen (N), Phosphate (P) and Potassium (K)], nitrogen is the only one that usually needs to be replenished every year, particularly for cereals, which comprise more than half of the cultivated areas worldwide. For example, inorganic nitrogenous fertilizers such as ammonium nitrate, potassium nitrate, or urea, typically accounts for 40% of the costs associated with crops such as corn and wheat.

Nitrogen is an essential macronutrient for the plant, responsible for biosynthesis of amino and nucleic acids, prosthetic groups, plant hormones, plant chemical defenses, etc. In addition, nitrogen is often the rate-limiting element in plant growth and all field crops have a fundamental dependence on inorganic nitrogen. Thus, nitrogen is translocated to the shoot, where it is stored in the leaves and stalk during the rapid step of plant development and up until flowering. In corn for example, plants accumulate the bulk of their organic nitrogen during the period of grain germination, and until flowering. Once fertilization of the plant has occurred, grains begin to form and become the main sink of plant nitrogen. The stored nitrogen can be then redistributed from the leaves and stalk that served as storage compartments until grain formation.

Since fertilizer is rapidly depleted from most soil types, it must be supplied to growing crops two or three times during the growing season. In addition, the low nitrogen use efficiency (NUE) of the main crops (e.g., in the range of only 30-70%) negatively affects the input expenses for the farmer, due to the excess fertilizer applied. Moreover, the over and inefficient use of fertilizers are major factors responsible for environmental problems such as eutrophication of groundwater, lakes, rivers and seas, nitrate pollution in drinking water which can cause methemoglobinemia, phosphate pollution, atmospheric pollution and the like. However, in spite of the negative impact of fertilizers on the environment, and the limits on fertilizer use, which have been legislated in several countries, the use of fertilizers is expected to increase in order support food and fiber production for rapid population growth on limited land resources. For example, it has been estimated that by 2050, more than 150 million tons of nitrogenous fertilizer will be used worldwide annually.

Increased use efficiency of nitrogen by plants should enable crops to be cultivated with lower fertilizer input, or alternatively to be cultivated on soils of poorer quality and would therefore have significant economic impact in both developed and developing agricultural systems.

Genetic improvement of fertilizer use efficiency (FUE) in plants can be generated either via traditional breeding or via genetic engineering.

Attempts to generate plants with increased FUE have been described in U.S. Pat. Appl. No. 20020046419 to Choo, et al.; U.S. Pat. Appl. No. 2005010879 to Edgerton et al.; U.S. Pat. Appl. No. 20060179511 to Chomet et al.; Good, A, et al. 2007 (Engineering nitrogen use efficiency with alanine aminotransferase. Canadian Journal of Botany 85: 252-262); and Good A G et al. 2004 (Trends Plant Sci. 9:597-605).

Yanagisawa et al. (Proc. Natl. Acad. Sci. U.S.A. 2004 101:7833-8) describe Dof1 transgenic plants which exhibit improved growth under low-nitrogen conditions.

U.S. Pat. No. 6,084,153 to Good et al. discloses the use of a stress responsive promoter to control the expression of Alanine Amine Transferase (AlaAT) and transgenic canola plants with improved drought and nitrogen deficiency tolerance when compared to control plants.

The global shortage of water supply, desertification, abiotic stress (ABS) conditions (e.g., drought, salinity, osmoticum, flood, suboptimal temperatures such as cold and heat, toxic chemical pollution, radiation, nutrient deficiencies, and the like) together with the presence of limited nitrogen and fertilizer sources cause substantial damage to agricultural plants such as major alterations in the plant metabolism, cell death, and decreases in plant growth and crop productivity.

Drought is a gradual phenomenon, which involves periods of abnormally dry weather that persists long enough to produce serious hydrologic imbalances such as crop damage, water supply shortage and increased susceptibility to various diseases.

Salinity affects one in five hectares of irrigated land. None of the top five food crops, i.e., wheat, corn, rice, potatoes, and soybean, can tolerate excessive salt. Detrimental effects of salt on plants result from both water deficit, which leads to osmotic stress (similar to drought stress), and the effect of excess sodium ions on critical biochemical processes. As with freezing and drought, high salt causes water deficit; and the presence of high salt makes it difficult for plant roots to extract water from their environment. Thus, salination of soils that are used for agricultural production is a significant and increasing problem in regions that rely heavily on agriculture, and is worsen by over-utilization, over-fertilization and water shortage, typically caused by climatic change and the demands of increasing population.

Extreme temperatures such as suboptimal or heat temperatures affect plant growth and development through the whole plant life cycle. Thus, low temperatures reduce germination rate and high temperatures result in leaf necrosis. In addition, mature plants that are exposed to excess of heat may experience heat shock, which may arise in various organs, including leaves and particularly fruit, when transpiration is insufficient to overcome heat stress. Heat also damages cellular structures, including organelles and cytoskeleton, and impairs membrane function. Heat shock may produce a decrease in overall protein synthesis, accompanied by expression of heat shock proteins, e.g., chaperones, which are involved in refolding proteins denatured by heat. High-temperature damage to pollen almost always occurs in conjunction with drought stress, and rarely occurs under well-watered conditions. Combined stress can alter plant metabolism in novel ways. Excessive chilling conditions, e.g., low, but above freezing, temperatures affect crops of tropical origins, such as soybean, rice, maize, and cotton. Typical chilling damage includes wilting, necrosis, chlorosis or leakage of ions from cell membranes. Excessive light conditions, which occur under clear atmospheric conditions subsequent to cold late summer/autumn nights, can lead to photoinhibition of photosynthesis (disruption of photosynthesis). In addition, chilling may lead to yield losses and lower product quality through the delayed ripening of maize.

Nutrient deficiencies cause adaptations of the root architecture, particularly notably for example is the root proliferation within nutrient rich patches to increase nutrient uptake. Nutrient deficiencies cause also the activation of plant metabolic pathways which maximize the absorption, assimilation and distribution processes such as by activating architectural changes. Engineering the expression of the triggered genes may cause the plant to exhibit the architectural changes and enhanced metabolism also under other conditions.

In addition, it is widely known that the plants usually respond to water deficiency by creating a deeper root system that allows access to moisture located in deeper soil layers. Triggering this effect will allow the plants to access nutrients and water located in deeper soil horizons particularly those readily dissolved in water like nitrates.

Yield is affected by various factors, such as, the number and size of the plant organs, plant architecture (for example, the number of branches), grains set length, number of filled grains, vigor (e.g. seedling), growth rate, root development, utilization of water, nutrients (e.g., nitrogen) and fertilizers, and stress tolerance.

Crops such as, corn, rice, wheat, canola and soybean account for over half of total human caloric intake, whether through direct consumption of the seeds themselves or through consumption of meat products raised on processed seeds or forage. Seeds are also a source of sugars, proteins and oils and metabolites used in industrial processes. The ability to increase plant yield, whether through increase dry matter accumulation rate, modifying cellulose or lignin composition, increase stalk strength, enlarge meristem size, change of plant branching pattern, erectness of leaves, increase in fertilization efficiency, enhanced seed dry matter accumulation rate, modification of seed development, enhanced seed filling or by increasing the content of oil, starch or protein in the seeds would have many applications in agricultural and non-agricultural uses such as in the biotechnological production of pharmaceuticals, antibodies or vaccines.

WO publication No. 2009/013750 discloses genes, constructs and methods of increasing abiotic stress tolerance, biomass and/or yield in plants generated thereby.

WO publication No. 2008/122980 discloses genes constructs and methods for increasing oil content, growth rate and biomass of plants.

WO publication No. 2008/075364 discloses polynucleotides involved in plant fiber development and methods of using same.

WO publication No. 2007/049275 discloses isolated polypeptides, polynucleotides encoding same, transgenic plants expressing same and methods of using same for increasing fertilizer use efficiency, plant abiotic stress tolerance and biomass.

WO publication No. 2004/104162 discloses methods of increasing abiotic stress tolerance and/or biomass in plants and plants generated thereby.

WO publication No. 2005/121364 discloses polynucleotides and polypeptides involved in plant fiber development and methods of using same for improving fiber quality, yield and/or biomass of a fiber producing plant.

WO publication No. 2007/020638 discloses methods of increasing abiotic stress tolerance and/or biomass in plants and plants generated thereby.

SUMMARY OF THE INVENTION

According to an aspect of some embodiments of the present invention there is provided a method of increasing nitrogen use efficiency, fertilizer use efficiency, yield, growth rate, vigor, biomass, oil content and/or abiotic stress tolerance of a plant, comprising expressing within the plant an exogenous polynucleotide comprising a nucleic acid sequence at least 80% identical to SEQ ID NO: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2521 or 2522, thereby increasing the nitrogen use efficiency, fertilizer use efficiency, yield, growth rate, vigor, biomass, oil content and/or abiotic stress tolerance of the plant.

According to an aspect of some embodiments of the present invention there is provided a method of increasing nitrogen use efficiency, fertilizer use efficiency, yield, growth rate, vigor, biomass, oil content and/or abiotic stress tolerance of a plant, comprising expressing within the plant an exogenous polynucleotide comprising the nucleic acid sequence selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522, 3, 5, 6, 9, 10, 14, 15, 20, 61, 62, 129, 288, 294, 307, 363, 667, 668, 669, 670, 672, 2398-2413, 2456 and 2457, thereby increasing the nitrogen use efficiency, fertilizer use efficiency, yield, growth rate, vigor, biomass, oil content and/or abiotic stress tolerance of the plant.

According to an aspect of some embodiments of the present invention there is provided a method of increasing nitrogen use efficiency, fertilizer use efficiency, yield, growth rate, vigor, biomass, oil content and/or abiotic stress tolerance of a plant, comprising expressing within the plant an exogenous polynucleotide comprising a nucleic acid sequence encoding a polypeptide at least 80% identical to SEQ ID NO: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2562 or 2563, thereby increasing the nitrogen use efficiency, fertilizer use efficiency, yield, growth rate, vigor, biomass, oil content and/or abiotic stress tolerance of the plant.

According to an aspect of some embodiments of the present invention there is provided a method of increasing nitrogen use efficiency, fertilizer use efficiency, yield, growth rate, vigor, biomass, oil content and/or abiotic stress tolerance of a plant, comprising expressing within the plant an exogenous polynucleotide comprising a nucleic acid sequence encoding a polypeptide selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563, 138-143, 146, 148, 150-152, 157, 162, 198, 265, 1334-1350, 1352-1364, 1426-1428, 1458, 1460, 1732-1734, 1737-1738, 2523-2532, 2542 and 2543, thereby increasing the nitrogen use efficiency, fertilizer use efficiency, yield, growth rate, vigor, biomass, oil content and/or abiotic stress tolerance of the plant.

According to an aspect of some embodiments of the present invention there is provided a method of increasing nitrogen use efficiency, fertilizer use efficiency and/or oil content of a plant, comprising expressing within the plant an exogenous polynucleotide comprising a nucleic acid sequence at least 80% identical to SEQ ID NO: 3, 5, 6, 9, 10, 14, 15, 288, 294, 2398-2412 or 2413, thereby increasing the nitrogen use efficiency, fertilizer use efficiency, and/or oil content of the plant.

According to an aspect of some embodiments of the present invention there is provided a method of increasing nitrogen use efficiency, fertilizer use efficiency and/or oil content of a plant, comprising expressing within the plant an exogenous polynucleotide comprising the nucleic acid sequence selected from the group consisting of SEQ ID NOs: 3, 5, 6, 9, 10, 14, 15, 288, 294, 2398-2413, thereby increasing the nitrogen use efficiency, fertilizer use efficiency and/or oil content of the plant.

According to an aspect of some embodiments of the present invention there is provided a method of increasing nitrogen use efficiency, fertilizer use efficiency and/or oil content of a plant, comprising expressing within the plant an exogenous polynucleotide comprising a nucleic acid sequence encoding a polypeptide at least 80% identical to SEQ ID NO: 138-153, 1334-1350, 1352-1364, 1458, 1460, 2523-2531 or 2532, thereby increasing the nitrogen use efficiency, fertilizer use efficiency and/or oil content of the plant.

According to an aspect of some embodiments of the present invention there is provided a method of increasing nitrogen use efficiency, fertilizer use efficiency and/or oil content of a plant, comprising expressing within the plant an exogenous polynucleotide comprising a nucleic acid sequence encoding a polypeptide selected from the group consisting of SEQ ID NOs: 138-153, 1334-1350, 1352-1364, 1458, 1460, 2523-2532, thereby increasing the nitrogen use efficiency, fertilizer use efficiency and/or oil content of the plant.

According to an aspect of some embodiments of the present invention there is provided an isolated polynucleotide comprising a nucleic acid sequence at least 80% identical to SEQ ID NO: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2521 or 2522, wherein the nucleic acid sequence is capable of increasing nitrogen use efficiency, fertilizer use efficiency, yield, growth rate, vigor, biomass, oil content and/or abiotic stress of a plant.

According to an aspect of some embodiments of the present invention there is provided an isolated polynucleotide comprising the nucleic acid sequence selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522, 3, 5, 6, 9, 10, 14, 15, 20, 61, 62, 129, 288, 294, 307, 363, 667, 668, 669, 670, 672, 2398-2413, 2456 and 2457.

According to an aspect of some embodiments of the present invention there is provided an isolated polynucleotide comprising a nucleic acid sequence encoding a polypeptide which comprises an amino acid sequence at least 80% homologous to the amino acid sequence set forth in SEQ ID NO: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2562 or 2563, wherein the amino acid sequence is capable of increasing nitrogen use efficiency, fertilizer use efficiency, yield, growth rate, vigor, biomass, oil content and/or abiotic stress tolerance of a plant.

According to an aspect of some embodiments of the present invention there is provided an isolated polynucleotide comprising a nucleic acid sequence encoding a polypeptide which comprises the amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563, 138-143, 146, 148, 150-152, 157, 162, 198, 265, 1334-1350, 1352-1364, 1426-1428, 1458, 1460, 1732-1734, 1737-1738, 2523-2532, 2542 and 2543.

According to an aspect of some embodiments of the present invention there is provided a nucleic acid construct comprising the isolated polynucleotide of the invention, and a promoter for directing transcription of the nucleic acid sequence in a host cell.

According to an aspect of some embodiments of the present invention there is provided an isolated polypeptide comprising an amino acid sequence at least 80% homologous to SEQ ID NO: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2562 or 2563, wherein the amino acid sequence is capable of increasing nitrogen use efficiency, fertilizer use efficiency, yield, growth rate, vigor, biomass, oil content and/or abiotic stress tolerance of a plant.

According to an aspect of some embodiments of the present invention there is provided an isolated polypeptide comprising the amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563, 138-143, 146, 148, 150-152, 157, 162, 198, 265, 1334-1350, 1352-1364, 1426-1428, 1458, 1460, 1732-1734, 1737-1738, 2523-2532, 2542 and 2543.

According to an aspect of some embodiments of the present invention there is provided a plant cell exogenously expressing the polynucleotide of the invention, or the nucleic acid construct of the invention.

According to an aspect of some embodiments of the present invention there is provided a plant cell exogenously expressing the polypeptide of the invention.

According to some embodiments of the invention, the nucleic acid sequence is as set forth in SEQ ID NO: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2521 or 2522.

According to some embodiments of the invention, the polynucleotide consists of the nucleic acid sequence selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522.

According to some embodiments of the invention, the nucleic acid sequence encodes an amino acid sequence at least 80% homologous to SEQ ID NO: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2562 or 2563.

According to some embodiments of the invention, the nucleic acid sequence encodes the amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563.

According to some embodiments of the invention, the nucleic acid sequence is as set forth in SEQ ID NO: 3, 5, 6, 9, 10, 14, 15, 288, 294, 2398-2412 or 2413.

According to some embodiments of the invention, the polynucleotide consists of the nucleic acid sequence selected from the group consisting of SEQ ID NOs: 3, 5, 6, 9, 10, 14, 15, 288, 294, 2398-2413.

According to some embodiments of the invention, the nucleic acid sequence encodes an amino acid sequence at least 80% homologous to SEQ ID NO: 138-153, 1334-1350, 1352-1364, 1458, 1460, 2523-2531 or 2532.

According to some embodiments of the invention, the nucleic acid sequence encodes the amino acid sequence selected from the group consisting of SEQ ID NOs: 138-153, 1334-1350, 1352-1364, 1458, 1460, 2523-2532.

According to some embodiments of the invention, the plant cell forms part of a plant.

According to some embodiments of the invention, the method further comprising growing the plant expressing the exogenous polynucleotide under the abiotic stress.

According to some embodiments of the invention, the abiotic stress is selected from the group consisting of salinity, drought, water deprivation, flood, etiolation, low temperature, high temperature, heavy metal toxicity, anaerobiosis, nutrient deficiency, nutrient excess, atmospheric pollution and UV irradiation.

According to some embodiments of the invention, the yield comprises seed yield or oil yield.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A—An image of a photograph of plants taken following 10 days on agar plates. FIG. 3B—An image of root analysis in which the length of the root measured is represented by a red arrow.

DESCRIPTION OF SPECIFIC EMBODIMENTS OF THE INVENTION

Figure 1:
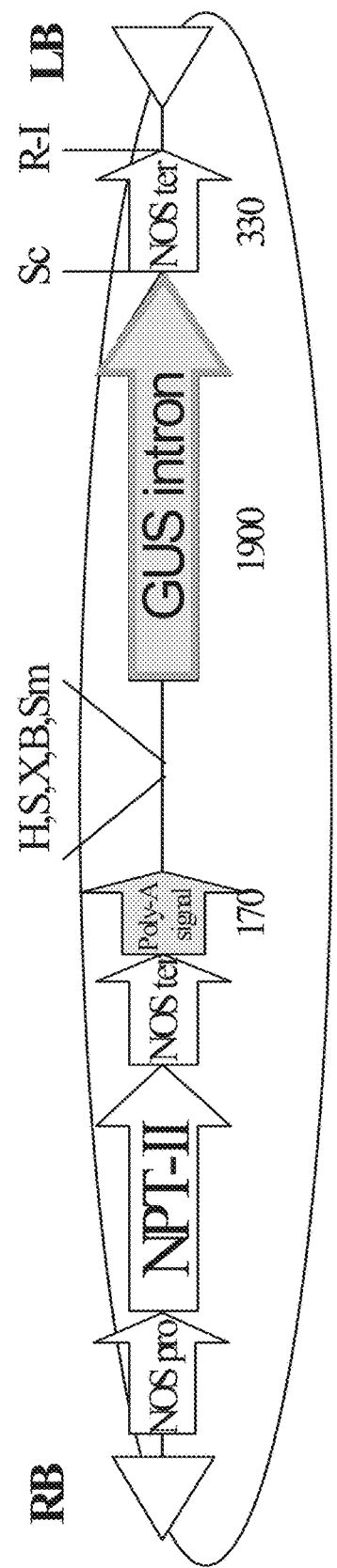
FIG. 1 is a schematic illustration of the pGI binary plasmid used for expressing the isolated polynucleotide sequences of some embodiments of the invention. RB—T-DNA right border; LB—T-DNA left border; H—HindIII restriction enzyme; X—XbaI restriction enzyme; B—BamHI restriction enzyme; S—SalI restriction enzyme; Sm—SmaI restriction enzyme; R-I—EcoRI restriction enzyme; Sc—SacI/SstI/Ecl136II; (numbers)—Length in base-pairs; NOS pro=nopaline synthase promoter; NPT-II=neomycin phosphotransferase gene; NOS ter=nopaline synthase terminator; Poly-A signal (polyadenylation signal); GUSintron—the GUS reporter gene (coding sequence and intron) The isolated polynucleotide sequences of the invention were cloned into the vector while replacing the GUS-intron reporter gene
Figure 2:
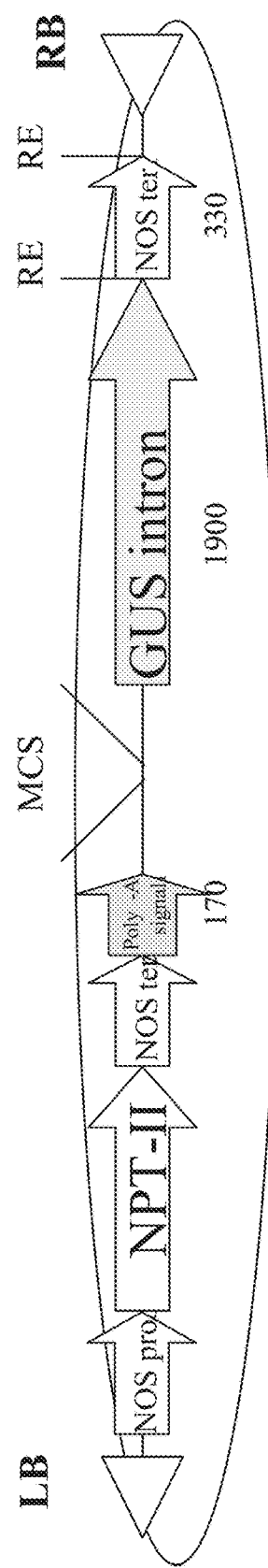
FIG. 2 is a schematic illustration of the modified pGI binary plasmid used for expressing the isolated polynucleotide sequences of the invention. RB—T-DNA right border; LB—T-DNA left border; MCS—Multiple cloning site; RE—any restriction enzyme; (numbers)—Length in base-pairs; NOS pro=nopaline synthase promoter; NPT-II=neomycin phosphotransferase gene; NOS ter=nopaline synthase terminator; Poly-A signal (polyadenylation signal); GUSintron—the GUS reporter gene (coding sequence and intron) The isolated polynucleotide sequences of the invention were cloned into the vector while replacing the GUS-intron reporter gene.

The present invention, in some embodiments thereof, relates to isolated polynucleotides and polypeptides, expression vectors comprising same and transgenic plants expressing same and, more particularly, but not exclusively, to methods of increasing nitrogen use efficiency, yield, biomass, vigor, growth rate, oil content and abiotic stress tolerance of a plant using same.

Before explaining at least one embodiment of the invention in detail, it is to be understood that the invention is not necessarily limited in its application to the details set forth in the following description or exemplified by the Examples.

The invention is capable of other embodiments or of being practiced or carried out in various ways.

While reducing the present invention to practice, the present inventors have identified novel polypeptides and polynucleotides which can be used to increase nitrogen use efficiency, fertilizer use efficiency, water use efficiency, yield, growth rate, biomass, oil content, vigor and/or abiotic stress tolerance of a plant.

Thus, as shown in the Examples section which follows, the present inventors have utilized bioinformatics tools to generate digital expression profiles of gene clusters which expression level is associated with various conditions and stresses such as nutrient deficiency, cold, salinity, drought, heat stress, etiolation, waterlogging and oxidative stress (Tables 1-19; Example 1 of the Examples section which follows), and based on the expression profiles have identified genes which are expected to enhance nitrogen use efficiency, biomass, growth rate, yield, vigor, oil content and/or abiotic stress tolerance of a plant (Table 20; polynucleotide SEQ ID NOs: 1-137; polypeptides SEQ ID NOs: 138-269; Example 1 of the Examples section which follows). Homologous polypeptides and polynucleotides having the same function were also identified (Table 21, polynucleotide SEQ ID NOs: 270-1333; polypeptide SEQ ID NOs: 1334-2397; Example 2 of the Examples section which follows). To test the effect of the isolated genes on the trait-of-interest, the polynucleotides were cloned into binary vectors (Table 23, polynucleotide SEQ ID NOs: 2398-2522; Example 3 of the Examples section which follows) and the predicted proteins were identified (Table 23, Example 3). Transgenic plants over-expressing the identified polynucleotides were found to exhibit increased nitrogen use efficiency, yield, biomass, photosynthetic areas and growth rate (Tables 24-521 Examples 5, 6 and 7 of the Examples section which follows), as well as increased abiotic stress tolerance (e.g., under salinity stress; Tables 53-55, Example 8 of the Examples section which follows). Altogether, these results suggest the use of the novel polynucleotides and polypeptides of the invention and homologous sequences thereof for increasing nitrogen use efficiency, fertilizer use efficiency, yield (including oil yield, seed yield and oil content), growth rate, biomass, vigor and/or abiotic stress tolerance of a plant.

Thus, according to an aspect of some embodiments of the invention, there is provided method of increasing fertilizer use efficiency, nitrogen use efficiency, yield, growth rate, vigor, biomass, oil content and/or abiotic stress tolerance of a plant, comprising expressing within the plant an exogenous polynucleotide comprising a nucleic acid sequence at least 80% identical to SEQ ID NO: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2521 or 2522, thereby increasing the nitrogen use efficiency, fertilizer use efficiency, yield, growth rate, vigor, biomass, oil content, water use efficiency and/or abiotic stress tolerance of the plant.

As used herein the phrase "fertilizer use efficiency" refers to the metabolic process(es) which lead to an increase in the plant's yield, biomass, vigor, and growth rate per fertilizer unit applied. The metabolic process can be the uptake, spread, absorbent, accumulation, relocation (within the plant) and use of one or more of the minerals and organic moieties absorbed by the plant, such as nitrogen, phosphates and/or potassium.

As used herein the phrase "fertilizer-limiting conditions" refers to growth conditions which include a level (e.g., concentration) of a fertilizer applied which is below the level needed for normal plant metabolism, growth, reproduction and/or viability.

As used herein the phrase "nitrogen use efficiency (NUE)" refers to the metabolic process(es) which lead to an increase in the plant's yield, biomass, vigor, and growth rate per nitrogen unit applied. The metabolic process can be the uptake, spread, absorbent, accumulation, relocation (within the plant) and use of nitrogen absorbed by the plant.

As used herein the phrase "nitrogen-limiting conditions" refers to growth conditions which include a level (e.g., concentration) of nitrogen (e.g., ammonium or nitrate) applied which is below the level needed for normal plant metabolism, growth, reproduction and/or viability.

Improved plant NUE and FUE is translated in the field into either harvesting similar quantities of yield, while implementing less fertilizers, or increased yields gained by implementing the same levels of fertilizers. Thus, improved NUE or FUE has a direct effect on plant yield in the field. Thus, the polynucleotides and polypeptides of some embodiments of the invention positively affect plant yield, seed yield, and plant biomass. In addition, the benefit of improved plant NUE will certainly improve crop quality and biochemical constituents of the seed such as protein yield and oil yield.

As used herein the phrase "plant yield" refers to the amount (as determined by weight or size) or quantity (numbers) of tissue produced per plant or per growing season. Hence increased yield could affect the economic benefit one can obtain from the plant in a certain growing area and/or growing time.

It should be noted that a plant yield can be affected by various parameters including, but not limited to, plant biomass; plant vigor; growth rate; seed yield; seed or grain quantity; seed or grain quality; oil yield; content of oil, starch and/or protein in harvested organs (e.g., seeds or vegetative parts of the plant); number of flowers (florets) per panicle (expressed as a ratio of number of filled seeds over number of primary panicles); harvest index; number of plants grown per area; number and size of harvested organs per plant and per area; number of plants per growing area (density); number of harvested organs in field; total leaf area; carbon assimilation and carbon partitioning (the distribution/allocation of carbon within the plant); resistance to shade; number of harvestable organs (e.g. seeds), seeds per pod, weight per seed; and modified architecture [such as increase stalk diameter, thickness or improvement of physical properties (e.g. elasticity)].

As used herein the phrase "plant biomass" refers to the amount (measured in grams of air-dry tissue) of a tissue produced from the plant in a growing season, which could also determine or affect the plant yield or the yield per growing area. An increase in plant biomass can be in the whole plant or in parts thereof such as aboveground (harvestable) parts, vegetative biomass, roots and seeds.

As used herein the phrase "growth rate" refers to the increase in plant organ size or mass per time (can be measured in cm$^2$ per day, day or as the regression coefficient of along time course).

As used herein the phrase "plant vigor" refers to the amount (measured by weight) of tissue produced by the plant in a given time. Hence increased vigor could determine or affect the plant yield or the yield per growing time or growing area. In addition, early vigor (seed and/or seedling) result with improved field stand.

As used herein the phrase "seed yield" refers to the number or weight of the seeds per plant, seeds per pod, or per growing area or to the weight of a single seed, or to the oil extracted per seed. Hence seed yield can be affected by seed dimensions (e.g., length, width, perimeter, area and/or volume), number of (filled) seeds and seed filling rate and by seed oil content. Hence increase seed yield per plant could affect the economic benefit one can obtain from the plant in a certain growing area and/or growing time; and increase seed yield per growing area could be achieved by increasing seed yield per plant, and/or by increasing number of plants grown on the same given area.

The term "seed" (also referred to as "grain" or "kernel") as used herein refers to a small embryonic plant enclosed in a covering called the seed coat (usually with some stored food), the product of the ripened ovule of gymnosperm and angiosperm plants which occurs after fertilization and some growth within the mother plant.

The phrase "oil content" as used herein refers to the amount of lipids in a given plant organ, either the seeds (seed oil content) or the vegetative portion of the plant (vegetative oil content) and is typically expressed as percentage of dry weight (10% humidity of seeds) or wet weight (for vegetative portion).

It should be noted that oil content is affected by intrinsic oil production of a tissue (e.g., seed, vegetative portion), as well as the mass or size of the oil-producing tissue per plant or per growth period.

In one embodiment, increase in oil content of the plant can be achieved by increasing the size/mass of a plant's tissue(s) which comprise oil per growth period. Thus, increased oil content of a plant can be achieved by increasing the yield, growth rate, biomass and vigor of the plant.

It should be noted that a plant yield can be determined under stress (e.g., abiotic stress, nitrogen-limiting conditions) or non-stress (normal) conditions.

As used herein, the phrase "non-stress conditions" refers to the growth conditions (e.g., water, temperature, light-dark cycles, humidity, salt concentration, fertilizer concentration in soil, nutrient supply such as nitrogen, phosphorous and/or potassium), which enable normal metabolism, growth, reproduction and/or viability of a plant at any stage in its life cycle (from seed to mature plant and back to seed again). It should be noted that while the non-stress conditions may include some mild variations from the optimal conditions (which vary from one type/species of a plant to another), such variations do not cause the plant to cease growing without the capacity to resume growth.

The phrase "abiotic stress" as used herein refers to any adverse effect on metabolism, growth, reproduction and/or viability of a plant. Accordingly, abiotic stress can be induced by suboptimal environmental growth conditions such as, for example, salinity, water deprivation, flooding, freezing, low or high temperature, heavy metal toxicity, anaerobiosis, nutrient deficiency, atmospheric pollution or UV irradiation. The implications of abiotic stress are discussed in the Background section.

The phrase "abiotic stress tolerance" as used herein refers to the ability of a plant to endure an abiotic stress without suffering a substantial alteration in metabolism, growth, productivity and/or viability.

As used herein the phrase "water use efficiency (WUE)" refers to the level of organic matter produced per unit of water consumed by the plant, i.e., the dry weight of a plant in relation to the plant's water use, e.g., the biomass produced per unit transpiration.

As used herein the term "increasing" refers to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, increase in nitrogen use efficiency, fertilizer use efficiency, yield, growth rate, vigor, biomass, oil content, water use efficiency and/or abiotic stress tolerance of a plant as compared to a native plant [i.e., a plant not modified with the biomolecules (polynucleotide or polypeptides) of the invention, e.g., a non-transformed plant of the same species which is grown under the same growth conditions).

As used herein, the phrase "exogenous polynucleotide" refers to a heterologous nucleic acid sequence which may not be naturally expressed within the plant or which overexpression in the plant is desired. The exogenous polynucleotide may be introduced into the plant in a stable or transient manner, so as to produce a ribonucleic acid (RNA) molecule and/or a polypeptide molecule. It should be noted that the exogenous polynucleotide may comprise a nucleic acid sequence which is identical or partially homologous to an endogenous nucleic acid sequence of the plant.

According to some embodiments of the invention the exogenous polynucleotide comprises a nucleic acid sequence which is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the nucleic acid sequence selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522.

Identity (e.g., percent homology) can be determined using any homology comparison software, including for example, the BlastN software of the National Center of Biotechnology Information (NCBI) such as by using default parameters.

According to some embodiments of the invention the exogenous polynucleotide is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522.

According to some embodiments of the invention the exogenous polynucleotide is set forth by SEQ ID NO: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2521 or 2522.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a plant cell.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the invention, the exogenous polynucleotide of the invention encodes a polypeptide having an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563.

Homology (e.g., percent homology) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

One option to identify orthologues in monocot plant species is by performing a reciprocal blast search. This may be done by a first blast involving blasting the sequence-of-interest against any sequence database, such as the publicly available NCBI database which may be found at: Hypertext Transfer Protocol://World Wide Web (dot) ncbi (dot) nlm (dot) nih (dot) gov. If orthologues in rice were sought, the sequence-of-interest would be blasted against, for example, the 28,469 full-length cDNA clones from Oryza sativa Nipponbare available at NCBI. The blast results may be filtered. The full-length sequences of either the filtered results or the non-filtered results are then blasted back (second blast) against the sequences of the organism from which the sequence-of-interest is derived. The results of the first and second blasts are then compared. An orthologue is identified when the sequence resulting in the highest score (best hit) in the first blast identifies in the second blast the query sequence (the original sequence-of-interest) as the best hit. Using the same rational a paralogue (homolog to a gene in the same organism) is found. In case of large sequence families, the ClustalW program may be used [Hypertext Transfer Protocol://World Wide Web (dot) ebi (dot) ac (dot) uk/Tools/clustalw2/index (dot) html], followed by a neighbor-joining tree (Hypertext Transfer Protocol://en (dot) wikipedia (dot) org/wiki/Neighbor-joining) which helps visualizing the clustering.

According to some embodiments of the invention, the exogenous polynucleotide encodes a polypeptide consisting of the amino acid sequence set forth by SEQ ID NO: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2562 or 2563.

According to an aspect of some embodiments of the invention there is provided a method of increasing nitrogen use efficiency, fertilizer use efficiency, yield, growth rate, vigor, biomass, oil content and/or abiotic stress tolerance of a plant. The method is effected by expressing within the plant an exogenous polynucleotide. comprising the nucleic acid sequence selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522, 3, 5, 6, 9, 10, 14, 15, 20, 61, 62, 129, 288, 294, 307, 363, 667, 668, 669, 670, 672, 2398-2413, 2456 and 2457, thereby increasing the nitrogen use efficiency, fertilizer use efficiency, yield, growth rate, vigor, biomass, oil content and/or abiotic stress tolerance of the plant.

According to some embodiments of the invention the exogenous polynucleotide is set forth by SEQ ID NO: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522, 3, 5, 6, 9, 10, 14, 15, 20, 61, 62, 129, 288, 294, 307, 363, 667, 668, 669, 670, 672, 2398-2413, 2456 or 2457.

According to some embodiments of the invention, the exogenous polynucleotide of the invention encodes a polypeptide having an amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563, 138-143, 146, 148, 150-152, 157, 162, 198, 265, 1334-1350, 1352-1364, 1426-1428, 1458, 1460, 1732-1734, 1737-1738, 2523-2532, 2542 and 2543, thereby increasing the nitrogen use efficiency, fertilizer use efficiency, yield, growth rate, vigor, biomass, oil content and/or abiotic stress tolerance of the plant.

According to an aspect of some embodiments of the invention there is provided a method of increasing nitrogen use efficiency, fertilizer use efficiency and/or oil content of a plant. The method is effected by expressing within the plant an exogenous polynucleotide comprising a nucleic acid sequence at least 80% identical to SEQ ID NO: 3, 5, 6, 9, 10, 14, 15, 288, 294, 2398-2412 or 2413, thereby increasing the nitrogen use efficiency, fertilizer use efficiency, and/or oil content of the plant.

According to some embodiments of the invention the exogenous polynucleotide comprises a nucleic acid sequence which is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the nucleic acid sequence selected from the group consisting of SEQ ID NOs: 3, 5, 6, 9, 10, 14, 15, 288, 294, 2398-2413.

According to some embodiments of the invention the exogenous polynucleotide is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs: 3, 5, 6, 9, 10, 14, 15, 288, 294, 2398-2413.

According to some embodiments of the invention the exogenous polynucleotide is set forth by SEQ ID NO: 3, 5, 6, 9, 10, 14, 15, 288, 294, 2398-2412 or 2413.

According to some embodiments of the invention, the exogenous polynucleotide of the invention encodes a polypeptide having an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to the amino acid sequence selected from the group consisting of SEQ ID NOs: 138-153, 1334-1350, 1352-1364, 1458, 1460, 2523-2532.

According to some embodiments of the invention, the exogenous polynucleotide encodes a polypeptide consisting of the amino acid sequence set forth by SEQ ID NO: 138-153, 1334-1350, 1352-1364, 1458, 1460, 2523-2531 or 2532.

Nucleic acid sequences encoding the polypeptides of the present invention may be optimized for expression. Non-limiting examples of optimized nucleic acid sequences are provided in SEQ ID NOs: 2415, 2420, 2428, 2430, 2431, 2436, 2437, 2441, 2444, 2445, 2446, 2451, 2456, 2468, 2471, 2478, 2481, 2484, 2520 and 2522 (Table 23). Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N[(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A Table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization Tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage Table having been statistically determined based on the data present in Genbank.

By using the above Tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

According to some embodiments of the invention, the exogenous polynucleotide is a non-coding RNA.

As used herein the phrase 'non-coding RNA" refers to an RNA molecule which does not encode an amino acid sequence (a polypeptide). Examples of such non-coding RNA molecules include, but are not limited to, an antisense RNA, a pre-miRNA (precursor of a microRNA), or a precursor of a Piwi-interacting RNA (piRNA).

According to a specific embodiment the non-coding polynucleotide comprises the nucleic acid sequence of SEQ ID NO: 64 or 2459 (NUE512).

Thus, the invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The invention provides an isolated polynucleotide comprising a nucleic acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, e.g., 100% identical to the polynucleotide selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522.

According to some embodiments of the invention the nucleic acid sequence is capable of increasing nitrogen use efficiency, fertilizer use efficiency, yield, growth rate, vigor, biomass, oil content, abiotic stress tolerance and/or water use efficiency of a plant.

According to some embodiments of the invention the isolated polynucleotide comprising the nucleic acid sequence selected from the group consisting of SEQ ID NOs: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522, 3, 5, 6, 9, 10, 14, 15, 20, 61, 62, 129, 288, 294, 307, 363, 667, 668, 669, 670, 672, 2398-2413, 2456 and 2457.

According to some embodiments of the invention the isolated polynucleotide is set forth by SEQ ID NO: 2506, 2512, 2442, 2496, 2446, 1, 2, 4, 7, 8, 11, 12, 13, 16-19, 21-60, 63-128, 130-137, 270-287, 289-293, 295-306, 308-362, 364-666, 671, 673-1333, 2414-2441, 2443-2445, 2447-2455, 2458-2495, 2497-2505, 2507-2511, 2513-2522, 3, 5, 6, 9, 10, 14, 15, 20, 61, 62, 129, 288, 294, 307, 363, 667, 668, 669, 670, 672, 2398-2413, 2456 or 2457.

The invention provides an isolated polynucleotide comprising a nucleic acid sequence encoding a polypeptide which comprises an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to the amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563.

According to some embodiments of the invention the amino acid sequence is capable of increasing nitrogen use efficiency, fertilizer use efficiency, yield, growth rate, vigor, biomass, oil content, abiotic stress tolerance and/or water use efficiency of a plant.

The invention provides an isolated polynucleotide comprising a nucleic acid sequence encoding a polypeptide which comprises the amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563, 138-143, 146, 148, 150-152, 157, 162, 198, 265, 1334-1350, 1352-1364, 1426-1428, 1458, 1460, 1732-1734, 1737-1738, 2523-2532, 2542 and 2543.

The invention provides an isolated polypeptide comprising an amino acid sequence at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563.

According to some embodiments of the invention, the polypeptide comprising an amino acid sequence selected from the group consisting of SEQ ID NOs: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563, 138-143, 146, 148, 150-152, 157, 162, 198, 265, 1334-1350, 1352-1364, 1426-1428, 1458, 1460, 1732-1734, 1737-1738, 2523-2532, 2542 and 2543.

According to some embodiments of the invention, the polypeptide is set forth by SEQ ID NO: 2557, 2560, 184, 238, 188, 154-156, 158-161, 163-183, 185-187, 189-197, 200-237, 239-264, 266-269, 1351, 1365-1425, 1429-1457, 1459, 1461-1730, 1735, 1739-2397, 2533-2541, 2544-2556, 2558, 2559, 2561-2563, 138-143, 146, 148, 150-152, 157, 162, 198, 265, 1334-1350, 1352-1364, 1426-1428, 1458, 1460, 1732-1734, 1737-1738, 2523-2532, 2542 or 2543.

The invention also encompasses fragments of the above described polypeptides and polypeptides having mutations, such as deletions, insertions or substitutions of one or more amino acids, either naturally occurring or man induced, either randomly or in a targeted fashion.

The term "plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum* mopane, *Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalypfus* spp., *Euclea schimperi, Eulalia vilosa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp., *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barely, rye, oat, peanut, pea, lentil and alfalfa, cotton, rapeseed, canola, pepper, sunflower, tobacco, eggplant, eucalyptus, a tree, an ornamental plant, a perennial grass and a forage crop. Alternatively algae and other non-Viridiplantae can be used for the methods of the present invention.

According to some embodiments of the invention, the plant used by the method of the invention is a crop plant such as rice, maize, wheat, barley, peanut, potato, sesame, olive tree, palm oil, banana, soybean, sunflower, canola, sugarcane, alfalfa, millet, leguminosae (bean, pea), flax, lupinus, rapeseed, tobacco, poplar and cotton.

According to some embodiments of the invention, there is provided a plant cell exogenously expressing the polynucleotide of some embodiments of the invention, the nucleic acid construct of some embodiments of the invention and/or the polypeptide of some embodiments of the invention.

According to some embodiments of the invention, expressing the exogenous polynucleotide of the invention within the plant is effected by transforming one or more cells of the plant with the exogenous polynucleotide, followed by generating a mature plant from the transformed cells and cultivating the mature plant under conditions suitable for expressing the exogenous polynucleotide within the mature plant.

According to some embodiments of the invention, the transformation is effected by introducing to the plant cell a nucleic acid construct which includes the exogenous polynucleotide of some embodiments of the invention and at least one promoter for directing transcription of the exogenous polynucleotide in a host cell (a plant cell). Further details of suitable transformation approaches are provided hereinbelow.

According to some embodiments of the invention, there is provided a nucleic acid construct comprising the isolated polynucleotide of the invention, and a promoter for directing transcription of the nucleic acid sequence of the isolated polynucleotide in a host cell.

According to some embodiments of the invention, the isolated polynucleotide is operably linked to the promoter sequence.

A coding nucleic acid sequence is "operably linked" to a regulatory sequence (e.g., promoter) if the regulatory sequence is capable of exerting a regulatory effect on the coding sequence linked thereto.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

Any suitable promoter sequence can be used by the nucleic acid construct of the present invention. Preferably the promoter is a constitutive promoter, a tissue-specific, or an abiotic stress-inducible promoter.

Suitable constitutive promoters include, for example, CaMV 35S promoter (SEQ ID NO: 3063; Odell et al., Nature 313:810-812, 1985); *Arabidopsis* At6669 promoter (SEQ ID NO:3064; see PCT Publication No. WO04081173A2); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al, Plant J November; 2(6):837-44, 1992); ubiquitin (Christensen et al, Plant Mol. Biol. 18: 675-689, 1992); Rice cyclophilin (Bucholz et al, Plant Mol Biol. 25(5):837-43, 1994); Maize H3 histone (Lepetit et al, Mol. Gen. Genet. 231: 276-285, 1992); Actin 2 (An et al, Plant J. 10(1); 107-121, 1996) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al Plant Mol Biol, 143). 323-32 1990), napA (Stalberg, et al, Planta 199: 515-519, 1996), Wheat SPA (Albani et al, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMBO3:1409-15, 1984), Barley ltrl promoter, barley B1, C, D hordein (Theor Appl Gen 98:1253-62, 1999; Plant J 4:343-55, 1993; Mol Gen Genet 250:750-60, 1996), Barley DOF (Mena et al, The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al, Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (PMB 32:1029-35, 1996)], embryo specific promoters [e.g., rice OSH1 (Sato et al, Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], and flower-specific promoters [e.g., AtPRP4, chalene synthase (chsA) (Van der Meer, et al., Plant Mol. Biol. 15, 95-109, 1990), LAT52 (Twell et al Mol. Gen Genet. 217:240-245; 1989), apetala-3].

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267).

The nucleic acid construct of some embodiments of the invention can further include an appropriate selectable marker and/or an origin of replication. According to some embodiments of the invention, the nucleic acid construct utilized is a shuttle vector, which can propagate both in E. coli (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol, Plant. Mol. Biol. (1991) 42:205-225; Shimamoto et al, Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Galon et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since processes which increase oil content, yield, growth rate, biomass, vigor and/or abiotic stress tolerance of a plant can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior effect on oil content, yield, growth rate, biomass, vigor and/or abiotic stress tolerance.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic messenger RNA including all the different exogenous polynucleotide sequences. To enable co-translation of the different polypeptides encoded by the polycistronic messenger RNA, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance, water use efficiency, fertilizer use efficiency, growth, biomass, yield and/or vigor traits, using conventional plant breeding techniques.

According to some embodiments of the invention, the method further comprising growing the plant expressing the exogenous polynucleotide under the abiotic stress.

Non-limiting examples of abiotic stress conditions include, salinity, drought, water deprivation, excess of water (e.g., flood, waterlogging), etiolation, low temperature, high temperature, heavy metal toxicity, anaerobiosis, nutrient deficiency, nutrient excess, atmospheric pollution and UV irradiation.

Thus, the invention encompasses plants exogenously expressing the polynucleotide(s), the nucleic acid constructs and/or polypeptide(s) of the invention. Once expressed within the plant cell or the entire plant, the level of the polypeptide encoded by the exogenous polynucleotide can be determined by methods well known in the art such as, activity assays, Western blots using antibodies capable of specifically binding the polypeptide, Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-in situ hybridization.

In addition, the endogenous homolog of the exogenous polynucleotide or polypeptide of the invention, or a fragment of the endogenous homolog (e.g. introns or untranslated regions) in the plant can be used as a marker for marker assisted selection (MAS), in which a marker is used for indirect selection of a genetic determinant or determinants of a trait of interest (e.g., biomass, growth rate, oil content, yield, abiotic stress tolerance). These genes (DNA or RNA sequence) may contain or be linked to polymorphic sites or genetic markers on the genome such as restriction fragment length polymorphism (RFLP), microsatellites and single nucleotide polymorphism (SNP), DNA fingerprinting (DFP), amplified fragment length polymorphism (AFLP), expression level polymorphism, polymorphism of the encoded polypeptide and any other polymorphism at the DNA or RNA sequence.

Examples of marker assisted selections include, but are not limited to, selection for a morphological trait (e.g., a gene that affects form, coloration, male sterility or resistance such as the presence or absence of awn, leaf sheath coloration, height, grain color, aroma of rice); selection for a biochemical trait (e.g., a gene that encodes a protein that can be extracted and observed; for example, isozymes and storage proteins); selection for a biological trait (e.g., pathogen races or insect biotypes based on host pathogen or host parasite interaction can be used as a marker since the genetic constitution of an organism can affect its susceptibility to pathogens or parasites).

The polynucleotides and polypeptides described hereinabove can be used in a wide range of economical plants, in a safe and cost effective manner.

Plant lines exogenously expressing the polynucleotide or the polypeptide of the invention are screened to identify those that show the greatest increase of the desired plant trait.

Following is a non-limiting description of assays which can be used to determine the effect of the transgene (the exogenous polynucleotide of some embodiments of the invention) or is encoded polypeptide on the trait-of-interest in a plant.

The main parameters of efficiency used to define plant Nitrogen (N) metabolism include nitrogen-uptake efficiency, nitrogen utilization efficiency, and nitrogen-use efficiency The Nitrogen-uptake efficiency [the amount of N in above ground biomass (grams of nitrogen)/N applied (grams/hectare)] is the total amount of nitrogen incorporated by the plant and is a function of the "uptake" (the plant's transport capacity), the metabolic efficiency of the assimilation process and the rate of plant size development, since the mass of stalk and leaves created during growth are the actual Nitrogen-storage organs. The fraction of the assimilated Nitrogen found in a shoot that is ultimately transferred to the grain (yield) is controlled enzymatically, and thus can be affected by transgenic manipulation. This parameter is, in effect, equal to the Nitrogen Use efficiency (NUE). Better grain-to-shoot N-partitioning most likely will improve yield and protein content of the grain.

Similarly, the same calculations of use and utilization efficiencies can be made for other macronutrients such as Phosphorous (P) and Potassium (K), which have a direct correlation with yield and general plant tolerance.

Fertilizer Use Efficiency

To analyze whether the transgenic plants are more responsive to fertilizers, plants are grown in agar plates or pots with a limited amount of fertilizer, as described, for example, in Examples 5-7 of the Example section which follows and in Yanagisawa et al (Proc Natl Acad Sci USA. 2004; 101:7833-8). The plants are analyzed for their overall size, time to flowering, yield, protein content of shoot and/or grain. The parameters checked are the overall size of the mature plant, its wet and dry weight, the weight of the seeds yielded, the average seed size and the number of seeds produced per plant. Other parameters that may be tested are: the chlorophyll content of leaves (as nitrogen plant status and the degree of leaf verdure is highly correlated), amino acid and the total protein content of the seeds or other plant parts such as leaves or shoots, oil content, etc. Similarly, instead of providing nitrogen at limiting amounts, phosphate or potassium can be added at increasing concentrations. Again, the same parameters measured are the same as listed above. In this way, nitrogen use efficiency (NUE), phosphate use efficiency (PUE) and potassium use efficiency (KUE) are assessed, checking the ability of the transgenic plants to thrive under nutrient restraining conditions.

Nitrogen Use Efficiency

To analyze whether the transgenic Arabidopsis plants are more responsive to nitrogen, plant are grown in 0.75-1.5 mM (nitrogen deficient conditions) or 6-15 mM (optimal nitrogen concentration). Plants are allowed to grow for additional 20-40 days or until seed production. The plants are then analyzed for their overall size, time to flowering, yield, protein content of shoot and/or grain/seed production. The parameters checked can be the overall size of the plant, wet and dry weight, the weight of the seeds yielded, the average seed size and the number of seeds produced per plant. Other parameters that may be tested are: the chlorophyll content of leaves (as nitrogen plant status and the degree of leaf greenness is highly correlated), amino acid and the total protein content of the seeds or other plant parts such as leaves or shoots and oil content. Transformed plants not exhibiting substantial physiological and/or morphological effects, or exhibiting higher measured parameters levels than wild-type plants, are identified as nitrogen use efficient plants.

Nitrogen Determination

The procedure for N (nitrogen) concentration determination in the structural parts of the plants involves the potassium persulfate digestion method to convert organic N to $NO_3^-$ (Purcell and King 1996 Argon. J. 88:111-113, the modified $Cd^-$ mediated reduction of $NO_3^-$ to $NO_2^-$ (Vodovotz 1996 Biotechniques 20:390-394) and the measurement of nitrite by the Griess assay (Vodovotz 1996, supra). The absorbance values are measured at 550 nm against a standard curve of $NaNO_2$. The procedure is described in details in Samonte et al. 2006 Agron. J. 98:168-176.

Germination Tests

Germination tests compare the percentage of seeds from transgenic plants that could complete the germination process to the percentage of seeds from control plants that are treated in the same manner. Normal conditions are considered for example, incubations at 22° C. under 22-hour light 2-hour dark daily cycles. Evaluation of germination and seedling vigor is conducted between 4 and 14 days after planting. The basal media is 50% MS medium (Murashige and Skoog, 1962 Plant Physiology 15, 473-497).

Germination is checked also at unfavorable conditions such as cold (incubating at temperatures lower than 10° C. instead of 22° C.) or using seed inhibition solutions that contain high concentrations of an osmolyte such as sorbitol (at concentrations of 50 mM, 100 mM, 200 mM, 300 mM, 500 mM, and up to 1000 mM) or applying increasing concentrations of salt (of 50 mM, 100 mM, 200 mM, 300 mM, 500 mM NaCl).

The effect of the transgene on plant's vigor, growth rate, biomass, yield and/or oil content can be determined using known methods.

Plant Vigor

The plant vigor can be calculated by the increase in growth parameters such as leaf area, fiber length, rosette diameter, plant fresh weight and the like per time.

Growth Rate

The growth rate can be measured using digital analysis of growing plants. For example, images of plants growing in greenhouse on plot basis can be captured every 3 days and the rosette area can be calculated by digital analysis. Rosette area growth is calculated using the difference of rosette area between days of sampling divided by the difference in days between samples.

Evaluation of growth rate can be done by measuring plant biomass produced, rosette area, leaf size or root length per time (can be measured in $cm^2$ per day of leaf area).

Relative growth area can be calculated using Formula I.

Relative growth area rate=$(\Delta$ Area/$\Delta t)*(1/$Area $t_0)$     Formula I:

$\Delta t$ is the current analyzed image day subtracted from the initial day (t–t0). Thus, the relative growth area rate is in units of 1/day and length growth rate is in units of 1/day.

Alternatively, the relative growth rate of the area can be calculated as the regression coefficient along time course.

Seed Yield

Evaluation of the seed yield per plant can be done by measuring the amount (weight or size) or quantity (i.e., number) of dry seeds produced and harvested from 8-16 plants and divided by the number of plants.

For example, the total seeds from 8-16 plants can be collected, weighted using e.g., an analytical balance and the total weight can be divided by the number of plants. Seed yield per growing area can be calculated in the same manner while taking into account the growing area given to a single plant. Increase seed yield per growing area could be achieved by increasing seed yield per plant, and/or by increasing number of plants capable of growing in a given area.

In addition, seed yield can be determined via the weight of 1000 seeds. The weight of 1000 seeds can be determined as follows: seeds are scattered on a glass tray and a picture is taken. Each sample is weighted and then using the digital analysis, the number of seeds in each sample is calculated.

The 1000 seeds weight can be calculated using formula II:

1000 Seed Weight=number of seed in sample/sample weight×1000     Formula II:

The Harvest Index can be calculated using Formula III

Harvest Index=Average seed yield per plant/Average dry weight     Formula III:

Grain Protein Concentration

Grain protein content (grams grain protein $m^{-2}$) is estimated as the product of the mass of grain N (nitrogen) [grams grain Nitrogen $m^{-2}$] multiplied by the N/protein conversion ratio of k-5.13 (Mosse 1990, supra). The grain protein concentration is estimated as the ratio of grain protein content per unit mass of the grain (grams grain protein $kg^{-1}$ grain).

Fiber Length

Fiber length can be measured using fibrograph. The fibrograph system was used to compute length in terms of "Upper Half Mean" length. The upper half mean (UHM) is the average length of longer half of the fiber distribution. The fibrograph measures length in span lengths at a given percentage point (Hypertext Transfer Protocol://World Wide Web (dot) cottoninc (dot) com/ClassificationofCotton/?Pg=4#Length).

Oil Content

The oil content of a plant can be determined by extraction of the oil from the seed or the vegetative portion of the plant. Briefly, lipids (oil) can be removed from the plant (e.g., seed) by grinding the plant tissue in the presence of specific solvents (e.g., hexane or petroleum ether) and extracting the oil in a continuous extractor. Indirect oil content analysis can be carried out using various known methods such as Nuclear Magnetic Resonance (NMR) Spectroscopy, which measures the resonance energy absorbed by hydrogen atoms in the liquid state of the sample [See for example, Conway T F. and Earle F R., 1963, Journal of the American Oil Chemists' Society; Springer Berlin/Heidelberg, ISSN: 0003-021X (Print) 1558-9331 (Online)]; the Near Infrared (NI) Spectroscopy, which utilizes the absorption of near infrared energy (1100-2500 nm) by the sample; and a method described in WO/2001/023884, which is based on extracting oil a solvent, evaporating the solvent in a gas stream which forms oil particles, and directing a light into the gas stream and oil particles which forms a detectable reflected light.

The effect of the transgene or its encoded polypeptide on abiotic stress tolerance can be determined using known methods.

Abiotic Stress Tolerance

Transformed (i.e., expressing the transgene) and non-transformed (wild type) plants are exposed to an abiotic stress condition, such as water deprivation, suboptimal temperature (low temperature, high temperature), nutrient deficiency, nutrient excess, a salt stress condition, osmotic stress, heavy metal toxicity, anaerobiosis, atmospheric pollution and UV irradiation.

Salinity Tolerance Assay

Transgenic plants with tolerance to high salt concentrations are expected to exhibit better germination, seedling vigor or growth in high salt. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium [e.g., 50% Murashige-Skoog medium (MS medium)]. Since different plants vary considerably in their tolerance to salinity, the salt concentration in the irrigation water, growth solution, or growth medium can be adjusted according to the specific characteristics of the specific plant cultivar or variety, so as to inflict a mild or moderate effect on the physiology and/or morphology of the plants (for guidelines as to appropriate concentration see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein).

For example, a salinity tolerance test can be performed by irrigating plants at different developmental stages with increasing concentrations of sodium chloride (for example 50 mM, 100 mM, 200 mM, 400 mM NaCl) applied from the bottom and from above to ensure even dispersal of salt. Following exposure to the stress condition the plants are frequently monitored until substantial physiological and/or morphological effects appear in wild type plants. Thus, the external phenotypic appearance, degree of wilting and overall success to reach maturity and yield progeny are compared between control and transgenic plants. Quantitative parameters of tolerance measured include, but are not limited to, the average wet and dry weight, the weight of the seeds yielded, the average seed size and the number of seeds produced per plant. Transformed plants not exhibiting substantial physiological and/or morphological effects, or exhibiting higher biomass than wild-type plants, are identified as abiotic stress tolerant plants.

Osmotic Tolerance Test

Osmotic stress assays (including sodium chloride and mannitol assays) are conducted to determine if an osmotic stress phenotype was sodium chloride-specific or if it was a general osmotic stress related phenotype. Plants which are tolerant to osmotic stress may have more tolerance to drought and/or freezing. For salt and osmotic stress germination experiments, the medium is supplemented for example with 50 mM, 100 mM, 200 mM NaCl or 100 mM, 200 mM NaCl, 400 mM mannitol, 500 mM sorbitol or 15 g (grams) PEG [Polyethylene Glycol 8000].

Drought Tolerance Assay/Osmoticum Assay

Tolerance to drought is performed to identify the genes conferring better plant survival after acute water deprivation. To analyze whether the transgenic plants are more tolerant to drought, an osmotic stress produced by the non-ionic osmolyte sorbitol in the medium can be performed. Control and transgenic plants are germinated and grown in plant-agar plates for 4 days, after which they are transferred to plates containing 500 mM sorbitol. The treatment causes growth retardation, then both control and transgenic plants are compared, by measuring plant weight (wet and dry), yield, and by growth rates measured as time to flowering.

Conversely, soil-based drought screens are performed with plants overexpressing the polynucleotides detailed above. Seeds from control *Arabidopsis* plants, or other transgenic plants overexpressing the polypeptide of the invention are germinated and transferred to pots. Drought stress is obtained after irrigation is ceased accompanied by placing the pots on absorbent paper to enhance the soil-drying rate. Transgenic and control plants are compared to each other when the majority of the control plants develop severe wilting. Plants are re-watered after obtaining a significant fraction of the control plants displaying a severe wilting. Plants are ranked comparing to controls for each of two criteria: tolerance to the drought conditions and recovery (survival) following re-watering.

Cold Stress Tolerance

To analyze cold stress, mature (25 day old) plants are transferred to 4° C. chambers for 1 or 2 weeks, with constitutive light. Later on plants are moved back to greenhouse. Two weeks later damages from chilling period, resulting in growth retardation and other phenotypes, are compared between both control and transgenic plants, by measuring plant weight (wet and dry), and by comparing growth rates measured as time to flowering, plant size, yield, and the like.

Heat Stress Tolerance

Heat stress tolerance is achieved by exposing the plants to temperatures above 34° C. for a certain period. Plant tolerance is examined after transferring the plants back to 22° C. for recovery and evaluation after 5 days relative to internal controls (non-transgenic plants) or plants not exposed to neither cold or heat stress.

Water Use Efficiency can be determined as the biomass produced per unit transpiration. To analyze WUE, leaf relative water content can be measured in control and transgenic plants. Fresh weight (FW) is immediately recorded; then leaves are soaked for 8 hours in distilled water at room temperature in the dark, and the turgid weight (TW) is recorded. Total dry weight (DW) is recorded after drying the leaves at 60° C. to a constant weight. Relative water content (RWC) is calculated according to the following Formula IV:

$$RWC=[(FW-DW)/(TW-DW)]\times 100 \quad \text{Formula IV}$$

Thus, the invention is of high agricultural value for promoting the yield of commercially desired crops (e.g., biomass of vegetative organ such as poplar wood, or reproductive organ such as number of seeds or seed biomass) under normal or growth-limiting conditions (e.g., nitrogen-deficient conditions, abiotic stress).

Any of the transgenic plants described hereinabove or parts thereof may be processed to produce a feed, meal, protein or oil preparation, such as for ruminant animals.

The transgenic plants described hereinabove, which exhibit an increased oil content can be used to produce plant oil (by extracting the oil from the plant).

The plant oil (including the seed oil and/or the vegetative portion oil) produced according to the method of the invention may be combined with a variety of other ingredients. The specific ingredients included in a product are determined according to the intended use. Exemplary products include animal feed, raw material for chemical modification, biodegradable plastic, blended food product, edible oil, biofuel, cooking oil, lubricant, biodiesel, snack food, cosmetics, and fermentation process raw material. Exemplary products to be incorporated to the plant oil include animal feeds, human food products such as extruded snack foods, breads, as a food binding agent, aquaculture feeds, fermentable mixtures, food supplements, sport drinks, nutritional food bars, multi-vitamin supplements, diet drinks, and cereal foods.

According to some embodiments of the invention, the oil comprises a seed oil and/or a vegetative portion oil.

According to some embodiments of the invention, the plant cell forms a part of a plant.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

All the information contained therein is incorporated herein by reference.

Example 1

Identifying Genes which Increase Nitroge Use Efficiency, Fertilizer Use Efficiency, Yield, Oil Content, Biomass and/or Abiotic Stress Tolerance Genes which can increase nitrogen use efficiency (NUE), fertilizer use efficiency (FUE), yield, oil content, biomass and/or abiotic stress tolerance (ABST) were identified using several data mining and bioinformatics tools.

All nucleotide sequence datasets used here were originated from publicly available databases. Sequence data from 76 different plant species was introduced into a single, comprehensive database. Other information on gene expression, protein annotation, enzymes and pathways were also incorporated. Major databases used include:

Genomes
- *Arabidopsis* genome [TAIR genome version 6 (Hypertext Transfer Protocol://World Wide Web (dot) *arabidopsis* (dot) org/)]
- Rice genome [IRGSP build 4.0 (Hypertext Transfer Protocol://rgp (dot) dna (dot) affrc (dot) go (dot) jp/IRGSP/)].
- Poplar [*Populus trichocarpa* release 1.1 from JGI (assembly release v1.0) (Hypertext Transfer Protocol://World Wide Web (dot) genome (dot) jgi-psf (dot) org/)]
- Brachypodium [JGI 4× assembly, Hypertext Transfer Protocol://World Wide Web (dot) brachpodium (dot) org)]
- Soybean [DOE-JGI SCP, version Glyma0 (Hypertext Transfer Protocol://World Wide Web (dot) phytozome (dot) net/)]
- Grape [French-Italian Public Consortium for Grapevine Genome Characterization grapevine genome (Hypertext Transfer Protocol://World Wide Web (dot) genoscope (dot) cns (dot) fr/)]
- Castobean [TIGR/J Craig Venter Institute 4× assembly [(Hypertext Transfer Protocol://msc (dot) jcvi (dot) org/r_communis]
- *Sorghum* [DOE-JGI SCP, version Sbi1 [Hypertext Transfer Protocol://World Wide Web (dot) phytozome (dot) net/(].
- Partially assembled genome of Maize [Hypertext Transfer Protocol://maizesequence (dot) org/]

Expressed EST and mRNA Sequences were Extracted from the Following Databases:
- GenBank (Hypertext Transfer Protocol://World Wide Web (dot) ncbi (dot) nlm (dot) nih (dot) gov/Genbank/).
- RefSeq (Hypertext Transfer Protocol://World Wide Web (dot) ncbi (dot) nlm (dot) nih (dot) gov/RefSeq/).
- TAIR (Hypertext Transfer Protocol://World Wide Web (dot) *arabidopsis* (dot) org/).

Protein and Pathway Databases
- Uniprot (Hypertext Transfer Protocol://World Wide Web (dot) expasy (dot) uniprot (dot) org/).

AraCyc (Hypertext Transfer Protocol://World Wide Web (dot) arabidopsis (dot) org/biocyc/index (dot) jsp).
ENZYME (Hypertext Transfer Protocol://expasy (dot) org/enzyme/).
Microarray Datasets were Downloaded from:
GEO (Hypertext Transfer Protocol://World Wide Web (dot) ncbi (dot) nlm (dot) nih (dot) gov/geo/)
TAIR (Hypertext Transfer Protocol://World Wide Web (dot) arabidopsis (dot) org/).
Proprietary cotton fiber microarray data (PCT Publication No. WO2008/075364)
Proprietary microarray data on *Arabidopsis* ecotypes (PCT Publication No. WO2008/122980).
QTL (Quantitative Trailt Locus) Information
Gramene (Hypertext Transfer Protocol://World Wide Web (dot) gramene (dot) org/qtl/).

Database assembly was performed to enable to build a wide, rich, reliable annotated and easy to analyze database comprised of publicly available genomic mRNA, and ESTs DNA sequences, data from various crops as well as gene expression, protein annotation and pathway data QTLs, and other relevant information.

Database assembly is comprised of a toolbox of gene refining, structuring, annotation and analysis tools enabling to construct a tailored database for each gene discovery project. Gene refining and structuring tools enable to reliably detect splice variants and antisense transcripts, generating understanding of various potential phenotypic outcomes of a single gene. The capabilities of the "LEADS" platform of Compugen LTD for analyzing human genome have been confirmed and accepted by the scientific community [see e.g., "Widespread Antisense Transcription", Yelin, et al. (2003) Nature Biotechnology 21, 379-85; "Splicing of Alu Sequences", Lev-Maor, et al. (2003) Science 300 (5623), 1288-91; "Computational analysis of alternative splicing using EST tissue information", Xie H et al. Genomics 2002], and have been proven most efficient in plant genomics as well.

EST Clustering and Gene Assembly

For clustering and assembly *Arabidopsis*, rice, grape, *sorghum*, brachypodium and soybean genes the present inventors used "genomic LEADS" version. This tool allows most accurate clustering of ESTs and mRNA sequences on genome, and predicts gene structure as well as alternative splicing events and anti-sense transcription.

Gene Annotation

Predicted genes and proteins were annotated as follows:

Sequences blast search [Hypertext Transfer Protocol://blast (dot) ncbi (dot) nlm (dot) nih (dot) gov/Blast (dot) cgi] against all plant UniProt [Hypertext Transfer Protocol://World Wide Web (dot) uniprot (dot) org/] was performed. Open reading frames of each putative transcript were analyzed and longest ORF with higher number of homologues was selected as predicted protein of the transcript. The predicted proteins were analyzed by InterPro [Hypertext Transfer Protocol://World Wide Web (dot) ebi (dot) ac (dot) uk/interpro/].

Blast against proteins from AraCyc and ENZYME databases was used to map the predicted transcripts to AraCyc pathways.

Predicted proteins from different species were compared using blast algorithm [Hypertext Transfer Protocol://World Wide Web (dot) ncbi (dot) nlm (dot) nih (dot) gov/Blast (dot) cgi] to validate the accuracy of the predicted protein sequence, and for efficient detection of orthologs.

Gene Expression Profiling

Few data sources were exploited for gene expression profiling, namely microarray data and digital expression profile (as mentioned above). According to gene expression profile, a correlation analysis was performed to identify genes which are co-regulated under different developmental stages and environmental conditions.

Publicly available microarray datasets were downloaded from NCBI GEO sites, renormalized, and integrated into the database. Expression profile was one of the most important resource data for identifying genes important for NUE, ABST, yield, biomass increment and/or FUE. Moreover, when homolog genes from different crops were found to be associated with increase of NUE, ABST, FUE, biomass, yield or oil content, the genes were marked as "highly predictive" to improve the trait.

A digital expression profile summary was compiled for each cluster according to all keywords included in the sequence records comprising the cluster. Digital expression, also known as electronic Northern Blot, is a tool that displays virtual expression profile based on the EST sequences forming the gene cluster. The tool can provide the expression profile of a cluster in terms of plant anatomy (e.g. tissues/organs in which the gene is expressed), developmental stage (the developmental stages at which a gene can be found) and profile of treatment (provides the physiological conditions under which a gene is expressed such as drought, cold, pathogen infection, etc). Given a random distribution of ESTs in the different clusters, the digital expression provides a probability value that describes the probability of a cluster having a total of N ESTs to contain X ESTs from a certain collection of libraries. For the probability calculations the following parameters were taken into consideration: a) the number of ESTs in the cluster; b) the number of ESTs of the implicated and related libraries; and c) the overall number of ESTs available, representing the species. Thereby clusters with low probability values are highly enriched with ESTs from the group of libraries of interest indicating a specialized expression.

The results of the digital and microarray gene expression data are provided in Tables 1-19, hereinbelow.

Below are summarized the key criteria used to select the genes which expression thereof in a plant can be used to increase NUE, FUE, biomass, yield, oil content and ABST. The overexpression Fold ("Fold") is calculated as the ratio between the number of ESTs found in a gene or an orthologue group for a certain category ("Keyword") and the number of expected ESTs according to a normal distribution. A probabilistic value (P-value) was estimated for the calculated overexpression folds. Genes were selected based on the results presented in Tables 1-19 below and other computational filtering combined with manual curation as detailed below.

NUE242, NUE244, NUE234, NUE239, NUE240, NUE514, NUE523, NUE533, NUE538, NUE548, NUE549, NUE241, NUE235, NUE251, NUE587 and NUE582 were selected since they are highly expressed in roots and under nutrient deficient conditions (as shown in Tables 1 and 2, hereinbelow).

TABLE 1

Digital expression of NUE242, NUE244, NUE234, NUE239, NUE240, NUE514, NUE523, NUE533, NUE538, NUE548, NUE549, NUE241, NUE235, NUE251, NUE587 and NUE582 in different tissues

| | Anatomy | | | | | | | |
|---|---|---|---|---|---|---|---|---|
| | germinating seed | | root | | seedling | | shoot | |
| Genes | fold | p-value | fold | p-value | fold | p-value | fold | p-value |
| NUE242 | | | 10.57 | 2.68E−12 | | | 1.00 | 5.47E−01 |
| NUE244 | 1.00 | 4.48E−02 | 3.00 | 1.06E−03 | 1.40 | 1.67E−01 | 2.00 | 2.03E−01 |
| NUE234 | | | 6.89 | 1.80E−24 | | | | |
| NUE239 | | | 7.26 | 1.87E−21 | | | | |
| NUE240 | | | 12.70 | 4.65E−40 | | | | |
| NUE514 | 1.97 | 2.69E−01 | 2.95 | 7.95E−60 | 0.78 | 1 | 0.39 | 9.99E−01 |
| NUE523 | | | 2.15 | 1.17E−05 | 1.11 | 4.45E−01 | 1.33 | 1.31E−01 |
| NUE533 | | | 2.96 | 5.39E−04 | 0.76 | 8.43E−01 | | |
| NUE538 | | | 3.47 | 1.05E−06 | 0.96 | 6.20E−01 | | |
| NUE548 | | | 1.72 | 1.06E−02 | 0.65 | 8.48E−01 | 0.60 | 9.41E−01 |
| NUE549 | | | 1.51 | 7.86E−06 | 2.52 | 7.38E−13 | 0.19 | 1 |
| NUE241 | | | 3.32 | 7.66E−03 | 1.00 | 4.05E−01 | 0.88 | 6.88E−01 |
| NUE235 | 1.00 | 2.95E−02 | 4.94 | 1.12E−06 | 0.48 | 9.46E−01 | | |
| NUE251 | | | 2.72 | 3.33E−05 | | | | |
| NUE587 | | | 2.39 | 2.20E−02 | 2.56 | 1.10E−01 | | |
| NUE582 | | | 2.00 | 6.00E−08 | 1.19 | 2.80E−01 | 1.89 | 7.60E−06 |

Table 1. Digital expression of the indicated genes in germinating seed, root, seedling and shoots. Provided are the fold increase and the calculated p-values. Results were considered statistically significant if the p-value was lower than 0.05. Blank cells indicate that either the gene is not expressed or data is not available.

TABLE 2

Digital expression of NUE242, NUE244, NUE234, NUE239, NUE240, NUE514, NUE523, NUE533, NUE538, NUE548, NUE549, NUE241, NUE235, NUE251, NUE587 and NUE582 under different growth conditions

| | Treatment | | | | | | | | | |
|---|---|---|---|---|---|---|---|---|---|---|
| | drought | | etiolation | | heat stress | | nutrient deficiencies | | waterlogging | |
| Genes | fold | p-value | fold | p-value | fold | p-value | fold | p-value | fold | p-value |
| NUE242 | | | | | 1.00 | 4.69E−02 | 5.00 | 8.06E−06 | | |
| NUE244 | | | 4.00 | 1.40E−02 | | | 7.00 | 2.93E−06 | 1.00 | 1.50E−01 |
| NUE234 | 3.00 | 2.51E−03 | | | | | 2.93 | 1.71E−02 | | |
| NUE239 | 8.00 | 5.17E−11 | | | | | 17.36 | 2.11E−27 | | |
| NUE240 | 4.00 | 1.44E−05 | | | | | 26.09 | 6.02E−35 | | |
| NUE514 | 0.14 | 1 | 0.49 | 9.96E−01 | 1.16 | 5.14E−01 | 5.75 | 1.26E−38 | 3.54 | 1.95E−04 |
| NUE523 | 1.53 | 1.07E−01 | | | | | 4.35 | 5.73E−04 | 1.94 | 2.76E−01 |
| NUE533 | 1.00 | 6.19E−01 | | | | | 4.00 | 3.57E−03 | | |
| NUE538 | 1.69 | 2.10E−01 | | | | | 7.00 | 2.32E−06 | 5.00 | 2.30E−05 |
| NUE548 | 0.76 | 7.80E−01 | | | | | 9.60 | 1.24E−09 | | |
| NUE549 | 1.91 | 8.07E−07 | | | | | 4.08 | 6.20E−12 | 9.58 | 8.54E−30 |
| NUE241 | | | | | | | 3.00 | 8.97E−03 | | |
| NUE235 | 2.00 | 1.50E−01 | | | | | 6.00 | 2.61E−06 | | |
| NUE251 | 1.89 | 9.79E−02 | | | | | 3.00 | 4.85E−02 | 8.00 | 2.04E−08 |
| NUE587 | 4.50 | 1.73E−03 | | | | | 3.00 | 4.71E−03 | | |
| NUE582 | 0.63 | 9.51E−01 | | | | | 3.20 | 4.00E−02 | 0.97 | 6.10E−01 |

Table 2. Digital expression of the indicated genes under drought, etiolation, heat stress, nutrient deficiencies and waterlogging. Provided are the fold increase and the calculated p-values. Results were considered statistically significant if the p-value was lower than 0.05. Blank cells indicate that either the gene is not expressed or data is not available.

NUE229, NUE248, NUE254, NUE542, NUE562, NUE237, NUE221, NUE585 and NUE588 were selected because of their high expression in roots and under drought stress conditions (as shown in Tables 3 and 4, below).

TABLE 3

Digital expression of NUE229, NUE248, NUE254, NUE542, NUE562, NUE237, NUE221, NUE585 and NUE588 in different tissues

| | Anatomy | | | | | | | | | |
|---|---|---|---|---|---|---|---|---|---|---|
| | leaf | | seed | | root | | seedling | | shoot | |
| Genes | fold | p-value | fold | p-value | fold | p-value | fold | p-value | fold | p-value |
| NUE229 | | | | | 4.64 | 2.79E−04 | | | | |
| NUE248 | 1.19 | 5.06E−01 | | | 3.56 | 6.36E−03 | | | | |
| NUE254 | 2.26 | 1.35E−02 | | | 7.90 | 5.32E−22 | 0.33 | 9.53E−01 | 1.55 | 1.46E−01 |
| NUE542 | | | | | 4.22 | 9.75E−04 | | | | |
| NUE562 | 2.75 | 2.40E−02 | | | 3.32 | 3.79E−08 | 0.71 | 9.32E−01 | 0.62 | 9.66E−01 |
| NUE237 | 0.50 | 9.00E−01 | | | 5.35 | 5.22E−11 | 1.21 | 2.97E−01 | 0.50 | 9.67E−01 |
| NUE221 | | | | | 4.15 | 2.33E−04 | 0.63 | 8.74E−01 | 1.41 | 2.48E−01 |
| NUE585 | 2.00 | 1.20E−01 | | | 6.00 | 1.34E−04 | | | | |
| NUE588 | 0.99 | 6.00E−01 | | | 2.56 | 7.16E−05 | 0.65 | 9.64E−01 | 1.30 | 1.29E−01 |

Table 3. Digital expression of the indicated genes in leaf, seed, root, seedling and shoots. Provided are the fold increase and the calculated p-values. Results were considered statistically significant if the p-value was lower than 0.05. Blank cells indicate that either the gene is not expressed or data is not available.

TABLE 4

Digital expression of NUE229, NUE248, NUE254, NUE542, NUE562, NUE237, NUE221 and NUE588 under different growth conditions

| | Treatment | | | | | | | |
|---|---|---|---|---|---|---|---|---|
| | cold | | drought | | etiolation | | salinity | |
| Genes | fold | p-value | fold | p-value | fold | p-value | fold | p-value |
| NUE229 | | | 4.00 | 6.53E−03 | | | | |
| NUE248 | | | 4.00 | 6.02E−03 | | | | |
| NUE254 | | | 3.13 | 1.29E−02 | | | 1.00 | 3.67E−01 |
| NUE542 | | | 3.00 | 3.50E−02 | | | 6.00 | 1.61E−10 |
| NUE562 | 0.70 | 0.760127 | 2.75 | 3.66E−02 | 0.98 | 0.57666 | 4.35 | 2.80E−03 |
| NUE237 | | | 6.00 | 3.30E−04 | | | | |
| NUE221 | | | 4.00 | 1.38E−03 | 1.60 | 0.28739 | | |
| NUE585 | | | 2.00 | 5.13E−02 | | | | |
| NUE588 | 2.10 | 0.173185 | 2.73 | 3.76E−02 | 1.39 | 0.185271 | 0.72 | 7.53E−01 |

Table 4. Digital expression of the indicated genes under cold, drought, etiolation and salinity. Provided are the fold increase and the calculated p-values. Results were considered statistically significant if the p-value was lower than 0.05. Blank cells indicate that either the gene is not expressed or data is not available.

NUE252 and MAB106, NUE265, NUE553, NUE513, NUE579, NUE580, NUE256, NUE227 and NUE223 were selected because of their high expression under etiolation growth conditions (as shown in Table 5).

TABLE 5

Digital expression of NUE252, MAB106, NUE265, NUE553, NUE513, NUE579, NUE580, NUE256, NUE227 and NUE223 under different growth conditions

| | Treatment | | | | | | | |
|---|---|---|---|---|---|---|---|---|
| | drought | | etiolation | | heat | | heavy metal | |
| Genes | fold | p-value | fold | p-value | fold | p-value | fold | p-value |
| NUE252 | 1.28 | 4.2E−01 | 5.67 | 2.0E−11 | | | | |
| MAB106 | 0.49 | 8.7E−01 | 10.17 | 5.2E−71 | | | | |
| NUE265 | | | 1.90 | 4.9E−02 | 4.00 | 2.6E−03 | 2.26 | 7.2E−02 |
| NUE553 | | | 1.92 | 4.4E−02 | | | | |
| NUE513 | 1.05 | 5.7E−01 | 3.75 | 1.5E−04 | | | | |
| NUE579 | 0.27 | 9.8E−01 | 3.18 | 1.9E−05 | | | | |
| NUE580 | 1.00 | 5.6E−01 | 3.16 | 3.8E−02 | | | | |
| NUE256 | 1.84 | 5.9E−02 | 2.03 | 9.9E−03 | 3.43 | 4.7E−03 | | |
| NUE227 | | | 4.74 | 3.4E−03 | | | | |
| NUE223 | 1.40 | 4.19E−01 | 4.17 | 5.6E−09 | | | | |

Table 5. Digital expression of the indicated genes under drought, etiolation, heat and heavy metal. Provided are the fold increase and the calculated p-values. Results were considered statistically significant if the p-value was lower than 0.05. Note the high expression of NUE252 and MAB106 under etiolation. Blank cells indicate that either the gene is not expressed or data is not available.

TABLE 6

Digital expression of NUE252, MAB106, NUE265, NUE553, NUE513, NUE579, NUE580, NUE256, NUE227 and NUE223 under different growth conditions

| | Treatment | | | | | |
|---|---|---|---|---|---|---|
| | salinity | | oxidative stress | | waterlogging | |
| Genes | fold | p-value | fold | p-value | fold | p-value |
| NUE252 | | | | | | |
| MAB106 | | | | | | |
| NUE265 | 3.00 | 6.3E−02 | | | | |
| NUE553 | | | | | | |
| NUE513 | | | | | | |
| NUE579 | | | | | | |
| NUE580 | | | | | | |
| NUE256 | 2.96 | 8.2E−02 | | | | |
| NUE227 | | | | | | |
| NUE223 | 2.85 | 8.91E−02 | | | 2.00 | 2.31E−02 |

Table 6. Digital expression of the indicated genes under salinity, oxidative stress and waterlogging. Provided are the fold increase and the calculated p-values. Results were considered statistically significant if the p-value was lower than 0.05. Blank cells indicate that either the gene is not expressed or data is not available.

NUE224, NUE230, NUE255, NUE245, NUE237, NUE233, NUE231, NUE228, NUE225 and NUE249 were selected because of their high expression in roots and expressed when treated with plant hormones intrinsically related to plant growth and development (as shown in Tables 7, 8 and 9).

TABLE 7

Digital expression of NUE224, NUE230, NUE255, NUE245, NUE237, NUE233, NUE231, NUE228, NUE225 and NUE249 in different tissues

| | Anatomy | | | | | | | | | |
|---|---|---|---|---|---|---|---|---|---|---|
| | leaf | | callus | | root | | seedling | | shoot | |
| Genes | fold | p-value | fold | p-value | fold | p-value | fold | p-value | fold | p-value |
| NUE224 | 1.20 | 4.0E−01 | 0.49 | 9.9E−01 | 7.26 | 4.1E−30 | 1.64 | 8.4E−03 | 1.04 | 5.0E−01 |
| NUE230 | 0.71 | 8.3E−01 | 1.35 | 1.4E−02 | 2.76 | 7.1E−09 | 0.59 | 1.0E+00 | 1.16 | 2.1E−01 |
| NUE255 | | | | | 4.00 | 3.3E−03 | | | | |
| NUE245 | 1.48 | 2.5E−01 | 0.32 | 1.0E+00 | 2.14 | 4.4E−03 | 1.03 | 4.8E−01 | 1.53 | 3.2E−02 |
| NUE237 | 0.47 | 8.8E−01 | 1.39 | 1.0E−01 | 5.12 | 1.3E−10 | 1.14 | 3.7E−01 | 0.47 | 9.8E−01 |
| NUE233 | | | 1.73 | 4.4E−02 | 4.19 | 9.9E−05 | 0.95 | 6.2E−01 | 1.28 | 3.3E−01 |
| NUE231 | | | 0.75 | 7.8E−01 | 8.66 | 4.6E−10 | 0.30 | 9.7E−01 | | |
| NUE228 | 0.17 | 1.0E+00 | 2.29 | 2.4E−12 | 4.75 | 3.2E−23 | | | 0.13 | 1.0E+00 |
| NUE225 | | | | | 11.25 | 0 | 2.41 | 1.0E−14 | 0.10 | 1.0E+00 |
| NUE249 | | | | | 5.78 | 4.17E−05 | | | | |

Table 7. Digital expression of the indicated genes in leaf, callus, root, seedling and shoot. Provided are the fold increase and the calculated p-values. Results were considered statistically significant if the p-value was lower than 0.05. Blank cells indicate that either the gene is not expressed or data is not available.

TABLE 8

Digital expression of NUE224, NUE230, NUE255, NUE245, NUE237, NUE233, NUE231, NUE228, NUE225 and NUE249 under different growth conditions and treatments

| | Treatment | | | | | |
|---|---|---|---|---|---|---|
| | plant development hormones | | drought | | etiolation | |
| Genes | fold | p-value | fold | p-value | fold | p-value |
| NUE224 | 4.75 | 1.7E−06 | | | 1.51 | 1.4E−01 |
| NUE230 | 2.74 | 2.1E−04 | 0.31 | 9.6E−01 | | |
| NUE255 | 4.00 | 1.4E−04 | | | | |
| NUE245 | 2.67 | 1.1E−02 | 1.28 | 4.6E−01 | | |
| NUE237 | 4.26 | 5.9E−04 | 6.00 | 4.2E−04 | | |
| NUE233 | 11.74 | 2.5E−10 | | | | |
| NUE231 | 10.00 | 3.4E−10 | | | | |
| NUE228 | 4.48 | 3.0E−09 | | | | |
| NUE225 | 3.45 | 3.6E−07 | | | | |
| NUE249 | 2.00 | 3.0E−02 | | | | |

Table 8. Digital expression of the indicated genes under plant development hormones, drought and etiolation. Provided are the fold increase and the calculated p-values. Results were considered statistically significant if the p-value was lower than 0.05. Blank cells indicate that either the gene is not expressed or data is not available.

TABLE 9

Digital expression of NUE224, NUE230, NUE255, NUE245, NUE237, NUE233, NUE231, NUE228, NUE225 and NUE249 under different growth treatments

| | Treatment | | | | | |
|---|---|---|---|---|---|---|
| | waterlogging | | photoperiod response | | salinity | |
| Genes | fold | p-value | fold | p-value | fold | p-value |
| NUE224 | | | | | | |
| NUE230 | | | | | 1.26 | 4.3E−01 |
| NUE255 | | | | | | |
| NUE245 | 2.00 | 2.7E−02 | | | 0.87 | 6.9E−01 |
| NUE237 | | | | | | |
| NUE233 | | | | | | |
| NUE231 | | | | | | |
| NUE228 | | | | | | |

TABLE 9-continued

Digital expression of NUE224, NUE230, NUE255, NUE245, NUE237, NUE233, NUE231, NUE228, NUE225 and NUE249 under different growth treatments

| | Treatment | | | | | |
|---|---|---|---|---|---|---|
| | waterlogging | | photoperiod response | | salinity | |
| Genes | fold | p-value | fold | p-value | fold | p-value |
| NUE225 | 21.00 | 3.4E−26 | | | 28.53 | 5.6E−82 |
| NUE249 | | | 2.00 | 4.0E−03 | | |

Table 9. Digital expression of the indicated genes under waterlogging, photoperiod response and salinity. Provided are the fold increase and the calculated p-values. Results were considered statistically significant if the p-value was lower than 0.05. Blank cells indicate that either the gene is not expressed or data is not available.

NUE268, NUE574 and NUE575 were selected because of their high expression in callus (a tissue with high cell division rate) and induced when treated with plant growth and development related hormones (as shown in Table 10, below).

TABLE 10

Digital expression of NUE268, NUE574 and NUE575 in various tissues and under different conditions and treatments

| | | | NUE268 | NUE574 | NUE575 |
|---|---|---|---|---|---|
| Anatomy | leaf | fold | 0.84 | 1.24 | |
| | | p-value | 0.8 | 4.8E−01 | |
| | callus | fold | 2.37 | 2.28 | 2.47 |
| | | p-value | 6.0E−19 | 2.0E−04 | 2.5E−07 |
| | root | fold | 0.41 | 0.31 | 1.20 |
| | | p-value | 1 | 9.7E−01 | 3.8E−01 |
| | seedling | fold | 0.34 | 1.23 | 0.45 |
| | | p-value | 1 | 3.1E−01 | 9.9E−01 |
| | shoot | fold | 0.59 | 0.16 | 0.91 |
| | | p-value | 9.9E−01 | 1.0E+00 | 6.6E−01 |
| Treatment | plant development hormones | fold | 4.46 | 2.80 | 1.84 |
| | | p-value | 1.4E−12 | 5.5E−02 | 1.7E−01 |
| | drought | fold | | 2.00 | |
| | | p-value | | 1.7E−01 | |
| | etiolation | fold | 0.20 | 0.35 | 0.23 |
| | | p-value | 1.0E+00 | 9.5E−01 | 9.9E−01 |
| | waterlogging | fold | | | |
| | | p-value | | | |
| | photoperiod response | fold | 3.32 | | |
| | | p-value | 3.4E−02 | | |
| | salinity | fold | | 1.00 | |
| | | p-value | | 4.3E−01 | |

Table 10. Digital expression of the indicated genes in various tissues (leaf, callus, root, seedling and shoot) and under various treatment or conditions (plant development hormones, drought, etiolation, waterlogging, photoperiod response and salinity. Provided are the fold increase and the calculated p-values. Results were considered statistically significant if the p-value was lower than 0.05. Note the significant fold expression in callus and under plant development hormones.

CT75, CT7, CT76, CT71, CT74, CT11, CT20, CT81, CT22, CT82, CT3, CT40, CT1, CT6, CT27, CT2, NUE269, NUE545 and NUE544, were selected based on their high expression in cotton fiber, which formation is strongly related to cell elongation (Tables 11 and 12 below) and therefore are expected to have a positive effect on root development under normal conditions, nitrogen deficient conditions, fertilizer shortage and/or water deficiencies conditions as well as for increasing oil content.

TABLE 11

Digital expression of CT75, CT7, CT76, CT71, CT74, CT11, CT20, CT81, CT22, CT82, CT3, CT40, CT1, CT6, CT27, CT2, NUE269, NUE545 and NUE544 in different tissues

| | Anatomy | | | | | | | |
|---|---|---|---|---|---|---|---|---|
| | cotton fiber | | fruit | | seed | | root | |
| Gene Name | fold | p-value | fold | p-value | fold | p-value | fold | p-value |
| CT75 | 1.63 | 9.3E−13 | | | | | | |
| CT7 | 1.65 | 6.3E−16 | | | | | | |
| CT76 | 1.21 | 1.9E−01 | | | | | | |
| CT71 | 1.6 | 1.3E−28 | | | | | | |
| CT74 | 1.68 | 2.4E−89 | | | | | | |
| CT11 | 1.49 | 4.4E−04 | | | | | | |
| CT20 | 1.68 | 1.1E−14 | | | | | 0.6 | 8.1E−01 |
| CT81 | 1.37 | 9.8E−04 | | | | | | |
| CT22 | 0.92 | 7.4E−01 | | | | | | |
| CT82 | 1.31 | 3.6E−01 | | | | | | |
| CT3 | 1.87 | 1.4E−14 | | | | | | |
| CT40 | 1.27 | 1.9E−03 | | | | | 0.59 | 8.2E−01 |
| CT1 | 1.53 | 2.4E−09 | | | | | | |
| CT6 | 1.46 | 6.3E−09 | | | | | | |
| CT27 | 0.65 | 9.0E−01 | | | | | | |
| CT2 | 1.43 | 1.7E−03 | | | | | | |
| NUE269 | 1.50 | 2.5E−02 | | | | | | |
| NUE545 | 1.39 | 4.6E−03 | | | | | 1 | 4.5E−01 |
| NUE544 | 1.73 | 1.5E−03 | | | | | | |

Table 11. Digital expression of the indicated genes in cotton fibers, fruit, seed and root. Provided are the fold increase and the calculated p-values. Results were considered statistically significant if the p-value was lower than 0.05. Note the significant fold expression in cotton fiber. Blank cells indicate that either the gene is not expressed or data is not available.

TABLE 12

Digital expression of CT75, CT7, CT76, CT71, CT74, CT11, CT20, CT81, CT22, CT82, CT3, CT40, CT1, CT6, CT27, CT2, NUE269, NUE545 and NUE544

| | Anatomy | | | | | |
|---|---|---|---|---|---|---|
| | seedling | | stem | | leaf | |
| Gene Name | fold | p-value | fold | p-value | fold | p-value |
| CT75 | | | | | | |
| CT7 | 0.08 | 1 | | | 0.44 | 9.0E−01 |
| CT76 | | | | | | |
| CT71 | 0.17 | 1 | | | | |
| CT74 | 0.17 | 1 | | | | |
| CT11 | | | | | | |
| CT20 | 0.55 | 0.97 | | | | |
| CT81 | 1.6 | 0.08 | | | | |
| CT22 | | | | | | |
| CT82 | | | | | | |
| CT3 | | | | | | |
| CT40 | | | | | 0.52 | 0.86 |
| CT1 | 0.54 | 0.97 | | | | |
| CT6 | | | 0.17 | 0.99 | | |
| CT27 | | | | | | |
| CT2 | 0.21 | 0.99 | | | | |
| NUE269 | | | | | | |
| NUE545 | | | | | 0.63 | 8.0E−01 |
| NUE544 | 0.6 | 8.3E−01 | | | | |

Table 12. Digital expression of the indicated genes in seedling, stem and leaf. Provided are the fold increase and the calculated p-values. Results were considered statistically significant if the p-value was lower than 0.05. Blank cells indicate that either the gene is not expressed or data is not available.

Plants growing under low nitrogen conditions or harsh drought conditions suffer from severe leaf senescence. NUE525, NUE535, NUE565, NUE578, NUE515 and NUE591 were selected as genes highly induced in leaves and under nutrient deficiencies of drought stress conditions (as shown in Tables 13 and 14, below). In addition, NUE578 shows strong induction in plants affected by heat stress.

TABLE 13

Digital expression of NUE525, NUE535, NUE565, NUE578, NUE515 and NUE591 in different tissues

| | Anatomy | | | | | | | |
|---|---|---|---|---|---|---|---|---|
| | Leaf | | Root | | Flower | | Callus | |
| Genes | fold | p-value | fold | p-value | fold | p-value | fold | p-value |
| NUE525 | 2.54 | 4.4E−06 | 0.93 | 6.6E−01 | 0.28 | 1.0E+00 | | |
| NUE535 | 8.10 | 1.4E−11 | | | | | | |
| NUE565 | 4.78 | 3.3E−03 | | | | | | |
| NUE578 | 2.41 | 9.1E−04 | | | 0.20 | 1.0E+00 | | |
| NUE515 | 3.67 | 2.2E−02 | 1.36 | 4.4E−01 | 1.00 | 3.7E−01 | | |
| NUE591 | 3.41 | 1.3E−02 | 1.40 | 3.6E−01 | 1.59 | 2.9E−01 | | |

Table 13. Digital expression of the indicated genes in leaf, root, flower and callus. Provided are the fold increase and the calculated p-values. Results were considered statistically significant if the p-value was lower than 0.05. Note the fold expression in leaf. Blank cells indicate that either the gene is not expressed or data is not available.

TABLE 14

Digital expression of NUE525, NUE535, NUE565, NUE578, NUE515 and NUE591 under different conditions

| | Treatment | | | | | | | |
|---|---|---|---|---|---|---|---|---|
| | Nutrient deficiency | | Drought | | Salinity | | Heat | |
| Genes | fold | p-value | fold | p-value | fold | p-value | fold | p-value |
| NUE525 | 3.19 | 1.2E−02 | 0.54 | 9.4E−01 | 1.29 | 4.6E−01 | | |
| NUE535 | | | 4.06 | 6.7E−03 | | | | |
| NUE565 | | | 3.00 | 2.3E−02 | | | | |
| NUE578 | | | 4.25 | 2.7E−05 | 1.00 | 4.0E−01 | 8.05 | 3.8E−08 |
| NUE515 | | | 3.00 | 2.6E−02 | | | | |
| NUE591 | | | 7.00 | 2.7E−05 | | | | |

Table 14. Digital expression of the indicated genes under nutrient deficiency, drought, salinity and heat. Provided are the fold increase and the calculated p-values. Results were considered statistically significant if the p-value was lower than 0.05. Note the fold expression under nutrient deficiency and drought. Blank cells indicate that either the gene is not expressed or data is not available.

NUE520, NUE521, NUE560, NUE563 and NUE573 were selected as genes that can improve seedling vigor under nitrogen stress conditions. NUE520, NUE521, NUE560 were selected as genes that are highly expressed in whole seedlings and are highly induced under drought stress. NUE563 was selected as a gene that is highly induced in seedling leaves and is induced under salinity stress. NUE573 is induced in seedling roots and under salinity stress (see Tables 15 and 16).

TABLE 15

Digital expression of NUE520, NUE521, NUE560, NUE563 and NUE573 in different tissues

| | Anatomy | | | | | | | |
|---|---|---|---|---|---|---|---|---|
| | Leaf | | Root | | Flower | | Seedling | |
| Genes | fold | p-value | fold | p-value | fold | p-value | fold | p-value |
| NUE520 | 1.80 | 8.0E−02 | 0.88 | 6.9E−01 | 1.34 | 1.4E−02 | 1.87 | 9.1E−05 |
| NUE521 | | | 1.43 | 2.7E−01 | 1.06 | 4.4E−01 | 1.78 | 2.1E−02 |
| NUE560 | 2.68 | 6.2E−02 | 0.66 | 8.2E−01 | 0.57 | 9.8E−01 | 3.67 | 1.2E−09 |
| NUE563 | 5.07 | 6.7E−05 | 0.28 | 9.8E−01 | 0.14 | 1.0E+00 | 5.30 | 4.7E−24 |
| NUE573 | 0.17 | 1.0E+00 | 8.59 | 3.2E−47 | | | 2.00 | 3.0E−03 |

Table 15. Digital expression of the indicated genes in leaf, root, flower and seedling. Provided are the fold increase and the calculated p-values. Results were considered statistically significant if the p-value was lower than 0.05. Note the fold expression in leaf (NUE563), root (NUE573) and seedling (NUE520, NUE521, NUE560, NUE563 and NUE573). Blank cells indicate that either the gene is not expressed or data is not available.

TABLE 16

Digital expression of NUE520, NUE521, NUE560, NUE563 and NUE573 under different conditions

| | Treatment | | | | | | | |
|---|---|---|---|---|---|---|---|---|
| | Nutrient deficiencies | | Drought | | Heat | | Salinity | |
| Genes | fold | p-value | fold | p-value | fold | p-value | fold | p-value |
| NUE520 | | | 3.96 | 1.1E−03 | 8.00 | 5.5E−06 | 2.60 | 6.9E−02 |
| NUE521 | | | 6.00 | 1.3E−04 | | | 1.00 | 4.5E−01 |
| NUE560 | | | 5.00 | 5.9E−04 | | | | |
| NUE563 | | | | | | | 3.00 | 2.4E−02 |
| NUE573 | | | 1.73 | 1.3E−01 | | | 2.00 | 5.4E−02 |

Table 16. Digital expression of the indicated genes under nutrient deficiency, drought, heat and salinity. Provided are the fold increase and the calculated p-values. Results were considered statistically significant if the p-value was lower than 0.05. Note the fold expression under drought (NUE520, NUE521, NUE560) and salinity (NUE563 and NUE573). Blank cells indicate that either the gene is not expressed or data is not available.

Seedlings and cell culture are fast growing tissues. Furthermore, emerging root seedlings elongate very fast to reach available water and nitrogen at deeper soils. NUE520, NUE211, NUE564 and NUE567 were selected for their high expression in root seedlings and/or whole seedlings, while NUE519 was selected for its high expression in root seedlings and cell cultures (see Table 17).

TABLE 17

Digital expression of NUE520, NUE211, NUE564, NUE567, and NUE519 in different tissues

| | | | NUE211 | NUE564 | NUE567 | NUE519 |
|---|---|---|---|---|---|---|
| Anatomy | Leaf | fold | 1.76 | 3.39 | | |
| | | p-value | 2.0E−01 | 2.5E−03 | | |
| | Cell suspension | fold | 0.24 | | | 8.00 |
| | | p-value | 9.9E−01 | | | 8.4E−12 |
| | Root | fold | 1.91 | 3.50 | 6.11 | 3.21 |
| | | p-value | 4.6E−02 | 1.1E−03 | 6.9E−06 | 5.1E−05 |
| | Seedling | fold | 2.01 | 3.687807 | | |
| | | p-value | 1.2E−03 | 5.9E−03 | | |

TABLE 17-continued

Digital expression of NUE520, NUE211, NUE564,
NUE567, and NUE519 in different tissues

|  |  | NUE211 | NUE564 | NUE567 | NUE519 |
|---|---|---|---|---|---|
| Shoot | fold | 1.29 | 0.21 |  |  |
|  | p-value | 2.0E−01 | 1.0E+00 |  |  |

Table 17. Digital expression of the indicated genes in leaf, cell suspension, root, seedling and shoot. Provided are the fold increase and the calculated p-values. Results were considered statistically significant if the p-value was lower than 0.05. Note the fold expression in root (NUE211, NUE564, NUE567 and NUE519) and seedling (NUE211 and NUE564). Blank cells indicate that either the gene is not expressed or data is not available.

NUE528, NUE571, NUE531 and NUE590 are induced by cold stress. Cold stress reduces plant photosynthesis and produces similar effect to that observed in plants growing under nitrogen deficiency (see Table 18).

TABLE 18

Digital expression of NUE528, NUE571, NUE531 and NUE590 under different conditions

| | Treatment | | | | | | | | | |
|---|---|---|---|---|---|---|---|---|---|---|
| | Nutrient deficiencies | | Cold | | Heat | | Salinity | | Drought | |
| Genes | fold | p-value | fold | p-value | fold | p-value | fold | p-value | fold | p-value |
| NUE528 | 2.47 | 0.08 | 3.00 | 5.2E−04 |  |  |  |  |  |  |
| NUE571 |  |  | 7.24 | 5.8E−09 |  |  |  |  |  |  |
| NUE531 |  |  | 6.00 | 4.5E−04 |  |  |  |  |  |  |
| NUE590 |  |  | 1.00 | 3.9E−02 |  |  | 1 | 2.9E−01 | 1 | 2.9E−01 |

Table 18. Digital expression of the indicated genes under nutrient deficiencies, cold, heat, salinity and drought. Provided are the fold increase and the calculated p-values. Results were considered statistically significant if the p-value was lower than 0.05. Note the fold expression under nutrient deficiencies (NUE528) and cold (NUE528, 571, 531 and 590). Blank cells indicate that either the gene is not expressed or data is not available.

NUE206 was selected based on its digital expression analysis. It showed that NUE206 is highly expressed in roots (2.4 fold $p<0.05$) and indications of being induced by cold (2.2 fold $p<0.08$). NUE208 and NUE210 are tomato genes that are expressed in fruit and during fruit ripening, respectively. These stages are considered important for maintaining high cell turgor. NUE209 is a putative HB2 homeodomain protein highly expressed in flower buds. It was selected as a gene that belongs to an orthologue group of genes that are highly induced by plant developmental hormones such as auxins (5 fold $p<0.002$), and in tissues that maintain high cell turgor such as the fruit pulp (3 fold $p<0.00098$) and callus (2 fold $p<0.0003$). NUE246 was selected because of its high expression in fruit pericarp (3.7 fold $p<0.01$) and because it is highly induced by drought (4 fold, $p<0.0013$). NUE516 is a putative Pto kinase interactor selected for its induction under drought conditions (3.2 fold, $p<0.03$) and prior to flowering stage (2.0 fold $p<0.02$). NUE527 was chosen because of its expression in different nutrient deficiencies (3.7 fold $p<0.002$) being mainly expressed under phosphate deficiency (4 fold, $p<0.006$). NUE547, which is a Putative Ca(2+)-dependent nuclease, was selected as a gene induced in flowers during pre-anthesis stage (2.0 fold $p<0.04$). NUE551 is an uncharacterized protein that was classified and chosen as a gene that is induced in flowers (2.6 fold $p<0.007$) and is involved in plant carbon metabolism (GO:0005975 carbohydrate metabolism). NUE554 was characterized as TBP-binding protein-like who is induced in shoots (1.8 fold $p<8e-09$) during blister and/or milking grain filling stage (3.4 fold $p<1e-08$). NUE583 is an uncharacterized protein highly expressed in flowers (2.5 fold $p<0.006$) and significantly induced by cytokinins (4.0 fold $p<2e-05$). NUE584 is an unknown protein highly induced in shoots and roots (6.0 fold $p<8e-07$) and overrepresented under nutrient deficiency conditions (6.0 fold $p<1e-08$) and drought (3.0 fold $p<0.03$). NUE592 is an unknown protein induced by phosphate deficiency (2.0 fold $p<0.05$) and by stress related hormones (6.1 fold $p<2E-05$)

Other NUE and MAB genes were selected based on their induced expression in different Microarrays experiments. The experiments selected from the Gene Expression Omnibus (Hypertext Transfer Protocol://World Wide Web (dot) ncbi (dot) nlm (dot) nih (dot) gov/geo/) were abiotic stresses (drought, salinity) GSE6901, nitrogen deficiency GSE4409, cold GSE3326, rice atlas GSE6893, and auxin GSE3350. From TAIR (Hypertext Transfer Protocol://World Wide Web (dot) arabidopsis (dot) org/servlets/Search?type=expr&search_action=new_search) the experiments on salinity 1007966888, osmoticum 1007966835, cold 1007966553 and ABA application 1007964750 were chosen, and from Nascarrays (Hypertext Transfer Protocol://affymetrix (dot) arabidopsis (dot) info/narrays/experiment-browse (dot) pl) an experiment on Nitrogen deficiency NASCARRAYS-136 was chosen. Furthermore, a Proprietary cotton fiber microarray data was used to detect the expression of the genes in cotton fiber or root specifically (PCT Publication No: WO 2008/075364)

Based on the analysis of the microarray experiments described above NUE222 was selected because it is highly expressed under nitrogen deficiency, salinity and because it is strongly induced by ABA (see Table 19, hereinbelow). NUE267 and NUE206 were selected as these genes are highly induced by salinity, cold and ABA. NUE212 is a cotton gene specifically expressed in roots. MAB52 was selected because it is induced by drought. MAB53 was selected because it is induced by nitrogen deficiency and it is a functional orthologue of MAB106. NUE566 and NUE568 were selected for their high expression in leaves when compared to their expression in roots). NUE570 was selected because it is highly overrepresented in EST's libraries of leaves (5 fold $p<0.001$) and is induced by salinity in the microarray experiment. NUE540 is expressed in roots and is related to root hair cell differentiation (GO:0048765). NUE539, NUE543, NUE576 and NUE577 were selected for being highly induced under nitrogen deficiency. NUE577 was also selected for being induced under salinity and cold stress. NUE569 was selected for being induced under salinity and osmoticum conditions. NUE586 was selected for being inducted when treated with the growth hormone auxin. NUE253 was selected as a highly expressed gene under nitrogen deficiency and salinity and NUE593 was selected as a highly expressed gene under salinity conditions

TABLE 19

Microarray expression analysis of NUE222, NUE267, NUE206, NUE212, MAB52, MAB53, NUE539, NUE543, NUE576, NUE566, NUE568, NUE569, NUE570, NUE572, NUE581, NUE540, NUE586, NUE577, NUE253 and NUE593

| Gene Name | Fold Salinity | Fold Drought | Fold Osmoticum | Fold Nitrogen Deficiency | Fold Cold | Fold ABA | Fold Roots | Fold Shoot | Fold Auxin |
|---|---|---|---|---|---|---|---|---|---|
| NUE222 | 5.0 | | | 2.0 | | 3.0 | | | |
| NUE267 | 3.0 | | | | 4.4 | 3.5 | | | |
| NUE206 | 4.0 | | | | 10.0 | 6.0 | | | |
| NUE212 | | | | | | | 12.0 | | |
| MAB52 | | 1.6 | | | | | | | |
| MAB53 | | | | 1.9 | | | | | |
| NUE539 | | | | 4.4 | | | | | |
| NUE543 | | | | 2.1 | | | | | |
| NUE576 | | | | 3.3 | | | | | |
| NUE566 | | | | | | | | 2.3 | |
| NUE568 | | | | | | | | 22.0 | |
| NUE569 | 1.5 | | 1.6 | | | | | | |
| NUE570 | 6.2 | | | | | | | | |
| NUE572 | 1.2 | | | | 2.1 | | | | |
| NUE581 | 20.9 | | | | | 7.0 | | | |
| NUE540 | | | | | | | 2.0 | | |
| NUE586 | | | | | | | | | 3.1 |
| NUE577 | 2.1 | | | 1.9 | 4.4 | | | | |
| NUE253 | 1.8 | | | 1.6 | | | | | |
| NUE593 | 2.0 | | | | | | | | |

Table 19: Microarray expression analysis of the indicated genes under salinity, drought, osmoticum, nitrogen deficiency, cold, ABA (abscisic acid) conditions and in roots, shoot and auxin. Blank cells indicate that either the gene is not expressed.

NUE49, NUE50 and NUE102 are variants of previously described genes that were originally selected for yield and NUE improvement (PCT Publication No. WO2007/049275) Overall 137 genes were identified to have a major impact on nitrogen use efficiency, fertilizer use efficiency, yield (e.g., seed yield, oil yield, grain quantity and/or quality), growth rate, vigor, biomass, oil content, abiotic stress tolerance and/or water use efficiency when expression thereof is increased in plants. The identified genes, their curated polynucleotide and polypeptide sequences, as well as their updated sequences according to GenBank database are summarized in Table 20, hereinbelow.

TABLE 20

Genes which affect nitrogen use efficiency, fertilizer use efficiency, yield, growth rate, vigor, biomass, oil content, abiotic stress tolerance and/or water use efficiency

| Gene Name | Cluster Name | Organism | Polyn. SEQ ID NO: | Polyp. SEQ ID NO: |
|---|---|---|---|---|
| CT1 | cotton\|gb164\|AI725990 | cotton | 1 | 138 |
| CT11 | cotton\|gb164\|AI725968 | cotton | 2 | 139 |
| CT2 | cotton\|gb164\|AI727334 | cotton | 3 | 140 |
| CT20 | cotton\|gb164\|AI726497 | cotton | 4 | 141 |
| CT22 | cotton\|gb164\|BG440027 | cotton | 5 | 142 |
| CT27 | cotton\|gb164\|AF336280 | cotton | 6 | 143 |
| CT3 | cotton\|gb164\|AI725456 | cotton | 7 | 144 |
| CT40 | cotton\|gb164\|BE052317 | cotton | 8 | 145 |
| CT6 | cotton\|gb164\|AI726479 | cotton | 9 | 146 |
| CT7 | cotton\|gb164\|AI727027 | cotton | 10 | 147 |
| CT71 | cotton\|gb164\|AI725508 | cotton | 11 | 148 |
| CT74 | cotton\|gb164\|AI725950 | cotton | 12 | 149 |
| CT75 | cotton\|gb164\|AI726599 | cotton | 13 | 150 |
| CT76 | cotton\|gb164\|AI726155 | cotton | 14 | 151 |
| CT81 | cotton\|gb164\|AI726693 | cotton | 15 | 152 |
| CT82 | cotton\|gb164\|BQ402794 | cotton | 16 | 153 |

TABLE 20-continued

Genes which affect nitrogen use efficiency, fertilizer use efficiency, yield, growth rate, vigor, biomass, oil content, abiotic stress tolerance and/or water use efficiency

| Gene Name | Cluster Name | Organism | Polyn. SEQ ID NO: | Polyp. SEQ ID NO: |
|---|---|---|---|---|
| MAB106 | barley\|gb157.2\|AL450627 | barley | 17 | 154 |
| MAB52 | rice\|gb157.2\|AU070543 | rice | 18 | 155 |
| MAB53 | rice\|gb157.2\|BI805919 | rice | 19 | 156 |
| NUE102 | maize\|gb170\|AI974922 | maize | 20 | 157 |
| NUE206 | arabidopsis\|gb165\|AT4G24960 | arabidopsis | 21 | 158 |
| NUE208 | tomato\|gb164\|BG124666 | tomato | 22 | 159 |
| NUE209 | tomato\|gb164\|BG134403 | tomato | 23 | 160 |
| NUE210 | tomato\|gb157\|TOMTRALTAB | tomato | 24 | 161 |
| NUE211 | rice\|gb157.2\|AU174544 | rice | 25 | 162 |
| NUE212 | cotton\|gb164\|CO081293 | cotton | 26 | 163 |
| NUE221 | rice\|gb157.2\|BI305241 | rice | 27 | 164 |
| NUE222 | arabidopsis\|gb165\|AT1G31820 | arabidopsis | 28 | 165 |
| NUE223 | rice\|gb157.2\|AW069985 | rice | 29 | 166 |
| NUE224 | rice\|gb157.2\|AW155063 | rice | 30 | 167 |
| NUE225 | rice\|gb157.2\|BE039221 | rice | 31 | 168 |
| NUE227 | rice\|gb157.2\|AU056888 | rice | 32 | 169 |
| NUE228 | rice\|gb157.2\|AA753730 | rice | 33 | 170 |
| NUE229 | maize\|gb164\|AW455682 | maize | 34 | 171 |
| NUE230 | rice\|gb157.2\|AA749861 | rice | 35 | 172 |
| NUE231 | rice\|gb157.2\|AK108994 | rice | 36 | 173 |
| NUE233 | rice\|gb157.2\|CB640732 | rice | 37 | 174 |
| NUE234 | poplar\|gb157.2\|BU868634 | poplar | 38 | 175 |
| NUE235 | soybean\|gb162\|CA852963 | soybean | 39 | 176 |
| NUE237 | rice\|gb157.2\|BI811377 | rice | 40 | 177 |
| NUE239 | poplar\|gb157.2\|BU880014 | poplar | 41 | 178 |
| NUE240 | poplar\|gb157.2\|AJ407707 | poplar | 42 | 179 |
| NUE241 | tomato\|gb164\|BG129806 | tomato | 43 | 180 |
| NUE242 | tomato\|gb164\|BG791300 | tomato | 44 | 181 |
| NUE244 | soybean\|gb162\|CF808561 | soybean | 45 | 182 |
| NUE245 | rice\|gb157.2\|AT003383 | rice | 46 | 183 |
| NUE246 | grape\|gb160\|CF207859 | grape | 47 | 184 |
| NUE248 | maize\|gb157\|BG354535 | maize | 48 | 185 |
| NUE249 | rice\|gb157.2\|AU029933 | rice | 49 | 186 |
| NUE250 | rice\|gb157.2\|AK102239 | rice | 50 | 187 |
| NUE251 | sorghum\|gb161. xeno\|AI947781 | sorghum | 51 | 188 |
| NUE252 | arabidopsis\|gb165\|AT1G58030 | arabidopsis | 52 | 189 |
| NUE253 | rice\|gb157.2\|AF145730 | rice | 53 | 190 |
| NUE254 | maize\|gb164\|AI600563 | maize | 54 | 191 |
| NUE255 | rice\|gb157.2\|CB000630 | rice | 55 | 192 |
| NUE256 | wheat\|gb154\|TG__BE216912 | wheat | 56 | 193 |
| NUE265 | rice\|gb157.2\|BE039218 | rice | 57 | 194 |
| NUE267 | arabidopsis\|gb165\|AT5G60680 | arabidopsis | 58 | 195 |
| NUE268 | rice\|gb157.2\|AA750934 | rice | 59 | 196 |
| NUE269 | cotton\|gb164\|AI730085 | cotton | 60 | 197 |
| NUE49 | maize\|gb154\|AW037179 | maize | 61 | 198 |
| NUE50 | maize\|gb164\|AW287760 | maize | 62 | 199 |
| NUE511 | maize\|gb157\|AW360667 | maize | 63 | 200 |
| NUE512 | arabidopsis\|gb157.2\|AT5G23460 | arabidopsis | 64 | 201 |
| NUE513 | arabidopsis\|gb157.2\|AT3G26100 | arabidopsis | 65 | 202 |
| NUE514 | soybean\|gb162\|SOYHPR | soybean | 66 | 203 |
| NUE515 | arabidopsis\|gb165\|AT1G44920 | arabidopsis | 67 | 204 |
| NUE515 | arabidopsis\|gb157.2\|AT1G44920__P1 | arabidopsis | 67 | 266 |
| NUE516 | arabidopsis\|gb157.2\|AT1G48210 | arabidopsis | 68 | 205 |
| NUE519 | wheat\|gb164\|BE445396 | wheat | 69 | 206 |
| NUE520 | rice\|gb157.2\|BI305493 | rice | 70 | 207 |
| NUE521 | rice\|gb157.2\|AU077950 | rice | 71 | 208 |
| NUE523 | sorghum\|gb161.xeno\|AI901439 | sorghum | 72 | 209 |
| NUE525 | sorghum\|gb161.xeno\|AW052978 | sorghum | 73 | 210 |
| NUE527 | sorghum\|gb161.xeno\|AW055409 | sorghum | 74 | 211 |
| NUE528 | sorghum\|gb161.xeno\|AI372194 | sorghum | 75 | 212 |
| NUE531 | rice\|gb157.2\|BI805136 | rice | 76 | 213 |
| NUE532 | maize\|gb164\|AW054475 | maize | 77 | 214 |
| NUE533 | soybean\|gb166\|AW350050 | soybean | 78 | 215 |
| NUE535 | sorghum\|gb161.crp\|BE599042 | sorghum | 79 | 216 |
| NUE536 | maize\|gb164\|BQ279657 | maize | 80 | 217 |
| NUE537 | barley\|gb157.2\|AJ234408 | barley | 81 | 218 |
| NUE538 | sorghum\|gb161.xeno\|AW923729 | sorghum | 82 | 219 |
| NUE539 | rice\|gb157.2\|AW155216 | rice | 83 | 220 |
| NUE540 | arabidopsis\|gb157.2\|AT1G13980 | arabidopsis | 84 | 221 |
| NUE542 | arabidopsis\|gb157.2\|AT3G46280 | arabidopsis | 85 | 222 |
| NUE543 | rice\|gb157.2\|AK063415 | rice | 86 | 223 |
| NUE544 | cotton\|gb164\|BQ412384 | cotton | 87 | 224 |
| NUE545 | cotton\|gb164\|AI055737 | cotton | 88 | 225 |
| NUE547 | sorghum\|gb161.xeno\|BI139559 | sorghum | 89 | 226 |

TABLE 20-continued

Genes which affect nitrogen use efficiency, fertilizer use efficiency, yield, growth rate, vigor, biomass, oil content, abiotic stress tolerance and/or water use efficiency

| Gene Name | Cluster Name | Organism | Polyn. SEQ ID NO: | Polyp. SEQ ID NO: |
|---|---|---|---|---|
| NUE548 | sorghum\|gb161.xeno\|BQ279657 | sorghum | 90 | 227 |
| NUE549 | sorghum\|gb161.xeno\|AF019147 | sorghum | 91 | 228 |
| NUE550 | canola\|gb161\|EE559843 | canola | 92 | 229 |
| NUE551 | barley\|gb157.3\|BE420701 | barley | 93 | 230 |
| NUE553 | barley\|gb157.3\|BE421829 | barley | 94 | 231 |
| NUE554 | sorghum\|gb161.xeno\|AA011880 | sorghum | 95 | 232 |
| NUE560 | rice\|gb157.2\|BE229552 | rice | 96 | 233 |
| NUE562 | rice\|gb157.2\|BE039784 | rice | 97 | 234 |
| NUE563 | rice\|gb157.2\|AU057884 | rice | 98 | 235 |
| NUE564 | maize\|gb164\|AI619269 | maize | 99 | 236 |
| NUE565 | arabidopsis\|gb157.2\|AT5G15080 | arabidopsis | 100 | 237 |
| NUE566 | arabidopsis\|gb165\|AT2G43700 | arabidopsis | 101 | 238 |
| NUE567 | arabidopsis\|gb165\|AT1G60680 | arabidopsis | 102 | 239 |
| NUE568 | arabidopsis\|gb165\|AT1G78450 | arabidopsis | 103 | 240 |
| NUE569 | arabidopsis\|gb165\|AT2G03890 | arabidopsis | 104 | 241 |
| NUE570 | arabidopsis\|gb165\|AT1G43910 | arabidopsis | 105 | 242 |
| NUE571 | arabidopsis\|gb157.2\|AT1G47530 | arabidopsis | 106 | 243 |
| NUE572 | arabidopsis\|gb157.2\|AT2G24240 | arabidopsis | 107 | 244 |
| NUE573 | arabidopsis\|gb165\|AT4G15390 | arabidopsis | 108 | 245 |
| NUE574 | rice\|gb157.2\|BI807603 | rice | 109 | 246 |
| NUE575 | rice\|gb157.2\|AU068829 | rice | 110 | 247 |
| NUE576 | rice\|gb157.2\|AA752451 | rice | 111 | 248 |
| NUE577 | arabidopsis\|gb165\|AT1G67800 | arabidopsis | 112 | 249 |
| NUE578 | wheat\|gb164\|BE401454 | wheat | 113 | 250 |
| NUE579 | arabidopsis\|gb165\|AT1G70850 | arabidopsis | 114 | 251 |
| NUE580 | arabidopsis\|gb165\|AT2G35880 | arabidopsis | 115 | 252 |
| NUE581 | arabidopsis\|gb165\|AT1G12845 | arabidopsis | 116 | 253 |
| NUE582 | sorghum\|gb161.xeno\|T18303 | sorghum | 117 | 254 |
| NUE583 | rice\|gb157.2\|AU172665 | rice | 118 | 255 |
| NUE584 | sorghum\|gb161.crp\|AW923545 | sorghum | 119 | 256 |
| NUE585 | arabidopsis\|gb165\|AT1G71900 | arabidopsis | 120 | 257 |
| NUE586 | arabidopsis\|gb165\|AT1G72320 | arabidopsis | 121 | 258 |
| NUE587 | sorghum\|gb161.xeno\|AW672541 | sorghum | 122 | 259 |
| NUE588 | rice\|gb157.2\|AA750816 | rice | 123 | 260 |
| NUE590 | sorghum\|gb161.xeno\|AI622209 | sorghum | 124 | 261 |
| NUE591 | sorghum\|gb161.xeno\|BE123399 | sorghum | 125 | 262 |
| NUE592 | sorghum\|gb161.xeno\|AI901557 | sorghum | 126 | 263 |
| NUE593 | arabidopsis\|gb165\|AT2G04066 | arabidopsis | 127 | 264 |
| CT82 | cotton\|gb164\|BQ402794_T1 | cotton | 128 | 153 |
| NUE102 | maize\|gb164\|AI974922_T1 | maize | 129 | 265 |
| NUE211 | rice\|gb157.2\|AU174544_T1 | rice | 130 | 162 |
| NUE212 | cotton\|gb164\|CO081293_T1 | cotton | 131 | 163 |
| NUE269 | cotton\|gb164\|AI730085_T1 | cotton | 132 | 197 |
| NUE519 | wheat\|gb164\|BE445396_T1 | wheat | 133 | 206 |
| NUE535 | sorghum\|gb161.xeno\|BE599042_T1 | sorghum | 134 | 267 |
| NUE537 | barley\|gb157.2\|AJ234408_T1 | barley | 135 | 218 |
| NUE544 | cotton\|gb164\|BQ412384_T1 | cotton | 136 | 268 |
| NUE584 | sorghum\|gb161.xeno\|AW923465_T1 | sorghum | 137 | 269 |

Table 20. Provided are polynucleotides (polyn.) and polypeptides (polyp.) which affect nitrogen use efficiency, fertilizer use efficiency, yield, growth rate, vigor, biomass, oil content, abiotic stress tolerance and/or water use efficiency of a plant.

Example 2

Identification of Homologues which Affect NUE, FUE, Yield, Growth Rate, Vigor, Biomass, Oil Content, ABST and WUE The concepts of orthology and paralogy have been applied to functional characterizations and classifications on the scale of whole-genome comparisons. Orthologs and paralogs constitute two major types of homologs: The first evolved from a common ancestor by specialization, and the latter are related by duplication events. It is assumed that paralogs arising from ancient duplication events are likely to have diverged in function while true orthologs are more likely to retain identical function over evolutionary time.

To further investigate and identify putative ortholog genes of genes affecting nitrogen use efficiency, fertilizer use efficiency, yield (e.g., seed yield, oil yield, biomass, grain quantity and/or quality), growth rate, vigor, biomass, oil content, abiotic stress tolerance and/or water use efficiency (presented in Table 20, above) all sequences were aligned using the BLAST (/Basic Local Alignment Search Tool/). Sequences sufficiently similar were tentatively grouped. These putative orthologs were further organized under a Phylogram—a branching diagram (tree) assumed to be a representation of the evolutionary relationships among the biological taxa. Putative ortholog groups were analyzed as to their agreement with the phylogram and in cases of disagreements these ortholog groups were broken accordingly. Expression data was analyzed and the EST libraries were classified using a fixed vocabulary of custom terms such as developmental stages (e.g., genes showing similar expression profile through development with up regulation at specific stage, such as at the seed filling stage) and/or plant organ (e.g., genes showing similar expression profile across their organs with up regulation at specific organs such as root). The annotations from all the ESTs clustered to a gene were analyzed statistically by comparing their frequency in the cluster versus their abundance in the database, allowing the construction of a numeric and graphic expression profile of that gene, which is termed "digital expression". The rationale of using these two complementary methods with methods of phenotypic association studies of QTLs, and phenotype expression correlation is based on the assumption that true orthologs are likely to retain identical function over evolutionary time. These methods provide different sets of indications on function similarities between two homologous genes, similarities in the sequence level—identical amino acids in the protein domains and similarity in expression profiles.

The search and identification of homologous genes involves the screening of sequence information available, for example, in public databases, which include but are not limited to the DNA Database of Japan (DDBJ), Genbank, and the European Molecular Biology Laboratory Nucleic Acid Sequence Database (EMBL) or versions thereof or the MIPS database. A number of different search algorithms have been developed, including but not limited to the suite of programs referred to as BLAST programs. There are five implementations of BLAST, three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., Genome Analysis, I: 543, 1997). Such methods involve alignment and comparison of sequences. The BLAST algorithm calculates percent sequence identity and performs a statistical analysis of the similarity between the two sequences. The software for performing BLAST analysis is publicly available through the National Centre for Biotechnology Information. Other such software or algorithms are GAP, BESTFIT, FASTA and TFASTA. GAP uses the algorithm of Needleman and Wunsch (J. Mol. Biol. 48: 443-453, 1970) to find the alignment of two complete sequences that maximizes the number of matches and minimizes the number of gaps.

The homologous genes may belong to the same gene family. The analysis of a gene family may be carried out using sequence similarity analysis. To perform this analysis one may use standard programs for multiple alignments e.g. Clustal W. A neighbor-joining tree of the proteins homologous to the genes of some embodiments of the invention may be used to provide an overview of structural and ancestral relationships. Sequence identity may be calculated using an alignment program as described above. It is expected that other plants will carry a similar functional gene (orthologue) or a family of similar genes and those genes will provide the same preferred phenotype as the genes presented here. Advantageously, these family members may be useful in the methods of some embodiments of the invention. Example of other plants include, but not limited to, barley (*Hordeum vulgare*), Arabidopsis (*Arabidopsis thaliana*), maize (*Zea mays*), cotton (*Gossypium*), Oilseed rape (*Brassica napus*), Rice (*Oryza sativa*), Sugar cane (*Saccharum officinarum*), Sorghum (*Sorghum bicolor*), Soybean (*Glycine max*), Sunflower (*Helianthus annuus*), Tomato (*Lycopersicon esculentum*) and Wheat (*Triticum aestivum*).

The above-mentioned analyses for sequence homology is preferably carried out on a full-length sequence, but may also be based on a comparison of certain regions such as conserved domains. The identification of such domains would also be well within the realm of the person skilled in the art and would involve, for example, a computer readable format of the nucleic acids of some embodiments of the invention, the use of alignment software programs and the use of publicly available information on protein domains, conserved motifs and boxes. This information is available in the PRODOM (Hypertext Transfer Protocol://World Wide Web (dot) biochem (dot) ucl (dot) ac (dot) uk/bsm/db-browser/protocol/prodomqry (dot) html), PIR (Hypertext Transfer Protocol://pir (dot) Georgetown (dot) edu/) or Pfam (Hypertext Transfer Protocol://World Wide Web (dot) sanger (dot) ac (dot) uk/Software/Pfam/) database. Sequence analysis programs designed for motif searching may be used for identification of fragments, regions and conserved domains as mentioned above. Preferred computer programs include, but are not limited to, MEME, SIGNALSCAN, and GENESCAN.

A person skilled in the art may use the homologous sequences provided herein to find similar sequences in other species and other organisms. Homologues of a protein encompass, peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (conservative changes, such as similar hydrophobicity, hydrophilicity, antigenicity, propensity to form or break a-helical structures or 3-sheet structures). Conservative substitution Tables are well known in the art [see for example Creighton (1984) Proteins. W.H. Freeman and Company]. Homologues of a nucleic acid encompass nucleic acids having nucleotide substitutions, deletions and/or insertions relative to the unmodified nucleic acid in question and having similar biological and functional activity as the unmodified nucleic acid from which they are derived.

Table 21, hereinbelow, lists a summary of orthologous and homologous sequences of the polynucleotide sequences (SEQ ID NOs: 1-137) and polypeptide sequences (SEQ ID NOs: 138-269) presented in Table 20, which were identified using BLAST (TBLASTN and BlastP programs) having at least 80% identity to the selected polypeptides and which are expected to posses the same role in NUE, ABST, FUE, WUE, biomass increment, growth rate increment, yield, vigor and/or oil content of plants.

TABLE 21

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 270 | cacao\|gb167\|CU484898 | cacao | 1334 | 138 | cotton\|gb164\|AI725990 | 88.2 | blastp |
| 271 | cotton\|gb164\|AI726705 | cotton | 1335 | 138 | cotton\|gb164\|AI725990 | 86.9 | blastp |
| 272 | almond\|gb157.2\|AY947462 | almond | 1336 | 139 | cotton\|gb164\|AI725968 | 85.7 | blastp |
| 273 | apple\|gb157.3\|CO415932 | apple | 1337 | 139 | cotton\|gb164\|AI725968 | 83.5 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 274 | bean\|gb167\|CA902463 | bean | 1338 | 139 | cotton\|gb164\|AI725968 | 87.9 | blastp |
| 275 | cacao\|gb167\|CU519200 | cacao | 1339 | 139 | cotton\|gb164\|AI725968 | 95.5 | blastp |
| 276 | citrus\|gb166\|CK936045 | citrus | 1340 | 139 | cotton\|gb164\|AI725968 | 92.4 | blastp |
| 277 | cotton\|gb164\|AI728519 | cotton | 1341 | 139 | cotton\|gb164\|AI725968 | 90.7 | blastp |
| 278 | grape\|gb160\|AF373604 | grape | 1342 | 139 | cotton\|gb164\|AI725968 | 86.2 | blastp |
| 279 | lotus\|gb157.2\|AY770405 | lotus | 1343 | 139 | cotton\|gb164\|AI725968 | 85.7 | blastp |
| 280 | medicago\|gb157.2\|BI311053 | medicago | 1344 | 139 | cotton\|gb164\|AI725968 | 87.4 | blastp |
| 281 | papaya\|gb165\|GFXEU141966X1 | papaya | 1345 | 139 | cotton\|gb164\|AI725968 | 90.1 | blastp |
| 282 | poplar\|gb170\|BU882889 | poplar | 1346 | 139 | cotton\|gb164\|AI725968 | 87.6 | blastp |
| 283 | poplar\|gb170\|CV256507 | poplar | 1347 | 139 | cotton\|gb164\|AI725968 | 83.9 | blastp |
| 284 | prunus\|gb167\|AJ825116 | prunus | 1348 | 139 | cotton\|gb164\|AI725968 | 85.2 | blastp |
| 285 | soybean\|gb168\|BE659913 | soybean | 1349 | 139 | cotton\|gb164\|AI725968 | 87.4 | blastp |
| 286 | soybean\|gb168\|BE659915 | soybean | 1350 | 139 | cotton\|gb164\|AI725968 | 85.2 | blastp |
| 287 | spurge\|gb161\|DV143720 | spurge | 1351 | 139 | cotton\|gb164\|AI725968 | 84.75 | tblastn |
| 288 | cotton\|gb164\|AI726482 | cotton | 1352 | 140 | cotton\|gb164\|AI727334 | 98.1 | blastp |
| 289 | cacao\|gb167\|CU473257 | cacao | 1353 | 141 | cotton\|gb164\|AI726497 | 87.4 | blastp |
| 290 | cotton\|gb164\|BF272326 | cotton | 1354 | 141 | cotton\|gb164\|AI726497 | 83.3 | blastp |
| 291 | cotton\|gb164\|AI729672 | cotton | 1355 | 144 | cotton\|gb164\|AI725456 | 83.7 | blastp |
| 292 | cotton\|gb164\|CB350460 | cotton | 1356 | 145 | cotton\|gb164\|BE052317 | 87.8 | blastp |
| 293 | cotton\|gb164\|DV437946 | cotton | 1357 | 145 | cotton\|gb164\|BE052317 | 87.8 | blastp |
| 294 | cotton\|gb164\|AI726435 | cotton | 1358 | 146 | cotton\|gb164\|AI726479 | 95.1 | blastp |
| 295 | cacao\|gb167\|CF972823 | cacao | 1359 | 148 | cotton\|gb164\|AI725508 | 81.4 | blastp |
| 296 | cotton\|gb164\|AI725520 | cotton | 1360 | 148 | cotton\|gb164\|AI725508 | 81.8 | blastp |
| 297 | cotton\|gb164\|BE054381 | cotton | 1361 | 148 | cotton\|gb164\|AI725508 | 85.4 | blastp |
| 298 | cotton\|gb164\|AI726610 | cotton | 1362 | 149 | cotton\|gb164\|AI725950 | 86.8 | blastp |
| 299 | cotton\|gb164\|AI731567 | cotton | 1363 | 149 | cotton\|gb164\|AI725950 | 96.4 | blastp |
| 300 | cotton\|gb164\|AI726627 | cotton | 1364 | 150 | cotton\|gb164\|AI726599 | 96.4 | blastp |
| 301 | brachypodium\|gb169\|BE425417 | brachypodium | 1365 | 154 | barley\|gb157.2\|AL450627 | 84.7 | blastp |
| 302 | leymus\|gb166\|EG388830 | leymus | 1366 | 154 | barley\|gb157.2\|AL450627 | 86.4 | blastp |
| 303 | pseudoroegneria\|gb167\|FF340314 | pseudoroegneria | 1367 | 154 | barley\|gb157.2\|AL450627 | 89.4 | blastp |
| 304 | wheat\|gb164\|BE429931 | wheat | 1368 | 154 | barley\|gb157.2\|AL450627 | 89.4 | blastp |
| 305 | switchgrass\|gb167\|DN142225 | switchgrass | 1369 | 156 | rice\|gb157.2\|BI805919 | 82.5 | blastp |
| 306 | brachypodium\|gb169\|BE425715 | brachypodium | 1370 | 157 | maize\|gb170\|AI974922 | 85.2 | blastp |
| 306 | brachypodium\|gb169\|BE425715 | brachypodium | 1370 | 265 | maize\|gb164\|AI974922 | 81 | blastp |
| 307 | maize\|gb170\|BG320615 | maize | 1371 | 157 | maize\|gb170\|AI974922 | 92.1 | blastp |
| 307 | maize\|gb170\|BG320615 | maize | 1371 | 265 | maize\|gb164\|AI974922 | 86 | blastp |
| 308 | maize\|gb170\|CF023721 | maize | 1372 | 157 | maize\|gb170\|AI974922 | 89.1 | blastp |
| 308 | maize\|gb170\|CF023721 | maize | 1372 | 265 | maize\|gb164\|AI974922 | 87.5 | blastp |
| 309 | maize\|gb170\|CF059393 | maize | 1373 | 157 | maize\|gb170\|AI974922 | 87.6 | blastp |
| 309 | maize\|gb170\|CF059393 | maize | 1373 | 265 | maize\|gb164\|AI974922 | 86 | blastp |
| 310 | maize\|gb170\|SRR014551S0286097 | maize | 1374 | 265 | maize\|gb164\|AI974922 | 88.1 | blastp |
| 310 | maize\|gb170\|SRR014551S0286097 | maize | 1374 | 157 | maize\|gb170\|AI974922 | 85.1 | blastp |
| 311 | rice\|gb170\|OS11G09020 | rice | 1375 | 265 | maize\|gb164\|AI974922 | 83.56 | tblastn |
| 311 | rice\|gb170\|OS11G09020 | rice | 1375 | 157 | maize\|gb170\|AI974922 | 80.1 | blastp |
| 312 | rice\|gb170\|OS12G08090 | rice | 1376 | 157 | maize\|gb170\|AI974922 | 86 | blastp |
| 312 | rice\|gb170\|OS12G08090 | rice | 1376 | 265 | maize\|gb164\|AI974922 | 81.3 | blastp |
| 313 | rice\|gb170\|OS12G08130 | rice | 1377 | 157 | maize\|gb170\|AI974922 | 86.2 | blastp |
| 313 | rice\|gb170\|OS12G08130 | rice | 1377 | 265 | maize\|gb164\|AI974922 | 81.5 | blastp |
| 314 | sorghum\|gb161.crp\|BE358811 | sorghum | 1378 | 157 | maize\|gb170\|AI974922 | 95.6 | blastp |
| 314 | sorghum\|gb161.crp\|BE358811 | sorghum | 1378 | 265 | maize\|gb164\|AI974922 | 89.8 | blastp |
| 315 | sorghum\|gb161.crp\|BG052599 | sorghum | 1379 | 157 | maize\|gb170\|AI974922 | 89.1 | blastp |
| 315 | sorghum\|gb161.crp\|BG052599 | sorghum | 1379 | 265 | maize\|gb164\|AI974922 | 87.5 | blastp |
| 316 | sorghum\|gb161.crp\|BG464355 | sorghum | 1380 | 157 | maize\|gb170\|AI974922 | 91 | blastp |
| 316 | sorghum\|gb161.crp\|BG464355 | sorghum | 1380 | 265 | maize\|gb164\|AI974922 | 85.6 | blastp |
| 317 | sorghum\|gb161.crp\|BG488442 | sorghum | 1381 | 157 | maize\|gb170\|AI974922 | 89.1 | blastp |
| 317 | sorghum\|gb161.crp\|BG488442 | sorghum | 1381 | 265 | maize\|gb164\|AI974922 | 87.7 | blastp |
| 318 | sorghum\|gb161.crp\|SBGWP027891 | sorghum | 1382 | 157 | maize\|gb170\|AI974922 | 87.6 | blastp |
| 318 | sorghum\|gb161.crp\|SBGWP027891 | sorghum | 1382 | 265 | maize\|gb164\|AI974922 | 86 | blastp |
| 319 | wheat\|gb164\|BI479031 | wheat | 1383 | 265 | maize\|gb164\|AI974922 | 81.74 | tblastn |
| 319 | wheat\|gb164\|BI479031 | wheat | 1383 | 157 | maize\|gb170\|AI974922 | 80.33 | tblastn |
| 320 | b_rapa\|gb162\|BG544047 | b_rapa | 1384 | 158 | arabidopsis\|gb165\|AT4G24960 | 87.5 | blastp |
| 321 | b_rapa\|gb162\|EX087649 | b_rapa | 1385 | 158 | arabidopsis\|gb165\|AT4G24960 | 82.2 | blastp |
| 322 | canola\|gb161\|DY020042 | canola | 1386 | 158 | arabidopsis\|gb165\|AT4G24960 | 86.8 | blastp |
| 323 | radish\|gb164\|EV538867 | radish | 1387 | 158 | arabidopsis\|gb165\|AT4G24960 | 84.4 | blastp |
| 324 | radish\|gb164\|EV544902 | radish | 1388 | 158 | arabidopsis\|gb165\|AT4G24960 | 85.1 | blastp |
| 325 | radish\|gb164\|EX746928 | radish | 1389 | 158 | arabidopsis\|gb165\|AT4G24960 | 84.4 | blastp |
| 326 | radish\|gb164\|EX748244 | radish | 1390 | 158 | arabidopsis\|gb165\|AT4G24960 | 83.9 | blastp |
| 327 | thellungiella\|gb167\|BY812778 | thellungiella | 1391 | 158 | arabidopsis\|gb165\|AT4G24960 | 84.3 | blastp |
| 328 | apple\|gb157.3\|CN876940 | apple | 1392 | 159 | tomato\|gb164\|BG124666 | 81.7 | blastp |
| 329 | apple\|gb157.3\|CN944710 | apple | 1393 | 159 | tomato\|gb164\|BG124666 | 81.7 | blastp |
| 330 | apricot\|gb157.2\|CB819340 | apricot | 1394 | 159 | tomato\|gb164\|BG124666 | 82.3 | blastp |
| 331 | b_oleracea\|gb161\|AM057864 | b_oleracea | 1395 | 159 | tomato\|gb164\|BG124666 | 80.6 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 332 | b_rapa\|gb162\|EE527690 | b_rapa | 1396 | 159 | tomato\|gb164\|BG124666 | 80.6 | blastp |
| 333 | cacao\|gb167\|CU493876 | cacao | 1397 | 159 | tomato\|gb164\|BG124666 | 80.3 | blastp |
| 334 | canola\|gb161\|CD830518 | canola | 1398 | 159 | tomato\|gb164\|BG124666 | 80 | blastp |
| 335 | canola\|gb161\|CX279110 | canola | 1399 | 159 | tomato\|gb164\|BG124666 | 80.6 | blastp |
| 336 | cassava\|gb164\|DV454217 | cassava | 1400 | 159 | tomato\|gb164\|BG124666 | 82.3 | blastp |
| 337 | catharanthus\|gb166\|EG557732 | catharanthus | 1401 | 159 | tomato\|gb164\|BG124666 | 81.1 | blastp |
| 338 | citrus\|gb166\|CB290240 | citrus | 1402 | 159 | tomato\|gb164\|BG124666 | 83.4 | blastp |
| 339 | coffea\|gb157.2\|DV694449 | coffea | 1403 | 159 | tomato\|gb164\|BG124666 | 83.4 | blastp |
| 340 | cotton\|gb164\|AI727100 | cotton | 1404 | 159 | tomato\|gb164\|BG124666 | 83.7 | blastp |
| 341 | cynara\|gb167\|GE589728 | cynara | 1405 | 159 | tomato\|gb164\|BG124666 | 80 | blastp |
| 342 | ipomoea\|gb157.2\|EE875432 | ipomoea | 1406 | 159 | tomato\|gb164\|BG124666 | 81.7 | blastp |
| 343 | kiwi\|gb166\|FG405906 | kiwi | 1407 | 159 | tomato\|gb164\|BG124666 | 81.6 | blastp |
| 344 | peach\|gb157.2\|BU044342 | peach | 1408 | 159 | tomato\|gb164\|BG124666 | 84 | blastp |
| 345 | pepper\|gb157.2\|CA514905 | pepper | 1409 | 159 | tomato\|gb164\|BG124666 | 93.1 | blastp |
| 346 | periwinkle\|gb164\|EG557732 | periwinkle | 1410 | 159 | tomato\|gb164\|BG124666 | 81.1 | blastp |
| 347 | petunia\|gb166\|CV294973 | petunia | 1411 | 159 | tomato\|gb164\|BG124666 | 88.7 | tblastn |
| 348 | poplar\|gb170\|BU867493 | poplar | 1412 | 159 | tomato\|gb164\|BG124666 | 85.2 | blastp |
| 349 | prunus\|gb167\|BU044342 | prunus | 1413 | 159 | tomato\|gb164\|BG124666 | 84 | blastp |
| 350 | safflower\|gb162\|EL399778 | safflower | 1414 | 159 | tomato\|gb164\|BG124666 | 81.71 | tblastn |
| 351 | soybean\|gb168\|AL371264 | soybean | 1415 | 159 | tomato\|gb164\|BG124666 | 81.1 | blastp |
| 352 | soybean\|gb168\|BE661867 | soybean | 1416 | 159 | tomato\|gb164\|BG124666 | 80.6 | blastp |
| 353 | spurge\|gb161\|DV121886 | spurge | 1417 | 159 | tomato\|gb164\|BG124666 | 80.6 | blastp |
| 354 | strawberry\|gb164\|DY670203 | strawberry | 1418 | 159 | tomato\|gb164\|BG124666 | 82.4 | blastp |
| 355 | sunflower\|gb162\|EL460579 | sunflower | 1419 | 159 | tomato\|gb164\|BG124666 | 80 | tblastn |
| 356 | thellungiella\|gb167\|DN773683 | thellungiella | 1420 | 159 | tomato\|gb164\|BG124666 | 80.6 | blastp |
| 357 | tobacco\|gb162\|EB445785 | tobacco | 1421 | 159 | tomato\|gb164\|BG124666 | 90.9 | blastp |
| 358 | potato\|gb157.2\|BG098579 | potato | 1422 | 160 | tomato\|gb164\|BG134403 | 97.1 | blastp |
| 359 | potato\|gb157.2\|CK246251 | potato | 1423 | 160 | tomato\|gb164\|BG134403 | 96.7 | blastp |
| 360 | potato\|gb157.2\|CK246610 | potato | 1424 | 160 | tomato\|gb164\|BG134403 | 96 | blastp |
| 361 | brachypodium\|gb169\|BF260689 | brachypodium | 1425 | 162 | rice\|gb157.2\|AU174544 | 88.6 | tblastn |
| 362 | maize\|gb170\|AI676864 | maize | 1426 | 162 | rice\|gb157.2\|AU174544 | 86.9 | blastp |
| 363 | rice\|gb170\|OS02G44980 | rice | 1427 | 162 | rice\|gb157.2\|AU174544 | 80.6 | blastp |
| 364 | sorghum\|gb161.crp\|BF704932 | sorghum | 1428 | 162 | rice\|gb157.2\|AU174544 | 89 | blastp |
| 365 | rice\|gb170\|OS12G38010 | rice | 1429 | 168 | rice\|gb157.2\|BE039221 | 91.14 | tblastn |
| 366 | rice\|gb170\|OS12G38270 | rice | 1430 | 168 | rice\|gb157.2\|BE039221 | 81.2 | blastp |
| 367 | rice\|gb170\|OS10G38040 | rice | 1431 | 169 | rice\|gb157.2\|AU056888 | 98.1 | blastp |
| 368 | maize\|gb170\|BQ528487 | maize | 1432 | 170 | rice\|gb157.2\|AA753730 | 89.1 | blastp |
| 369 | sorghum\|gb161.crp\|CD221960 | sorghum | 1433 | 170 | rice\|gb157.2\|AA753730 | 87.1 | blastp |
| 370 | switchgrass\|gb167\|DN149767 | switchgrass | 1434 | 170 | rice\|gb157.2\|AA753730 | 86.7 | blastp |
| 371 | sorghum\|gb161.crp\|SBGWP095487 | sorghum | 1435 | 171 | maize\|gb164\|AW455682 | 89.3 | blastp |
| 372 | sugarcane\|gb157.3\|CA172410 | sugarcane | 1436 | 171 | maize\|gb164\|AW455682 | 89 | blastp |
| 373 | switchgrass\|gb167\|DN144560 | switchgrass | 1437 | 171 | maize\|gb164\|AW455682 | 85.2 | blastp |
| 374 | brachypodium\|gb169\|BE404970 | brachypodium | 1438 | 172 | rice\|gb157.2\|AA749861 | 88.7 | blastp |
| 375 | cenchrus\|gb166\|EB654111 | cenchrus | 1439 | 172 | rice\|gb157.2\|AA749861 | 87 | blastp |
| 376 | leymus\|gb166\|EG400906 | leymus | 1440 | 172 | rice\|gb157.2\|AA749861 | 83.6 | blastp |
| 377 | maize\|gb170\|AW018173 | maize | 1441 | 172 | rice\|gb157.2\|AA749861 | 90 | blastp |
| 378 | maize\|gb170\|LLAI637139 | maize | 1442 | 172 | rice\|gb157.2\|AA749861 | 88.9 | blastp |
| 379 | sorghum\|gb161.crp\|AI783434 | sorghum | 1443 | 172 | rice\|gb157.2\|AA749861 | 90.5 | blastp |
| 380 | sugarcane\|gb157.3\|BU925706 | sugarcane | 1444 | 172 | rice\|gb157.2\|AA749861 | 91.2 | blastp |
| 381 | switchgrass\|gb167\|DN142209 | switchgrass | 1445 | 172 | rice\|gb157.2\|AA749861 | 91 | blastp |
| 382 | switchgrass\|gb167\|DN142636 | switchgrass | 1446 | 172 | rice\|gb157.2\|AA749861 | 90.7 | blastp |
| 383 | wheat\|gb164\|BE398863 | wheat | 1447 | 172 | rice\|gb157.2\|AA749861 | 80.9 | blastp |
| 384 | wheat\|gb164\|BE404970 | wheat | 1448 | 172 | rice\|gb157.2\|AA749861 | 81.7 | blastp |
| 385 | wheat\|gb164\|BE418290 | wheat | 1449 | 172 | rice\|gb157.2\|AA749861 | 82 | blastp |
| 386 | maize\|gb170\|BM895695 | maize | 1450 | 173 | rice\|gb157.2\|AK108994 | 84.5 | blastp |
| 387 | rice\|gb170\|OS04G55740 | rice | 1451 | 173 | rice\|gb157.2\|AK108994 | 94.7 | blastp |
| 388 | sorghum\|gb161.crp\|BM895695 | sorghum | 1452 | 173 | rice\|gb157.2\|AK108994 | 82.2 | blastp |
| 389 | brachypodium\|gb169\|CA684980 | brachypodium | 1453 | 174 | rice\|gb157.2\|CB640732 | 87.2 | blastp |
| 390 | maize\|gb170\|AW562805 | maize | 1454 | 174 | rice\|gb157.2\|CB640732 | 87.1 | blastp |
| 391 | sorghum\|gb161.crp\|CD219694 | sorghum | 1455 | 174 | rice\|gb157.2\|CB640732 | 87.7 | blastp |
| 392 | soybean\|gb168\|AL366192 | soybean | 1456 | 174 | rice\|gb157.2\|CB640732 | 80.38 | tblastn |
| 393 | poplar\|gb170\|AI166596 | poplar | 1457 | 175 | poplar\|gb157.2\|BU868634 | 88.2 | blastp |
| 394 | castorbean\|gb160\|AJ605572 | castorbean | 1458 | 176 | soybean\|gb162\|CA852963 | 81 | blastp |
| 395 | chestnut\|gb170\|SRR006296S0014660 | chestnut | 1459 | 176 | soybean\|gb162\|CA852963 | 80.08 | tblastn |
| 396 | citrus\|gb166\|CK740163 | citrus | 1460 | 176 | soybean\|gb162\|CA852963 | 80.08 | tblastn |
| 397 | cowpea\|gb166\|FF394551 | cowpea | 1461 | 176 | soybean\|gb162\|CA852963 | 90.7 | blastp |
| 398 | medicago\|gb157.2\|AA660751 | medicago | 1462 | 176 | soybean\|gb162\|CA852963 | 87.9 | blastp |
| 399 | peanut\|gb167\|EH042453 | peanut | 1463 | 176 | soybean\|gb162\|CA852963 | 88.66 | tblastn |
| 400 | soybean\|gb168\|BU547671 | soybean | 1464 | 176 | soybean\|gb162\|CA852963 | 97.2 | blastp |
| 401 | barley\|gb157.3\|BE194421 | barley | 1465 | 177 | rice\|gb157.2\|BI811377 | 81.5 | blastp |
| 402 | brachypodium\|gb169\|BE424330 | brachypodium | 1466 | 177 | rice\|gb157.2\|BI811377 | 82.4 | blastp |
| 403 | leymus\|gb166\|EG376396 | leymus | 1467 | 177 | rice\|gb157.2\|BI811377 | 81.8 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 404 | pseudoroegneria\|gb167\|FF349876 | pseudoroegneria | 1468 | 177 | rice\|gb157.2\|BI811377 | 82.1 | blastp |
| 405 | sugarcane\|gb157.3\|CA099115 | sugarcane | 1469 | 177 | rice\|gb157.2\|BI811377 | 81 | blastp |
| 406 | wheat\|gb164\|BE424330 | wheat | 1470 | 177 | rice\|gb157.2\|BI811377 | 81.82 | tblastn |
| 407 | wheat\|gb164\|BE516775 | wheat | 1471 | 177 | rice\|gb157.2\|BI811377 | 82.1 | blastp |
| 408 | antirrhinum\|gb166\|AJ560033 | antirrhinum | 1472 | 180 | tomato\|gb164\|BG129806 | 82.9 | blastp |
| 409 | antirrhinum\|gb166\|AJ801252 | antirrhinum | 1473 | 180 | tomato\|gb164\|BG129806 | 83.3 | blastp |
| 410 | apple\|gb157.3\|AU301287 | apple | 1474 | 180 | tomato\|gb164\|BG129806 | 86.9 | blastp |
| 411 | apple\|gb157.3\|CN488989 | apple | 1475 | 180 | tomato\|gb164\|BG129806 | 84.7 | blastp |
| 412 | apple\|gb157.3\|CN864173 | apple | 1476 | 180 | tomato\|gb164\|BG129806 | 84.7 | blastp |
| 413 | apple\|gb157.3\|CN869339 | apple | 1477 | 180 | tomato\|gb164\|BG129806 | 87.4 | blastp |
| 414 | aquilegia\|gb157.3\|DR939874 | aquilegia | 1478 | 180 | tomato\|gb164\|BG129806 | 81.5 | blastp |
| 415 | arabidopsis\|gb165\|AT1G04750 | arabidopsis | 1479 | 180 | tomato\|gb164\|BG129806 | 81.5 | blastp |
| 416 | arabidopsis\|gb165\|AT2G33120 | arabidopsis | 1480 | 180 | tomato\|gb164\|BG129806 | 82 | blastp |
| 417 | artemisia\|gb164\|EY060063 | artemisia | 1481 | 180 | tomato\|gb164\|BG129806 | 84.7 | blastp |
| 418 | artemisia\|gb164\|EY073689 | artemisia | 1482 | 180 | tomato\|gb164\|BG129806 | 84.7 | blastp |
| 419 | avocado\|gb164\|CK762777 | avocado | 1483 | 180 | tomato\|gb164\|BG129806 | 82.9 | blastp |
| 420 | avocado\|gb164\|CV461025 | avocado | 1484 | 180 | tomato\|gb164\|BG129806 | 80.6 | blastp |
| 421 | b_oleracea\|gb161\|AM386735 | b_oleracea | 1485 | 180 | tomato\|gb164\|BG129806 | 80.6 | blastp |
| 422 | b_oleracea\|gb161\|CB617574 | b_oleracea | 1486 | 180 | tomato\|gb164\|BG129806 | 81.6 | blastp |
| 423 | b_rapa\|gb162\|CA992099 | b_rapa | 1487 | 180 | tomato\|gb164\|BG129806 | 80.2 | blastp |
| 424 | b_rapa\|gb162\|CV544695 | b_rapa | 1488 | 180 | tomato\|gb164\|BG129806 | 82.4 | blastp |
| 425 | b_rapa\|gb162\|DN961220 | b_rapa | 1489 | 180 | tomato\|gb164\|BG129806 | 82.1 | blastp |
| 426 | b_rapa\|gb162\|DY008890 | b_rapa | 1490 | 180 | tomato\|gb164\|BG129806 | 82.4 | blastp |
| 427 | b_rapa\|gb162\|EX034829 | b_rapa | 1491 | 180 | tomato\|gb164\|BG129806 | 80.6 | blastp |
| 428 | banana\|gb167\|FF558354 | banana | 1492 | 180 | tomato\|gb164\|BG129806 | 80.4 | blastp |
| 429 | banana\|gb167\|FL658702 | banana | 1493 | 180 | tomato\|gb164\|BG129806 | 82 | blastp |
| 430 | barley\|gb157.3\|BE413339 | barley | 1494 | 180 | tomato\|gb164\|BG129806 | 80.8 | blastp |
| 431 | basilicum\|gb157.3\|DY343103 | basilicum | 1495 | 180 | tomato\|gb164\|BG129806 | 84.1 | blastp |
| 432 | bean\|gb167\|CA898578 | bean | 1496 | 180 | tomato\|gb164\|BG129806 | 83.8 | blastp |
| 433 | bean\|gb167\|CA899486 | bean | 1497 | 180 | tomato\|gb164\|BG129806 | 87.2 | blastp |
| 434 | bean\|gb167\|CA907867 | bean | 1498 | 180 | tomato\|gb164\|BG129806 | 87.4 | blastp |
| 435 | brachypodium\|gb169\|BE417694 | brachypodium | 1499 | 180 | tomato\|gb164\|BG129806 | 80.2 | blastp |
| 436 | cacao\|gb167\|CA798042 | cacao | 1500 | 180 | tomato\|gb164\|BG129806 | 83.3 | blastp |
| 437 | cacao\|gb167\|CU474349 | cacao | 1501 | 180 | tomato\|gb164\|BG129806 | 90.5 | blastp |
| 438 | cacao\|gb167\|CU478046 | cacao | 1502 | 180 | tomato\|gb164\|BG129806 | 85.1 | blastp |
| 439 | canola\|gb161\|CD816574 | canola | 1503 | 180 | tomato\|gb164\|BG129806 | 82.4 | blastp |
| 440 | canola\|gb161\|CD818619 | canola | 1504 | 180 | tomato\|gb164\|BG129806 | 80.2 | blastp |
| 441 | canola\|gb161\|CD826636 | canola | 1505 | 180 | tomato\|gb164\|BG129806 | 82.9 | blastp |
| 442 | canola\|gb161\|CD841484 | canola | 1506 | 180 | tomato\|gb164\|BG129806 | 82.4 | blastp |
| 443 | canola\|gb161\|CN734885 | canola | 1507 | 180 | tomato\|gb164\|BG129806 | 81.5 | blastp |
| 444 | canola\|gb161\|DW998530 | canola | 1508 | 180 | tomato\|gb164\|BG129806 | 82.1 | blastp |
| 445 | canola\|gb161\|DY028580 | canola | 1509 | 180 | tomato\|gb164\|BG129806 | 82.5 | blastp |
| 446 | canola\|gb161\|EE483345 | canola | 1510 | 180 | tomato\|gb164\|BG129806 | 80.2 | blastp |
| 447 | cassava\|gb164\|BM259789 | cassava | 1511 | 180 | tomato\|gb164\|BG129806 | 84.2 | blastp |
| 448 | cassava\|gb164\|CK645968 | cassava | 1512 | 180 | tomato\|gb164\|BG129806 | 84.7 | blastp |
| 449 | cassava\|gb164\|DV446794 | cassava | 1513 | 180 | tomato\|gb164\|BG129806 | 82.4 | blastp |
| 450 | castorbean\|gb160\|EE255473 | castorbean | 1514 | 180 | tomato\|gb164\|BG129806 | 82.9 | blastp |
| 451 | castorbean\|gb160\|EE255572 | castorbean | 1515 | 180 | tomato\|gb164\|BG129806 | 85.1 | blastp |
| 452 | castorbean\|gb160\|EE259993 | castorbean | 1516 | 180 | tomato\|gb164\|BG129806 | 86 | blastp |
| 453 | centaurea\|gb166\|EH728993 | centaurea | 1517 | 180 | tomato\|gb164\|BG129806 | 84.3 | blastp |
| 454 | centaurea\|gb166\|EH737653 | centaurea | 1518 | 180 | tomato\|gb164\|BG129806 | 83.33 | tblastn |
| 455 | centaurea\|gb166\|EH743515 | centaurea | 1519 | 180 | tomato\|gb164\|BG129806 | 84.7 | blastp |
| 456 | centaurea\|gb166\|EH747496 | centaurea | 1520 | 180 | tomato\|gb164\|BG129806 | 82 | blastp |
| 457 | chestnut\|gb170\|SRR006295S0000799 | chestnut | 1521 | 180 | tomato\|gb164\|BG129806 | 84.7 | blastp |
| 458 | chestnut\|gb170\|SRR006295S0000895 | chestnut | 1522 | 180 | tomato\|gb164\|BG129806 | 85.7 | blastp |
| 459 | cichorium\|gb166\|DT212405 | cichorium | 1523 | 180 | tomato\|gb164\|BG129806 | 83.33 | tblastn |
| 460 | cichorium\|gb166\|DT212482 | cichorium | 1524 | 180 | tomato\|gb164\|BG129806 | 84.7 | blastp |
| 461 | cichorium\|gb166\|EH686887 | cichorium | 1525 | 180 | tomato\|gb164\|BG129806 | 82.88 | tblastn |
| 462 | citrus\|gb166\|BE205677 | citrus | 1526 | 180 | tomato\|gb164\|BG129806 | 88.3 | blastp |
| 463 | citrus\|gb166\|CB290704 | citrus | 1527 | 180 | tomato\|gb164\|BG129806 | 83.3 | blastp |
| 464 | citrus\|gb166\|CF830698 | citrus | 1528 | 180 | tomato\|gb164\|BG129806 | 83.8 | blastp |
| 465 | coffea\|gb157.2\|CF588660 | coffea | 1529 | 180 | tomato\|gb164\|BG129806 | 82.9 | blastp |
| 466 | coffea\|gb157.2\|DV665256 | coffea | 1530 | 180 | tomato\|gb164\|BG129806 | 80.5 | blastp |
| 467 | cotton\|gb164\|AI055143 | cotton | 1531 | 180 | tomato\|gb164\|BG129806 | 82.4 | blastp |
| 468 | cotton\|gb164\|AI726538 | cotton | 1532 | 180 | tomato\|gb164\|BG129806 | 82.43 | tblastn |
| 469 | cotton\|gb164\|BF268281 | cotton | 1533 | 180 | tomato\|gb164\|BG129806 | 88.3 | blastp |
| 470 | cotton\|gb164\|BF270800 | cotton | 1534 | 180 | tomato\|gb164\|BG129806 | 85.1 | blastp |
| 471 | cotton\|gb164\|BF274309 | cotton | 1535 | 180 | tomato\|gb164\|BG129806 | 88.8 | blastp |
| 472 | cowpea\|gb166\|FF382703 | cowpea | 1536 | 180 | tomato\|gb164\|BG129806 | 84.2 | blastp |
| 473 | cowpea\|gb166\|FF385500 | cowpea | 1537 | 180 | tomato\|gb164\|BG129806 | 87.4 | blastp |
| 474 | cowpea\|gb166\|FF388694 | cowpea | 1538 | 180 | tomato\|gb164\|BG129806 | 88 | blastp |
| 475 | cycas\|gb166\|CB090084 | cycas | 1539 | 180 | tomato\|gb164\|BG129806 | 80.6 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 476 | cynara\|gb167\|GE583641 | cynara | 1540 | 180 | tomato\|gb164\|BG129806 | 81.98 | tblastn |
| 477 | cynara\|gb167\|GE586008 | cynara | 1541 | 180 | tomato\|gb164\|BG129806 | 80.18 | tblastn |
| 478 | dandelion\|gb161\|DY820375 | dandelion | 1542 | 180 | tomato\|gb164\|BG129806 | 84.23 | tblastn |
| 479 | dandelion\|gb161\|DY822153 | dandelion | 1543 | 180 | tomato\|gb164\|BG129806 | 85.1 | blastp |
| 480 | fescue\|gb161\|DT686644 | fescue | 1544 | 180 | tomato\|gb164\|BG129806 | 82.9 | blastp |
| 481 | ginger\|gb164\|DY354490 | ginger | 1545 | 180 | tomato\|gb164\|BG129806 | 82.9 | blastp |
| 482 | ginger\|gb164\|DY357009 | ginger | 1546 | 180 | tomato\|gb164\|BG129806 | 81.53 | tblastn |
| 483 | grape\|gb160\|BQ797249 | grape | 1547 | 180 | tomato\|gb164\|BG129806 | 84.2 | blastp |
| 484 | grape\|gb160\|CA814878 | grape | 1548 | 180 | tomato\|gb164\|BG129806 | 83.4 | blastp |
| 485 | grape\|gb160\|CB009359 | grape | 1549 | 180 | tomato\|gb164\|BG129806 | 83.8 | blastp |
| 486 | ipomoea\|gb157.2\|BJ554498 | ipomoea | 1550 | 180 | tomato\|gb164\|BG129806 | 90.1 | blastp |
| 487 | ipomoea\|gb157.2\|BJ555833 | ipomoea | 1551 | 180 | tomato\|gb164\|BG129806 | 89.6 | blastp |
| 488 | ipomoea\|gb157.2\|BJ565525 | ipomoea | 1552 | 180 | tomato\|gb164\|BG129806 | 89.6 | blastp |
| 489 | ipomoea\|gb157.2\|DQ016990 | ipomoea | 1553 | 180 | tomato\|gb164\|BG129806 | 82 | blastp |
| 490 | kiwi\|gb166\|FG428824 | kiwi | 1554 | 180 | tomato\|gb164\|BG129806 | 81.5 | blastp |
| 491 | lettuce\|gb157.2\|DW046480 | lettuce | 1555 | 180 | tomato\|gb164\|BG129806 | 85.1 | blastp |
| 492 | lettuce\|gb157.2\|DW051770 | lettuce | 1556 | 180 | tomato\|gb164\|BG129806 | 80.6 | blastp |
| 493 | lettuce\|gb157.2\|DW054433 | lettuce | 1557 | 180 | tomato\|gb164\|BG129806 | 84.7 | blastp |
| 494 | lettuce\|gb157.2\|DW104005 | lettuce | 1558 | 180 | tomato\|gb164\|BG129806 | 83.8 | blastp |
| 495 | lettuce\|gb157.2\|DW148893 | lettuce | 1559 | 180 | tomato\|gb164\|BG129806 | 84.7 | blastp |
| 496 | liriodendron\|gb166\|CK761427 | liriodendron | 1560 | 180 | tomato\|gb164\|BG129806 | 81.1 | blastp |
| 497 | lovegrass\|gb167\|EH189433 | lovegrass | 1561 | 180 | tomato\|gb164\|BG129806 | 81.5 | blastp |
| 498 | maize\|gb170\|AI621444 | maize | 1562 | 180 | tomato\|gb164\|BG129806 | 83 | blastp |
| 499 | maize\|gb170\|AI901672 | maize | 1563 | 180 | tomato\|gb164\|BG129806 | 81.5 | blastp |
| 500 | medicago\|gb157.2\|AL371369 | medicago | 1564 | 180 | tomato\|gb164\|BG129806 | 81.3 | blastp |
| 501 | medicago\|gb157.2\|AW127543 | medicago | 1565 | 180 | tomato\|gb164\|BG129806 | 85.3 | blastp |
| 502 | medicago\|gb157.2\|AW329342 | medicago | 1566 | 180 | tomato\|gb164\|BG129806 | 81.5 | blastp |
| 503 | melon\|gb165\|AM743036 | melon | 1567 | 180 | tomato\|gb164\|BG129806 | 82.9 | blastp |
| 504 | melon\|gb165\|DV633620 | melon | 1568 | 180 | tomato\|gb164\|BG129806 | 80.6 | blastp |
| 505 | nuphar\|gb166\|ES730054 | nuphar | 1569 | 180 | tomato\|gb164\|BG129806 | 81.2 | blastp |
| 506 | oak\|gb170\|CU639508 | oak | 1570 | 180 | tomato\|gb164\|BG129806 | 85.7 | blastp |
| 507 | oak\|gb170\|SRR006307S0008904 | oak | 1571 | 180 | tomato\|gb164\|BG129806 | 84.7 | blastp |
| 508 | oil_palm\|gb166\|CN599846 | oil_palm | 1572 | 180 | tomato\|gb164\|BG129806 | 82 | blastp |
| 509 | onion\|gb162\|CF440003 | onion | 1573 | 180 | tomato\|gb164\|BG129806 | 82.43 | tblastn |
| 510 | papaya\|gb165\|AM904122 | papaya | 1574 | 180 | tomato\|gb164\|BG129806 | 84.2 | blastp |
| 511 | papaya\|gb165\|EX245134 | papaya | 1575 | 180 | tomato\|gb164\|BG129806 | 83.8 | blastp |
| 512 | peach\|gb157.2\|BU040787 | peach | 1576 | 180 | tomato\|gb164\|BG129806 | 88.7 | blastp |
| 513 | peach\|gb157.2\|BU048627 | peach | 1577 | 180 | tomato\|gb164\|BG129806 | 81.53 | tblastn |
| 514 | peanut\|gb167\|EH042957 | peanut | 1578 | 180 | tomato\|gb164\|BG129806 | 88.4 | blastp |
| 515 | peanut\|gb167\|EH044861 | peanut | 1579 | 180 | tomato\|gb164\|BG129806 | 83 | blastp |
| 516 | pepper\|gb157.2\|CA520584 | pepper | 1580 | 180 | tomato\|gb164\|BG129806 | 82.4 | blastp |
| 517 | petunia\|gb166\|CV296853 | petunia | 1581 | 180 | tomato\|gb164\|BG129806 | 82.9 | blastp |
| 518 | pineapple\|gb157.2\|DT337519 | pineapple | 1582 | 180 | tomato\|gb164\|BG129806 | 83.3 | blastp |
| 519 | poplar\|gb170\|AI166018 | poplar | 1583 | 180 | tomato\|gb164\|BG129806 | 86.9 | blastp |
| 520 | poplar\|gb170\|BI120322 | poplar | 1584 | 180 | tomato\|gb164\|BG129806 | 82.9 | blastp |
| 521 | poplar\|gb170\|BI128184 | poplar | 1585 | 180 | tomato\|gb164\|BG129806 | 81.1 | blastp |
| 522 | poplar\|gb170\|BU818354 | poplar | 1586 | 180 | tomato\|gb164\|BG129806 | 87.8 | blastp |
| 523 | poplar\|gb170\|CB240411 | poplar | 1587 | 180 | tomato\|gb164\|BG129806 | 81.1 | blastp |
| 524 | potato\|gb157.2\|BG590329 | potato | 1588 | 180 | tomato\|gb164\|BG129806 | 80.3 | blastp |
| 525 | potato\|gb157.2\|BG886984 | potato | 1589 | 180 | tomato\|gb164\|BG129806 | 82.9 | blastp |
| 526 | potato\|gb157.2\|BI406651 | potato | 1590 | 180 | tomato\|gb164\|BG129806 | 100 | blastp |
| 527 | prunus\|gb167\|BU040787 | prunus | 1591 | 180 | tomato\|gb164\|BG129806 | 88.7 | blastp |
| 528 | prunus\|gb167\|BU048627 | prunus | 1592 | 180 | tomato\|gb164\|BG129806 | 85.6 | blastp |
| 529 | pseudoroegneria\|gb167\|FF341379 | pseudoroegneria | 1593 | 180 | tomato\|gb164\|BG129806 | 81.2 | blastp |
| 530 | radish\|gb164\|EV527352 | radish | 1594 | 180 | tomato\|gb164\|BG129806 | 82.5 | blastp |
| 531 | radish\|gb164\|EV528724 | radish | 1595 | 180 | tomato\|gb164\|BG129806 | 82 | blastp |
| 532 | radish\|gb164\|EV532638 | radish | 1596 | 180 | tomato\|gb164\|BG129806 | 82 | blastp |
| 533 | radish\|gb164\|EV535212 | radish | 1597 | 180 | tomato\|gb164\|BG129806 | 82.5 | blastp |
| 534 | radish\|gb164\|EV544241 | radish | 1598 | 180 | tomato\|gb164\|BG129806 | 82 | blastp |
| 535 | radish\|gb164\|EV549527 | radish | 1599 | 180 | tomato\|gb164\|BG129806 | 81.98 | tblastn |
| 536 | radish\|gb164\|EV567707 | radish | 1600 | 180 | tomato\|gb164\|BG129806 | 82 | blastp |
| 537 | radish\|gb164\|EW724564 | radish | 1601 | 180 | tomato\|gb164\|BG129806 | 82 | blastp |
| 538 | radish\|gb164\|EX755021 | radish | 1602 | 180 | tomato\|gb164\|BG129806 | 80.7 | blastp |
| 539 | rice\|gb170\|OS03G58840 | rice | 1603 | 180 | tomato\|gb164\|BG129806 | 82.9 | blastp |
| 540 | rice\|gb170\|OS07G09600 | rice | 1604 | 180 | tomato\|gb164\|BG129806 | 82.9 | blastp |
| 541 | safflower\|gb162\|EL373980 | safflower | 1605 | 180 | tomato\|gb164\|BG129806 | 84.7 | blastp |
| 542 | safflower\|gb162\|EL381462 | safflower | 1606 | 180 | tomato\|gb164\|BG129806 | 83.8 | blastp |
| 543 | safflower\|gb162\|EL389501 | safflower | 1607 | 180 | tomato\|gb164\|BG129806 | 81.5 | blastp |
| 544 | safflower\|gb162\|EL404279 | safflower | 1608 | 180 | tomato\|gb164\|BG129806 | 84.7 | blastp |
| 545 | senecio\|gb170\|DY663178 | senecio | 1609 | 180 | tomato\|gb164\|BG129806 | 81.08 | tblastn |
| 546 | sorghum\|gb161.crp\|AW282206 | sorghum | 1610 | 180 | tomato\|gb164\|BG129806 | 81.5 | blastp |
| 547 | sorghum\|gb161.crp\|AW565015 | sorghum | 1611 | 180 | tomato\|gb164\|BG129806 | 83 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 548 | soybean\|gb168\|AL371369 | soybean | 1612 | 180 | tomato\|gb164\|BG129806 | 87.8 | blastp |
| 549 | soybean\|gb168\|AL371370 | soybean | 1613 | 180 | tomato\|gb164\|BG129806 | 87.6 | blastp |
| 550 | soybean\|gb168\|AL374552 | soybean | 1614 | 180 | tomato\|gb164\|BG129806 | 87.4 | blastp |
| 551 | soybean\|gb168\|AL384290 | soybean | 1615 | 180 | tomato\|gb164\|BG129806 | 86.7 | blastp |
| 552 | soybean\|gb168\|BE658783 | soybean | 1616 | 180 | tomato\|gb164\|BG129806 | 84.7 | blastp |
| 553 | soybean\|gb168\|BE660085 | soybean | 1617 | 180 | tomato\|gb164\|BG129806 | 85.1 | blastp |
| 554 | spurge\|gb161\|DV113185 | spurge | 1618 | 180 | tomato\|gb164\|BG129806 | 83.8 | blastp |
| 555 | spurge\|gb161\|DV115533 | spurge | 1619 | 180 | tomato\|gb164\|BG129806 | 86.5 | blastp |
| 556 | spurge\|gb161\|DV129528 | spurge | 1620 | 180 | tomato\|gb164\|BG129806 | 82.4 | blastp |
| 557 | strawberry\|gb164\|CO380944 | strawberry | 1621 | 180 | tomato\|gb164\|BG129806 | 87.4 | blastp |
| 558 | strawberry\|gb164\|DY667942 | strawberry | 1622 | 180 | tomato\|gb164\|BG129806 | 83.8 | blastp |
| 559 | sugarcane\|gb157.3\|CA066679 | sugarcane | 1623 | 180 | tomato\|gb164\|BG129806 | 81.53 | tblastn |
| 560 | sugarcane\|gb157.3\|CA070863 | sugarcane | 1624 | 180 | tomato\|gb164\|BG129806 | 83 | blastp |
| 561 | sugarcane\|gb157.3\|CA073069 | sugarcane | 1625 | 180 | tomato\|gb164\|BG129806 | 82.5 | blastp |
| 562 | sugarcane\|gb157.3\|CA098212 | sugarcane | 1626 | 180 | tomato\|gb164\|BG129806 | 81.1 | blastp |
| 563 | sugarcane\|gb157.3\|CA105955 | sugarcane | 1627 | 180 | tomato\|gb164\|BG129806 | 83 | blastp |
| 564 | sugarcane\|gb157.3\|CA125341 | sugarcane | 1628 | 180 | tomato\|gb164\|BG129806 | 83 | blastp |
| 565 | sunflower\|gb162\|CD848438 | sunflower | 1629 | 180 | tomato\|gb164\|BG129806 | 83.8 | blastp |
| 566 | sunflower\|gb162\|CD855829 | sunflower | 1630 | 180 | tomato\|gb164\|BG129806 | 84.7 | blastp |
| 567 | sunflower\|gb162\|DY909391 | sunflower | 1631 | 180 | tomato\|gb164\|BG129806 | 84.7 | blastp |
| 568 | sunflower\|gb162\|EL423569 | sunflower | 1632 | 180 | tomato\|gb164\|BG129806 | 83.3 | blastp |
| 569 | sunflower\|gb162\|EL429220 | sunflower | 1633 | 180 | tomato\|gb164\|BG129806 | 85.1 | blastp |
| 570 | switchgrass\|gb167\|DN143573 | switchgrass | 1634 | 180 | tomato\|gb164\|BG129806 | 82.4 | blastp |
| 571 | switchgrass\|gb167\|DN151435 | switchgrass | 1635 | 180 | tomato\|gb164\|BG129806 | 82.9 | blastp |
| 572 | switchgrass\|gb167\|FE607763 | switchgrass | 1636 | 180 | tomato\|gb164\|BG129806 | 83 | blastp |
| 573 | switchgrass\|gb167\|FE624609 | switchgrass | 1637 | 180 | tomato\|gb164\|BG129806 | 84.2 | blastp |
| 574 | thellungiella\|gb167\|BY802757 | thellungiella | 1638 | 180 | tomato\|gb164\|BG129806 | 81.5 | blastp |
| 575 | tobacco\|gb162\|DV157924 | tobacco | 1639 | 180 | tomato\|gb164\|BG129806 | 82.4 | blastp |
| 576 | tobacco\|gb162\|EB426444 | tobacco | 1640 | 180 | tomato\|gb164\|BG129806 | 96.4 | tblastn |
| 577 | tobacco\|gb162\|EB426574 | tobacco | 1641 | 180 | tomato\|gb164\|BG129806 | 84.7 | blastp |
| 578 | tobacco\|gb162\|EB677916 | tobacco | 1642 | 180 | tomato\|gb164\|BG129806 | 94.1 | blastp |
| 579 | tomato\|gb164\|BG135003 | tomato | 1643 | 180 | tomato\|gb164\|BG129806 | 84.2 | blastp |
| 580 | tomato\|gb164\|BG629456 | tomato | 1644 | 180 | tomato\|gb164\|BG129806 | 82.9 | blastp |
| 581 | triphysaria\|gb164\|DR172719 | triphysaria | 1645 | 180 | tomato\|gb164\|BG129806 | 82.3 | blastp |
| 582 | triphysaria\|gb164\|EY126667 | triphysaria | 1646 | 180 | tomato\|gb164\|BG129806 | 83.8 | blastp |
| 583 | triphysaria\|gb164\|EY128979 | triphysaria | 1647 | 180 | tomato\|gb164\|BG129806 | 83.8 | blastp |
| 584 | walnuts\|gb166\|CV198306 | walnuts | 1648 | 180 | tomato\|gb164\|BG129806 | 85.7 | blastp |
| 585 | wheat\|gb164\|BE400499 | wheat | 1649 | 180 | tomato\|gb164\|BG129806 | 80.8 | blastp |
| 586 | wheat\|gb164\|BE417694 | wheat | 1650 | 180 | tomato\|gb164\|BG129806 | 81.2 | blastp |
| 587 | wheat\|gb164\|CA595472 | wheat | 1651 | 180 | tomato\|gb164\|BG129806 | 81.2 | blastp |
| 588 | zamia\|gb166\|FD768487 | zamia | 1652 | 180 | tomato\|gb164\|BG129806 | 80.2 | blastp |
| 589 | barley\|gb157.3\|AL450674 | barley | 1653 | 183 | rice\|gb157.2\|AT003383 | 85.7 | blastp |
| 590 | brachypodium\|gb169\|BE424284 | brachypodium | 1654 | 183 | rice\|gb157.2\|AT003383 | 83.4 | blastp |
| 591 | fescue\|gb161\|DT675288 | fescue | 1655 | 183 | rice\|gb157.2\|AT003383 | 85.4 | blastp |
| 592 | leymus\|gb166\|CN466264 | leymus | 1656 | 183 | rice\|gb157.2\|AT003383 | 84.6 | blastp |
| 593 | maize\|gb170\|AI438809 | maize | 1657 | 183 | rice\|gb157.2\|AT003383 | 84.4 | blastp |
| 594 | maize\|gb170\|AI977870 | maize | 1658 | 183 | rice\|gb157.2\|AT003383 | 82.8 | blastp |
| 595 | maize\|gb170\|LLDQ245361 | maize | 1659 | 183 | rice\|gb157.2\|AT003383 | 85.7 | blastp |
| 596 | pseudoroegneria\|gb167\|FF341007 | pseudoroegneria | 1660 | 183 | rice\|gb157.2\|AT003383 | 85.7 | blastp |
| 597 | rye\|gb164\|BE586725 | rye | 1661 | 183 | rice\|gb157.2\|AT003383 | 85.7 | blastp |
| 598 | sorghum\|gb161.crp\|AW565030 | sorghum | 1662 | 183 | rice\|gb157.2\|AT003383 | 82.9 | blastp |
| 599 | sugarcane\|gb157.3\|CA084082 | sugarcane | 1663 | 183 | rice\|gb157.2\|AT003383 | 83.1 | blastp |
| 600 | switchgrass\|gb167\|DN142592 | switchgrass | 1664 | 183 | rice\|gb157.2\|AT003383 | 86.4 | blastp |
| 601 | switchgrass\|gb167\|DN145453 | switchgrass | 1665 | 183 | rice\|gb157.2\|AT003383 | 85 | blastp |
| 602 | wheat\|gb164\|BE424284 | wheat | 1666 | 183 | rice\|gb157.2\|AT003383 | 85.7 | blastp |
| 603 | wheat\|gb164\|BE498139 | wheat | 1667 | 183 | rice\|gb157.2\|AT003383 | 85.3 | blastp |
| 604 | wheat\|gb164\|BF200880 | wheat | 1668 | 183 | rice\|gb157.2\|AT003383 | 85.1 | blastp |
| 605 | wheat\|gb164\|CA620728 | wheat | 1669 | 183 | rice\|gb157.2\|AT003383 | 81.67 | tblastn |
| 606 | brachypodium\|gb169\|AJ476542 | brachypodium | 1670 | 185 | maize\|gb157\|BG354535 | 91 | blastp |
| 607 | leymus\|gb166\|EG388555 | leymus | 1671 | 185 | maize\|gb157\|BG354535 | 88.3 | blastp |
| 608 | pseudoroegneria\|gb167\|FF346414 | pseudoroegneria | 1672 | 185 | maize\|gb157\|BG354535 | 88.9 | blastp |
| 609 | rice\|gb170\|OS01G51190 | rice | 1673 | 185 | maize\|gb157\|BG354535 | 91.57 | tblastn |
| 610 | sorghum\|gb161.crp\|AW283867 | sorghum | 1674 | 185 | maize\|gb157\|BG354535 | 98.8 | blastp |
| 611 | wheat\|gb164\|AL820971 | wheat | 1675 | 185 | maize\|gb157\|BG354535 | 88.3 | blastp |
| 612 | maize\|gb170\|BI388811 | maize | 1676 | 186 | rice\|gb157.2\|AU029933 | 82.8 | blastp |
| 613 | sorghum\|gb161.crp\|DR807282 | sorghum | 1677 | 186 | rice\|gb157.2\|AU029933 | 82 | blastp |
| 614 | rice\|gb157.2\|OS01G05169 | rice | 1678 | 187 | rice\|gb157.2\|AK102239 | 82.5 | blastp |
| 615 | brachypodium\|gb169\|BE421953 | brachypodium | 1679 | 188 | sorghum\|gb161.xeno\|AI947781 | 81.97 | tblastn |
| 616 | maize\|gb170\|AI947781 | maize | 1680 | 188 | sorghum\|gb161.xeno\|AI947781 | 95.8 | blastp |
| 617 | rice\|gb170\|OS01G65100 | rice | 1681 | 188 | sorghum\|gb161.xeno\|AI947781 | 87 | blastp |
| 618 | switchgrass\|gb167\|DN144961 | switchgrass | 1682 | 188 | sorghum\|gb161.xeno\|AI947781 | 90.2 | tblastn |
| 619 | canola\|gb161\|EE417585 | canola | 1683 | 189 | arabidopsis\|gb165\|AT1G58030 | 89 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 620 | radish\|gb164\|EV566943 | radish | 1684 | 189 | arabidopsis\|gb165\|AT1G58030 | 89.47 | tblastn |
| 621 | barley\|gb157.3\|BE412663 | barley | 1685 | 191 | maize\|gb164\|AI600563 | 84.2 | blastp |
| 622 | brachypodium\|gb169\|BE407009 | brachypodium | 1686 | 191 | maize\|gb164\|AI600563 | 88.6 | blastp |
| 623 | rice\|gb170\|OS04G56290 | rice | 1687 | 191 | maize\|gb164\|AI600563 | 88.1 | blastp |
| 624 | sorghum\|gb161.crp\|AI622153 | sorghum | 1688 | 191 | maize\|gb164\|AI600563 | 95.3 | blastp |
| 625 | sugarcane\|gb157.3\|CA067412 | sugarcane | 1689 | 191 | maize\|gb164\|AI600563 | 95 | blastp |
| 626 | switchgrass\|gb167\|DN150103 | switchgrass | 1690 | 191 | maize\|gb164\|AI600563 | 93.5 | blastp |
| 627 | wheat\|gb164\|BE407009 | wheat | 1691 | 191 | maize\|gb164\|AI600563 | 87.5 | blastp |
| 628 | rice\|gb157.2\|OS01G03530 | rice | 1692 | 192 | rice\|gb157.2\|CB000630 | 99.8 | blastp |
| 629 | barley\|gb157.3\|BF066082 | barley | 1693 | 193 | wheat\|gb154\|TG_BE216912 | 88.03 | tblastn |
| 630 | barley\|gb157.3\|HVU08135 | barley | 1694 | 193 | wheat\|gb154\|TG_BE216912 | 81.7 | blastp |
| 631 | brachypodium\|gb169\|HVU08135 | brachypodium | 1695 | 193 | wheat\|gb154\|TG_BE216912 | 91.1 | blastp |
| 632 | fescue\|gb161\|DT682842 | fescue | 1696 | 193 | wheat\|gb154\|TG_BE216912 | 86.5 | blastp |
| 633 | leymus\|gb166\|CD808858 | leymus | 1697 | 193 | wheat\|gb154\|TG_BE216912 | 97.4 | blastp |
| 634 | maize\|gb170\|AI491463 | maize | 1698 | 193 | wheat\|gb154\|TG_BE216912 | 84.3 | blastp |
| 635 | maize\|gb170\|AI601031 | maize | 1699 | 193 | wheat\|gb154\|TG_BE216912 | 84.9 | blastp |
| 636 | pseudoroegneria\|gb167\|FF347239 | pseudoroegneria | 1700 | 193 | wheat\|gb154\|TG_BE216912 | 98.3 | blastp |
| 637 | rice\|gb170\|OS03G56670 | rice | 1701 | 193 | wheat\|gb154\|TG_BE216912 | 85 | blastp |
| 638 | rye\|gb164\|BE636806 | rye | 1702 | 193 | wheat\|gb154\|TG_BE216912 | 84 | blastp |
| 639 | sorghum\|gb161.crp\|AI861201 | sorghum | 1703 | 193 | wheat\|gb154\|TG_BE216912 | 85.4 | blastp |
| 640 | switchgrass\|gb167\|DN144671 | switchgrass | 1704 | 193 | wheat\|gb154\|TG_BE216912 | 84.4 | blastp |
| 641 | wheat\|gb164\|BE213564 | wheat | 1705 | 193 | wheat\|gb154\|TG_BE216912 | 91.5 | blastp |
| 642 | wheat\|gb164\|BE216912 | wheat | 1706 | 193 | wheat\|gb154\|TG_BE216912 | 89.8 | blastp |
| 643 | wheat\|gb164\|BE415875 | wheat | 1707 | 193 | wheat\|gb154\|TG_BE216912 | 93.5 | blastp |
| 644 | wheat\|gb164\|CK217408 | wheat | 1708 | 193 | wheat\|gb154\|TG_BE216912 | 83.12 | tblastn |
| 645 | wheat\|gb164\|DR737269 | wheat | 1709 | 193 | wheat\|gb154\|TG_BE216912 | 82.25 | tblastn |
| 646 | leymus\|gb166\|EG400892 | leymus | 1710 | 194 | rice\|gb157.2\|BE039218 | 81.9 | blastp |
| 647 | b_oleracea\|gb161\|AM059989 | b_oleracea | 1711 | 195 | arabidopsis\|gb165\|AT5G60680 | 80.6 | blastp |
| 648 | canola\|gb161\|DW997913 | canola | 1712 | 195 | arabidopsis\|gb165\|AT5G60680 | 81.2 | blastp |
| 649 | bean\|gb167\|CA898406 | bean | 1713 | 196 | rice\|gb157.2\|AA750934 | 80.5 | blastp |
| 650 | cacao\|gb167\|CU469591 | cacao | 1714 | 196 | rice\|gb157.2\|AA750934 | 80.6 | blastp |
| 651 | cassava\|gb164\|CK641441 | cassava | 1715 | 196 | rice\|gb157.2\|AA750934 | 80.9 | blastp |
| 652 | castorbean\|gb160\|T15009 | castorbean | 1716 | 196 | rice\|gb157.2\|AA750934 | 80.2 | blastp |
| 653 | cowpea\|gb166\|FC457559 | cowpea | 1717 | 196 | rice\|gb157.2\|AA750934 | 80.2 | blastp |
| 654 | cowpea\|gb166\|FC461906 | cowpea | 1718 | 196 | rice\|gb157.2\|AA750934 | 80.3 | blastp |
| 655 | maize\|gb170\|W21620 | maize | 1719 | 196 | rice\|gb157.2\|AA750934 | 87.6 | blastp |
| 656 | oil_palm\|gb166\|CN601354 | oil_palm | 1720 | 196 | rice\|gb157.2\|AA750934 | 81.1 | blastp |
| 657 | papaya\|gb165\|EX264224 | papaya | 1721 | 196 | rice\|gb157.2\|AA750934 | 80 | blastp |
| 658 | pineapple\|gb157.2\|CO730751 | pineapple | 1722 | 196 | rice\|gb157.2\|AA750934 | 81.6 | blastp |
| 659 | sorghum\|gb161.crp\|W21620 | sorghum | 1723 | 196 | rice\|gb157.2\|AA750934 | 87.4 | blastp |
| 660 | soybean\|gb168\|AL373484 | soybean | 1724 | 196 | rice\|gb157.2\|AA750934 | 80.9 | blastp |
| 661 | soybean\|gb168\|AW348141 | soybean | 1725 | 196 | rice\|gb157.2\|AA750934 | 80.4 | blastp |
| 662 | soybean\|gb168\|AW587090 | soybean | 1726 | 196 | rice\|gb157.2\|AA750934 | 80.4 | blastp |
| 663 | sugarcane\|gb157.3\|BQ535675 | sugarcane | 1727 | 196 | rice\|gb157.2\|AA750934 | 86.8 | blastp |
| 664 | switchgrass\|gb167\|DN140694 | switchgrass | 1728 | 196 | rice\|gb157.2\|AA750934 | 86.1 | blastp |
| 665 | switchgrass\|gb167\|DN141888 | switchgrass | 1729 | 196 | rice\|gb157.2\|AA750934 | 85.8 | blastp |
| 666 | switchgrass\|gb167\|FE603746 | switchgrass | 1730 | 196 | rice\|gb157.2\|AA750934 | 85.3 | blastp |
| 667 | maize\|gb170\|BE129570 | maize | 1731 | 198 | maize\|gb154\|AW037179 | 96.1 | blastp |
| 668 | maize\|gb170\|BI478834 | maize | 1732 | 198 | maize\|gb154\|AW037179 | 92.9 | blastp |
| 669 | rice\|gb170\|OS02G54730 | rice | 1733 | 198 | maize\|gb154\|AW037179 | 81.4 | blastp |
| 670 | sorghum\|gb161.crp\|BE129570 | sorghum | 1734 | 198 | maize\|gb154\|AW037179 | 91.8 | blastp |
| 671 | sorghum\|gb161.crp\|CD231473 | sorghum | 1735 | 199 | maize\|gb164\|AW287760 | 81.98 | tblastn |
| 672 | sugarcane\|gb157.3\|CA089926 | sugarcane | 1736 | 199 | maize\|gb164\|AW287760 | 88.56 | tblastn |
| 673 | switchgrass\|gb167\|FL699406 | switchgrass | 1737 | 199 | maize\|gb164\|AW287760 | 85.3 | blastp |
| 674 | switchgrass\|gb167\|FL727557 | switchgrass | 1738 | 199 | maize\|gb164\|AW287760 | 81.9 | blastp |
| 675 | sorghum\|gb161.crp\|BF480947 | sorghum | 1739 | 200 | maize\|gb157\|AW360667 | 96.1 | blastp |
| 676 | sugarcane\|gb157.3\|CA069365 | sugarcane | 1740 | 200 | maize\|gb157\|AW360667 | 97.2 | blastp |
| 677 | apple\|gb157.3\|CN873722 | apple | 1741 | 202 | arabidopsis\|gb157.2\|AT3G26100 | 80.26 | tblastn |
| 678 | chestnut\|gb170\|SRR006295S0001486 | chestnut | 1742 | 202 | arabidopsis\|gb157.2\|AT3G26100 | 82.2 | blastp |
| 679 | cotton\|gb164\|AI728964 | cotton | 1743 | 202 | arabidopsis\|gb157.2\|AT3G26100 | 80.3 | blastp |
| 680 | grape\|gb160\|CB004507 | grape | 1744 | 202 | arabidopsis\|gb157.2\|AT3G26100 | 80.3 | blastp |
| 681 | papaya\|gb165\|EX243430 | papaya | 1745 | 202 | arabidopsis\|gb157.2\|AT3G26100 | 82.8 | blastp |
| 682 | poplar\|gb170\|AI165788 | poplar | 1746 | 202 | arabidopsis\|gb157.2\|AT3G26100 | 80.26 | tblastn |
| 683 | poplar\|gb170\|BI071804 | poplar | 1747 | 202 | arabidopsis\|gb157.2\|AT3G26100 | 80.75 | blastp |
| 684 | bean\|gb167\|CV538336 | bean | 1748 | 203 | soybean\|gb162\|SOYHPR | 80.83 | tblastn |
| 685 | bean\|gb167\|PVU72768 | bean | 1749 | 203 | soybean\|gb162\|SOYHPR | 85.8 | blastp |
| 686 | clover\|gb162\|BB932705 | clover | 1750 | 203 | soybean\|gb162\|SOYHPR | 83.3 | blastp |
| 687 | cowpea\|gb166\|FC457443 | cowpea | 1751 | 203 | soybean\|gb162\|SOYHPR | 87.92 | tblastn |
| 688 | medicago\|gb157.2\|AL366760 | medicago | 1752 | 203 | soybean\|gb162\|SOYHPR | 84.7 | blastp |
| 689 | medicago\|gb157.2\|AW328889 | medicago | 1753 | 203 | soybean\|gb162\|SOYHPR | 80.52 | tblastn |
| 690 | medicago\|gb157.2\|AW329415 | medicago | 1754 | 203 | soybean\|gb162\|SOYHPR | 83.67 | tblastn |
| 691 | medicago\|gb157.2\|AW329734 | medicago | 1755 | 203 | soybean\|gb162\|SOYHPR | 85.11 | tblastn |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 692 | soybean\|gb168\|S44202 | soybean | 1756 | 203 | soybean\|gb162\|SOYHPR | 95.7 | blastp |
| 693 | b_rapa\|gb162\|CV544929 | b_rapa | 1757 | 266 | arabidopsis\|gb157.2\|AT1G44920 | 80.38 | tblastn |
| 693 | b_rapa\|gb162\|CV544929 | b_rapa | 1757 | 204 | arabidopsis\|gb165\|AT1G44920 | 80.15 | tblastn |
| 694 | radish\|gb164\|EV525414 | radish | 1758 | 266 | arabidopsis\|gb157.2\|AT1G44920 | 81.3 | blastp |
| 694 | radish\|gb164\|EV525414 | radish | 1758 | 204 | arabidopsis\|gb165\|AT1G44920 | 80.7 | blastp |
| 695 | thellungiella\|gb167\|DN777579 | thellungiella | 1759 | 266 | arabidopsis\|gb157.2\|AT1G44920 | 81.7 | blastp |
| 695 | thellungiella\|gb167\|DN777579 | thellungiella | 1759 | 204 | arabidopsis\|gb165\|AT1G44920 | 81.1 | blastp |
| 696 | arabidopsis\|gb165\|AT3G17410 | arabidopsis | 1760 | 205 | arabidopsis\|gb157.2\|AT1G48210 | 87.1 | blastp |
| 697 | b_oleracea\|gb161\|AM385784 | b_oleracea | 1761 | 205 | arabidopsis\|gb157.2\|AT1G48210 | 87.4 | blastp |
| 698 | b_rapa\|gb162\|DN962030 | b_rapa | 1762 | 205 | arabidopsis\|gb157.2\|AT1G48210 | 83.52 | tblastn |
| 699 | b_rapa\|gb162\|EX020680 | b_rapa | 1763 | 205 | arabidopsis\|gb157.2\|AT1G48210 | 85.4 | blastp |
| 700 | b_rapa\|gb162\|EX025892 | b_rapa | 1764 | 205 | arabidopsis\|gb157.2\|AT1G48210 | 85.99 | tblastn |
| 701 | canola\|gb161\|CX278279 | canola | 1765 | 205 | arabidopsis\|gb157.2\|AT1G48210 | 86.3 | blastp |
| 702 | canola\|gb161\|EG021170 | canola | 1766 | 205 | arabidopsis\|gb157.2\|AT1G48210 | 83.79 | tblastn |
| 703 | radish\|gb164\|EV525080 | radish | 1767 | 205 | arabidopsis\|gb157.2\|AT1G48210 | 87.6 | blastp |
| 704 | radish\|gb164\|EV543636 | radish | 1768 | 205 | arabidopsis\|gb157.2\|AT1G48210 | 85.4 | blastp |
| 705 | radish\|gb164\|EY895533 | radish | 1769 | 205 | arabidopsis\|gb157.2\|AT1G48210 | 84.7 | blastp |
| 706 | thellungiella\|gb167\|DN774052 | thellungiella | 1770 | 205 | arabidopsis\|gb157.2\|AT1G48210 | 87.4 | blastp |
| 707 | wheat\|gb164\|AL822688 | wheat | 1771 | 206 | wheat\|gb164\|BE445396 | 92.9 | blastp |
| 708 | wheat\|gb164\|CD869154 | wheat | 1772 | 206 | wheat\|gb164\|BE445396 | 92.9 | blastp |
| 709 | banana\|gb167\|ES432415 | banana | 1773 | 208 | rice\|gb157.2\|AU077950 | 85.3 | blastp |
| 710 | barley\|gb157.3\|BI948762 | barley | 1774 | 208 | rice\|gb157.2\|AU077950 | 81.5 | blastp |
| 711 | barley\|gb157.3\|BJ453298 | barley | 1775 | 208 | rice\|gb157.2\|AU077950 | 94.2 | blastp |
| 712 | citrus\|gb166\|CF419725 | citrus | 1776 | 208 | rice\|gb157.2\|AU077950 | 80.8 | blastp |
| 713 | cotton\|gb164\|BF277609 | cotton | 1777 | 208 | rice\|gb157.2\|AU077950 | 81.5 | blastp |
| 714 | fescue\|gb161\|CK801460 | fescue | 1778 | 208 | rice\|gb157.2\|AU077950 | 91.1 | blastp |
| 715 | maize\|gb170\|AI619081 | maize | 1779 | 208 | rice\|gb157.2\|AU077950 | 97.7 | blastp |
| 716 | maize\|gb170\|AW216176 | maize | 1780 | 208 | rice\|gb157.2\|AU077950 | 87.8 | blastp |
| 717 | maize\|gb170\|BG841543 | maize | 1781 | 208 | rice\|gb157.2\|AU077950 | 97.7 | blastp |
| 718 | maize\|gb170\|H89383 | maize | 1782 | 208 | rice\|gb157.2\|AU077950 | 86.9 | blastp |
| 719 | onion\|gb162\|CF447150 | onion | 1783 | 208 | rice\|gb157.2\|AU077950 | 80 | blastp |
| 720 | pseudoroegneria\|gb167\|FF343595 | pseudoroegneria | 1784 | 208 | rice\|gb157.2\|AU077950 | 94.2 | blastp |
| 721 | rice\|gb170\|OS05G36110 | rice | 1785 | 208 | rice\|gb157.2\|AU077950 | 86.2 | blastp |
| 722 | sorghum\|gb161.crp\|AI783327 | sorghum | 1786 | 208 | rice\|gb157.2\|AU077950 | 96.5 | blastp |
| 723 | sorghum\|gb161.crp\|H89383 | sorghum | 1787 | 208 | rice\|gb157.2\|AU077950 | 87.9 | blastp |
| 724 | sugarcane\|gb157.3\|BQ479039 | sugarcane | 1788 | 208 | rice\|gb157.2\|AU077950 | 98.1 | blastp |
| 725 | switchgrass\|gb167\|DN144476 | switchgrass | 1789 | 208 | rice\|gb157.2\|AU077950 | 96.9 | blastp |
| 726 | switchgrass\|gb167\|FE642599 | switchgrass | 1790 | 208 | rice\|gb157.2\|AU077950 | 87.5 | blastp |
| 727 | wheat\|gb164\|BG909438 | wheat | 1791 | 208 | rice\|gb157.2\|AU077950 | 93.4 | blastp |
| 728 | wheat\|gb164\|CA497850 | wheat | 1792 | 208 | rice\|gb157.2\|AU077950 | 81.9 | blastp |
| 729 | wheat\|gb164\|CA658427 | wheat | 1793 | 208 | rice\|gb157.2\|AU077950 | 94.2 | blastp |
| 730 | cenchrus\|gb166\|EB654920 | cenchrus | 1794 | 209 | sorghum\|gb161.xeno\|AI901439 | 82.2 | blastp |
| 731 | maize\|gb170\|AI855209 | maize | 1795 | 209 | sorghum\|gb161.xeno\|AI901439 | 89.4 | blastp |
| 732 | sugarcane\|gb157.3\|BU102825 | sugarcane | 1796 | 209 | sorghum\|gb161.xeno\|AI901439 | 96.2 | blastp |
| 733 | switchgrass\|gb167\|DN146789 | switchgrass | 1797 | 209 | sorghum\|gb161.xeno\|AI901439 | 81.2 | blastp |
| 734 | maize\|gb170\|AI944302 | maize | 1798 | 210 | sorghum\|gb161.xeno\|AW052978 | 93.5 | blastp |
| 735 | sugarcane\|gb157.3\|BQ534346 | sugarcane | 1799 | 210 | sorghum\|gb161.xeno\|AW052978 | 93.5 | blastp |
| 736 | switchgrass\|gb167\|FL722616 | switchgrass | 1800 | 210 | sorghum\|gb161.xeno\|AW052978 | 86.1 | blastp |
| 737 | barley\|gb157.3\|BE413281 | barley | 1801 | 211 | sorghum\|gb161.xeno\|AW055409 | 88.3 | blastp |
| 738 | leymus\|gb166\|EG382167 | leymus | 1802 | 211 | sorghum\|gb161.xeno\|AW055409 | 88.5 | blastp |
| 739 | maize\|gb170\|AI855325 | maize | 1803 | 211 | sorghum\|gb161.xeno\|AW055409 | 93.5 | blastp |
| 740 | rice\|gb170\|OS01G09010 | rice | 1804 | 211 | sorghum\|gb161.xeno\|AW055409 | 88.8 | blastp |
| 741 | switchgrass\|gb167\|DN145994 | switchgrass | 1805 | 211 | sorghum\|gb161.xeno\|AW055409 | 93 | blastp |
| 742 | wheat\|gb164\|BE414789 | wheat | 1806 | 211 | sorghum\|gb161.xeno\|AW055409 | 88.5 | blastp |
| 743 | barley\|gb157.3\|BE437905 | barley | 1807 | 212 | sorghum\|gb161.xeno\|AI372194 | 82.43 | tblastn |
| 744 | brachypodium\|gb169\|BE437905 | brachypodium | 1808 | 212 | sorghum\|gb161.xeno\|AI372194 | 80.2 | blastp |
| 745 | leymus\|gb166\|EG394243 | leymus | 1809 | 212 | sorghum\|gb161.xeno\|AI372194 | 80.4 | blastp |
| 746 | maize\|gb170\|BG320821 | maize | 1810 | 212 | sorghum\|gb161.xeno\|AI372194 | 94.5 | blastp |
| 747 | maize\|gb170\|LLT23330 | maize | 1811 | 212 | sorghum\|gb161.xeno\|AI372194 | 96.2 | blastp |
| 748 | rice\|gb170\|OS08G45240 | rice | 1812 | 212 | sorghum\|gb161.xeno\|AI372194 | 82.2 | blastp |
| 749 | sugarcane\|gb157.3\|CA073529 | sugarcane | 1813 | 212 | sorghum\|gb161.xeno\|AI372194 | 97.9 | blastp |
| 750 | switchgrass\|gb167\|DN145055 | switchgrass | 1814 | 212 | sorghum\|gb161.xeno\|AI372194 | 94.9 | blastp |
| 751 | wheat\|gb164\|BE404004 | wheat | 1815 | 212 | sorghum\|gb161.xeno\|AI372194 | 81.59 | tblastn |
| 752 | maize\|gb170\|AI939746 | maize | 1816 | 213 | rice\|gb157.2\|BI805136 | 80 | blastp |
| 753 | rice\|gb170\|OS08G44840 | rice | 1817 | 213 | rice\|gb157.2\|BI805136 | 99.8 | blastp |
| 754 | wheat\|gb164\|BE400051 | wheat | 1818 | 213 | rice\|gb157.2\|BI805136 | 80.54 | tblastn |
| 755 | barley\|gb157.3\|AL506838 | barley | 1819 | 214 | maize\|gb164\|AW054475 | 86.9 | blastp |
| 756 | brachypodium\|gb169\|BE406703 | brachypodium | 1820 | 214 | maize\|gb164\|AW054475 | 90.9 | blastp |
| 757 | rice\|gb170\|OS01G13730 | rice | 1821 | 214 | maize\|gb164\|AW054475 | 92.7 | blastp |
| 758 | sorghum\|gb161.crp\|AI739896 | sorghum | 1822 | 214 | maize\|gb164\|AW054475 | 97.8 | blastp |
| 759 | sugarcane\|gb157.3\|BQ479038 | sugarcane | 1823 | 214 | maize\|gb164\|AW054475 | 97.8 | blastp |
| 760 | switchgrass\|gb167\|FE622691 | switchgrass | 1824 | 214 | maize\|gb164\|AW054475 | 95.1 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 761 | wheat\|gb164\|BE406703 | wheat | 1825 | 214 | maize\|gb164\|AW054475 | 86.7 | blastp |
| 762 | apple\|gb157.3\|AU301405 | apple | 1826 | 215 | soybean\|gb166\|AW350050 | 93.1 | blastp |
| 763 | arabidopsis\|gb165\|AT2G27600 | arabidopsis | 1827 | 215 | soybean\|gb166\|AW350050 | 91 | blastp |
| 764 | b_rapa\|gb162\|CV546524 | b_rapa | 1828 | 215 | soybean\|gb166\|AW350050 | 90.6 | blastp |
| 765 | b_rapa\|gb162\|EX019335 | b_rapa | 1829 | 215 | soybean\|gb166\|AW350050 | 89.9 | blastp |
| 766 | barley\|gb157.3\|BE438944 | barley | 1830 | 215 | soybean\|gb166\|AW350050 | 87.5 | blastp |
| 767 | basilicum\|gb157.3\|DY330212 | basilicum | 1831 | 215 | soybean\|gb166\|AW350050 | 88 | blastp |
| 768 | bean\|gb167\|CA896847 | bean | 1832 | 215 | soybean\|gb166\|AW350050 | 98.4 | blastp |
| 769 | brachypodium\|gb169\|BE405668 | brachypodium | 1833 | 215 | soybean\|gb166\|AW350050 | 87.9 | blastp |
| 770 | cacao\|gb167\|CA794307 | cacao | 1834 | 215 | soybean\|gb166\|AW350050 | 93.1 | blastp |
| 771 | canola\|gb161\|CD814779 | canola | 1835 | 215 | soybean\|gb166\|AW350050 | 88.7 | blastp |
| 772 | canola\|gb161\|DY024749 | canola | 1836 | 215 | soybean\|gb166\|AW350050 | 90.8 | blastp |
| 773 | castorbean\|gb160\|EG661556 | castorbean | 1837 | 215 | soybean\|gb166\|AW350050 | 93.1 | blastp |
| 774 | chestnut\|gb170\|SRR006295S0002595 | chestnut | 1838 | 215 | soybean\|gb166\|AW350050 | 92.9 | blastp |
| 775 | citrus\|gb166\|CF830344 | citrus | 1839 | 215 | soybean\|gb166\|AW350050 | 93.8 | blastp |
| 776 | cotton\|gb164\|AI726326 | cotton | 1840 | 215 | soybean\|gb166\|AW350050 | 94 | blastp |
| 777 | cotton\|gb164\|AI729650 | cotton | 1841 | 215 | soybean\|gb166\|AW350050 | 91.5 | blastp |
| 778 | cotton\|gb164\|AI731487 | cotton | 1842 | 215 | soybean\|gb166\|AW350050 | 89.5 | blastp |
| 779 | cotton\|gb164\|AI731657 | cotton | 1843 | 215 | soybean\|gb166\|AW350050 | 92.2 | blastp |
| 780 | cowpea\|gb166\|FF395986 | cowpea | 1844 | 215 | soybean\|gb166\|AW350050 | 94.2 | blastp |
| 781 | iceplant\|gb164\|AF165422 | iceplant | 1845 | 215 | soybean\|gb166\|AW350050 | 91.3 | blastp |
| 782 | lettuce\|gb157.2\|DW049083 | lettuce | 1846 | 215 | soybean\|gb166\|AW350050 | 90.8 | blastp |
| 783 | lettuce\|gb157.2\|DW059917 | lettuce | 1847 | 215 | soybean\|gb166\|AW350050 | 83.9 | blastp |
| 784 | maize\|gb170\|AI615072 | maize | 1848 | 215 | soybean\|gb166\|AW350050 | 89.9 | blastp |
| 785 | maize\|gb170\|AI714627 | maize | 1849 | 215 | soybean\|gb166\|AW350050 | 89.7 | blastp |
| 786 | medicago\|gb157.2\|AW329426 | medicago | 1850 | 215 | soybean\|gb166\|AW350050 | 91.94 | tblastn |
| 787 | pine\|gb157.2\|AL751019 | pine | 1851 | 215 | soybean\|gb166\|AW350050 | 88.2 | blastp |
| 788 | pine\|gb157.2\|BE643751 | pine | 1852 | 215 | soybean\|gb166\|AW350050 | 86.8 | blastp |
| 789 | poplar\|gb170\|AI166646 | poplar | 1853 | 215 | soybean\|gb166\|AW350050 | 91.7 | blastp |
| 790 | poplar\|gb170\|BI069748 | poplar | 1854 | 215 | soybean\|gb166\|AW350050 | 90.8 | blastp |
| 791 | poplar\|gb170\|BI070062 | poplar | 1855 | 215 | soybean\|gb166\|AW350050 | 81.7 | blastp |
| 792 | poplar\|gb170\|CN549423 | poplar | 1856 | 215 | soybean\|gb166\|AW350050 | 81.6 | blastp |
| 793 | potato\|gb157.2\|BG096555 | potato | 1857 | 215 | soybean\|gb166\|AW350050 | 87.4 | blastp |
| 794 | potato\|gb157.2\|BI177056 | potato | 1858 | 215 | soybean\|gb166\|AW350050 | 90.8 | blastp |
| 795 | rice\|gb170\|OS01G04814 | rice | 1859 | 215 | soybean\|gb166\|AW350050 | 90.8 | blastp |
| 796 | sorghum\|gb161.crp\|BE366383 | sorghum | 1860 | 215 | soybean\|gb166\|AW350050 | 90.6 | blastp |
| 797 | soybean\|gb168\|AW329426 | soybean | 1861 | 215 | soybean\|gb166\|AW350050 | 94 | blastp |
| 798 | soybean\|gb168\|AW719488 | soybean | 1862 | 215 | soybean\|gb166\|AW350050 | 94 | blastp |
| 799 | soybean\|gb168\|AW719867 | soybean | 1863 | 215 | soybean\|gb166\|AW350050 | 97.5 | blastp |
| 800 | spikemoss\|gb165\|FE429017 | spikemoss | 1864 | 215 | soybean\|gb166\|AW350050 | 85.3 | blastp |
| 801 | spruce\|gb162\|CO217587 | spruce | 1865 | 215 | soybean\|gb166\|AW350050 | 88.2 | blastp |
| 802 | strawberry\|gb164\|CO816822 | strawberry | 1866 | 215 | soybean\|gb166\|AW350050 | 92.4 | blastp |
| 803 | sugarcane\|gb157.3\|BQ533539 | sugarcane | 1867 | 215 | soybean\|gb166\|AW350050 | 90.6 | blastp |
| 804 | sunflower\|gb162\|CD849902 | sunflower | 1868 | 215 | soybean\|gb166\|AW350050 | 90.57 | tblastn |
| 805 | sunflower\|gb162\|DY927633 | sunflower | 1869 | 215 | soybean\|gb166\|AW350050 | 82.3 | blastp |
| 806 | switchgrass\|gb167\|DN142133 | switchgrass | 1870 | 215 | soybean\|gb166\|AW350050 | 90.3 | blastp |
| 807 | tomato\|gb164\|AI637361 | tomato | 1871 | 215 | soybean\|gb166\|AW350050 | 90.6 | blastp |
| 808 | tomato\|gb164\|BE459090 | tomato | 1872 | 215 | soybean\|gb166\|AW350050 | 87.2 | blastp |
| 809 | triphysaria\|gb164\|DR175699 | triphysaria | 1873 | 215 | soybean\|gb166\|AW350050 | 90.3 | blastp |
| 810 | wheat\|gb164\|BE405903 | wheat | 1874 | 215 | soybean\|gb166\|AW350050 | 87.9 | blastp |
| 811 | maize\|gb170\|BG316566 | maize | 1875 | 267 | sorghum\|gb161.xeno\|BE599042 | 98.87 | tblastn |
| 811 | maize\|gb170\|BG316566 | maize | 1875 | 216 | sorghum\|gb161.crp\|BE599042 | 96.8 | blastp |
| 812 | rice\|gb170\|OS11G10420 | rice | 1876 | 267 | sorghum\|gb161.xeno\|BE599042 | 93.57 | tblastn |
| 812 | rice\|gb170\|OS11G10420 | rice | 1876 | 216 | sorghum\|gb161.crp\|BE599042 | 88 | blastp |
| 813 | aquilegia\|gb157.3\|DR921243 | aquilegia | 1877 | 217 | maize\|gb164\|BQ279657 | 80.7 | blastp |
| 814 | avocado\|gb164\|CK766314 | avocado | 1878 | 217 | maize\|gb164\|BQ279657 | 80.5 | blastp |
| 815 | brachypodium\|gb169\|BE492967 | brachypodium | 1879 | 217 | maize\|gb164\|BQ279657 | 85.7 | blastp |
| 815 | brachypodium\|gb169\|BE492967 | brachypodium | 1879 | 227 | sorghum\|gb161.xeno\|BQ279657 | 84.7 | blastp |
| 816 | castorbean\|gb160\|EE255906 | castorbean | 1880 | 217 | maize\|gb164\|BQ279657 | 81.3 | blastp |
| 816 | castorbean\|gb160\|EE255906 | castorbean | 1880 | 227 | sorghum\|gb161.xeno\|BQ279657 | 81 | blastp |
| 817 | centaurea\|gb166\|EH728846 | centaurea | 1881 | 217 | maize\|gb164\|BQ279657 | 80.08 | tblastn |
| 818 | chestnut\|gb170\|SRR006295S0011600 | chestnut | 1882 | 217 | maize\|gb164\|BQ279657 | 81.3 | blastp |
| 818 | chestnut\|gb170\|SRR006295S0011600 | chestnut | 1882 | 227 | sorghum\|gb161.xeno\|BQ279657 | 80.6 | blastp |
| 819 | citrus\|gb166\|CB305147 | citrus | 1883 | 217 | maize\|gb164\|BQ279657 | 81.4 | blastp |
| 819 | citrus\|gb166\|CB305147 | citrus | 1883 | 227 | sorghum\|gb161.xeno\|BQ279657 | 81.3 | blastp |
| 820 | cotton\|gb164\|CO121350 | cotton | 1884 | 217 | maize\|gb164\|BQ279657 | 82.4 | tblastn |
| 820 | cotton\|gb164\|CO121350 | cotton | 1884 | 227 | sorghum\|gb161.xeno\|BQ279657 | 81.41 | tblastn |
| 821 | kiwi\|gb166\|FG403767 | kiwi | 1885 | 217 | maize\|gb164\|BQ279657 | 80.5 | blastp |
| 822 | leymus\|gb166\|EG376319 | leymus | 1886 | 217 | maize\|gb164\|BQ279657 | 90.3 | blastp |
| 822 | leymus\|gb166\|EG376319 | leymus | 1886 | 227 | sorghum\|gb161.xeno\|BQ279657 | 89.6 | blastp |
| 823 | papaya\|gb165\|EX229221 | papaya | 1887 | 217 | maize\|gb164\|BQ279657 | 81.3 | blastp |
| 823 | papaya\|gb165\|EX229221 | papaya | 1887 | 227 | sorghum\|gb161.xeno\|BQ279657 | 81 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 824 | potato\|gb157.2\|BE341318 | potato | 1888 | 217 | maize\|gb164\|BQ279657 | 81.3 | blastp |
| 824 | potato\|gb157.2\|BE341318 | potato | 1888 | 227 | sorghum\|gb161.xeno\|BQ279657 | 81.3 | blastp |
| 825 | pseudoroegneria\|gb167\|FF342296 | pseudoroegneria | 1889 | 217 | maize\|gb164\|BQ279657 | 89.9 | blastp |
| 825 | pseudoroegneria\|gb167\|FF342296 | pseudoroegneria | 1889 | 227 | sorghum\|gb161.xeno\|BQ279657 | 89.2 | blastp |
| 826 | rice\|gb170\|OS03G21914 | rice | 1890 | 217 | maize\|gb164\|BQ279657 | 90.6 | blastp |
| 826 | rice\|gb170\|OS03G21914 | rice | 1890 | 227 | sorghum\|gb161.xeno\|BQ279657 | 89.9 | blastp |
| 827 | rice\|gb170\|OS03G50620 | rice | 1891 | 217 | maize\|gb164\|BQ279657 | 88.2 | blastp |
| 827 | rice\|gb170\|OS03G50620 | rice | 1891 | 227 | sorghum\|gb161.xeno\|BQ279657 | 87.2 | blastp |
| 828 | sugarcane\|gb157.3\|BQ536934 | sugarcane | 1892 | 227 | sorghum\|gb161.xeno\|BQ279657 | 99.3 | blastp |
| 828 | sugarcane\|gb157.3\|BQ536934 | sugarcane | 1892 | 217 | maize\|gb164\|BQ279657 | 98.1 | blastp |
| 829 | sugarcane\|gb157.3\|CA096803 | sugarcane | 1893 | 227 | sorghum\|gb161.xeno\|BQ279657 | 98.9 | blastp |
| 829 | sugarcane\|gb157.3\|CA096803 | sugarcane | 1893 | 217 | maize\|gb164\|BQ279657 | 97.8 | blastp |
| 830 | sunflower\|gb162\|BU018368 | sunflower | 1894 | 217 | maize\|gb164\|BQ279657 | 80.2 | blastp |
| 831 | switchgrass\|gb167\|FL773351 | switchgrass | 1895 | 227 | sorghum\|gb161.xeno\|BQ279657 | 94.8 | blastp |
| 831 | switchgrass\|gb167\|FL773351 | switchgrass | 1895 | 217 | maize\|gb164\|BQ279657 | 94 | blastp |
| 832 | tobacco\|gb162\|DV158876 | tobacco | 1896 | 217 | maize\|gb164\|BQ279657 | 80.9 | blastp |
| 832 | tobacco\|gb162\|DV158876 | tobacco | 1896 | 227 | sorghum\|gb161.xeno\|BQ279657 | 80.2 | blastp |
| 833 | tomato\|gb164\|BG124565 | tomato | 1897 | 217 | maize\|gb164\|BQ279657 | 80.9 | blastp |
| 833 | tomato\|gb164\|BG124565 | tomato | 1897 | 227 | sorghum\|gb161.xeno\|BQ279657 | 80.6 | blastp |
| 834 | wheat\|gb164\|BE492967 | wheat | 1898 | 217 | maize\|gb164\|BQ279657 | 89.9 | blastp |
| 834 | wheat\|gb164\|BE492967 | wheat | 1898 | 227 | sorghum\|gb161.xeno\|BQ279657 | 89.2 | blastp |
| 835 | wheat\|gb164\|BQ168983 | wheat | 1899 | 217 | maize\|gb164\|BQ279657 | 90.3 | blastp |
| 835 | wheat\|gb164\|BQ168983 | wheat | 1899 | 227 | sorghum\|gb161.xeno\|BQ279657 | 89.6 | blastp |
| 836 | fescue\|gb161\|CK801026 | fescue | 1900 | 218 | barley\|gb157.2\|AJ234408 | 87 | blastp |
| 837 | pseudoroegneria\|gb167\|FF340368 | pseudoroegneria | 1901 | 218 | barley\|gb157.2\|AJ234408 | 92.1 | blastp |
| 838 | rice\|gb170\|OS07G05360 | rice | 1902 | 218 | barley\|gb157.2\|AJ234408 | 81.2 | blastp |
| 839 | wheat\|gb164\|BE213379 | wheat | 1903 | 218 | barley\|gb157.2\|AJ234408 | 92.1 | blastp |
| 840 | wheat\|gb164\|BE401132 | wheat | 1904 | 218 | barley\|gb157.2\|AJ234408 | 90 | blastp |
| 841 | wheat\|gb164\|BE401288 | wheat | 1905 | 218 | barley\|gb157.2\|AJ234408 | 90.7 | blastp |
| 842 | wheat\|gb164\|CA654680 | wheat | 1906 | 218 | barley\|gb157.2\|AJ234408 | 84.89 | tblastn |
| 843 | wheat\|gb164\|CA695915 | wheat | 1907 | 218 | barley\|gb157.2\|AJ234408 | 88.49 | tblastn |
| 844 | maize\|gb170\|AW433364 | maize | 1908 | 219 | sorghum\|gb161.xeno\|AW923729 | 87.9 | blastp |
| 845 | sorghum\|gb161.crp\|AW922411 | sorghum | 1909 | 219 | sorghum\|gb161.xeno\|AW923729 | 81.1 | blastp |
| 846 | sugarcane\|gb157.3\|CA068925 | sugarcane | 1910 | 219 | sorghum\|gb161.xeno\|AW923729 | 91.1 | blastp |
| 847 | switchgrass\|gb167\|DN144528 | switchgrass | 1911 | 219 | sorghum\|gb161.xeno\|AW923729 | 86.8 | blastp |
| 848 | switchgrass\|gb167\|DN144587 | switchgrass | 1912 | 219 | sorghum\|gb161.xeno\|AW923729 | 85.8 | blastp |
| 849 | switchgrass\|gb167\|FL758275 | switchgrass | 1913 | 219 | sorghum\|gb161.xeno\|AW923729 | 80.1 | blastp |
| 850 | castorbean\|gb160\|MDL29813M001539 | castorbean | 1914 | 221 | arabidopsis\|gb157.2\|AT1G13980 | 83.3 | blastp |
| 851 | poplar\|gb170\|BU886496 | poplar | 1915 | 221 | arabidopsis\|gb157.2\|AT1G13980 | 82 | blastp |
| 852 | soybean\|gb168\|BM308552 | soybean | 1916 | 221 | arabidopsis\|gb157.2\|AT1G13980 | 81.2 | blastp |
| 853 | maize\|gb170\|BM072861 | maize | 1917 | 226 | sorghum\|gb161.xeno\|BI139559 | 95.5 | blastp |
| 854 | rice\|gb170\|OS01G07200 | rice | 1918 | 226 | sorghum\|gb161.xeno\|BI139559 | 83.5 | blastp |
| 855 | sugarcane\|gb157.3\|CA112539 | sugarcane | 1919 | 226 | sorghum\|gb161.xeno\|BI139559 | 88.25 | tblastn |
| 856 | barley\|gb157.3\|BE412997 | barley | 1920 | 228 | sorghum\|gb161.xeno\|AF019147 | 84.1 | blastp |
| 857 | brachypodium\|gb169\|BE403874 | brachypodium | 1921 | 228 | sorghum\|gb161.xeno\|AF019147 | 83 | blastp |
| 858 | fescue\|gb161\|DT680716 | fescue | 1922 | 228 | sorghum\|gb161.xeno\|AF019147 | 81 | blastp |
| 859 | leymus\|gb166\|CN466335 | leymus | 1923 | 228 | sorghum\|gb161.xeno\|AF019147 | 83.4 | blastp |
| 860 | maize\|gb170\|AF019147 | maize | 1924 | 228 | sorghum\|gb161.xeno\|AF019147 | 91.7 | blastp |
| 861 | maize\|gb170\|AI948311 | maize | 1925 | 228 | sorghum\|gb161.xeno\|AF019147 | 90 | blastp |
| 862 | rice\|gb170\|OS04G55650 | rice | 1926 | 228 | sorghum\|gb161.xeno\|AF019147 | 85.2 | blastp |
| 863 | sugarcane\|gb157.3\|BQ536348 | sugarcane | 1927 | 228 | sorghum\|gb161.xeno\|AF019147 | 97.9 | blastp |
| 864 | switchgrass\|gb167\|DN140659 | switchgrass | 1928 | 228 | sorghum\|gb161.xeno\|AF019147 | 91.8 | blastp |
| 865 | switchgrass\|gb167\|DN141292 | switchgrass | 1929 | 228 | sorghum\|gb161.xeno\|AF019147 | 90.8 | blastp |
| 866 | wheat\|gb164\|BE403874 | wheat | 1930 | 228 | sorghum\|gb161.xeno\|AF019147 | 83.9 | blastp |
| 867 | wheat\|gb164\|BE405077 | wheat | 1931 | 228 | sorghum\|gb161.xeno\|AF019147 | 84.5 | blastp |
| 868 | b_rapa\|gb162\|EX027120 | b_rapa | 1932 | 229 | canola\|gb161\|EE559843 | 94.1 | blastp |
| 869 | brachypodium\|gb169\|BF202681 | brachypodium | 1933 | 230 | barley\|gb157.3\|BE420701 | 90.9 | blastp |
| 870 | maize\|gb170\|LLAI629913 | maize | 1934 | 230 | barley\|gb157.3\|BE420701 | 87 | blastp |
| 871 | pseudoroegneria\|gb167\|FF340034 | pseudoroegneria | 1935 | 230 | barley\|gb157.3\|BE420701 | 96.8 | blastp |
| 872 | rice\|gb170\|OS07G44660 | rice | 1936 | 230 | barley\|gb157.3\|BE420701 | 88.6 | blastp |
| 873 | sorghum\|gb161.crp\|AW282627 | sorghum | 1937 | 230 | barley\|gb157.3\|BE420701 | 88.3 | blastp |
| 874 | switchgrass\|gb167\|FE609054 | switchgrass | 1938 | 230 | barley\|gb157.3\|BE420701 | 88.1 | blastp |
| 875 | brachypodium\|gb169\|BE421829 | brachypodium | 1939 | 231 | barley\|gb157.3\|BE421829 | 90.2 | blastp |
| 875 | brachypodium\|gb169\|BE421829 | brachypodium | 1939 | 235 | rice\|gb157.2\|AU057884 | 82.6 | blastp |
| 875 | brachypodium\|gb169\|BE421829 | brachypodium | 1939 | 261 | sorghum\|gb161.xeno\|AI622209 | 81.1 | blastp |
| 876 | fescue\|gb161\|DT679850 | fescue | 1940 | 231 | barley\|gb157.3\|BE421829 | 95.3 | blastp |
| 876 | fescue\|gb161\|DT679850 | fescue | 1940 | 235 | rice\|gb157.2\|AU057884 | 84.1 | blastp |
| 876 | fescue\|gb161\|DT679850 | fescue | 1940 | 261 | sorghum\|gb161.xeno\|AI622209 | 81.6 | blastp |
| 877 | leymus\|gb166\|EG396605 | leymus | 1941 | 231 | barley\|gb157.3\|BE421829 | 96.3 | blastp |
| 877 | leymus\|gb166\|EG396605 | leymus | 1941 | 235 | rice\|gb157.2\|AU057884 | 83.6 | blastp |
| 877 | leymus\|gb166\|EG396605 | leymus | 1941 | 261 | sorghum\|gb161.xeno\|AI622209 | 83.1 | blastp |
| 878 | maize\|gb170\|AI622209 | maize | 1942 | 261 | sorghum\|gb161.xeno\|AI622209 | 94 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 878 | maize\|gb170\|AI622209 | maize | 1942 | 235 | rice\|gb157.2\|AU057884 | 82.9 | blastp |
| 878 | maize\|gb170\|AI622209 | maize | 1942 | 231 | barley\|gb157.3\|BE421829 | 81.8 | blastp |
| 879 | sugarcane\|gb157.3\|CA123704 | sugarcane | 1943 | 261 | sorghum\|gb161.xeno\|AI622209 | 93.5 | blastp |
| 879 | sugarcane\|gb157.3\|CA123704 | sugarcane | 1943 | 231 | barley\|gb157.3\|BE421829 | 86.5 | blastp |
| 879 | sugarcane\|gb157.3\|CA123704 | sugarcane | 1943 | 235 | rice\|gb157.2\|AU057884 | 84.6 | blastp |
| 880 | switchgrass\|gb167\|FE619680 | switchgrass | 1944 | 261 | sorghum\|gb161.xeno\|AI622209 | 91 | blastp |
| 880 | switchgrass\|gb167\|FE619680 | switchgrass | 1944 | 235 | rice\|gb157.2\|AU057884 | 85.4 | blastp |
| 880 | switchgrass\|gb167\|FE619680 | switchgrass | 1944 | 231 | barley\|gb157.3\|BE421829 | 82.7 | blastp |
| 881 | switchgrass\|gb167\|FE630609 | switchgrass | 1945 | 261 | sorghum\|gb161.xeno\|AI622209 | 89.6 | blastp |
| 881 | switchgrass\|gb167\|FE630609 | switchgrass | 1945 | 235 | rice\|gb157.2\|AU057884 | 84 | blastp |
| 881 | switchgrass\|gb167\|FE630609 | switchgrass | 1945 | 231 | barley\|gb157.3\|BE421829 | 81.9 | blastp |
| 882 | wheat\|gb164\|BE497607 | wheat | 1946 | 231 | barley\|gb157.3\|BE421829 | 96.8 | blastp |
| 882 | wheat\|gb164\|BE497607 | wheat | 1946 | 235 | rice\|gb157.2\|AU057884 | 84.6 | blastp |
| 882 | wheat\|gb164\|BE497607 | wheat | 1946 | 261 | sorghum\|gb161.xeno\|AI622209 | 82.6 | blastp |
| 883 | wheat\|gb164\|BF428660 | wheat | 1947 | 231 | barley\|gb157.3\|BE421829 | 96.8 | blastp |
| 883 | wheat\|gb164\|BF428660 | wheat | 1947 | 235 | rice\|gb157.2\|AU057884 | 85.6 | blastp |
| 883 | wheat\|gb164\|BF428660 | wheat | 1947 | 261 | sorghum\|gb161.xeno\|AI622209 | 82.6 | blastp |
| 884 | barley\|gb157.3\|BE411922 | barley | 1948 | 232 | sorghum\|gb161.xeno\|AA011880 | 81 | blastp |
| 885 | brachypodium\|gb169\|BE398696 | brachypodium | 1949 | 232 | sorghum\|gb161.xeno\|AA011880 | 82.3 | blastp |
| 886 | cenchrus\|gb166\|EB652789 | cenchrus | 1950 | 232 | sorghum\|gb161.xeno\|AA011880 | 92.3 | blastp |
| 887 | cotton\|gb164\|DT574337 | cotton | 1951 | 232 | sorghum\|gb161.xeno\|AA011880 | 95.9 | blastp |
| 888 | leymus\|gb166\|CN465754 | leymus | 1952 | 232 | sorghum\|gb161.xeno\|AA011880 | 81.1 | blastp |
| 889 | maize\|gb170\|AA011880 | maize | 1953 | 232 | sorghum\|gb161.xeno\|AA011880 | 95.9 | blastp |
| 890 | maize\|gb170\|LLCD979368 | maize | 1954 | 232 | sorghum\|gb161.xeno\|AA011880 | 95.9 | blastp |
| 891 | pseudoroegneria\|gb167\|FF344484 | pseudoroegneria | 1955 | 232 | sorghum\|gb161.xeno\|AA011880 | 83.3 | blastp |
| 892 | rice\|gb170\|OS07G46750 | rice | 1956 | 232 | sorghum\|gb161.xeno\|AA011880 | 87.9 | blastp |
| 893 | sugarcane\|gb157.3\|BQ535840 | sugarcane | 1957 | 232 | sorghum\|gb161.xeno\|AA011880 | 97.3 | blastp |
| 894 | sugarcane\|gb157.3\|BQ536355 | sugarcane | 1958 | 232 | sorghum\|gb161.xeno\|AA011880 | 94 | blastp |
| 895 | sugarcane\|gb157.3\|CA065609 | sugarcane | 1959 | 232 | sorghum\|gb161.xeno\|AA011880 | 83.94 | tblastn |
| 896 | sugarcane\|gb157.3\|CA075754 | sugarcane | 1960 | 232 | sorghum\|gb161.xeno\|AA011880 | 93.3 | blastp |
| 897 | sugarcane\|gb157.3\|CA078921 | sugarcane | 1961 | 232 | sorghum\|gb161.xeno\|AA011880 | 98.6 | blastp |
| 898 | switchgrass\|gb167\|DN141728 | switchgrass | 1962 | 232 | sorghum\|gb161.xeno\|AA011880 | 91.5 | blastp |
| 899 | switchgrass\|gb167\|DN145078 | switchgrass | 1963 | 232 | sorghum\|gb161.xeno\|AA011880 | 92.4 | blastp |
| 900 | wheat\|gb164\|BE398306 | wheat | 1964 | 232 | sorghum\|gb161.xeno\|AA011880 | 82.8 | blastp |
| 901 | wheat\|gb164\|BE398696 | wheat | 1965 | 232 | sorghum\|gb161.xeno\|AA011880 | 81.4 | blastp |
| 902 | wheat\|gb164\|BE423010 | wheat | 1966 | 232 | sorghum\|gb161.xeno\|AA011880 | 82.8 | blastp |
| 903 | wheat\|gb164\|CA484184 | wheat | 1967 | 232 | sorghum\|gb161.xeno\|AA011880 | 97.7 | blastp |
| 904 | barley\|gb157.3\|BE413465 | barley | 1968 | 233 | rice\|gb157.2\|BE229552 | 87.4 | blastp |
| 905 | brachypodium\|gb169\|BE413465 | brachypodium | 1969 | 233 | rice\|gb157.2\|BE229552 | 86.5 | blastp |
| 906 | leymus\|gb166\|EG379179 | leymus | 1970 | 233 | rice\|gb157.2\|BE229552 | 87.1 | blastp |
| 907 | maize\|gb170\|T26952 | maize | 1971 | 233 | rice\|gb157.2\|BE229552 | 87.7 | blastp |
| 908 | sorghum\|gb161.crp\|BG549557 | sorghum | 1972 | 233 | rice\|gb157.2\|BE229552 | 87.7 | blastp |
| 909 | sugarcane\|gb157.3\|CA099583 | sugarcane | 1973 | 233 | rice\|gb157.2\|BE229552 | 88.3 | blastp |
| 910 | switchgrass\|gb167\|FE610789 | switchgrass | 1974 | 233 | rice\|gb157.2\|BE229552 | 85.6 | blastp |
| 911 | switchgrass\|gb167\|FL748149 | switchgrass | 1975 | 233 | rice\|gb157.2\|BE229552 | 88 | blastp |
| 912 | wheat\|gb164\|BE430330 | wheat | 1976 | 233 | rice\|gb157.2\|BE229552 | 86.83 | tblastn |
| 913 | wheat\|gb164\|BE490164 | wheat | 1977 | 233 | rice\|gb157.2\|BE229552 | 87.1 | blastp |
| 914 | wheat\|gb164\|BF201086 | wheat | 1978 | 233 | rice\|gb157.2\|BE229552 | 87.4 | blastp |
| 915 | amborella\|gb166\|CD484126 | amborella | 1979 | 234 | rice\|gb157.2\|BE039784 | 96 | blastp |
| 916 | amborella\|gb166\|CK760819 | amborella | 1980 | 234 | rice\|gb157.2\|BE039784 | 97.4 | blastp |
| 917 | antirrhinum\|gb166\|AJ558674 | antirrhinum | 1981 | 234 | rice\|gb157.2\|BE039784 | 89.4 | blastp |
| 918 | antirrhinum\|gb166\|AJ559850 | antirrhinum | 1982 | 234 | rice\|gb157.2\|BE039784 | 91.4 | blastp |
| 919 | antirrhinum\|gb166\|AJ787300 | antirrhinum | 1983 | 234 | rice\|gb157.2\|BE039784 | 91.4 | blastp |
| 920 | antirrhinum\|gb166\|AJ789533 | antirrhinum | 1984 | 234 | rice\|gb157.2\|BE039784 | 91.4 | blastp |
| 921 | apple\|gb157.3\|CN489349 | apple | 1985 | 234 | rice\|gb157.2\|BE039784 | 90.7 | blastp |
| 922 | apple\|gb157.3\|CN496576 | apple | 1986 | 234 | rice\|gb157.2\|BE039784 | 91.4 | blastp |
| 923 | apple\|gb157.3\|CN995013 | apple | 1987 | 234 | rice\|gb157.2\|BE039784 | 90.7 | blastp |
| 924 | apricot\|gb157.2\|CB819597 | apricot | 1988 | 234 | rice\|gb157.2\|BE039784 | 92.7 | blastp |
| 925 | apricot\|gb157.2\|CV044080 | apricot | 1989 | 234 | rice\|gb157.2\|BE039784 | 93.4 | blastp |
| 926 | aquilegia\|gb157.3\|DR915026 | aquilegia | 1990 | 234 | rice\|gb157.2\|BE039784 | 94.7 | blastp |
| 927 | arabidopsis\|gb165\|AT2G36160 | arabidopsis | 1991 | 234 | rice\|gb157.2\|BE039784 | 90.7 | blastp |
| 928 | arabidopsis\|gb165\|AT3G11510 | arabidopsis | 1992 | 234 | rice\|gb157.2\|BE039784 | 91.4 | blastp |
| 929 | arabidopsis\|gb165\|AT3G52580 | arabidopsis | 1993 | 234 | rice\|gb157.2\|BE039784 | 91.4 | blastp |
| 930 | artemisia\|gb164\|EY033322 | artemisia | 1994 | 234 | rice\|gb157.2\|BE039784 | 89.4 | blastp |
| 931 | artemisia\|gb164\|EY038655 | artemisia | 1995 | 234 | rice\|gb157.2\|BE039784 | 88.1 | blastp |
| 932 | artemisia\|gb164\|EY050701 | artemisia | 1996 | 234 | rice\|gb157.2\|BE039784 | 89.4 | blastp |
| 933 | avocado\|gb164\|CK753882 | avocado | 1997 | 234 | rice\|gb157.2\|BE039784 | 93.4 | blastp |
| 934 | b_juncea\|gb164\|EVGN00033609170815 | b_juncea | 1998 | 234 | rice\|gb157.2\|BE039784 | 92.7 | blastp |
| 935 | b_juncea\|gb164\|EVGN00191625522759 | b_juncea | 1999 | 234 | rice\|gb157.2\|BE039784 | 92.7 | blastp |
| 936 | b_juncea\|gb164\|EVGN00422623890637 | b_juncea | 2000 | 234 | rice\|gb157.2\|BE039784 | 84.8 | blastp |
| 937 | b_juncea\|gb164\|EVGN00544912222373 | b_juncea | 2001 | 234 | rice\|gb157.2\|BE039784 | 93.4 | blastp |
| 938 | b_juncea\|gb164\|EVGN00716011751939 | b_juncea | 2002 | 234 | rice\|gb157.2\|BE039784 | 92.1 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 939 | b_juncea\|gb164\|EVGN00888211982122 | b_juncea | 2003 | 234 | rice\|gb157.2\|BE039784 | 92.1 | blastp |
| 940 | b_juncea\|gb164\|EVGN01248609033239 | b_juncea | 2004 | 234 | rice\|gb157.2\|BE039784 | 92.7 | blastp |
| 941 | b_oleracea\|gb161\|DY026232 | b_oleracea | 2005 | 234 | rice\|gb157.2\|BE039784 | 93.4 | blastp |
| 942 | b_oleracea\|gb161\|DY026495 | b_oleracea | 2006 | 234 | rice\|gb157.2\|BE039784 | 92.7 | blastp |
| 943 | b_oleracea\|gb161\|DY026867 | b_oleracea | 2007 | 234 | rice\|gb157.2\|BE039784 | 93.4 | blastp |
| 944 | b_oleracea\|gb161\|DY027139 | b_oleracea | 2008 | 234 | rice\|gb157.2\|BE039784 | 92.7 | blastp |
| 945 | b_oleracea\|gb161\|DY028093 | b_oleracea | 2009 | 234 | rice\|gb157.2\|BE039784 | 92.7 | blastp |
| 946 | b_oleracea\|gb161\|ES942246 | b_oleracea | 2010 | 234 | rice\|gb157.2\|BE039784 | 92.7 | blastp |
| 947 | b_rapa\|gb162\|BG544390 | b_rapa | 2011 | 234 | rice\|gb157.2\|BE039784 | 92.7 | blastp |
| 948 | b_rapa\|gb162\|CA992255 | b_rapa | 2012 | 234 | rice\|gb157.2\|BE039784 | 92.7 | blastp |
| 949 | b_rapa\|gb162\|CV433769 | b_rapa | 2013 | 234 | rice\|gb157.2\|BE039784 | 92.7 | blastp |
| 950 | b_rapa\|gb162\|CV433783 | b_rapa | 2014 | 234 | rice\|gb157.2\|BE039784 | 93.4 | blastp |
| 951 | b_rapa\|gb162\|CX265694 | b_rapa | 2015 | 234 | rice\|gb157.2\|BE039784 | 93.4 | blastp |
| 952 | b_rapa\|gb162\|CX270426 | b_rapa | 2016 | 234 | rice\|gb157.2\|BE039784 | 92.7 | blastp |
| 953 | b_rapa\|gb162\|CX270426 | b_rapa | 2017 | 234 | rice\|gb157.2\|BE039784 | 93.4 | blastp |
| 954 | b_rapa\|gb162\|DY008989 | b_rapa | 2018 | 234 | rice\|gb157.2\|BE039784 | 93.4 | blastp |
| 955 | b_rapa\|gb162\|EE525926 | b_rapa | 2019 | 234 | rice\|gb157.2\|BE039784 | 92.7 | blastp |
| 956 | b_rapa\|gb162\|L33661 | b_rapa | 2020 | 234 | rice\|gb157.2\|BE039784 | 93.4 | blastp |
| 957 | banana\|gb167\|DN240239 | banana | 2021 | 234 | rice\|gb157.2\|BE039784 | 96.7 | blastp |
| 958 | banana\|gb167\|ES433381 | banana | 2022 | 234 | rice\|gb157.2\|BE039784 | 96.7 | blastp |
| 959 | banana\|gb167\|FF558372 | banana | 2023 | 234 | rice\|gb157.2\|BE039784 | 96.7 | blastp |
| 960 | banana\|gb167\|FF558518 | banana | 2024 | 234 | rice\|gb157.2\|BE039784 | 97.4 | blastp |
| 961 | banana\|gb167\|FL662140 | banana | 2025 | 234 | rice\|gb157.2\|BE039784 | 91.4 | blastp |
| 962 | barley\|gb157.3\|AL501882 | barley | 2026 | 234 | rice\|gb157.2\|BE039784 | 96 | blastp |
| 963 | barley\|gb157.3\|BE412576 | barley | 2027 | 234 | rice\|gb157.2\|BE039784 | 97.4 | blastp |
| 964 | barley\|gb157.3\|BQ768399 | barley | 2028 | 234 | rice\|gb157.2\|BE039784 | 82.8 | blastp |
| 965 | barley\|gb157.3\|DN183050 | barley | 2029 | 234 | rice\|gb157.2\|BE039784 | 80.9 | blastp |
| 966 | basilicum\|gb157.3\|DY331402 | basilicum | 2030 | 234 | rice\|gb157.2\|BE039784 | 91.4 | blastp |
| 967 | basilicum\|gb157.3\|DY344099 | basilicum | 2031 | 234 | rice\|gb157.2\|BE039784 | 90.1 | blastp |
| 968 | bean\|gb167\|CA897110 | bean | 2032 | 234 | rice\|gb157.2\|BE039784 | 91.4 | blastp |
| 969 | bean\|gb167\|CA897113 | bean | 2033 | 234 | rice\|gb157.2\|BE039784 | 91.4 | blastp |
| 970 | beet\|gb162\|BQ060487 | beet | 2034 | 234 | rice\|gb157.2\|BE039784 | 94 | blastp |
| 971 | brachypodium\|gb169\|BE398957 | brachypodium | 2035 | 234 | rice\|gb157.2\|BE039784 | 94.04 | tblastn |
| 972 | brachypodium\|gb169\|BE402469 | brachypodium | 2036 | 234 | rice\|gb157.2\|BE039784 | 97.35 | tblastn |
| 973 | brachypodium\|gb169\|BE403589 | brachypodium | 2037 | 234 | rice\|gb157.2\|BE039784 | 95.4 | blastp |
| 974 | brachypodium\|gb169\|BE406789 | brachypodium | 2038 | 234 | rice\|gb157.2\|BE039784 | 96.7 | blastp |
| 975 | bruguiera\|gb166\|BP949576 | bruguiera | 2039 | 234 | rice\|gb157.2\|BE039784 | 91.39 | tblastn |
| 976 | cacao\|gb167\|CA796567 | cacao | 2040 | 234 | rice\|gb157.2\|BE039784 | 93.4 | blastp |
| 977 | cacao\|gb167\|CU473326 | cacao | 2041 | 234 | rice\|gb157.2\|BE039784 | 92.1 | blastp |
| 978 | canola\|gb161\|AY196093 | canola | 2042 | 234 | rice\|gb157.2\|BE039784 | 93.4 | blastp |
| 979 | canola\|gb161\|CD811632 | canola | 2043 | 234 | rice\|gb157.2\|BE039784 | 93.4 | blastp |
| 980 | canola\|gb161\|CD812906 | canola | 2044 | 234 | rice\|gb157.2\|BE039784 | 92.7 | blastp |
| 981 | canola\|gb161\|CD820445 | canola | 2045 | 234 | rice\|gb157.2\|BE039784 | 93.4 | blastp |
| 982 | canola\|gb161\|CD822523 | canola | 2046 | 234 | rice\|gb157.2\|BE039784 | 92.7 | blastp |
| 983 | canola\|gb161\|CD823758 | canola | 2047 | 234 | rice\|gb157.2\|BE039784 | 92.7 | blastp |
| 984 | canola\|gb161\|CD827084 | canola | 2048 | 234 | rice\|gb157.2\|BE039784 | 92.7 | blastp |
| 985 | canola\|gb161\|CD829044 | canola | 2049 | 234 | rice\|gb157.2\|BE039784 | 92.7 | blastp |
| 986 | canola\|gb161\|CD840491 | canola | 2050 | 234 | rice\|gb157.2\|BE039784 | 92.7 | blastp |
| 987 | canola\|gb161\|CN730264 | canola | 2051 | 234 | rice\|gb157.2\|BE039784 | 93.4 | blastp |
| 988 | canola\|gb161\|CN731838 | canola | 2052 | 234 | rice\|gb157.2\|BE039784 | 92.7 | blastp |
| 989 | canola\|gb161\|CX190513 | canola | 2053 | 234 | rice\|gb157.2\|BE039784 | 92.7 | blastp |
| 990 | canola\|gb161\|CX280454 | canola | 2054 | 234 | rice\|gb157.2\|BE039784 | 92.7 | blastp |
| 991 | canola\|gb161\|CX280565 | canola | 2055 | 234 | rice\|gb157.2\|BE039784 | 92.7 | blastp |
| 992 | canola\|gb161\|H07559 | canola | 2056 | 234 | rice\|gb157.2\|BE039784 | 92.7 | blastp |
| 993 | cassava\|gb164\|CK647007 | cassava | 2057 | 234 | rice\|gb157.2\|BE039784 | 95.4 | blastp |
| 994 | cassava\|gb164\|CK650413 | cassava | 2058 | 234 | rice\|gb157.2\|BE039784 | 95.4 | blastp |
| 995 | cassava\|gb164\|CK652715 | cassava | 2059 | 234 | rice\|gb157.2\|BE039784 | 95.4 | blastp |
| 996 | castorbean\|gb160\|MDL29693M002016 | castorbean | 2060 | 234 | rice\|gb157.2\|BE039784 | 93.4 | blastp |
| 997 | castorbean\|gb160\|T14945 | castorbean | 2061 | 234 | rice\|gb157.2\|BE039784 | 93.4 | blastp |
| 998 | catharanthus\|gb166\|EG556977 | catharanthus | 2062 | 234 | rice\|gb157.2\|BE039784 | 88.7 | blastp |
| 999 | catharanthus\|gb166\|EG557933 | catharanthus | 2063 | 234 | rice\|gb157.2\|BE039784 | 93.4 | blastp |
| 1000 | cenchrus\|gb166\|EB656767 | cenchrus | 2064 | 234 | rice\|gb157.2\|BE039784 | 94.7 | blastp |
| 1001 | cenchrus\|gb166\|EB664187 | cenchrus | 2065 | 234 | rice\|gb157.2\|BE039784 | 97.4 | blastp |
| 1002 | centaurea\|gb166\|EH724794 | centaurea | 2066 | 234 | rice\|gb157.2\|BE039784 | 91.4 | blastp |
| 1003 | centaurea\|gb166\|EH739148 | centaurea | 2067 | 234 | rice\|gb157.2\|BE039784 | 91.4 | blastp |
| 1004 | centaurea\|gb166\|EH748001 | centaurea | 2068 | 234 | rice\|gb157.2\|BE039784 | 90.7 | blastp |
| 1005 | centaurea\|gb166\|EH753801 | centaurea | 2069 | 234 | rice\|gb157.2\|BE039784 | 91.4 | blastp |
| 1006 | centaurea\|gb166\|EH780000 | centaurea | 2070 | 234 | rice\|gb157.2\|BE039784 | 91.4 | blastp |
| 1007 | cherry\|gb157.2\|EE488074 | cherry | 2071 | 234 | rice\|gb157.2\|BE039784 | 92.05 | tblastn |
| 1008 | chestnut\|gb170\|SRR006295S0002784 | chestnut | 2072 | 234 | rice\|gb157.2\|BE039784 | 94 | blastp |
| 1009 | chestnut\|gb170\|SRR006295S0004532 | chestnut | 2073 | 234 | rice\|gb157.2\|BE039784 | 93.4 | blastp |
| 1010 | chestnut\|gb170\|SRR006295S0010942 | chestnut | 2074 | 234 | rice\|gb157.2\|BE039784 | 94 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 1011 | chlamydomonas\|gb162\|AW676072 | chlamydomonas | 2075 | 234 | rice\|gb157.2\|BE039784 | 85.6 | blastp |
| 1012 | cichorium\|gb166\|DT211087 | cichorium | 2076 | 234 | rice\|gb157.2\|BE039784 | 89.4 | blastp |
| 1013 | cichorium\|gb166\|DT214005 | cichorium | 2077 | 234 | rice\|gb157.2\|BE039784 | 91.4 | blastp |
| 1014 | cichorium\|gb166\|EL356717 | cichorium | 2078 | 234 | rice\|gb157.2\|BE039784 | 91.4 | blastp |
| 1015 | cichorium\|gb166\|EL365574 | cichorium | 2079 | 234 | rice\|gb157.2\|BE039784 | 91.4 | blastp |
| 1016 | citrus\|gb166\|BQ623292 | citrus | 2080 | 234 | rice\|gb157.2\|BE039784 | 94.7 | blastp |
| 1017 | citrus\|gb166\|BQ624114 | citrus | 2081 | 234 | rice\|gb157.2\|BE039784 | 93.4 | blastp |
| 1018 | coffea\|gb157.2\|BQ449109 | coffea | 2082 | 234 | rice\|gb157.2\|BE039784 | 93.4 | blastp |
| 1019 | coffea\|gb157.2\|DV673676 | coffea | 2083 | 234 | rice\|gb157.2\|BE039784 | 92.7 | blastp |
| 1020 | cotton\|gb164\|AI726845 | cotton | 2084 | 234 | rice\|gb157.2\|BE039784 | 92.7 | blastp |
| 1021 | cotton\|gb164\|AI730068 | cotton | 2085 | 234 | rice\|gb157.2\|BE039784 | 92.1 | blastp |
| 1022 | cotton\|gb164\|BE054711 | cotton | 2086 | 234 | rice\|gb157.2\|BE039784 | 92.7 | blastp |
| 1023 | cotton\|gb164\|BF271677 | cotton | 2087 | 234 | rice\|gb157.2\|BE039784 | 92.1 | blastp |
| 1024 | cotton\|gb164\|CD485874 | cotton | 2088 | 234 | rice\|gb157.2\|BE039784 | 81.46 | tblastn |
| 1025 | cotton\|gb164\|DV849004 | cotton | 2089 | 234 | rice\|gb157.2\|BE039784 | 92.1 | blastp |
| 1026 | cotton\|gb164\|ES792938 | cotton | 2090 | 234 | rice\|gb157.2\|BE039784 | 92.1 | blastp |
| 1027 | cowpea\|gb166\|FC459672 | cowpea | 2091 | 234 | rice\|gb157.2\|BE039784 | 91.4 | blastp |
| 1028 | cowpea\|gb166\|FF384317 | cowpea | 2092 | 234 | rice\|gb157.2\|BE039784 | 81.6 | blastp |
| 1029 | cowpea\|gb166\|FF385803 | cowpea | 2093 | 234 | rice\|gb157.2\|BE039784 | 91.4 | blastp |
| 1030 | cowpea\|gb166\|FF389079 | cowpea | 2094 | 234 | rice\|gb157.2\|BE039784 | 83.4 | blastp |
| 1031 | cowpea\|gb166\|FF391295 | cowpea | 2095 | 234 | rice\|gb157.2\|BE039784 | 90.7 | blastp |
| 1032 | cryptomeria\|gb166\|BP173938 | cryptomeria | 2096 | 234 | rice\|gb157.2\|BE039784 | 92.7 | blastp |
| 1033 | cryptomeria\|gb166\|BW994122 | cryptomeria | 2097 | 234 | rice\|gb157.2\|BE039784 | 92.7 | blastp |
| 1034 | cycas\|gb166\|EX923616 | cycas | 2098 | 234 | rice\|gb157.2\|BE039784 | 92.1 | blastp |
| 1035 | cycas\|gb166\|EX924938 | cycas | 2099 | 234 | rice\|gb157.2\|BE039784 | 91.39 | tblastn |
| 1036 | cynara\|gb167\|GE586142 | cynara | 2100 | 234 | rice\|gb157.2\|BE039784 | 91.4 | blastp |
| 1037 | cynara\|gb167\|GE586173 | cynara | 2101 | 234 | rice\|gb157.2\|BE039784 | 91.4 | blastp |
| 1038 | cynara\|gb167\|GE591726 | cynara | 2102 | 234 | rice\|gb157.2\|BE039784 | 90.1 | blastp |
| 1039 | dandelion\|gb161\|DY804347 | dandelion | 2103 | 234 | rice\|gb157.2\|BE039784 | 91.4 | blastp |
| 1040 | dandelion\|gb161\|DY807877 | dandelion | 2104 | 234 | rice\|gb157.2\|BE039784 | 91.4 | blastp |
| 1041 | eucalyptus\|gb166\|CB967799 | eucalyptus | 2105 | 234 | rice\|gb157.2\|BE039784 | 94.7 | blastp |
| 1042 | eucalyptus\|gb166\|CT980941 | eucalyptus | 2106 | 234 | rice\|gb157.2\|BE039784 | 94.7 | blastp |
| 1043 | fescue\|gb161\|DT679829 | fescue | 2107 | 234 | rice\|gb157.2\|BE039784 | 98 | blastp |
| 1044 | fescue\|gb161\|DT682674 | fescue | 2108 | 234 | rice\|gb157.2\|BE039784 | 96 | blastp |
| 1045 | fescue\|gb161\|DT688310 | fescue | 2109 | 234 | rice\|gb157.2\|BE039784 | 98 | blastp |
| 1046 | flax\|gb157.3\|CV478813 | flax | 2110 | 234 | rice\|gb157.2\|BE039784 | 89.4 | tblastn |
| 1047 | ginger\|gb164\|DY372231 | ginger | 2111 | 234 | rice\|gb157.2\|BE039784 | 97.4 | blastp |
| 1048 | grape\|gb160\|BQ796073 | grape | 2112 | 234 | rice\|gb157.2\|BE039784 | 94.7 | blastp |
| 1049 | grape\|gb160\|BQ796330 | grape | 2113 | 234 | rice\|gb157.2\|BE039784 | 93.4 | blastp |
| 1050 | grape\|gb160\|BQ800180 | grape | 2114 | 234 | rice\|gb157.2\|BE039784 | 94 | blastp |
| 1051 | iceplant\|gb164\|BE034755 | iceplant | 2115 | 234 | rice\|gb157.2\|BE039784 | 93.4 | blastp |
| 1052 | iceplant\|gb164\|CA833881 | iceplant | 2116 | 234 | rice\|gb157.2\|BE039784 | 92.7 | blastp |
| 1053 | ipomoea\|gb157.2\|BJ554031 | ipomoea | 2117 | 234 | rice\|gb157.2\|BE039784 | 94.7 | blastp |
| 1054 | ipomoea\|gb157.2\|BJ555694 | ipomoea | 2118 | 234 | rice\|gb157.2\|BE039784 | 92.72 | tblastn |
| 1055 | ipomoea\|gb157.2\|BJ557693 | ipomoea | 2119 | 234 | rice\|gb157.2\|BE039784 | 94.7 | blastp |
| 1056 | ipomoea\|gb157.2\|BU691365 | ipomoea | 2120 | 234 | rice\|gb157.2\|BE039784 | 94 | blastp |
| 1057 | kiwi\|gb166\|FG404658 | kiwi | 2121 | 234 | rice\|gb157.2\|BE039784 | 92.7 | blastp |
| 1058 | kiwi\|gb166\|FG404746 | kiwi | 2122 | 234 | rice\|gb157.2\|BE039784 | 92.1 | blastp |
| 1059 | kiwi\|gb166\|FG408063 | kiwi | 2123 | 234 | rice\|gb157.2\|BE039784 | 94 | blastp |
| 1060 | lettuce\|gb157.2\|DW078606 | lettuce | 2124 | 234 | rice\|gb157.2\|BE039784 | 91.4 | blastp |
| 1061 | leymus\|gb166\|EG388410 | leymus | 2125 | 234 | rice\|gb157.2\|BE039784 | 96 | blastp |
| 1062 | liriodendron\|gb166\|CK743464 | liriodendron | 2126 | 234 | rice\|gb157.2\|BE039784 | 94.7 | blastp |
| 1063 | liriodendron\|gb166\|CO998653 | liriodendron | 2127 | 234 | rice\|gb157.2\|BE039784 | 93.4 | blastp |
| 1064 | lotus\|gb157.2\|AI967817 | lotus | 2128 | 234 | rice\|gb157.2\|BE039784 | 90.1 | blastp |
| 1065 | lotus\|gb157.2\|CB826697 | lotus | 2129 | 234 | rice\|gb157.2\|BE039784 | 89.4 | blastp |
| 1066 | lovegrass\|gb167\|DN480258 | lovegrass | 2130 | 234 | rice\|gb157.2\|BE039784 | 99.3 | blastp |
| 1067 | lovegrass\|gb167\|EH183996 | lovegrass | 2131 | 234 | rice\|gb157.2\|BE039784 | 98.7 | blastp |
| 1068 | maize\|gb170\|AI612306 | maize | 2132 | 234 | rice\|gb157.2\|BE039784 | 97.4 | blastp |
| 1069 | maize\|gb170\|AI967032 | maize | 2133 | 234 | rice\|gb157.2\|BE039784 | 98.7 | blastp |
| 1070 | maize\|gb170\|AI979679 | maize | 2134 | 234 | rice\|gb157.2\|BE039784 | 85.71 | tblastn |
| 1071 | maize\|gb170\|AW054617 | maize | 2135 | 234 | rice\|gb157.2\|BE039784 | 97.4 | blastp |
| 1072 | maize\|gb170\|AW165569 | maize | 2136 | 234 | rice\|gb157.2\|BE039784 | 97.4 | blastp |
| 1073 | maize\|gb170\|LLBU037867 | maize | 2137 | 234 | rice\|gb157.2\|BE039784 | 94.7 | tblastn |
| 1074 | maize\|gb170\|LLDQ244878 | maize | 2138 | 234 | rice\|gb157.2\|BE039784 | 92.7 | blastp |
| 1075 | maize\|gb170\|LLDQ245962 | maize | 2139 | 234 | rice\|gb157.2\|BE039784 | 92.1 | blastp |
| 1076 | maize\|gb170\|T18275 | maize | 2140 | 234 | rice\|gb157.2\|BE039784 | 97.4 | blastp |
| 1077 | marchantia\|gb166\|BJ841500 | marchantia | 2141 | 234 | rice\|gb157.2\|BE039784 | 89.4 | blastp |
| 1078 | marchantia\|gb166\|C95799 | marchantia | 2142 | 234 | rice\|gb157.2\|BE039784 | 92.1 | blastp |
| 1079 | medicago\|gb157.2\|AA660312 | medicago | 2143 | 234 | rice\|gb157.2\|BE039784 | 89.4 | blastp |
| 1080 | medicago\|gb157.2\|AA660491 | medicago | 2144 | 234 | rice\|gb157.2\|BE039784 | 88.7 | blastp |
| 1081 | melon\|gb165\|AM713905 | melon | 2145 | 234 | rice\|gb157.2\|BE039784 | 94 | blastp |
| 1082 | melon\|gb165\|AM719737 | melon | 2146 | 234 | rice\|gb157.2\|BE039784 | 84.1 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 1083 | melon\|gb165\|AM719902 | melon | 2147 | 234 | rice\|gb157.2\|BE039784 | 92.76 | tblastn |
| 1084 | melon\|gb165\|EB714362 | melon | 2148 | 234 | rice\|gb157.2\|BE039784 | 94 | blastp |
| 1085 | mesostigma\|gb166\|DN254866 | mesostigma | 2149 | 234 | rice\|gb157.2\|BE039784 | 86.3 | blastp |
| 1086 | millet\|gb161\|CD724748 | millet | 2150 | 234 | rice\|gb157.2\|BE039784 | 96 | blastp |
| 1087 | millet\|gb161\|CD725398 | millet | 2151 | 234 | rice\|gb157.2\|BE039784 | 92.72 | tblastn |
| 1088 | nuphar\|gb166\|CD475044 | nuphar | 2152 | 234 | rice\|gb157.2\|BE039784 | 94 | blastp |
| 1089 | nuphar\|gb166\|CK757845 | nuphar | 2153 | 234 | rice\|gb157.2\|BE039784 | 94 | blastp |
| 1090 | nuphar\|gb166\|CK767949 | nuphar | 2154 | 234 | rice\|gb157.2\|BE039784 | 93.4 | blastp |
| 1091 | oak\|gb170\|DB996865 | oak | 2155 | 234 | rice\|gb157.2\|BE039784 | 93.4 | blastp |
| 1092 | oak\|gb170\|DB998068 | oak | 2156 | 234 | rice\|gb157.2\|BE039784 | 94 | blastp |
| 1093 | oak\|gb170\|DN949738 | oak | 2157 | 234 | rice\|gb157.2\|BE039784 | 94 | blastp |
| 1094 | oil_palm\|gb166\|EL681750 | oil_palm | 2158 | 234 | rice\|gb157.2\|BE039784 | 96 | blastp |
| 1095 | oil_palm\|gb166\|EL930220 | oil_palm | 2159 | 234 | rice\|gb157.2\|BE039784 | 96 | blastp |
| 1096 | oil_palm\|gb166\|EL930363 | oil_palm | 2160 | 234 | rice\|gb157.2\|BE039784 | 96 | blastp |
| 1097 | onion\|gb162\|BQ580074 | onion | 2161 | 234 | rice\|gb157.2\|BE039784 | 96 | blastp |
| 1098 | papaya\|gb165\|EX231620 | papaya | 2162 | 234 | rice\|gb157.2\|BE039784 | 92.7 | blastp |
| 1099 | papaya\|gb165\|EX252393 | papaya | 2163 | 234 | rice\|gb157.2\|BE039784 | 92.7 | blastp |
| 1100 | peach\|gb157.2\|BU040848 | peach | 2164 | 234 | rice\|gb157.2\|BE039784 | 93.4 | blastp |
| 1101 | peanut\|gb167\|CD037918 | peanut | 2165 | 234 | rice\|gb157.2\|BE039784 | 92.1 | blastp |
| 1102 | peanut\|gb167\|CX018155 | peanut | 2166 | 234 | rice\|gb157.2\|BE039784 | 92.1 | blastp |
| 1103 | pepper\|gb157.2\|BM061978 | pepper | 2167 | 234 | rice\|gb157.2\|BE039784 | 92.1 | blastp |
| 1104 | pepper\|gb157.2\|BM062219 | pepper | 2168 | 234 | rice\|gb157.2\|BE039784 | 92.7 | blastp |
| 1105 | pepper\|gb157.2\|BM066627 | pepper | 2169 | 234 | rice\|gb157.2\|BE039784 | 92.7 | blastp |
| 1106 | periwinkle\|gb164\|EG556977 | periwinkle | 2170 | 234 | rice\|gb157.2\|BE039784 | 88.7 | blastp |
| 1107 | periwinkle\|gb164\|EG557933 | periwinkle | 2171 | 234 | rice\|gb157.2\|BE039784 | 93.4 | blastp |
| 1108 | physcomitrella\|gb157\|AW127039 | physcomitrella | 2172 | 234 | rice\|gb157.2\|BE039784 | 89.4 | tblastn |
| 1109 | physcomitrella\|gb157\|BQ827306 | physcomitrella | 2173 | 234 | rice\|gb157.2\|BE039784 | 88.7 | blastp |
| 1110 | pine\|gb157.2\|AW010184 | pine | 2174 | 234 | rice\|gb157.2\|BE039784 | 92.7 | blastp |
| 1111 | pine\|gb157.2\|BX248872 | pine | 2175 | 234 | rice\|gb157.2\|BE039784 | 93.4 | blastp |
| 1112 | pine\|gb157.2\|BX251919 | pine | 2176 | 234 | rice\|gb157.2\|BE039784 | 92.7 | blastp |
| 1113 | pine\|gb157.2\|DR102094 | pine | 2177 | 234 | rice\|gb157.2\|BE039784 | 82.1 | blastp |
| 1114 | pine\|gb157.2\|H75266 | pine | 2178 | 234 | rice\|gb157.2\|BE039784 | 92.7 | blastp |
| 1115 | poplar\|gb170\|AI162468 | poplar | 2179 | 234 | rice\|gb157.2\|BE039784 | 96 | blastp |
| 1116 | poplar\|gb170\|AI163154 | poplar | 2180 | 234 | rice\|gb157.2\|BE039784 | 93.4 | blastp |
| 1117 | poplar\|gb170\|AI164614 | poplar | 2181 | 234 | rice\|gb157.2\|BE039784 | 94 | blastp |
| 1118 | poplar\|gb170\|AI164759 | poplar | 2182 | 234 | rice\|gb157.2\|BE039784 | 94.7 | blastp |
| 1119 | poppy\|gb166\|FE964530 | poppy | 2183 | 234 | rice\|gb157.2\|BE039784 | 92.1 | blastp |
| 1120 | poppy\|gb166\|FE965652 | poppy | 2184 | 234 | rice\|gb157.2\|BE039784 | 91.4 | blastp |
| 1121 | potato\|gb157.2\|AW906248 | potato | 2185 | 234 | rice\|gb157.2\|BE039784 | 92.7 | blastp |
| 1122 | potato\|gb157.2\|BF459889 | potato | 2186 | 234 | rice\|gb157.2\|BE039784 | 92.1 | blastp |
| 1123 | potato\|gb157.2\|BG350431 | potato | 2187 | 234 | rice\|gb157.2\|BE039784 | 92.1 | blastp |
| 1124 | potato\|gb157.2\|BG351012 | potato | 2188 | 234 | rice\|gb157.2\|BE039784 | 92.1 | blastp |
| 1125 | potato\|gb157.2\|BG351586 | potato | 2189 | 234 | rice\|gb157.2\|BE039784 | 92.05 | tblastn |
| 1126 | prunus\|gb167\|BQ641170 | prunus | 2190 | 234 | rice\|gb157.2\|BE039784 | 92.7 | blastp |
| 1127 | prunus\|gb167\|BU040848 | prunus | 2191 | 234 | rice\|gb157.2\|BE039784 | 93.4 | blastp |
| 1128 | pseudoroegneria\|gb167\|FF343278 | pseudoroegneria | 2192 | 234 | rice\|gb157.2\|BE039784 | 97.4 | blastp |
| 1129 | pseudoroegneria\|gb167\|FF349878 | pseudoroegneria | 2193 | 234 | rice\|gb157.2\|BE039784 | 96 | blastp |
| 1130 | radish\|gb164\|EV527917 | radish | 2194 | 234 | rice\|gb157.2\|BE039784 | 92.7 | blastp |
| 1131 | radish\|gb164\|EV528399 | radish | 2195 | 234 | rice\|gb157.2\|BE039784 | 92.1 | blastp |
| 1132 | radish\|gb164\|EV535656 | radish | 2196 | 234 | rice\|gb157.2\|BE039784 | 92.7 | blastp |
| 1133 | radish\|gb164\|EV535984 | radish | 2197 | 234 | rice\|gb157.2\|BE039784 | 92.7 | blastp |
| 1134 | radish\|gb164\|EV538012 | radish | 2198 | 234 | rice\|gb157.2\|BE039784 | 92.7 | blastp |
| 1135 | radish\|gb164\|EV543948 | radish | 2199 | 234 | rice\|gb157.2\|BE039784 | 92.7 | blastp |
| 1136 | radish\|gb164\|EV544942 | radish | 2200 | 234 | rice\|gb157.2\|BE039784 | 92.7 | blastp |
| 1137 | radish\|gb164\|EV545164 | radish | 2201 | 234 | rice\|gb157.2\|BE039784 | 92.7 | blastp |
| 1138 | radish\|gb164\|EV565378 | radish | 2202 | 234 | rice\|gb157.2\|BE039784 | 92.05 | tblastn |
| 1139 | radish\|gb164\|EV565564 | radish | 2203 | 234 | rice\|gb157.2\|BE039784 | 92.7 | blastp |
| 1140 | radish\|gb164\|EV565962 | radish | 2204 | 234 | rice\|gb157.2\|BE039784 | 92.7 | blastp |
| 1141 | radish\|gb164\|EV569172 | radish | 2205 | 234 | rice\|gb157.2\|BE039784 | 92.7 | blastp |
| 1142 | radish\|gb164\|EV571678 | radish | 2206 | 234 | rice\|gb157.2\|BE039784 | 92.7 | blastp |
| 1143 | radish\|gb164\|EW714068 | radish | 2207 | 234 | rice\|gb157.2\|BE039784 | 92.7 | blastp |
| 1144 | radish\|gb164\|EW715107 | radish | 2208 | 234 | rice\|gb157.2\|BE039784 | 92.7 | blastp |
| 1145 | radish\|gb164\|EW715768 | radish | 2209 | 234 | rice\|gb157.2\|BE039784 | 92.7 | blastp |
| 1146 | radish\|gb164\|EX755320 | radish | 2210 | 234 | rice\|gb157.2\|BE039784 | 92.1 | blastp |
| 1147 | radish\|gb164\|EX762413 | radish | 2211 | 234 | rice\|gb157.2\|BE039784 | 92.7 | blastp |
| 1148 | radish\|gb164\|EX762524 | radish | 2212 | 234 | rice\|gb157.2\|BE039784 | 92.1 | blastp |
| 1149 | radish\|gb164\|EX762893 | radish | 2213 | 234 | rice\|gb157.2\|BE039784 | 92.7 | blastp |
| 1150 | radish\|gb164\|EY902515 | radish | 2214 | 234 | rice\|gb157.2\|BE039784 | 92.1 | blastp |
| 1151 | radish\|gb164\|EY916898 | radish | 2215 | 234 | rice\|gb157.2\|BE039784 | 92.7 | blastp |
| 1152 | radish\|gb164\|T25179 | radish | 2216 | 234 | rice\|gb157.2\|BE039784 | 92.7 | blastp |
| 1153 | rice\|gb170\|OS02G06700 | rice | 2217 | 234 | rice\|gb157.2\|BE039784 | 98 | blastp |
| 1154 | rose\|gb157.2\|EC586094 | rose | 2218 | 234 | rice\|gb157.2\|BE039784 | 92.1 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 1155 | rye\|gb164\|BE494213 | rye | 2219 | 234 | rice\|gb157.2\|BE039784 | 96.69 | tblastn |
| 1156 | safflower\|gb162\|EL401182 | safflower | 2220 | 234 | rice\|gb157.2\|BE039784 | 90.7 | blastp |
| 1157 | safflower\|gb162\|EL403588 | safflower | 2221 | 234 | rice\|gb157.2\|BE039784 | 90.1 | blastp |
| 1158 | safflower\|gb162\|EL408982 | safflower | 2222 | 234 | rice\|gb157.2\|BE039784 | 86.09 | tblastn |
| 1159 | senecio\|gb170\|DY663041 | senecio | 2223 | 234 | rice\|gb157.2\|BE039784 | 88.7 | blastp |
| 1160 | sorghum\|gb161.crp\|AW120027 | sorghum | 2224 | 234 | rice\|gb157.2\|BE039784 | 98.7 | blastp |
| 1161 | sorghum\|gb161.crp\|BE238630 | sorghum | 2225 | 234 | rice\|gb157.2\|BE039784 | 98.7 | blastp |
| 1162 | sorghum\|gb161.crp\|BE367365 | sorghum | 2226 | 234 | rice\|gb157.2\|BE039784 | 98.7 | blastp |
| 1163 | soybean\|gb168\|AI967817 | soybean | 2227 | 234 | rice\|gb157.2\|BE039784 | 92.1 | blastp |
| 1164 | soybean\|gb168\|AJ388676 | soybean | 2228 | 234 | rice\|gb157.2\|BE039784 | 92.1 | blastp |
| 1165 | soybean\|gb168\|AW349445 | soybean | 2229 | 234 | rice\|gb157.2\|BE039784 | 91.4 | blastp |
| 1166 | spikemoss\|gb165\|DN837720 | spikemoss | 2230 | 234 | rice\|gb157.2\|BE039784 | 87.4 | blastp |
| 1167 | spikemoss\|gb165\|FE450939 | spikemoss | 2231 | 234 | rice\|gb157.2\|BE039784 | 87.4 | blastp |
| 1168 | spruce\|gb162\|CO216116 | spruce | 2232 | 234 | rice\|gb157.2\|BE039784 | 92.1 | blastp |
| 1169 | spruce\|gb162\|CO227952 | spruce | 2233 | 234 | rice\|gb157.2\|BE039784 | 92.1 | blastp |
| 1170 | spruce\|gb162\|DR449297 | spruce | 2234 | 234 | rice\|gb157.2\|BE039784 | 84.8 | blastp |
| 1171 | spruce\|gb162\|DR449808 | spruce | 2235 | 234 | rice\|gb157.2\|BE039784 | 82.1 | blastp |
| 1172 | spruce\|gb162\|DR474303 | spruce | 2236 | 234 | rice\|gb157.2\|BE039784 | 80.8 | blastp |
| 1173 | spruce\|gb162\|DR534167 | spruce | 2237 | 234 | rice\|gb157.2\|BE039784 | 82.1 | blastp |
| 1174 | spruce\|gb162\|DR579185 | spruce | 2238 | 234 | rice\|gb157.2\|BE039784 | 80.8 | blastp |
| 1175 | spurge\|gb161\|BE095303 | spurge | 2239 | 234 | rice\|gb157.2\|BE039784 | 92.72 | tblastn |
| 1176 | spurge\|gb161\|DV124297 | spurge | 2240 | 234 | rice\|gb157.2\|BE039784 | 91.4 | blastp |
| 1177 | strawberry\|gb164\|CO380977 | strawberry | 2241 | 234 | rice\|gb157.2\|BE039784 | 92.1 | blastp |
| 1178 | strawberry\|gb164\|CO817246 | strawberry | 2242 | 234 | rice\|gb157.2\|BE039784 | 93.4 | blastp |
| 1179 | strawberry\|gb164\|EX670929 | strawberry | 2243 | 234 | rice\|gb157.2\|BE039784 | 85.5 | blastp |
| 1180 | sugarcane\|gb157.3\|BQ529920 | sugarcane | 2244 | 234 | rice\|gb157.2\|BE039784 | 97.35 | tblastn |
| 1181 | sugarcane\|gb157.3\|BQ533000 | sugarcane | 2245 | 234 | rice\|gb157.2\|BE039784 | 98.7 | blastp |
| 1182 | sugarcane\|gb157.3\|CA076561 | sugarcane | 2246 | 234 | rice\|gb157.2\|BE039784 | 97.4 | blastp |
| 1183 | sugarcane\|gb157.3\|CA102375 | sugarcane | 2247 | 234 | rice\|gb157.2\|BE039784 | 96.03 | tblastn |
| 1184 | sugarcane\|gb157.3\|CA123229 | sugarcane | 2248 | 234 | rice\|gb157.2\|BE039784 | 96 | blastp |
| 1185 | sugarcane\|gb157.3\|CA137141 | sugarcane | 2249 | 234 | rice\|gb157.2\|BE039784 | 98.7 | blastp |
| 1186 | sugarcane\|gb157.3\|CA230074 | sugarcane | 2250 | 234 | rice\|gb157.2\|BE039784 | 92.72 | tblastn |
| 1187 | sunflower\|gb162\|AJ318263 | sunflower | 2251 | 234 | rice\|gb157.2\|BE039784 | 90.1 | blastp |
| 1188 | sunflower\|gb162\|CD848093 | sunflower | 2252 | 234 | rice\|gb157.2\|BE039784 | 91.4 | blastp |
| 1189 | sunflower\|gb162\|CD848805 | sunflower | 2253 | 234 | rice\|gb157.2\|BE039784 | 90.1 | blastp |
| 1190 | sunflower\|gb162\|EL430967 | sunflower | 2254 | 234 | rice\|gb157.2\|BE039784 | 82.8 | blastp |
| 1191 | switchgrass\|gb167\|DN149917 | switchgrass | 2255 | 234 | rice\|gb157.2\|BE039784 | 96.7 | blastp |
| 1192 | switchgrass\|gb167\|DN150990 | switchgrass | 2256 | 234 | rice\|gb157.2\|BE039784 | 98.7 | blastp |
| 1193 | switchgrass\|gb167\|FE599497 | switchgrass | 2257 | 234 | rice\|gb157.2\|BE039784 | 96 | blastp |
| 1194 | switchgrass\|gb167\|FE608350 | switchgrass | 2258 | 234 | rice\|gb157.2\|BE039784 | 96.7 | blastp |
| 1195 | switchgrass\|gb167\|FE625398 | switchgrass | 2259 | 234 | rice\|gb157.2\|BE039784 | 80.13 | tblastn |
| 1196 | switchgrass\|gb167\|FE627660 | switchgrass | 2260 | 234 | rice\|gb157.2\|BE039784 | 98.7 | blastp |
| 1197 | switchgrass\|gb167\|FE634044 | switchgrass | 2261 | 234 | rice\|gb157.2\|BE039784 | 98 | blastp |
| 1198 | switchgrass\|gb167\|FE637032 | switchgrass | 2262 | 234 | rice\|gb157.2\|BE039784 | 97.4 | blastp |
| 1199 | switchgrass\|gb167\|FL948269 | switchgrass | 2263 | 234 | rice\|gb157.2\|BE039784 | 82.12 | tblastn |
| 1200 | switchgrass\|gb167\|GD043911 | switchgrass | 2264 | 234 | rice\|gb157.2\|BE039784 | 80.13 | tblastn |
| 1201 | tamarix\|gb166\|EG966933 | tamarix | 2265 | 234 | rice\|gb157.2\|BE039784 | 93.4 | blastp |
| 1202 | tamarix\|gb166\|EG972900 | tamarix | 2266 | 234 | rice\|gb157.2\|BE039784 | 82.8 | blastp |
| 1203 | thellungiella\|gb167\|BY818453 | thellungiella | 2267 | 234 | rice\|gb157.2\|BE039784 | 94 | blastp |
| 1204 | thellungiella\|gb167\|DN775374 | thellungiella | 2268 | 234 | rice\|gb157.2\|BE039784 | 94 | blastp |
| 1205 | tobacco\|gb162\|AM816373 | tobacco | 2269 | 234 | rice\|gb157.2\|BE039784 | 81.5 | blastp |
| 1206 | tobacco\|gb162\|CN498843 | tobacco | 2270 | 234 | rice\|gb157.2\|BE039784 | 82.2 | blastp |
| 1207 | tobacco\|gb162\|CV019114 | tobacco | 2271 | 234 | rice\|gb157.2\|BE039784 | 91.4 | blastp |
| 1208 | tobacco\|gb162\|CV020233 | tobacco | 2272 | 234 | rice\|gb157.2\|BE039784 | 91.4 | blastp |
| 1209 | tobacco\|gb162\|CV021807 | tobacco | 2273 | 234 | rice\|gb157.2\|BE039784 | 92.7 | blastp |
| 1210 | tobacco\|gb162\|NTU66262 | tobacco | 2274 | 234 | rice\|gb157.2\|BE039784 | 90.7 | blastp |
| 1211 | tomato\|gb164\|BG123159 | tomato | 2275 | 234 | rice\|gb157.2\|BE039784 | 92.1 | blastp |
| 1212 | tomato\|gb164\|BG123562 | tomato | 2276 | 234 | rice\|gb157.2\|BE039784 | 92.7 | blastp |
| 1213 | tomato\|gb164\|U21078 | tomato | 2277 | 234 | rice\|gb157.2\|BE039784 | 92.7 | blastp |
| 1214 | triphysaria\|gb164\|BM357412 | triphysaria | 2278 | 234 | rice\|gb157.2\|BE039784 | 92.7 | blastp |
| 1215 | triphysaria\|gb164\|EX988766 | triphysaria | 2279 | 234 | rice\|gb157.2\|BE039784 | 91.4 | blastp |
| 1216 | triphysaria\|gb164\|EX990185 | triphysaria | 2280 | 234 | rice\|gb157.2\|BE039784 | 91.4 | blastp |
| 1217 | triphysaria\|gb164\|EX992752 | triphysaria | 2281 | 234 | rice\|gb157.2\|BE039784 | 91.4 | blastp |
| 1218 | volvox\|gb162\|AW676072 | volvox | 2282 | 234 | rice\|gb157.2\|BE039784 | 85 | blastp |
| 1219 | walnuts\|gb166\|CV197623 | walnuts | 2283 | 234 | rice\|gb157.2\|BE039784 | 92.1 | blastp |
| 1220 | walnuts\|gb166\|EL891118 | walnuts | 2284 | 234 | rice\|gb157.2\|BE039784 | 94.7 | blastp |
| 1221 | wheat\|gb164\|AL827137 | wheat | 2285 | 234 | rice\|gb157.2\|BE039784 | 97.4 | blastp |
| 1222 | wheat\|gb164\|BE398647 | wheat | 2286 | 234 | rice\|gb157.2\|BE039784 | 96 | blastp |
| 1223 | wheat\|gb164\|BE398957 | wheat | 2287 | 234 | rice\|gb157.2\|BE039784 | 97.4 | blastp |
| 1224 | wheat\|gb164\|BE405321 | wheat | 2288 | 234 | rice\|gb157.2\|BE039784 | 96 | blastp |
| 1225 | wheat\|gb164\|BE406789 | wheat | 2289 | 234 | rice\|gb157.2\|BE039784 | 95.4 | blastp |
| 1226 | wheat\|gb164\|BJ240969 | wheat | 2290 | 234 | rice\|gb157.2\|BE039784 | 80.79 | tblastn |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 1227 | wheat\|gb164\|BM135152 | wheat | 2291 | 234 | rice\|gb157.2\|BE039784 | 82.9 | blastp |
| 1228 | wheat\|gb164\|CA616908 | wheat | 2292 | 234 | rice\|gb157.2\|BE039784 | 94.7 | tblastn |
| 1229 | wheat\|gb164\|CJ652504 | wheat | 2293 | 234 | rice\|gb157.2\|BE039784 | 93.4 | blastp |
| 1230 | wheat\|gb164\|DN829631 | wheat | 2294 | 234 | rice\|gb157.2\|BE039784 | 80.92 | tblastn |
| 1231 | zamia\|gb166\|DY032098 | zamia | 2295 | 234 | rice\|gb157.2\|BE039784 | 91.4 | blastp |
| 1232 | barley\|gb157.3\|BE412461 | barley | 2296 | 236 | maize\|gb164\|AI619269 | 87.9 | blastp |
| 1233 | brachypodium\|gb169\|BE404324 | brachypodium | 2297 | 236 | maize\|gb164\|AI619269 | 86.4 | blastp |
| 1234 | cenchrus\|gb166\|EB653779 | cenchrus | 2298 | 236 | maize\|gb164\|AI619269 | 94.8 | blastp |
| 1235 | fescue\|gb161\|DT696747 | fescue | 2299 | 236 | maize\|gb164\|AI619269 | 85.6 | blastp |
| 1236 | leymus\|gb166\|EG375640 | leymus | 2300 | 236 | maize\|gb164\|AI619269 | 88.8 | blastp |
| 1237 | lovegrass\|gb167\|EH189611 | lovegrass | 2301 | 236 | maize\|gb164\|AI619269 | 92 | blastp |
| 1238 | maize\|gb170\|AI944307 | maize | 2302 | 236 | maize\|gb164\|AI619269 | 94.4 | blastp |
| 1239 | oat\|gb164\|BE439172 | oat | 2303 | 236 | maize\|gb164\|AI619269 | 85.58 | tblastn |
| 1240 | pseudoroegneria\|gb167\|FF354244 | pseudoroegneria | 2304 | 236 | maize\|gb164\|AI619269 | 88.4 | blastp |
| 1241 | rice\|gb170\|OS02G53790 | rice | 2305 | 236 | maize\|gb164\|AI619269 | 89.3 | blastp |
| 1242 | rice\|gb170\|OS07G43170 | rice | 2306 | 236 | maize\|gb164\|AI619269 | 90.1 | blastp |
| 1243 | sorghum\|gb161.crp\|AW011679 | sorghum | 2307 | 236 | maize\|gb164\|AI619269 | 95.8 | blastp |
| 1244 | sorghum\|gb161.crp\|CD231888 | sorghum | 2308 | 236 | maize\|gb164\|AI619269 | 90.6 | blastp |
| 1245 | sugarcane\|gb157.3\|CA072943 | sugarcane | 2309 | 236 | maize\|gb164\|AI619269 | 95.3 | blastp |
| 1246 | sugarcane\|gb157.3\|CA090072 | sugarcane | 2310 | 236 | maize\|gb164\|AI619269 | 95.8 | blastp |
| 1247 | switchgrass\|gb167\|DN145249 | switchgrass | 2311 | 236 | maize\|gb164\|AI619269 | 92.5 | blastp |
| 1248 | switchgrass\|gb167\|FE626130 | switchgrass | 2312 | 236 | maize\|gb164\|AI619269 | 93.4 | blastp |
| 1249 | arabidopsis\|gb165\|AT3G01300 | arabidopsis | 2313 | 237 | arabidopsis\|gb157.2\|AT5G15080 | 83.3 | blastp |
| 1250 | b_rapa\|gb162\|CA992096 | b_rapa | 2314 | 237 | arabidopsis\|gb157.2\|AT5G15080 | 82.5 | blastp |
| 1251 | canola\|gb161\|EE473973 | canola | 2315 | 237 | arabidopsis\|gb157.2\|AT5G15080 | 82.3 | blastp |
| 1252 | arabidopsis\|gb165\|AT1G60690 | arabidopsis | 2316 | 239 | arabidopsis\|gb165\|AT1G60680 | 84.1 | blastp |
| 1253 | arabidopsis\|gb165\|AT1G60710 | arabidopsis | 2317 | 239 | arabidopsis\|gb165\|AT1G60680 | 83.2 | blastp |
| 1254 | arabidopsis\|gb165\|AT1G60730 | arabidopsis | 2318 | 239 | arabidopsis\|gb165\|AT1G60680 | 84.44 | tblastn |
| 1255 | b_rapa\|gb162\|ES935213 | b_rapa | 2319 | 239 | arabidopsis\|gb165\|AT1G60680 | 82.1 | blastp |
| 1256 | canola\|gb161\|CD815566 | canola | 2320 | 239 | arabidopsis\|gb165\|AT1G60680 | 80.6 | blastp |
| 1257 | canola\|gb161\|CD819004 | canola | 2321 | 239 | arabidopsis\|gb165\|AT1G60680 | 81.5 | blastp |
| 1258 | canola\|gb161\|DY003163 | canola | 2322 | 239 | arabidopsis\|gb165\|AT1G60680 | 81.8 | blastp |
| 1259 | radish\|gb164\|EV524749 | radish | 2323 | 239 | arabidopsis\|gb165\|AT1G60680 | 81.6 | blastp |
| 1260 | radish\|gb164\|EV544729 | radish | 2324 | 239 | arabidopsis\|gb165\|AT1G60680 | 81.8 | blastp |
| 1261 | b_rapa\|gb162\|EX018587 | b_rapa | 2325 | 242 | arabidopsis\|gb165\|AT1G43910 | 85.3 | blastp |
| 1262 | canola\|gb161\|EE452442 | canola | 2326 | 242 | arabidopsis\|gb165\|AT1G43910 | 91.5 | blastp |
| 1263 | radish\|gb164\|EX749875 | radish | 2327 | 243 | arabidopsis\|gb157.2\|AT1G47530 | 91.94 | tblastn |
| 1264 | arabidopsis\|gb165\|AT4G30940 | arabidopsis | 2328 | 244 | arabidopsis\|gb157.2\|AT2G24240 | 88.3 | blastp |
| 1265 | castorbean\|gb160\|EG675736 | castorbean | 2329 | 244 | arabidopsis\|gb157.2\|AT2G24240 | 83.6 | blastp |
| 1266 | cotton\|gb164\|CO495384 | cotton | 2330 | 244 | arabidopsis\|gb157.2\|AT2G24240 | 83.3 | blastp |
| 1267 | nicotiana_benthamiana\|gb162\|CK280239 | nicotiana_benthamiana | 2331 | 244 | arabidopsis\|gb157.2\|AT2G24240 | 80.1 | blastp |
| 1268 | poplar\|gb170\|CA822859 | poplar | 2332 | 244 | arabidopsis\|gb157.2\|AT2G24240 | 81.2 | blastp |
| 1269 | poplar\|gb170\|CV237453 | poplar | 2333 | 244 | arabidopsis\|gb157.2\|AT2G24240 | 81.8 | blastp |
| 1270 | potato\|gb157.2\|CK243505 | potato | 2334 | 244 | arabidopsis\|gb157.2\|AT2G24240 | 83.1 | blastp |
| 1271 | soybean\|gb168\|AW586330 | soybean | 2335 | 244 | arabidopsis\|gb157.2\|AT2G24240 | 80.3 | blastp |
| 1272 | soybean\|gb168\|BP073481 | soybean | 2336 | 244 | arabidopsis\|gb157.2\|AT2G24240 | 80.4 | blastp |
| 1273 | barley\|gb157.3\|AL502083 | barley | 2337 | 246 | rice\|gb157.2\|BI807603 | 89.93 | tblastn |
| 1274 | brachypodium\|gb169\|BE471061 | brachypodium | 2338 | 246 | rice\|gb157.2\|BI807603 | 90.3 | blastp |
| 1275 | maize\|gb170\|AW066842 | maize | 2339 | 246 | rice\|gb157.2\|BI807603 | 88.1 | blastp |
| 1276 | maize\|gb170\|CF021466 | maize | 2340 | 246 | rice\|gb157.2\|BI807603 | 81 | blastp |
| 1277 | maize\|gb170\|LLCD975615 | maize | 2341 | 246 | rice\|gb157.2\|BI807603 | 88.8 | blastp |
| 1278 | maize\|gb170\|T12700 | maize | 2342 | 246 | rice\|gb157.2\|BI807603 | 91.8 | blastp |
| 1279 | sorghum\|gb161.crp\|AW066842 | sorghum | 2343 | 246 | rice\|gb157.2\|BI807603 | 92.9 | blastp |
| 1280 | sorghum\|gb161.crp\|AW747438 | sorghum | 2344 | 246 | rice\|gb157.2\|BI807603 | 82.1 | blastp |
| 1281 | sugarcane\|gb157.3\|BU925651 | sugarcane | 2345 | 246 | rice\|gb157.2\|BI807603 | 88.27 | tblastn |
| 1282 | switchgrass\|gb167\|FL745129 | switchgrass | 2346 | 246 | rice\|gb157.2\|BI807603 | 91.8 | blastp |
| 1283 | wheat\|gb164\|BE471061 | wheat | 2347 | 246 | rice\|gb157.2\|BI807603 | 89.7 | blastp |
| 1284 | rice\|gb170\|OS01G09340 | rice | 2348 | 247 | rice\|gb157.2\|AU068829 | 86.29 | tblastn |
| 1285 | brachypodium\|gb169\|AV835247 | brachypodium | 2349 | 248 | rice\|gb157.2\|AA752451 | 86.7 | blastp |
| 1286 | maize\|gb170\|BG835950 | maize | 2350 | 248 | rice\|gb157.2\|AA752451 | 80.7 | blastp |
| 1287 | sorghum\|gb161.crp\|BE598733 | sorghum | 2351 | 248 | rice\|gb157.2\|AA752451 | 81.4 | blastp |
| 1288 | sugarcane\|gb157.3\|CA101548 | sugarcane | 2352 | 248 | rice\|gb157.2\|AA752451 | 84.5 | blastp |
| 1289 | switchgrass\|gb167\|FE639520 | switchgrass | 2353 | 248 | rice\|gb157.2\|AA752451 | 88.9 | blastp |
| 1290 | barley\|gb157.3\|AL511842 | barley | 2354 | 250 | wheat\|gb164\|BE401454 | 98.4 | blastp |
| 1291 | brachypodium\|gb169\|BE488258 | brachypodium | 2355 | 250 | wheat\|gb164\|BE401454 | 93.4 | blastp |
| 1292 | fescue\|gb161\|DT699211 | fescue | 2356 | 250 | wheat\|gb164\|BE401454 | 90.2 | blastp |
| 1293 | leymus\|gb166\|CD808752 | leymus | 2357 | 250 | wheat\|gb164\|BE401454 | 97.6 | blastp |
| 1294 | pseudoroegneria\|gb167\|FF347865 | pseudoroegneria | 2358 | 250 | wheat\|gb164\|BE401454 | 99.2 | blastp |
| 1295 | rice\|gb170\|OS08G45190 | rice | 2359 | 250 | wheat\|gb164\|BE401454 | 81.9 | blastp |
| 1296 | sorghum\|gb161.crp\|AW287236 | sorghum | 2360 | 250 | wheat\|gb164\|BE401454 | 83.7 | blastp |
| 1297 | wheat\|gb164\|BE488191 | wheat | 2361 | 250 | wheat\|gb164\|BE401454 | 99.2 | blastp |
| 1298 | arabidopsis\|gb165\|AT1G70830 | arabidopsis | 2362 | 251 | arabidopsis\|gb165\|AT1G70850 | 85.4 | blastp |

TABLE 21-continued

Homologues of the identified polynucleotides and polypeptides which affect nitrogen use efficiency, fertilizer use efficiency, yield, growth rate, vigor, biomass, oil content, abiotic stress tolerance and/or water use efficiency of a plant

| Polyn. SEQ ID NO: | Cluster name | Organism | Polyp. SEQ ID | Homology to SEQ ID NO: | Core cluster name | % global identity | Algorithm |
|---|---|---|---|---|---|---|---|
| 1299 | arabidopsis\|gb165\|AT1G70830T4 | arabidopsis | 2363 | 251 | arabidopsis\|gb165\|AT1G70850 | 88.24 | tblastn |
| 1300 | barley\|gb157.3\|BE420890 | barley | 2364 | 254 | sorghum\|gb161.xeno\|T18303 | 81.5 | blastp |
| 1301 | brachypodium\|gb169\|BE401954 | brachypodium | 2365 | 254 | sorghum\|gb161.xeno\|T18303 | 83 | blastp |
| 1302 | cenchrus\|gb166\|EB656949 | cenchrus | 2366 | 254 | sorghum\|gb161.xeno\|T18303 | 89.1 | blastp |
| 1303 | fescue\|gb161\|DT686385 | fescue | 2367 | 254 | sorghum\|gb161.xeno\|T18303 | 80.1 | blastp |
| 1304 | leymus\|gb166\|CN466500 | leymus | 2368 | 254 | sorghum\|gb161.xeno\|T18303 | 82.2 | blastp |
| 1305 | maize\|gb170\|AF093538 | maize | 2369 | 254 | sorghum\|gb161.xeno\|T18303 | 91.3 | blastp |
| 1306 | maize\|gb170\|T18303 | maize | 2370 | 254 | sorghum\|gb161.xeno\|T18303 | 94.9 | blastp |
| 1307 | pseudoroegneria\|gb167\|FF348742 | pseudoroegneria | 2371 | 254 | sorghum\|gb161.xeno\|T18303 | 81.2 | blastp |
| 1308 | rice\|gb170\|OS09G19734T3 | rice | 2372 | 254 | sorghum\|gb161.xeno\|T18303 | 83.7 | blastp |
| 1309 | sugarcane\|gb157.3\|BQ533149 | sugarcane | 2373 | 254 | sorghum\|gb161.xeno\|T18303 | 97.5 | blastp |
| 1310 | switchgrass\|gb167\|DN141290 | switchgrass | 2374 | 254 | sorghum\|gb161.xeno\|T18303 | 89.1 | blastp |
| 1311 | switchgrass\|gb167\|DN141310 | switchgrass | 2375 | 254 | sorghum\|gb161.xeno\|T18303 | 89.5 | blastp |
| 1312 | wheat\|gb164\|BE406144 | wheat | 2376 | 254 | sorghum\|gb161.xeno\|T18303 | 81.5 | blastp |
| 1313 | wheat\|gb164\|BF200548 | wheat | 2377 | 254 | sorghum\|gb161.xeno\|T18303 | 81.9 | blastp |
| 1314 | wheat\|gb164\|X77733 | wheat | 2378 | 254 | sorghum\|gb161.xeno\|T18303 | 81.2 | blastp |
| 1315 | maize\|gb170\|CD936650 | maize | 2379 | 269 | sorghum\|gb161.xeno\|AW923465 | 89.12 | tblastn |
| 1315 | maize\|gb170\|CD936650 | maize | 2379 | 256 | sorghum\|gb161.crp\|AW923545 | 88.85 | tblastn |
| 1316 | aquilegia\|gb157.3\|DR915439 | aquilegia | 2380 | 257 | arabidopsis\|gb165\|AT1G71900 | 81.1 | blastp |
| 1317 | arabidopsis\|gb165\|AT1G34470 | arabidopsis | 2381 | 257 | arabidopsis\|gb165\|AT1G71900 | 80.11 | tblastn |
| 1318 | castorbean\|gb160\|EE258327 | castorbean | 2382 | 257 | arabidopsis\|gb165\|AT1G71900 | 81 | blastp |
| 1319 | castorbean\|gb160\|MDL29728M000834 | castorbean | 2383 | 257 | arabidopsis\|gb165\|AT1G71900 | 81.56 | tblastn |
| 1320 | grape\|gb160\|CB035795 | grape | 2384 | 257 | arabidopsis\|gb165\|AT1G71900 | 82.4 | blastp |
| 1321 | radish\|gb164\|EW714634 | radish | 2385 | 257 | arabidopsis\|gb165\|AT1G71900 | 89.74 | tblastn |
| 1322 | maize\|gb170\|CF021816 | maize | 2386 | 259 | sorghum\|gb161.xeno\|AW672541 | 88.3 | blastp |
| 1323 | maize\|gb170\|CO527882 | maize | 2387 | 259 | sorghum\|gb161.xeno\|AW672541 | 85 | blastp |
| 1324 | switchgrass\|gb167\|FE626524 | switchgrass | 2388 | 259 | sorghum\|gb161.xeno\|AW672541 | 85.4 | blastp |
| 1325 | sugarcane\|gb157.3\|CA069240 | sugarcane | 2389 | 262 | sorghum\|gb161.xeno\|BE123399 | 89.08 | tblastn |
| 1326 | sugarcane\|gb157.3\|CA078694 | sugarcane | 2390 | 262 | sorghum\|gb161.xeno\|BE123399 | 88.4 | blastp |
| 1327 | maize\|gb170\|AI901557 | maize | 2391 | 263 | sorghum\|gb161.xeno\|AI901557 | 86.2 | blastp |
| 1328 | sorghum\|gb161.crp\|AW286491 | sorghum | 2392 | 263 | sorghum\|gb161.xeno\|AI901557 | 98.5 | blastp |
| 1329 | sugarcane\|gb157.3\|CA068682 | sugarcane | 2393 | 263 | sorghum\|gb161.xeno\|AI901557 | 93.9 | blastp |
| 1330 | switchgrass\|gb167\|DN146139 | switchgrass | 2394 | 263 | sorghum\|gb161.xeno\|AI901557 | 83.6 | blastp |
| 1331 | switchgrass\|gb167\|FE604486 | switchgrass | 2395 | 263 | sorghum\|gb161.xeno\|AI901557 | 82.7 | blastp |
| 1332 | maize\|gb170\|CD945482 | maize | 2396 | 265 | maize\|gb164\|AI974922 | 81.53 | tblastn |
| 1333 | sorghum\|gb161.crp\|BE599314 | sorghum | 2397 | 265 | maize\|gb164\|AI974922 | 80.49 | tblastn |

Table 21: Provided are the homologous polypeptides (polypep.) and polynucleotides (polynucl.) of the genes and polypeptides identified in Table 20, which are capable of increase nitrogen use efficiency, fertilizer use efficiency, yield, growth rate, vigor, biomass, oil content, abiotic stress tolerance and/or water use efficiency of a plant. Homology was calculated as % of identity over the aligned sequences. The query sequences were polypeptide sequences SEQ ID NOs: 138-269 and the subject sequences are polypeptide sequences or nucleotide sequences which were dynamically translated in all six reading frames identified in the database based on greater than 80% identity to the query polypeptide sequences.

Example 3

Gene Cloning and Generation of Binary Vectors for Expression in Plants

Cloning Strategy

Genes presented in Examples 1 and 2 above were cloned into binary vectors for the generation of transgenic plants. For cloning, the full-length open reading frames (ORF) were first identified. EST clusters and in some cases mRNA sequences were analyzed to identify the entire open reading frame of each gene, by comparing the results of several translation algorithms to known proteins from other plant species.

In order to clone the full-length cDNAs, Reverse Transcription followed by PCR (RT-PCR) was performed on total RNA extracted from leaves, roots, fibers or other plant tissues, growing under either normal, nutrient deficient or other abiotic stress conditions. Total RNA extraction, production of cDNA and PCR amplification was performed using standard protocols described elsewhere (Sambrook J., E. F. Fritsch, and T. Maniatis. 1989. Molecular Cloning. A Laboratory Manual., 2nd Ed. Cold Spring Harbor Laboratory Press, New York.), which are well known to those skilled in the art. PCR products were purified using PCR purification kit (Qiagen) and sequencing of the amplified PCR products was performed, using ABI 377 sequencer (Applied Biosystems). In case of none or weak PCR product bands were visible on Ethidium Bromide—stained 1% agarose gels, 0.1-1 μL of the PCR product was used as a DNA template, and PCR amplification was effected using either the same or new set of primers, designed internally to the first set of primers. In such cases, the set of primers which is expected to produce the longer PCR product is designated External primers set (EF and ER for External-Forward and External-Reverse, respectively), and the set of primers which expected to produce the shorter PCR product is designated Nested primers set (NF and NR for Nested-Forward and Nested-Reverse, respectively), as illustrated in Table 22 below. Cloning of the cotton genes CT75, CT7, CT76, CT71, CT74, CT11, CT20, CT81, CT22, CT82, CT3, CT40, CT1, CT6, CT27 and CT2 was performed using only one set of primers, as detailed in WO Publication No: WO2005/121364.

To facilitate cloning of the cDNAs, a 7-12 bp extension was added to the 5' prime end of most of the primers. The primer extension includes an endonuclease restriction site (Table 22). The restriction sites were selected using two parameters: (a). The site does not exist in the cDNA sequence; and (b). The restriction sites in the forward and reverse primers are designed such that the digested cDNA is inserted in the sense formation into the binary vector utilized for transformation. Table 22, hereinbelow, provides the primers designation, restriction endonuclease sites added for the subsequent cloning, and sequences of each primer used for the amplification of the genes of the some embodiments of the invention.

TABLE 22

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE227 | SalI, | NUE227_EF_SalI | TTAGTCGACAGAGA AGAGGCAAGAACAA CTAG | 2564 | 101-F | GCTATGACCATGATT ACGCC | 2860 | pGXN |
| | XbaI | NUE227_ER_XbaI | TATCTAGACGATCG GTGTCCACTGTACA G | 2565 | | | | |
| | | NUE227_NF_SalI | TTAGTCGACACTAG CTGCATGGCAATGG | 2566 | | | | |
| | | NUE227_NR_XbaI | TTAGTCGACACTAG CTGCATGGCAATGG | 2567 | NUE227_NR_XbaI | TATCTAGATTAACGC GTTGATCGATCAGC | 2861 | |
| NUE233 | SalI, | NUE233_EF_SalI | TTAGTCGACCTCGA AATCCTTCCCAAGA C | 2568 | | | | pKsJ or Topo |
| | XbaI | NUE233_ER_XbaI | TATCTAGAGTCACA GAATAGTACACGTA CACAAC | 2569 | | | | |
| | | NUE233_NF_SalI | TTAGTCGACCGCAC GCTTCTCCATTTC | 2570 | | | | |
| | | NUE233_NR_XbaI | TATCTAGATCAAAC TAAGTACTCCAGTA ACAAC | 2571 | | | | |
| NUE237 | SalI, | NUE237_EF_SalI | AAAGTCGACCCTCT CTCTCGTTTCGATT CC | 2572 | 35S_1F | GGAGAGGACAGGCTT CTTGAG | 2862 | pGXN |
| | XbaI | NUE237_ER_XbaI | ATTCTAGATCAACC ACATAGCCTAGAGC AC | 2573 | NUE237_NR_XbaI | ACTCTAGAACTCTAT TAACAATGCACGGAG | 2863 | |
| | | NUE237_NF_SalI | AAAGTCGACAGATT CGATCCAACCAAAC C | 2574 | | | | |
| | | NUE237_NR_XbaI | ACTCTAGAACTCTA TTAACAATGCACGG AG | 2575 | | | | |
| NUE241 | SalI, | NUE241_EF_SalI | AAAGTCGACAATTC TTCTTTGTTTGCTT GC | 2576 | 35S_1F | GGAGAGGACAGGCTT CTTGAG | 2864 | pGXN |
| | XbaI | NUE241_ER_XbaI | ATTCTAGATAAATG CTGATATAGGACAA AGC | 2577 | NUE241_NR_XbaI | ATTCTAGATCACAAT AGAAACATCCTCCCT C | 2865 | |
| | | NUE241_NF_SalI | AAAGTCGACGAAGA AAACCCACAAAACC AG | 2578 | | | | |
| | | NUE241_NR_XbaI | ATTCTAGATCACAA TAGAAACATCCTCC CTC | 2579 | | | | |
| NUE242 | XbaI, | NUE242_EF_XbaI | TATCTAGAGAGAAG AGAGAGACTTTGAA GATG | 2580 | p35S_F2 | GGACAGGCTTCTTGA GATCCT | 2866 | pGXN |
| | SacI | NUE242_ER_SacI | TGAGCTCTTAAGAG TAGACACAACTCCT GCG | 2581 | NUE242_NR_SacI | TGAGCTCTTATTAGG AAGCAACTTCAAGAA ATG | 2867 | |
| | SalI, | NUE242_NF_SalI | TTAGTCGACTGAAG ATGGAAGCAAACTC TAAC | 2582 | | | | |
| | SacI | NUE242_NR_SacI | TGAGCTCTTATTAG GAAGCAACTTCAAG AAATG | 2583 | | | | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE255 | EcoRV | NUE255_EF_EcoRV | ATGATATCCCTCCAACCTCTCTCCCAAC | 2584 | p35S_F2 | GGACAGGCTTCTTGAGATCCT | 2868 | Topo |
| | | NUE255_ER_EcoRV | TAGATATCGATTGCTTCTTGTACTCTGATCATC | 2585 | NUE255_NR_EcoRV | TAGATATCTCATCATTTGATCAGCTTTAGCG | 2869 | |
| | | NUE255_NR_EcoRV | ATGATATCCAAGAATTAAGGTGTAGCAACC | 2586 | | | | |
| | | NUE255_NR_EcoRV | TAGATATCTCATCATTTGATCAGCTTTAGCG | 2587 | | | | |
| NUE269 | SalI, XbaI | NUE269_NF_SalI | TATGTCGACACAAGGAAATGATGGCTATTG | 2588 | 35S_1F | GGAGAGGACAGGCTTCTTGAG | 2870 | pGXN |
| | | NUE269_NR_XbaI | TATCTAGACACCACAACATGATAGCTTTTG | 2589 | NUE269_NR_XbaI | TATCTAGACACCACAACATGATAGCTTTTG | 2871 | |
| NUE521 | Sal, Xba | NUE521_NF_Sal | AAGGTCGACCTGGGAGCTAGCTTTGGAG | 2590 | p35S_F2 | GGACAGGCTTCTTGAGATCCT | 2872 | pGXN |
| | | NUE521_ER_Xba | ACTCTAGATCACACCGATTCCACACATAAC | 2591 | NUE521_NR_Xba | CGTCTAGATCAGATCGTGTTGAGCACTTGAGC | 2873 | |
| | | NUE521_NF_Sal | AAGGTCGACCTGGGAGCTAGCTTTGGAG | 2592 | | | | |
| | | NUE521_NR_Xba | CGTCTAGATCAGATCGTGTTGAGCACTTGAGC | 2593 | | | | |
| NUE554 | SmaI, SacI | NUE554_EF_SmaI | TCCCGGGCTCCGTCTCTAGGGTTTGAG | 2594 | 35S_1F | GGAGAGGACAGGCTTCTTGAG | 2874 | pGXN |
| | | NUE554_ER_SacI | TGAGCTCTCAGTGATTGGAACTCTAGATCTTG | 2595 | NUE554_ER_SacI | TGAGCTCTCAGTGATTGGAACTCTAGATCTTG | 2875 | |
| NUE562 | XbaI, SacI | NUE562_EF_XbaI | TATCTAGACTTGAGCTAGGGTTTTATCGC | 2596 | 35S_1F | GGAGAGGACAGGCTTCTTGAG | 2876 | pGXN |
| | | NUE562_ER_SacI | TGAGCTCTTAATGCAGACGGTAACATCTAGG | 2597 | NUE562_NR_SacI | TGAGCTCTTATGAAGATTACAGCCTCCTACC | 2877 | |
| | | NUE562_NF_XbaI | TATCTAGAAACAATGTCCGGGAGGAAGAAGAC | 2598 | | | | |
| | | NUE562_NR_SacI | TGAGCTCTTATGAAGATTACAGCCTCCTACC | 2599 | | | | |
| NUE567 | Sal, Xba | NUE567_EF_Sal | AGAGTCGACGTGACATAAAATCCATGGCTG | 2600 | 35S_1F | GGAGAGGACAGGCTTCTTGAG | 2878 | pGXN |
| | | NUE567_ER_Xba | TATCTAGATCAGCTTACACAAGCCCTTAGCA | 2601 | NUE567_NR_Xba | ACCTCTAGATCATTAAGTGGCTTTCCAGGAAG | 2879 | |
| | | NUE567_NF_Sal | GAGGTCGACAATCCATGGCTGAAGCTTG | 2602 | | | | |
| | | NUE567_NR_Xba | ACCTCTAGATCATTAAGTGGCTTTCCAGGAAG | 2603 | | | | |
| NUE568 | Sal, Xba | NUE568_EF_Sal | AGAGTCGACCGCAACGGAAAACAAATC | 2604 | 35S_1F | GGAGAGGACAGGCTTCTTGAG | 2880 | pGXN |
| | | NUE568_ER_Xba | TATCTAGAAGATAGGCTTATCTCAATGGCT | 2605 | NUE568_NR_Xba | TATCTAGATCATGTTCACTGAGTAACGATACTAACAG | 2881 | |
| | | NUE568_NF_Sal | TAGGTCGACACAAATCCGCCAATGGAAG | 2606 | | | | |
| | | NUE568_NR_Xba | TATCTAGATCATGTTCACTGAGTAACGATACTAACAG | 2607 | | | | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE573 | Sal, EF | NUE573_Sal | TAGGTCGACGAGAG AAATCCATGGAGAC G | 2608 | 35S_1F | GGAGAGGACAGGCTT CTTGAG | 2882 | pKsJ |
| | Sac | NUE573_ER_Sac | CGAGCTCAATTTCA GTACAGGATTTAAA CC | 2609 | NUE573_NR_Sac | CGAGCTCTCAGTACA GGATTTAAACCAAGA CA | 2883 | |
| | Sma, NF | NUE573_Sma | ACCCGGGAGACGAT GACGATGAAGGTTG | 2610 | | | | |
| | Sac NR | NUE573_Sac | CGAGCTCTCAGTAC AGGATTTAAACCAA GACA | 2611 | | | | |
| NUE575 | EcoRV | NUE575_NF_EcoRV | AAGATATCCCAAAC ACCAAACCCTCG | 2612 | NUE575_NF_EcoRV | AAGATATCCCAAACA CCAAACCCTCG | 2884 | pKsJ |
| | | NUE575_NR_EcoRV | TAGATATCTCATCA TATTCCTAGCTTAT CAACCTC | 2613 | 101_R | AAGTTGGGTAACGCC AGGGT | 2885 | |
| NUE585 | SalI, EF | NUE585_SalI | AAAGTCGACCGATT TCTGCTTCGATCTC TAC | 2614 | 35S_1F | GGAGAGGACAGGCTT CTTGAG | 2886 | pGXN |
| | XbaI | NUE585_ER_XbaI | ATTCTAGACCTTCT TCGATCTTCTTGAA CC | 2615 | NUE585_NR_XbaI | ATTCTAGATTAGTTT GCAGTTATCGCAGTG G | 2887 | |
| | | NUE585_NF_SalI | AAAGTCGACGTCTG GGTCGAAGTTAAAT AGG | 2616 | | | | |
| | | NUE585_NR_XbaI | ATTCTAGATTAGTT TGCAGTTATCGCAG TGG | 2617 | | | | |
| NUE587 | SalI, EF | NUE587_SalI | AAAGTCGACGTTCC ATTGGAGGAGAATC G | 2618 | 35S_1F | GGAGAGGACAGGCTT CTTGAG | 2888 | pGXN |
| | XbaI | NUE587_ER_XbaI | ATTCTAGATTCAAA AGGAAAATGGAGAG G | 2619 | NUE587_NR_XbaI | ATTCTAGATTATTTC AAACATGAAATGAGT TGC | 2889 | |
| | | NUE587_NF_SalI | AAAGTCGACAAAGG CTTGGAAAGGAAGG | 2620 | | | | |
| | | NUE587_NR_XbaI | ATTCTAGATTATTT CAAACATGAAATGA GTTGC | 2621 | | | | |
| NUE528 | Sac EF | NUE528_Sac | AGAGCTCAACCCTA ACGTTTCGATCG | 2622 | 101F | GCTATGACCATGATT ACGCC | 2890 | pGXN |
| | SalI, ER | NUE528_Sac | TGAGCTCTTCCAGA AGTAGCATCTTTCG | 2623 | NUE528_NR_Sac | TGAGCTCTGGCCTTC ACCCTCTATATCTC | 2891 | |
| | | NUE528_NF_SalI | AATGTCGACGAAGC GTCTGAGCCAGTCC | 2624 | | | | |
| | | NUE528_NR_Sac | TGAGCTCTGGCCTT CACCCTCTATATCT C | 2625 | | | | |
| NUE535 | Sal, NF | NUE535_Sal | ATTGTCGACGAGTA TGCTTTCCGATGGG | 2626 | 101_F | GCTATGACCATGATT ACGCC | 2892 | pGXN |
| | XbaI | NUE535_NR_XbaI | TTTCTAGACTATGA ATGAATCCGTGACT CTTG | 2627 | NUE535_NR_XbaI | TTTCTAGACTATGAA TGAATCCGTGACTCT TG | 2893 | |
| NUE538 | Sal, EF | NUE538_Sal | ATTGTCGACCACGA CCATTCTTCATTTT CC | 2628 | NUE538_EF_Sal | ATTGTCGACCACGAC CATTCTTCATTTTCC | 2894 | pKSJ |
| | Sma ER | NUE538_Sma | TCCCGGGTTAGAAC TGAGTCTGAAAGGA TGG | 2629 | NOS R | GCGGGACTCTAATCA TAAAAACC | 2895 | |
| NUE548 | Sal NF | NUE548_Sal | AATGTCGACGTCCT AATACTATACTCGC AATCC | 2630 | 101_F | GCTATGACCATGATT ACGCC | 2896 | pGXN |
| | Xba NR | NUE548_Xba | AATCTAGATCAACC AACTAGTTTGCAGC TCCT | 2631 | NUE548_NR_Xba | AATCTAGATCAACCA ACTAGTTTGCAGCTC CT | 2897 | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE537 | Sal, | NUE537_NF_Sal | TAAGTCGACCAAACAACATGTCTGCCTGTG | 2632 | 101_ER | GAAACACCATCTTCGTTCTTG | 2898 | pGXN |
|  | Xba | NUE537_NR_Xba | ATTCTAGATTAACACATCGTTTGGTGCATAGC | 2633 | NUE537_NF_Sal | TAAGTCGACCAAACAACATGTCTGCCTGTG | 2899 |  |
| NUE551 | Sal, | NUE551_NF_Sal | AATGTCGACGTTGATCAGTCAGCCCACTTC | 2634 | NUE551_seqF | GTCAAGCTGTGCTGTCTTCC | 2900 | pGXN |
|  | Xba | NUE551_ER_Xba | TATCTAGAGACATAATCCATCAACGGTTG | 2635 | 101_ER | GAAACACCATCTTCGTTCTTG | 2901 |  |
| NUE553 | Xba. | NUE553_EF_Xba | AATCTAGACTCACGAATCCACCGATCAG | 2636 | NUE553_NF_Xba | AATCTAGAGACACGGACCGAACAGCTAG | 2902 | pGXN |
|  | Sma | NUE553_ER_Sma | TCCCGGGACACACATCATGGCTGTTACAG | 2637 | NOS_R | GCGGGACTCTAATCATAAAAACC | 2903 |  |
|  |  | NUE553_NF_Xba | AATCTAGAGACACGGACCGAACAGCTAG | 2638 |  |  |  |  |
|  |  | NUE553_NR_Sma | TCCCGGGCGACTTCATATACAGACGGATG | 2639 |  |  |  |  |
| NUE511 | Xba. | NUE511_EF_Xba | AATCTAGAGATTAGGAGCAGGGACCAATC | 2640 | NUE511_EF_Xba | AATCTAGAGATTAGGAGCAGGGACCAATC | 2904 | pGXN |
|  | Sac | NUE511_NR_Sac | TGAGCTCTTAGGTACATGATGACATTTCAGCA | 2641 | 101_ER | GAAACACCATCTTCGTTCTTG | 2905 |  |
| NUE512 | Xba. | NUE512_NF_Xba | AATCTAGACCTATTGCTCATGATGTTTGA | 2642 | NUE512_NF_Xba | AATCTAGACCTATTGCTCATGATGTTTGA | 2906 | pGXN |
|  | Sac | NUE512_NR_Sac | TGAGCTCTTACAAAGGCAGGAAATACAGAAG | 2643 | Nos_R | GCGGGACTCTAATCATAAAAACC | 2907 |  |
| NUE542 | XbaI, | NUE542_EF_XbaI | TATCTAGAAATTTAGCTCGTTGATGATGG | 2644 | NUE542_seqF | GTACGTCTCCGTCCGACAAC | 2908 | pGXN |
|  | SacI | NUE542_ER_sacI | TGAGCTCCTAGTGTCCATGTCAATGATGTC | 2645 | 101_ER | GAAACACCATCTTCGTTCTTG | 2909 |  |
|  |  | NUE542_NF_XbaI | TATCTAGATAGCTCGTTGATGATGGAGG | 2646 |  |  |  |  |
|  |  | NUE542_NR_SacI | TGAGCTCTTATCCATGTCAATGATGTCCATC | 2647 |  |  |  |  |
| NUE569 | SalI | NUE569_NF_SalI | AAAGTCGACGCTACTGCTTCTTCTGTTCACC | 2648 | 35S_1F | GGAGAGGACAGGCTTCTTGAG | 2910 | pGXN |
|  | SacI | NUE569_NR_SacI | TGAGCTCTACTACCATAGAACTGAAGAAGAAGTC | 2649 | NUE569_seqR | GAGATGGAGCCTTGTCATGA | 2911 |  |
| NUE244 | SalI, | NUE244_NF_SalI | TTAGTCGACTAGACTGATGGGAAGTGTTCC | 2650 | 35S_1F | GGAGAGGACAGGCTTCTTGAG | 2912 | pGXN |
|  | XbaI | NUE244_NR_XbaI | TATCTAGACTACTACACGGATTGCCCAAAC | 2651 | NUE244_NR_XbaI | TATCTAGACTACTACACGGATTGCCCAAAC | 2913 |  |
| NUE577 |  | NUE577_NF_XbaI | AATCTAGAGTTTATCTTGTTTTGGGTTTGG | 2652 | 35S_1F | GGAGAGGACAGGCTTCTTGAG | 2914 | TopoB |
|  |  | NUE577_NR_SmaI | TCCCGGGGTGAAAGATCTCAGACCACCTC | 2653 | NUE577_NR_SmaI | TCCCGGGGTGAAAGATCTCAGACCACCTC | 2915 |  |
| NUE253 | XbaI, | NUE253_EF_XbaI | TATCTAGACTTCTTCCTCCATATCACACG | 2654 | 35S_1F | GGAGAGGACAGGCTTCTTGAG | 2916 | pKSJ |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| | SmaI | NUE253_ER_SmaI | TCCCGGGTCACGTG GCATGCATGATCTG | 2655 | | | | |
| | | NUE253_NF_XbaI | TATCTAGAAACAAT GGATGGGGAGGAGG AC | 2656 | NUE253_NR_SmaI | TCCCGGGTCATCACT CGCTCTCGAATTCC | 2917 | |
| | | NUE253_NR_SmaI | TCCCGGGTCATCAC TCGCTCTCGAATTC C | 2657 | | | | |
| NUE583 | XbaI. | NUE583_EF_XbaI | TATCTAGACACGAA TCAACCCACCAGAG | 2658 | 35S_1F | GGAGAGGACAGGCTT CTTGAG | 2918 | pGXN |
| | SacI | NUE583_ER_SacI | TGAGCTCTCAATGC CGATCATCAGTGCT AAG | 2659 | NUE583_NR_SacI | TGAGCTCTCATCAGA ACCGGAAGAAGTTGG | 2919 | |
| | | NUE583_NF_XbaI | TATCTAGAAACAAT GCCTTGGGTTTATC ATCC | 2660 | | | | |
| | | NUE583_NR_SacI | TGAGCTCTCATCAG AACCGGAAGAAGTT GG | 2661 | | | | |
| NUE235 | XbaI, | NUE235_EF_XbaI | TATCTAGAATTGAG CAGAGGAGCCATG | 2662 | 35S_1F | GGAGAGGACAGGCTT CTTGAG | 2920 | pGXN |
| | SacI | NUE235_ER_SacI | TGAGCTCCTACACA GGGTGCCAGATCTC | 2663 | NUE235_NR_SacI | TGAGCTCTTAAGTGC AAGTTGTCAATCCTA TTG | 2921 | |
| | | NUE235_NF_XbaI | TATCTAGAGGAGCC ATGGCCAAAATC | 2664 | | | | |
| | | NUE235_NR_SacI | TGAGCTCTTAAGTG CAAGTTGTCAATCC TATTG | 2665 | | | | |
| NUE231 GA | | | | | 35S_1F | GGAGAGGACAGGCTT CTTGAG | 2922 | |
| | | | | | NUE231_GA_R | CCTGAGAGGCGATC ATATC | 2923 | |
| NUE513 | XbaI, | NUE513_NF_XbaI | AATCTAGAGATGAT GGTTTGATGCAGAT G | 2666 | 35S_1F | GGAGAGGACAGGCTT CTTGAG | 2924 | pKSJ |
| | SmaI | NUE513_NR_SmaI | TCCCGGGCTAACGT AGTTTCTTACCAAC CAAAC | 2667 | NUE513_seqR | CTGCTTTGACATGGC TTAGAC | 2925 | |
| NUE516 | SalI, | NUE516_NF_SalI | AATGTCGACGAGAG AAGGGTGTAATGAG CTG | 2668 | p35S_F2 | GGACAGGCTTCTTGA GATCCT | 2926 | pGXN |
| | XbaI | NUE516_NR_XbaI | TATCTAGATCATCA GTAGGGGTTCCTAT GTGG | 2669 | NUE516_NR_XbaI | TATCTAGATCATCAG TAGGGGTTCCTATGT GG | 2927 | |
| NUE223 | SalI, | NUE223_NF_SalI | AAAGTCGACCAAGA GGTAGCACATCCTC TCC | 2670 | 35S_1F | GGAGAGGACAGGCTT CTTGAG | 2928 | pGXN |
| | XbaI | NUE223_NR_XbaI | ATTCTAGACCGGAT TGAACTAATTAACG AC | 2671 | NUE223_NR_XbaI | ATTCTAGACCGGATT GAACTAATTAACGAC | 2929 | |
| NUE540 | SalI, | NUE540_NF_SalI | AAAGTCGACAGGAA GATTGTGAGCATTG AAG | 2672 | 35S_1F | GGAGAGGACAGGCTT CTTGAG | 2930 | pGXN |
| | XbaI | NUE540_NR_XbaI | ATTCTAGACACCTA ATGATCTCACTTGT AAGG | 2673 | NUE540_ER_NdeI | CATACCAACATGTTC GACCAC | 2931 | |
| NUE544 | SalI, | NUE544_EF_SalI | TTAGTCGACAGCCT TGCCTTGTTTCTTC | 2674 | 35S_1F | GGAGAGGACAGGCTT CTTGAG | 2932 | pKSJ |
| | SmaI | NUE544_ER_SmaI | TCCCGGGCAACTTA TACACTCAACCAAA GC | 2675 | NUE544_NR_SmaI | TCCCGGGCTTTCATC CATGTGTGCAGTG | 2933 | |
| | | NUE544_NF_SalI | TTAGTCGACCATAC ACACAGTGAGAG GTAGG | 2676 | | | | |
| | | NUE544_NR_SmaI | TCCCGGGCTTTCAT CCATGTGTGCAGTG | 2677 | | | | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE560 | XbaI, | NUE560_EF_XbaI | AATCTAGAAGAAACCCAGAGGAGCAGC | 2678 | 35S_1F | GGAGAGGACAGGCTTCTTGAG | 2934 | pGXN |
| | SacI | NUE560_ER_SacI | CGAGCTCAAGGGATTATTATTGCAGGTTG | 2679 | NUE560_NR_SacI | TGAGCTCCTACTTCTAGGCCTTGTTGCTGC | 2935 | |
| | | NUE560_NF_XbaI | AATCTAGAGAAGCAGGAAGGAAGCAGAG | 2680 | | | | |
| | | NUE560_NR_SacI | TGAGCTCCTACTTCTAGGCCTTGTTGCTGC | 2681 | | | | |
| NUE563 | XbaI, | NUE563_EF_XbaI | AATCTAGAGATAACATCAGTAGTTCGCAGC | 2682 | NUE563_NF_XbaI | ATTCTAGATCACAGCAACACAATCACCAC | 2936 | pGXN |
| | SacI | NUE563_ER_SacI | CGAGCTCAACACACTCACACCAAAAGTCC | 2683 | 101_R | AAGTTGGGTAACGCCAGGGT | 2937 | |
| | | NUE563_NF_XbaI | ATTCTAGATCACAGCAACACAATCACCAC | 2684 | | | | |
| | | NUE563_NR_SacI | TGAGCTCCACTGCTACTGAAGGCAAATTC | 2685 | | | | |
| NUE565 | XbaI, | NUE565_EF_XbaI | ATTCTAGATTTTCCTGGATTTTGTTTCTC | 2686 | 35S_1F | GGAGAGGACAGGCTTCTTGAG | 2938 | pGXN |
| | SacI | NUE565_ER_SacI | TGAGCTCTCAATTAAAGAGTTACCCTAACG | 2687 | NUE565_NR_SacI | TGAGCTCCTACTTGAGCCTTCTAGCTCTGTTC | |  |
| | | NUE565_NF_XbaI | ATTCTAGAGATTTGGGGAAAAGCTATGG | 2688 | | | | |
| | | NUE565_NR_SacI | TGAGCTCCTACTTGAGCCTTCTAGCTCTGTTC | 2689 | | | | |
| NUE566 | SalI | NUE566_EF_SalI | TACGTCGACTTCACATGTCTTGACTAGTTCATATG | 2690 | 35S_1F | GGAGAGGACAGGCTTCTTGAG | 2940 | Topo |
| | | NUE566_ER_SalI | TAAGTCGACACGATACATTCAATACAATCACC | 2691 | NUE566_R | CGAAGGCATAGACGTCTGTC | 2941 | |
| | | NUE566_NF_SalI | TTAGTCGACCTTCCATCATGCTCCCAAAG | 2692 | | | | |
| | | NUE566_NR_SalI | TAAGTCGACTCAACTCAGCATCACGTCTCAGC | 2693 | | | | |
| NUE586 | SalI, | NUE586_EF_SalI | AATGTCGACTCGTTTCTCCTCTAACGTCAAC | 2694 | 35S_1F | GGAGAGGACAGGCTTCTTGAG | 2942 | pKSJ |
| | SamI | NUE586_ER_SmaI | TCCCGGGTCAGCAGCTCTCTGTCTGTTAC | 2695 | NUE586_R | CATCGAAGCACTTCTCAACTG | 2943 | |
| | | NUE586_NF_SalI | ATAGTCGACGTTTAACATAGTTGGGGCTAGG | 2696 | | | | |
| | | NUE586_NR_SmaI | CCCCGGGATAAGCCAGGAGATGAAAGGAG | 2697 | | | | |
| NUE588 | SalI, | NUE588_NF_SalI | AAAGTCGACGATCGAAAAGAGAAGAGGAGC | 2698 | 35S_1F | GGAGAGGACAGGCTTCTTGAG | 2944 | pGXN |
| | XbaI | NUE588_NR_XbaI | ATTCTAGACTAATCTCTCTCCCTCCCTCC | 2699 | NUE588_NR_XbaI | ATTCTAGACTAATCTCTCTCCCTCCCTCC | 2945 | |
| NUE591 GA | | | | | 35S_1F | GGAGAGGACAGGCTTCTTGAG | 2946 | |
| | | | | | NUE591_GA_R | CTCTTGCAGCTCTTGATCTTC | 2947 | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE206 | XbaI, | NUE206_EF_XbaI | ATTCTAGAATTTACACAGACTTGTCGCTCTC | 2700 | 35S_1F | GGAGAGGACAGGCTTCTTGAG | 2948 | pGN |
|  | SalI | NUE206_ER_XbaI | TATCTAGACTTCTGATTCAGTGACTGTGAGC | 2701 | NUE206_NR_XbaI | TATCTAGATCATCAGTGACTGTGAGCCTCGT | 2949 |  |
|  |  | NUE206_NF_SalI | ATAGTCGACAACAATGGACAAATTTTGGAC | 2702 |  |  |  |  |
|  |  | NUE206_NR_XbaI | TATCTAGATCATCAGTGACTGTGAGCCTCGT | 2703 |  |  |  |  |
| NUE208 | XbaI, | NUE208_EF_XbaI | AATCTAGACTGAAAGAGAGAGAGGTATGGC | 2704 | 35S_1F | GGAGAGGACAGGCTTCTTGAG | 2950 | pGN |
|  | SacI | NUE208_ER_SacI | TGAGCTCTGAATTAGTCATCTATTGGGTCC | 2705 | NUE208_NR_SacI | TGAGCTCTTATTAGTCATCTATTGGGTCCTGAG | 2951 |  |
|  |  | NUE208_NF_XbaI | TATCTAGAAACAATGGCAGGTGAGGCAACTC | 2706 |  |  |  |  |
|  |  | NUE208_NR_SacI | TGAGCTCTTATTAGTCATCTATTGGGTCCTGAG | 2707 |  |  |  |  |
| NUE209 | SalI, | NUE209_EF_SalI | AATGTCGACTTTGTGATGACCCTTTTAAGG | 2708 | 35S_1F | GGAGAGGACAGGCTTCTTGAG | 2952 | pGN |
|  | XbaI | NUE209_ER_XbaI | ATTCTAGAGGTAGTTAGCCGGTCATGTTG | 2709 | NUE209_NR_XbaI | ATTCTAGATTATTAGCCGGTCATGTTGTAGTC | 2953 |  |
|  |  | NUE209_NF_SalI | AATGTCGACAACAATGGATTGGGAAAAACAGC | 2710 |  |  |  |  |
|  |  | NUE209_NR_XbaI | ATTCTAGATTATTAGCCGGTCATGTTGTAGTC | 2711 |  |  |  |  |
| NUE210 | SalI | NUE210_EF_SalI | TGAGTCGACGTCTTGAAATGTTTGGTGGGT | 2712 | 35S_1F | GGAGAGGACAGGCTTCTTGAG | 2954 | pGN |
|  | XbaI | NUE210_ER_XbaI | TATCTAGACTTACTTGCCCTTTGCTTATGA | 2713 | NUE210_NR_XbaI | TGTCTAGACTATGCTATGAGGAAAGAAACTAAGC | 2955 |  |
|  |  | NUE210_NF_SalI | AATGTCGACAACAATGTTTGGTGGGTTCAATGTG | 2714 |  |  |  |  |
|  |  | NUE210_NR_XbaI | TGTCTAGACTATGCTATGAGGAAAGAAACTAAGC | 2715 |  |  |  |  |
| NUE211 GeneArt |  |  |  |  | 35S_1F | GGAGAGGACAGGCTTCTTGAG | 2956 |  |
|  |  |  |  |  | NOS_R | GCGGGACTCTAATCATAAAAACC | 2957 |  |
| NUE212 | XbaI, | NUE212_EF_XbaI | ATTCTAGAATATCATAATGAAAGGGATTCG | 2716 | 35S_1F | GGAGAGGACAGGCTTCTTGAG | 2958 | pGN |
|  | SacI | NUE212_ER_SacI | TGAGCTCCCATTAGAACCGAGACTGAAG | 2717 | NUE212_NEW_NR_SacI | TGAGCTCTTATTAGAACCGAGACTGAAGATACTTA | 2959 |  |
|  |  | NUE212_NF_XbaI | TATCTAGAAACAATGAAAGGGATTCGCTCC | 2718 |  |  |  |  |
|  |  | NUE212_NR_SacI | TGAGCTCTTATTAGAACCGAGACTGAAGATACTTA | 2719 |  |  |  |  |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE221 | EcoRV | NUE221_EF_EcoRV | AAGATATCAATGAC TTTCCCCATCTATC C | 2720 | 35S_1F | GGAGAGGACAGGCTT CTTGAG | 2960 | pKSJ |
| | | NUE221_ER_EcoRV | ACGATATCAATCGA CCAACAACTAACAT TAC | 2721 | NUE221_NR_EcoRV | ATGATATCCATTACA TGTGTGTATCCGACG | 2961 | |
| | | NUE221_NF_EcoRV | AAGATATCCTTCTA ATAATCAACCGACA GG | 2722 | | | | |
| | | NUE221_NR_EcoRV | ATGATATCCATTAC ATGTGTGTATCCGA CG | 2723 | | | | |
| NUE222 | SalI, | NUE222_EF_SalI | ATAGTCGACGGGAA GTATCATTAGTTCA TTACC | 2724 | NUE222_seq_F1 | AGTTGCATCGATCTT GATCTTG | 2962 | pGN |
| | XbaI | NUE222_ER_XbaI | TATCTAGACTAGTA TCCCTAACGTAACA AAGACTC | 2725 | 101_ER | CTGCAAGGCGATTAA GTTGG | 2963 | |
| | | NUE222_NF_SalI | AATGTCGACTTACC ATGGGAGACTATAA CATG | 2726 | | | | |
| | | NUE222_NR_XbaI | TATCTAGACTACTA ACGTAACAAAGACT CTTCACA | 2727 | | | | |
| NUE229 | XbaI | NUE229_EF_XbaI | TATCTAGACTGTCT GTTTGCCTGTCGAG | 2728 | NUE229_seq_F1 | GCAAGGTTAGCTTCA TGACG | 2964 | pGN |
| | SmaI | NUE229_ER_SmaI | TCCCGGGATACTCA AATCAAATGAAAGT CCG | 2729 | 101_ER | GAAACACCATCTTCG TTCTTG | 2965 | |
| | | NUE229_NF_XbaI | CATCTAGACAACAA TGGCGAGGATGATC | 2730 | | | | |
| | | NUE229_NR_SmaI | TCCCGGGTTAGATA GAAGTTTATCCCAT CAGGG | 2731 | | | | |
| NUE254 | SalI | NUE254_EF_SalI | AATGTCGACAGTCT GCACTGGAAGGACA G | 2732 | NUE254_NF_SalI | AATGTCGACCTGGAA GGACAGCATGTCG | 2966 | pGN |
| | XbaI | NUE254_ER_XbaI | TATCTAGACTTGTT GCCAGCATCTCTTA TG | 2733 | 101_R | AAGTTGGGTAACGCC AGGGT | 2967 | |
| | | NUE254_NF_SalI | AATGTCGACCTGGA AGGACAGCATGTCG | 2734 | | | | |
| | | NUE254_NR_XbaI | TATCTAGACTATGA CTAGCTGATGGAGT CCTCC | 2735 | | | | |
| NUE267 | | NUE267_F | CTTCTTCAATGGCG ACGG | 2736 | NUE267_F | CTTCTTCAATGGCGA CGG | 2968 | Topo |
| | | NUE267_R | TAGTCATGCAAATA TTTAATCTTGGAAC CC | 2737 | 101_ER | GAAACACCATCTTCG TTCTTG | 2969 | |
| NUE519 | SalI, | NUE519_NF_SalI | TTAGTCGACTTAAG ATGGCCAAGGTTAA CG | 2738 | NUE519_NF_SalI | TTAGTCGACTTAAGA TGGCCAAGGTTAACG | 2970 | pGN |
| | XbaI | NUE519_NR_XbaI | TATCTAGACTAATG CCGTTGCTTCTAGT AATAG | 2739 | 101_ER | CTGCAAGGCGATTAA GTTGG | 2971 | |
| NUE549 | XbaI, | NUE549_EF_XbaI | TATCTAGATCCTCT CCCTAGCTAGCAAG | 2740 | NUE549_seq_F3 | CAGCTGTGGAAGGCA TCAAC | 2972 | pGN |
| | SacI | NUE549_ER_SacI | TGAGCTCCTAATCA CCCTGGCTGTTGAC | 2741 | 101_R | AAGTTGGGTAACGCC AGGGT | 2973 | |
| | | NUE549_NF_XbaI | TATCTAGATCCCTA GCTAGCAAGCTCTA G | 2742 | | | | |
| | | NUE549_NR_SacI | TGAGCTCCCTTAAT GCCATGCTGCG | 2743 | | | | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE572 | XbaI, | NUE572_NF_XbaI | ATTCTAGATACATCGTCTTCACCTAATTTTC | 2744 | 35S_1F | GGAGAGGACAGGCTTCTTGAG | 2974 | pGN |
|  | SacI | NUE572_NR_SacI | CGAGCTCAACAAGCAAAACTAAACGTGAAC | 2745 | NUE572_NR_SacI | CGAGCTCAACAAGCAAACTAAACGTGAAC | 2975 |  |
| NUE592 | EcoRV | NUE592_EF_EcoRV | ATGATATCAAATCCGGTGGAC | 2746 | 35S_1F | GGAGAGGACAGGCTTCTTGAG | 2976 | pKSJ |
|  |  | NUE592_ER_EcoRV | TAGATATCCAACACTCACTAGGGAGCACAG | 2747 | NUE592_NR_EcoRV | TAGATATCGTTGAACGCTCCACATCATG | 2977 |  |
|  |  | NUE592_NF_EcoRV | TAGATATCAGAATTCGCAGGGATGCC | 2748 |  |  |  |  |
|  |  | NUE592_NR_EcoRV | TAGATATCGTTGAACGCTCCACATCATG | 2749 |  |  |  |  |
| NUE248 | XbaI, | NUE248_NF_XbaI | GCTCTAGAAGGCGAGATGTGGGAGTC | 2750 | NUE248_NF_XbaI | GCTCTAGAAGGCGAGATGTGGGAGTC | 2978 | pGN |
|  | SacI | NUE248_NR_SacI | TGAGCTCCTACTAGGCCTTCTCCTTTGTTG | 2751 | NOS_R | GCGGGACTCTAATCATAAAAACC | 2979 |  |
| NUE590 | SacI | NUE590_EF_XbaI | AATCTAGACAACTGCAACTGCAACTAGC | 2752 | 35S_1F | GGAGAGGACAGGCTTCTTGAG | 2980 | TopoB |
|  |  | NUE590_ER_SacI | CGAGCTCACAGCTAAACATCAATCCTCTTC | 2753 |  |  |  |  |
|  |  | NUE590_NF_SacI | TGAGCTCTGCAAGCAATCACCAGTTTG | 2754 | NUE590_NR_SacI | TGAGCTCCTCATTTTATTTGCTGCGTG | 2981 |  |
|  |  | NUE590_NR_SacI | TGAGCTCCTCATTTTATTTGCTGCGTG | 2755 |  |  |  |  |
| NUE245 GA |  |  |  |  | 35S_1F | GGAGAGGACAGGCTTCTTGAG | 2982 |  |
|  |  |  |  |  | NUE245_GA_R1 | CTCGGTGTTCTTGATGGTCAC | 2983 |  |
| NUE520 FA |  |  |  |  | 35S_1F | GGAGAGGACAGGCTTCTTGAG | 2984 |  |
|  |  |  |  |  | NUE520_GA_R2 | TTCTTGACCTTGGTCAGCTTG | 2985 |  |
| NUE574 | SmaI | NUE574_EF_SmaI | Agattagtcccaaagattattcg | 2756 | 35S_1F | GGAGAGGACAGGCTTCTTGAG | 2986 | Topo |
|  |  | NUE574_ER_SmaI | Gacattgtggggaagctact | 2757 | NUE574_NR_SmaI | gcatgtaattgtagcttctttt | 2987 |  |
|  |  | NUE574_NF_SmaI | Gatacaaagaattctttctttt | 2758 |  |  |  |  |
|  |  | NUE574_NR_SmaI | gcatgtaattgtagctttctttt | 2759 |  |  |  |  |
| NUE224 | XbaI. | NUE224_EF_XbaI | TATCTAGAGTTTGCTTGCTTACCAGGAG | 2760 | p35S_F1 | GGAGAGGACAGGCTTCTTGAG | 2988 | pGXN |
|  | SmaI | NUE224_ER_SmaI | TCCCGGGTTAGCAGCATCGATCGTACACTAG | 2761 | NUE224_ER_SmaI | TCCCGGGTTAGCAGCATCGATCGTACACTAG | 2989 |  |
| NUE225 | SalI, | NUE225_NF_SalI | AATGTCGACGAGTTTACAAGAGACCCAGACG | 2762 | p35S_F1 | GGAGAGGACAGGCTTCTTGAG | 2990 | pGXN |
|  | XbaI | NUE225_NR_XbaI | ACTCTAGAATTCAGTCATAGATCGCCTTG | 2763 | NUE225_NR_XbaI | ACTCTAGAATTCAGTCATAGATCGCCTTG | 2991 |  |
| NUE230 GA |  |  |  |  | p35S_F1 | GGAGAGGACAGGCTTCTTGAG | 2992 |  |
|  |  |  |  |  | NUE230_GA_R1 | GGATCTTGATGTACACGTTTGG | 2993 |  |
| NUE234 GA |  |  |  |  | p35S_F1 | GGAGAGGACAGGCTTCTTGAG | 2994 |  |
|  |  |  |  |  | NUE234_GA_R1 | CGATGTTGCACCTCTTTGG | 2995 |  |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE239 GA | | | | | p35S_F1 NUE239_ GA_R1 | GGAGAGGACAGGCTT CTTGAG CGAAATCCTCTGGGA ATGAC | 2996 2997 | |
| NUE240 GA | | | | | p35S_F1 NUE240_ GA_R1 | GGAGAGGACAGGCTT CTTGAG CCTCAGTAGAGAGAG ACTCGTCG | 2998 2999 | |
| NUE246 GA | | | | | p35S_F1 NUE246_ GA_R1 | GGAGAGGACAGGCTT CTTGAG CAACACTTGCATCAC CCTAGTC | 3000 3001 | |
| NUE249 GA | | | | | p35S_F1 NUE249_ GA_R1 | GGAGAGGACAGGCTT CTTGAG CCACCTCAAGAACAG TAACGAG | 3002 3003 | |
| NUE250 GA | | | | | p35S_F1 NUE250_ GA_R1 | GGAGAGGACAGGCTT CTTGAG GAAGGTAGAGTGCAG CATGG | 3004 3005 | |
| NUE252 | XbaI, SacI | NUE252_ EF_XbaI NUE252_ ER_SacI NUE252_ NF_XbaI NUE252_ NR_SacI | TATCTAGATTGGTC ACAGGGGATAGGC TGAGCTCCTAAGAT GCTGCTTTCTCAGA CTATG TATCTAGAGAAATT GTGTTTGTTTGATG GG TGAGCTCCTACTAT GCCAAAGAACCTTC ATG | 2764 2765 2766 2767 | p35S_F1 NUE252_ SacI NR_ | GGAGAGGACAGGCTT CTTGAG TGAGCTCCTACTATG CCAAAGAACCTTCAT G | 3006 3007 | pGXN |
| NUE265 | XbaI, SacI | NUE265_ NF_XbaI NUE265_ NR_SacI | TATCTAGAGAGAAA TGACAAGTGTCTGG AAG TGAGCTCGGAGTGA TCACTACTGCTTCT CC | 2768 2769 | p35S_F1 NUE265_ NR_SacI | GGAGAGGACAGGCTT CTTGAG TGAGCTCGGAGTGAT CACTACTGCTTCTCC | 3008 3009 | pGXN |
| NUE268 | SalI, XbaI | NUE268_ NF_SalI NUE268_ NR_XbaI | AATGTCGACTGAAG ATGGCTGACGATTT G TATCTAGACTAGTC TTAGCCACCACCAG AAC | 2770 2771 | p35S_F1 NUE268_ NR_XbaI | GGAGAGGACAGGCTT CTTGAG TATCTAGACTAGTCT TAGCCACCACCAGAA C | 3010 3011 | pGXN |
| NUE514 | XbaI, SacI | NUE514_ EF_XbaI NUE514_ ER_SacI NUE514_ NF_XbaI NUE514_ NR_SacI | AATCTAGAGGATTG AGACATGCACTTAA CAG TGAGCTCTTTTGAG CACCTCTTATTTAG C AATCTAGAACTCAT CAGCAACTACAACG TG TGAGCTCCTACAAT ACACCTCTTGACAT CCTTC | 2772 2773 2774 2775 | p35S_F1 NUE514_ NR_SacI | GGAGAGGACAGGCTT CTTGAG TGAGCTCCTACAATA CACCTCTTGACATCC TTC | 3012 3013 | pGXN |
| NUE515 | SalI, XbaI | NUE515_ NF_SalI NUE515_ NR_XbaI | TAAGTCGACGATAC AATGAGAATGTTAG TTCTTC TATCTAGATCATCA CCATCGTCTTATCA ATGAAG | 2776 2777 | p35S_F1 NUE515_ NR_XbaI | GGAGAGGACAGGCTT CTTGAG TATCTAGATCATCAC CATCGTCTTATCAAT GAAG | 3014 3015 | pGXN |
| NUE523 | SmaI, | NUE523_ EF_SmaI | ACCCGGGTCGTCTC ATCAATTCAAGATC C | 2778 | p35S_F1 | GGAGAGGACAGGCTT CTTGAG | 3016 | Topo |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| | SacI | NUE523_ER_SacI | TGAGCTCCCCTTCAAACTAATCAATCTTG | 2779 | NUE523_ER_SacI | TGAGCTCCCCTTCAAACTAATCAATCTTG | 3-17 | |
| NUE525 GA | | | | | p35S_F1 | GGAGAGGACAGGCTTCTTGAG | 3018 | pQXYN |
| | | | | | NUE525_GA_R | GTACTGAAGCTCGTCCTGGAC | 3019 | |
| NUE527 | XbaI | NUE527_EF_XbaI | AATCTAGAAAGAGCACCACCAGAGCAG | 2780 | p35S_F1 | GGAGAGGACAGGCTTCTTGAG | 3020 | pKSJ |
| | EcoRV | NUE527_ER_EcoRV | TTGATATCCTTTATGTCACCATTCATCTCAG | 2781 | NUE527_ER_EcoRV | TTGATATCCTTTATGTCACCATTCATCTCAG | 3021 | |
| NUE532 | XbaI, | NUE532_EF_XbaI | AATCTAGACTGGTTTAGGAGACGAAAAGG | 2782 | p35S_F1 | GGAGAGGACAGGCTTCTTGAG | 3022 | pGXN |
| | SacI | NUE532_ER_SacI | AGAGCTCCTATCTCAACTCCATCGCCTCAG | 2783 | NUE532_NR_SacI | AGAGCTCCTACTACTCAACTTCTCTGATGATTCTC | 3023 | |
| | | NUE532_NF_XbaI | AATCTAGAAGTGCTCTCCGGTTTGAGG | 2784 | | | | |
| | | NUE532_NR_SacI | AGAGCTCCTACTACTCAACTTCTCTGATGATTCTC | 2785 | | | | |
| NUE533 GA | | | | | p35S_F1 | GGAGAGGACAGGCTTCTTGAG | 3024 | pQXYN |
| | | | | | NUE533_GA_R | GGTTAGACACGAGCTTCTCAGAC | 3025 | |
| NUE536 | XbaI, | NUE536_EF_XbaI | ATTCTAGAGCCTTCTGATTCCCACTCC | 2786 | p35S_F1 | GGAGAGGACAGGCTTCTTGAG | 3026 | pGXN |
| | SacI | NUE536_ER_SacI | TGAGCTCTGGAGTATCTGGTTTAGTTCGTC | 2787 | NUE536_NR_SacI | CGAGCTCAAAGTCTCACTCCGCACTACAC | 3027 | |
| | | NUE536_NF_XbaI | AATCTAGACCTACTATACTTGCAACCTCTCC | 2788 | | | | |
| | | NUE536_NR_SacI | CGAGCTCAAAGTCTCACTCCGCACTACAC | 2789 | | | | |
| NUE547 GA | | | | | p35S_F1 | GGAGAGGACAGGCTTCTTGAG | 3028 | pQXYN |
| | | | | | NUE547_GA_R | GTGTGCAGCTCGAACTTGG | 3029 | |
| NUE550 | SmaI | NUE550_EF_SmaI | ACCCGGGGTAACACTATCAAGAGACGATGAAG | 2790 | p35S_F1 | GGACAGGCTTCTTGAGATCCT | 3030 | pKSJ |
| | | NUE550_ER_SmaI | TCCCGGGGTTTACATTGTTCTCGTTTCAAATC | 2791 | NUE550_NR_SmaI | TCCCGGGAATCTTTATTAACGAAACAGCAG | 3031 | |
| | | NUE550_NF_SmaI | ACCCGGGCTATCAAGAGACGATGAAGGTG | 2792 | | | | |
| | | NUE550_NR_SmaI | TCCCGGGAATCTTTATTAACGAAACAGCAG | 2793 | | | | |
| NUE564 | XbaI, | NUE564_EF_XbaI | AATCTAGACTTCAAGCAGGCAGCACAC | 2794 | p35S_F1 | GGAGAGGACAGGCTTCTTGAG | 3032 | pGXN |
| | SacI | NUE564_ER_SacI | CGAGCTCAAAGGGTCCATCATAATCACAG | 2795 | NUE564_NR_SacI | TGAGCTCCTACATGTCCCTTAGATTGCTCTATTC | 3033 | |
| | | NUE564_NF_XbaI | TATCTAGAGGAAACCTTGAGCCATGG | 2796 | | | | |
| | | NUE564_NR_SacI | TGAGCTCCTACATGTCCCTTAGATTGCTCTATTC | 2797 | | | | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE576 | SalI, | NUE576_EF_SalI | AAAGTCGACAGGAACAGCAACAAAAGTAAGC | 2798 | p35S_F1 | GGAGAGGACAGGCTTCTTGAG | 3034 | pGXN |
| | SmaI | NUE576_ER_SmaI | TCCCGGGCTAAACTGTCCCATTCTGCGTG | 2799 | NUE576_NR_SmaI | TCCCGGGCTAAGTAGCATGAGTCTAGAGCTTGG | 3035 | |
| | | NUE576_NF_SalI | AAAGTCGACCAACAACCACACACACTCACAG | 2800 | | | | |
| | | NUE576_NR_SmaI | TCCCGGGCTAAGTAGCATGAGTCTAGAGCTTGG | 2801 | | | | |
| NUE579 | SalI, | NUE579_NF_SalI | AATGTCGACTCTCAAAACCCTAACTGTTTCC | 2802 | p35S_F1 | GGAGAGGACAGGCTTCTTGAG | 3036 | pGXN |
| | XbaI | NUE579_NR_XbaI | ATTCTAGACAGGATAATAGATAGTCACACGAGG | 2803 | NUE579_NR_XbaI | ATTCTAGACAGGATAATAGATAGTCACACGAGG | 3037 | |
| NUE581 | SalI, | NUE581_EF_SalI | AAAGTCGACCAAAAGAATCTGTCTTCTTCTCTG | 2804 | p35S_F1 | GGAGAGGACAGGCTTCTTGAG | 3038 | pGXN |
| | XbaI | NUE581_ER_XbaI | ATTCTAGACTATCCAAGAAGGAACAATGAGG | 2805 | NUE581_NR_XbaI | ACTCTAGATTAGAACCACAAAAGATTACAACATC | 3039 | |
| | | NUE581_NF_SalI | AAAGTCGACGGTAAAATATCTTTCTTGTGCAG | 2806 | | | | |
| | | NUE581_NR_XbaI | ACTCTAGATTAGAACCACAAAAGATTACAACATC | 2807 | | | | |
| MAB52 GA | | | | | 6669F | TCAGCCACCCAAACCATGAC | 3040 | pGN |
| | | | | | MAB52_R_Seq | GAAGTCCTGAGACCGTTGATAG | 3041 | |
| MAB106 | | MAB106_EF | GTTCCAGTTGAGCGAGCAG | 2808 | T7_1 | TACGACTCACTATAGGGCGA | 3042 | pGN |
| | EcoRV, | MAB106_ER_EcoRV | TTGATATCCCAGTCTGTTTATTGCATCATC | 2809 | MAB106_NR_EcoRV | AAGATATCGTGCTAAACTATACATCAAACGTG | 3043 | |
| | PstI | MAB106_NF_PstI | AACTGCAGGATCATCCTCACATTGCGAG | 2810 | | | | |
| | | MAB106_NR_EcoRV | AAGATATCGTGCTAAACTATACATCAAACGTG | 2811 | | | | |
| NUE251 GA | | | | | 35S_F1 | GGAGAGGACAGGCTTCTTGAG | 3044 | |
| | | | | | NUE251_GA_R | GAAGTACCACCAGTTGAAGAAGC | 3045 | |
| NUE545 | SalI, | NUE545_NF_SalI | TATGTCGACAGGTTATGGGAAGAAGCTAG | 2812 | NUE545_F | GCAACAATTGTGGAGTCAACAC | 3046 | pGXN |
| | XbaI | NUE545_NR_XbaI | TATCTAGATCATCAGTAGCCACGAACTTGTCTAG | 2813 | 101_R | AAGTTGGGTAACGCCAGGGT | 3047 | |
| NUE570 | Sal, | NUE570_NF_Sal | TTCGTCGACTAAGCACAAATGGCGACTC | 2814 | NUE570_SeqF | CTTTGAGACGTTAGCTGTTGAG | 3048 | pKSJ |
| | Sma | NUE570_NR_Sma | ACCCGGGTCAAGGAGCTGAAACACTAGAGTTACT | 2815 | 101_R | AAGTTGGGTAACGCCAGGGT | 3049 | |
| NUE571 | Sal, | NUE571_NF_Sal | GTAGTCGACTTCACATGGGAAGGATAAGAC | 2816 | NUE571_NF_Sal | GTAGTCGACTTCACATGGGAAGGATAAGAC | 3050 | pGXN |
| | Xba | NUE571_NR_Xba | AATCTAGATCACTGATATAGTCCACGTCCTAAGG | 2817 | 101_R | AAGTTGGGTAACGCCAGGGT | 3051 | |

TABLE 22-continued

PCR primers used for cloning and for screening positive clones

| Gene ID | Enz. | Primers for cloning | | SEQ ID NO: | Primers for screening | | SEQ ID NO: | Plas. |
|---|---|---|---|---|---|---|---|---|
| NUE578 | XbaI, | NUE578_EF_XbaI | AATCTAGAATATCCTCCCATTCTCATTCTG | 2818 | 35S_1F | GGAGAGGACAGGCTTCTTGAG | 3052 | pGXN |
| | SmaI | NUE578_ER_SmaI | TCCCGGGCTAATGCAATCTCCAACTCCAAG | 2819 | NUE578_NR_SmaI | TCCCGGGCTAAGAAAAGGTAGGAGAAGGAAGG | 3053 | |
| | | NUE578_NF_XbaI | AATCTAGAAGCGGAGAAGAGGAAGGAG | 2820 | | | | |
| | | NUE578_NR_SmaI | TCCCGGGCTAAGAAAGGTAGGAGAAGGAAGG | 2821 | | | | |
| NUE580 | XbaI, | NUE580_NF_XbaI | AATCTAGACGGAATATACATTTGCTTTGTG | 2822 | 35S_1F | GGAGAGGACAGGCTTCTTGAG | 3054 | pGXN |
| | SmaI | NUE580_NR_SmaI | TCCCGGGCTACTGCTGAATGCTCTCTTTGC | 2823 | NUE580_NR_SmaI | TCCCGGGCTACTGCTGAATGCTCTCTTTGC | 3055 | |
| NUE582 | XbaI | NUE582_NF_XbaI | AATCTAGAAATCATCCTTCCCCAACCTC | 2824 | 35S_1F | GGAGAGGACAGGCTTCTTGAG | 3056 | pGXN |
| | SmaI | NUE582_NR_SmaI | CCCCGGGACCCAAACAGTCATGCTAGG | 2825 | NUE582_NR_SmaI | CCCCGGGACCCAAACAGTCATGCTAGG | 3057 | |
| NUE584 | SalI, | NUE584_NF_SalI | AAAGTCGACAAGGTTGGAGATTGTGAAATTG | 2826 | 35S_1F | GGAGAGGACAGGCTTCTTGAG | 3058 | pGXN |
| | SacI | NUE584_NR_SacI | CGAGCTCATACTCTACGTTCCCGTGTGG | 2827 | NUE584_NR_SacI | CGAGCTCATACTCTACGTTCCCGTGTGG | 3059 | |
| NUE593 GA | | | | | 35S_1F | GGAGAGGACAGGCTTCTTGAG | 3060 | |
| | | | | | NUE593_GA_R | GTAGCCTGAACAGCAGAACC | 3061 | |
| CT1 | SmaI | Reverse | AAGTTGGGTAACGCCAGGGT | 2828 | | | | pKS |
| | SacI | Forward | GGTGGCTCCTACAAATGCCATC | 2829 | | | | |
| CT11 | SmaI | Reverse | AAGTTGGGTAACGCCAGGGT | 2830 | | | | pKS |
| | SacI | Forward | GGTGGCTCCTACAAATGCCATC | 2831 | | | | |
| CT2 | XbaI | Reverse | AAGTTGGGTAACGCCAGGGT | 2832 | | | | pKS |
| | | Forward | ATGGGGCAACATCACTTGGG | 2833 | | | | |
| CT20 | SmaI | Reverse | AAGTTGGGTAACGCCAGGGT | 2834 | | | | pKS |
| | SacI | Forward | GGTGGCTCCTACAAATGCCATC | 2835 | | | | |
| CT22 | SmaI | Reverse | AAGTTGGGTAACGCCAGGGT | 2836 | | | | pKS |
| | SacI | Forward | GGTGGCTCCTACAAATGCCATC | 2837 | | | | |
| CT27 | SmaI | Reverse | AAGTTGGGTAACGCCAGGGT | 2838 | | | | pKS |
| | EcoRV | Forward | GGTGGCTCCTACAAATGCCATC | 2839 | | | | |
| CT3 | SmaI | Reverse | AAGTTGGGTAACGCCAGGGT | 2840 | | | | pKS |
| | SacI | Forward | GGTGGCTCCTACAAATGCCATC | 2841 | | | | |
| CT40 | SmaI | Reverse | AAGTTGGGTAACGCCAGGGT | 2842 | | | | pKS |
| | SacI | Forward | GGTGGCTCCTACAAATGCCATC | 2843 | | | | |

TABLE 22-continued

PCR primers used for cloning and for screening positive clones

| Gene ID | Enz. | Primers for cloning | | SEQ ID NO: | Primers for screening | SEQ ID NO: | Plas. |
|---|---|---|---|---|---|---|---|
| CT6 | SmaI | Reverse | AAGTTGGGTAACGCCAGGGT | 2844 | | | pKS |
| | SacI | Forward | GGTGGCTCCTACAAATGCCATC | 2845 | | | |
| CT7 | SmaI | Reverse | AAGTTGGGTAACGCCAGGGT | 2846 | | | pKS |
| | EcoRV | Forward | GGTGGCTCCTACAAATGCCATC | 2847 | | | |
| CT71 | XbaI | Reverse | AAGTTGGGTAACGCCAGGGT | 2848 | | | pKS |
| | SacI | Forward | GGTGGCTCCTACAAATGCCATC | 2849 | | | |
| CT74 | SmaI | Reverse | AAGTTGGGTAACGCCAGGGT | 2850 | | | pKS |
| | SacI | Forward | GGTGGCTCCTACAAATGCCATC | 2851 | | | |
| CT75 | SmaI | Reverse | AAGTTGGGTAACGCCAGGGT | 2852 | | | pKS |
| | EcoRV | Forward | GGTGGCTCCTACAAATGCCATC | 2853 | | | |
| CT76 | SmaI | Reverse | AAGTTGGGTAACGCCAGGGT | 2854 | | | pKS |
| | SacI | Forward | GGTGGCTCCTACAAATGCCATC | 2855 | | | |
| CT81 | SmaI | Reverse | AAGTTGGGTAACGCCAGGGT | 2856 | | | pKS |
| | SacI | Forward | GGTGGCTCCTACAAATGCCATC | 2857 | | | |
| CT82 | SmaI | Reverse | AAGTTGGGTAACGCCAGGGT | 2858 | | | pKS |
| | SacI | Forward | GGTGGCTCCTACAAATGCCATC | 2859 | | | |

Table 22: Provided are the sequences of the primers used for cloning the indicated genes and for screening of cloned binary plasmids. Primers are provided from 5' → 3'. "EF" = external forward primer; "ER" = external reverse primer; "NF" = nested forward primer; "NR" = nested reverse primer. Unless indicated otherwise, all genes were cloned from RNA molecules. "GA" = GeneArt, synthetically prepared genes; "Enz." = Enzyme; "Plas." = Plasmid.

Each digested PCR product was inserted into a high copy vector originated from pBlue-script KS plasmid vector (pBlue-script KS plasmid vector, Hypertext Transfer Protocol://World Wide Web (dot) stratagene (dot) com/manuals/212205 (dot) pdf). In case of the high copy vector originated from pBlue-script KS plasmid vector (pGN) PCR product was inserted in the high copy plasmid upstream to the NOS terminator (SEQ ID NO:3064) originated from pBI 101.3 binary vector (GenBank Accession No. U12640, nucleotides 4417 to 4693). In other cases the PCR product was inserted into the pCR®-BluntII-TOPO® high copy vector (Zero-Blunt® TOPO® PCR cloning Kit, Invitrogene). Some of the genes were synthetically synthesized ordered from a commercial supplier (GeneArt, GmbH) those genes were received into the pQXYN, pGXN high copy vectors obtained from the suppliers.

Sequencing of the inserted genes was performed, using the ABI 377 sequencer (Applied Biosystems). In some cases, after confirming the sequences of the cloned genes, the cloned cDNA accompanied with the NOS terminator was introduced into the binary vectors pGI containing the 35S promoter via digestion with appropriate restriction endonucleases. In other cases the cloned cDNA accompanied with the 35S promoter was introduced into the pGI vector. In any case the insert was followed by single copy of the NOS terminator (SEQ ID NO: 3064). The digested products and the linearized plasmid vector were ligated using T4 DNA ligase enzyme (Roche, Switzerland)

For some of the cloned polynucleotides, instead of amplifying the sequence from cDNA, synthetic sequences were ordered from a commercial supplier (GeneArt, GmbH). Thus, no primers were used for the amplification of the synthetic genes. To optimize the coding sequences of the synthetic genes, codon-usage Tables calculated from plant transcriptomes were used (example of such Tables can be found in the Codon Usage Database available online at Hypertext Transfer Protocol://World Wide Web (dot) kazusa (dot) or (dot) jp/codon/). The optimized coding sequences is designed in a way that no changes are introduced in the encoded amino acid sequence while using codons preferred for expression in dicotyledonous plants mainly tomato and *Arabidopsis*; and monocotyledonous plants such as maize. Such optimized sequences promote better translation rate and therefore higher protein expression levels. To the optimized sequences flanking additional unique restriction enzymes sites were added- to facilitate the cloning of the genes into the binary vectors.

The pPI and pGI binary vector plasmids were used to introduce the gene constructs into plants. pPI plasmid was constructed by inserting a synthetic poly-(A) signal sequence, originating from pGL3 basic plasmid vector (Promega, Acc. No. U47295; bp 4658-4811) into the HindIII restriction site of the binary vector pBI101.3 (Clontech, Acc. No. U12640). In some cases the backbone binary plasmid used was pGI which is similar to pPI but the GUS gene was replaced by the GUS-Intron gene (Vancanneyt. G, et al MGG 220, 245-50, 1990). pPI or pGI plasmid was used to clone the polynucleotide sequences, initially under the control of 35S promoter [Odell, J T, et al. Nature 313, 810-812 (28 Feb. 1985); SEQ ID NO: 3063] or *Arabidopsis thaliana* promoter At6669 (SEQ ID NO:3064, PCT Publication No. WO2004/104162). The At6669 or the CaMV 35S promoter sequence (set forth in SEQ ID NO: 3063) is inserted in the pPI or pGI binary vector, upstream to the cloned genes by using the restriction enzymes HindIII and SalI or BamHI (Roche, Switzerland). The digested PCR product and the linearized plasmid vector were ligated using T4 DNA ligase enzyme (Roche, Switzerland), as described above.

60 µL of *E. coli*, strain DH5-α competent cells (about $10^9$ cells/mL) were transformed using 1 µl of ligation reaction mixture by electroporation, using a MicroPulser electroporator (Biorad), 0.2 cm cuvettes (Biorad) and EC-2 electroporation program (Biorad). *E. coli* cells were grown on 0.8 mL LB liquid medium at 37° C. for 1 hrs and 0.2 mL of the cell suspension were plated on LB-agar plates supplemented with the antibiotics kanamycin 50 mg/L (Sigma). Plates were then incubated at 37° C. for 16 hrs. Bacteria colonies were grown and expression was confirmed by PCR amplification using the primers sets detailed in Table 22, above, which were designed to span the inserted sequence in the binary vector.

PCR products were separated on 1.5% agarose gels and product sizes were estimated by comparing to DNA ladder (MBI Fermentas).

TABLE 23

Cloned sequences

| SEQ ID NO: of cloned or synthetic gene | Gene Name | SEQ ID NO: of the encoded polypeptide | Cluster | Cloning Method |
|---|---|---|---|---|
| 2398 | CT1 | 2523 | cotton\|gb164\|AI725990_T1 | cloned |
| 2399 | CT11 | 2524 | cotton\|gb164\|AI725968_T1 | cloned |
| 2400 | CT2 | 2525 | cotton\|gb164\|AI727334_T1 | cloned |
| 2401 | CT20 | 2526 | cotton\|gb164\|AI726497_T1 | cloned |
| 2402 | CT22 | 2527 | cotton\|gb164\|BG440027_T1 | cloned |
| 2403 | CT27 | 2528 | cotton\|gb164\|AF336280_T1 | cloned |
| 2404 | CT3 | 144 | cotton\|gb164\|AI725456_T1 | cloned |
| 2405 | CT40 | 145 | cotton\|gb164\|BE052317_T1 | cloned |
| 2406 | CT6 | 2529 | cotton\|gb164\|AI726479_T1 | cloned |
| 2407 | CT7 | 147 | cotton\|gb164\|AI727027_T1 | cloned |
| 2408 | CT71 | 148 | cotton\|gb164\|AI725508_T1 | cloned |
| 2409 | CT74 | 149 | cotton\|gb164\|AI725950_T1 | cloned |
| 2410 | CT75 | 2530 | cotton\|gb164\|AI726599_T1 | cloned |
| 2411 | CT76 | 2531 | cotton\|gb164\|AI726155_T1 | cloned |
| 2412 | CT81 | 2532 | cotton\|gb164\|AI726693_T1 | cloned |
| 2413 | CT82 | 153 | cotton\|gb164\|BQ402794_T1 | cloned |
| 2414 | MAB106 | 154 | barley\|gb157.2\|AL450627_T1 | cloned |
| 2415 | MAB52 | 155 | rice\|gb157.2\|AU070543_T1 | synthesized_optimized |
| 2416 | NUE206 | 158 | arabidopsis\|gb165\|AT4G2490_T1 | cloned |
| 2417 | NUE208 | 2533 | tomato\|gb164\|BG124666_T1 | cloned |
| 2418 | NUE209 | 160 | tomato\|gb164\|BG134403_T1 | cloned |
| 2419 | NUE210 | 2534 | tomato\|gb157\|TOMTRALTAB_T1 | cloned |
| 2420 | NUE211 | 162 | rice\|gb157.2\|AU174544_T1 | synthesized_optimized |
| 2421 | NUE212 | 163 | cotton\|gb164\|CO081293_T1 | cloned |
| 2422 | NUE221 | 164 | rice\|gb157.2\|BI305241_T1 | cloned |
| 2423 | NUE222 | 165 | arabidopsis\|gb165\|AT1G31820_T1 | cloned |
| 2424 | NUE223 | 166 | rice\|gb157.2\|AW069985_T1 | cloned |
| 2425 | NUE224 | 167 | rice\|gb157.2\|AW155063_T1 | cloned |
| 2426 | NUE225 | 168 | rice\|gb157.2\|BE039221_T1 | cloned |
| 2427 | NUE227 | 169 | rice\|gb157.2\|AU056888_T1 | cloned |
| 2428 | NUE228 | 170 | rice\|gb157.2\|AA753730_T1 | synthesized_optimized |
| 2429 | NUE229 | 2535 | maize\|gb164\|AW455682_T1 | cloned |
| 2430 | NUE230 | 172 | rice\|gb157.2\|AA749861_T1 | synthesized_optimized |
| 2431 | NUE231 | 173 | rice\|gb157.2\|AK108994_T1 | synthesized_optimized |
| 2432 | NUE233 | 174 | rice\|gb157.2\|CB640732_T1 | cloned |
| 2433 | NUE234 | 175 | poplar\|gb157.2\|BU868634_T1 | synthesized_optimized |
| 2434 | NUE235 | 176 | soybean\|gb162\|CA852963_T1 | cloned |
| 2435 | NUE237 | 177 | rice\|gb157.2\|BI811377_T1 | cloned |
| 2436 | NUE239 | 178 | poplar\|gb157.2\|BU880014_T1 | synthesized_optimized |
| 2437 | NUE240 | 179 | poplar\|gb157.2\|AJ407707_T1 | synthesized_optimized |
| 2438 | NUE241 | 180 | tomato\|gb164\|BG129806_T1 | cloned |
| 2439 | NUE242 | 2536 | tomato\|gb164\|BG791300_T1 | cloned |
| 2440 | NUE244 | 182 | soybean\|gb162\|CF808561_T1 | cloned |
| 2441 | NUE245 | 2537 | rice\|gb157.2\|AT003383_T1 | synthesized_optimized |
| 2442 | NUE246 | 184 | grape\|gb160\|CF207859_T1 | synthesized |
| 2443 | NUE248 | 2538 | maize\|gb157\|BG354535_T1 | cloned |
| 2444 | NUE249 | 186 | rice\|gb157.2\|AU029933_T1 | synthesized_optimized |
| 2445 | NUE250 | 187 | rice\|gb157.2\|AK102239_T1 | synthesized_optimized |
| 2446 | NUE251 | 188 | *sorghum*\|gb161.xeno\|AI947781_T1 | synthesized_optimized |
| 2447 | NUE252 | 189 | *arabidopsis*\|gb165\|AT1G58030_T1 | cloned |

TABLE 23-continued

Cloned sequences

| SEQ ID NO: of cloned or synthetic gene | Gene Name | SEQ ID NO: of the encoded polypeptide | Cluster | Cloning Method |
|---|---|---|---|---|
| 2448 | NUE253 | 190 | rice\|gb157.2\|AF145730_T1 | cloned |
| 2449 | NUE254 | 2539 | maize\|gb164\|AI600563_T1 | cloned |
| 2450 | NUE255 | 2540 | rice\|gb157.2\|CB000630_T1 | cloned |
| 2451 | NUE256 | 193 | wheat\|gb164\|BE415875_T1 | synthesized_optimized |
| 2452 | NUE265 | 194 | rice\|gb157.2\|BE039218_T1 | cloned |
| 2453 | NUE267 | 195 | *arabidopsis*\|gb165\|AT5G60680_T1 | cloned |
| 2454 | NUE268 | 196 | rice\|gb157.2\|AA750934_T1 | cloned |
| 2455 | NUE269 | 2541 | cotton\|gb164\|AI730085_T1 | cloned |
| 2456 | NUE49 | 2542 | maize\|gb154\|AW037179_T1 | synthesized_optimized |
| 2457 | NUE50 | 2543 | maize\|gb164\|AW287760_T1 | cloned |
| 2458 | NUE511 | 2544 | maize\|gb157\|AW360667_T1 | cloned |
| 2459 | NUE512 | 201 | *arabidopsis*\|gb157.2\|AT5G23460_T1 | cloned |
| 2460 | NUE513 | 2545 | *arabidopsis*\|gb157.2\|AT3G26100_T1 | cloned |
| 2461 | NUE514 | 2546 | soybean\|gb162\|SOYHPR_T1 | cloned |
| 2462 | NUE515 | 2547 | *arabidopsis*\|gb165\|AT1G44920_T1 | cloned |
| 2463 | NUE516 | 205 | *arabidopsis*\|gb157.2\|AT1G48210_T1 | cloned |
| 2464 | NUE519 | 2548 | wheat\|gb164\|BE445396_T1 | cloned |
| 2465 | NUE520 | 207 | rice\|gb157.2\|BI305493_T1 | synthesized |
| 2466 | NUE521 | 208 | rice\|gb157.2\|AU077950_T1 | cloned |
| 2467 | NUE523 | 209 | *sorghum*\|gb161.xeno\|AI901439_T1 | cloned |
| 2468 | NUE525 | 210 | *sorghum*\|gb161.xeno\|AW052978_T1 | synthesized_optimized |
| 2469 | NUE527 | 211 | *sorghum*\|gb161.xeno\|AW055409_T1 | cloned |
| 2470 | NUE528 | 212 | *sorghum*\|gb161.xeno\|AI372194_T1 | cloned |
| 2471 | NUE531 | 213 | rice\|gb157.2\|BI805136_T1 | synthesized_optimized |
| 2472 | NUE532 | 214 | maize\|gb164\|AW054475_T1 | cloned |
| 2473 | NUE533 | 215 | soybean\|gb166\|AW350050_T1 | cloned |
| 2474 | NUE535 | 2549 | *sorghum*\|gb161.crp\|BE599042_T1 | cloned |
| 2475 | NUE536 | 217 | maize\|gb164\|BQ279657_T1 | cloned |
| 2476 | NUE537 | 218 | barley\|gb157.2\|AJ234408_T1 | cloned |
| 2477 | NUE538 | 219 | *sorghum*\|gb161.xeno\|AW923729_T1 | cloned |
| 2478 | NUE539 | 220 | rice\|gb157.2\|AW155216_T1 | synthesized_optimized |
| 2479 | NUE540 | 2550 | *arabidopsis*\|gb157.2\|AT1G13980_T1 | cloned |
| 2480 | NUE542 | 2551 | *arabidopsis*\|gb157.2\|AT3G46280_T1 | cloned |
| 2481 | NUE543 | 223 | rice\|gb157.2\|AK063415_T1 | synthesized_optimized |
| 2482 | NUE544 | 2552 | cotton\|gb164\|BQ412384_T1 | cloned |
| 2483 | NUE545 | 2553 | cotton\|gb164\|AI055737_T1 | cloned |
| 2484 | NUE547 | 226 | *sorghum*\|gb161.xeno\|BI139559_T1 | synthesized_optimized |
| 2485 | NUE548 | 227 | *sorghum*\|gb161.xeno\|BQ279657_T1 | cloned |
| 2486 | NUE549 | 228 | *sorghum*\|gb161.xeno\|AF019147_T1 | cloned |
| 2487 | NUE550 | 229 | canola\|gb161\|EE559843_T1 | cloned |
| 2488 | NUE551 | 2554 | barley\|gb157.3\|BE420701_T1 | cloned |
| 2489 | NUE553 | 231 | barley\|gb157.3\|BE421829_T1 | cloned |
| 2490 | NUE554 | 232 | *sorghum*\|gb161.xeno\|AA011880_T1 | cloned |
| 2491 | NUE560 | 233 | rice\|gb157.2\|BE229552_T1 | cloned |
| 2492 | NUE562 | 2555 | rice\|gb157.2\|BE039784_T1 | cloned |
| 2493 | NUE563 | 235 | rice\|gb157.2\|AU057884_T1 | cloned |
| 2494 | NUE564 | 236 | maize\|gb164\|AI619269_T1 | cloned |
| 2495 | NUE565 | 237 | *arabidopsis*\|gb157.2\|AT5G15080_T1 | cloned |
| 2496 | NUE566 | 238 | *arabidopsis*\|gb165\|AT2G43700_T1 | cloned |
| 2497 | NUE567 | 239 | *arabidopsis*\|gb165\|AT1G60680_T1 | cloned |
| 2498 | NUE568 | 240 | *arabidopsis*\|gb165\|AT1G78450_T1 | cloned |
| 2499 | NUE569 | 241 | *arabidopsis*\|gb165\|AT2G03890_T1 | cloned |
| 2500 | NUE570 | 242 | *arabidopsis*\|gb165\|AT1G43910_T1 | cloned |
| 2501 | NUE571 | 243 | *arabidopsis*\|gb157.2\|AT1G47530_T1 | cloned |
| 2502 | NUE572 | 244 | *arabidopsis*\|gb157.2\|AT2G24240_T1 | cloned |
| 2503 | NUE573 | 245 | *arabidopsis*\|gb165\|AT4G15390_T1 | cloned |
| 2504 | NUE574 | 2556 | rice\|gb157.2\|BI807603_T1 | cloned |
| 2505 | NUE575 | 247 | rice\|gb157.2\|AU068829_T1 | cloned |
| 2506 | NUE576 | 2557 | rice\|gb157.2\|AA752451_T1 | cloned |
| 2507 | NUE577 | 249 | *arabidopsis*\|gb165\|AT1G67800_T1 | cloned |
| 2508 | NUE578 | 250 | wheat\|gb164\|BE401454_T1 | cloned |
| 2509 | NUE579 | 2558 | *arabidopsis*\|gb165\|AT1G70850_T1 | cloned |
| 2510 | NUE580 | 2559 | *arabidopsis*\|gb165\|AT2G35880_T1 | cloned |
| 2511 | NUE581 | 253 | *arabidopsis*\|gb165\|AT1G12845_T1 | cloned |
| 2512 | NUE582 | 2560 | *sorghum*\|gb161.xeno\|T18303_T1 | cloned |
| 2513 | NUE583 | 255 | rice\|gb157.2\|AU172665_T1 | cloned |
| 2514 | NUE584 | 2561 | *sorghum*\|gb161.crp\|AW923545_T1 | cloned |
| 2515 | NUE585 | 257 | *arabidopsis*\|gb165\|AT1G71900_T1 | cloned |

TABLE 23-continued

Cloned sequences

| SEQ ID NO: of cloned or synthetic gene | Gene Name | SEQ ID NO: of the encoded polypeptide | Cluster | Cloning Method |
|---|---|---|---|---|
| 2516 | NUE586 | 2562 | arabidopsis\|gb165\|AT1G72320__T1 | cloned |
| 2517 | NUE587 | 259 | sorghum\|gb161.xeno\|AW672541__T1 | cloned |
| 2518 | NUE588 | 260 | rice\|gb157.2\|AA750816__T1 | cloned |
| 2519 | NUE590 | 2563 | sorghum\|gb161.xeno\|AI622209__T1 | cloned |
| 2520 | NUE591 | 262 | sorghum\|gb161.xeno\|BE123399__T1 | synthesized_optimized |
| 2521 | NUE592 | 263 | sorghum\|gb161.xeno\|AI901557__T1 | cloned |
| 2522 | NUE593 | 264 | arabidopsis\|gb165\|AT2G04066__T1 | synthesized_optimized |

Table 23. Provided are the cloned or synthetically produced genes and their encoded polypeptides, along with the sequence identifiers, organisms from which the genes were cloned.

Example 4

Generation of Transgenic Plants Expressing the Polynucleotides of Some Embodiments of the Invention Arabidopsis transformation was performed according to Clough S J, Bent A F. (1998) Floral dip: a simplified method for Agrobacterium-mediated transformation of Arabidopsis thaliana. Plant J. 16(6): 735-43; and Desfeux C, Clough S J, Bent A F. (20000 Female reproductive tissues are the primary targets of Agrobacterium-mediated transformation by the Arabidopsis floral-dip method. Plant Physiol. 123(3): 895-904.). Briefly—Arabidopsis thaliana var Columbia ($T_0$ plants) were transformed using the Floral Dip procedure described by Clough S J and Bent A F (10) and by Desfeux C et al. (11), with minor modifications. Arabidopsis thaliana Columbia (Col0) $T_0$ Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hour light/dark cycles. The $T_0$ plants were ready for transformation six days prior to anthesis. Single colonies of Agrobacterium carrying the binary vectors harboring the polynucleotides of some embodiments of the invention were cultured in LB medium supplemented with kanamycin (50 mg/L) and gentamycin (50 mg/L). The cultures were incubated at 28° C. for 48 hrs under vigorous shaking and centrifuged at 4000 rpm for 5 minutes. The pellets comprising Agrobacterium cells were resuspended in a transformation medium which contained half-strength (2.15 g/L) Murashige-Skoog (MS) medium (Duchefa); 0.044 µM benzylamino purine (Sigma); 112 µg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was performed by inverting each plant into an Agrobacterium suspension such that the flowering stem is submerged for 3-5 seconds. Each inoculated $T_0$ plant was immediately placed in a plastic tray, then covered with clear plastic dome to maintain humidity and kept in the dark at room temperature for 18 hrs to facilitate infection and transformation. Transformed (transgenic) plants were then uncovered and transferred to a greenhouse for recovery and maturation. The transgenic $T_0$ plants were grown in the greenhouse for 3-5 weeks until siliques maturation, and then seeds were harvested and kept at room temperature until sowing.

For generating T1 and $T_2$ transgenic plants harboring the polynucleotides of some embodiments of the invention, seeds collected from transgenic $T_0$ plants were surface-sterilized by soaking in 70% ethanol for 1 minute, followed by soaking in 5% sodium hypochlorite and 0.05% Triton X-100 for 5 minutes. The surface-sterilized seeds were thoroughly washed in sterile distilled water then placed on culture plates containing half-strength Murashige-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital $T_1$ Arabidopsis plants were transferred to fresh culture plates for another week of incubation. Following incubation, the $T_1$ plants were removed from culture plates and planted in growth mix contained in 250 ml pots. The transgenic plants were allowed to grow in a greenhouse to maturity. Seeds harvested from $T_1$ plants were cultured and grown to maturity as $T_2$ plants under the same conditions as used for culturing and growing the $T_1$ plants. At least 10 independent transformation events were created from each construct for which bulk of T2 seeds were collected.

The NUE584 (SEQ ID NO: 2514), NUE253 (SEQ ID NO: 2448), NUE533 (SEQ ID NO: 2473), NUE577 (SEQ ID NO: 2507), NUE590 (SEQ ID NO: 2519) and NUE562 (SEQ ID NO: 2492) genes were cloned, introduced in Arabidopsis and T2 seeds were produced.

NUE540 (SEQ ID NO: 2479), NUE549 (SEQ ID NO: 2486), and NUE533 (SEQ ID NO: 2473) developed purple healthy plants, suggesting increased vigor of the transgenic plants.

NUE591 (SEQ ID NO: 2520) produced light green plants. This phenotype relates the gene to the photosynthetic capacity of the plant at different nitrogen fertilization levels.

Example 5

Assay 1: Improved Nitrogen Use Efficiency In Vitro (Tissue Culture Assay)

Surface sterilized seeds were sown in basal media [50% Murashige-Skoog medium (MS) supplemented with 0.8% plant agar as solidifying agent] in the presence of Kanamycin (used as a selecting agent). After sowing, plates were transferred for 2-3 days for stratification at 4° C. and then grown at 25° C. under 12-hour light 12-hour dark daily cycles for 7 to 10 days. At this time point, seedlings randomly chosen were carefully transferred to plates containing ½ MS media (15 mM N) for the normal nitrogen concentration treatment and 0.75 mM nitrogen for the low nitrogen concentration treatments. Each plate contained 5 seedlings of the same transgenic event, and 3-4 different plates (replicates) for each event. For each polynucleotide of the invention at least four independent transformation events were analyzed from each construct. Plants expressing the polynucleotides of the invention were compared to the average measurement of the control plants (empty vector or GUS reporter gene under the same promoter) used in the same experiment.

Digital Imaging

A laboratory image acquisition system, which consists of a digital reflex camera (Canon EOS 300D) attached with a 55 mm focal length lens (Canon EF-S series), mounted on a reproduction device (Kaiser RS), which includes 4 light units (4×150 Watts light bulb) and located in a darkroom, was used for capturing images of plantlets sawn in agar plates.

Figure 3B:
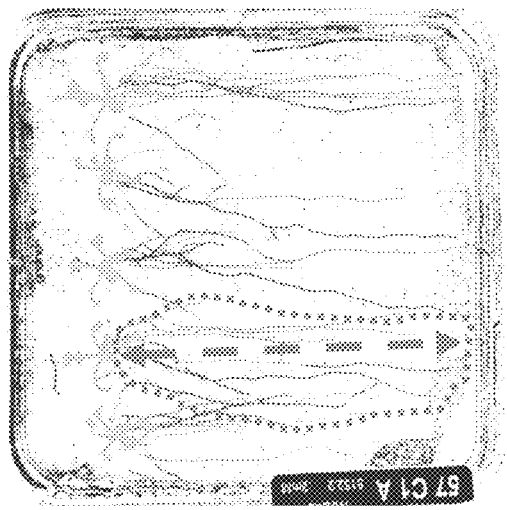
FIGS. 3A-3B are images depicting visualization of root development of plants grown in transparent agar plates. The different transgenes were grown in transparent agar plates for 10 days and the plates were photographed every 3-4 days starting at day 1.
Figure 3A:
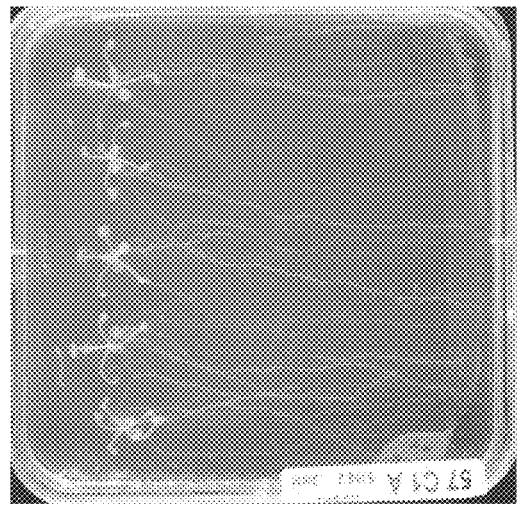

The image capturing process was repeated every 3-4 days starting at day 1 till day 10 (see for example the images in FIGS. 3A-3B). An image analysis system was used, which consists of a personal desktop computer (Intel P4 3.0 GHz processor) and a public domain program—ImageJ 1.39 [Java based image processing program which was developed at the U.S. National Institutes of Health and freely available on the internet at Hypertext Transfer Protocol://rsbweb (dot) nih (dot) gov/]. Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Seedling Analysis

Using the digital analysis seedling data was calculated, including leaf area, root coverage and root length.

The relative growth rate for the various seedling parameters was calculated according to the following formulas V, VI and VII.

Relative growth rate of leaf area=Regression coefficient of leaf area along time course.　　　Formula V:

Relative growth rate of root coverage=Regression coefficient of root coverage along time course.　　　Formula VI:

Relative growth rate of root length=Regression coefficient of root coverage along time course.　　　Formula VII:

At the end of the experiment, plantlets were removed from the media and weighed for the determination of plant fresh weight. Plantlets were then dried for 24 hours at 60° C., and weighed again to measure plant dry weight for later statistical analysis. Growth rate was determined by comparing the leaf area coverage, root coverage and root length, between each couple of sequential photographs, and results were used to resolve the effect of the gene introduced on plant vigor under optimal conditions. Similarly, the effect of the gene introduced on biomass accumulation, under optimal conditions, was determined by comparing the plants' fresh and dry weight to that of control plants (containing an empty vector or the GUS reporter gene under the same promoter). From every construct created, 3-5 independent transformation events were examined in replicates.

Statistical Analyses

To identify genes conferring significantly improved plant vigor or enlarged root architecture, the results obtained from the transgenic plants were compared to those obtained from control plants. To identify outperforming genes and constructs, results from the independent transformation events tested were analyzed separately. To evaluate the effect of a gene event over a control the data was analyzed by Student's t-test and the p-value was calculated. Results were considered significant if $p \leq 0.1$. The JMP statistics software package was used (Version 5.2.1, SAS Institute Inc., Cary, N.C., USA).

Experimental Results

The genes presented in Tables 24-25, hereinbelow, were found to improve nitrogen use efficiency (NUE) by producing larger plant biomass when grown under limiting nitrogen growth conditions, compared to control plants.

Tables 24 and 25 depict analyses of plant biomass (plant fresh and dry weight and leaf area) when grown under limiting nitrogen conditions [low nitrogen or nitrogen deficient conditions (0.75 mM N)] in plants overexpressing the polynucleotides of some embodiments of the invention under the regulation of a constitutive promoter (35S). Evaluation of each gene was performed by testing the performance of several events. Some of the genes were evaluated in more than one tissue culture assay and the second experiment confirmed the significant increment in plant biomass. Event with p-value <0.1 was considered statistically significant.

TABLE 24

Transgenic plants exogenously expressing the polynucleotides of some embodiments of the invention exhibit improved plant biomass (fresh and dry weight) under nitrogen deficient conditions

| Gene Name | Event # | Plant Biomass Fresh Weight [mg] | | | Gene Name | Event # | Plant Biomass Dry Weight [mg] | | |
|---|---|---|---|---|---|---|---|---|---|
| | | Average | p-value | % incr. | | | Average | p-value | % incr. |
| CT11 | 4892.1 | 204.50 | 6.3E−02 | 16.5 | CT11 | 4894.3 | 7.80 | 7.7E−02 | 39.29 |
| Control | | 175.55 | | | CT11 | 4892.3 | 8.85 | 1.3E−01 | 58.04 |
| CT22 | 5023.1 | 184.08 | 2.6E−04 | 43.5 | CT11 | 4892.2 | 7.85 | 4.5E−02 | 40.18 |
| Control | | 128.24 | | | CT11 | 4893.2 | 5.98 | 6.8E−01 | 6.70 |
| CT27 | 5033.7 | 195.00 | 3.2E−02 | 55.4 | CT11 | 4892.1 | 9.20 | 3.7E−02 | 64.29 |
| CT27 | 5031.4 | 150.93 | 3.2E−01 | 20.3 | Control | | 5.60 | | |
| CT27 | 5035.2 | 233.40 | 2.7E−02 | 86.0 | CT27 | 5033.7 | 7.68 | 1.2E−01 | 37.05 |
| CT27 | 5033.6 | 150.63 | 4.2E−01 | 20.0 | CT27 | 5031.4 | 6.73 | 2.2E−01 | 20.09 |
| CT27 | 5033.4 | 179.95 | 1.8E−01 | 43.4 | CT27 | 5035.2 | 9.68 | 4.3E−02 | 72.77 |
| CT27 | 5033.8 | 189.30 | 2.0E−02 | 50.9 | CT27 | 5033.6 | 6.40 | 3.1E−01 | 14.29 |
| CT27 | 5033.5 | 146.98 | 3.6E−01 | 17.1 | CT27 | 5033.4 | 8.03 | 1.4E−01 | 43.30 |
| Control | | 125.47 | | | CT27 | 5033.8 | 7.60 | 7.7E−02 | 35.71 |
| CT6 | 4943.1 | 184.30 | 8.3E−02 | 46.9 | CT27 | 5033.5 | 6.40 | 9.6E−02 | 14.29 |
| CT6 | 4941.4 | 188.38 | 3.0E−02 | 50.1 | Control | | 5.60 | | |
| Control | | 125.47 | | | CT6 | 4943.1 | 7.78 | 1.9E−01 | 38.84 |
| CT76 | 5044.6 | 213.08 | 1.8E−01 | 21.4 | CT6 | 4941.4 | 9.60 | 1.3E−03 | 71.43 |

TABLE 24-continued

Transgenic plants exogenously expressing the polynucleotides of some embodiments of the invention exhibit improved plant biomass (fresh and dry weight) under nitrogen deficient conditions

| Gene Name | Event # | Plant Biomass Fresh Weight [mg] | | | Gene Name | Event # | Plant Biomass Dry Weight [mg] | | |
|---|---|---|---|---|---|---|---|---|---|
| | | Average | p-value | % incr. | | | Average | p-value | % incr. |
| CT76 | 5041.5 | 250.50 | 1.6E−01 | 42.7 | Control | | 5.60 | | |
| CT76 | 5043.5 | 207.00 | 2.5E−01 | 17.9 | CT76 | 5044.6 | 7.83 | 1.1E−01 | 22.21 |
| CT76 | 5041.7 | 204.53 | 1.6E−01 | 16.5 | CT76 | 5041.5 | 9.10 | 2.0E−01 | 42.12 |
| CT76 | 5041.9 | 209.00 | 8.4E−02 | 19.1 | CT76 | 5043.5 | 11.05 | 1.7E−02 | 72.57 |
| CT76 | 5041.6 | 256.10 | 9.0E−02 | 45.9 | CT76 | 5041.7 | 7.35 | 1.9E−01 | 14.79 |
| Control | | 175.55 | | | CT76 | 5041.9 | 7.33 | 2.0E−01 | 14.40 |
| CT81 | 4992.1 | 223.50 | 1.8E−02 | 27.3 | CT76 | 5041.6 | 9.28 | 9.6E−02 | 44.85 |
| Control | | 175.55 | | | Control | | 6.40 | | |
| NUE208 | 8354.8 | 118.28 | 9.1E−02 | 17.3 | CT81 | 4992.1 | 9.60 | 7.2E−04 | 49.93 |
| NUE208 | 8351.3 | 138.15 | 8.5E−02 | 37.0 | CT81 | 4993.5 | 6.60 | 8.0E−01 | 3.07 |
| NUE208 | 8355.3 | 128.53 | 4.9E−02 | 27.5 | Control | | 6.40 | | |
| NUE208 | 8351.5 | 112.93 | 3.5E−01 | 12.0 | NUE206 | 6731.2 | 7.65 | 8.4E−01 | 4.97 |
| Control | | 100.81 | | | NUE206 | 6732.9 | 10.70 | 7.4E−02 | 46.83 |
| NUE209 | 8191.2 | 135.83 | 4.0E−01 | 34.7 | NUE206 | 6732.5 | 7.98 | 7.0E−01 | 9.43 |
| NUE209 | 8192.13 | 118.85 | 2.3E−01 | 17.9 | Control | | 7.2875 | | |
| NUE209 | 8192.14 | 160.40 | 1.7E−01 | 59.1 | NUE208 | 8354.8 | 6.05 | 1.0E−01 | 55.63 |
| NUE209 | 8191.5 | 119.28 | 1.9E−01 | 18.3 | NUE208 | 8351.3 | 7.95 | 4.3E−02 | 104.50 |
| NUE209 | 8192.1 | 134.45 | 4.5E−01 | 33.4 | NUE208 | 8355.3 | 6.63 | 9.8E−03 | 70.42 |
| Control | | 100.81 | | | NUE208 | 8351.5 | 6.33 | 1.0E−02 | 62.70 |
| NUE211 | 8265.1 | 118.48 | 6.7E−02 | 47.0 | Control | | 3.89 | | |
| Control | | 80.58 | | | NUE209 | 8191.2 | 6.20 | 2.2E−01 | 59.49 |
| NUE212 | 8331.1 | 115.18 | 4.7E−01 | 14.2 | NUE209 | 8192.13 | 5.80 | 4.4E−02 | 49.20 |
| NUE212 | 8335.2 | 182.98 | 6.6E−03 | 81.5 | NUE209 | 8192.14 | 7.58 | 6.3E−02 | 94.86 |
| NUE212 | 8334.1 | 121.25 | 2.6E−01 | 20.3 | NUE209 | 8191.5 | 7.85 | 5.2E−02 | 101.93 |
| NUE212 | 8331.4 | 177.68 | 1.1E−01 | 76.2 | NUE209 | 8192.1 | 5.85 | 9.5E−02 | 50.48 |
| Control | | 100.81 | | | Control | | 3.89 | | |
| NUE221 | 9802.8 | 134.30 | 1.6E−01 | 18.0 | NUE210 | 8202.1 | 4.83 | 4.9E−01 | 24.12 |
| NUE221 | 9806.1 | 138.60 | 9.0E−02 | 21.8 | NUE210 | 8202.2 | 6.35 | 6.3E−03 | 63.34 |
| Control | | 113.81 | | | NUE210 | 8201.3 | 5.50 | 4.7E−02 | 41.48 |
| NUE222 | 8851.4 | 131.68 | 5.8E−03 | 44.1 | Control | | 3.89 | | |
| NUE222 | 8854.1 | 108.37 | 6.9E−02 | 18.6 | NUE212 | 8334.1 | 5.18 | 2.2E−01 | 42.76 |
| NUE222 | 8853.2 | 119.23 | 1.9E−02 | 30.4 | NUE212 | 8332.1 | 3.83 | 7.5E−01 | 5.52 |
| NUE222 | 8851.3 | 161.75 | 2.1E−02 | 77.0 | NUE212 | 8331.4 | 4.75 | 6.6E−02 | 31.03 |
| Control | | 91.40 | | | Control | | 3.63 | | |
| NUE227 | 9851.2 | 102.75 | 1.2E−01 | 26.1 | NUE221 | 9806.1 | 6.025 | 1.9E−01 | 18.7 |
| NUE227 | 9854.2 | 84.70 | 8.3E−01 | 4.0 | Control | | 5.075 | | |
| NUE227 | 9853.4 | 102.83 | 2.9E−01 | 26.2 | NUE222 | 8851.4 | 4.03 | 7.9E−01 | 3.54 |
| NUE227 | 9853.1 | 103.23 | 1.3E−01 | 26.7 | NUE222 | 8853.2 | 4.65 | 2.2E−01 | 19.61 |
| NUE227 | 9852.3 | 101.98 | 1.4E−01 | 25.2 | NUE222 | 8851.3 | 6.45 | 3.3E−03 | 65.92 |
| Control | | 81.48 | | | Control | | 3.89 | | |
| NUE230 | 9154.2 | 181.58 | 2.3E−02 | 48.8 | NUE224 | 9002.2 | 6.93 | 2.1E−02 | 39.55 |
| NUE230 | 9151.2 | 125.18 | 8.8E−01 | 2.6 | NUE224 | 9001.3 | 6.83 | 2.8E−01 | 37.70 |
| Control | | 122.05 | | | Control | | 4.96 | | |
| NUE231 | 10633.3 | 138.98 | 8.5E−02 | 22.1 | NUE227 | 9851.2 | 4.90 | 3.6E−01 | 24.05 |
| Control | | 113.81 | | | NUE227 | 9854.2 | 4.60 | 4.8E−01 | 16.46 |
| NUE233 | 10174.3 | 156.40 | 3.7E−02 | 60.8 | NUE227 | 9853.4 | 4.55 | 5.3E−01 | 15.19 |
| NUE233 | 10174.1 | 176.20 | 4.0E−03 | 81.2 | NUE227 | 9853.1 | 4.83 | 1.4E−01 | 22.15 |
| NUE233 | 10173.7 | 103.68 | 7.4E−01 | 6.6 | NUE227 | 9852.3 | 5.18 | 7.7E−02 | 31.01 |
| Control | | 97.24 | | | Control | | 3.95 | | |
| NUE233 | 10174.1 | 117.95 | 8.1E−03 | 37.2 | NUE228 | 10092.2 | 6.75 | 2.8E−02 | 35.34 |
| NUE233 | 10173.7 | 95.40 | 4.6E−01 | 10.9 | Control | | 4.99 | | |
| Control | | 86.00 | | | NUE230 | 9154.2 | 7.83 | 2.2E−02 | 57.68 |
| NUE235 | 9691.1 | 175.50 | 3.2E−01 | 43.8 | NUE230 | 9151.2 | 5.40 | 5.4E−01 | 8.82 |
| NUE235 | 9693.3 | 178.60 | 3.1E−03 | 46.3 | NUE230 | 9153.3 | 5.28 | 6.9E−01 | 6.30 |
| NUE235 | 9694.3 | 156.28 | 2.1E−01 | 28.0 | NUE230 | 9153.1 | 5.48 | 3.3E−01 | 10.33 |
| Control | | 122.05 | | | Control | | 4.96 | | |
| NUE237 | 9651.1 | 159.43 | 1.6E−01 | 30.6 | NUE231 | 10633.3 | 8.425 | 1.0E−05 | 66.0 |
| NUE237 | 9654.4 | 170.70 | 4.1E−02 | 39.9 | Control | | 5.075 | | |
| NUE237 | 9654.1 | 128.70 | 7.1E−01 | 5.4 | NUE233 | 10174.3 | 6.05 | 5.1E−02 | 44.05 |
| NUE237 | 9653.3 | 133.33 | 6.1E−01 | 9.2 | NUE233 | 10174.1 | 8.15 | 2.7E−03 | 94.05 |
| Control | | 122.05 | | | NUE233 | 10173.7 | 4.45 | 7.3E−01 | 5.95 |
| NUE239 | 9192.3 | 168.58 | 5.1E−02 | 27.4 | Control | | 4.20 | | |
| NUE239 | 9192.1 | 142.68 | 1.7E−01 | 7.8 | NUE235 | 9694.2 | 5.25 | 7.9E−01 | 5.79 |
| NUE239 | 9191.2 | 136.75 | 5.8E−01 | 3.3 | NUE235 | 9691.1 | 7.28 | 1.6E−01 | 46.60 |
| Control | | 132.34 | | | NUE235 | 9694.4 | 5.83 | 4.1E−01 | 17.38 |
| NUE240 | 9172.1 | 157.53 | 5.3E−03 | 19.0 | NUE235 | 9693.3 | 7.28 | 6.0E−02 | 46.60 |
| NUE240 | 9174.3 | 143.65 | 1.7E−01 | 8.5 | NUE235 | 9694.3 | 7.88 | 1.5E−02 | 58.69 |
| Control | | 132.34 | | | Control | | 4.96 | | |
| NUE241 | 9632.5 | 133.63 | 1.4E−01 | 64.0 | NUE237 | 9651.1 | 7.03 | 3.2E−01 | 41.56 |
| NUE241 | 9631.3 | 148.18 | 3.8E−03 | 81.9 | NUE237 | 9654.4 | 8.88 | 2.0E−02 | 78.84 |

TABLE 24-continued

Transgenic plants exogenously expressing the polynucleotides of some embodiments of the invention exhibit improved plant biomass (fresh and dry weight) under nitrogen deficient conditions

| | | Plant Biomass Fresh Weight [mg] | | | | | Plant Biomass Dry Weight [mg] | | |
|---|---|---|---|---|---|---|---|---|---|
| Gene Name | Event # | Average | p-value | % incr. | Gene Name | Event # | Average | p-value | % incr. |
| NUE241 | 9632.3 | 137.60 | 8.0E−03 | 68.9 | NUE237 | 9654.1 | 6.23 | 6.5E−02 | 25.44 |
| NUE241 | 9632.4 | 131.93 | 1.9E−02 | 61.9 | NUE237 | 9653.3 | 7.08 | 8.5E−02 | 42.57 |
| Control | | 81.48 | | | Control | | 4.96 | | |
| NUE242 | 9212.1 | 124.50 | 2.7E−02 | 48.7 | NUE239 | 9191.1 | 9.00 | 5.3E−02 | 60.71 |
| NUE242 | 9214.1 | 89.98 | 7.5E−01 | 7.4 | NUE239 | 9191.2 | 6.13 | 5.2E−01 | 9.38 |
| NUE242 | 9211.2 | 95.30 | 4.3E−01 | 13.8 | Control | | 5.60 | | |
| NUE242 | 9213.4 | 125.50 | 2.8E−02 | 49.9 | NUE240 | 9172.4 | 7.35 | 3.5E−02 | 18.55 |
| Control | | 83.75 | | | NUE240 | 9174.3 | 6.53 | 6.1E−01 | 5.24 |
| NUE244 | 9061.1 | 119.60 | 2.8E−03 | 30.9 | Control | | 6.20 | | |
| NUE244 | 9061.5 | 148.80 | 1.4E−01 | 62.8 | NUE241 | 9633.4 | 5.68 | 6.1E−02 | 43.67 |
| Control | | 91.40 | | | NUE241 | 9632.3 | 6.55 | 1.3E−02 | 65.82 |
| NUE246 | 9033.6 | 140.75 | 1.4E−01 | 41.2 | NUE241 | 9632.2 | 6.20 | 4.4E−02 | 56.96 |
| NUE246 | 9033.8 | 111.20 | 4.8E−01 | 11.6 | NUE241 | 9632.4 | 5.68 | 7.9E−04 | 43.67 |
| NUE246 | 9033.4 | 148.63 | 2.7E−03 | 49.1 | Control | | 3.95 | | |
| NUE246 | 9034.1 | 138.50 | 6.0E−03 | 39.0 | NUE246 | 9033.6 | 4.40 | 3.2E−01 | 19.32 |
| NUE246 | 9031.1 | 131.63 | 3.5E−01 | 32.1 | NUE246 | 9033.8 | 5.13 | 1.8E−01 | 38.98 |
| Control | | 99.68 | | | NUE246 | 9033.4 | 4.73 | 8.2E−02 | 28.14 |
| NUE248 | 8981.5 | 197.35 | 1.3E−02 | 30.1 | NUE246 | 9034.1 | 6.43 | 1.7E−02 | 74.46 |
| Control | | 151.66 | | | NUE246 | 9031.1 | 4.80 | 2.5E−01 | 30.17 |
| NUE249 | 9124.2 | 82.68 | 9.2E−01 | 3.4 | Control | | 3.69 | | |
| NUE249 | 9121.4 | 125.13 | 2.0E−03 | 56.5 | NUE248 | 8981.5 | 7.98 | 6.0E−02 | 23.17 |
| NUE249 | 9123.3 | 89.55 | 2.3E−01 | 12.0 | NUE248 | 8984.1 | 6.75 | 7.1E−01 | 4.25 |
| Control | | 79.94 | | | NUE248 | 8981.2 | 7.35 | 3.3E−01 | 13.51 |
| NUE250 | 9132.1 | 149.53 | 4.6E−02 | 22.5 | Control | | 6.48 | | |
| NUE250 | 9133.2 | 193.20 | 1.3E−02 | 58.3 | NUE249 | 9124.2 | 5.05 | 7.6E−01 | 11.60 |
| NUE250 | 9132.2 | 152.38 | 1.8E−01 | 24.8 | NUE249 | 9121.4 | 5.50 | 2.3E−02 | 21.55 |
| NUE250 | 9134.1 | 205.50 | 5.0E−02 | 68.4 | Control | | 4.53 | | |
| Control | | 122.05 | | | NUE250 | 9132.1 | 7.38 | 4.8E−02 | 48.61 |
| NUE251 | 10181.3 | 175.35 | 4.7E−03 | 80.3 | NUE250 | 9133.2 | 7.95 | 2.5E−03 | 60.20 |
| NUE251 | 10183.2 | 127.58 | 1.7E−01 | 31.2 | NUE250 | 9132.2 | 7.23 | 1.0E−01 | 45.59 |
| NUE251 | 10183.1 | 118.03 | 3.6E−01 | 21.4 | NUE250 | 9134.1 | 8.03 | 1.1E−02 | 61.71 |
| Control | | 97.24 | | | Control | | 4.96 | | |
| NUE252 | 9011.3 | 252.23 | 1.3E−02 | 40.9 | NUE251 | 10181.3 | 7.03 | 2.9E−02 | 67.26 |
| NUE252 | 9012.2 | 201.53 | 3.1E−01 | 12.5 | NUE251 | 10183.2 | 5.35 | 2.6E−01 | 27.38 |
| Control | | 179.06 | | | NUE251 | 10183.1 | 4.93 | 4.6E−01 | 17.26 |
| NUE256 | 10063.4 | 127.55 | 1.7E−01 | 31.2 | Control | | 4.2 | | |
| NUE256 | 10064.1 | 155.88 | 3.1E−02 | 60.3 | NUE256 | 10063.4 | 5.78 | 1.0E−01 | 37.50 |
| NUE256 | 10061.2 | 158.93 | 1.1E−02 | 63.4 | NUE256 | 10064.1 | 7.40 | 1.0E−02 | 76.19 |
| NUE256 | 10062.4 | 147.40 | 1.4E−01 | 51.6 | NUE256 | 10061.2 | 6.35 | 1.8E−02 | 51.19 |
| NUE256 | 10063.2 | 134.18 | 1.9E−01 | 38.0 | NUE256 | 10062.4 | 7.43 | 1.4E−01 | 76.79 |
| NUE256 | 10061.1 | 101.35 | 8.3E−01 | 4.2 | NUE256 | 10063.2 | 5.73 | 1.4E−01 | 36.31 |
| Control | | 97.24 | | | NUE256 | 10061.1 | 4.40 | 8.0E−01 | 4.76 |
| NUE256 | 10061.2 | 104.20 | 5.5E−01 | 21.2 | Control | | 4.20 | | |
| NUE256 | 10061.4 | 127.68 | 1.8E−01 | 48.5 | NUE512 | 9284.3 | 4.65 | 6.8E−01 | 5.38 |
| NUE256 | 10063.2 | 88.28 | 8.5E−01 | 2.6 | NUE512 | 9282.3 | 7.78 | 1.3E−02 | 76.20 |
| Control | | 86.00 | | | NUE512 | 9284.4 | 6.70 | 2.6E−02 | 51.84 |
| NUE268 | 8992.1 | 108.25 | 4.3E−01 | 10.4 | Control | | 4.41 | | |
| NUE268 | 8996.3 | 118.68 | 5.5E−01 | 21.0 | NUE515 | 9713.6 | 6.725 | 2.4E−02 | 32.5 |
| NUE268 | 8996.5 | 177.25 | 8.4E−02 | 80.8 | Control | | 5.075 | | |
| NUE268 | 8996.2 | 112.10 | 3.7E−01 | 14.3 | NUE516 | 9291.1 | 5.78 | 2.4E−01 | 16.37 |
| Control | | 98.05 | | | NUE516 | 9291.4 | 7.43 | 2.7E−02 | 49.62 |
| NUE269 | 9104.1 | 93.80 | 3.0E−01 | 23.1 | NUE516 | 9293.2 | 5.78 | 4.3E−01 | 16.37 |
| NUE269 | 9101.3 | 94.65 | 6.2E−03 | 24.2 | Control | | 4.96 | | |
| Control | | 76.20 | | | NUE519 | 9371.2 | 11.75 | 4.8E−02 | 89.52 |
| NUE512 | 9284.2 | 166.53 | 6.1E−05 | 73.7 | NUE519 | 9371.1 | 8.50 | 1.5E−02 | 37.10 |
| NUE512 | 9284.3 | 112.35 | 2.1E−01 | 17.2 | NUE519 | 9372.2 | 6.60 | 6.7E−01 | 6.45 |
| NUE512 | 9282.3 | 181.10 | 1.3E−02 | 88.9 | Control | | 6.20 | | |
| NUE512 | 9284.4 | 171.70 | 7.6E−02 | 79.1 | NUE525 | 9531.2 | 5.25 | 3.6E−01 | −10.45 |
| Control | | 95.88 | | | NUE525 | 9534.1 | 5.40 | 4.4E−01 | −7.89 |
| NUE515 | 9712.5 | 116.43 | 8.6E−01 | 2.3 | NUE525 | 9531.3 | 6.73 | 4.4E−01 | 14.71 |
| NUE515 | 9713.6 | 148.18 | 2.0E−02 | 30.2 | NUE525 | 9533.1 | 7.43 | 1.2E−02 | 26.65 |
| Control | | 113.81 | | | NUE525 | 9531.1 | 7.20 | 9.9E−02 | 22.81 |
| NUE514 | 9404.1 | 113.98 | 8.5E−02 | 36.1 | Control | | 5.86 | | |
| NUE514 | 9403.2 | 94.58 | 1.2E−01 | 12.9 | NUE531 | 10083.1 | 6.58 | 4.2E−02 | 31.83 |
| NUE514 | 9402.5 | 99.38 | 3.5E−01 | 18.7 | NUE531 | 10082.2 | 6.25 | 1.6E−01 | 25.31 |
| Control | | 83.75 | | | NUE531 | 10081.4 | 8.50 | 2.4E−02 | 70.43 |
| NUE516 | 9291.1 | 128.58 | 6.7E−01 | 5.3 | NUE531 | 10081.5 | 8.03 | 2.5E−02 | 60.90 |
| NUE516 | 9291.4 | 165.93 | 1.5E−01 | 35.9 | Control | | 4.99 | | |
| NUE516 | 9293.2 | 139.73 | 5.7E−01 | 14.5 | NUE532 | 9222.4 | 6.15 | 3.5E−05 | 44.71 |
| Control | | 122.05 | | | NUE532 | 9222.1 | 6.98 | 1.3E−02 | 64.12 |

TABLE 24-continued

Transgenic plants exogenously expressing the polynucleotides of some embodiments of the invention exhibit improved plant biomass (fresh and dry weight) under nitrogen deficient conditions

| Gene Name | Event # | Plant Biomass Fresh Weight [mg] | | | Gene Name | Event # | Plant Biomass Dry Weight [mg] | | |
|---|---|---|---|---|---|---|---|---|---|
| | | Average | p-value | % incr. | | | Average | p-value | % incr. |
| NUE519 | 9371.2 | 182.10 | 1.5E−02 | 37.6 | NUE532 | 9223.3 | 5.53 | 1.4E−01 | 30.00 |
| Control | | 132.34 | | | NUE532 | 9224.4 | 4.43 | 4.4E−01 | 4.12 |
| NUE521 | 9363.1 | 107.40 | 3.1E−01 | 28.2 | Control | | 4.25 | | |
| NUE521 | 9362.2 | 119.80 | 2.6E−02 | 43.0 | NUE536 | 9233.3 | 6.03 | 4.8E−03 | 63.39 |
| NUE521 | 9361.2 | 136.10 | 3.5E−04 | 62.5 | NUE536 | 9234.1 | 4.55 | 3.3E−01 | 23.39 |
| NUE521 | 9361.3 | 104.15 | 3.8E−01 | 24.4 | NUE536 | 9231.3 | 4.08 | 5.7E−01 | 10.51 |
| NUE521 | 9363.4 | 132.95 | 5.8E−03 | 58.7 | NUE536 | 9232.4 | 3.98 | 6.1E−01 | 7.80 |
| Control | | 83.75 | | | Control | | 3.69 | | |
| NUE523 | 9412.5 | 190.08 | 2.4E−01 | 25.3 | NUE537 | 9391.1 | 5.08 | 3.5E−01 | 15.01 |
| NUE523 | 9414.2 | 192.23 | 1.9E−01 | 26.7 | NUE537 | 9393.2 | 4.53 | 9.2E−01 | 2.55 |
| NUE523 | 9412.1 | 187.50 | 2.8E−02 | 23.6 | NUE537 | 9394.4 | 5.90 | 2.8E−01 | 33.71 |
| Control | | 151.66 | | | NUE537 | 9391.2 | 5.53 | 2.2E−01 | 25.21 |
| NUE527 | 9201.1 | 111.28 | 3.2E−03 | 273.7 | NUE537 | 9393.3 | 5.63 | 2.7E−02 | 27.48 |
| NUE527 | 9202.6 | 51.70 | 2.1E−02 | 73.6 | Control | | 4.41 | | |
| NUE527 | 9203.2 | 49.77 | 4.3E−02 | 67.1 | NUE539 | 10101.5 | 6.78 | 4.4E−03 | 61.31 |
| NUE527 | 9204.1 | 45.83 | 3.0E−01 | 53.9 | NUE539 | 10103.5 | 5.63 | 1.7E−01 | 33.93 |
| Control | | 29.78 | | | NUE539 | 10101.2 | 7.43 | 4.4E−02 | 76.79 |
| NUE531 | 10083.1 | 159.05 | 9.2E−02 | 38.1 | NUE539 | 10101.7 | 7.05 | 2.3E−02 | 67.86 |
| NUE531 | 10082.2 | 154.43 | 1.6E−02 | 34.1 | NUE539 | 10103.4 | 4.88 | 3.6E−01 | 16.07 |
| NUE531 | 10081.4 | 173.70 | 5.9E−02 | 50.8 | Control | | 4.20 | | |
| NUE531 | 10081.5 | 154.38 | 1.9E−02 | 34.0 | NUE542 | 9333.2 | 8.35 | 2.6E−02 | 89.24 |
| Control | | 115.16 | | | NUE542 | 9334.1 | 4.80 | 5.2E−01 | 8.78 |
| NUE531 | 10081.4 | 128.20 | 3.4E−02 | 49.1 | NUE542 | 9331.3 | 4.83 | 6.9E−01 | 9.35 |
| NUE531 | 10083.2 | 91.95 | 6.4E−01 | 6.9 | NUE542 | 9334.3 | 4.65 | 8.1E−01 | 5.38 |
| NUE531 | 10081.5 | 165.43 | 5.5E−02 | 92.4 | Control | | 4.41 | | |
| Control | | 86.00 | | | NUE548 | 9095.2 | 8.05 | 2.6E−01 | 44.07 |
| NUE532 | 9222.4 | 143.08 | 9.9E−02 | 70.8 | NUE548 | 9095.4 | 8.60 | 4.7E−02 | 53.91 |
| NUE532 | 9222.1 | 106.98 | 2.3E−01 | 27.7 | NUE548 | 9091.1 | 6.43 | 3.0E−01 | 14.99 |
| NUE532 | 9223.3 | 100.20 | 1.3E−01 | 19.6 | Control | | 5.59 | | |
| Control | | 83.75 | | | NUE549 | 9343.7 | 7.67 | 2.2E−02 | 54.88 |
| NUE532 | 9222.4 | 118.33 | 7.6E−02 | 41.3 | Control | | 4.95 | | |
| NUE532 | 9222.1 | 170.88 | 1.1E−01 | 104.0 | NUE550 | 9143.1 | 5.75 | 3.9E−04 | 35.29 |
| NUE532 | 9223.3 | 115.80 | 3.1E−01 | 38.3 | NUE550 | 9143.4 | 6.85 | 7.3E−03 | 61.18 |
| NUE532 | 9223.5 | 104.90 | 7.7E−01 | 25.3 | NUE550 | 9142.2 | 6.45 | 1.6E−02 | 51.76 |
| NUE532 | 9224.4 | 110.48 | 6.3E−01 | 31.9 | Control | | 4.25 | | |
| Control | | 98.05 | | | NUE553 | 9181.5 | 5.55 | 7.6E−02 | 30.59 |
| NUE535 | 9082.2 | 32.95 | 4.7E−01 | 10.7 | NUE553 | 9184.3 | 4.58 | 6.3E−01 | 7.65 |
| NUE535 | 9086.2 | 73.97 | 3.2E−02 | 148.4 | NUE553 | 9182.2 | 4.70 | 2.4E−01 | 10.59 |
| NUE535 | 9086.3 | 51.43 | 6.0E−02 | 72.7 | Control | | 4.25 | | |
| NUE535 | 9081.1 | 61.90 | 1.9E−01 | 107.9 | NUE554 | 9114.3 | 4.33 | 9.4E−01 | 1.76 |
| NUE535 | 9084.4 | 57.00 | 9.3E−03 | 91.4 | NUE554 | 9115.2 | 6.88 | 1.3E−02 | 61.76 |
| Control | | 29.78 | | | NUE554 | 9114.2 | 5.35 | 1.8E−02 | 25.88 |
| NUE537 | 9391.1 | 131.75 | 2.2E−01 | 37.4 | NUE554 | 9115.3 | 4.45 | 5.9E−01 | 4.71 |
| NUE537 | 9393.2 | 110.88 | 3.9E−01 | 15.6 | Control | | 4.25 | | |
| NUE537 | 9394.4 | 214.60 | 6.4E−02 | 123.8 | NUE564 | 9242.3 | 4.55 | 6.7E−05 | 114.12 |
| NUE537 | 9391.2 | 141.33 | 3.2E−02 | 47.4 | NUE564 | 9243.2 | 4.03 | 7.8E−02 | 89.41 |
| NUE537 | 9393.3 | 136.40 | 2.1E−04 | 42.3 | NUE564 | 9242.4 | 3.28 | 3.6E−02 | 54.12 |
| Control | | 95.88 | | | NUE564 | 9242.2 | 3.90 | 7.6E−02 | 83.53 |
| NUE538 | 9782.4 | 108.85 | 2.7E−01 | 33.6 | NUE564 | 9243.4 | 4.35 | 2.2E−06 | 104.71 |
| NUE538 | 9781.4 | 95.73 | 4.5E−01 | 17.5 | Control | | 2.13 | | |
| NUE538 | 9781.1 | 94.65 | 2.6E−01 | 16.2 | NUE567 | 9263.2 | 3.15 | 2.1E−01 | 48.24 |
| NUE538 | 9782.1 | 145.73 | 8.8E−02 | 78.9 | NUE567 | 9261.3 | 3.05 | 1.8E−02 | 43.53 |
| Control | | 81.48 | | | NUE567 | 9263.3 | 3.28 | 8.5E−03 | 54.12 |
| NUE539 | 10101.5 | 163.80 | 2.4E−02 | 68.5 | NUE567 | 9261.4 | 3.28 | 5.9E−03 | 54.12 |
| NUE539 | 10103.5 | 124.98 | 2.8E−01 | 28.5 | Control | | 2.13 | | |
| NUE539 | 10101.2 | 177.98 | 2.7E−02 | 83.0 | NUE569 | 9384.4 | 2.63 | 3.0E−01 | 23.53 |
| NUE539 | 10101.7 | 162.73 | 2.5E−02 | 67.3 | NUE569 | 9381.2 | 5.20 | 1.8E−02 | 144.71 |
| NUE539 | 10103.4 | 105.13 | 7.6E−01 | 8.1 | NUE569 | 9381.5 | 2.90 | 5.3E−01 | 36.47 |
| Control | | 97.24 | | | NUE569 | 9381.3 | 4.53 | 1.3E−01 | 112.94 |
| NUE542 | 9333.2 | 165.80 | 6.0E−02 | 72.9 | NUE569 | 9384.2 | 3.58 | 4.5E−01 | 68.24 |
| NUE542 | 9331.3 | 150.08 | 9.7E−02 | 56.5 | Control | | 2.13 | | |
| NUE542 | 9334.3 | 153.73 | 2.9E−03 | 60.3 | NUE570 | 9311.4 | 4.23 | 1.6E−01 | 98.82 |
| NUE542 | 9332.1 | 167.08 | 1.0E−01 | 74.3 | NUE570 | 9313.3 | 3.85 | 5.1E−02 | 81.18 |
| Control | | 95.88 | | | NUE570 | 9314.4 | 3.58 | 8.1E−01 | 68.24 |
| NUE542 | 9333.2 | 169.30 | 1.0E−01 | 38.7 | NUE570 | 9314.1 | 4.25 | 4.3E−02 | 100.00 |
| NUE542 | 9332.1 | 165.13 | 3.6E−02 | 35.3 | NUE570 | 9312.3 | 4.33 | 4.8E−01 | 103.53 |
| Control | | 122.05 | | | Control | | 2.13 | | |
| NUE543 | 10051.2 | 99.90 | 1.4E−01 | 22.6 | NUE571 | 9304.2 | 4.28 | 1.1E−02 | 101.18 |
| NUE543 | 10051.6 | 113.23 | 1.8E−01 | 39.0 | NUE571 | 9304.3 | 4.15 | 1.7E−02 | 95.29 |
| NUE543 | 10053.1 | 97.10 | 3.1E−01 | 19.2 | NUE571 | 9303.2 | 5.13 | 6.8E−05 | 141.18 |

TABLE 24-continued

Transgenic plants exogenously expressing the polynucleotides of some embodiments of the invention exhibit improved plant biomass (fresh and dry weight) under nitrogen deficient conditions

| Gene Name | Event # | Plant Biomass Fresh Weight [mg] Average | p-value | % incr. | Gene Name | Event # | Plant Biomass Dry Weight [mg] Average | p-value | % incr. |
|---|---|---|---|---|---|---|---|---|---|
| NUE543 | 10054.2 | 121.08 | 9.3E−03 | 48.6 | NUE571 | 9302.3 | 3.63 | 7.7E−02 | 70.59 |
| Control | | 81.48 | | | NUE571 | 9301.4 | 3.90 | 1.9E−02 | 83.53 |
| NUE544 | 9764.1 | 143.68 | 3.0E−02 | 33.9 | Control | | 2.13 | | |
| NUE544 | 9763.4 | 115.60 | 4.9E−01 | 7.7 | NUE572 | 9321.3 | 3.35 | 2.6E−02 | 57.65 |
| NUE544 | 9764.2 | 127.50 | 1.6E−01 | 18.8 | NUE572 | 9321.1 | 4.50 | 2.2E−02 | 111.76 |
| NUE544 | 9763.3 | 123.08 | 3.5E−02 | 14.7 | NUE572 | 9322.1 | 3.03 | 1.2E−01 | 42.35 |
| Control | | 107.29 | | | NUE572 | 9324.3 | 4.10 | 1.5E−02 | 92.94 |
| NUE549 | 9343.7 | 142.03 | 1.9E−02 | 19.6 | NUE572 | 9322.2 | 3.63 | 1.2E−02 | 70.59 |
| Control | | 118.75 | | | Control | | 2.13 | | |
| NUE550 | 9141.3 | 109.05 | 5.0E−01 | 11.2 | NUE573 | 9491.4 | 5.65 | 3.2E−01 | 14.14 |
| NUE550 | 9143.1 | 136.53 | 1.7E−01 | 39.2 | NUE573 | 9491.1 | 6.18 | 1.2E−01 | 24.75 |
| NUE550 | 9143.4 | 161.73 | 1.3E−02 | 64.9 | NUE573 | 9493.2 | 5.53 | 3.2E−01 | 11.78 |
| NUE550 | 9142.2 | 131.30 | 5.7E−02 | 33.9 | Control | | 4.95 | | |
| Control | | 98.05 | | | NUE574 | 10364.2 | 5.73 | 2.9E−01 | 11.98 |
| NUE553 | 9181.5 | 52.48 | 2.2E−04 | 76.2 | NUE574 | 10366.2 | 7.08 | 5.3E−02 | 38.39 |
| NUE553 | 9184.1 | 57.30 | 3.2E−03 | 92.4 | Control | | 5.11 | | |
| NUE553 | 9184.3 | 82.23 | 1.3E−05 | 176.2 | NUE576 | 9791.3 | 6.70 | 8.6E−04 | 69.62 |
| NUE553 | 9185.2 | 56.35 | 8.3E−04 | 89.3 | NUE576 | 9792.4 | 5.18 | 6.6E−02 | 31.01 |
| NUE553 | 9182.2 | 68.93 | 8.8E−03 | 131.5 | NUE576 | 9794.1 | 4.78 | 4.0E−01 | 20.89 |
| Control | | 29.78 | | | NUE576 | 9793.3 | 5.65 | 8.4E−04 | 43.04 |
| NUE554 | 9115.2 | 215.73 | 3.9E−02 | 120.0 | Control | | 3.95 | | |
| NUE554 | 9114.2 | 116.98 | 1.9E−01 | 19.3 | NUE581 | 9723.6 | 5.875 | 2.7E−01 | 15.8 |
| Control | | 98.05 | | | NUE581 | 9724.9 | 5.425 | 6.3E−01 | 6.9 |
| NUE564 | 9242.3 | 120.53 | 8.6E−03 | 25.7 | Control | | 5.075 | | |
| NUE564 | 9243.2 | 130.18 | 2.3E−02 | 35.8 | NUE582 | 9564.2 | 5.28 | 5.6E−01 | 6.30 |
| NUE564 | 9242.2 | 221.87 | 6.4E−02 | 131.4 | NUE582 | 9562.4 | 6.45 | 1.8E−01 | 29.97 |
| NUE564 | 9243.4 | 121.85 | 1.0E−01 | 27.1 | NUE582 | 9561.2 | 6.95 | 1.4E−03 | 40.05 |
| Control | | 95.88 | | | Control | | 4.96 | | |
| NUE567 | 9263.2 | 133.50 | 8.5E−02 | 39.2 | NUE583 | 9673.1 | 5.80 | 1.1E−01 | 46.84 |
| NUE567 | 9261.2 | 133.75 | 2.6E−01 | 39.5 | NUE583 | 9673.2 | 4.33 | 2.7E−01 | 9.49 |
| Control | | 95.88 | | | NUE583 | 9671.2 | 5.28 | 2.1E−01 | 33.54 |
| NUE568 | 9461.2 | 164.90 | 7.0E−02 | 38.9 | NUE583 | 9671.1 | 4.88 | 3.7E−01 | 23.42 |
| Control | | 118.75 | | | Control | | 3.95 | | |
| NUE569 | 9381.2 | 97.40 | 1.5E−01 | 20.5 | NUE585 | 9662.4 | 4.65 | 3.3E−01 | 26.10 |
| NUE569 | 9381.3 | 108.85 | 7.3E−02 | 34.7 | NUE585 | 9661.5 | 4.78 | 5.4E−02 | 29.49 |
| NUE569 | 9384.2 | 93.95 | 9.3E−02 | 16.2 | NUE585 | 9661.3 | 3.90 | 6.6E−01 | 5.76 |
| Control | | 80.83 | | | NUE585 | 9662.1 | 4.00 | 6.9E−01 | 8.47 |
| NUE570 | 9311.4 | 127.53 | 1.3E−01 | 33.0 | NUE585 | 9661.1 | 4.43 | 2.5E−01 | 20.00 |
| NUE570 | 9314.1 | 135.55 | 3.8E−01 | 41.4 | Control | | 3.69 | | |
| NUE570 | 9312.3 | 143.83 | 3.5E−02 | 50.0 | NUE586 | 9751.1 | 5.38 | 1.9E−01 | 22.86 |
| Control | | 95.88 | | | NUE586 | 9751.7 | 6.43 | 1.4E−01 | 46.86 |
| NUE573 | 9491.1 | 135.18 | 6.0E−02 | 13.8 | NUE586 | 9752.1 | 8.15 | 3.7E−04 | 86.29 |
| Control | | 118.75 | | | Control | | 4.38 | | |
| NUE574 | 10364.2 | 110.48 | 2.1E−02 | 28.5 | NUE587 | 9643.2 | 7.45 | 8.6E−03 | 70.29 |
| NUE574 | 10362.2 | 89.95 | 7.8E−01 | 4.6 | NUE587 | 9643.1 | 5.58 | 9.3E−02 | 27.43 |
| NUE574 | 10366.2 | 153.38 | 8.1E−02 | 78.3 | NUE587 | 9642.2 | 4.50 | 8.7E−01 | 2.86 |
| Control | | 86.00 | | | NUE587 | 9641.3 | 6.88 | 4.2E−02 | 57.14 |
| NUE576 | 9791.3 | 164.75 | 1.6E−02 | 102.2 | Control | | 4.38 | | |
| NUE576 | 9792.3 | 90.20 | 4.8E−01 | 10.7 | NUE588 | 9591.3 | 5.03 | 5.9E−02 | 36.27 |
| NUE576 | 9792.4 | 106.40 | 1.0E−01 | 30.6 | NUE588 | 9591.4 | 3.75 | 9.4E−01 | 1.69 |
| NUE576 | 9794.1 | 108.43 | 1.9E−01 | 33.1 | NUE588 | 9592.2 | 4.68 | 3.7E−01 | 26.78 |
| NUE576 | 9793.3 | 136.93 | 6.6E−02 | 68.1 | NUE588 | 9592.4 | 4.98 | 1.7E−01 | 34.92 |
| Control | | 81.48 | | | NUE588 | 9592.1 | 3.98 | 7.2E−01 | 7.80 |
| NUE583 | 9673.4 | 171.65 | 5.2E−03 | 99.6 | Control | | 3.69 | | |
| NUE583 | 9673.2 | 117.30 | 3.2E−03 | 36.4 | NUE592 | 9744.5 | 9.000 | 3.7E−07 | 77.3 |
| Control | | 86.00 | | | NUE592 | 9747.5 | 7.900 | 2.1E−05 | 55.7 |
| NUE585 | 9662.4 | 135.60 | 1.7E−01 | 36.0 | Control | | 5.075 | | |
| NUE585 | 9661.5 | 122.20 | 6.2E−02 | 22.6 | | | | | |
| Control | | 99.68 | | | | | | | |
| NUE586 | 9751.1 | 153.83 | 2.1E−01 | 88.8 | | | | | |
| NUE586 | 9752.1 | 194.23 | 2.2E−02 | 138.4 | | | | | |
| Control | | 129.73 | | | | | | | |
| NUE587 | 9643.2 | 156.78 | 2.0E−01 | 92.4 | | | | | |
| NUE587 | 9641.3 | 180.28 | 6.6E−02 | 121.3 | | | | | |
| Control | | 129.73 | | | | | | | |

TABLE 24-continued

Transgenic plants exogenously expressing the polynucleotides of some embodiments of the invention exhibit improved plant biomass (fresh and dry weight) under nitrogen deficient conditions

| Gene Name | Event # | Plant Biomass Fresh Weight [mg] Average | p-value | % incr. | Gene Name | Event # | Plant Biomass Dry Weight [mg] Average | p-value | % incr. |
|---|---|---|---|---|---|---|---|---|---|
| NUE592 | 9744.5 | 187.48 | 1.8E−06 | 64.7 | | | | | |
| NUE592 | 9747.5 | 155.45 | 5.0E−03 | 36.6 | | | | | |
| Control | | 113.81 | | | | | | | |

Table 24: Analyses of plant biomass (plant fresh and dry weight) of transgenic plants overexpressing the exogenous polynucleotides of some embodiments of the invention (using the cloned or synthetic genes listed in Table 23 above) under the regulation of a constitutive promoter (35S) when grown under limiting nitrogen conditions [low nitrogen or nitrogen deficient conditions (0.75 mM N)] as compared to control plants.
"Incr." = increment.

TABLE 25

Transgenic plants exogenously expressing the polynucleotides of some embodiments of the invention exhibit improved plant biomass (leaf area) under nitrogen deficient conditions

| Gene Name | Event # | Leaf Area [cm$^2$] Average | p-value | % increment |
|---|---|---|---|---|
| CT11 | 4894.3 | 0.70 | 4.9E−02 | 43.10 |
| CT11 | 4892.3 | 0.77 | 4.0E−02 | 57.27 |
| CT11 | 4892.2 | 0.65 | 7.4E−02 | 33.68 |
| CT11 | 4893.2 | 0.51 | 6.3E−01 | 4.12 |
| CT11 | 4892.1 | 0.93 | 1.2E−02 | 91.25 |
| Control | | 0.49 | | |
| CT27 | 5033.7 | 0.40 | 8.2E−01 | 3.15 |
| CT27 | 5031.4 | 0.59 | 7.3E−04 | 50.88 |
| CT27 | 5035.2 | 0.52 | 9.6E−03 | 33.43 |
| CT27 | 5033.4 | 0.45 | 5.2E−01 | 14.02 |
| Control | | 0.39 | | |
| CT6 | 4943.1 | 0.58 | 1.1E−01 | 47.28 |
| CT6 | 4941.4 | 0.56 | 6.0E−02 | 43.93 |
| Control | | 0.39 | | |
| CT76 | 5044.6 | 0.58 | 2.9E−01 | 19.76 |
| CT76 | 5041.5 | 0.74 | 1.1E−01 | 50.86 |
| CT76 | 5043.5 | 0.81 | 2.8E−04 | 66.21 |
| CT76 | 5041.9 | 0.79 | 5.4E−02 | 61.76 |
| CT76 | 5041.6 | 0.80 | 7.2E−03 | 64.90 |
| Control | | 0.49 | | |
| CT81 | 4992.1 | 0.70 | 3.0E−04 | 44.35 |
| CT81 | 4993.6 | 0.50 | 8.2E−01 | 3.08 |
| CT81 | 4993.5 | 0.59 | 3.2E−01 | 20.36 |
| CT81 | 4992.2 | 0.69 | 8.9E−02 | 41.46 |
| Control | | 0.49 | | |
| NUE206 | 6731.2 | 0.34 | 1.4E−02 | 30.90 |
| NUE206 | 6732.7 | 0.30 | 1.9E−01 | 15.55 |
| Control | | 0.26 | | |
| NUE208 | 8354.8 | 0.33 | 4.7E−01 | 8.19 |
| NUE208 | 8351.3 | 0.43 | 5.8E−02 | 44.03 |
| NUE208 | 8355.3 | 0.37 | 7.4E−02 | 22.98 |
| NUE208 | 8351.5 | 0.31 | 7.3E−01 | 3.72 |
| Control | | 0.30 | | |
| NUE209 | 8192.13 | 0.39 | 1.6E−01 | 30.67 |
| NUE209 | 8192.14 | 0.47 | 5.9E−02 | 56.92 |
| NUE209 | 8191.5 | 0.32 | 6.9E−01 | 4.74 |
| Control | | 0.30 | | |
| NUE209 | 8192.13 | 0.45 | 4.7E−03 | 34.55 |
| NUE209 | 8191.5 | 0.51 | 2.8E−02 | 53.15 |
| NUE209 | 8192.14 | 0.40 | 1.5E−01 | 20.45 |
| Control | | 0.33 | | |
| NUE211 | 8265.1 | 0.35 | 7.9E−02 | 17.46 |
| Control | | 0.30 | | |
| NUE212 | 8335.2 | 0.43 | 1.7E−03 | 43.62 |
| NUE212 | 8334.1 | 0.33 | 5.3E−01 | 10.76 |
| NUE212 | 8331.4 | 0.44 | 3.5E−02 | 44.45 |
| Control | | 0.30 | | |
| NUE221 | 9801.1 | 0.500 | 1.0E−01 | 20.5 |
| NUE221 | 9802.8 | 0.505 | 8.2E−02 | 21.8 |
| NUE221 | 9806.1 | 0.666 | 4.2E−06 | 60.5 |
| Control | | 0.415 | | |
| NUE224 | 9001.3 | 0.62 | 1.7E−03 | 38.99 |
| Control | | 0.44 | | |
| NUE225 | 9732.8 | 0.445 | 5.6E−01 | 7.2 |
| NUE225 | 9734.5 | 0.484 | 1.8E−01 | 16.6 |
| NUE225 | 9734.9 | 0.439 | 6.4E−01 | 5.7 |
| Control | | 0.415 | | |
| NUE230 | 9154.2 | 0.52 | 7.3E−02 | 17.73 |
| NUE230 | 9151.2 | 0.50 | 1.2E−01 | 12.59 |
| Control | | 0.44 | | |
| NUE231 | 10633.3 | 0.573 | 2.8E−04 | 38.1 |
| Control | | 0.415 | | |
| NUE233 | 10174.3 | 0.47 | 8.4E−03 | 54.39 |
| NUE233 | 10174.1 | 0.75 | 2.8E−04 | 146.46 |
| NUE233 | 10172.5 | 0.32 | 6.6E−01 | 6.03 |
| NUE233 | 10173.7 | 0.39 | 3.5E−02 | 26.43 |
| Control | | 0.31 | | |
| NUE237 | 9651.1 | 0.52 | 4.4E−01 | 17.13 |
| NUE237 | 9654.4 | 0.57 | 1.1E−01 | 29.19 |
| NUE237 | 9654.1 | 0.54 | 2.2E−02 | 21.91 |
| Control | | 0.44 | | |
| NUE239 | 9191.1 | 0.66 | 4.6E−02 | 57.34 |
| Control | | 0.42 | | |
| NUE240 | 9172.2 | 0.68 | 1.4E−03 | 63.63 |
| NUE240 | 9174.3 | 0.55 | 7.7E−02 | 32.26 |
| Control | | 0.42 | | |
| NUE240 | 9174.2 | 0.54 | 7.7E−01 | 4.29 |
| NUE240 | 9172.1 | 0.71 | 7.8E−03 | 35.86 |
| NUE240 | 9174.3 | 0.57 | 4.2E−01 | 9.74 |
| Control | | 0.52 | | |
| NUE241 | 9633.4 | 0.56 | 2.1E−05 | 47.36 |
| NUE241 | 9632.2 | 0.44 | 1.4E−01 | 15.74 |
| NUE241 | 9632.4 | 0.49 | 2.4E−01 | 28.11 |
| Control | | 0.38 | | |
| NUE241 | 9631.3 | 0.53 | 3.9E−03 | 36.03 |
| NUE241 | 9632.3 | 0.54 | 7.5E−02 | 40.72 |
| NUE241 | 9632.4 | 0.49 | 1.1E−01 | 26.49 |
| Control | | 0.39 | | |
| NUE242 | 9212.1 | 0.56 | 2.9E−02 | 50.18 |
| NUE242 | 9213.4 | 0.43 | 1.3E−01 | 14.72 |
| Control | | 0.37 | | |
| NUE246 | 9033.6 | 0.44 | 8.7E−01 | 3.16 |
| NUE246 | 9033.8 | 0.51 | 1.8E−01 | 21.26 |
| NUE246 | 9033.4 | 0.50 | 2.6E−01 | 18.30 |
| NUE246 | 9034.1 | 0.64 | 2.1E−02 | 52.45 |
| NUE246 | 9031.1 | 0.49 | 4.7E−01 | 15.11 |
| Control | | 0.42 | | |
| NUE248 | 8981.5 | 0.58 | 4.6E−02 | 38.97 |

TABLE 25-continued

Transgenic plants exogenously expressing the polynucleotides of some embodiments of the invention exhibit improved plant biomass (leaf area) under nitrogen deficient conditions

| Gene Name | Event # | Leaf Area [cm$^2$] Average | p-value | % increment |
|---|---|---|---|---|
| NUE248 | 8981.2 | 0.51 | 3.1E−02 | 22.19 |
| Control | | 0.42 | | |
| NUE251 | 10181.3 | 0.54 | 7.6E−06 | 75.63 |
| NUE251 | 10183.2 | 0.42 | 2.3E−02 | 38.78 |
| NUE251 | 10183.1 | 0.42 | 5.4E−03 | 38.58 |
| Control | | 0.31 | | |
| NUE251 | 10183.2 | 0.84 | 1.0E−02 | 72.56 |
| NUE251 | 10182.1 | 0.57 | 1.2E−01 | 18.26 |
| Control | | 0.49 | | |
| NUE256 | 10063.4 | 0.43 | 6.3E−01 | 5.53 |
| NUE256 | 10064.1 | 0.54 | 1.3E−02 | 30.76 |
| NUE256 | 10061.1 | 0.45 | 5.2E−01 | 10.87 |
| Control | | 0.41 | | |
| NUE256 | 10063.4 | 0.58 | 6.6E−02 | 90.27 |
| NUE256 | 10064.1 | 0.59 | 1.1E−02 | 94.09 |
| NUE256 | 10061.2 | 0.68 | 9.5E−06 | 122.00 |
| NUE256 | 10062.2 | 0.64 | 8.2E−03 | 108.97 |
| NUE256 | 10063.2 | 0.52 | 9.2E−03 | 68.33 |
| Control | | 0.31 | | |
| NUE256 | 10061.2 | 0.75 | 5.3E−05 | 53.75 |
| NUE256 | 10061.4 | 0.71 | 1.4E−02 | 46.02 |
| NUE256 | 10063.2 | 0.52 | 4.1E−01 | 6.83 |
| Control | | 0.49 | | |
| NUE268 | 8996.5 | 0.65 | 4.3E−02 | 21.87 |
| Control | | 0.53 | | |
| NUE511 | 9273.1 | 0.47 | 4.7E−01 | 13.04 |
| NUE511 | 9271.2 | 0.54 | 2.2E−02 | 28.41 |
| Control | | 0.42 | | |
| NUE512 | 9282.3 | 0.72 | 2.1E−02 | 68.37 |
| NUE512 | 9284.4 | 0.60 | 7.8E−03 | 39.86 |
| Control | | 0.43 | | |
| NUE514 | 9404.1 | 0.49 | 1.1E−02 | 30.78 |
| NUE514 | 9402.2 | 0.41 | 5.1E−01 | 10.03 |
| NUE514 | 9403.2 | 0.42 | 1.5E−01 | 12.66 |
| NUE514 | 9402.5 | 0.42 | 5.1E−01 | 13.45 |
| Control | | 0.37 | | |
| NUE515 | 9712.5 | 0.454 | 4.5E−01 | 9.4 |
| NUE515 | 9713.6 | 0.648 | 1.7E−05 | 56.1 |
| Control | | 0.415 | | |
| NUE520 | 9771.4 | 0.40 | 3.1E−03 | 31.70 |
| Control | | 0.31 | | |
| NUE521 | 9362.2 | 0.50 | 7.5E−02 | 33.38 |
| NUE521 | 9361.2 | 0.43 | 1.6E−01 | 14.92 |
| NUE521 | 9363.4 | 0.57 | 1.3E−03 | 54.08 |
| Control | | 0.37 | | |
| NUE521 | 9363.4 | 0.63 | 8.6E−02 | 31.31 |
| Control | | 0.48 | | |
| NUE523 | 9412.5 | 0.59 | 1.9E−01 | 40.65 |
| NUE523 | 9414.2 | 0.48 | 1.6E−01 | 16.08 |
| NUE523 | 9412.1 | 0.65 | 7.4E−03 | 55.07 |
| Control | | 0.42 | | |
| NUE525 | 9531.2 | 0.44 | 2.9E−01 | 15.42 |
| NUE525 | 9534.1 | 0.45 | 3.8E−01 | 17.35 |
| NUE525 | 9531.3 | 0.51 | 6.2E−02 | 34.94 |
| NUE525 | 9533.1 | 0.54 | 6.9E−02 | 42.25 |
| NUE525 | 9531.1 | 0.49 | 2.7E−03 | 29.15 |
| Control | | 0.38 | | |
| NUE527 | 9201.1 | 0.44 | 6.7E−02 | 22.51 |
| Control | | 0.36 | | |
| NUE528 | 9072.1 | 0.48 | 4.5E−02 | 17.39 |
| NUE528 | 9073.1 | 0.42 | 7.8E−01 | 3.17 |
| Control | | 0.41 | | |
| NUE531 | 10083.1 | 0.74 | 2.0E−02 | 31.74 |
| NUE531 | 10082.2 | 0.69 | 3.0E−02 | 22.95 |
| NUE531 | 10081.4 | 0.75 | 8.8E−02 | 32.91 |
| NUE531 | 10081.5 | 0.75 | 1.3E−01 | 33.71 |
| Control | | 0.56 | | |
| NUE535 | 9082.2 | 0.37 | 4.1E−01 | 22.10 |
| NUE535 | 9084.2 | 0.37 | 4.6E−02 | 22.19 |
| NUE535 | 9081.1 | 0.43 | 1.7E−01 | 41.23 |
| NUE535 | 9083.1 | 0.63 | 2.8E−03 | 105.40 |
| NUE535 | 9084.4 | 0.46 | 8.7E−03 | 50.93 |
| Control | | 0.31 | | |
| NUE537 | 9391.2 | 0.65 | 1.6E−02 | 51.35 |
| NUE537 | 9393.3 | 0.76 | 3.4E−03 | 76.76 |
| Control | | 0.43 | | |
| NUE539 | 10101.5 | 0.53 | 1.2E−02 | 74.32 |
| NUE539 | 10103.5 | 0.50 | 6.6E−05 | 63.28 |
| NUE539 | 10101.2 | 0.60 | 7.3E−05 | 96.27 |
| NUE539 | 10101.7 | 0.68 | 3.9E−03 | 121.77 |
| NUE539 | 10103.4 | 0.32 | 8.9E−01 | 4.57 |
| Control | | 0.31 | | |
| NUE542 | 9333.2 | 0.56 | 2.0E−02 | 25.55 |
| Control | | 0.44 | | |
| NUE543 | 10051.2 | 0.43 | 4.6E−01 | 11.78 |
| NUE543 | 10051.6 | 0.52 | 1.7E−02 | 33.53 |
| Control | | 0.39 | | |
| NUE544 | 9764.2 | 0.49 | 9.7E−02 | 19.20 |
| Control | | 0.41 | | |
| NUE548 | 9095.2 | 0.59 | 3.4E−03 | 41.28 |
| NUE548 | 9095.3 | 0.47 | 3.1E−01 | 13.55 |
| NUE548 | 9092.2 | 0.55 | 1.8E−01 | 32.59 |
| Control | | 0.42 | | |
| NUE548 | 9095.2 | 0.67 | 3.3E−01 | 10.81 |
| NUE548 | 9095.4 | 0.82 | 5.7E−02 | 36.33 |
| NUE548 | 9091.1 | 0.71 | 2.4E−02 | 17.16 |
| Control | | 0.60 | | |
| NUE568 | 9471.3 | 0.54 | 3.5E−02 | 18.92 |
| NUE568 | 9472.2 | 0.64 | 3.6E−04 | 41.93 |
| Control | | 0.45 | | |
| NUE573 | 9491.4 | 0.59 | 6.8E−02 | 29.98 |
| NUE573 | 9491.1 | 0.51 | 6.1E−01 | 13.35 |
| NUE573 | 9494.3 | 0.52 | 2.8E−01 | 14.77 |
| Control | | 0.45 | | |
| NUE574 | 10364.2 | 0.63 | 8.1E−04 | 28.96 |
| NUE574 | 10366.2 | 0.81 | 4.0E−03 | 66.05 |
| Control | | 0.49 | | |
| NUE576 | 9791.3 | 0.47 | 8.9E−02 | 21.80 |
| NUE576 | 9792.3 | 0.39 | 9.8E−01 | 0.42 |
| NUE576 | 9792.4 | 0.48 | 1.5E−01 | 24.25 |
| NUE576 | 9794.1 | 0.46 | 1.3E−01 | 19.07 |
| NUE576 | 9793.3 | 0.49 | 6.6E−02 | 25.95 |
| Control | | 0.39 | | |
| NUE581 | 9723.6 | 0.449 | 5.0E−01 | 8.3 |
| NUE581 | 9724.9 | 0.583 | 1.5E−03 | 40.6 |
| Control | | 0.415 | | |
| NUE582 | 9562.4 | 0.54 | 7.0E−02 | 21.31 |
| NUE582 | 9561.2 | 0.51 | 6.2E−02 | 14.15 |
| Control | | 0.44 | | |
| NUE583 | 9673.1 | 0.56 | 6.5E−02 | 46.13 |
| NUE583 | 9673.4 | 0.91 | 2.1E−02 | 88.22 |
| NUE583 | 9673.2 | 0.65 | 8.8E−02 | 34.45 |
| Control | | 0.49 | | |
| NUE586 | 9751.7 | 0.52 | 3.8E−01 | 11.42 |
| NUE586 | 9752.1 | 0.62 | 1.1E−02 | 31.98 |
| Control | | 0.47 | | |
| NUE586 | 9751.7 | 0.50 | 2.3E−01 | 23.80 |
| NUE586 | 9751.3 | 0.42 | 6.9E−01 | 3.28 |
| NUE586 | 9752.4 | 0.53 | 3.2E−02 | 30.20 |
| NUE586 | 9752.1 | 0.53 | 2.9E−01 | 30.75 |
| Control | | 0.41 | | |
| NUE587 | 9643.2 | 0.58 | 1.5E−02 | 24.86 |
| Control | | 0.47 | | |
| NUE592 | 9741.7 | 0.462 | 3.7E−01 | 11.3 |
| NUE592 | 9744.5 | 0.721 | 4.3E−08 | 73.7 |
| NUE592 | 9747.4 | 0.472 | 2.7E−01 | 13.8 |
| NUE592 | 9747.5 | 0.711 | 1.0E−07 | 71.4 |
| Control | | | | |

Table 25: Analyses of plant biomass (leaf area) of transgenic plants overexpressing the exogenous polynucleotides of some embodiments of the invention (using the cloned or synthetic genes listed in Table 23 above) under the regulation of a constitutive promoter (35S) when grown under limiting nitrogen conditions [low nitrogen or nitrogen deficient conditions (0.75 mM N)] as compared to control plants.

The genes presented in Table 26, hereinbelow, have improved plant NUE since they produced larger root biomass when grown under limiting nitrogen growth conditions, compared to control plants. Plants producing larger root biomass have better possibilities to absorb larger amount of nitrogen from soil.

Table 26 depicts analyses of root biomass (root length and root coverage) when grown under limiting nitrogen conditions [low nitrogen or nitrogen deficient conditions (0.75 mM N)] in plants overexpressing the polynucleotides of some embodiments of the invention under the regulation of a constitutive promoter (35S). Evaluation of each gene was performed by testing the performance of several events. Some of the genes were evaluated in more than one tissue culture assay and the second experiment confirmed the significant increment in root performance. Event with p-value <0.1 was considered statistically significant.

TABLE 26

Transgenic plants exogenously expressing the polynucleotides of some embodiments of the invention exhibit improved root performance under nitrogen deficient conditions

| | | Roots Length [cm] | | | | | Roots Coverage [cm$^2$] | | |
|---|---|---|---|---|---|---|---|---|---|
| Gene Name | Event # | Ave. | p-value | % incr. | Gene Name | Event # | Ave. | p-value | % incr. |
| CT1 | 4844.5 | 3.445 | 1.1E−01 | 19.68 | CT11 | 4894.3 | 8.833 | 4.1E−01 | 16.49 |
| CT1 | 4841.2 | 3.580 | 2.6E−01 | 24.38 | CT11 | 4892.2 | 8.345 | 6.3E−01 | 10.06 |
| Control | | 2.879 | | | CT11 | 4892.1 | 9.792 | 8.1E−02 | 29.14 |
| CT27 | 5035.2 | 4.246 | 1.7E−03 | 47.50 | Control | | 7.582 | | |
| Control | | 2.879 | | | CT22 | 5023.1 | 4.110 | 2.1E−01 | 49.46 |
| CT27 | 5033.4 | 4.384 | 2.4E−02 | 29.17 | Control | | 2.750 | | |
| Control | | 3.394 | | | CT27 | 5031.4 | 5.380 | 5.8E−01 | 10.31 |
| CT75 | 4873.4 | 4.829 | 3.9E−01 | 9.29 | CT27 | 5033.4 | 6.993 | 1.0E−01 | 43.38 |
| CT75 | 4873.3 | 6.119 | 2.2E−03 | 38.51 | Control | | 4.877 | | |
| Control | | 4.418 | | | CT27 | 5035.2 | 5.220 | 3.8E−02 | 89.83 |
| CT76 | 5044.6 | 3.723 | 1.9E−01 | 9.70 | Control | | 2.750 | | |
| CT76 | 5041.5 | 4.025 | 3.1E−02 | 18.59 | CT6 | 4943.1 | 7.564 | 2.3E−01 | 55.08 |
| CT76 | 5043.5 | 3.614 | 6.2E−01 | 6.49 | CT6 | 4941.4 | 7.260 | 1.8E−01 | 48.86 |
| CT76 | 5041.6 | 3.651 | 2.9E−01 | 7.58 | Control | | 4.877 | | |
| CT76 | 5041.9 | 3.970 | 5.6E−02 | 16.98 | CT75 | 4873.4 | 5.384 | 6.2E−01 | 10.40 |
| Control | | 3.394 | | | CT75 | 4873.3 | 6.378 | 1.6E−01 | 30.78 |
| NUE206 | 6731.2 | 4.717 | 1.4E−03 | 36.19 | Control | | 4.877 | | |
| NUE206 | 6732.9 | 3.952 | 1.7E−01 | 14.11 | CT76 | 5044.6 | 4.762 | 2.6E−02 | 39.62 |
| NUE206 | 6732.5 | 3.624 | 7.7E−01 | 4.64 | CT76 | 5041.5 | 4.729 | 6.0E−02 | 38.66 |
| Control | | 3.463 | | | CT76 | 5043.5 | 5.470 | 1.3E−01 | 60.38 |
| NUE208 | 8355.3 | 4.721 | 7.5E−02 | 36.30 | CT76 | 5041.9 | 5.282 | 1.3E−02 | 54.87 |
| Control | | 3.463 | | | Control | | 3.410 | | |
| NUE209 | 8192.14 | 4.584 | 5.7E−02 | 32.34 | NUE206 | 6731.2 | 7.467 | 1.3E−01 | 95.14 |
| Control | | 3.463 | | | NUE206 | 6732.7 | 4.706 | 3.7E−01 | 22.98 |
| NUE212 | 8331.1 | 5.110 | 2.1E−01 | 9.85 | Control | | 3.826 | | |
| NUE212 | 8332.2 | 5.868 | 9.1E−02 | 26.14 | NUE206 | 6731.2 | 6.249 | 2.8E−02 | 92.41 |
| NUE212 | 8331.4 | 4.910 | 5.8E−01 | 5.55 | NUE206 | 6732.5 | 4.433 | 4.0E−01 | 36.49 |
| Control | | 4.652 | | | Control | | 3.248 | | |
| NUE221 | 9801.1 | 4.34 | 1.6E−01 | 13.5 | NUE208 | 8354.8 | 4.799 | 5.0E−01 | 17.29 |
| NUE221 | 9801.7 | 3.84 | 9.0E−01 | 0.4 | NUE208 | 8351.3 | 5.763 | 7.7E−02 | 40.86 |
| NUE221 | 9802.8 | 4.68 | 2.1E−02 | 22.5 | Control | | 4.091 | | |
| Control | | 3.82 | | | NUE209 | 8192.13 | 5.110 | 7.0E−02 | 24.91 |
| NUE222 | 8854.1 | 4.997 | 7.0E−02 | 7.48 | NUE209 | 8192.14 | 5.450 | 1.7E−01 | 33.21 |
| Control | | 4.649 | | | Control | | 4.091 | | |
| NUE223 | 9613.1 | 4.236 | 5.0E−01 | 10.38 | NUE209 | 8192.14 | 5.624 | 5.5E−02 | 73.16 |
| NUE223 | 9611.5 | 5.091 | 6.8E−03 | 32.67 | Control | | 3.248 | | |
| NUE223 | 9612.3 | 4.868 | 1.6E−01 | 26.86 | NUE210 | 8202.2 | 5.208 | 1.0E−01 | 27.29 |
| Control | | 3.837 | | | Control | | 4.091 | | |
| NUE225 | 9731.7 | 4.58 | 4.0E−02 | 20.0 | NUE212 | 8335.2 | 6.338 | 2.8E−02 | 54.92 |
| NUE225 | 9731.8 | 4.30 | 2.0E−01 | 12.5 | NUE212 | 8334.1 | 4.541 | 3.4E−01 | 10.99 |
| NUE225 | 9732.8 | 4.09 | 4.7E−01 | 6.9 | NUE212 | 8331.4 | 6.188 | 1.3E−01 | 51.26 |
| NUE225 | 9734.5 | 4.07 | 4.9E−01 | 6.5 | Control | | 4.091 | | |
| NUE225 | 9734.9 | 4.26 | 2.3E−01 | 11.5 | NUE212 | 8332.2 | 8.847 | 2.5E−01 | 56.56 |
| Control | | 3.82 | | | NUE212 | 8331.4 | 6.998 | 2.5E−01 | 23.84 |
| NUE228 | 10092.2 | 4.242 | 1.4E−01 | 13.89 | Control | | 5.651 | | |
| NUE228 | 10093.1 | 4.106 | 2.5E−01 | 10.23 | NUE221 | 9801.1 | 5.06 | 1.4E−01 | 29.7 |
| Control | | 3.725 | | | NUE221 | 9802.8 | 5.89 | 1.2E−03 | 50.9 |
| NUE231 | 10631.3 | 4.27 | 2.3E−01 | 11.6 | NUE221 | 9806.1 | 4.39 | 5.4E−01 | 12.3 |
| NUE231 | 10631.4 | 4.08 | 4.8E−01 | 6.8 | Control | | | | |
| NUE231 | 10633.3 | 4.34 | 1.6E−01 | 13.5 | NUE223 | 9613.1 | 5.411 | 2.9E−01 | 16.86 |
| Control | | 3.82 | | | NUE223 | 9612.3 | 5.162 | 2.9E−01 | 11.49 |
| NUE233 | 10174.3 | 3.942 | 4.0E−01 | 7.65 | Control | | 4.630 | | |
| NUE233 | 10174.1 | 4.973 | 2.8E−02 | 35.83 | NUE223 | 9611.5 | 8.701 | 1.9E−02 | 67.39 |
| NUE233 | 10173.5 | 4.903 | 2.0E−02 | 33.89 | NUE223 | 9612.3 | 6.493 | 2.6E−01 | 24.90 |
| NUE233 | 10172.5 | 4.240 | 1.3E−01 | 15.78 | Control | | 5.198 | | |
| NUE233 | 10173.7 | 4.289 | 1.7E−01 | 17.14 | NUE225 | 9731.7 | 4.77 | 2.7E−01 | 22.1 |
| Control | | 3.662 | | | Control | | 3.90 | | |
| NUE233 | 10174.1 | 4.253 | 1.5E−02 | 16.86 | NUE228 | 10092.2 | 5.763 | 7.2E−02 | 34.52 |
| NUE233 | 10173.5 | 4.101 | 3.7E−01 | 12.66 | NUE228 | 10093.3 | 5.099 | 1.5E−01 | 19.02 |
| NUE233 | 10172.5 | 3.911 | 1.0E−01 | 7.44 | NUE228 | 10093.1 | 5.468 | 1.2E−01 | 27.63 |

TABLE 26-continued

Transgenic plants exogenously expressing the polynucleotides of some embodiments of the invention exhibit improved root performance under nitrogen deficient conditions

| | | Roots Length [cm] | | | | | Roots Coverage [cm²] | | |
|---|---|---|---|---|---|---|---|---|---|
| Gene Name | Event # | Ave. | p-value | % incr. | Gene Name | Event # | Ave. | p-value | % incr. |
| NUE233 | 10173.7 | 4.544 | 1.3E-01 | 24.84 | Control | | 4.284 | | |
| Control | | 3.640 | | | NUE231 | 10631.3 | 4.31 | 5.9E-01 | 10.5 |
| NUE234 | 9162.1 | 4.574 | 9.8E-02 | 23.62 | NUE231 | 10631.4 | 4.87 | 2.1E-01 | 24.8 |
| Control | | 3.700 | | | NUE231 | 10633.3 | 6.21 | 3.6E-03 | 59.1 |
| NUE235 | 9693.4 | 4.908 | 6.4E-02 | 22.32 | Control | | | | |
| NUE235 | 9691.1 | 4.310 | 4.9E-01 | 1017.43 | NUE233 | 101.74.3 | 4.340 | 2.8E-01 | 24.27 |
| NUE235 | 9694.4 | 4.347 | 4.0E-01 | 8.36 | NUE233 | 10174.1 | 7.195 | 2.6E-04 | 106.04 |
| NUE235 | 9694.3 | 5.377 | 3.4E-02 | 34.03 | NUE233 | 10173.5 | 4.086 | 3.5E-01 | 17.00 |
| Control | | 4.012 | | | NUE233 | 10173.7 | 4.955 | 5.4E-02 | 41.90 |
| NUE239 | 9192.3 | 5.241 | 4.4E-04 | 36.59 | Control | | 3.492 | | |
| NUE239 | 9192.1 | 4.041 | 5.6E-01 | 5.31 | NUE235 | 9693.4 | 6.311 | 7.2E-03 | 44.37 |
| NUE239 | 9191.2 | 4.081 | 4.2E-01 | 6.35 | NUE235 | 9691.1 | 5.246 | 3.3E-02 | 20.00 |
| Control | | 3.837 | | | NUE235 | 9694.4 | 5.145 | 1.4E-01 | 17.69 |
| NUE240 | 9172.1 | 4.624 | 1.3E-02 | 20.49 | NUE235 | 9694.3 | 6.927 | 4.8E-02 | 58.46 |
| Control | | 3.837 | | | Control | | 4.371 | | |
| NUE241 | 9633.4 | 6.137 | 3.4E-06 | 52.97 | NUE237 | 9654.4 | 7.760 | 1.1E-01 | 38.68 |
| NUE241 | 9632.3 | 4.772 | 2.4E-01 | 18.94 | NUE237 | 9654.1 | 7.127 | 3.0E-01 | 27.37 |
| NUE241 | 9632.2 | 5.157 | 3.2E-04 | 28.54 | Control | | 5.596 | | |
| NUE241 | 9632.4 | 5.016 | 2.0E-01 | 25.02 | NUE239 | 9192.3 | 8.844 | 6.5E-05 | 70.14 |
| Control | | 4.012 | | | NUE239 | 9191.2 | 5.903 | 2.8E-01 | 13.55 |
| NUE242 | 9212.1 | 4.373 | 4.9E-01 | 6.96 | Control | | 5.198 | | |
| NUE242 | 9211.2 | 4.328 | 5.2E-01 | 5.86 | NUE240 | 9172.2 | 5.902 | 5.7E-02 | 27.47 |
| NUE242 | 9213.4 | 5.474 | 1.3E-03 | 33.89 | NUE240 | 9174.3 | 5.530 | 1.2E-01 | 19.43 |
| Control | | 4.088 | | | Control | | 4.630 | | |
| NUE242 | 9212.1 | 4.552 | 1.0E-01 | 29.06 | NUE240 | 9172.1 | 7.568 | 1.8E-02 | 45.59 |
| Control | | 3.527 | | | Control | | 5.198 | | |
| NUE245 | 10641.7 | 4.388 | 9.4E-02 | 20.56 | NUE241 | 9633.4 | 9.643 | 7.2E-07 | 120.61 |
| NUE245 | 10641.8 | 4.657 | 7.4E-03 | 27.95 | NUE241 | 9632.3 | 5.344 | 3.9E-01 | 22.26 |
| NUE245 | 10643.4 | 3.906 | 2.1E-01 | 7.31 | NUE241 | 9632.2 | 6.559 | 3.6E-02 | 50.05 |
| Control | | 3.640 | | | NUE241 | 9632.4 | 6.451 | 1.3E-01 | 47.58 |
| NUE246 | 9033.4 | 4.695 | 4.8E-01 | 7.49 | Control | | 4.371 | | |
| NUE246 | 9031.1 | 5.062 | 8.4E-02 | 15.90 | NUE241 | 9632.5 | 5.170 | 5.1E-01 | 15.54 |
| Control | | 4.368 | | | NUE241 | 9632.3 | 6.198 | 8.3E-02 | 38.51 |
| NUE250 | 9134.1 | 4.593 | 1.6E-01 | 5.15 | NUE241 | 9632.4 | 5.754 | 1.6E-01 | 28.58 |
| NUE250 | 9132.2 | 4.590 | 3.3E-01 | 5.09 | Control | | 4.475 | | |
| Control | | 4.088 | | | NUE242 | 9212.1 | 5.873 | 4.1E-01 | 11.59 |
| NUE251 | 10181.3 | 3.907 | 2.6E-01 | 7.34 | NUE242 | 9213.4 | 8.125 | 1.6E-02 | 54.40 |
| NUE251 | 10183.2 | 4.763 | 7.9E-02 | 30.87 | Control | | 5.262 | | |
| Control | | 3.640 | | | NUE242 | 9212.1 | 5.679 | 1.2E-01 | 67.87 |
| NUE256 | 10063.4 | 5.259 | 1.4E-02 | 3 | NUE242 | 3.4 | 4.572 | 2.4E-01 | 35.15 |
| NUE256 | 10064.1 | 4.734 | 2.3E-02 | 29.28 | Control | | 3.383 | | |
| NUE256 | 10061.2 | 4.281 | 1.3E-01 | 16.92 | NUE245 | 10641.8 | 4.795 | 1.3E-01 | 22.01 |
| NUE256 | 10062.4 | 3.855 | 7.0E-01 | 5.28 | Control | | 3.930 | | |
| NUE256 | 10063.2 | 5.276 | 5.5E-03 | 44.10 | NUE246 | 9033.8 | 6.003 | 2.5E-01 | 20.21 |
| Control | | 3.662 | | | NUE246 | 9033.4 | 5.693 | 4.7E-01 | 14.00 |
| NUE512 | 9284.3 | 4.875 | 1.0E-01 | 17.48 | NUE246 | 9034.1 | 6.292 | 1.7E-01 | 25.99 |
| NUE512 | 9282.3 | 4.442 | 4.4E-01 | 7.05 | NUE246 | 9031.1 | 7.329 | 6.6E-03 | 46.77 |
| NUE512 | 9284.4 | 6.172 | 3.9E-04 | 48.73 | Control | | 4.994 | | |
| Control | | 4.150 | | | NUE250 | 9134.1 | 5.762 | 4.8E-01 | 9.49 |
| NUE513 | 9681.6 | 5.009 | 1.7E-03 | 30.52 | NUE250 | 9132.2 | 7.281 | 2.7E-01 | 38.35 |
| NUE513 | 9683.2 | 4.506 | 8.6E-02 | 17.42 | Control | | 5.262 | | |
| Control | | 3.837 | | | NUE251 | 10181.3 | 4.289 | 1.9E-01 | 22.81 |
| NUE514 | 9404.1 | 4.333 | 5.3E-01 | 5.99 | NUE251 | 10183.2 | 4.689 | 1.4E-01 | 34.27 |
| NUE514 | 9404.5 | 4.906 | 4.1E-02 | 20.00 | NUE251 | 10183.1 | 4.709 | 1.9E-01 | 34.86 |
| NUE514 | 9403.2 | 4.451 | 6.9E-02 | 8.87 | Control | | 3.492 | | |
| NUE514 | 9402.5 | 4.644 | 2.1E-01 | 13.59 | NUE251 | 10183.2 | 6.691 | 3.8E-02 | 70.25 |
| Control | | 4.088 | | | NUE251 | 10181.1 | 4.687 | 4.8E-01 | 19.25 |
| NUE514 | 9403.2 | 4.874 | 2.1E-02 | 38.20 | Control | | 3.930 | | |
| NUE514 | 9402.5 | 4.044 | 2.9E-01 | 14.65 | NUE256 | 10063.4 | 7.393 | 2.9E-02 | 111.70 |
| Control | | 3.527 | | | NUE256 | 10064.1 | 7.214 | 2.6E-02 | 106.59 |
| NUE515 | 9712.5 | 4.43 | 1.0E-01 | 15.9 | NUE256 | 10061.2 | 6.139 | 2.2E-03 | 75.81 |
| NUE515 | 9712.6 | 4.05 | 5.0E-01 | 5.8 | NUE256 | 10062.4 | 6.337 | 7.9E-02 | 81.46 |
| NUE515 | 9713.6 | 5.34 | 1.0E-04 | 39.7 | NUE256 | 10063.2 | 6.594 | 1.7E-02 | 88.81 |
| Control | | 3.82 | | | Control | | 3.492 | | |
| NUE520 | 9771.4 | 4.327 | 6.9E-02 | 16.16 | NUE256 | 10061.3 | 4.798 | 3.9E-02 | 22.09 |
| NUE520 | 9771.7 | 4.332 | 1.7E-01 | 16.28 | NUE256 | 10061.2 | 5.141 | 1.9E-02 | 30.82 |

TABLE 26-continued

Transgenic plants exogenously expressing the polynucleotides of some embodiments of the invention exhibit improved root performance under nitrogen deficient conditions

| | | Roots Length [cm] | | | | | Roots Coverage [cm²] | | |
|---|---|---|---|---|---|---|---|---|---|
| Gene Name | Event # | Ave. | p-value | % incr. | Gene Name | Event # | Ave. | p-value | % incr. |
| NUE520 | 9771.2 | 4.303 | 1.2E-01 | 15.52 | NUE256 | 10061.4 | 5.617 | 9.8E-02 | 42.92 |
| NUE520 | 9771.3 | 4.345 | 1.6E-01 | 16.66 | NUE256 | 10063.2 | 5.303 | 1.5E-02 | 34.95 |
| Control | | 3.725 | | | Control | | 3.930 | | |
| NUE520 | 9771.4 | 4.377 | 1.4E-01 | 19.54 | NUE268 | 8996.5 | 7.789 | 1.6E-02 | 40.04 |
| NUE520 | 9771.2 | 4.684 | 3.1E-02 | 27.93 | Control | | 5.562 | | |
| NUE520 | 9771.3 | 3.878 | 5.2E-01 | 5.90 | NUE512 | 9284.3 | 4.930 | 1.1E-01 | 21.84 |
| Control | | 3.662 | | | NUE512 | 9282.3 | 5.873 | 1.4E-01 | 45.13 |
| NUE523 | 9412.5 | 4.031 | 3.9E-01 | 14.28 | NUE512 | 9284.4 | 7.912 | 1.6E-03 | 95.53 |
| NUE523 | 9414.2 | 5.032 | 1.5E-03 | 42.68 | Control | | 4.047 | | |
| NUE523 | 9413.4 | 3.766 | 2.8E-01 | 6.78 | NUE513 | 9681.6 | 6.591 | 3.6E-02 | 26.79 |
| Control | | 3.527 | | | Control | | 5.198 | | |
| NUE523 | 9412.5 | 5.066 | 6.2E-01 | 7.98 | NUE514 | 9404.5 | 6.570 | 9.0E-02 | 24.84 |
| NUE523 | 9414.2 | 5.879 | 2.1E-04 | 25.30 | Control | | 5.262 | | |
| Control | | 4.692 | | | NUE514 | 9403.2 | 5.579 | 1.2E-02 | 64.94 |
| NUE525 | 9531.2 | 5.029 | 1.0E-03 | 25.34 | NUE514 | 9402.5 | 4.299 | 3.2E-01 | 27.09 |
| NUE525 | 9534.1 | 5.116 | 4.0E-02 | 27.51 | Control | | 3.383 | | |
| NUE525 | 9533.1 | 4.471 | 2.8E-01 | 11.43 | NUE515 | 9712.5 | 4.93 | 26.3 | 1.9E-01 |
| NUE525 | 9531.1 | 5.184 | 1.9E-01 | 29.21 | NUE515 | 9712.6 | 4.09 | 4.7 | 8.1E-01 |
| Control | | 4.012 | | | NUE515 | 9713.6 | 7.39 | 89.4 | 1.9E-05 |
| NUE531 | 10081.5 | 5.029 | 9.2E-02 | 35.00 | Control | | 3.90 | | |
| Control | | 3.725 | | | NUE519 | 9371.2 | 7.868 | 4.7E-01 | 51.36 |
| NUE531 | 10083.3 | 4.502 | 2.7E-03 | 23.69 | NUE519 | 9371.1 | 7.813 | 1.7E-01 | 50.30 |
| NUE531 | 10081.4 | 3.894 | 1.4E-01 | 6.98 | Control | | 5.198 | | |
| NUE531 | 10083.2 | 4.655 | 3.2E-02 | 9 | NUE520 | 1.4 | 4.820 | 3.0E-01 | 12.51 |
| NUE531 | 10081.5 | 5.026 | 2.1E-02 | 8 | NUE520 | 1.7 | 5.879 | 1.4E-02 | 37.23 |
| Control | | 3.640 | | | NUE520 | 9771.2 | 6.392 | 3.3E-02 | 49.20 |
| NUE536 | 9233.3 | 5.416 | 1.2E-02 | 24.00 | NUE520 | 9771.3 | 7.265 | 1.4E-02 | 69.57 |
| Control | | 4.368 | | | Control | | 4.284 | | |
| NUE539 | 10101.5 | 4.107 | 4.7E-01 | 12.17 | NUE520 | 9771.4 | 6.158 | 1.8E-02 | 76.34 |
| NUE539 | 10103.5 | 4.561 | 5.0E-02 | 24.57 | NUE520 | 9771.2 | 6.839 | 1.7E-02 | 95.84 |
| NUE539 | 10101.7 | 4.953 | 2.0E-02 | 35.27 | NUE520 | 9771.3 | 5.440 | 5.3E-03 | 55.77 |
| Control | | 3.662 | | | NUE520 | 9773.1 | 4.655 | 9.8E-02 | 33.29 |
| NUE539 | 10101.7 | 4.344 | 8.5E-02 | 19.36 | Control | | 3.492 | | |
| Control | | 3.640 | | | NUE521 | 9362.2 | 4.458 | 3.1E-01 | 31.79 |
| NUE543 | 10051.1 | 4.030 | 3.5E-01 | 8.20 | NUE521 | 9363.4 | 5.071 | 5.6E-02 | 49.90 |
| NUE543 | 10052.3 | 4.347 | 8.1E-02 | 16.70 | Control | | 3.383 | | |
| NUE543 | 10053.1 | 4.034 | 4.0E-01 | 8.29 | NUE523 | 9412.5 | 4.834 | 3.0E-01 | 42.92 |
| Control | | 3.725 | | | NUE523 | 9414.2 | 5.371 | 1.7E-04 | 58.79 |
| NUE563 | 9452.3 | 5.668 | 7.3E-02 | 41.27 | Control | | 3.383 | | |
| NUE563 | 9451.2 | 4.348 | 2.6E-01 | 8.38 | NUE523 | 9413.3 | 6.532 | 5.1E-01 | 20.78 |
| NUE563 | 9452.1 | 4.415 | 3.9E-01 | 104-.0 | NUE523 | 9414.2 | 8.479 | 4.6E-02 | 56.78 |
| Control | | 4.012 | | | Control | | 5.408 | | |
| NUE566 | 9513.1 | 4.306 | 4.5E-01 | 7.32 | NUE525 | 9531.2 | 6.497 | 1.7E-04 | 48.62 |
| NUE566 | 9512.2 | 4.118 | 6.3E-01 | 2.63 | NUE525 | 9534.1 | 6.805 | 6.9E-02 | 55.67 |
| NUE566 | 9512.4 | 4.411 | 3.9E-01 | 9.95 | NUE525 | 9531.3 | 4.928 | 6.1E-01 | 12.73 |
| NUE566 | 9512.1 | 5.392 | 9.6E-02 | 34.39 | NUE525 | 9533.1 | 7.002 | 3.6E-02 | 60.17 |
| NUE566 | 9514.1 | 5.583 | 1.8E-05 | 39.15 | NUE525 | 9531.1 | 8.063 | 1.5E-01 | 84.46 |
| Control | | 4.012 | | | Control | | 4.371 | | |
| NUE574 | 10363.4 | 4.132 | 3.5E-01 | 13.52 | NUE531 | 10083.3 | 4.905 | 2.4E-02 | 24.81 |
| NUE574 | 10366.2 | 4.697 | 7.2E-02 | 29.04 | NUE531 | 10081.4 | 6.308 | 1.3E-02 | 60.52 |
| NUE574 | 10366.1 | 4.264 | 6.0E-03 | 17.15 | NUE531 | 10083.2 | 5.480 | 8.6E-02 | 39.45 |
| Control | | 3.640 | | | NUE531 | 10081.5 | 7.516 | 4.3E-02 | 91.25 |
| NUE581 | 9724.9 | 4.35 | 1.5E-01 | 13.8 | Control | | 3.930 | | |
| Control | | 3.82 | | | NUE536 | 9233.3 | 7.107 | 3.3E-02 | 42.30 |
| NUE583 | 9673.4 | 5.145 | 8.6E-02 | 41.35 | Control | | 4.994 | | |
| NUE583 | 9673.2 | 4.621 | 1.6E-02 | 26.95 | NUE537 | 9393.3 | 7.508 | 5.7E-02 | 85.53 |
| NUE583 | 9671.2 | 4.181 | 1.0E-01 | 14.88 | Control | | 4.047 | | |
| NUE583 | 9671.1 | 3.903 | 3.2E-01 | 7.24 | NUE539 | 10101.5 | 5.026 | 1.1E-01 | 43.93 |
| Control | | 3.640 | | | NUE539 | 10103.5 | 5.622 | 7.6E-03 | 60.99 |
| NUE586 | 9751.1 | 4.510 | 4.7E-01 | 7.36 | NUE539 | 10101.7 | 6.622 | 4.1E-03 | 89.62 |
| NUE586 | 9751.7 | 5.845 | 3.0E-03 | 39.13 | Control | | 3.492 | | |
| NUE586 | 9751.3 | 5.259 | 7.3E-02 | 25.20 | NUE543 | 10051.1 | 5.204 | 9.1E-02 | 21.47 |
| NUE586 | 9752.2 | 4.903 | 1.1E-01 | 16.71 | NUE543 | 10052.3 | 4.978 | 2.0E-01 | 16.20 |
| NUE586 | 9752.1 | 6.626 | 1.3E-05 | 57.73 | NUE543 | 10051.2 | 5.086 | 3.6E-01 | 18.73 |
| Control | | 4.201 | | | Control | | 4.284 | | |
| NUE586 | 9751.1 | 5.290 | 3.0E-01 | 13.71 | NUE544 | 9764.2 | 8.303 | 9.5E-02 | 46.92 |
| NUE586 | 9751.6 | 6.090 | 1.6E-03 | 30.92 | NUE544 | 9763.3 | 6.821 | 1.1E-01 | 20.71 |
| NUE586 | 9751.3 | 5.181 | 3.1E-01 | 11.38 | Control | | 5.651 | | |

TABLE 26-continued

Transgenic plants exogenously expressing the polynucleotides of some embodiments of the invention exhibit improved root performance under nitrogen deficient conditions

| | | Roots Length [cm] | | | | | Roots Coverage [cm$^2$] | | |
|---|---|---|---|---|---|---|---|---|---|
| Gene Name | Event # | Ave. | p-value | % incr. | Gene Name | Event # | Ave. | p-value | % incr. |
| NUE586 | 9752.4 | 5.952 | 2.9E−03 | 27.96 | NUE548 | 9095.2 | 7.731 | 2.2E−01 | 46.90 |
| NUE586 | 9752.1 | 6.660 | 2.1E−04 | 43.17 | NUE548 | 9095.4 | 7.888 | 1.3E−01 | 49.89 |
| Control | | 4.652 | | | NUE548 | 9091.1 | 6.011 | 2.7E−01 | 14.23 |
| NUE593 | 10391.2 | 4.849 | 8.9E−03 | 30.18 | Control | | 5.262 | | |
| NUE593 | 10394.1 | 4.390 | 2.4E−01 | 5 | NUE554 | 5.2 | 7.603 | 3.2E−02 | 36.68 |
| NUE593 | 10394.2 | 4.698 | 3.3E−02 | 26.13 | Control | | 5.562 | | |
| Control | | 3.725 | | | NUE563 | 9452.3 | 9.266 | 1.7E−01 | 111.97 |
| NUE592 | 9741.7 | 4.08 | 4.8E−01 | 6.8 | NUE563 | 9451.2 | 6.068 | 1.3E−01 | 38.82 |
| NUE592 | 9747.4 | 4.00 | 6.2E−01 | 4.8 | NUE563 | 9452.1 | 5.145 | 1.2E−01 | 17.70 |
| NUE592 | 9747.5 | 4.70 | 1.8E−02 | 23.0 | Control | | 4.371 | | |
| Control | | 3.82 | | | NUE566 | 9513.1 | 5.537 | 2.0E−01 | 26.67 |
| | | | | | NUE566 | 9512.2 | 5.086 | 1.3E−01 | 16.36 |
| | | | | | NUE566 | 9512.1 | 7.608 | 1.0E−01 | 74.05 |
| | | | | | NUE566 | 9514.1 | 7.752 | 2.2E−03 | 77.33 |
| | | | | | Control | | 4.371 | | |
| | | | | | NUE569 | 9381.2 | 5.147 | 2.8E−02 | 21.78 |
| | | | | | Control | | 4.226 | | |
| | | | | | NUE570 | 9311.4 | 4.965 | 5.6E−01 | 22.69 |
| | | | | | NUE570 | 9314.4 | 5.327 | 8.0E−02 | 31.63 |
| | | | | | NUE570 | 9314.1 | 5.093 | 3.3E−01 | 25.85 |
| | | | | | Control | | 4.047 | | |
| | | | | | NUE574 | 10364.2 | 4.318 | 1.9E−01 | 9.88 |
| | | | | | NUE574 | 10366.2 | 7.430 | 5.1E−02 | 89.06 |
| | | | | | NUE574 | 10366.1 | 5.260 | 5.6E−02 | 33.83 |
| | | | | | Control | | 3.930 | | |
| | | | | | NUE581 | 9723.6 | 4.16 | 7.4E | 6.5 |
| | | | | | NUE581 | 9724.9 | 4.93 | 1.9E | 26.3 |
| | | | | | Control | | 3.90 | | |
| | | | | | NUE583 | 9673.4 | 8.986 | 1.7E−02 | 128.64 |
| | | | | | NUE583 | 9673.2 | 6.359 | 5.0E−02 | 61.80 |
| | | | | | NUE583 | 9671.2 | 4.956 | 1.0E−01 | 26.11 |
| | | | | | Control | | 3.930 | | |
| | | | | | NUE586 | 9751.1 | 5'324 | 5.1E−01 | 14.00 |
| | | | | | NUE586 | 9751.7 | 8.938 | 2.6E−02 | 91.38 |
| | | | | | NUE586 | 9751.3 | 6.250 | 8.3E−02 | 33.83 |
| | | | | | NUE586 | 9752.2 | 5.566 | 3.7E−01 | 19.18 |
| | | | | | NUE586 | 9752.1 | 10.320 | 9.6E−04 | 120.99 |
| | | | | | Control | | 4.670 | | |
| | | | | | NUE586 | 9751.1 | 7.261 | 2.8E−01 | 28.49 |
| | | | | | NUE586 | 9751.6 | 7.902 | 4.2E−02 | 39.83 |
| | | | | | NUE586 | 9751.7 | 6.250 | 6.0E−01 | 10.60 |
| | | | | | NUE586 | 9751.3 | 7.274 | 9.2E−02 | 28.71 |
| | | | | | NUE586 | 9752.4 | 8.572 | 6.8E−03 | 51.70 |
| | | | | | NUE586 | 9752.1 | 9.922 | 5.6E−02 | 75.58 |
| | | | | | Control | | 5.651 | | |
| | | | | | NUE587 | 9643.2 | 7'007 | 7.6E−02 | 50.03 |
| | | | | | Control | | 4.670 | | |
| | | | | | NUE592 | 9741.7 | 4.20 | 7.0E | 7.7 |
| | | | | | NUE592 | 9747.5 | 5.31 | 7.3E | 36.0 |
| | | | | | Control | | 3.90 | | |
| | | | | | NUE593 | 10391.2 | 5.167 | 2.6E−01 | 20.60 |
| | | | | | NUE593 | 10394.2 | 6.009 | 9.4E−02 | 40.25 |
| | | | | | Control | | 4.284 | | |

Table 26: Analyses of root performance (root length and coverage) of transgenic plants overexpressing the exogenous polynucleotides of some embodiments of the invention (using the cloned or synthetic genes listed in Table 23 above) under the regulation of a constitutive promoter (35S) when grown under limiting nitrogen conditions [low nitrogen or nitrogen deficient conditions (0.75 mM N)] as compared to control plants.
"Ave." = Average;
"Incr." = increment.

The genes presented in Tables 27 and 28, hereinbelow, have improved plant growth rate when grown under limiting nitrogen growth conditions, compared to control plants. Plants showing fast growth rate confirm a better plant establishment in soil under nitrogen deficient conditions. Faster growth was observed when growth rate of leaf area as well as root length and coverage was measured.

Table 27 and 28 depict analyses of plant growth rate of the leaf area, root coverage and root length when grown under limiting nitrogen conditions [low nitrogen or nitrogen deficient conditions (0.75 mM N)] in plants overexpressing the polynucleotides of some embodiments of the invention under the regulation of a constitutive promoter (35S). Evaluation of each gene was performed by testing the performance of several events. Some of the genes were evaluated in more than one tissue culture assay and the second experiment confirmed the significant increment in growth rate. Event with p-value <0.1 was considered statistically significant.

TABLE 27

Transgenic plants exogenously expressing the polynucleotides of some embodiments of the invention exhibit improved plant growth rate (relative growth rate of leaf area and root coverage) under nitrogen deficient conditions

| | | RGR Of Leaf Area | | | | | RGR Of Roots Coverage | | |
|---|---|---|---|---|---|---|---|---|---|
| Gene Name | Event # | Average | p-value | % Incr. | Gene Name | Event # | Average | p-value | % Incr. |
| CT11 | 4892.3 | 0.043 | 3.1E−01 | 14.75 | CT11 | 4894.3 | 1.07 | 2.6E−01 | 18.78 |
| CT11 | 4893.2 | 0.054 | 7.0E−02 | 43.87 | CT11 | 4892.2 | 1.02 | 4.7E−01 | 12.68 |
| Control | | 0.038 | | | CT11 | 4892.1 | 1.17 | 4.9E−02 | 29.43 |
| CT11 | 4894.3 | 0.071 | 3.2E−02 | 37.85 | Control | | 0.90 | | |
| CT11 | 4892.3 | 0.077 | 6.5E−03 | 47.95 | CT22 | 5023.1 | 0.49 | 6.6E−02 | 51.49 |
| CT11 | 4892.2 | 0.066 | 8.1E−02 | 27.89 | Control | | 0.32 | | |
| Control | | 0.052 | | | CT27 | 5033.7 | 0.51 | 5.1E−01 | 59.31 |
| CT27 | 5031.4 | 0.059 | 2.1E−03 | 56.19 | CT27 | 5031.4 | 0.66 | 4.4E−01 | 106.25 |
| CT27 | 5035.2 | 0.050 | 3.7E−02 | 31.33 | CT27 | 5035.2 | 0.48 | 3.3E−01 | 50.35 |
| Control | | 0.038 | | | CT27 | 5033.6 | 0.46 | 1.9E−01 | 41.98 |
| CT27 | 5035.2 | 0.052 | 1.4E−02 | 47.58 | CT27 | 5033.4 | 0.81 | 5.0E−02 | 152.27 |
| Control | | 0.035 | | | CT27 | 5033.8 | 0.36 | 4.5E−02 | 12.91 |
| CT27 | 5033.4 | 0.047 | 1.9E−01 | 28.65 | Control | | 0.32 | | |
| CT27 | 5033.8 | 0.062 | 1.7E−04 | 66.84 | CT6 | 4943.1 | 0.93 | 4.7E−02 | 60.75 |
| Control | | 0.037 | | | CT6 | 4941.4 | 0.88 | 3.3E−02 | 52.53 |
| CT6 | 4943.1 | 0.058 | 1.9E−02 | 54.43 | Control | | 0.58 | | |
| CT6 | 4941.4 | 0.058 | 1.2E−02 | 52.74 | CT75 | 4873.3 | 0.75 | 1.1E−01 | 30.24 |
| Control | | 0.038 | | | Control | | 0.58 | | |
| CT76 | 5044.6 | 0.059 | 3.8E−01 | 13.49 | CT76 | 5041.5 | 1.29 | 5.2E−02 | 43.20 |
| CT76 | 5041.5 | 0.075 | 2.9E−02 | 44.40 | CT76 | 5043.5 | 1.24 | 5.2E−02 | 37.15 |
| CT76 | 5043.5 | 0.082 | 2.8E−04 | 58.85 | CT76 | 5041.6 | 1.01 | 4.7E−01 | 11.99 |
| CT76 | 5041.9 | 0.084 | 4.2E−03 | 62.25 | Control | | 0.90 | | |
| CT76 | 5041.6 | 0.086 | 5.5E−04 | 65.56 | CT76 | 5044.6 | 0.59 | 3.6E−02 | 49.62 |
| Control | | 0.052 | | | CT76 | 5043.5 | 0.67 | 1.9E−02 | 71.45 |
| CT76 | 5044.6 | 0.044 | 2.9E−01 | 18.54 | CT76 | 5041.6 | 0.46 | 4.1E−01 | 17.98 |
| CT76 | 5041.5 | 0.050 | 5.8E−02 | 36.83 | CT76 | 5041.9 | 0.64 | 8.3E−03 | 64.17 |
| CT76 | 5043.5 | 0.075 | 1.6E−07 | 103.60 | Control | | 0.39 | | |
| CT76 | 5041.6 | 0.053 | 9.2E−03 | 43.71 | NUE206 | 6731.2 | 0.88 | 6.1E−03 | 107.33 |
| CT76 | 5041.9 | 0.055 | 7.7E−03 | 48.95 | NUE206 | 6732.7 | 0.54 | 2.5E−01 | 28.14 |
| Control | | 0.037 | | | Control | | 0.42 | | |
| CT81 | 4992.1 | 0.074 | 1.9E−03 | 43.33 | NUE206 | 6731.2 | 0.73 | 3.0E−04 | 103.93 |
| CT81 | 4993.5 | 0.061 | 2.8E−01 | 17.47 | NUE206 | 6732.9 | 0.46 | 1.5E−01 | 29.09 |
| CT81 | 4992.2 | 0.072 | 2.3E−02 | 38.79 | NUE206 | 6732.5 | 0.51 | 1.5E−01 | 42.93 |
| Control | | 0.052 | | | Control | | 0.36 | | |
| NUE206 | 6731.2 | 0.035 | 2.0E−02 | 39.25 | NUE208 | 8354.8 | 0.58 | 3.9E−01 | 18.43 |
| NUE206 | 6732.7 | 0.032 | 6.4E−02 | 28.96 | NUE208 | 8351.3 | 0.71 | 3.7E−02 | 44.72 |
| Control | | 0.025 | | | Control | | 0.49 | | |
| NUE208 | 8351.3 | 0.046 | 1.0E−02 | 54.30 | NUE208 | 8355.3 | 0.72 | 9.1E−03 | 100.13 |
| NUE208 | 8355.3 | 0.038 | 9.5E−02 | 28.29 | Control | | 0.36 | | |
| Control | | 0.030 | | | NUE209 | 8192.13 | 0.63 | 1.3E−01 | 28.43 |
| NUE208 | 8355.3 | 0.073 | 2.0E−02 | 55.84 | NUE209 | 8192.14 | 0.65 | 1.1E−01 | 32.34 |
| Control | | 0.047 | | | Control | | 0.49 | | |
| NUE209 | 8192.13 | 0.043 | 3.2E−02 | 44.12 | NUE209 | 8192.14 | 0.65 | 4.0E−03 | 79.86 |
| NUE209 | 8192.14 | 0.047 | 6.9E−03 | 60.54 | Control | | 0.36 | | |
| Control | | 0.030 | | | NUE212 | 8332.2 | 0.64 | 2.2E−02 | 70.92 |
| NUE209 | 8192.13 | 0.047 | 2.2E−02 | 38.99 | NUE212 | 8334.1 | 0.61 | 1.5E−01 | 63.17 |
| NUE209 | 8191.5 | 0.055 | 4.8E−04 | 64.77 | Control | | 0.37 | | |
| NUE209 | 8192.14 | 0.041 | 1.2E−01 | 22.52 | NUE212 | 8335.2 | 0.75 | 1.1E−02 | 52.25 |
| Control | | 0.033 | | | NUE212 | 8331.4 | 0.76 | 2.4E−02 | 54.17 |
| NUE209 | 8192.14 | 0.071 | 2.5E−03 | 52.94 | Control | | 0.49 | | |
| NUE209 | 8191.3 | 0.057 | 2.2E−01 | 22.44 | NUE212 | 8332.2 | 1.08 | 2.7E−02 | 58.34 |
| Control | | 0.047 | | | NUE212 | 8331.4 | 0.87 | 1.6E−01 | 27.37 |
| NUE212 | 8335.2 | 0.041 | 1.9E−02 | 40.11 | Control | | 0.68 | | |
| NUE212 | 8331.4 | 0.046 | 8.8E−03 | 54.77 | NUE223 | 9611.5 | 1.06 | 8.9E−04 | 67.16 |
| Control | | 0.030 | | | NUE223 | 9612.3 | 0.77 | 2.3E−01 | 21.00 |
| NUE212 | 8332.1 | 0.062 | 4.8E−03 | 50.03 | Control | | 0.63 | | |
| Control | | 0.041 | | | NUE228 | 10092.2 | 0.70 | 2.0E−02 | 41.76 |
| NUE224 | 9001.3 | 0.064 | 5.9E−04 | 41.00 | NUE228 | 10093.3 | 0.61 | 1.5E−01 | 23.30 |
| Control | | 0.045 | | | NUE228 | 10093.1 | 0.66 | 5.5E−02 | 33.53 |
| NUE230 | 9154.2 | 0.054 | 8.1E−02 | 19.70 | Control | | 0.49 | | |
| NUE230 | 9151.2 | 0.052 | 1.5E−01 | 14.88 | NUE233 | 10174.3 | 0.52 | 2.2E−01 | 27.38 |
| Control | | 0.045 | | | NUE233 | 10174.1 | 0.86 | 1.1E−05 | 111.13 |
| NUE230 | 9153.3 | 0.046 | 3.5E−02 | 23.46 | NUE233 | 10173.7 | 0.59 | 4.2E−02 | 45.30 |
| Control | | 0.038 | | | Control | | 0.41 | | |
| NUE233 | 10174.3 | 0.047 | 2.8E−03 | 52.81 | NUE233 | 10174.1 | 0.56 | 8.1E−02 | 22.89 |
| NUE233 | 10174.1 | 0.075 | 5.3E−09 | 141.80 | NUE233 | 10173.7 | 0.72 | 2.7E−03 | 57.48 |
| NUE233 | 10173.7 | 0.040 | 4.3E−02 | 28.55 | Control | | 0.46 | | |
| Control | | 0.031 | | | NUE234 | 9162.1 | 0.51 | 5.1E−02 | 39.40 |
| NUE237 | 9651.1 | 0.051 | 4.5E−01 | 12.77 | Control | | 0.37 | | |
| NUE237 | 9654.4 | 0.059 | 2.5E−02 | 31.14 | NUE235 | 9693.4 | 0.68 | 2.5E−03 | 44.45 |
| NUE237 | 9654.1 | 0.056 | 2.6E−02 | 24.39 | NUE235 | 9691.1 | 0.56 | 2.0E−01 | 18.18 |

TABLE 27-continued

Transgenic plants exogenously expressing the polynucleotides of some embodiments of the invention exhibit improved plant growth rate (relative growth rate of leaf area and root coverage) under nitrogen deficient conditions

| | RGR Of Leaf Area | | | | RGR Of Roots Coverage | | | |
|---|---|---|---|---|---|---|---|---|
| Gene Name | Event # | Average | p-value | % Incr. | Gene Name | Event # | Average | p-value | % Incr. |
| Control | | 0.045 | | | NUE235 | 9694.4 | 0.55 | 2.3E−01 | 15.87 |
| NUE239 | 9191.1 | 0.063 | 1.3E−02 | 58.77 | NUE235 | 9694.3 | 0.76 | 1.1E−03 | 60.48 |
| Control | | 0.040 | | | Control | | 0.47 | | |
| NUE239 | 9192.3 | 0.061 | 5.3E−02 | 25.48 | NUE237 | 9654.4 | 0.93 | 7.8E−02 | 39.79 |
| Control | | 0.048 | | | NUE237 | 9654.1 | 0.84 | 2.4E−01 | 26.90 |
| NUE240 | 9172.2 | 0.067 | 1.5E−03 | 68.99 | Control | | 0.66 | | |
| NUE240 | 9174.3 | 0.052 | 1.4E−01 | 29.40 | NUE239 | 9191.1 | 0.75 | 6.5E−02 | 36.48 |
| Control | | 0.040 | | | Control | | 0.55 | | |
| NUE240 | 9172.1 | 0.068 | 4.1E−03 | 41.05 | NUE239 | 9192.3 | 1.08 | 7.2E−05 | 71.00 |
| Control | | 0.048 | | | NUE239 | 9191.2 | 0.73 | 3.5E−01 | 14.79 |
| NUE241 | 9633.4 | 0.053 | 4.5E−04 | 58.65 | Control | | 0.63 | | |
| NUE241 | 9632.2 | 0.042 | 7.6E−02 | 26.55 | NUE240 | 9172.2 | 0.73 | 5.1E−02 | 33.21 |
| NUE241 | 9632.4 | 0.045 | 6.8E−02 | 35.24 | NUE240 | 9174.3 | 0.68 | 1.4E−01 | 23.94 |
| Control | | 0.033 | | | Control | | 0.55 | | |
| NUE241 | 9632.3 | 0.056 | 2.2E−02 | 43.54 | NUE240 | 9172.1 | 0.93 | 8.4E−03 | 46.95 |
| Control | | 0.039 | | | Control | | 0.63 | | |
| NUE242 | 9212.1 | 0.053 | 4.2E−03 | 49.38 | NUE241 | 9633.4 | 1.05 | 5.1E−09 | 121.17 |
| NUE242 | 9213.4 | 0.041 | 2.2E−01 | 15.83 | NUE241 | 9632.3 | 0.56 | 3.0E−01 | 17.76 |
| Control | | 0.036 | | | NUE241 | 9632.2 | 0.70 | 4.2E−03 | 47.48 |
| NUE245 | 10641.7 | 0.064 | 3.3E−02 | 39.30 | NUE241 | 9632.4 | 0.68 | 2.6E−02 | 42.78 |
| Control | | 0.046 | | | Control | | 0.47 | | |
| NUE246 | 9033.8 | 0.047 | 5.0E−01 | 13.54 | NUE241 | 9632.3 | 0.73 | 8.7E−02 | 37.63 |
| NUE246 | 9033.4 | 0.053 | 1.8E−01 | 27.65 | NUE241 | 9632.4 | 0.68 | 1.8E−01 | 28.48 |
| NUE246 | 9034.1 | 0.067 | 1.3E−02 | 63.07 | Control | | 0.53 | | |
| Control | | 0.041 | | | NUE242 | 9214.1 | 0.82 | 5.3E−01 | 34.65 |
| NUE248 | 8981.5 | 0.059 | 1.8E−02 | 42.38 | NUE242 | 9213.4 | 0.98 | 4.4E−04 | 61.42 |
| Control | | 0.041 | | | Control | | 0.61 | | |
| NUE250 | 9132.1 | 0.051 | 2.9E−01 | 13.50 | NUE242 | 9212.1 | 0.69 | 2.3E−03 | 76.75 |
| NUE250 | 9132.2 | 0.051 | 4.2E−01 | 12.43 | NUE242 | 9213.4 | 0.55 | 4.3E−02 | 40.32 |
| NUE250 | 9134.1 | 0.055 | 5.3E−02 | 21.91 | Control | | 0.39 | | |
| Control | | 0.045 | | | NUE245 | 10641.7 | 0.67 | 5.7E−03 | 46.73 |
| NUE251 | 10181.3 | 0.052 | 3.2E−05 | 67.47 | NUE245 | 10641.8 | 0.57 | 4.6E−02 | 24.96 |
| NUE251 | 10183.2 | 0.044 | 1.1E−02 | 41.23 | NUE245 | 10643.4 | 0.50 | 4.1E−01 | 10.90 |
| NUE251 | 10183.1 | 0.043 | 1.1E−02 | 38.27 | Control | | 0.46 | | |
| Control | | 0.031 | | | NUE246 | 9033.8 | 0.72 | 2.4E−01 | 22.81 |
| NUE251 | 10183.2 | 0.084 | 2.2E−05 | 83.75 | NUE246 | 9033.4 | 0.69 | 3.8E−01 | 17.06 |
| NUE251 | 10182.1 | 0.057 | 8.1E−02 | 23.66 | NUE246 | 9034.1 | 0.78 | 1.5E−01 | 32.69 |
| NUE251 | 10181.1 | 0.048 | 7.3E−01 | 4.28 | NUE246 | 9031.1 | 0.90 | 1.2E−02 | 52.58 |
| Control | | 0.046 | | | Control | | 0.59 | | |
| NUE256 | 10063.4 | 0.045 | 4.9E−01 | 10.33 | NUE248 | 8981.5 | 0.70 | 7.3E−02 | 30.02 |
| NUE256 | 10064.1 | 0.057 | 1.5E−02 | 37.35 | Control | | 0.53 | | |
| Control | | 0.041 | | | NUE250 | 9134.1 | 0.68 | 3.3E−01 | 12.73 |
| NUE256 | 10063.4 | 0.061 | 8.1E−04 | 96.42 | NUE250 | 9132.2 | 0.89 | 3.6E−02 | 46.62 |
| NUE256 | 10064.1 | 0.063 | 1.3E−05 | 104.87 | Control | | 0.61 | | |
| NUE256 | 10061.2 | 0.065 | 1.0E−07 | 110.14 | NUE251 | 10183.2 | 0.81 | 8.3E−05 | 77.68 |
| NUE256 | 10062.4 | 0.062 | 2.3E−05 | 99.98 | NUE251 | 10181.1 | 0.56 | 1.8E−01 | 24.08 |
| NUE256 | 10063.2 | 0.054 | 1.7E−04 | 74.87 | Control | | 0.46 | | |
| Control | | 0.031 | | | NUE254 | 8972.4 | 0.74 | 6.0E−02 | 38.45 |
| NUE256 | 10061.2 | 0.071 | 6.0E−04 | 55.03 | Control | | 0.53 | | |
| NUE256 | 10061.4 | 0.068 | 4.1E−03 | 47.93 | NUE256 | 10063.4 | 0.88 | 2.3E−04 | 115.25 |
| NUE256 | 10063.2 | 0.051 | 3.9E−01 | 11.43 | NUE256 | 10064.1 | 0.89 | 1.6E−04 | 117.15 |
| Control | | 0.046 | | | NUE256 | 10061.2 | 0.74 | 5.9E−04 | 81.36 |
| NUE511 | 9271.2 | 0.056 | 2.6E−02 | 50.68 | NUE256 | 10062.4 | 0.77 | 4.0E−03 | 87.01 |
| Control | | 0.040 | | | NUE256 | 10063.2 | 0.78 | 7.9E−04 | 90.93 |
| NUE512 | 9282.3 | 0.072 | 3.6E−04 | 68.22 | Control | | 0.41 | | |
| NUE512 | 9284.4 | 0.059 | 8.0E−03 | 38.67 | NUE256 | 10061.3 | 0.55 | 7.7E−02 | 20.48 |
| Control | | 0.043 | | | NUE256 | 10061.2 | 0.61 | 1.1E−02 | 34.76 |
| NUE514 | 9404.1 | 0.047 | 3.4E−02 | 30.81 | NUE256 | 10061.4 | 0.67 | 6.4E−03 | 46.55 |
| NUE514 | 9402.2 | 0.041 | 3.3E−01 | 14.01 | NUE256 | 10063.2 | 0.63 | 6.6E−03 | 39.24 |
| NUE514 | 9403.2 | 0.042 | 1.7E−01 | 17.39 | Control | | 0.46 | | |
| Control | | 0.036 | | | NUE268 | 8996.5 | 0.95 | 7.5E−03 | 46.67 |
| NUE516 | 9291.1 | 0.051 | 3.6E−01 | 12.83 | Control | | 0.65 | | |
| NUE516 | 9291.4 | 0.058 | 5.2E−02 | 28.67 | NUE512 | 9284.3 | 0.59 | 1.2E−01 | 24.74 |
| Control | | 0.045 | | | NUE512 | 9282.3 | 0.72 | 1.5E−02 | 51.97 |
| NUE519 | 9371.2 | 0.065 | 7.6E−02 | 34.99 | NUE512 | 9284.4 | 0.94 | 7.5E−06 | 98.41 |
| NUE519 | 9371.1 | 0.059 | 1.7E−01 | 22.69 | Control | | 0.47 | | |
| Control | | 0.048 | | | NUE513 | 9681.6 | 0.77 | 1.4E−01 | 21.72 |
| NUE521 | 9362.2 | 0.050 | 7.7E−03 | 41.00 | Control | | 0.63 | | |
| NUE521 | 9361.2 | 0.041 | 3.1E−01 | 15.27 | NUE514 | 9404.1 | 0.72 | 2.6E−01 | 17.95 |
| NUE521 | 9363.4 | 0.056 | 1.4E−04 | 56.51 | NUE514 | 9404.5 | 0.79 | 2.9E−02 | 30.17 |
| Control | | 0.036 | | | Control | | 0.61 | | |

TABLE 27-continued

Transgenic plants exogenously expressing the polynucleotides of some embodiments of the invention exhibit improved plant growth rate (relative growth rate of leaf area and root coverage) under nitrogen deficient conditions

| | | RGR Of Leaf Area | | | | | RGR Of Roots Coverage | | |
|---|---|---|---|---|---|---|---|---|---|
| Gene Name | Event # | Average | p-value | % Incr. | Gene Name | Event # | Average | p-value | % Incr. |
| NUE521 | 9362.2 | 0.057 | 3.4E−01 | 16.01 | NUE514 | 9403.2 | 0.67 | 3.9E−05 | 71.81 |
| NUE521 | 9363.4 | 0.065 | 6.3E−02 | 31.54 | NUE514 | 9402.5 | 0.52 | 5.8E−02 | 34.24 |
| Control | | 0.049 | | | Control | | 0.39 | | |
| NUE523 | 9412.5 | 0.048 | 4.9E−02 | 33.67 | NUE519 | 9371.2 | 0.97 | 5.6E−02 | 52.96 |
| NUE523 | 9414.2 | 0.043 | 9.2E−02 | 20.21 | NUE519 | 9371.1 | 0.96 | 2.5E−02 | 51.45 |
| Control | | 0.036 | | | Control | | 0.63 | | |
| NUE523 | 9412.5 | 0.058 | 7.6E−02 | 41.83 | NUE520 | 9771.4 | 0.59 | 2.1E−01 | 20.79 |
| NUE523 | 9414.2 | 0.049 | 2.2E−01 | 19.88 | NUE520 | 9771.7 | 0.72 | 9.4E−03 | 47.07 |
| NUE523 | 9412.1 | 0.062 | 5.2E−03 | 49.67 | NUE520 | 9771.2 | 0.78 | 4.4E−03 | 59.79 |
| Control | | 0.041 | | | NUE520 | 9771.3 | 0.89 | 5.5E−04 | 81.39 |
| NUE525 | 9531.2 | 0.043 | 8.9E−02 | 27.96 | Control | | 0.49 | | |
| NUE525 | 9534.1 | 0.042 | 1.4E−01 | 27.19 | NUE520 | 9771.4 | 0.76 | 1.5E−03 | 85.18 |
| NUE525 | 9531.3 | 0.046 | 3.9E−02 | 36.82 | NUE520 | 9771.2 | 0.83 | 3.7E−04 | 102.18 |
| NUE525 | 9533.1 | 0.048 | 1.6E−02 | 42.76 | NUE520 | 9771.3 | 0.66 | 5.4E−03 | 60.90 |
| NUE525 | 9531.1 | 0.045 | 3.5E−02 | 36.14 | NUE520 | 9773.1 | 0.57 | 1.1E−01 | 39.32 |
| Control | | 0.033 | | | Control | | 0.41 | | |
| NUE531 | 10083.1 | 0.070 | 5.6E−02 | 24.91 | NUE521 | 9362.2 | 0.55 | 5.4E−02 | 39.89 |
| NUE531 | 10082.2 | 0.067 | 1.1E−01 | 20.04 | NUE521 | 9361.3 | 0.46 | 2.1E−01 | 18.65 |
| NUE531 | 10081.4 | 0.070 | 1.2E−01 | 24.78 | NUE521 | 9363.4 | 0.63 | 1.4E−03 | 61.36 |
| NUE531 | 10081.5 | 0.073 | 8.2E−02 | 30.25 | Control | | 0.39 | | |
| Control | | 0.056 | | | NUE523 | 9412.5 | 0.58 | 5.0E−02 | 49.67 |
| NUE531 | 10081.4 | 0.051 | 4.0E−01 | 11.96 | NUE523 | 9414.2 | 0.63 | 9.9E−06 | 61.62 |
| NUE531 | 10081.5 | 0.090 | 1.3E−05 | 95.63 | Control | | 0.39 | | |
| Control | | 0.046 | | | NUE523 | 9413.3 | 0.80 | 2.6E−01 | 24.87 |
| NUE532 | 9222.4 | 0.050 | 1.6E−01 | 40.00 | NUE523 | 9414.2 | 1.03 | 3.8E−03 | 60.15 |
| Control | | 0.036 | | | Control | | 0.64 | | |
| NUE535 | 9082.2 | 0.040 | 1.7E−01 | 29.19 | NUE523 | 9412.5 | 1.03 | 5.0E−02 | 44.09 |
| NUE535 | 9084.2 | 0.037 | 2.0E−01 | 17.89 | NUE523 | 9414.2 | 1.05 | 7.8E−03 | 47.15 |
| NUE535 | 9081.1 | 0.045 | 4.7E−02 | 45.68 | Control | | 0.71 | | |
| NUE535 | 9083.1 | 0.059 | 9.9E−06 | 91.43 | NUE525 | 9531.2 | 0.71 | 1.1E−03 | 50.16 |
| NUE535 | 9084.4 | 0.046 | 6.1E−03 | 49.99 | NUE525 | 9534.1 | 0.76 | 3.0E−03 | 59.45 |
| Control | | 0.031 | | | NUE525 | 9531.3 | 0.55 | 3.9E−01 | 15.44 |
| NUE537 | 9391.2 | 0.067 | 8.9E−04 | 57.56 | NUE525 | 9533.1 | 0.75 | 1.1E−03 | 57.42 |
| NUE537 | 9393.3 | 0.078 | 3.4E−06 | 83.37 | NUE525 | 9531.1 | 0.88 | 9.0E−04 | 85.07 |
| Control | | 0.043 | | | Control | | 0.47 | | |
| NUE539 | 10103.5 | 0.060 | 7.5E−02 | 45.45 | NUE527 | 9201.2 | 0.91 | 6.0E−02 | 39.82 |
| Control | | 0.041 | | | Control | | 0.65 | | |
| NUE539 | 10101.5 | 0.052 | 6.3E−04 | 68.95 | NUE528 | 9073.1 | 0.91 | 8.8E−02 | 33.70 |
| NUE539 | 10103.5 | 0.052 | 2.7E−05 | 67.92 | Control | | 0.68 | | |
| NUE539 | 10101.2 | 0.058 | 4.6E−06 | 85.91 | NUE531 | 10081.4 | 0.65 | 1.2E−01 | 33.32 |
| NUE539 | 10101.7 | 0.067 | 1.3E−06 | 115.49 | NUE531 | 10081.5 | 0.95 | 6.1E−03 | 93.18 |
| Control | | 0.031 | | | Control | | 0.49 | | |
| NUE542 | 9333.2 | 0.058 | 1.7E−02 | 27.22 | NUE531 | 10083.3 | 0.56 | 5.7E−02 | 22.09 |
| Control | | 0.045 | | | NUE531 | 10081.4 | 0.76 | 2.5E−04 | 67.03 |
| NUE543 | 10051.2 | 0.043 | 4.9E−01 | 11.08 | NUE531 | 10051.6 | 0.65 | 7.4E−03 | 42.46 |
| NUE543 | 10051.6 | 0.052 | 2.6E−02 | 32.97 | NUE531 | 10081.5 | 0.88 | 5.5E−05 | 94.20 |
| Control | | 0.039 | | | Control | | 0.46 | | |
| NUE548 | 9095.2 | 0.058 | 1.9E−02 | 45.78 | NUE535 | 9084.2 | 0.87 | 1.1E−01 | 34.81 |
| NUE548 | 9092.2 | 0.054 | 1.1E−01 | 34.83 | Control | | 0.65 | | |
| Control | | 0.040 | | | NUE536 | 9233.3 | 0.85 | 2.7E−02 | 45.06 |
| NUE548 | 9095.2 | 0.067 | 2.0E−01 | 16.93 | Control | | 0.59 | | |
| NUE548 | 9095.4 | 0.082 | 6.7E−03 | 43.33 | NUE537 | 9393.2 | 0.50 | 9.3E−02 | 28.21 |
| NUE548 | 9091.1 | 0.070 | 7.8E−02 | 21.75 | NUE537 | 9393.3 | 0.49 | 8.0E−02 | 25.71 |
| Control | | 0.057 | | | Control | | 0.39 | | |
| NUE554 | 9115.2 | 0.067 | 8.8E−02 | 26.21 | NUE537 | 9393.3 | 0.92 | 5.4E−04 | 95.13 |
| Control | | 0.053 | | | Control | | 0.47 | | |
| NUE560 | 9424.3 | 0.069 | 4.8E−02 | 39.85 | NUE539 | 10101.5 | 0.62 | 3.4E−02 | 50.84 |
| Control | | 0.049 | | | NUE539 | 10103.5 | 0.66 | 6.2E−03 | 61.79 |
| NUE564 | 9242.2 | 0.066 | 8.5E−03 | 54.86 | NUE539 | 10101.7 | 0.80 | 2.0E−04 | 96.01 |
| Control | | 0.043 | | | Control | | 0.41 | | |
| NUE566 | 9512.1 | 0.052 | 2.2E−02 | 56.47 | NUE544 | 9764.2 | 1.00 | 2.7E−02 | 46.55 |
| Control | | 0.033 | | | NUE544 | 9763.3 | 0.80 | 2.7E−01 | 17.81 |
| NUE567 | 9263.3 | 0.053 | 1.8E−01 | 25.10 | Control | | 0.68 | | |
| Control | | 0.043 | | | NUE545 | 9482.4 | 0.61 | 7.1E−02 | 28.80 |
| NUE568 | 9471.3 | 0.051 | 2.9E−01 | 14.08 | Control | | 0.47 | | |
| NUE568 | 9472.2 | 0.062 | 5.2E−03 | 40.02 | NUE548 | 9095.2 | 0.72 | 1.2E−01 | 30.12 |
| Control | | 0.045 | | | Control | | 0.55 | | |
| NUE570 | 9314.1 | 0.064 | 6.7E−02 | 32.94 | NUE548 | 9095.2 | 0.96 | 1.5E−02 | 57.39 |
| Control | | 0.048 | | | NUE548 | 9095.4 | 0.97 | 4.3E−03 | 59.52 |
| NUE573 | 9491.4 | 0.058 | 6.1E−02 | 30.87 | NUE548 | 9091.1 | 0.74 | 1.1E−01 | 22.28 |
| NUE573 | 9494.3 | 0.055 | 1.4E−01 | 23.73 | Control | | 0.61 | | |

TABLE 27-continued

Transgenic plants exogenously expressing the polynucleotides of some embodiments of the invention exhibit improved plant growth rate (relative growth rate of leaf area and root coverage) under nitrogen deficient conditions

| | RGR Of Leaf Area | | | | RGR Of Roots Coverage | | | |
|---|---|---|---|---|---|---|---|---|
| Gene Name | Event # | Average | p-value | % Incr. | Gene Name | Event # | Average | p-value | % Incr. |
| Control | | 0.045 | | | NUE550 | 9141.3 | 0.83 | 1.4E−01 | 28.42 |
| NUE574 | 10364.2 | 0.062 | 1.0E−02 | 34.44 | Control | | 0.65 | | |
| NUE574 | 10362.2 | 0.048 | 6.7E−01 | 5.59 | NUE554 | 9115.2 | 0.93 | 1.7E−02 | 43.12 |
| NUE574 | 10366.2 | 0.079 | 6.5E−05 | 72.54 | Control | | 0.65 | | |
| Control | | 0.046 | | | NUE563 | 9452.3 | 1.02 | 3.8E−03 | 114.90 |
| NUE576 | 9791.3 | 0.046 | 2.5E−01 | 17.12 | NUE563 | 9451.2 | 0.65 | 3.0E−02 | 36.75 |
| NUE576 | 9792.4 | 0.050 | 9.0E−02 | 27.76 | Control | | 0.47 | | |
| NUE576 | 9794.1 | 0.048 | 9.8E−02 | 24.04 | NUE564 | 9242.3 | 0.58 | 2.0E−01 | 21.75 |
| NUE576 | 9793.3 | 0.048 | 1.4E−01 | 22.67 | NUE564 | 9242.2 | 0.71 | 3.1E−02 | 49.74 |
| Control | | 0.039 | | | NUE564 | 9243.4 | 0.65 | 9.3E−02 | 37.10 |
| NUE582 | 9562.4 | 0.056 | 4.1E−02 | 24.61 | Control | | 0.47 | | |
| Control | | 0.045 | | | NUE566 | 9513.1 | 0.58 | 1.3E−01 | 23.35 |
| NUE583 | 9673.1 | 0.056 | 3.2E−02 | 43.43 | NUE566 | 9512.2 | 0.56 | 1.7E−01 | 17.73 |
| Control | | 0.039 | | | NUE566 | 9512.1 | 0.79 | 5.1E−03 | 67.15 |
| NUE583 | 9673.4 | 0.092 | 3.5E−05 | 100.45 | NUE566 | 9514.1 | 0.86 | 2.8E−05 | 80.42 |
| NUE583 | 9673.2 | 0.063 | 2.5E−02 | 38.28 | Control | | 0.47 | | |
| Control | | 0.046 | | | NUE567 | 9263.3 | 0.66 | 7.7E−02 | 39.99 |
| NUE586 | 9751.6 | 0.047 | 4.2E−01 | 12.92 | Control | | 0.47 | | |
| NUE586 | 9751.7 | 0.049 | 3.1E−01 | 19.09 | NUE567 | 9263.3 | 0.97 | 5.0E−02 | 42.53 |
| NUE586 | 9752.4 | 0.057 | 2.6E−02 | 36.93 | Control | | 0.68 | | |
| NUE586 | 9752.1 | 0.058 | 1.0E−01 | 39.90 | NUE569 | 9381.2 | 0.60 | 8.8E−02 | 20.49 |
| Control | | 0.041 | | | NUE569 | 9381.5 | 0.59 | 2.1E−01 | 19.31 |
| | | | | | Control | | 0.50 | | |
| | | | | | NUE570 | 9311.4 | 0.60 | 2.9E−01 | 27.17 |
| | | | | | NUE570 | 9314.4 | 0.64 | 4.5E−02 | 35.92 |
| | | | | | NUE570 | 9314.1 | 0.61 | 1.6E−01 | 29.32 |
| | | | | | Control | | 0.47 | | |
| | | | | | NUE570 | 9314.4 | 0.63 | 2.6E−01 | 26.50 |
| | | | | | NUE570 | 9314.1 | 0.81 | 1.1E−02 | 64.12 |
| | | | | | Control | | 0.50 | | |
| | | | | | NUE571 | 9304.2 | 0.84 | 1.4E−01 | 30.16 |
| | | | | | Control | | 0.64 | | |
| | | | | | NUE574 | 10364.2 | 0.51 | 2.5E−01 | 12.29 |
| | | | | | NUE574 | 10366.2 | 0.91 | 7.6E−05 | 99.71 |
| | | | | | NUE574 | 10366.1 | 0.63 | 6.2E−03 | 38.15 |
| | | | | | Control | | 0.46 | | |
| | | | | | NUE583 | 9673.4 | 1.08 | 7.4E−07 | 136.31 |
| | | | | | NUE583 | 9673.2 | 0.76 | 3.4E−04 | 67.32 |
| | | | | | NUE583 | 9671.2 | 0.58 | 3.4E−02 | 27.94 |
| | | | | | Control | | 0.46 | | |
| | | | | | NUE586 | 9751.7 | 1.08 | 4.4E−04 | 90.56 |
| | | | | | NUE586 | 9751.3 | 0.73 | 1.3E−01 | 28.69 |
| | | | | | NUE586 | 9752.1 | 1.23 | 1.1E−06 | 117.25 |
| | | | | | Control | | 0.57 | | |
| | | | | | NUE586 | 9751.1 | 0.86 | 1.9E−01 | 26.09 |
| | | | | | NUE586 | 9751.6 | 0.93 | 5.1E−02 | 35.91 |
| | | | | | NUE586 | 9751.3 | 0.89 | 9.6E−02 | 30.27 |
| | | | | | NUE586 | 9752.4 | 1.02 | 9.5E−03 | 49.17 |
| | | | | | NUE586 | 9752.1 | 1.16 | 6.5E−03 | 69.78 |
| | | | | | Control | | 0.68 | | |
| | | | | | NUE587 | 9643.2 | 0.85 | 2.3E−02 | 50.29 |
| | | | | | Control | | 0.57 | | |
| | | | | | NUE593 | 10394.2 | 0.72 | 1.5E−02 | 46.89 |
| | | | | | Control | | 0.49 | | |

Table 27: Analyses of plant growth rate (relative growth rate of leaf area and root coverage) of transgenic plants overexpressing the exogenous polynucleotides of some embodiments of the invention (using the cloned or synthetic genes listed in Table 23 above) under the regulation of a constitutive promoter (35S) when grown under limiting nitrogen conditions [low nitrogen or nitrogen deficient conditions (0.75 mM N)] as compared to control plants.

"Incr." = increment;

"RGR" = relative growth rate.

TABLE 28

Transgenic plants exogenously expressing the polynucleotides of some embodiments of the invention exhibit improved plant growth rate (relative growth rate of root length) under nitrogen deficient conditions

| Gene Name | Event # | RGR Of Roots Length Average | p-value | % incr. |
|---|---|---|---|---|
| CT1 | 4841.1 | 0.325 | 4.6E−01 | 14.92 |
| CT1 | 4844.5 | 0.386 | 3.9E−02 | 36.53 |
| CT1 | 4841.2 | 0.399 | 5.1E−02 | 41.25 |
| Control | | 0.282 | | |
| CT11 | 4892.1 | 0.612 | 9.8E−02 | 15.48 |
| Control | | 0.530 | | |
| CT22 | 5023.1 | 0.373 | 9.6E−02 | 32.01 |
| Control | | 0.282 | | |
| CT27 | 5033.4 | 0.394 | 5.2E−02 | 29.10 |
| CT27 | 5033.8 | 0.350 | 2.6E−01 | 14.96 |
| Control | | 0.305 | | |
| CT6 | 4945.8 | 0.460 | 2.1E−01 | 17.91 |
| CT6 | 4943.1 | 0.548 | 2.0E−02 | 40.56 |
| Control | | 0.390 | | |
| CT75 | 4873.4 | 0.473 | 1.5E−01 | 21.17 |
| CT75 | 4873.3 | 0.532 | 1.3E−02 | 36.39 |
| Control | | 0.390 | | |
| CT76 | 5044.6 | 0.408 | 1.1E−02 | 33.88 |
| CT76 | 5043.5 | 0.389 | 7.9E−02 | 27.59 |
| CT76 | 5041.9 | 0.381 | 6.4E−02 | 25.11 |
| Control | | 0.305 | | |
| NUE206 | 6731.2 | 0.496 | 5.5E−03 | 49.81 |
| NUE206 | 6732.7 | 0.395 | 1.8E−01 | 19.18 |
| Control | | 0.331 | | |
| NUE206 | 6731.2 | 0.501 | 1.2E−05 | 64.61 |
| NUE206 | 6732.9 | 0.417 | 8.6E−03 | 37.13 |
| Control | | 0.304 | | |
| NUE208 | 8351.3 | 0.477 | 7.4E−02 | 22.59 |
| Control | | 0.389 | | |
| NUE208 | 8355.3 | 0.500 | 7.9E−04 | 64.40 |
| Control | | 0.304 | | |
| NUE209 | 8192.13 | 0.506 | 1.6E−02 | 30.23 |
| NUE209 | 8192.14 | 0.475 | 9.5E−02 | 22.29 |
| Control | | 0.389 | | |
| NUE209 | 8191.2 | 0.421 | 5.1E−02 | 36.60 |
| NUE209 | 8192.13 | 0.394 | 7.1E−02 | 27.85 |
| NUE209 | 8191.5 | 0.410 | 3.0E−02 | 32.93 |
| Control | | 0.308 | | |
| NUE209 | 8192.14 | 0.452 | 5.1E−03 | 48.66 |
| Control | | 0.304 | | |
| NUE210 | 8202.2 | 0.462 | 9.4E−02 | 18.92 |
| Control | | 0.389 | | |
| NUE210 | 6755.3 | 0.421 | 3.2E−02 | 36.49 |
| Control | | 0.308 | | |
| NUE212 | 8332.2 | 0.455 | 1.7E−02 | 47.71 |
| NUE212 | 8334.1 | 0.426 | 1.6E−01 | 38.40 |
| Control | | 0.308 | | |
| NUE212 | 8331.4 | 0.504 | 2.3E−02 | 29.68 |
| Control | | 0.389 | | |
| NUE212 | 8331.1 | 0.584 | 6.4E−02 | 24.96 |
| NUE212 | 8332.2 | 0.597 | 8.7E−02 | 27.76 |
| NUE212 | 8331.4 | 0.567 | 1.3E−01 | 21.20 |
| Control | | 0.468 | | |
| NUE223 | 9611.5 | 0.537 | 4.1E−03 | 35.20 |
| NUE223 | 9612.3 | 0.466 | 2.5E−01 | 17.18 |
| Control | | 0.397 | | |
| NUE228 | 10092.2 | 0.426 | 5.6E−02 | 29.90 |
| NUE228 | 10093.3 | 0.422 | 8.2E−02 | 28.77 |
| NUE228 | 10093.1 | 0.408 | 1.1E−01 | 24.40 |
| Control | | 0.328 | | |
| NUE233 | 10174.3 | 0.391 | 3.9E−01 | 14.35 |
| NUE233 | 10174.1 | 0.471 | 4.7E−02 | 37.60 |
| NUE233 | 10173.5 | 0.461 | 5.6E−02 | 34.78 |
| NUE233 | 10172.5 | 0.412 | 2.3E−01 | 20.55 |
| NUE233 | 10173.7 | 0.407 | 2.8E−01 | 19.07 |
| Control | | 0.342 | | |
| NUE233 | 10174.1 | 0.404 | 1.2E−03 | 29.24 |
| NUE233 | 10173.5 | 0.362 | 2.5E−01 | 15.71 |
| NUE233 | 10172.5 | 0.362 | 6.0E−02 | 15.79 |
| NUE233 | 10173.7 | 0.436 | 3.6E−03 | 39.35 |
| Control | | 0.313 | | |
| NUE234 | 9162.1 | 0.426 | 5.9E−02 | 25.45 |
| Control | | 0.340 | | |
| NUE235 | 9693.4 | 0.451 | 1.4E−02 | 25.62 |
| NUE235 | 9694.3 | 0.517 | 4.3E−04 | 43.98 |
| Control | | 0.359 | | |
| NUE239 | 9191.1 | 0.435 | 3.5E−01 | 10.73 |
| NUE239 | 9194.3 | 0.482 | 4.7E−02 | 22.75 |
| Control | | 0.393 | | |
| NUE239 | 9192.3 | 0.565 | 2.7E−04 | 42.18 |
| NUE239 | 9192.1 | 0.447 | 2.6E−01 | 12.34 |
| NUE239 | 9191.2 | 0.449 | 2.2E−01 | 13.06 |
| Control | | 0.397 | | |
| NUE240 | 9172.2 | 0.490 | 1.2E−02 | 24.73 |
| Control | | 0.393 | | |
| NUE240 | 9172.1 | 0.507 | 1.4E−02 | 27.47 |
| Control | | 0.397 | | |
| NUE241 | 9633.4 | 0.554 | 8.4E−07 | 54.27 |
| NUE241 | 9632.3 | 0.407 | 2.8E−01 | 13.32 |
| NUE241 | 9632.2 | 0.466 | 1.7E−03 | 29.87 |
| NUE241 | 9632.4 | 0.432 | 1.5E−01 | 20.52 |
| Control | | 0.359 | | |
| NUE242 | 9212.1 | 0.429 | 2.2E−01 | 13.68 |
| NUE242 | 9213.4 | 0.544 | 4.7E−05 | 44.09 |
| Control | | 0.377 | | |
| NUE242 | 9212.1 | 0.462 | 1.1E−03 | 54.42 |
| NUE242 | 9211.2 | 0.403 | 7.9E−02 | 34.60 |
| NUE242 | 9213.4 | 0.347 | 2.6E−01 | 16.09 |
| Control | | 0.299 | | |
| NUE245 | 10643.1 | 0.351 | 2.1E−01 | 12.20 |
| NUE245 | 10641.7 | 0.414 | 3.8E−03 | 32.32 |
| NUE245 | 10641.8 | 0.434 | 2.5E−04 | 38.90 |
| NUE245 | 10643.4 | 0.377 | 2.2E−02 | 20.56 |
| Control | | 0.313 | | |
| NUE246 | 9033.4 | 0.504 | 1.2E−01 | 21.54 |
| NUE246 | 9034.1 | 0.510 | 1.4E−01 | 22.94 |
| NUE246 | 9031.1 | 0.524 | 5.4E−02 | 26.35 |
| Control | | 0.414 | | |
| NUE250 | 9134.1 | 0.433 | 1.4E−01 | 14.91 |
| NUE250 | 9132.2 | 0.482 | 2.4E−02 | 27.68 |
| Control | | 0.377 | | |
| NUE251 | 10183.1 | 0.460 | 6.6E−02 | 34.46 |
| Control | | 0.342 | | |
| NUE251 | 10181.3 | 0.337 | 3.8E−01 | 7.88 |
| NUE251 | 10183.2 | 0.485 | 1.4E−04 | 55.27 |
| NUE251 | 10182.1 | 0.391 | 3.4E−02 | 25.13 |
| NUE251 | 10183.1 | 0.323 | 6.8E−01 | 3.24 |
| NUE251 | 10181.1 | 0.361 | 2.5E−01 | 15.54 |
| Control | | 0.313 | | |
| NUE252 | 9011.3 | 0.468 | 6.8E−03 | 24.03 |
| NUE252 | 9012.2 | 0.438 | 1.2E−01 | 16.22 |
| NUE252 | 9013.2 | 0.458 | 8.4E−02 | 21.40 |
| Control | | 0.377 | | |
| NUE254 | 8972.4 | 0.508 | 2.7E−03 | 27.22 |
| Control | | 0.399 | | |
| NUE256 | 10063.4 | 0.507 | 1.5E−02 | 48.06 |
| NUE256 | 10064.1 | 0.525 | 4.0E−03 | 53.43 |
| NUE256 | 10061.2 | 0.431 | 1.4E−01 | 26.08 |
| NUE256 | 10063.2 | 0.518 | 6.8E−03 | 51.45 |
| Control | | 0.342 | | |
| NUE256 | 10061.3 | 0.383 | 6.3E−02 | 22.55 |
| NUE256 | 10061.2 | 0.368 | 6.1E−02 | 17.75 |
| NUE256 | 10061.4 | 0.432 | 3.7E−04 | 38.10 |
| NUE256 | 10063.2 | 0.434 | 3.8E−05 | 38.83 |
| Control | | 0.313 | | |
| NUE512 | 9282.3 | 0.479 | 5.0E−02 | 22.43 |
| NUE512 | 9284.4 | 0.525 | 3.4E−03 | 34.40 |
| Control | | 0.391 | | |
| NUE513 | 9681.4 | 0.489 | 1.7E−01 | 18.01 |
| NUE513 | 9683.5 | 0.518 | 8.4E−02 | 24.96 |
| Control | | 0.414 | | |
| NUE513 | 9681.6 | 0.475 | 6.5E−02 | 19.62 |

TABLE 28-continued

Transgenic plants exogenously expressing the polynucleotides of some embodiments of the invention exhibit improved plant growth rate (relative growth rate of root length) under nitrogen deficient conditions

| Gene Name | Event # | RGR Of Roots Length Average | p-value | % incr. |
|---|---|---|---|---|
| Control | | 0.397 | | |
| NUE513 | 9683.5 | 0.515 | 8.4E−02 | 16.54 |
| Control | | 0.442 | | |
| NUE514 | 9404.1 | 0.471 | 2.5E−02 | 24.98 |
| NUE514 | 9402.2 | 0.445 | 9.9E−02 | 17.92 |
| NUE514 | 9404.5 | 0.493 | 4.6E−03 | 30.81 |
| NUE514 | 9403.2 | 0.443 | 4.8E−02 | 17.37 |
| NUE514 | 9402.5 | 0.503 | 3.8E−03 | 33.24 |
| Control | | 0.377 | | |
| NUE514 | 9404.1 | 0.371 | 3.0E−02 | 23.82 |
| NUE514 | 9403.2 | 0.471 | 4.9E−05 | 57.43 |
| NUE514 | 9402.5 | 0.442 | 9.5E−04 | 47.79 |
| Control | | 0.299 | | |
| NUE519 | 9371.2 | 0.513 | 1.3E−01 | 29.00 |
| NUE519 | 9371.1 | 0.555 | 1.8E−02 | 39.76 |
| Control | | 0.397 | | |
| NUE520 | 9771.4 | 0.486 | 2.5E−03 | 48.07 |
| NUE520 | 9771.7 | 0.471 | 1.1E−02 | 43.62 |
| NUE520 | 9771.2 | 0.463 | 9.8E−03 | 41.14 |
| NUE520 | 9771.3 | 0.463 | 2.4E−02 | 41.09 |
| Control | | 0.328 | | |
| NUE520 | 9771.4 | 0.476 | 3.4E−02 | 39.14 |
| NUE520 | 9771.2 | 0.478 | 3.0E−02 | 39.79 |
| Control | | 0.342 | | |
| NUE521 | 9362.2 | 0.414 | 1.2E−02 | 38.49 |
| NUE521 | 9361.3 | 0.383 | 8.8E−03 | 27.99 |
| NUE521 | 9363.4 | 0.456 | 1.0E−04 | 52.49 |
| Control | | 0.299 | | |
| NUE523 | 9412.5 | 0.410 | 2.6E−02 | 36.99 |
| NUE523 | 9414.2 | 0.495 | 1.1E−06 | 65.32 |
| NUE523 | 9412.1 | 0.364 | 7.6E−02 | 21.51 |
| NUE523 | 9413.4 | 0.372 | 3.3E−02 | 24.28 |
| Control | | 0.299 | | |
| NUE523 | 9412.5 | 0.525 | 1.7E−01 | 18.63 |
| NUE523 | 9414.2 | 0.552 | 6.9E−03 | 24.85 |
| Control | | 0.442 | | |
| NUE525 | 9531.2 | 0.465 | 3.5E−03 | 29.55 |
| NUE525 | 9534.1 | 0.506 | 5.7E−04 | 40.93 |
| NUE525 | 9531.1 | 0.494 | 4.1E−03 | 37.67 |
| Control | | 0.359 | | |
| NUE531 | 10082.2 | 0.413 | 1.1E−01 | 25.96 |
| NUE531 | 10081.5 | 0.451 | 5.6E−02 | 37.34 |
| Control | | 0.328 | | |
| NUE531 | 10083.3 | 0.387 | 8.0E−03 | 23.90 |
| NUE531 | 10082.2 | 0.359 | 2.2E−01 | 14.68 |
| NUE531 | 10081.4 | 0.366 | 5.7E−02 | 17.00 |
| NUE531 | 10083.2 | 0.445 | 5.0E−04 | 42.20 |
| NUE531 | 10081.5 | 0.478 | 2.9E−05 | 52.87 |
| Control | | 0.313 | | |
| NUE536 | 9233.3 | 0.511 | 8.2E−02 | 23.25 |
| Control | | 0.414 | | |
| NUE537 | 9393.2 | 0.409 | 2.5E−03 | 36.75 |
| NUE537 | 9393.3 | 0.415 | 1.8E−03 | 38.64 |
| Control | | 0.299 | | |
| NUE537 | 9393.3 | 0.496 | 1.4E−02 | 26.83 |
| Control | | 0.391 | | |
| NUE539 | 10101.5 | 0.454 | 9.5E−02 | 32.65 |
| NUE539 | 10103.5 | 0.436 | 1.2E−01 | 27.43 |
| NUE539 | 10101.7 | 0.527 | 4.4E−03 | 53.99 |
| Control | | 0.342 | | |
| NUE539 | 10101.7 | 0.420 | 2.4E−03 | 34.28 |
| Control | | 0.313 | | |
| NUE544 | 9764.2 | 0.581 | 9.7E−02 | 24.20 |
| Control | | 0.468 | | |
| NUE548 | 9095.2 | 0.495 | 3.1E−02 | 31.12 |
| NUE548 | 9095.4 | 0.541 | 1.3E−03 | 43.44 |
| NUE548 | 9091.1 | 0.436 | 8.2E−02 | 15.49 |
| Control | | 0.377 | | |
| NUE550 | 9141.3 | 0.469 | 9.2E−02 | 27.80 |
| Control | | 0.367 | | |
| NUE563 | 9452.3 | 0.513 | 4.5E−03 | 42.86 |
| Control | | 0.359 | | |
| NUE566 | 9512.1 | 0.448 | 7.9E−02 | 24.77 |
| NUE566 | 9514.1 | 0.530 | 1.3E−05 | 47.65 |
| Control | | 0.359 | | |
| NUE570 | 9314.4 | 0.477 | 6.1E−02 | 22.12 |
| NUE570 | 9314.1 | 0.436 | 3.3E−01 | 11.56 |
| Control | | 0.391 | | |
| NUE570 | 9314.1 | 0.522 | 5.4E−02 | 26.80 |
| Control | | 0.411 | | |
| NUE574 | 10363.4 | 0.384 | 9.0E−02 | 22.79 |
| NUE574 | 10364.2 | 0.369 | 3.4E−02 | 18.18 |
| NUE574 | 10362.2 | 0.372 | 4.0E−02 | 19.10 |
| NUE574 | 10366.2 | 0.505 | 1.3E−05 | 61.62 |
| NUE574 | 10366.1 | 0.403 | 1.8E−03 | 28.75 |
| Control | | 0.313 | | |
| NUE583 | 9673.1 | 0.337 | 3.3E−01 | 7.83 |
| NUE583 | 9673.4 | 0.511 | 4.9E−04 | 63.57 |
| NUE583 | 9673.2 | 0.445 | 1.3E−04 | 42.20 |
| NUE583 | 9671.2 | 0.373 | 5.7E−02 | 19.44 |
| NUE583 | 9671.1 | 0.356 | 1.3E−01 | 13.96 |
| Control | | 0.313 | | |
| NUE586 | 9751.1 | 0.466 | 3.8E−01 | 12.01 |
| NUE586 | 9751.7 | 0.561 | 1.4E−02 | 34.87 |
| NUE586 | 9752.1 | 0.616 | 6.6E−04 | 48.10 |
| Control | | 0.416 | | |
| NUE586 | 9751.6 | 0.578 | 9.9E−02 | 23.61 |
| NUE586 | 9751.3 | 0.544 | 2.5E−01 | 16.32 |
| NUE586 | 9752.4 | 0.585 | 6.0E−02 | 25.16 |
| NUE586 | 9752.1 | 0.611 | 3.8E−02 | 30.58 |
| Control | | 0.468 | | |
| NUE593 | 10394.2 | 0.446 | 2.9E−02 | 35.91 |
| Control | | 0.328 | | |

Table 28: Analyses of plant growth rate (relative growth rate of root length) of transgenic plants overexpressing the exogenous polynucleotides of some embodiments of the invention (using the cloned or synthetic genes listed in Table 23 above) under the regulation of a constitutive promoter (35S) when grown under limiting nitrogen conditions [low nitrogen or nitrogen deficient conditions (0.75 mM N)] as compared to control plants. "Incr." = increment; "RGR" = relative growth rate.

The genes presented in Tables 29 and 30, hereinbelow, have improved plant NUE since they produced larger plant biomass when grown under standard nitrogen growth conditions, compared to control plants, indicating the high ability of the plant to better metabolize the nitrogen present in the medium.

Tables 29 and 30 depict analyses of plant biomass (plant fresh and dry weight and leaf area) when grown under standard nitrogen conditions [normal or regular growth conditions (15 mM N)] in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 29

Transgenic plants exogenously expressing the polynucleotides of some embodiments of the invention exhibit improved plant biomass (fresh and dry weight) under standard nitrogen conditions

| Gene Name | Event # | Plant Fresh Weight [mg] Average | p-value | % incr. | Gene Name | Event # | Plant Dry Weight [mg] Average | p-value | % incr. |
|---|---|---|---|---|---|---|---|---|---|
| CT1 | 4841.1 | 224.68 | 5.7E−03 | 44.54 | CT11 | 4894.3 | 10.93 | 1.0E−01 | 57.88 |
| CT1 | 4844.3 | 220.28 | 1.3E−01 | 41.71 | CT11 | 4892.2 | 11.00 | 2.3E−02 | 58.84 |
| Control | | 155.44 | | | CT11 | 4892.3 | 9.35 | 1.6E−01 | 35.02 |
| CT11 | 4892.2 | 327.13 | 1.2E−02 | 41.78 | CT11 | 4893.2 | 7.20 | 7.0E−01 | 3.97 |
| CT11 | 4892.3 | 321.38 | 4.4E−02 | 39.29 | CT11 | 4892.1 | 12.40 | 1.0E−01 | 79.06 |
| Control | | 230.73 | | | Control | | 6.93 | | |
| CT11 | 4893.2 | 293.83 | 1.8E−02 | 70.30 | CT11 | 4894.2 | 6.70 | 5.8E−01 | 8.06 |
| Control | | 172.54 | | | CT11 | 4893.2 | 12.73 | 5.8E−03 | 105.24 |
| CT22 | 5023.1 | 249.48 | 1.3E−02 | 60.50 | Control | | 6.20 | | |
| Control | | 155.44 | | | CT27 | 5033.6 | 7.40 | 1.9E−01 | 79.39 |
| CT27 | 5033.6 | 234.13 | 1.1E−01 | 148.18 | CT27 | 5033.8 | 7.50 | 9.2E−02 | 81.82 |
| CT27 | 5033.8 | 192.50 | 8.4E−03 | 104.05 | CT27 | 5033.5 | 5.55 | 1.9E−01 | 34.55 |
| CT27 | 5033.5 | 143.73 | 3.1E−01 | 52.35 | Control | | 4.13 | | |
| Control | | 94.34 | | | CT27 | 5033.7 | 8.23 | 1.5E−01 | 32.66 |
| CT27 | 5033.7 | 224.58 | 1.2E−01 | 30.16 | CT27 | 5035.2 | 13.10 | 2.1E−04 | 111.29 |
| CT27 | 5035.2 | 343.65 | 2.2E−02 | 99.17 | CT27 | 5031.4 | 9.28 | 8.2E−03 | 49.60 |
| CT27 | 5031.4 | 255.88 | 3.0E−03 | 48.30 | CT27 | 5033.6 | 8.15 | 2.7E−01 | 31.45 |
| Control | | 172.54 | | | CT27 | 5033.4 | 7.95 | 4.7E−02 | 28.23 |
| CT76 | 5041.7 | 292.55 | 5.6E−02 | 26.80 | CT27 | 5033.8 | 8.90 | 2.5E−02 | 43.55 |
| CT76 | 5043.5 | 415.05 | 1.4E−03 | 79.89 | CT27 | 5033.5 | 7.63 | 2.1E−01 | 22.98 |
| Control | | 230.73 | | | Control | | 6.20 | | |
| CT76 | 5044.6 | 239.08 | 2.1E−03 | 153.43 | CT6 | 4943.1 | 7.83 | 3.2E−01 | 26.21 |
| CT76 | 5041.5 | 209.10 | 1.6E−03 | 121.65 | CT6 | 4945.9 | 7.63 | 1.8E−01 | 22.98 |
| CT76 | 5043.5 | 272.60 | 2.7E−02 | 188.96 | CT6 | 4941.4 | 9.28 | 2.9E−02 | 49.60 |
| CT76 | 5041.6 | 124.75 | 3.9E−02 | 32.24 | Control | | 6.20 | | |
| CT76 | 5041.9 | 245.20 | 7.1E−02 | 159.92 | CT75 | 4874.4 | 9.35 | 1.2E−02 | 50.81 |
| Control | | 94.34 | | | Control | | 6.20 | | |
| CT81 | 4992.1 | 381.73 | 3.3E−04 | 65.45 | CT76 | 5044.6 | 9.40 | 1.6E−01 | 35.74 |
| CT81 | 4992.2 | 305.85 | 2.8E−01 | 32.56 | CT76 | 5043.5 | 17.23 | 7.8E−06 | 148.74 |
| Control | | 230.73 | | | CT76 | 5041.6 | 10.03 | 9.7E−02 | 44.89 |
| NUE209 | 8192.14 | 217.23 | 3.8E−02 | 86.30 | Control | | 6.93 | | |
| Control | | 116.60 | | | CT76 | 5044.6 | 7.43 | 5.8E−02 | 80.00 |
| NUE210 | 8202.1 | 279.53 | 1.1E−01 | 139.73 | CT76 | 5041.5 | 9.70 | 1.0E−04 | 135.15 |
| NUE210 | 8201.3 | 250.90 | 4.8E−02 | 115.18 | CT76 | 5041.7 | 5.03 | 4.5E−01 | 21.82 |
| Control | | 116.60 | | | CT76 | 5043.5 | 10.88 | 1.3E−02 | 163.64 |
| NUE211 | 8263.5 | 162.35 | 5.0E−02 | 31.43 | CT76 | 5041.9 | 8.95 | 1.1E−02 | 116.97 |
| Control | | 123.53 | | | Control | | 4.13 | | |
| NUE212 | 8332.1 | 253.75 | 1.0E−01 | 105.42 | CT81 | 4992.1 | 11.20 | 4.1E−02 | 61.73 |
| NUE212 | 8335.2 | 169.28 | 4.9E−02 | 37.03 | CT81 | 4993.5 | 8.60 | 3.6E−01 | 24.19 |
| Control | | 123.53 | | | CT81 | 4992.2 | 8.63 | 3.4E−01 | 24.55 |
| NUE212 | 8335.2 | 221.83 | 2.0E−02 | 90.24 | CT81 | 4995.5 | 7.90 | 3.8E−01 | 14.08 |
| NUE212 | 8331.4 | 163.88 | 2.7E−01 | 40.54 | Control | | 6.93 | | |
| Control | | 116.60 | | | NUE206 | 6732.9 | 13.68 | 7.9E−03 | 43.38 |
| NUE212 | 8332.1 | 116.43 | 1.8E−01 | 29.34 | NUE206 | 6731.2 | 14.13 | 4.3E−01 | 48.19 |
| NUE212 | 8334.1 | 128.33 | 8.1E−02 | 42.56 | NUE206 | 6732.5 | 12.98 | 1.8E−02 | 36.04 |
| NUE212 | 8331.4 | 143.63 | 3.0E−02 | 59.56 | NUE206 | 6732.2 | 10.98 | 3.6E−01 | 15.07 |
| Control | | 90.01 | | | Control | | 9.54 | | |
| NUE221 | 9802.8 | 149.35 | 3.9E−03 | 58.7 | NUE208 | 8354.8 | 8.20 | 2.7E−02 | 78.75 |
| NUE221 | 9806.1 | 209.18 | 1.7E−08 | 122.3 | NUE208 | 8355.3 | 5.78 | 3.3E−01 | 25.89 |
| Control | | 94.09 | | | Control | | 4.59 | | |
| NUE222 | 8851.3 | 240.70 | 6.1E−02 | 106.43 | NUE208 | 8354.8 | 6.15 | 3.1E−02 | 14.42 |
| NUE222 | 8852.4 | 138.15 | 3.1E−01 | 18.48 | Control | | 5.38 | | |
| Control | | 116.60 | | | NUE208 | 8354.8 | 16.45 | 1.9E−03 | 72.48 |
| NUE224 | 9002.4 | 279.08 | 6.1E−02 | 32.66 | NUE208 | 8354.5 | 15.58 | 2.4E−03 | 63.30 |
| Control | | 210.36 | | | NUE208 | 8355.3 | 12.40 | 9.6E−02 | 30.01 |
| NUE224 | 9002.4 | 159.13 | 2.6E−01 | 14.58 | Control | | 9.54 | | |
| NUE224 | 9002.2 | 268.95 | 3.8E−03 | 93.66 | NUE209 | 8192.1 | 7.73 | 1.5E−01 | 68.39 |
| NUE224 | 9001.3 | 181.65 | 3.2E−02 | 30.80 | NUE209 | 8191.5 | 7.13 | 7.1E−02 | 55.31 |
| Control | | 138.88 | | | Control | | 4.59 | | |
| NUE225 | 9732.8 | 117.00 | 2.2E−01 | 24.4 | NUE209 | 8191.5 | 10.83 | 6.2E−01 | 162.42 |
| Control | | 94.09 | | | NUE209 | 8191.3 | 15.40 | 6.3E−03 | |
| NUE227 | 9853.1 | 197.68 | 9.4E−02 | 55.51 | Control | | 9.54 | | |
| Control | | 127.11 | | | NUE210 | 8202.1 | 10.95 | 1.0E−02 | 138.69 |
| NUE229 | 8862.2 | 75.00 | 1.2E−02 | 26.32 | NUE210 | 8201.3 | 8.98 | 5.5E−02 | 95.64 |
| NUE229 | 8862.5 | 74.03 | 1.3E−01 | 24.67 | Control | | 4.59 | | |
| NUE229 | 8864.2 | 84.93 | 3.9E−02 | 43.03 | NUE210 | 8202.1 | 4.28 | 2.4E−02 | 41.91 |
| Control | | 59.38 | | | NUE210 | 8751.4 | 4.33 | 1.1E−01 | 43.57 |
| NUE230 | 9154.6 | 171.38 | 4.4E−01 | 23.40 | NUE210 | 6755.3 | 3.85 | 2.4E−01 | 27.80 |
| NUE230 | 9151.2 | 203.78 | 3.1E−02 | 46.73 | NUE210 | 8201.2 | 3.93 | 2.1E−01 | 30.29 |
| Control | | 138.88 | | | Control | | 3.01 | | |
| NUE231 | 10633.3 | 199.70 | 1.6E−07 | 112.2 | NUE211 | 8265.1 | 7.38 | 8.8E−02 | 60.76 |
| Control | | 94.09 | | | Control | | 4.59 | | |
| NUE233 | 10174.3 | 139.08 | 9.0E−02 | 44.46 | NUE212 | 8335.2 | 9.53 | 7.3E−02 | 107.63 |

TABLE 29-continued

Transgenic plants exogenously expressing the polynucleotides of some embodiments of the invention exhibit improved plant biomass (fresh and dry weight) under standard nitrogen conditions

| Gene Name | Event # | Plant Fresh Weight [mg] Average | p-value | % incr. | Gene Name | Event # | Plant Dry Weight [mg] Average | p-value | % incr. |
|---|---|---|---|---|---|---|---|---|---|
| NUE233 | 10174.1 | 190.05 | 5.5E−04 | 97.40 | Control | | 4.59 | | |
| NUE233 | 10173.7 | 143.98 | 3.5E−03 | 49.55 | NUE212 | 8334.1 | 4.20 | 7.4E−02 | 39.42 |
| Control | | 96.28 | | | NUE212 | 8331.4 | 5.08 | 5.7E−02 | 68.46 |
| NUE235 | 9694.2 | 171.15 | 1.0E−01 | 23.24 | Control | | 3.01 | | |
| NUE235 | 9691.1 | 172.20 | 7.8E−02 | 24.00 | NUE221 | 9802.8. | 7.50 | 2.5E−03 | 56.3 |
| NUE235 | 9693.3 | 194.48 | 5.4E−02 | 40.04 | NUE221 | 9806.1. | 9.08 | 3.5E−06 | 89.1 |
| Control | | 138.88 | | | Control | | 4.80 | | |
| NUE237 | 9651.1 | 293.05 | 3.8E−02 | 111.02 | NUE222 | 8851.3 | 11.60 | 4.2E−02 | 152.86 |
| NUE237 | 9652.3 | 167.10 | 1.1E−01 | 20.32 | Control | | 4.59 | | |
| NUE237 | 9654.4 | 195.80 | 1.4E−01 | 40.99 | NUE224 | 9002.2 | 10.13 | 5.4E−02 | 83.67 |
| Control | | 138.88 | | | NUE224 | 9001.3 | 7.03 | 1.1E−01 | 27.44 |
| NUE237 | 9651.1 | 191.70 | 1.8E−02 | 26.32 | Control | | 5.51 | | |
| Control | | 151.76 | | | NUE227 | 9851.2 | 5.88 | 1.4E−01 | 24.34 |
| NUE239 | 9192.1 | 245.53 | 3.6E−02 | 56.82 | NUE227 | 9853.1 | 8.88 | 4.0E−02 | 87.83 |
| Control | | 156.56 | | | Control | | 4.73 | | |
| NUE240 | 9172.1 | 212.68 | 7.3E−02 | 35.84 | NUE228 | 10092 | 7.90 | 2.0E−01 | 45.29 |
| NUE240 | 9174.3 | 255.50 | 2.6E−01 | | NUE228 | 10093 | 7.98 | 8.6E−02 | 46.67 |
| Control | | 156.56 | | | NUE228 | 10093 | 6.68 | 5.3E−03 | 22.76 |
| NUE241 | 9631.3 | 166.03 | 6.6E−02 | 30.61 | Control | | 5.44 | | |
| NUE241 | 9632.5 | 185.58 | 1.4E−02 | 45.99 | NUE229 | 8862.2 | 3.90 | 4.1E−02 | 30.54 |
| NUE241 | 9632.4 | 219.43 | 8.4E−03 | 72.62 | NUE229 | 8862.5 | 3.80 | 2.7E−01 | 27.20 |
| Control | | 127.11 | | | NUE229 | 8864.2 | 4.45 | 2.9E−02 | 48.95 |
| NUE242 | 9212.1 | 140.78 | 3.9E−02 | 59.41 | Control | | 2.99 | | |
| NUE242 | 9214.1 | 129.18 | 1.5E−01 | 46.27 | NUE230 | 9154.2 | 7.38 | 1.0E−01 | 33.79 |
| NUE242 | 9213.2 | 101.43 | 3.7E−01 | 14.85 | NUE230 | 9151.2 | 7.48 | 5.8E−02 | 35.60 |
| NUE242 | 9213.4 | 146.30 | 3.0E−02 | 65.66 | Control | | 5.51 | | |
| Control | | 88.31 | | | NUE231 | 10632.2 | 5.53 | 4.1E−01 | 15.1 |
| NUE244 | 9061.1 | 164.20 | 8.9E−04 | 45.23 | NUE231 | 10633.3 | 11.43 | 2.0E−11 | 138.0 |
| NUE244 | 9061.5 | 143.40 | 4.8E−01 | 26.83 | Control | | 4.80 | | |
| Control | | 113.06 | | | NUE233 | 10174 | 6.13 | 1.2E−02 | 58.58 |
| NUE246 | 9033.6 | 273.05 | 8.9E−03 | 43.57 | NUE233 | 10174 | 8.63 | 2.1E−04 | 123.30 |
| NUE246 | 9033.4 | 241.48 | 4.8E−01 | 26.97 | NUE233 | 10174 | 5.10 | 8.2E−02 | 32.04 |
| NUE246 | 9034.1 | 224.08 | 2.5E−01 | 17.82 | Control | | 3.86 | | |
| NUE246 | 9031.1 | 232.65 | 3.3E−01 | 22.33 | NUE234 | 9163.5 | 4.28 | 8.7E−02 | 43.10 |
| Control | | 190.19 | | | NUE234 | 9162.1 | 4.60 | 1.3E−01 | 53.97 |
| NUE246 | 9034.1 | 160.45 | 1.8E−02 | 41.91 | Control | | 2.99 | | |
| Control | | 113.06 | | | NUE235 | 9694.2 | 7.35 | 2.2E−01 | 33.33 |
| NUE246 | 9033.4 | 185.78 | 4.3E−01 | 16.45 | NUE235 | 9691.1 | 7.90 | 1.4E−01 | 43.31 |
| NUE246 | 9033.8 | 205.95 | 1.8E−01 | 29.09 | NUE235 | 9693.3 | 6.98 | 6.2E−02 | 26.53 |
| NUE246 | 9034.1 | 228.95 | 2.4E−03 | 43.51 | Control | | 5.51 | | |
| Control | | 159.54 | | | NUE237 | 9651.1 | 10.20 | 2.9E−02 | 85.03 |
| NUE248 | 8982.4 | 275.80 | 2.2E−02 | 45.01 | NUE237 | 9652.3 | 6.68 | 6.3E−02 | 21.09 |
| NUE248 | 8981.5 | 343.28 | 1.1E−02 | 80.49 | NUE237 | 9654.4 | 8.25 | 1.1E−02 | 49.66 |
| NUE248 | 8984.1 | 294.45 | 1.5E−01 | 54.82 | Control | | 5.51 | | |
| NUE248 | 8981.2 | 245.25 | 1.1E−01 | 28.95 | NUE237 | 9651.1 | 6.98 | 4.0E−02 | 26.53 |
| Control | | 190.19 | | | Control | | 5.51 | | |
| NUE248 | 8982.4 | 118.75 | 1.6E−01 | 37.56 | NUE239 | 9191.2 | 8.80 | 7.6E−02 | 19.32 |
| NUE248 | 8984.1 | 124.38 | 2.5E−02 | 44.08 | Control | | 7.38 | | |
| NUE248 | 8981.5 | 140.05 | 4.8E−02 | 62.24 | NUE241 | 9631.3 | 6.43 | 8.5E−02 | 35.98 |
| NUE248 | 8983.1 | 114.05 | 3.2E−01 | 32.12 | NUE241 | 9632.5 | 8.33 | 2.8E−04 | 76.19 |
| Control | | 86.33 | | | NUE241 | 9632.3 | 6.55 | 1.6E−02 | 38.62 |
| NUE249 | 9122.5 | 145.73 | 4.6E−02 | 68.82 | NUE241 | 9632.4 | 8.03 | 1.0E−04 | 70.02 |
| NUE249 | 9121.4 | 112.83 | 3.6E−01 | 30.71 | Control | | 4.73 | | |
| NUE249 | 9123.3 | 107.98 | 2.1E−01 | 25.08 | NUE244 | 9061.1 | 5.65 | 6.3E−02 | 34.52 |
| Control | | 86.33 | | | NUE244 | 9061.5 | 5.88 | 6.7E−02 | 39.88 |
| NUE250 | 9133.2 | 182.70 | 4.3E−02 | 31.56 | Control | | 4.20 | | |
| NUE250 | 9134.1 | 216.85 | 2.5E−02 | 56.15 | NUE246 | 9033.6 | 8.98 | 2.9E−02 | 28.90 |
| Control | | 138.88 | | | NUE246 | 9033.4 | 8.28 | 3.1E−01 | 18.85 |
| NUE251 | 10181.3 | 143.00 | 4.0E−02 | 48.53 | Control | | 6.96 | | |
| NUE251 | 10183.2 | 146.38 | 2.4E−02 | 52.04 | NUE246 | 9034.1 | 5.60 | 7.3E−02 | 33.33 |
| NUE251 | 10183.1 | 128.05 | 3.6E−01 | 33.00 | Control | | 4.20 | | |
| Control | | 96.28 | | | NUE246 | 9033.4 | 6.28 | 1.7E−01 | 18.40 |
| NUE254 | 8972.2 | 173.28 | 8.8E−02 | 100.72 | NUE246 | 9033.8 | 8.63 | 5.2E−04 | 62.74 |
| NUE254 | 8974.1 | 130.38 | 4.1E−02 | 51.03 | NUE246 | 9034.1 | 8.35 | 2.5E−04 | 57.55 |
| Control | | 86.33 | | | Control | | 5.30 | | |
| NUE256 | 10063.4 | 132.65 | 1.4E−02 | 37.78 | NUE248 | 8982.4 | 9.88 | 2.2E−02 | 41.83 |
| NUE256 | 10064.1 | 212.63 | 1.5E−04 | 120.85 | NUE248 | 8981.5 | 11.78 | 1.3E−01 | 69.12 |
| NUE256 | 10061.2 | 151.98 | 1.2E−01 | 57.86 | NUE248 | 8984.1 | 10.25 | 4.1E−02 | 47.22 |
| NUE256 | 10062.4 | 152.75 | 1.5E−01 | 58.66 | NUE248 | 8981.2 | 7.55 | 6.5E−01 | 8.44 |
| NUE256 | 10063.2 | 162.50 | 2.1E−01 | 68.79 | Control | | 6.96 | | |
| Control | | 96.28 | | | NUE248 | 8984.1 | 7.15 | 1.2E−01 | 43.00 |
| NUE267 | 8962.1 | 185.23 | 1.6E−02 | 63.83 | NUE248 | 8981.5 | 8.65 | 1.9E−02 | 73.00 |
| Control | | 113.06 | | | Control | | 5.00 | | |

TABLE 29-continued

Transgenic plants exogenously expressing the polynucleotides of some embodiments of the invention exhibit improved plant biomass (fresh and dry weight) under standard nitrogen conditions

| Gene Name | Event # | Plant Fresh Weight [mg] Average | p-value | % incr. | Gene Name | Event # | Plant Dry Weight [mg] Average | p-value | % incr. |
|---|---|---|---|---|---|---|---|---|---|
| NUE268 | 8994.5 | 228.80 | 8.7E−02 | 64.46 | NUE250 | 9134.3 | 8.48 | 1.3E−02 | 49.67 |
| NUE268 | 8992.1 | 204.08 | 2.2E−01 | 46.69 | Control | | 5.66 | | |
| NUE268 | 8996.5 | 146.34 | 7.6E−02 | 5.19 | NUE250 | 9132.1 | 11.18 | 1.5E−01 | 102.72 |
| Control | | 139.13 | | | NUE250 | 9133.2 | 7.88 | 2.6E−02 | 42.86 |
| NUE269 | 9101.1 | 95.83 | 1.4E−02 | 79.28 | NUE250 | 9132.2 | 8.55 | 3.2E−02 | 55.10 |
| NUE269 | 9102.2 | 89.05 | 7.7E−05 | 66.60 | NUE250 | 9134.1 | 8.88 | 4.5E−02 | 61.00 |
| NUE269 | 9102.3 | 117.90 | 6.5E−02 | 120.58 | Control | | 5.51 | | |
| NUE269 | 9103.1 | 83.60 | 7.0E−02 | 56.41 | NUE250 | 9134.1 | 3.53 | 1.8E−01 | 17.99 |
| NUE269 | 9103.3 | 82.45 | 1.6E−02 | 54.26 | NUE250 | 9131.2 | 4.38 | 7.2E−02 | 46.44 |
| Control | | 53.45 | | | Control | | 2.99 | | |
| NUE512 | 9284.2 | 94.55 | 9.0E−02 | 20.60 | NUE251 | 10181 | 5.98 | 4.9E−02 | 54.69 |
| NUE512 | 9284.3 | 92.98 | 4.2E−01 | 18.59 | NUE251 | 10183 | 6.63 | 3.6E−03 | 71.52 |
| NUE512 | 9283.1 | 91.30 | 8.6E−02 | 16.45 | Control | | 3.86 | | |
| NUE512 | 9282.3 | 92.85 | 5.7E−02 | 18.43 | NUE254 | 8972.2 | 6.43 | 2.1E−02 | 52.98 |
| NUE512 | 9281.3 | 105.50 | 2.1E−01 | 34.57 | Control | | 4.20 | | |
| Control | | 78.40 | | | NUE254 | 8972.2 | 9.28 | 3.3E−02 | 85.50 |
| NUE514 | 9404.1 | 158.73 | 3.8E−02 | 79.73 | Control | | 5.00 | | |
| Control | | 88.31 | | | NUE256 | 10063 | 6.10 | 1.7E−03 | 57.93 |
| NUE515 | 9712.5 | 104.98 | 5.6E−01 | 11.6 | NUE256 | 10064 | 9.55 | 2.9E−07 | 147.25 |
| NUE515 | 9713.6 | 185.55 | 4.0E−06 | 97.2 | NUE256 | 10061 | 6.30 | 5.2E−02 | 63.11 |
| Control | | 94.09 | | | NUE256 | 10062 | 7.65 | 1.1E−01 | 98.06 |
| NUE516 | 9291.1 | 230.00 | 8.3E−02 | 65.62 | NUE256 | 10063 | 6.33 | 4.9E−03 | 63.75 |
| NUE516 | 9291.4 | 227.13 | 5.7E−02 | 63.55 | Control | | 3.86 | | |
| Control | | 138.88 | | | NUE267 | 8962.1 | 6.43 | 5.0E−03 | 52.98 |
| NUE520 | 9771.4 | 137.73 | 5.8E−02 | 43.05 | Control | | 4.20 | | |
| NUE520 | 9771.7 | 160.25 | 3.5E−03 | 66.45 | NUE268 | 8994.5 | 7.18 | 8.4E−02 | 59.44 |
| NUE520 | 9771.2 | 158.98 | 1.3E−02 | 65.13 | NUE268 | 8996.3 | 6.85 | 1.9E−02 | 52.22 |
| NUE520 | 9771.3 | 148.40 | 6.5E−02 | 54.14 | NUE268 | 8996.5 | 7.00 | 2.8E−03 | 55.56 |
| Control | | 96.28 | | | Control | | 4.50 | | |
| NUE521 | 9361.2 | 167.53 | 7.3E−05 | 89.70 | NUE512 | 9284.2 | 4.20 | 1.6E−02 | 46.72 |
| NUE521 | 9363.4 | 180.95 | 7.6E−03 | 104.90 | NUE512 | 9284.3 | 3.58 | 1.7E−01 | 24.89 |
| Control | | 88.31 | | | NUE512 | 9283.1 | 4.35 | 1.8E−02 | 51.97 |
| NUE523 | 9412.1 | 271.35 | 1.0E−01 | 42.67 | NUE512 | 9282.3 | 4.18 | 2.6E−02 | 45.85 |
| Control | | 190.19 | | | NUE512 | 9281.3 | 4.93 | 1.9E−02 | 72.05 |
| NUE523 | 9413.3 | 184.25 | 7.3E−02 | 28.51 | Control | | 2.86 | | |
| NUE523 | 9413.4 | 180.55 | 2.2E−01 | 25.93 | NUE512 | 9284.2 | 6.00 | 2.3E−03 | 53.35 |
| Control | | 143.37 | | | Control | | 3.91 | | |
| NUE527 | 9202.6 | 152.18 | 6.1E−01 | 9.38 | NUE514 | 9404.1 | 7.90 | 6.3E−02 | 61.64 |
| NUE527 | 9203.2 | 249.95 | 7.5E−02 | 79.66 | Control | | 4.89 | | |
| NUE527 | 9201.2 | 273.53 | 4.2E−04 | 96.60 | NUE515 | 9713.6 | 8.38 | 1.0E−04 | 74.5 |
| Control | | 139.13 | | | Control | | 4.80 | | |
| NUE527 | 9204.2 | 101.70 | 1.3E−02 | 90.27 | NUE519 | 9371.1 | 12.15 | 1.4E−01 | 64.75 |
| NUE527 | 9202.6 | 82.40 | 3.4E−02 | 54.16 | NUE519 | 9371.2 | 14.15 | 3.5E−01 | 91.86 |
| NUE527 | 9201.1 | 120.30 | 3.6E−03 | 125.07 | NUE519 | 9373.1 | 9.20 | 2.4E−01 | 24.75 |
| NUE527 | 9203.2 | 84.63 | 2.6E−03 | 58.33 | Control | | 7.38 | | |
| NUE527 | 9204.1 | 68.55 | 1.2E−01 | 28.25 | NUE520 | 9771.4 | 5.73 | 1.5E−01 | 48.22 |
| Control | | 53.45 | | | NUE520 | 9771.7 | 6.60 | 5.4E−02 | 70.87 |
| NUE532 | 9222.4 | 210.65 | 3.5E−01 | 51.41 | NUE520 | 9771.2 | 8.05 | 7.6E−03 | 108.41 |
| NUE532 | 9222.1 | 168.45 | 8.4E−02 | 21.08 | NUE520 | 9771.3 | 5.73 | 2.9E−02 | 48.22 |
| NUE532 | 9223.5 | 210.15 | 7.6E−02 | 51.05 | Control | | 3.86 | | |
| Control | | 139.13 | | | NUE523 | 9412.1 | 9.03 | 6.0E−02 | 29.62 |
| NUE535 | 9081.1 | 117.15 | 3.0E−01 | 21.68 | Control | | 6.96 | | |
| NUE535 | 9083.1 | 235.35 | 7.7E−02 | 144.46 | NUE527 | 9201.2 | 8.78 | 7.7E−02 | 95.00 |
| NUE535 | 9084.4 | 128.88 | 5.4E−02 | 33.86 | Control | | 4.50 | | |
| NUE535 | 9082.1 | 114.83 | 3.1E−01 | 19.27 | NUE531 | 10083 | 7.05 | 1.2E−01 | 29.66 |
| Control | | 96.28 | | | NUE531 | 10082 | 8.90 | 7.5E−02 | 63.68 |
| NUE535 | 9082.2 | 85.55 | 5.9E−03 | 60.06 | NUE531 | 10081 | 8.60 | 2.4E−01 | 58.16 |
| NUE535 | 9086.2 | 120.63 | 1.3E−02 | 125.68 | NUE531 | 10082 | 9.43 | 1.6E−02 | 73.33 |
| NUE535 | 9086.3 | 86.67 | 1.2E−01 | 62.15 | Control | | 5.44 | | |
| NUE535 | 9081.1 | 90.65 | 4.3E−03 | 69.60 | NUE531 | 10081 | 8.48 | 4.2E−02 | 32.13 |
| NUE535 | 9084.4 | 69.83 | 2.2E−02 | 30.64 | NUE531 | 10082 | 8.95 | 1.2E−01 | 39.53 |
| Control | | 53.45 | | | Control | | 6.41 | | |
| NUE537 | 9393.3 | 207.43 | 6.7E−02 | 30.28 | NUE532 | 9222.4 | 8.28 | 1.4E−01 | 83.89 |
| Control | | 159.21 | | | NUE532 | 9222.1 | 6.53 | 8.4E−02 | 45.00 |
| NUE538 | 9782.1 | 203.68 | 4.0E−02 | 60.23 | NUE532 | 9223.3 | 6.08 | 7.5E−02 | 35.00 |
| Control | | 127.11 | | | NUE532 | 9223.5 | 6.70 | 1.8E−01 | 48.89 |
| NUE539 | 10101.5 | 146.60 | 3.7E−03 | 52.27 | Control | | 4.50 | | |
| NUE539 | 10103.5 | 126.33 | 7.8E−02 | 31.21 | NUE535 | 9083.1 | 10.90 | 5.6E−02 | 182.20 |
| NUE539 | 10101.2 | 190.80 | 5.0E−03 | 98.18 | Control | | 3.86 | | |
| NUE539 | 10101.7 | 173.78 | 2.0E−04 | 80.50 | NUE537 | 9391.1 | 6.48 | 9.9E−02 | 65.50 |
| Control | | 96.28 | | | NUE537 | 9393.3 | 5.53 | 2.9E−01 | 41.21 |
| NUE542 | 9332.1 | 196.48 | 3.3E−02 | 41.48 | Control | | 3.91 | | |
| Control | | 138.88 | | | NUE538 | 9782.1 | 8.30 | 2.8E−05 | 75.66 |

TABLE 29-continued

Transgenic plants exogenously expressing the polynucleotides of some embodiments of the invention exhibit improved plant biomass (fresh and dry weight) under standard nitrogen conditions

| Gene Name | Event # | Plant Fresh Weight [mg] Average | p-value | % incr. | Gene Name | Event # | Plant Dry Weight [mg] Average | p-value | % incr. |
|---|---|---|---|---|---|---|---|---|---|
| NUE544 | 9763.3 | 169.78 | 8.8E-02 | 26.31 | Control | | 4.73 | | |
| Control | | 134.41 | | | NUE539 | 10102 | 6.83 | 1.4E-03 | 76.70 |
| NUE549 | 9343.6 | 200.95 | 9.7E-02 | 32.41 | NUE539 | 10101 | 9.15 | 2.0E-02 | 136.89 |
| NUE549 | 9343.7 | 205.95 | 2.8E-01 | 35.71 | NUE539 | 10102 | 7.80 | 1.6E-02 | 101.94 |
| Control | | 151.76 | | | Control | | 3.86 | | |
| NUE550 | 9144.4 | 128.13 | 5.6E-03 | 139.71 | NUE543 | 10052 | 5.90 | 7.1E-02 | 24.87 |
| NUE550 | 9141.3 | 116.60 | 5.0E-07 | 118.15 | Control | | 4.73 | | |
| NUE550 | 9143.1 | 124.23 | 1.9E-02 | 132.41 | NUE544 | 9764.2 | 8.25 | 1.1E-01 | 53.49 |
| NUE550 | 9143.4 | 98.70 | 5.2E-02 | 84.66 | NUE544 | 9763.3 | 8.25 | 2.7E-02 | 53.49 |
| Control | | 53.45 | | | Control | | 5.38 | | |
| NUE550 | 9143.1 | 197.68 | 2.6E-01 | 42.08 | NUE548 | 9095.2 | 7.50 | 7.6E-02 | 32.45 |
| NUE550 | 9143.4 | 174.85 | 1.4E-01 | 25.68 | NUE548 | 9095.4 | 8.18 | 1.7E-01 | 44.37 |
| NUE550 | 9142.2 | 240.83 | 7.2E-05 | 73.10 | NUE548 | 9091.1 | 7.68 | 2.1E-01 | 35.54 |
| Control | | 139.13 | | | Control | | 5.66 | | |
| NUE553 | 9181.5 | 76.85 | 1.9E-03 | 43.78 | NUE548 | 9095.2 | 10.17 | 2.7E-02 | 71.23 |
| NUE553 | 9185.2 | 74.85 | 2.4E-01 | 40.04 | NUE548 | 9092.2 | 8.15 | 8.9E-02 | 37.26 |
| NUE553 | 9184.3 | 61.65 | 5.6E-01 | 15.34 | Control | | 5.94 | | |
| NUE553 | 9182.2 | 72.28 | 1.3E-01 | 35.22 | NUE549 | 9343.7 | 7.25 | 6.9E-02 | 31.52 |
| Control | | 53.45 | | | Control | | 5.51 | | |
| NUE554 | 9111.4 | 135.30 | 6.7E-02 | 153.13 | NUE550 | 9141.3 | 5.80 | 3.0E-01 | 28.89 |
| Control | | 53.45 | | | NUE550 | 9143.4 | 5.73 | 8.3E-03 | 27.22 |
| NUE563 | 9453.2 | 270.58 | 1.2E-01 | 53.26 | NUE550 | 9142.2 | 8.08 | 1.6E-02 | 79.44 |
| NUE563 | 9452.3 | 207.35 | 4.2E-01 | 17.45 | Control | | 4.50 | | |
| NUE563 | 9451.2 | 273.50 | 4.7E-02 | 54.91 | NUE554 | 9115.2 | 6.40 | 4.5E-02 | 42.22 |
| Control | | 176.55 | | | Control | | 4.50 | | |
| NUE564 | 9242.3 | 113.35 | 4.7E-02 | 44.58 | NUE560 | 9424.3 | 8.85 | 1.7E-03 | 65.64 |
| NUE564 | 9242.4 | 90.95 | 8.5E-02 | 16.01 | NUE560 | 9422.1 | 6.88 | 4.7E-02 | 28.68 |
| NUE564 | 9244.1 | 94.08 | 1.3E-02 | 19.99 | Control | | 5.34 | | |
| Control | | 78.40 | | | NUE562 | 9252.8 | 8.43 | 3.0E-02 | 57.69 |
| NUE566 | 9512.4 | 257.28 | 1.4E-02 | 45.72 | Control | | 5.34 | | |
| Control | | 176.55 | | | NUE567 | 9261.3 | 4.10 | 6.3E-02 | 43.23 |
| NUE567 | 9263.2 | 130.00 | 7.3E-03 | 65.82 | Control | | 2.86 | | |
| NUE567 | 9261.3 | 93.50 | 8.4E-02 | 19.26 | NUE568 | 9471.3 | 7.63 | 1.8E-02 | 38.32 |
| NUE567 | 9261.4 | 112.75 | 2.2E-02 | 43.81 | Control | | 5.51 | | |
| NUE567 | 9263.3 | 84.55 | 5.9E-01 | 7.84 | NUE569 | 9381.2 | 4.40 | 1.7E-02 | 53.71 |
| Control | | 78.40 | | | NUE569 | 9381.5 | 4.90 | 9.0E-02 | 71.18 |
| NUE568 | 9471.3 | 230.43 | 4.1E-02 | 51.83 | NUE569 | 9381.3 | 4.73 | 2.4E-03 | 65.07 |
| NUE568 | 9461.2 | 186.87 | 2.5E-01 | 23.13 | Control | | 2.86 | | |
| NUE568 | 9474.4 | 187.77 | 2.0E-01 | 23.72 | NUE570 | 9311.3 | 3.63 | 1.4E-01 | 26.64 |
| NUE568 | 9472.2 | 195.70 | 3.0E-01 | 28.95 | NUE570 | 9313.3 | 4.33 | 4.3E-02 | 51.09 |
| NUE568 | 9462.3 | 172.65 | 5.1E-01 | 13.76 | NUE570 | 9314.4 | 4.78 | 8.5E-03 | 66.81 |
| Control | | 151.76 | | | NUE570 | 9314.1 | 4.33 | 3.0E-02 | 51.09 |
| NUE569 | 9384.4 | 90.90 | 2.1E-01 | 15.94 | NUE570 | 9312.3 | 5.23 | 4.2E-04 | 82.53 |
| NUE569 | 9381.2 | 124.28 | 7.9E-03 | 58.51 | Control | | 2.86 | | |
| NUE569 | 9381.5 | 130.40 | 4.3E-02 | 66.33 | NUE571 | 9304.2 | 8.98 | 5.6E-02 | 67.98 |
| NUE569 | 9381.3 | 99.18 | 1.7E-01 | 26.50 | NUE571 | 9303.2 | 8.63 | 2.3E-03 | 61.43 |
| NUE569 | 9384.2 | 99.08 | 9.4E-02 | 26.37 | NUE571 | 9301.4 | 7.13 | 6.3E-02 | 33.36 |
| Control | | 78.40 | | | Control | | 5.34 | | |
| NUE570 | 9313.3 | 110.70 | 1.2E-01 | 41.20 | NUE571 | 9304.3 | 6.50 | 2.4E-04 | 127.07 |
| NUE570 | 9314.4 | 119.08 | 1.2E-02 | 51.88 | NUE571 | 9304.2 | 6.05 | 2.8E-02 | 111.35 |
| NUE570 | 9314.1 | 109.93 | 8.7E-03 | 40.21 | NUE571 | 9303.2 | 4.98 | 4.1E-02 | 73.80 |
| NUE570 | 9312.3 | 149.30 | 8.0E-03 | 90.43 | NUE571 | 9301.4 | 4.13 | 4.1E-02 | 44.10 |
| Control | | 78.40 | | | NUE571 | 9302.3 | 4.03 | 3.4E-02 | 40.61 |
| NUE571 | 9304.2 | 212.53 | 1.1E-01 | 48.23 | Control | | 2.86 | | |
| NUE571 | 9303.2 | 240.93 | 3.8E-02 | 68.04 | NUE572 | 9321.3 | 4.95 | 9.0E-02 | 72.93 |
| NUE571 | 9302.1 | 177.58 | 4.0E-01 | 23.86 | NUE572 | 9324.3 | 4.55 | 2.4E-02 | 58.95 |
| NUE571 | 9301.4 | 209.80 | 1.0E-01 | 46.33 | NUE572 | 9321.1 | 4.80 | 4.7E-03 | 67.69 |
| NUE571 | 9302.3 | 199.13 | 2.6E-01 | 38.89 | NUE572 | 9322.2 | 4.35 | 1.5E-02 | 51.97 |
| Control | | 143.37 | | | Control | | 2.86 | | |
| NUE571 | 9304.3 | 124.43 | 1.2E-02 | 58.71 | NUE573 | 9491.4 | 7.28 | 1.8E-03 | 31.97 |
| NUE571 | 9304.2 | 123.90 | 4.5E-02 | 58.04 | Control | | 5.51 | | |
| NUE571 | 9303.2 | 106.00 | 1.7E-02 | 35.20 | NUE576 | 9793.3 | 8.03 | 7.1E-04 | 69.84 |
| Control | | 78.40 | | | Control | | 4.73 | | |
| NUE572 | 9322.1 | 124.90 | 3.5E-02 | 59.31 | NUE581 | 9723.6 | 6.28 | 9.3E-02 | 30.7 |
| NUE572 | 9324.3 | 115.85 | 2.7E-03 | 47.77 | NUE581 | 9724.9 | 8.15 | 2.0E-04 | 69.8 |
| NUE572 | 9321.1 | 101.00 | 3.1E-02 | 28.83 | Control | | 4.80 | | |
| NUE572 | 9322.2 | 98.05 | 1.1E-02 | 25.06 | NUE582 | 9561.1 | 6.90 | 2.6E-01 | 25.17 |
| Control | | 78.40 | | | NUE582 | 9562.4 | 7.88 | 3.3E-02 | 42.86 |
| NUE573 | 9491.1 | 226.63 | 4.7E-02 | 49.33 | NUE582 | 9561.2 | 8.95 | 3.0E-02 | 62.36 |
| Control | | 151.76 | | | Control | | 5.51 | | |
| NUE581 | 9723.6 | 125.85 | 9.7E-02 | 33.8 | NUE583 | 9673.4 | 11.28 | 6.2E-02 | 75.78 |
| NUE581 | 9724.5 | 99.23 | 7.8E-01 | 5.5 | NUE583 | 9673.2 | 7.70 | 4.3E-01 | 20.04 |
| NUE581 | 9724.9 | 165.35 | 2.0E-04 | 75.7 | Control | | 6.41 | | |

TABLE 29-continued

Transgenic plants exogenously expressing the polynucleotides of some embodiments of the invention exhibit improved plant biomass (fresh and dry weight) under standard nitrogen conditions

| Gene Name | Event # | Plant Fresh Weight [mg] Average | p-value | % incr. | Gene Name | Event # | Plant Dry Weight [mg] Average | p-value | % incr. |
|---|---|---|---|---|---|---|---|---|---|
| Control | | 94.09 | | | NUE585 | 9661.1 | 6.95 | 7.5E−02 | 31.13 |
| NUE582 | 9564.2 | 189.45 | 1.4E−01 | 36.42 | Control | | 5.30 | | |
| NUE582 | 9561.1 | 186.30 | 1.5E−01 | 34.15 | NUE587 | 9643.2 | 10.20 | 3.2E−02 | 85.03 |
| NUE582 | 9562.4 | 209.48 | 7.3E−02 | 50.84 | NUE587 | 9641.3 | 8.23 | 1.8E−01 | 49.21 |
| NUE582 | 9561.2 | 244.25 | 9.8E−02 | 75.88 | Control | | 5.51 | | |
| Control | | 138.88 | | | NUE592 | 9744.5 | 9.80 | 1.0E−07 | 104.2 |
| NUE583 | 9673.4 | 222.13 | 4.7E−02 | 54.28 | NUE592 | 9747.5 | 8.23 | 2.0E−04 | 71.4 |
| Control | | 143.97 | | | Control | | 4.80 | | |
| NUE585 | 9661.5 | 198.18 | 6.9E−02 | 24.22 | | | | | |
| NUE585 | 9661.1 | 194.93 | 2.6E−01 | 22.18 | | | | | |
| Control | | 159.54 | | | | | | | |
| NUE587 | 9643.2 | 242.53 | 4.2E−02 | 53.46 | | | | | |
| NUE587 | 9643.1 | 221.50 | 1.9E−01 | 40.16 | | | | | |
| NUE587 | 9642.5 | 169.73 | 7.0E−01 | 7.40 | | | | | |
| NUE587 | 9642.2 | 192.08 | 4.1E−01 | 21.54 | | | | | |
| NUE587 | 9641.3 | 268.95 | 3.5E−04 | 70.18 | | | | | |
| Control | | 158.04 | | | | | | | |
| NUE592 | 9741.7 | 115.18 | 2.6E−01 | 22.4 | | | | | |
| NUE592 | 9744.5 | 197.68 | 2.6E−07 | 110.1 | | | | | |
| NUE592 | 9747.4 | 118.53 | 1.9E−01 | 26.0 | | | | | |
| NUE592 | 9747.5 | 169.38 | 1.0E−04 | 80.0 | | | | | |
| Control | | 94.09 | | | | | | | |

Table 29: Analyses of plant biomass (plant fresh and dry weight) of transgenic plants overexpressing the exogenous polynucleotides of some embodiments of the invention (using the cloned or synthetic genes listed in Table 23 above) under the regulation of a constitutive promoter (35S) when grown under standard nitrogen conditions [normal or regular growth conditions (15 mM N)] as compared to control plants.
"Incr." = increment; "RGR" = relative growth rate.

TABLE 30

Transgenic plants exogenously expressing the polynucleotides of some embodiments of the invention exhibit improved plant biomass (leaf area) under standard nitrogen conditions

| Gene Name | Event # | Leaf Area cm² Average | p-value | % increment |
|---|---|---|---|---|
| CT11 | 4892.2 | 0.873 | 6.4E−03 | 72.49 |
| CT11 | 4892.3 | 0.809 | 1.6E−03 | 59.89 |
| CT11 | 4892.1 | 0.848 | 8.2E−02 | 67.56 |
| Control | | 0.506 | | |
| CT11 | 4894.2 | 0.474 | 8.2E−02 | 21.28 |
| CT11 | 4893.2 | 0.763 | 2.7E−02 | 94.95 |
| Control | | 0.391 | | |
| CT27 | 5033.8 | 0.645 | 3.8E−02 | 81.02 |
| CT27 | 5033.5 | 0.482 | 8.8E−02 | 35.52 |
| Control | | 0.356 | | |
| CT27 | 5033.7 | 0.495 | 6.9E−02 | 26.56 |
| CT27 | 5035.2 | 0.751 | 1.2E−02 | 92.06 |
| CT27 | 5031.4 | 0.582 | 1.3E−05 | 48.90 |
| CT27 | 5033.6 | 0.602 | 1.6E−02 | 53.79 |
| CT27 | 5033.4 | 0.575 | 1.3E−02 | 47.12 |
| CT27 | 5033.8 | 0.528 | 6.0E−03 | 34.95 |
| CT27 | 5033.5 | 0.446 | 5.8E−02 | 14.08 |
| Control | | 0.391 | | |
| CT6 | 4941.4 | 0.551 | 1.5E−04 | 40.90 |
| Control | | 0.391 | | |
| CT75 | 4872.5 | 0.506 | 1.0E−01 | 29.29 |
| CT75 | 4874.4 | 0.529 | 3.1E−02 | 35.35 |
| Control | | 0.391 | | |
| CT76 | 5044.6 | 0.702 | 8.6E−03 | 38.82 |
| CT76 | 5041.5 | 0.674 | 2.0E−01 | 33.22 |
| CT76 | 5041.7 | 0.596 | 1.4E−01 | 17.83 |
| CT76 | 5043.5 | 1.093 | 2.1E−05 | 116.09 |
| CT76 | 5041.6 | 0.779 | 4.9E−02 | 53.91 |
| CT76 | 5041.9 | 0.749 | 4.0E−03 | 48.14 |
| Control | | 0.506 | | |
| CT76 | 5044.6 | 0.663 | 1.6E−02 | 86.32 |
| CT76 | 5041.5 | 0.904 | 2.4E−03 | 153.77 |
| CT76 | 5043.5 | 0.850 | 1.8E−03 | 138.87 |
| CT76 | 5041.6 | 0.528 | 2.3E−02 | 48.40 |
| CT76 | 5041.9 | 0.696 | 6.3E−03 | 95.60 |
| Control | | 0.356 | | |
| CT81 | 4992.1 | 0.804 | 7.1E−02 | 58.98 |
| CT81 | 4992.2 | 0.778 | 3.4E−03 | 53.73 |
| Control | | 0.506 | | |
| NUE206 | 6732.5 | 0.707 | 3.6E−02 | 21.77 |
| Control | | 0.580 | | |
| NUE208 | 8354.8 | 0.765 | 1.1E−02 | 31.82 |
| NUE208 | 8354.5 | 0.727 | 1.3E−01 | 25.27 |
| NUE208 | 8355.3 | 0.763 | 5.7E−02 | 31.55 |
| Control | | 0.580 | | |
| NUE209 | 8192.14 | 0.458 | 2.2E−01 | 43.17 |
| NUE209 | 8191.5 | 0.430 | 7.0E−02 | 34.44 |
| Control | | 0.320 | | |
| NUE210 | 8201.3 | 0.485 | 1.1E−02 | 51.70 |
| Control | | 0.320 | | |
| NUE210 | 8202.1 | 0.414 | 1.3E−02 | 30.69 |
| NUE210 | 6755.3 | 0.474 | 5.8E−02 | 49.68 |
| Control | | 0.316 | | |
| NUE210 | 8201.2 | 0.275 | 1.5E−02 | 35.08 |
| Control | | 0.204 | | |
| NUE211 | 8265.1 | 0.253 | 7.2E−02 | 24.01 |
| NUE211 | 8263.5 | 0.370 | 4.7E−04 | 81.74 |
| Control | | 0.204 | | |
| NUE212 | 8335.1 | 0.332 | 6.3E−02 | 62.71 |
| NUE212 | 8334.1 | 0.277 | 5.9E−03 | 36.04 |
| NUE212 | 8331.4 | 0.268 | 1.1E−01 | 31.45 |
| Control | | 0.204 | | |
| NUE212 | 8335.2 | 0.490 | 1.2E−02 | 53.10 |
| Control | | 0.320 | | |
| NUE212 | 8332.1 | 0.390 | 7.7E−03 | 23.33 |
| NUE212 | 8334.1 | 0.420 | 2.1E−03 | 32.80 |

TABLE 30-continued

Transgenic plants exogenously expressing the polynucleotides of some embodiments of the invention exhibit improved plant biomass (leaf area) under standard nitrogen conditions

| Gene Name | Event # | Leaf Area cm² Average | p-value | % increment |
|---|---|---|---|---|
| NUE212 | 8331.4 | 0.430 | 2.3E−03 | 35.83 |
| Control | | 0.316 | | |
| NUE221 | 9801.10 | 0.47 | 5.6E−01 | 8.7 |
| NUE221 | 9802.8 | 0.59 | 1.0E−02 | 38.4 |
| NUE221 | 9806.1 | 0.72 | 1.0E−05 | 68.8 |
| Control | | 0.43 | | |
| NUE224 | 9002.2 | 0.525 | 1.3E−02 | 19.12 |
| NUE224 | 9001.3 | 0.542 | 9.6E−02 | 22.97 |
| Control | | 0.441 | | |
| NUE227 | 9851.2 | 0.531 | 1.9E−01 | 22.50 |
| NUE227 | 9853.1 | 0.628 | 2.1E−02 | 44.84 |
| NUE227 | 9852.3 | 0.550 | 6.8E−02 | 26.84 |
| Control | | 0.433 | | |
| NUE228 | 10092.2 | 0.691 | 2.5E−01 | 22.23 |
| NUE228 | 10093.3 | 0.759 | 3.6E−02 | 34.30 |
| NUE228 | 10093.1 | 0.646 | 1.7E−01 | 14.35 |
| Control | | 0.565 | | |
| NUE229 | 8864.2 | 0.430 | 2.4E−02 | 21.48 |
| Control | | 0.354 | | |
| NUE230 | 9154.2 | 0.559 | 1.3E−01 | 26.94 |
| NUE230 | 9151.2 | 0.519 | 8.3E−02 | 17.74 |
| Control | | 0.441 | | |
| NUE231 | 10631.3 | 0.46 | 5.9E−01 | 8.0 |
| NUE231 | 10632.2 | 0.50 | 2.7E−01 | 16.3 |
| NUE231 | 10633.3 | 0.74 | 3.9E−06 | 72.3 |
| Control | | 0.43 | | |
| NUE233 | 10174.3 | 0.512 | 7.7E−04 | 87.53 |
| NUE233 | 10174.1 | 0.735 | 5.1E−06 | 169.13 |
| NUE233 | 10173.7 | 0.398 | 2.9E−02 | 45.70 |
| Control | | 0.273 | | |
| NUE233 | 10174.1 | 0.820 | 1.2E−04 | 35.44 |
| Control | | 0.606 | | |
| NUE235 | 9694.2 | 0.516 | 1.0E−01 | 17.08 |
| NUE235 | 9694.3 | 0.578 | 2.6E−02 | 31.06 |
| Control | | 0.441 | | |
| NUE237 | 9651.1 | 0.710 | 3.7E−03 | 61.05 |
| NUE237 | 9654.4 | 0.566 | 1.9E−02 | 28.50 |
| NUE237 | 9654.1 | 0.634 | 1.4E−01 | 43.87 |
| Control | | 0.441 | | |
| NUE241 | 9631.3 | 0.670 | 6.8E−04 | 54.67 |
| NUE241 | 9632.5 | 0.626 | 1.2E−01 | 44.49 |
| NUE241 | 9632.4 | 0.601 | 1.1E−03 | 38.64 |
| Control | | 0.433 | | |
| NUE242 | 9214.1 | 0.726 | 5.0E−02 | 18.36 |
| Control | | 0.613 | | |
| NUE242 | 9212.1 | 0.542 | 4.1E−02 | 42.31 |
| NUE242 | 9213.4 | 0.518 | 1.3E−02 | 35.92 |
| Control | | 0.381 | | |
| NUE244 | 9061.5 | 0.473 | 4.8E−03 | 33.52 |
| Control | | 0.354 | | |
| NUE246 | 9033.8 | 0.740 | 3.2E−03 | 51.11 |
| NUE246 | 9034.1 | 0.582 | 6.5E−02 | 18.92 |
| NUE246 | 9031.1 | 0.572 | 6.9E−02 | 16.87 |
| Control | | 0.490 | | |
| NUE248 | 8981.5 | 0.803 | 7.2E−02 | 55.67 |
| Control | | 0.516 | | |
| NUE250 | 9132.1 | 0.744 | 8.5E−02 | 68.79 |
| NUE250 | 9133.2 | 0.528 | 2.0E−02 | 19.79 |
| NUE250 | 9132.2 | 0.517 | 1.8E−02 | 17.26 |
| NUE250 | 9134.1 | 0.525 | 1.8E−01 | 19.17 |
| Control | | 0.441 | | |
| NUE250 | 9134.1 | 0.444 | 4.1E−03 | 25.38 |
| Control | | 0.354 | | |
| NUE251 | 10181.3 | 0.599 | 1.1E−02 | 119.32 |
| NUE251 | 10183.2 | 0.467 | 2.4E−02 | 71.22 |
| NUE251 | 10183.1 | 0.408 | 2.7E−02 | 49.61 |
| NUE251 | 10181.1 | 0.397 | 7.3E−03 | 45.35 |
| Control | | 0.273 | | |
| NUE251 | 10181.3 | 0.600 | 6.2E−02 | 22.85 |
| Control | | 0.488 | | |
| NUE251 | 10183.2 | 0.713 | 2.9E−02 | 17.75 |
| Control | | 0.606 | | |
| NUE256 | 10063.4 | 0.479 | 4.6E−03 | 75.40 |
| NUE256 | 10064.1 | 0.707 | 1.5E−04 | 159.05 |
| NUE256 | 10061.2 | 0.601 | 9.0E−06 | 120.20 |
| NUE256 | 10062.4 | 0.588 | 1.2E−03 | 115.54 |
| NUE256 | 10063.2 | 0.507 | 3.2E−03 | 85.58 |
| Control | | 0.273 | | |
| NUE268 | 8996.5 | 0.730 | 6.1E−02 | 39.46 |
| Control | | 0.523 | | |
| NUE269 | 9103.3 | 0.448 | 8.1E−02 | 23.13 |
| Control | | 0.364 | | |
| NUE512 | 9284.2 | 0.531 | 4.8E−02 | 45.85 |
| NUE512 | 9282.3 | 0.748 | 1.2E−04 | 105.28 |
| NUE512 | 9284.4 | 0.442 | 5.3E−02 | 21.37 |
| Control | | 0.364 | | |
| NUE514 | 9404.1 | 0.796 | 1.2E−04 | 108.76 |
| NUE514 | 9402.2 | 0.449 | 2.1E−01 | 17.88 |
| NUE514 | 9403.2 | 0.452 | 2.3E−01 | 18.65 |
| Control | | 0.381 | | |
| NUE515 | 9712.6 | 0.49 | 3.5E−01 | 14.0 |
| NUE515 | 9713.6 | 0.66 | 5.0E−04 | 53.4 |
| Control | | 0.43 | | |
| NUE516 | 9291.1 | 0.516 | 2.0E−01 | 16.98 |
| NUE516 | 9291.4 | 0.639 | 6.0E−04 | 45.10 |
| Control | | 0.441 | | |
| NUE520 | 9771.4 | 0.465 | 1.6E−02 | 70.36 |
| NUE520 | 9771.7 | 0.482 | 1.4E−02 | 76.62 |
| NUE520 | 9771.2 | 0.415 | 2.7E−03 | 51.98 |
| NUE520 | 9771.3 | 0.360 | 1.5E−02 | 32.02 |
| Control | | 0.273 | | |
| NUE521 | 9363.4 | 0.716 | 4.6E−03 | 75.12 |
| Control | | 0.409 | | |
| NUE521 | 9361.2 | 0.525 | 4.8E−02 | 37.71 |
| NUE521 | 9363.4 | 0.582 | 2.5E−02 | 52.79 |
| Control | | 0.381 | | |
| NUE523 | 9412.1 | 0.752 | 2.0E−02 | 45.74 |
| Control | | 0.516 | | |
| NUE523 | 9412.5 | 0.526 | 5.2E−02 | 38.12 |
| NUE523 | 9414.2 | 0.487 | 3.3E−02 | 27.79 |
| Control | | 0.381 | | |
| NUE531 | 10083.1 | 0.809 | 7.9E−03 | 43.12 |
| NUE531 | 10082.2 | 0.705 | 3.0E−01 | 24.67 |
| NUE531 | 10081.4 | 0.900 | 1.5E−02 | 59.14 |
| NUE531 | 10081.5 | 0.866 | 3.8E−02 | 53.10 |
| Control | | 0.565 | | |
| NUE531 | 10081.4 | 0.789 | 7.0E−02 | 30.24 |
| NUE531 | 10081.5 | 0.816 | 2.0E−02 | 34.70 |
| Control | | 0.606 | | |
| NUE535 | 9084.2 | 0.430 | 1.9E−02 | 57.65 |
| NUE535 | 9083.1 | 0.822 | 4.7E−03 | 201.24 |
| NUE535 | 9084.4 | 0.436 | 1.4E−03 | 59.81 |
| NUE535 | 9082.1 | 0.381 | 1.6E−01 | 39.64 |
| Control | | 0.273 | | |
| NUE537 | 9391.1 | 0.526 | 8.2E−02 | 44.39 |
| NUE537 | 9393.2 | 0.459 | 7.1E−02 | 26.03 |
| NUE537 | 9394.4 | 0.471 | 3.3E−02 | 29.36 |
| NUE537 | 9391.2 | 0.575 | 1.1E−02 | 57.79 |
| NUE537 | 9393.3 | 0.733 | 5.0E−03 | 101.21 |
| Control | | 0.364 | | |
| NUE539 | 10101.5 | 0.510 | 3.6E−02 | 86.79 |
| NUE539 | 10103.5 | 0.432 | 1.6E−02 | 58.38 |
| NUE539 | 10101.2 | 0.638 | 3.5E−04 | 133.70 |
| NUE539 | 10101.7 | 0.641 | 6.5E−03 | 134.76 |
| Control | | 0.273 | | |
| NUE542 | 9333.2 | 0.535 | 4.4E−04 | 46.83 |
| NUE542 | 9331.3 | 0.455 | 7.7E−02 | 24.84 |
| NUE542 | 9332.1 | 0.411 | 2.9E−01 | 12.88 |
| Control | | 0.364 | | |
| NUE543 | 10052.3 | 0.556 | 2.0E−01 | 28.45 |
| NUE543 | 10051.6 | 0.530 | 2.6E−02 | 22.32 |
| Control | | 0.433 | | |
| NUE543 | 10051.2 | 0.759 | 7.7E−02 | 34.20 |
| NUE543 | 10051.6 | 0.682 | 1.0E−01 | 20.71 |

TABLE 30-continued

Transgenic plants exogenously expressing the polynucleotides of some embodiments of the invention exhibit improved plant biomass (leaf area) under standard nitrogen conditions

| Gene Name | Event # | Leaf Area $cm^2$ Average | p-value | % increment |
|---|---|---|---|---|
| Control | | 0.565 | | |
| NUE544 | 9763.3 | 0.596 | 1.8E−03 | 36.70 |
| Control | | 0.436 | | |
| NUE548 | 9091.1 | 0.783 | 1.2E−02 | 27.78 |
| Control | | 0.613 | | |
| NUE550 | 9144.3 | 0.436 | 4.0E−02 | 19.74 |
| Control | | 0.364 | | |
| NUE550 | 9143.1 | 0.558 | 1.4E−02 | 35.96 |
| Control | | 0.410 | | |
| NUE550 | 9141.3 | 0.622 | 2.0E−01 | 18.74 |
| NUE550 | 9142.2 | 0.664 | 5.7E−03 | 26.77 |
| Control | | 0.523 | | |
| NUE551 | 9351.1 | 0.566 | 7.6E−02 | 15.59 |
| Control | | 0.490 | | |
| NUE560 | 9424.3 | 0.537 | 8.5E−02 | 31.22 |
| NUE560 | 9422.1 | 0.581 | 2.0E−04 | 41.90 |
| Control | | 0.409 | | |
| NUE564 | 9244.1 | 0.520 | 7.9E−02 | 22.64 |
| Control | | 0.424 | | |
| NUE564 | 9242.3 | 0.415 | 5.6E−02 | 13.97 |
| NUE564 | 9243.2 | 0.469 | 7.6E−02 | 28.83 |
| NUE564 | 9242.2 | 0.585 | 4.5E−04 | 60.72 |
| Control | | 0.364 | | |
| NUE567 | 9263.2 | 0.510 | 2.5E−02 | 40.15 |
| NUE567 | 9261.3 | 0.415 | 3.4E−01 | 13.94 |
| NUE567 | 9261.2 | 0.400 | 6.0E−01 | 9.89 |
| NUE567 | 9263.3 | 0.453 | 3.9E−01 | 24.33 |
| Control | | 0.364 | | |
| NUE568 | 9471.3 | 0.613 | 4.5E−04 | 60.34 |
| NUE568 | 9472.2 | 0.689 | 3.5E−03 | 80.16 |
| Control | | 0.382 | | |
| NUE569 | 9381.2 | 0.576 | 1.6E−02 | 35.83 |
| NUE569 | 9381.3 | 0.507 | 1.7E−01 | 19.49 |
| Control | | 0.424 | | |
| NUE571 | 9304.2 | 0.752 | 4.6E−03 | 83.90 |
| NUE571 | 9301.1 | 0.623 | 1.4E−01 | 52.23 |
| NUE571 | 9303.2 | 0.545 | 6.6E−04 | 33.32 |
| NUE571 | 9302.1 | 0.574 | 1.3E−04 | 40.39 |
| NUE571 | 9302.3 | 0.524 | 9.1E−02 | 28.11 |
| Control | | 0.409 | | |
| NUE571 | 9301.4 | 0.492 | 6.1E−02 | 16.00 |
| Control | | 0.424 | | |
| NUE573 | 9491.1 | 0.511 | 1.5E−02 | 33.50 |
| NUE573 | 9491.4 | 0.539 | 2.3E−01 | 40.86 |
| Control | | 0.382 | | |
| NUE576 | 9794.1 | 0.503 | 1.2E−01 | 16.10 |
| NUE576 | 9793.3 | 0.641 | 9.9E−03 | 48.00 |
| Control | | 0.433 | | |
| NUE578 | 9524.3 | 0.551 | 3.2E−04 | 43.94 |
| NUE578 | 9524.1 | 0.477 | 2.2E−01 | 24.73 |

TABLE 30-continued

Transgenic plants exogenously expressing the polynucleotides of some embodiments of the invention exhibit improved plant biomass (leaf area) under standard nitrogen conditions

| Gene Name | Event # | Leaf Area $cm^2$ Average | p-value | % increment |
|---|---|---|---|---|
| Control | | 0.382 | | |
| NUE579 | 9701.3 | 0.481 | 8.3E−02 | 18.67 |
| Control | | 0.406 | | |
| NUE580 | 9554.4 | 0.483 | 2.0E−02 | 26.39 |
| Control | | 0.382 | | |
| NUE581 | 9723.6 | 0.53 | 1.3E−01 | 22.7 |
| NUE581 | 9724.9 | 0.74 | 2.9E−06 | 73.4 |
| Control | | 0.43 | | |
| NUE582 | 9562.4 | 0.567 | 2.6E−02 | 28.69 |
| NUE582 | 9561.2 | 0.649 | 3.4E−02 | 47.37 |
| Control | | 0.441 | | |
| NUE583 | 9673.4 | 1.065 | 4.9E−03 | 75.90 |
| NUE583 | 9673.2 | 0.773 | 8.5E−02 | 27.63 |
| Control | | 0.606 | | |
| NUE586 | 9751.6 | 0.551 | 3.4E−02 | 26.32 |
| NUE586 | 9751.7 | 0.628 | 2.7E−02 | 44.06 |
| NUE586 | 9752.4 | 0.479 | 8.0E−02 | 9.73 |
| NUE586 | 9752.1 | 0.609 | 2.0E−02 | 39.56 |
| Control | | 0.436 | | |
| NUE587 | 9643.2 | 0.780 | 4.2E−03 | 92.27 |
| NUE587 | 9641.3 | 0.503 | 1.9E−01 | 23.98 |
| Control | | 0.406 | | |
| NUE592 | 9744.5 | 0.89 | 1.0E−10 | 106.7 |
| NUE592 | 9747.5 | 0.59 | 1.0E−02 | 38.7 |
| Control | | 0.43 | | |

Table 30: Analyses of plant biomass (leaf area) of transgenic plants overexpressing the exogenous polynucleotides of some embodiments of the invention (using the cloned or synthetic genes listed in Table 23 above) under the regulation of a constitutive promoter (35S) when grown under standard nitrogen conditions [normal or regular growth conditions (15 mM N)] as compared to control plants.
"Incr." = increment; "RGR" = relative growth rate.

The genes presented in Table 31 hereinbelow, have improved plant NUE since they produced larger root biomass when grown under standard nitrogen growth conditions, compared to control plants. Plants producing larger root biomass have better possibilities to absorb larger amount of nitrogen from soil.

Table 31 depicts analyses of root performance (root length and coverage) when grown under standard nitrogen conditions [normal or regular growth conditions (15 mM N)] in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 31

Transgenic plants exogenously expressing the polynucleotides of some embodiments of the invention exhibit improved root performance (root length and coverage) under standard nitrogen conditions

| Gene Name | Event # | Roots Length [cm] Average | p-value | % incr. | Roots Coverage [$cm^2$] Average | p-value | % incr. |
|---|---|---|---|---|---|---|---|
| CT27 | 5033.6 | 3.341 | 1.8E−01 | 18.64 | 2.879 | 1.5E−01 | 31.17 |
| CT27 | 5033.4 | 3.362 | 1.6E−02 | 19.36 | 2.461 | 5.3E−01 | 12.11 |
| Control | | 2.817 | | | 2.195 | | |
| CT75 | 4873.4 | 4.223 | 8.1E−02 | 13.74 | 3.136 | 8.5E−01 | 2.38 |
| CT75 | 4873.3 | 5.290 | 9.1E−03 | 42.48 | 4.560 | 7.9E−02 | 48.88 |
| Control | | 3.713 | | | 3.063 | | |
| CT76 | 5043.5 | 4.908 | 7.0E−02 | 23.17 | 7.927 | 1.5E−02 | 101.19 |
| CT76 | 5041.6 | 4.286 | 4.2E−01 | 7.57 | 5.216 | 3.7E−01 | 32.41 |
| CT76 | 5041.9 | 4.051 | 7.2E−01 | 1.67 | 4.809 | 3.9E−02 | 22.05 |

TABLE 31-continued

Transgenic plants exogenously expressing the polynucleotides of some embodiments of the invention exhibit improved root performance (root length and coverage) under standard nitrogen conditions

| Gene Name | Event # | Roots Length [cm] | | | Roots Coverage [cm$^2$] | | |
|---|---|---|---|---|---|---|---|
| | | Average | p-value | % incr. | Average | p-value | % incr. |
| Control | | 3.984 | | | 3.940 | | |
| CT76 | 5041.5 | 4.273 | 5.4E−04 | 51.72 | 5.377 | 2.8E−03 | 144.94 |
| CT76 | 5043.5 | 2.837 | 9.1E−01 | 0.73 | 3.200 | 5.7E−03 | 45.76 |
| Control | | 2.817 | | | 2.195 | | |
| NUE206 | 6731.2 | 3.619 | 6.8E−02 | 28.05 | 3.376 | 3.5E−02 | 60.66 |
| NUE206 | 6732.7 | 3.311 | 6.7E−02 | 17.14 | 2.577 | 1.3E−01 | 22.63 |
| NUE206 | 6732.5 | 3.516 | 3.1E−02 | 24.42 | 2.894 | 1.3E−01 | 37.69 |
| NUE206 | 6732.1 | 3.347 | 2.0E−02 | 18.43 | 2.575 | 1.2E−01 | 22.53 |
| Control | | 2.826 | | | 2.102 | | |
| NUE206 | 6731.2 | 4.088 | 4.8E−02 | 36.80 | 5.469 | 3.2E−02 | 109.44 |
| NUE206 | 6732.5 | 4.106 | 1.2E−03 | 37.41 | 5.064 | 5.2E−03 | 93.92 |
| NUE206 | 6732.15 | 3.669 | 9.1E−02 | 22.78 | 4.031 | 2.4E−02 | 54.36 |
| Control | | 2.988 | | | 2.611 | | |
| NUE208 | 8351.3 | 3.930 | 2.9E−03 | 39.05 | 3.339 | 8.4E−03 | 58.86 |
| NUE208 | 8354.4 | 3.385 | 1.8E−01 | 19.76 | 2.828 | 1.3E−02 | 34.57 |
| Control | | 2.826 | | | 2.102 | | |
| NUE208 | 8355.3 | 3.393 | 6.0E−01 | 8.41 | 3.528 | 8.5E−02 | 48.07 |
| Control | | 3.130 | | | 2.382 | | |
| NUE208 | 8355.3 | 3.600 | 6.6E−02 | 20.47 | 3.969 | 8.6E−02 | 51.99 |
| Control | | 2.988 | | | 2.611 | | |
| NUE212 | 8332.2 | 4.896 | 6.1E−02 | 14.16 | 5.444 | 2.0E−02 | 27.45 |
| Control | | 4.289 | | | 4.272 | | |
| NUE221 | 9802.8 | | | | 3.72 | 4.9E−01 | 12.1 |
| Control | | | | | 3.32 | | |
| NUE223 | 9613.1 | 4.376 | 9.8E−02 | 18.05 | 5.480 | 4.0E−02 | 36.61 |
| NUE223 | 9612.3 | 4.426 | 8.7E−02 | 19.41 | 5.228 | 4.5E−02 | 30.32 |
| Control | | 3.707 | | | 4.012 | | |
| NUE230 | 9152.4 | 4.034 | 9.1E−03 | 17.77 | 3.441 | 1.1E−01 | 40.34 |
| Control | | 3.425 | | | 2.452 | | |
| NUE231 | 10631.3 | | | | 4.45 | 5.3E−02 | 34.2 |
| NUE231 | 10632.2 | 4.31 | 7.8E−03 | 14.7 | 4.64 | 2.3E−02 | 40.0 |
| NUE231 | 10633.3 | 4.84 | 7.0E−04 | 28.9 | 6.30 | 1.2E−06 | 90.1 |
| Control | | 3.76 | | | 3.32 | | |
| NUE233 | 10174.3 | 3.326 | 1.2E−01 | 16.40 | 2.879 | 3.3E−02 | 45.78 |
| NUE233 | 10174.1 | 4.581 | 3.9E−04 | 60.32 | 5.392 | 3.2E−04 | 173.01 |
| NUE233 | 10173.5 | 4.414 | 4.8E−04 | 54.47 | 2.865 | 1.1E−02 | 45.06 |
| NUE233 | 10172.5 | 3.581 | 3.5E−02 | 25.30 | 2.957 | 4.8E−03 | 49.73 |
| NUE233 | 10173.7 | 3.100 | 4.5E−01 | 8.48 | 2.613 | 1.9E−01 | 32.30 |
| Control | | 2.858 | | | 1.975 | | |
| NUE233 | 10174.1 | 4.375 | 1.3E−02 | 30.08 | 3.884 | 1.6E−01 | 18.86 |
| NUE233 | 10173.5 | 4.755 | 7.1E−04 | 41.36 | 4.746 | 2.3E−02 | 45.25 |
| Control | | 3.363 | | | 3.268 | | |
| NUE233 | 10174.1 | 4.357 | 5.8E−04 | 21.63 | 4.698 | 6.0E−03 | 39.12 |
| Control | | 3.582 | | | 3.377 | | |
| NUE237 | 9654.4 | 3.928 | 8.6E−01 | −1.32 | 4.729 | 1.0E−02 | 21.38 |
| NUE237 | 9654.1 | 4.951 | 4.0E−02 | 24.37 | 6.035 | 7.3E−02 | 54.90 |
| Control | | 3.981 | | | 3.896 | | |
| NUE237 | 9654.1 | 3.831 | 1.8E−01 | 11.85 | 4.235 | 2.3E−02 | 49.30 |
| Control | | 3.425 | | | 2.837 | | |
| NUE239 | 9191.2 | 4.379 | 2.1E−02 | 27.86 | 5.300 | 3.4E−02 | 86.84 |
| Control | | 3.707 | | | 4.012 | | |
| NUE241 | 9631.3 | 4.010 | 4.1E−01 | 5.60 | 3.785 | 1.4E−01 | 23.13 |
| NUE241 | 9632.5 | 5.084 | 4.2E−04 | 33.88 | 6.207 | 2.3E−03 | 101.95 |
| NUE241 | 9632.3 | 4.507 | 1.7E−01 | 18.69 | 4.237 | 2.3E−01 | 37.86 |
| Control | | 3.797 | | | 3.074 | | |
| NUE242 | 9213.4 | 4.696 | 5.9E−02 | 20.84 | 5.038 | 1.3E−01 | 28.12 |
| Control | | 3.886 | | | 3.933 | | |
| NUE246 | 9033.8 | 4.534 | 1.2E−01 | 14.09 | 5.522 | 6.1E−02 | 50.92 |
| Control | | 3.974 | | | 3.659 | | |
| NUE251 | 10181.3 | 3.824 | 2.7E−02 | 33.82 | 3.356 | 9.5E−03 | 69.93 |
| NUE251 | 10183.2 | 3.635 | 3.7E−02 | 27.20 | 3.158 | 3.6E−02 | 59.92 |
| NUE251 | 10183.1 | 3.726 | 6.2E−02 | 30.37 | 3.075 | 7.4E−02 | 55.70 |
| Control | | 2.858 | | | 1.975 | | |
| NUE251 | 10181.3 | 4.406 | 1.5E−03 | 30.98 | 4.945 | 2.9E−02 | 51.35 |
| Control | | 3.363 | | | 3.268 | | |
| NUE256 | 10063.4 | 4.545 | 1.0E−02 | 59.03 | 4.513 | 1.7E−02 | 128.53 |
| NUE256 | 10064.1 | 3.444 | 8.2E−02 | 20.53 | 3.655 | 3.0E−04 | 85.07 |
| NUE256 | 10061.2 | 3.398 | 6.3E−02 | 18.90 | 3.772 | 7.5E−05 | 91.01 |
| NUE256 | 10063.2 | 3.464 | 2.0E−01 | 21.21 | 3.617 | 7.2E−02 | 83.13 |
| Control | | 2.858 | | | 1.975 | | |
| NUE256 | 10061.3 | 4.011 | 8.5E−02 | 11.96 | 3.500 | 7.6E−01 | 3.66 |

TABLE 31-continued

Transgenic plants exogenously expressing the polynucleotides of
some embodiments of the invention exhibit improved root performance
(root length and coverage) under standard nitrogen conditions

| Gene Name | Event # | Roots Length [cm] | | | Roots Coverage [cm²] | | |
|---|---|---|---|---|---|---|---|
| | | Average | p-value | % incr. | Average | p-value | % incr. |
| Control | | 3.582 | | | 3.377 | | |
| NUE269 | 9104.1 | 4.116 | 9.0E−02 | 26.30 | 3.527 | 2.2E−01 | 28.77 |
| Control | | 3.259 | | | 2.739 | | |
| NUE512 | 9284.3 | 4.178 | 3.9E−01 | 14.99 | 3.222 | 6.3E−01 | 12.38 |
| NUE512 | 9282.3 | 3.683 | 8.6E−01 | 1.36 | 4.173 | 1.7E−02 | 45.56 |
| NUE512 | 9284.4 | 5.110 | 6.5E−04 | 40.66 | 3.987 | 3.4E−02 | 39.06 |
| Control | | 3.633 | | | 2.867 | | |
| NUE513 | 9681.6 | 4.639 | 2.5E−02 | 25.14 | 5.087 | 1.9E−01 | 26.81 |
| Control | | 3.707 | | | 4.012 | | |
| NUE513 | 9683.5 | 5.331 | 3.4E−02 | 20.24 | 4.960 | 9.1E−01 | 1.26 |
| Control | | 4.433 | | | 4.898 | | |
| NUE513 | 9683.5 | 5.216 | 1.6E−04 | 31.26 | 4.402 | 2.2E−01 | 20.31 |
| Control | | 3.974 | | | 3.659 | | |
| NUE514 | 9403.2 | 5.889 | 2.1E−04 | 54.38 | 6.448 | 1.4E−03 | 101.05 |
| Control | | 3.815 | | | 3.207 | | |
| NUE515 | 9712.6. | | | | 3.87 | 3.4E−01 | 16.6 |
| NUE515 | 9713.6. | | | | 4.19 | 1.3E−01 | 26.3 |
| Control | | | | | 3.32 | | |
| NUE520 | 9771.4 | 3.480 | 6.1E−02 | 21.77 | 3.356 | 7.8E−02 | 69.94 |
| NUE520 | 9771.2 | 3.487 | 5.7E−02 | 22.01 | 4.241 | 1.3E−02 | 114.72 |
| NUE520 | 9772.1 | 3.382 | 2.6E−01 | 18.35 | 3.936 | 4.7E−02 | 99.31 |
| NUE520 | 9771.3 | 3.284 | 2.0E−01 | 14.93 | 3.728 | 4.4E−03 | 88.78 |
| Control | | 2.858 | | | 1.975 | | |
| NUE523 | 9414.2 | 5.238 | 9.7E−02 | 18.15 | 4.912 | 9.9E−01 | 0.28 |
| Control | | 4.433 | | | 4.898 | | |
| NUE523 | 9412.5 | 4.589 | 2.1E−02 | 24.78 | 3.820 | 5.5E−01 | 11.95 |
| NUE523 | 9414.2 | 4.983 | 3.6E−02 | 35.48 | 4.310 | 1.6E−01 | 26.28 |
| Control | | 3.678 | | | 3.413 | | |
| NUE523 | 9412.5 | 3.997 | 5.3E−01 | 4.78 | 4.391 | 1.4E−02 | 36.91 |
| NUE523 | 9414.2 | 4.386 | 7.8E−02 | 14.98 | 4.588 | 1.8E−02 | 43.04 |
| Control | | 3.815 | | | 3.207 | | |
| NUE531 | 10083.3 | 4.413 | 5.7E−02 | 33.45 | 3.781 | 2.2E−01 | 24.13 |
| NUE531 | 10081.4 | 3.857 | 3.6E−02 | 16.65 | 4.484 | 3.8E−02 | 47.23 |
| NUE531 | 10081.5 | 4.377 | 3.6E−02 | 32.38 | 4.698 | 9.9E−02 | 54.25 |
| Control | | 3.306 | | | 3.046 | | |
| NUE531 | 10083.2 | 3.852 | 7.3E−02 | 14.51 | 3.992 | 6.0E−02 | 22.18 |
| Control | | 3.363 | | | 3.268 | | |
| NUE531 | 10083.3 | 4.256 | 9.0E−02 | 18.79 | 4.023 | 2.8E−01 | 19.16 |
| NUE531 | 10081.4 | 4.066 | 5.2E−02 | 13.49 | 4.864 | 3.7E−02 | 44.06 |
| NUE531 | 10081.5 | 4.240 | 1.7E−02 | 18.37 | 4.905 | 8.1E−02 | 45.26 |
| Control | | 3.582 | | | 3.377 | | |
| NUE535 | 9084.2 | 3.244 | 2.5E−01 | 13.51 | 3.005 | 9.7E−02 | 52.16 |
| NUE535 | 9083.1 | 3.300 | 2.3E−01 | 15.49 | 3.263 | 7.1E−02 | 65.20 |
| Control | | 2.858 | | | 1.975 | | |
| NUE537 | 9393.3 | 3.603 | 8.9E−01 | −0.83 | 4.005 | 4.8E−02 | 39.70 |
| Control | | 3.633 | | | 2.867 | | |
| NUE538 | 9782.1 | 3.805 | 9.8E−01 | 0.22 | 3.850 | 7.9E−02 | 25.26 |
| Control | | 3.797 | | | 3.074 | | |
| NUE538 | 9784.4 | 3.674 | 7.5E−02 | 16.79 | 2.729 | 4.6E−01 | 12.64 |
| NUE538 | 9783.4 | 4.332 | 6.1E−03 | 37.70 | 3.571 | 4.5E−02 | 47.38 |
| Control | | 3.146 | | | 2.423 | | |
| NUE539 | 10103.5 | 3.228 | 2.0E−01 | 12.96 | 2.727 | 1.5E−01 | 38.07 |
| NUE539 | 10101.7 | 3.736 | 1.6E−02 | 30.72 | 3.446 | 8.3E−03 | 74.48 |
| Control | | 2.858 | | | 1.975 | | |
| NUE543 | 10052.3 | 4.801 | 3.8E−03 | 26.44 | 4.373 | 4.7E−02 | 42.28 |
| Control | | 3.797 | | | 3.074 | | |
| NUE543 | 10051.1 | 4.064 | 2.9E−02 | 22.91 | 4.493 | 6.0E−02 | 47.51 |
| NUE543 | 10052.3 | 4.003 | 1.1E−01 | 21.06 | 3.953 | 2.1E−01 | 29.78 |
| Control | | 3.306 | | | 3.046 | | |
| NUE544 | 9764.1 | 3.603 | 9.6E−02 | 14.52 | 3.075 | 2.3E−02 | 26.92 |
| NUE544 | 9763.3 | 3.953 | 1.8E−02 | 25.66 | 3.096 | 3.0E−02 | 27.77 |
| Control | | 3.146 | | | 2.423 | | |
| NUE550 | 9141.3 | 4.453 | 4.6E−01 | 8.58 | 5.445 | 5.9E−02 | 35.65 |
| Control | | 4.101 | | | 4.014 | | |
| NUE551 | 9354.3 | 4.584 | 9.0E−02 | 23.66 | 5.375 | 1.3E−01 | 33.99 |
| Control | | 3.707 | | | 4.012 | | |
| NUE566 | 9512.2 | 5.004 | 3.0E−02 | 18.17 | 5.741 | 2.3E−01 | 27.49 |
| NUE566 | 9512.1 | 4.859 | 1.5E−01 | 14.75 | 5.807 | 3.0E−01 | 28.96 |
| Control | | 4.234 | | | 4.503 | | |
| NUE568 | 9471.3 | 3.796 | 2.4E−01 | 10.82 | 3.883 | 8.9E−02 | 36.89 |
| NUE568 | 9472.2 | 4.025 | 1.8E−01 | 17.50 | 4.944 | 9.7E−03 | 74.30 |
| NUE568 | 9462.3 | 4.519 | 4.8E−02 | 31.93 | 4.354 | 5.0E−02 | 53.47 |

TABLE 31-continued

Transgenic plants exogenously expressing the polynucleotides of
some embodiments of the invention exhibit improved root performance
(root length and coverage) under standard nitrogen conditions

| Gene Name | Event # | Roots Length [cm] | | | Roots Coverage [cm²] | | |
|---|---|---|---|---|---|---|---|
| | | Average | p-value | % incr. | Average | p-value | % incr. |
| Control | | 3.425 | | | 2.837 | | |
| NUE570 | 9311.4 | 4.279 | 3.0E−01 | 17.77 | 4.349 | 5.4E−02 | 51.70 |
| NUE570 | 9314.4 | 3.692 | 8.1E−01 | 1.63 | 4.044 | 2.8E−02 | 41.05 |
| Control | | 3.633 | | | 2.867 | | |
| NUE571 | 9304.2 | 3.841 | 7.5E−01 | 4.43 | 4.423 | 3.7E−01 | 29.60 |
| NUE571 | 9301.1 | 4.444 | 6.6E−02 | 20.84 | 5.020 | 1.1E−01 | 47.11 |
| Control | | 3.678 | | | 3.413 | | |
| NUE573 | 9491.1 | 3.948 | 7.6E−02 | 15.26 | 3.887 | 4.8E−02 | 37.01 |
| Control | | 3.425 | | | 2.837 | | |
| NUE574 | 10363.4 | 4.080 | 5.6E−02 | 13.90 | 4.326 | 2.0E−01 | 28.12 |
| NUE574 | 10366.1 | 4.893 | 3.3E−02 | 36.58 | 5.262 | 4.3E−02 | 55.84 |
| Control | | 3.582 | | | 3.377 | | |
| NUE576 | 9792.4 | 4.284 | 1.5E−01 | 12.82 | 4.322 | 2.3E−02 | 40.63 |
| Control | | 3.797 | | | 3.074 | | |
| NUE579 | 9701.3 | 3.965 | 9.9E−02 | 26.03 | 3.899 | 4.7E−02 | 60.90 |
| NUE579 | 9703.3 | 3.542 | 1.0E−01 | 12.60 | 2.797 | 4.7E−01 | 15.43 |
| Control | | 3.146 | | | 2.423 | | |
| NUE580 | 9553.2 | 4.418 | 4.7E−03 | 28.99 | 3.784 | 7.3E−02 | 33.40 |
| NUE580 | 9551.4 | 4.239 | 5.1E−02 | 23.75 | 4.282 | 1.5E−01 | 50.96 |
| NUE580 | 9554.4 | 4.158 | 8.9E−02 | 21.41 | 3.902 | 7.1E−02 | 37.54 |
| Control | | 3.425 | | | 2.837 | | |
| NUE582 | 9562.4 | 4.115 | 5.1E−01 | 3.38 | 4.951 | 7.6E−02 | 27.06 |
| Control | | 3.981 | | | 3.896 | | |
| NUE583 | 9673.4 | 4.319 | 2.2E−03 | 20.56 | 5.635 | 4.1E−03 | 66.89 |
| NUE583 | 9673.2 | 3.739 | 5.9E−01 | 4.36 | 4.595 | 1.5E−01 | 36.10 |
| Control | | 3.582 | | | 3.377 | | |
| NUE586 | 9752.1 | 6.394 | 2.6E−05 | 49.10 | 7.681 | 6.9E−05 | 79.81 |
| Control | | 4.289 | | | 4.272 | | |
| NUE586 | 9751.1 | 3.847 | 9.6E−02 | 22.28 | 3.171 | 2.3E−01 | 30.87 |
| NUE586 | 9751.7 | 4.956 | 9.5E−03 | 57.53 | 4.510 | 8.1E−02 | 86.12 |
| NUE586 | 9752.2 | 4.538 | 2.3E−04 | 44.25 | 3.478 | 1.6E−03 | 43.54 |
| NUE586 | 9751.3 | 4.047 | 2.8E−01 | 28.62 | 3.090 | 3.3E−01 | 27.54 |
| NUE586 | 9752.1 | 4.629 | 3.9E−02 | 47.13 | 4.232 | 1.4E−01 | 74.66 |
| Control | | 3.146 | | | 2.423 | | |
| NUE587 | 9643.2 | 3.473 | 3.4E−01 | 10.38 | 3.653 | 4.2E−02 | 50.77 |
| Control | | 3.146 | | | 2.423 | | |
| NUE593 | 10394.2 | 4.033 | 4.5E−02 | 21.96 | 3.941 | 3.7E−02 | 29.39 |
| NUE593 | 10393.2 | 3.719 | 6.3E−02 | 12.48 | 3.544 | 1.8E−01 | 16.38 |
| Control | | 3.306 | | | 3.046 | | |

Table 31: Analyses of root performance (root length and coverage) of transgenic plants overexpressing the exogenous polynucleotides of some embodiments of the invention (using the cloned or synthetic genes listed in Table 23 above) under the regulation of a constitutive promoter (35S) when grown under standard nitrogen conditions [normal or regular growth conditions (15 mM N)] as compared to control plants.
"Incr." = increment; "RGR" = relative growth rate.

The genes presented in Table 32, hereinbelow, have improved plant growth rate when grown under standard nitrogen growth conditions, compared to control plants. Faster growth was observed when growth rate of leaf area and root length and coverage was measured.

Table 32 depicts analyses of leaf area, root length and root coverage growth rate when grown under standard nitrogen conditions [normal or regular growth conditions (15 mM N)] in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 32

Transgenic plants exogenously expressing the polynucleotides of some embodiments
of the invention exhibit improved growth rate under standard nitrogen conditions

| Gene Name | Event # | RGR Of Leaf Area | | | RGR Of Roots Coverage | | | RGR Of Roots Length | | |
|---|---|---|---|---|---|---|---|---|---|---|
| | | Ave. | p-value | % incr. | Ave. | p-value | % incr. | Ave. | p-value | % incr. |
| CT11 | 4892.2 | 0.093 | 2.4E−04 | 76.02 | 0.584 | 7.8E−02 | 28.88 | 0.428 | 1.0E−01 | 17.45 |
| CT11 | 4892.3 | 0.082 | 1.3E−03 | 55.84 | 0.524 | 3.6E−01 | 15.68 | 0.397 | 4.0E−01 | 8.75 |
| CT11 | 4892.1 | 0.085 | 6.5E−03 | 61.71 | 0.490 | 6.8E−01 | 8.24 | 0.385 | 6.7E−01 | 5.43 |
| Control | | 0.053 | | | 0.453 | | | 0.365 | | |
| CT11 | 4894.2 | 0.049 | 2.0E−02 | 30.32 | | | | | | |
| CT11 | 4893.2 | 0.078 | 3.6E−05 | 107.01 | 0.550 | 3.4E−02 | 52.79 | 0.395 | 2.0E−01 | 21.56 |

TABLE 32-continued

Transgenic plants exogenously expressing the polynucleotides of some embodiments of the invention exhibit improved growth rate under standard nitrogen conditions

| Gene Name | Event # | RGR Of Leaf Area Ave. | p-value | % incr. | RGR Of Roots Coverage Ave. | p-value | % incr. | RGR Of Roots Length Ave. | p-value | % incr. |
|---|---|---|---|---|---|---|---|---|---|---|
| Control |  | 0.037 |  |  | 0.360 |  |  | 0.325 |  |  |
| CT27 | 5033.6 | 0.040 | 1.6E−01 | 22.17 | 0.347 | 4.1E−02 | 40.85 | 0.325 | 1.9E−02 | 36.08 |
| CT27 | 5033.4 | 0.047 | 3.2E−02 | 40.54 | 0.287 | 3.5E−01 | 16.49 | 0.296 | 5.9E−02 | 24.30 |
| CT27 | 5033.8 | 0.063 | 5.9E−05 | 90.98 | 0.357 | 1.0E−01 | 44.71 | 0.251 | 7.5E−01 | 5.19 |
| CT27 | 5033.5 | 0.049 | 3.7E−03 | 48.72 |  |  |  | 0.248 | 7.8E−01 | 3.85 |
| Control |  | 0.033 |  |  | 0.247 |  |  | 0.238 |  |  |
| CT27 | 5033.7 | 0.049 | 1.8E−02 | 31.77 |  |  |  |  |  |  |
| CT27 | 5035.2 | 0.079 | 8.4E−07 | 111.02 | 0.402 | 5.8E−01 | 11.56 | 0.343 | 7.1E−01 | 5.73 |
| CT27 | 5031.4 | 0.053 | 1.5E−03 | 41.85 |  |  |  |  |  |  |
| CT27 | 5033.6 | 0.058 | 4.6E−04 | 53.91 | 0.513 | 3.1E−02 | 42.39 | 0.357 | 5.4E−01 | 10.03 |
| CT27 | 5033.4 | 0.060 | 2.2E−05 | 59.59 | 0.547 | 3.2E−02 | 51.81 | 0.416 | 9.9E−02 | 28.01 |
| CT27 | 5033.8 | 0.055 | 3.8E−04 | 47.37 |  |  |  |  |  |  |
| CT27 | 5033.5 | 0.047 | 4.0E−02 | 25.25 |  |  |  |  |  |  |
| Control |  | 0.037 |  |  | 0.360 |  |  | 0.325 |  |  |
| CT6 | 4943.1 | 0.048 | 6.3E−02 | 27.13 | 0.378 | 8.1E−01 | 4.79 |  |  |  |
| Control |  | 0.037 |  |  | 0.360 |  |  | 0.325 |  |  |
| CT75 | 4872.5 | 0.055 | 2.1E−03 | 47.90 |  |  |  |  |  |  |
| CT75 | 4874.4 | 0.053 | 3.2E−03 | 42.55 |  |  |  |  |  |  |
| CT75 | 4874.7 | 0.054 | 6.7E−03 | 44.21 | 0.368 | 9.2E−01 | 2.17 |  |  |  |
| CT75 | 4873.3 | 0.052 | 1.3E−02 | 39.84 | 0.518 | 4.3E−02 | 43.91 | 0.415 | 1.1E−01 | 27.69 |
| Control |  | 0.037 |  |  | 0.360 |  |  | 0.325 |  |  |
| CT76 | 5044.6 | 0.072 | 2.6E−02 | 36.36 |  |  |  |  |  |  |
| CT76 | 5041.5 | 0.068 |  | 29.56 | 0.685 | 2.8E−02 | 51.34 | 0.403 | 4.7E−01 | 10.41 |
| CT76 | 5041.7 | 0.058 |  | 9.50 |  |  |  |  |  |  |
| CT76 | 5043.5 | 0.114 | 1.4E−07 | 115.19 | 0.961 | 9.5E−06 | 112.17 | 0.506 | 2.2E−03 | 38.75 |
| CT76 | 5041.6 | 0.082 | 7.3E−03 | 55.95 | 0.626 | 9.8E−02 | 38.15 | 0.448 | 5.4E−02 | 22.83 |
| CT76 | 5041.9 | 0.079 | 3.8E−03 | 49.27 | 0.571 | 9.6E−02 | 25.96 | 0.378 | 7.0E−01 | 3.74 |
| Control |  | 0.053 |  |  | 0.453 |  |  | 0.365 |  |  |
| CT76 | 5044.6 | 0.064 | 2.7E−05 | 92.67 | 0.283 | 4.2E−01 | 14.80 | 0.292 | 1.2E−01 | 22.42 |
| CT76 | 5041.5 | 0.094 | 9.7E−12 | 182.48 | 0.635 | 9.1E−08 | 157.51 | 0.384 | 2.8E−05 | 61.08 |
| CT76 | 5041.7 | 0.042 | 3.4E−02 | 25.46 |  |  |  |  |  |  |
| CT76 | 5043.5 | 0.091 | 1.1E−11 | 174.29 | 0.394 | 2.7E−03 | 59.72 | 0.300 | 4.2E−02 | 25.74 |
| CT76 | 5041.6 | 0.052 | 7.3E−05 | 55.70 | 0.287 | 3.9E−01 | 16.43 | 0.271 | 3.6E−01 | 13.45 |
| CT76 | 5041.9 | 0.066 | 4.5E−07 | 100.31 | 0.408 | 1.2E−03 | 65.59 | 0.317 | 9.7E−03 | 33.04 |
| Control |  | 0.033 |  |  | 0.247 |  |  | 0.238 |  |  |
| NUE206 | 6731.2 |  |  |  | 0.396 | 1.6E−03 | 78.33 | 0.369 | 8.5E−03 | 44.35 |
| NUE206 | 6732.1 |  |  |  | 0.297 | 1.5E−01 | 33.53 | 0.333 | 4.9E−02 | 30.52 |
| Control |  | 0.036 |  |  | 0.222 |  |  | 0.256 |  |  |
| NUE206 | 6731.2 | 0.063 | 6.3E−01 | 7.32 | 0.650 | 3.1E−05 | 125.39 | 0.435 | 4.9E−05 | 65.80 |
| NUE206 | 6732.5 | 0.074 | 9.5E−02 | 26.57 | 0.579 | 4.4E−06 | 100.85 | 0.389 | 8.9E−05 | 48.32 |
| NUE206 | 6732.2 | 0.059 | 9.2E−01 | 1.58 | 0.464 | 1.9E−03 | 60.76 | 0.365 | 4.6E−03 | 39.21 |
| Control |  | 0.058 |  |  | 0.288 |  |  | 0.262 |  |  |
| NUE208 | 8351.3 | 0.033 |  |  | 0.389 | 1.4E−03 | 74.92 | 0.397 | 1.9E−04 | 55.33 |
| Control |  | 0.036 |  |  | 0.222 |  |  | 0.256 |  |  |
| NUE208 | 8354.8 | 0.041 |  | 24.69 | 0.422 | 3.7E−02 | 51.73 | 0.393 | 8.2E−02 | 35.05 |
| NUE208 | 8355.3 | 0.037 |  | 13.69 | 0.418 | 3.5E−02 | 50.07 | 0.331 | 4.7E−01 | 13.65 |
| Control |  | 0.033 |  |  | 0.278 |  |  | 0.291 |  |  |
| NUE208 | 8354.8 | 0.076 | 9.1E−02 | 30.54 |  |  |  |  |  |  |
| NUE208 | 8354.5 | 0.073 | 1.8E−01 | 24.95 | 0.305 | 7.4E−01 | 5.73 | 0.276 | 6.4E−01 | 5.23 |
| NUE208 | 8355.3 | 0.079 | 5.8E−02 | 34.69 | 0.460 | 7.5E−03 | 59.54 | 0.362 | 3.1E−03 | 37.83 |
| NUE208 | 8351.5 | 0.059 | 9.0E−01 | 1.94 | 0.312 | 6.2E−01 | 8.27 | 0.315 | 9.1E−02 | 19.92 |
| Control |  | 0.058 |  |  | 0.288 |  |  | 0.262 |  |  |
| NUE209 | 8192.1 | 0.045 | 1.4E−01 | 36.98 | 0.450 | 1.9E−02 | 61.65 | 0.368 | 1.4E−01 | 26.60 |
| NUE209 | 8191.5 | 0.044 | 7.8E−02 | 34.71 | 0.295 | 7.7E−01 | 6.00 |  |  |  |
| Control |  | 0.033 |  |  | 0.278 |  |  | 0.291 |  |  |
| NUE209 | 8191.2 | 0.041 | 4.5E−02 | 31.45 | 0.330 | 4.3E−01 | 12.88 | 0.335 | 4.4E−01 | 12.06 |
| NUE209 | 8192.1 | 0.035 | 3.6E−01 | 14.35 |  |  |  |  |  |  |
| NUE209 | 8192.1 | 0.044 | 2.3E−02 | 40.98 |  |  |  |  |  |  |
| NUE209 | 8191.5 | 0.040 | 5.9E−02 | 30.43 |  |  |  |  |  |  |
| NUE209 | 8192.1 | 0.034 | 5.7E−01 | 9.26 |  |  |  |  |  |  |
| Control |  | 0.031 |  |  | 0.292 |  |  | 0.299 |  |  |
| NUE209 | 8192.1 |  |  |  | 0.345 |  | 19.74 | 0.365 | 1.4E−03 | 39.07 |
| NUE209 | 8192.1 |  |  |  | 0.487 | 9.6E−03 | 68.94 | 0.377 | 2.5E−02 | 43.59 |
| NUE209 | 8191.3 | 0.083 | 4.7E−02 | 41.92 |  |  |  |  |  |  |
| Control |  | 0.058 |  |  | 0.288 |  |  | 0.262 |  |  |
| NUE210 | 8202.1 | 0.049 | 3.9E−02 | 48.76 |  |  |  |  |  |  |
| NUE210 | 8201.3 | 0.049 | 9.7E−03 | 50.64 |  |  |  |  |  |  |
| Control |  | 0.033 |  |  | 0.278 |  |  | 0.291 |  |  |
| NUE210 | 8202.1 | 0.042 | 3.6E−02 | 34.98 | 0.403 | 4.8E−02 | 37.90 | 0.345 | 3.7E−01 | 15.40 |
| NUE210 | 6755.3 | 0.048 | 4.6E−03 | 55.18 | 0.423 | 1.9E−02 | 44.72 | 0.441 | 1.1E−02 | 47.78 |
| Control |  | 0.031 |  |  | 0.292 |  |  | 0.299 |  |  |
| NUE211 | 8263.5 | 0.038 | 7.6E−05 | 89.32 | 0.191 | 8.9E−02 | 58.43 | 0.215 | 5.7E−02 | 53.44 |

TABLE 32-continued

Transgenic plants exogenously expressing the polynucleotides of some embodiments of the invention exhibit improved growth rate under standard nitrogen conditions

| Gene Name | Event # | RGR Of Leaf Area | | | RGR Of Roots Coverage | | | RGR Of Roots Length | | |
|---|---|---|---|---|---|---|---|---|---|---|
| | | Ave. | p-value | % incr. | Ave. | p-value | % incr. | Ave. | p-value | % incr. |
| Control | | 0.020 | | | 0.121 | | | 0.140 | | |
| NUE212 | 8335.1 | 0.036 | 2.7E−03 | 82.84 | 0.216 | 5.8E−02 | 79.29 | 0.235 | 4.4E−02 | 68.20 |
| NUE212 | 8334.1 | 0.029 | 6.2E−03 | 46.65 | 0.131 | 7.9E−01 | 8.85 | 0.159 | 6.3E−01 | 13.62 |
| NUE212 | 8331.4 | 0.026 | 9.1E−02 | 31.28 | | | | 0.153 | 7.1E−01 | 9.70 |
| Control | | 0.020 | | | 0.121 | | | 0.140 | | |
| NUE212 | 8335.2 | 0.049 | 1.5E−02 | 48.76 | 0.314 | 5.6E−01 | 12.68 | | | |
| Control | | 0.033 | | | 0.278 | | | 0.291 | | |
| NUE212 | 8332.2 | 0.046 | 8.1E−01 | 3.53 | 0.656 | 4.5E−02 | 27.59 | 0.507 | 1.2E−01 | 19.17 |
| Control | | 0.044 | | | 0.514 | | | 0.426 | | |
| NUE212 | 8332.1 | 0.039 | 5.5E−02 | 26.08 | | | | | | |
| NUE212 | 8334.1 | 0.044 | 5.7E−03 | 41.96 | 0.316 | 6.2E−01 | 8.13 | 0.361 | 2.1E−01 | 20.73 |
| NUE212 | 8331.4 | 0.041 | 3.2E−02 | 31.53 | | | | 0.307 | 8.8E−01 | 2.62 |
| Control | | 0.031 | | | 0.292 | | | 0.299 | | |
| NUE222 | 8851.3 | 0.046 | 6.7E−02 | 41.29 | 0.365 | 2.2E−01 | 31.13 | 0.291 | 1.0E+00 | −0.102 |
| Control | | 0.033 | | | 0.278 | | | 0.291 | | |
| NUE223 | 9613.1 | | | | 0.659 | 3.7E−02 | 36.07 | 0.449 | 9.4E−02 | 19.43 |
| Control | | 0.068 | | | 0.484 | | | 0.376 | | |
| NUE224 | 9002.2 | 0.052 | 5.5E−02 | 23.49 | | | | | | |
| NUE224 | 9001.3 | 0.055 | 2.7E−02 | 30.04 | | | | | | |
| Control | | 0.042 | | | 0.445 | | | 0.370 | | |
| NUE224 | 9001.3 | 0.046 | 3.2E−02 | 28.75 | | | | | | |
| Control | | 0.036 | | | 0.279 | | | 0.316 | | |
| NUE227 | 9851.2 | 0.058 | 2.8E−02 | 35.17 | | | | | | |
| NUE227 | 9853.1 | 0.064 | 3.6E−03 | 49.89 | | | | | | |
| Control | | 0.043 | | | 0.349 | | | 0.360 | | |
| NUE228 | 10093 | 0.078 | 2.9E−02 | 39.70 | 0.355 | | 3.25 | 0.328 | | 16.65 |
| NUE228 | 10093 | 0.067 | 2.1E−01 | 20.98 | | | | 0.301 | | 7.24 |
| Control | | 0.056 | | | 0.344 | | | 0.281 | | |
| NUE229 | 8864.2 | 0.045 | 3.9E−02 | 26.44 | | | | | | |
| Control | | 0.036 | | | 0.279 | | | 0.316 | | |
| NUE230 | 9154.2 | 0.057 | 2.1E−02 | 35.25 | 0.461 | | 3.61 | | | |
| NUE230 | 9151.2 | 0.055 | 1.7E−02 | 29.70 | | | | | | |
| Control | | 0.042 | | | 0.445 | | | 0.370 | | |
| NUE230 | 9152.4 | 0.047 | 1.7E−01 | 29.87 | 0.378 | 7.6E−02 | 35.74 | 0.328 | 7.2E−01 | 3.71 |
| Control | | 0.036 | | | 0.279 | | | 0.316 | | |
| NUE233 | 10174 | 0.051 | 4.1E−06 | 93.04 | 0.340 | 1.4E−02 | 54.67 | 0.311 | 1.7E−01 | 31.25 |
| NUE233 | 10174 | 0.069 | 5.1E−11 | 160.30 | 0.624 | 8.1E−09 | 183.57 | 0.399 | 7.2E−03 | 68.42 |
| NUE233 | 10174 | 0.030 | 3.6E−01 | 13.97 | 0.314 | 4.1E−02 | 42.81 | 0.344 | 5.6E−02 | 45.20 |
| NUE233 | 10173 | 0.032 | 1.9E−01 | 19.26 | 0.342 | 9.3E−03 | 55.25 | 0.324 | 1.1E−01 | 36.68 |
| NUE233 | 10174 | 0.039 | 1.1E−02 | 45.92 | 0.299 | 1.2E−01 | 35.80 | 0.262 | 6.4E−01 | 10.75 |
| Control | | 0.026 | | | 0.220 | | | 0.237 | | |
| NUE233 | 10174 | 0.053 | 7.8E−01 | 4.51 | 0.451 | 3.0E−01 | 17.53 | 0.381 | 5.1E−02 | 32.89 |
| NUE233 | 10174 | | | | 0.538 | 2.8E−02 | 40.15 | 0.407 | 1.2E−02 | 41.78 |
| Control | | 0.051 | | | 0.384 | | | 0.287 | | |
| NUE234 | 9163.5 | 0.044 | 9.7E−02 | 22.24 | | | | | | |
| NUE234 | 9162.1 | 0.048 | 2.8E−02 | 32.38 | 0.381 | 7.4E−02 | 36.73 | 0.330 | 7.6E−01 | 4.39 |
| Control | | 0.036 | | | 0.279 | | | 0.316 | | |
| NUE235 | 9694.2 | 0.054 | 3.7E−02 | 27.26 | 0.475 | 6.0E−01 | 6.64 | | | |
| NUE235 | 9691.1 | 0.055 | 6.9E−02 | 31.10 | 0.454 | 8.9E−01 | 1.90 | 0.382 | 7.4E−01 | 3.28 |
| NUE235 | 9693.3 | 0.054 | 5.5E−02 | 28.28 | | | | | | |
| NUE235 | 9694.3 | 0.062 | 1.0E−03 | 46.88 | 0.583 | 1.9E−02 | 30.90 | 0.470 | 1.2E−02 | 27.17 |
| Control | | 0.042 | | | 0.445 | | | 0.370 | | |
| NUE237 | 9651.1 | 0.073 | 7.6E−06 | 74.28 | 0.508 | 2.1E−01 | 14.12 | | | |
| NUE237 | 9654.4 | 0.057 | 5.2E−03 | 36.61 | 0.553 | 2.5E−02 | 24.26 | 0.384 | 7.1E−01 | 3.83 |
| NUE237 | 9654.1 | 0.065 | 8.0E−03 | 53.61 | 0.680 | 5.8E−03 | 52.84 | 0.445 | 9.4E−02 | 20.30 |
| Control | | 0.042 | | | 0.445 | | | 0.370 | | |
| NUE237 | 9651.1 | 0.047 | 4.6E−02 | 31.99 | 0.331 | 9.7E−01 | 0.99 | | | |
| NUE237 | 9654.1 | 0.056 | 6.7E−03 | 58.85 | 0.493 | 9.9E−02 | 50.53 | 0.363 | 5.2E−01 | 13.15 |
| Control | | 0.036 | | | 0.327 | | | 0.321 | | |
| NUE241 | 9631.3 | 0.066 | 4.8E−04 | 52.60 | 0.452 | 5.0E−02 | 29.57 | 0.395 | 3.6E−01 | 9.92 |
| NUE241 | 9632.5 | 0.066 | 9.6E−03 | 52.36 | 0.733 | 8.9E−08 | 110.05 | 0.490 | 2.0E−03 | 36.33 |
| NUE241 | 9632.3 | 0.060 | 4.8E−02 | 39.27 | 0.494 | 5.1E−02 | 41.65 | 0.377 | 7.3E−01 | 4.72 |
| NUE241 | 9632.4 | 0.060 | 5.7E−03 | 38.59 | 0.428 | 1.8E−01 | 22.84 | | | |
| Control | | 0.043 | | | 0.349 | | | 0.360 | | |
| NUE242 | 9214.1 | 0.074 | 7.4E−02 | 25.97 | 0.460 | 8.2E−01 | 4.07 | 0.380 | 3.8E−01 | 13.95 |
| NUE242 | 9213.4 | 0.068 | 2.6E−01 | 16.65 | 0.588 | 8.2E−02 | 32.97 | 0.428 | 7.7E−02 | 28.57 |
| Control | | 0.059 | | | 0.442 | | | 0.333 | | |
| NUE242 | 9212.1 | 0.050 | 4.6E−02 | 43.13 | 0.374 | 8.2E−01 | 2.93 | | | |
| NUE242 | 9214.1 | 0.052 | 4.5E−02 | 47.68 | | | | | | |
| NUE242 | 9213.4 | 0.050 | 3.3E−02 | 41.82 | 0.504 | 1.6E−02 | 38.74 | 0.409 | 1.8E−01 | 20.10 |
| Control | | 0.035 | | | 0.363 | | | 0.341 | | |
| NUE244 | 9061.5 | 0.049 | 2.2E−03 | 35.40 | 0.347 | 1.9E−01 | 24.39 | 0.324 | 8.4E−01 | 2.40 |

TABLE 32-continued

Transgenic plants exogenously expressing the polynucleotides of some embodiments of the invention exhibit improved growth rate under standard nitrogen conditions

| Gene | | RGR Of Leaf Area | | | RGR Of Roots Coverage | | | RGR Of Roots Length | | |
|---|---|---|---|---|---|---|---|---|---|---|
| Name | Event # | Ave. | p-value | % incr. | Ave. | p-value | % incr. | Ave. | p-value | % incr. |
| Control | | 0.036 | | | 0.279 | | | 0.316 | | |
| NUE245 | 10642 | 0.080 | 7.9E−02 | 33.89 | 0.622 | 2.6E−02 | 60.99 | 0.397 | 2.9E−02 | 26.31 |
| Control | | 0.060 | | | 0.387 | | | 0.315 | | |
| NUE246 | 9033.8 | | | | 0.462 | 7.1E−02 | 30.62 | 0.400 | 2.0E−01 | 18.15 |
| Control | | 0.049 | | | 0.354 | | | 0.339 | | |
| NUE246 | 9033.6 | 0.053 | 5.9E−01 | 8.27 | | | | | | |
| NUE246 | 9033.4 | 0.053 | 5.4E−01 | 8.70 | 0.546 | 1.5E−01 | 30.07 | 0.410 | 2.1E−01 | 14.19 |
| NUE246 | 9033.8 | 0.075 | 3.8E−03 | 52.67 | 0.658 | 9.3E−03 | 56.72 | 0.436 | 4.3E−02 | 21.22 |
| NUE246 | 9034.1 | 0.060 | 1.3E−01 | 22.21 | | | | | | |
| NUE246 | 9031.1 | 0.057 | 2.3E−01 | 16.59 | 0.505 | 2.9E−01 | 20.28 | 0.424 | 6.6E−02 | 17.89 |
| Control | | 0.049 | | | 0.420 | | | 0.359 | | |
| NUE248 | 8981.5 | 0.085 | 3.9E−03 | 63.02 | 0.638 | 5.3E−01 | 11.57 | | | |
| Control | | 0.052 | | | 0.572 | | | 0.423 | | |
| NUE250 | 9132.1 | 0.078 | 1.3E−03 | 86.50 | 0.604 | 7.4E−02 | 35.67 | 0.386 | | 4.46 |
| NUE250 | 9132.2 | 0.054 | 4.2E−02 | 28.86 | | | | | | |
| NUE250 | 9134.1 | 0.051 | 1.3E−01 | 21.34 | | | | | | |
| Control | | 0.042 | | | 0.445 | | | 0.370 | | |
| NUE250 | 9134.1 | 0.043 | 6.6E−02 | 19.98 | 0.329 | 3.0E−01 | 17.87 | | | |
| Control | | 0.036 | | | 0.279 | | | 0.316 | | |
| NUE251 | 10181 | 0.059 | 5.5E−06 | 122.34 | 0.396 | 9.1E−04 | 80.08 | 0.349 | 5.2E−02 | 47.21 |
| NUE251 | 10183 | 0.048 | 2.3E−04 | 80.31 | 0.369 | 5.8E−03 | 67.70 | 0.343 | 5.7E−02 | 44.89 |
| NUE251 | 10183 | 0.042 | 2.5E−03 | 58.23 | 0.366 | 9.1E−03 | 66.32 | 0.377 | 1.9E−02 | 59.19 |
| NUE251 | 10181 | 0.039 | 5.8E−03 | 48.78 | 0.249 | 5.2E−01 | 13.16 | 0.240 | 9.5E−01 | 1.48 |
| Control | | 0.026 | | | 0.220 | | | 0.237 | | |
| NUE251 | 10181 | 0.063 | 1.5E−01 | 23.79 | 0.582 | 8.9E−03 | 51.43 | 0.381 | 3.8E−02 | 32.80 |
| Control | | 0.051 | | | 0.384 | | | 0.287 | | |
| NUE251 | 10183 | 0.072 | 9.1E−02 | 19.27 | | | | 0.324 | 6.6E−01 | 3.02 |
| Control | | 0.060 | | | 0.387 | | | 0.315 | | |
| NUE256 | 10063 | 0.050 | 7.6E−06 | 89.88 | 0.520 | 1.9E−05 | 136.35 | 0.410 | 6.7E−03 | 72.97 |
| NUE256 | 10064 | 0.076 | 2.0E−11 | 188.66 | 0.442 | 5.9E−05 | 100.99 | 0.356 | 3.4E−02 | 50.21 |
| NUE256 | 10061 | 0.056 | 5.0E−08 | 110.73 | 0.450 | 1.2E−05 | 104.36 | 0.330 | 8.2E−02 | 39.37 |
| NUE256 | 10062 | 0.054 | 2.3E−06 | 103.99 | 0.327 | 7.9E−02 | 48.64 | 0.272 | 5.3E−01 | 14.99 |
| NUE256 | 10063 | 0.051 | 9.1E−06 | 93.42 | 0.424 | 2.3E−03 | 92.64 | 0.335 | 1.0E−01 | 41.59 |
| Control | | 0.026 | | | 0.220 | | | 0.237 | | |
| NUE268 | 8996.5 | 0.072 | 7.2E−03 | 43.95 | | | | 0.388 | 7.2E−01 | 3.95 |
| Control | | 0.050 | | | 0.463 | | | 0.374 | | |
| NUE512 | 9284.2 | 0.052 | 3.6E−03 | 48.09 | 0.369 | 3.4E−01 | 18.49 | 0.372 | 9.7E−02 | 22.41 |
| NUE512 | 9282.3 | 0.073 | 4.5E−09 | 108.17 | 0.514 | 2.9E−03 | 64.80 | 0.403 | 2.2E−02 | 32.41 |
| NUE512 | 9284.4 | 0.041 | 1.5E−01 | 18.26 | 0.450 | 2.2E−02 | 44.50 | 0.390 | 5.3E−02 | 28.25 |
| Control | | 0.035 | | | 0.312 | | | 0.304 | | |
| NUE513 | 9683.5 | | | | | | | 0.511 | 5.7E−02 | 20.91 |
| Control | | 0.052 | | | 0.572 | | | 0.423 | | |
| NUE513 | 9683.5 | | | | 0.521 | | 24.10 | 0.512 | 1.8E−05 | 42.60 |
| Control | | 0.049 | | | 0.420 | | | 0.359 | | |
| NUE514 | 9404.1 | 0.082 | 7.9E−07 | 133.82 | 0.426 | 2.2E−01 | 17.18 | 0.377 | 4.6E−01 | 10.68 |
| NUE514 | 9402.2 | 0.044 | 1.7E−01 | 26.64 | 0.389 | 6.0E−01 | 7.20 | 0.356 | 7.5E−01 | 4.44 |
| NUE514 | 9403.2 | 0.046 | 1.3E−01 | 31.04 | 0.776 | 1.9E−07 | 113.56 | 0.565 | 8.5E−05 | 65.81 |
| Control | | 0.035 | | | 0.363 | | | 0.341 | | |
| NUE516 | 9291.1 | 0.054 | 4.3E−02 | 28.22 | 0.577 | 4.3E−02 | 29.59 | 0.407 | 3.9E−01 | 10.04 |
| NUE516 | 9291.4 | 0.064 | 8.4E−05 | 52.81 | 0.531 | 7.4E−02 | 19.37 | 0.392 | 5.9E−01 | 6.00 |
| Control | | 0.042 | | | 0.445 | | | 0.370 | | |
| NUE520 | 9771.4 | 0.049 | 5.8E−05 | 87.02 | 0.408 | 2.7E−03 | 85.53 | 0.370 | 1.7E−02 | 56.27 |
| NUE520 | 9771.7 | 0.050 | 6.3E−05 | 88.34 | 0.404 | 5.1E−03 | 83.74 | 0.372 | 2.1E−02 | 57.16 |
| NUE520 | 9771.2 | 0.042 | 8.9E−04 | 59.66 | 0.491 | 4.1E−05 | 122.92 | 0.330 | 1.1E−01 | 39.23 |
| NUE520 | 9772.1 | | | | 0.462 | 5.2E−04 | 109.90 | 0.301 | 2.6E−01 | 27.23 |
| NUE520 | 9771.3 | 0.035 | 3.8E−02 | 32.37 | 0.454 | 1.3E−04 | 106.42 | 0.346 | 5.1E−02 | 46.13 |
| NUE520 | 9773.1 | 0.023 | 4.8E−01 | −14.07 | 0.369 | 7.7E−02 | 67.68 | 0.329 | 2.3E−01 | 38.86 |
| Control | | 0.026 | | | 0.220 | | | 0.237 | | |
| NUE520 | 9771.4 | | | | 0.360 | 7.9E−01 | 4.93 | 0.352 | 6.6E−02 | 25.41 |
| NUE520 | 9771.7 | | | | 0.434 | 1.9E−01 | 26.37 | 0.377 | 2.5E−02 | 34.19 |
| Control | | 0.056 | | | 0.344 | | | 0.281 | | |
| NUE521 | 9362.2 | 0.051 | 4.7E−02 | 29.12 | 0.430 | 6.6E−01 | 9.02 | 0.375 | 6.4E−01 | 6.57 |
| NUE521 | 9363.4 | 0.073 | 5.8E−05 | 84.97 | 0.407 | 8.4E−01 | 3.33 | 0.349 | 9.6E−01 | −0.67 |
| Control | | 0.040 | | | 0.394 | | | 0.351 | | |
| NUE521 | 9361.2 | 0.051 | 3.9E−02 | 44.60 | 0.370 | 8.9E−01 | 1.86 | 0.349 | 8.6E−01 | 2.50 |
| NUE521 | 9363.4 | 0.059 | 3.0E−03 | 69.25 | 0.313 | 3.7E−01 | | | | |
| Control | | 0.035 | | | 0.363 | | | 0.341 | | |
| NUE523 | 9412.1 | 0.070 | 2.7E−02 | 35.53 | | | | | | |
| Control | | 0.052 | | | 0.572 | | | 0.423 | | |
| NUE523 | 9413.3 | 0.059 | 3.1E−02 | 49.30 | 0.466 | 4.2E−01 | 18.10 | 0.406 | 3.4E−01 | 15.59 |
| NUE523 | 9414.2 | 0.052 | 1.4E−01 | 30.19 | 0.516 | 8.7E−02 | 30.82 | 0.471 | 3.2E−02 | 34.02 |

TABLE 32-continued

Transgenic plants exogenously expressing the polynucleotides of some embodiments
of the invention exhibit improved growth rate under standard nitrogen conditions

| Gene | | RGR Of Leaf Area | | | RGR Of Roots Coverage | | | RGR Of Roots Length | | |
|---|---|---|---|---|---|---|---|---|---|---|
| Name | Event # | Ave. | p-value | % incr. | Ave. | p-value | % incr. | Ave. | p-value | % incr. |
| Control | | 0.040 | | | 0.394 | | | 0.351 | | |
| NUE523 | 9412.5 | 0.053 | 1.6E−02 | 51.59 | 0.522 | 3.6E−03 | 43.78 | 0.392 | 2.8E−01 | 15.04 |
| NUE523 | 9414.2 | 0.046 | 8.0E−02 | 32.35 | 0.523 | 4.2E−03 | 43.92 | 0.394 | 2.6E−01 | 15.82 |
| Control | | 0.035 | | | 0.363 | | | 0.341 | | |
| NUE527 | 9202.6 | 0.046 | 1.5E−01 | 22.86 | 0.375 | 2.0E−01 | 25.97 | 0.374 | 2.8E−02 | 46.88 |
| Control | | 0.038 | | | 0.297 | | | 0.254 | | |
| NUE531 | 10083 | 0.078 | 2.7E−02 | 40.47 | | | | 0.305 | 5.6E−01 | 8.47 |
| NUE531 | 10081 | 0.090 | 3.8E−03 | 62.13 | 0.535 | 7.9E−03 | 55.85 | 0.359 | 5.6E−02 | 27.85 |
| NUE531 | 10082 | 0.086 | 1.2E−02 | 55.40 | 0.554 | 1.3E−02 | 61.37 | 0.398 | 1.2E−02 | 41.80 |
| Control | | 0.056 | | | 0.344 | | | 0.281 | | |
| NUE531 | 10081 | 0.080 | 2.5E−02 | 32.77 | 0.578 | | 49.54 | 0.386 | | 22.62 |
| NUE531 | 10082 | 0.078 | 2.4E−02 | 30.60 | 0.581 | 1.5E−02 | 50.29 | 0.410 | 7.9E−04 | 30.44 |
| Control | | 0.060 | | | 0.387 | | | 0.315 | | |
| NUE535 | 9084.2 | 0.043 | 1.2E−03 | 62.38 | 0.345 | 2.6E−02 | 56.73 | 0.277 | 4.6E−01 | 17.08 |
| NUE535 | 9083.1 | 0.082 | 3.3E−09 | 211.11 | 0.388 | 5.6E−03 | 76.23 | 0.325 | 1.2E−01 | 37.19 |
| NUE535 | 9084.4 | 0.042 | 4.8E−04 | 59.66 | 0.246 | 5.8E−01 | 11.82 | 0.306 | 2.2E−01 | 29.02 |
| NUE535 | 9082.1 | 0.039 | 2.9E−02 | 46.36 | | | | | | |
| Control | | 0.026 | | | 0.220 | | | 0.237 | | |
| NUE537 | 9391.1 | 0.053 | 4.2E−03 | 51.98 | 0.444 | 6.2E−02 | 42.62 | 0.388 | 5.6E−02 | 27.48 |
| NUE537 | 9394.4 | 0.046 | 3.2E−02 | 31.60 | | | | | | |
| NUE537 | 9391.2 | 0.056 | 2.6E−04 | 60.43 | 0.385 | 2.0E−01 | 23.46 | 0.365 | 1.4E−01 | 19.94 |
| NUE537 | 9393.3 | 0.073 | 8.5E−07 | 109.66 | 0.481 | 1.3E−02 | 54.18 | 0.366 | 1.3E−01 | 20.35 |
| Control | | 0.035 | | | 0.312 | | | 0.304 | | |
| NUE538 | 9782.1 | 0.071 | 1.0E−03 | 64.80 | 0.474 | 2.4E−02 | 36.00 | 0.424 | 1.3E−01 | 17.89 |
| Control | | 0.043 | | | 0.349 | | | 0.360 | | |
| NUE538 | 9781.4 | 0.048 | 3.3E−01 | 15.40 | 0.405 | 5.9E−02 | 41.28 | 0.398 | 2.8E−02 | 31.83 |
| NUE538 | 9783.4 | 0.046 | 5.4E−01 | 9.73 | 0.414 | 9.5E−03 | 44.32 | 0.390 | 2.5E−02 | 29.10 |
| Control | | 0.042 | | | 0.287 | | | 0.302 | | |
| NUE539 | 10102 | 0.049 | 1.1E−03 | 83.56 | 0.307 | 1.3E−01 | 39.36 | 0.311 | 2.0E−01 | 31.26 |
| NUE539 | 10104 | 0.045 | 3.9E−04 | 69.52 | 0.317 | 6.6E−02 | 43.97 | 0.299 | 2.4E−01 | 26.34 |
| NUE539 | 10101 | 0.061 | 3.2E−08 | 129.48 | 0.266 | 3.2E−01 | 20.90 | 0.293 | 3.0E−01 | 23.62 |
| NUE539 | 10102 | 0.061 | 1.1E−06 | 132.28 | 0.410 | 5.3E−04 | 86.11 | 0.375 | 1.5E−02 | 58.30 |
| Control | | 0.026 | | | 0.220 | | | 0.237 | | |
| NUE539 | 10102 | | | | | | | 0.366 | 8.7E−02 | 27.65 |
| NUE539 | 10102 | | | | | | | 0.371 | 1.0E−01 | 29.42 |
| Control | | 0.051 | | | 0.384 | | | 0.287 | | |
| NUE542 | 9333.2 | 0.053 | 2.2E−04 | 50.87 | 0.445 | 3.5E−02 | 42.68 | 0.400 | 1.7E−02 | 31.61 |
| NUE542 | 9331.3 | 0.045 | 6.9E−02 | 27.12 | 0.450 | 6.4E−02 | 44.47 | 0.397 | 8.1E−02 | 30.56 |
| NUE542 | 9332.1 | 0.041 | 2.4E−01 | 16.04 | 0.414 | 8.3E−02 | 32.84 | 0.347 | 2.8E−01 | 14.05 |
| Control | | 0.035 | | | 0.312 | | | 0.304 | | |
| NUE543 | 10052 | 0.060 | 2.7E−02 | 39.61 | 0.505 | 8.0E−03 | 44.88 | 0.420 | 1.4E−01 | 16.75 |
| NUE543 | 10052 | 0.058 | 1.6E−02 | 33.92 | 0.399 | 3.4E−01 | 14.30 | | | |
| Control | | 0.043 | | | 0.349 | | | 0.360 | | |
| NUE543 | 10051 | 0.056 | 9.8E−01 | 0.47 | 0.509 | 2.1E−02 | 48.29 | 0.356 | 7.1E−02 | 26.63 |
| NUE543 | 10051 | 0.077 | 4.3E−02 | 39.35 | 0.452 | 1.5E−01 | 31.70 | 0.385 | 3.3E−02 | 36.96 |
| Control | | 0.056 | | | 0.344 | | | 0.281 | | |
| NUE544 | 9763.3 | 0.060 | 2.7E−02 | 35.77 | 0.602 | 2.4E−01 | 17.04 | | | |
| Control | | 0.044 | | | 0.514 | | | 0.426 | | |
| NUE544 | 9764.1 | 0.047 | 3.4E−01 | 11.45 | 0.367 | 7.3E−02 | 27.87 | 0.350 | 1.9E−01 | 15.92 |
| NUE544 | 9763.3 | 0.046 | 4.0E−01 | 9.93 | 0.358 | 1.0E−01 | 24.63 | 0.378 | 4.9E−02 | 24.94 |
| Control | | 0.042 | | | 0.287 | | | 0.302 | | |
| NUE548 | 9091.3 | 0.058 | 9.7E−01 | −0.55 | 0.489 | 5.6E−01 | 10.49 | 0.423 | 9.0E−02 | 26.90 |
| NUE548 | 9091.1 | 0.076 | 3.2E−02 | 29.54 | 0.578 | 1.1E−01 | 30.72 | 0.419 | 1.0E−01 | 25.87 |
| NUE548 | 9092.2 | 0.063 | 6.6E−01 | 6.64 | 0.686 | 2.4E−02 | 55.14 | 0.486 | 2.4E−02 | 45.86 |
| Control | | 0.059 | | | 0.442 | | | 0.333 | | |
| NUE549 | 9343.7 | 0.055 | 5.8E−03 | 53.63 | 0.362 | 7.2E−01 | 10.47 | | | |
| NUE549 | 9342.3 | 0.045 | 6.6E−02 | 26.67 | 0.330 | 9.7E−01 | 0.73 | 0.370 | 3.2E−01 | 15.10 |
| Control | | 0.036 | | | 0.327 | | | 0.321 | | |
| NUE550 | 9143.1 | 0.061 | 6.0E−02 | 36.03 | | | | 0.368 | | |
| Control | | 0.045 | | | 0.416 | | | | | |
| NUE550 | 9141.3 | 0.061 | 1.1E−01 | 21.68 | 0.651 | 1.3E−02 | 40.71 | 0.451 | 8.2E−02 | 20.82 |
| NUE550 | 9142.2 | 0.066 | 1.5E−02 | 31.25 | | | | | | |
| Control | | 0.050 | | | 0.463 | | | 0.374 | | |
| NUE560 | 9424.3 | 0.052 | 1.6E−02 | 31.56 | | | | 0.374 | | 6.54 |
| NUE560 | 9422.1 | 0.058 | 5.3E−04 | 46.65 | | | | | | |
| Control | | 0.040 | | | | | | 0.351 | | |
| NUE562 | 9252.8 | 0.055 | 4.1E−02 | 38.43 | | | | | | |
| Control | | 0.040 | | | | | | | | |
| NUE564 | 9243.2 | 0.049 | 8.7E−03 | 38.96 | 0.477 | 2.0E−02 | 53.10 | 0.356 | 2.2E−01 | 17.03 |
| NUE564 | 9242.2 | 0.060 | 7.6E−05 | 70.29 | 0.471 | 3.1E−02 | 51.25 | 0.452 | 8.2E−03 | 48.52 |
| NUE564 | 9243.4 | 0.045 | 8.0E−02 | 27.01 | 0.356 | 4.3E−01 | 14.34 | 0.349 | 2.8E−01 | 14.73 |
| Control | | 0.035 | | | 0.312 | | | 0.304 | | |
| NUE567 | 9263.2 | 0.047 | 1.8E−02 | 34.46 | | | | | | |

TABLE 32-continued

Transgenic plants exogenously expressing the polynucleotides of some embodiments of the invention exhibit improved growth rate under standard nitrogen conditions

| Gene Name | Event # | RGR Of Leaf Area | | | RGR Of Roots Coverage | | | RGR Of Roots Length | | |
|---|---|---|---|---|---|---|---|---|---|---|
| | | Ave. | p-value | % incr. | Ave. | p-value | % incr. | Ave. | p-value | % incr. |
| Control | | 0.035 | | | | | | | | |
| NUE568 | 9471.3 | 0.059 | 4.2E−05 | 65.16 | 0.458 | 8.3E−02 | 40.04 | 0.358 | 4.4E−01 | 11.62 |
| NUE568 | 9461.3 | 0.062 | 1.5E−03 | 73.11 | 0.424 | 3.6E−01 | 29.62 | 0.347 | 6.9E−01 | 8.17 |
| NUE568 | 9474.4 | 0.056 | 4.1E−03 | 57.42 | 0.353 | 7.6E−01 | 7.67 | 0.331 | 8.6E−01 | 3.00 |
| NUE568 | 9472.2 | 0.071 | 3.5E−07 | 99.64 | 0.567 | 4.6E−03 | 73.13 | 0.364 | 4.0E−01 | 13.42 |
| NUE568 | 9462.3 | 0.047 | 5.2E−02 | 32.21 | 0.478 | 5.4E−02 | 45.99 | 0.369 | 3.9E−01 | 14.82 |
| Control | | 0.036 | | | 0.327 | | | 0.321 | | |
| NUE569 | 9381.2 | 0.056 | 5.3E−03 | 36.52 | 0.391 | 9.1E−01 | 1.25 | | | |
| Control | | 0.041 | | | 0.386 | | | 0.353 | | |
| NUE569 | 9381.1 | 0.053 | 8.1E−03 | 52.48 | 0.474 | 6.6E−02 | 52.21 | 0.342 | 4.9E−01 | 12.36 |
| Control | | 0.035 | | | 0.312 | | | 0.304 | | |
| NUE570 | 9314.1 | 0.049 | 1.8E−01 | 40.41 | 0.439 | 2.2E−01 | 40.98 | 0.420 | 7.2E−02 | 38.13 |
| Control | | 0.041 | | | 0.386 | | | 0.353 | | |
| NUE570 | 9311.4 | 0.047 | 3.3E−02 | 32.96 | 0.530 | 5.0E−03 | 70.17 | 0.456 | 7.3E−03 | 49.83 |
| NUE570 | 9311.3 | 0.040 | 2.3E−01 | 15.28 | 0.426 | 7.1E−02 | 36.71 | 0.397 | 3.7E−02 | 30.73 |
| NUE570 | 9314.4 | 0.035 | 9.4E−01 | 0.90 | 0.479 | 7.4E−03 | 53.70 | 0.368 | 1.1E−01 | 21.10 |
| NUE570 | 9314.1 | | | | 0.418 | 7.8E−02 | 34.04 | 0.374 | 1.0E−01 | 22.95 |
| Control | | 0.035 | | | 0.312 | | | 0.304 | | |
| NUE571 | 9304.2 | 0.078 | 3.4E−06 | 95.35 | 0.542 | 1.3E−01 | 37.40 | 0.420 | 2.1E−01 | 19.40 |
| NUE571 | 9301.1 | 0.063 | 9.9E−03 | 59.31 | 0.576 | 2.9E−02 | 46.03 | 0.389 | 4.4E−01 | 10.81 |
| NUE571 | 9303.2 | 0.053 | 1.1E−03 | 33.00 | | | | | | |
| NUE571 | 9302.1 | 0.062 | 7.2E−06 | 56.48 | | | | | | |
| NUE571 | 9302.3 | 0.054 | 2.1E−02 | 36.15 | | | | | | |
| Control | | 0.040 | | | 0.394 | | | 0.351 | | |
| NUE571 | 9304.3 | 0.055 | 6.8E−02 | 33.34 | | | | | | |
| NUE571 | 9304.2 | 0.054 | 7.6E−02 | 32.37 | | | | | | |
| NUE571 | 9303.2 | 0.050 | 1.0E−01 | 22.33 | | | | | | |
| NUE571 | 9301.4 | 0.049 | 9.7E−02 | 19.07 | | | | | | |
| Control | | 0.041 | | | | | | | | |
| NUE572 | 9324.3 | 0.049 | 2.7E−02 | 24.30 | 0.410 | 8.0E−01 | 3.99 | 0.381 | 5.3E−01 | 8.40 |
| Control | | 0.040 | | | 0.394 | | | 0.351 | | |
| NUE573 | 9491.1 | 0.053 | 1.5E−03 | 49.67 | 0.457 | 7.9E−02 | 39.55 | 0.382 | 1.9E−01 | 19.03 |
| NUE573 | 9491.4 | 0.050 | 8.7E−02 | 40.83 | 0.470 | 8.2E−02 | 43.44 | 0.400 | 1.9E−01 | 24.64 |
| Control | | 0.036 | | | 0.327 | | | 0.321 | | |
| NUE574 | 10366 | 0.063 | 8.1E−01 | 4.39 | 0.610 | 7.5E−03 | 57.68 | 0.473 | 6.5E−04 | 50.50 |
| Control | | 0.060 | | | 0.387 | | | 0.315 | | |
| NUE575 | 9502.1 | 0.052 | 7.9E−03 | 46.87 | 0.446 | 1.1E−01 | 36.36 | 0.343 | 6.5E−01 | 6.83 |
| Control | | 0.036 | | | 0.327 | | | 0.321 | | |
| NUE576 | 9792.4 | 0.050 | 2.2E−01 | 16.55 | 0.504 | 3.9E−03 | 44.47 | 0.390 | 4.7E−01 | 8.39 |
| NUE576 | 9794.1 | 0.054 | 5.4E−02 | 26.15 | 0.357 | 8.7E−01 | 2.30 | 0.392 | 4.4E−01 | 9.02 |
| NUE576 | 9793.3 | 0.065 | 1.8E−03 | 51.97 | 0.386 | 4.4E−01 | 10.78 | | | |
| Control | | 0.043 | | | 0.349 | | | 0.360 | | |
| NUE578 | 9524.3 | 0.055 | 1.8E−04 | 54.47 | 0.374 | 5.1E−01 | 14.35 | 0.360 | 4.1E−01 | 12.25 |
| NUE578 | 9524.1 | 0.050 | 2.5E−02 | 41.80 | | | | | | |
| Control | | 0.036 | | | 0.327 | | | 0.321 | | |
| NUE579 | 9701.3 | 0.051 | 8.7E−02 | 21.86 | 0.456 | 3.9E−03 | 58.84 | 0.377 | 8.8E−02 | 24.61 |
| Control | | 0.042 | | | 0.287 | | | 0.302 | | |
| NUE580 | 9551.4 | 0.040 | 4.3E−01 | 13.32 | 0.479 | 9.3E−02 | 46.41 | 0.361 | 4.2E−01 | 12.46 |
| NUE580 | 9554.4 | 0.049 | 1.2E−02 | 36.68 | 0.462 | 7.3E−02 | 41.18 | 0.382 | 2.3E−01 | 18.93 |
| Control | | 0.036 | | | 0.327 | | | 0.321 | | |
| NUE582 | 9562.4 | 0.059 | 3.4E−03 | 40.45 | 0.591 | 8.2E−03 | 32.70 | 0.414 | 1.9E−01 | 12.08 |
| NUE582 | 9561.2 | 0.061 | 4.1E−03 | 45.60 | | | | | | |
| Control | | 0.042 | | | 0.445 | | | 0.370 | | |
| NUE583 | 9671.1 | 0.057 | 1.3E−01 | 32.70 | 0.499 | 2.2E−02 | 43.12 | 0.401 | 4.5E−01 | 11.60 |
| Control | | 0.043 | | | 0.349 | | | 0.360 | | |
| NUE583 | 9673.4 | 0.106 | 1.1E−05 | 77.51 | 0.663 | 2.0E−04 | 71.43 | 0.416 | 4.2E−05 | 32.10 |
| NUE583 | 9673.2 | 0.077 | 4.3E−02 | 28.35 | 0.533 | 5.6E−02 | 37.79 | 0.331 | 5.4E−01 | 5.30 |
| Control | | 0.060 | | | 0.387 | | | 0.315 | | |
| NUE586 | 9751.7 | 0.067 | 5.9E−03 | 49.93 | 0.548 | 6.5E−01 | 6.47 | | | |
| NUE586 | 9752.1 | 0.066 | 4.3E−03 | 47.72 | 0.855 | 4.1E−05 | 66.23 | 0.563 | 1.2E−02 | 32.27 |
| Control | | 0.044 | | | 0.514 | | | 0.426 | | |
| NUE586 | 9751.1 | 0.052 | 8.3E−02 | 24.79 | 0.379 | 9.5E−02 | 32.19 | 0.393 | 3.6E−02 | 30.10 |
| NUE586 | 9751.7 | 0.067 | 7.5E−03 | 60.10 | 0.529 | 1.7E−03 | 84.40 | 0.452 | 1.5E−03 | 49.64 |

TABLE 32-continued

Transgenic plants exogenously expressing the polynucleotides of some embodiments of the invention exhibit improved growth rate under standard nitrogen conditions

| Gene Name | Event # | RGR Of Leaf Area | | | RGR Of Roots Coverage | | | RGR Of Roots Length | | |
|---|---|---|---|---|---|---|---|---|---|---|
| | | Ave. | p-value | % incr. | Ave. | p-value | % incr. | Ave. | p-value | % incr. |
| NUE586 | 9752.2 | | | | 0.394 | 1.4E−02 | 37.21 | 0.390 | 2.6E−02 | 29.02 |
| NUE586 | 9752.1 | 0.055 | 5.8E−02 | 32.53 | 0.472 | 1.9E−02 | 64.61 | 0.400 | 4.5E−02 | 32.28 |
| Control | | 0.042 | | | 0.287 | | | 0.302 | | |
| NUE587 | 9643.2 | 0.083 | 2.5E−06 | 97.54 | 0.439 | 3.8E−03 | 52.93 | 0.314 | 7.6E−01 | 4.01 |
| Control | | 0.042 | | | 0.287 | | | 0.302 | | |
| NUE593 | 10394 | 0.074 | 1.4E−01 | 33.10 | 0.465 | 9.0E−02 | 35.46 | 0.368 | 6.3E−02 | 31.07 |
| Control | | 0.056 | | | 0.344 | | | 0.281 | | |

Table 32: Analyses of plant growth rate (leaf area, root coverage and root length) of transgenic plants overexpressing the exogenous polynucleotides of some embodiments of the invention (using the cloned or synthetic genes listed in Table 23 above) under the regulation of a constitutive promoter (35S) when grown under standard nitrogen conditions [normal or regular growth conditions (15 mM N)]as compared to control plants.
"Incr." = increment; "RGR" = relative growth rate; "Ave." = average.

Example 6

Assay 2: Nitrogen Use Efficiency: Yield and Plant Growth Rate at Limited and Optimal Nitrogen Concentration Under Greenhouse Conditions This assay follows the seed yield production, biomass formation and rosette area growth of plants grown in the greenhouse at nitrogen deficient of nitrogen standard fertilization conditions. Seeds were sown in agar media supplemented with ½ MS medium and a selection agent (Kanamycin). The $T_2$ transgenic seedlings were then transplanted to 1.7 trays filled with peat and perlite. The trays were irrigated with a solution containing constant nitrogen limiting conditions, which were achieved by irrigating the plants with a solution containing 1.5 mM inorganic nitrogen in the form of $KNO_3$, supplemented with 1 mM $KH_2PO_4$, 1 mM $MgSO_4$, 3.6 mM $K_2SO_4$, 2 mM $CaCl_2$ and microelements, while normal nitrogen levels were achieved by applying a solution of 6 mM inorganic nitrogen also in the form of $KNO_3$ with 1 mM $KH_2PO_4$, 1 mM $MgSO_4$, 2 mM $CaCl_2$ and microelements. All plants were grown in the greenhouse until mature seeds. Seeds were harvested separately to the above ground tissue, extracted and weight. Plant biomass (the above ground tissue) was also collected and dried for 1 week at 30° C.

Each construct was validated at its $T_2$ generation. Transgenic plants transformed with a construct conform by an empty vector carrying the 35S promoter and the selectable marker were used as controls.

The plants were analyzed for their overall size, growth rate, seed yield, 1,000-seed weight, dry matter and harvest index (HI—seed yield/dry matter). Transgenic plants performance was compared to control plants grown in parallel under the same conditions.

The experiment was planned in nested randomized plot distribution. For each gene of the invention three to five independent transformation events were analyzed from each construct.

Digital Imaging

A laboratory image acquisition system, which consists of a digital reflex camera (Canon EOS 300D) attached with a 55 mm focal length lens (Canon EF-S series), mounted on a reproduction device (Kaiser RS), which includes 4 light units (4×150 Watts light bulb) was used for capturing images of plant samples.

The image capturing process was repeated every 2 days starting from day 1 after transplanting till day 15. Same camera, placed in a custom made iron mount, was used for capturing images of larger plants sawn in white tubs in an environmental controlled greenhouse. During the capture process, the trays were placed beneath the iron mount, while avoiding direct sun light and casting of shadows.

An image analysis system was used, which consists of a personal desktop computer (Intel P4 3.0 GHz processor) and a public domain program—ImageJ 1.39 [Java based image processing program which was developed at the U.S. National Institutes of Health and freely available on the internet at Hypertext Transfer Protocol://rsbweb (dot) nih (dot) gov/]. Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Leaf Growth Analysis

Using the digital analysis leaves data was calculated, including leaf number, rosette area, rosette diameter, leaf blade area, plot coverage, leaf petiole length.

Vegetative growth rate: is the rate of growth of the plant as defined by formulas VIII, IX, X and XI Relative growth rate of leaf blade area=Regression coefficient of leaf area along time course.   Formula VIII:

Relative growth rate of rosette area=Regression coefficient of rosette area along time course.   Formula IX:

Relative growth rate of rosette diameter=Regression coefficient of rosette diameter along time course.   Formula X Relative growth rate of plot coverage=Regression coefficient of plot coverage along time course.   Formula XI Seeds Average Weight (Seed Weight or 1000 Seed Weight)

At the end of the experiment all seeds were collected. The seeds were scattered on a glass tray and a picture was taken. Using the digital analysis, the number of seeds in each sample was calculated.

Plant Dry Weight and Seed Yield

On about day 80 from sowing, the plants were harvested and left to dry at 30° C. in a drying chamber. The biomass and seed weight of each plot were measured and divided by the number of plants in each plot.

Dry weight=total weight of the vegetative portion above ground (excluding roots) after drying at 30° C. in a drying chamber;

Seed yield per plant=total seed weight per plant (grams).

The Harvest Index can be calculated using Formula III (as described above; Harvest Index=Average seed yield per plant/Average dry weight).

Statistical Analyses

To identify genes conferring significantly improved nitrogen use efficiency and yield production, the results obtained from the transgenic plants were compared to those obtained from control plants. To identify outperforming genes and constructs, results from the independent transformation events tested were analyzed separately. Data was analyzed using Student's t-test and results were considered significant if the p value was less than 0.1. The JMP statistics software package was used (Version 5.2.1, SAS Institute Inc., Cary, N.C., USA).

Experiment Results:

The genes presented in Tables 33, 34 and 35, hereinbelow, have improved plant NUE when grown at limiting nitrogen concentration levels. These genes produced higher seed yield, harvest index, seed weight (expressed as 1000-seed weight) and plant biomass [(as expressed as plant dry weight (DW)] when grown under limiting nitrogen growth conditions, compared to control.

Tables 33, 34 and 35 depict analyses of seed yield, harvest index, seed size (expressed as 1000-seed weight) when grown under limiting nitrogen conditions in plants overexpressing the polynucleotides of some embodiments of the invention under the regulation of a constitutive (35S). Evaluation of each gene was performed by testing the performance of several events. Some of the genes were evaluated in more than one tissue culture assay and the results obtained were repeated. Event with p-value <0.1 was considered statistically significant.

TABLE 33

Transgenic plants exogenously expressing the polynucleotides of some embodiments of the invention exhibit improved seed yield and weight (expressed as 1000-seed weight) under nitrogen deficient growth conditions.

| | Seed Yield | | | | | Seeds Weight | | | |
|---|---|---|---|---|---|---|---|---|---|
| Gene Name | Event # | Ave. | p-value | % incr. | Gene Name | Event # | Ave. | p-value | % incr. |
| NUE241 | 9631.6 | 0.169 | 1.3E−01 | 12.60 | NUE241 | 9632.3 | 0.020 | 2.5E−01 | 2.46 |
| NUE241 | 9631.4 | 0.150 | 9.7E−01 | 0.40 | NUE241 | 9631.4 | 0.020 | 6.4E−01 | 1.96 |
| Control | | 0.150 | | | Control | | 0.020 | | |
| NUE248 | 8982.3 | 0.144 | 3.6E−01 | 7.27 | NUE248 | 8982.4 | 0.023 | 4.1E−03 | 14.08 |
| Control | | 0.135 | | | NUE248 | 8982.3 | 0.021 | 4.3E−01 | 4.59 |
| NUE525 | 9534.1 | 0.161 | 6.7E−01 | 7.33 | NUE248 | 8981.1 | 0.021 | 7.2E−01 | 7.54 |
| NUE525 | 9531.3 | 0.169 | 5.6E−01 | 12.83 | NUE248 | 8983.1 | 0.021 | 7.3E−01 | 5.14 |
| NUE525 | 9533.4 | 0.162 | 7.0E−01 | 8.26 | Control | | 0.020 | | |
| NUE525 | 9531.1 | 0.166 | 1.0E−01 | 10.90 | NUE255 | 9431.4 | 0.021 | 1.0E−01 | 4.57 |
| Control | | 0.150 | | | Control | | 0.020 | | |
| NUE536 | 9234.1 | 0.157 | 6.1E−01 | 16.81 | NUE525 | 9533.1 | 0.022 | 2.1E−01 | 10.94 |
| Control | | 0.135 | | | NUE525 | 9531.3 | 0.020 | 7.6E−01 | 2.55 |
| NUE545 | 9482.4 | 0.184 | 1.7E−04 | 22.72 | Control | | 0.020 | | |
| Control | | 0.150 | | | NUE536 | 9234.1 | 0.020 | 6.0E−01 | 3.02 |
| NUE565 | 9443.4 | 0.204 | 1.8E−01 | 36.33 | NUE536 | 9231.3 | 0.021 | 5.3E−01 | 4.99 |
| Control | | 0.150 | | | Control | | 0.020 | | |
| NUE566 | 9514.3 | 0.163 | 1.6E−01 | 9.08 | NUE545 | 9482.4 | 0.020 | 7.1E−01 | 1.36 |
| NUE566 | 9514.1 | 0.172 | 7.0E−01 | 15.02 | Control | | 0.020 | | |
| Control | | 0.150 | | | NUE549 | 9343.6 | 0.023 | 2.7E−01 | 14.91 |
| NUE568 | 9471.3 | 0.160 | 1.8E−01 | 6.55 | NUE549 | 9342.3 | 0.021 | 5.1E−01 | 3.66 |
| Control | | 0.150 | | | Control | | 0.020 | | |
| NUE573 | 9493.4 | 0.172 | 3.8E−01 | 14.54 | NUE560 | 9424.1 | 0.023 | 1.3E−04 | 18.35 |
| NUE573 | 9491.2 | 0.181 | 3.3E−04 | 20.87 | NUE560 | 9424.3 | 0.021 | 8.0E−02 | 4.76 |
| NUE573 | 9492.2 | 0.155 | 8.9E−01 | 3.21 | NUE560 | 9422.1 | 0.020 | 3.1E−01 | 3.38 |
| Control | | 0.150 | | | Control | | 0.020 | | |
| NUE578 | 9524.1 | 0.147 | 9.3E−01 | −1.70 | NUE568 | 9461.2 | 0.024 | 1.3E−05 | 21.77 |
| Control | | 0.150 | | | Control | | 0.020 | | |
| NUE580 | 9552.3 | 0.180 | 1.9E−01 | 19.99 | NUE573 | 9491.2 | 0.023 | 1.1E−01 | 14.40 |
| Control | | 0.150 | | | NUE573 | 9492.2 | 0.021 | 3.6E−02 | 5.14 |
| NUE585 | 9661.1 | 0.150 | 1.8E−01 | 11.29 | Control | | 0.020 | | |
| Control | | 0.135 | | | NUE578 | 9524.1 | 0.022 | 8.2E−04 | 10.87 |
| | | | | | Control | | 0.020 | | |
| | | | | | NUE580 | 9551.3 | 0.025 | 7.2E−02 | 24.52 |
| | | | | | NUE580 | 9554.4 | 0.023 | 9.7E−02 | 14.78 |
| | | | | | Control | | 0.020 | | |
| | | | | | NUE585 | 9662.4 | 0.021 | 7.5E−02 | 6.26 |
| | | | | | NUE585 | 9661.1 | 0.022 | 5.2E−03 | 9.36 |
| | | | | | Control | | 0.020 | | |

Table 33: Analyses of seed yield and weight of transgenic plants overexpressing the exogenous polynucleotides of some embodiments of the invention (using the cloned or synthetic genes listed in Table 23 above) under the regulation of a constitutive promoter (35S) when grown under nitrogen deficient conditions (1.5 mM $KNO_3$, 1 mM $KH_2PO_4$, 1 mM $MgSO_4$, 3.6 mM $K_2SO_4$, 2 mM $CaCl_2$ and microelements) as compared to control plants. "Incr." = increment; "Ave." = average.

TABLE 34

Transgenic plants exogenously expressing the polynucleotides of some embodiments of the invention exhibit improved harvest index under nitrogen deficient growth conditions.

| | | Harvest Index | | |
|---|---|---|---|---|
| Gene Name | Event # | Average | p-value | % increment |
| NUE525 | 9534.1 | 0.321 | 1.9E−01 | 6.99 |
| NUE525 | 9533.1 | 0.319 | 7.0E−01 | 6.25 |
| NUE525 | 9533.4 | 0.322 | 4.8E−01 | 7.18 |
| NUE525 | 9531.1 | 0.356 | 3.5E−02 | 18.72 |
| Control | | 0.300 | | |
| NUE536 | 9234.1 | 0.344 | 6.9E−02 | 20.95 |
| NUE536 | 9231.3 | 0.298 | 3.7E−01 | 4.68 |
| Control | | 0.285 | | |
| NUE545 | 9482.4 | 0.328 | 2.0E−01 | 9.31 |
| Control | | 0.300 | | |
| NUE549 | 9341.1 | 0.337 | 2.9E−02 | 12.21 |
| NUE549 | 9342.3 | 0.322 | 6.8E−01 | 7.19 |
| Control | | 0.300 | | |
| NUE560 | 9424.3 | 0.316 | 9.5E−02 | 10.86 |
| NUE560 | 9422.1 | 0.318 | 8.2E−02 | 11.60 |
| Control | | 0.285 | | |
| NUE565 | 9443.4 | 0.335 | 3.9E−01 | 11.59 |
| Control | | 0.300 | | |
| NUE566 | 9514.1 | 0.351 | 5.8E−01 | 17.05 |
| Control | | 0.300 | | |

Table 34: Analyses of harvest index of transgenic plants overexpressing the exogenous polynucleotides of some embodiments of the invention (using the cloned or synthetic genes listed in Table 23 above) under the regulation of a constitutive promoter (35S) when grown under nitrogen deficient conditions (1.5 mM $KNO_3$, 1 mM $KH_2PO_4$, 1 mM $MgSO_4$, 3.6 mM $K_2SO_4$, 2 mM $CaCl_2$ and microelements) as compared to control plants.

TABLE 35

Transgenic plants exogenously expressing the polynucleotides of some embodiments of the invention exhibit improved dry weight under nitrogen deficient growth conditions

| | | Dry Weight | | |
|---|---|---|---|---|
| Gene Name | Event # | Average | p-value | % increment |
| NUE241 | 9631.6 | 0.569 | 5.2E−01 | 11.66 |
| NUE241 | 9632.3 | 0.613 | 8.0E−02 | 20.25 |
| Control | | 0.509 | | |
| NUE248 | 8982.3 | 0.534 | 2.9E−01 | 13.35 |
| Control | | 0.471 | | |
| NUE525 | 9531.3 | 0.600 | 4.3E−01 | 17.79 |
| Control | | 0.509 | | |
| NUE545 | 9482.4 | 0.561 | 2.9E−01 | 10.18 |
| Control | | 0.509 | | |
| NUE549 | 9342.2 | 0.541 | 7.3E−01 | 6.13 |
| NUE565 | 9444.1 | 0.589 | 6.5E−01 | 15.71 |
| NUE565 | 9443.4 | 0.609 | 3.4E−02 | 19.63 |
| Control | | 0.509 | | |
| NUE566 | 9514.3 | 0.637 | 5.2E−01 | 24.96 |
| Control | | 0.509 | | |
| NUE568 | 9471.3 | 0.515 | 8.9E−01 | 1.10 |
| NUE568 | 9462.3 | 0.639 | 1.4E−02 | 25.52 |
| Control | | 0.509 | | |
| NUE573 | 9493.4 | 0.581 | 2.9E−01 | 14.15 |
| NUE573 | 9491.2 | 0.613 | 3.4E−02 | 20.37 |
| NUE573 | 9492.2 | 0.683 | 4.2E−02 | 33.99 |
| Control | | 0.509 | | |
| NUE580 | 9552.3 | 0.561 | | 10.18 |
| NUE580 | 9551.3 | 0.634 | 2.4E−01 | 24.42 |
| NUE580 | 9554.4 | 0.526 | 7.0E−01 | 3.31 |
| Control | | 0.509 | | |
| NUE585 | 9661.1 | 0.519 | 4.6E−01 | 10.30 |
| Control | | 0.471 | | |

Table 35: Analyses of dry weight of transgenic plants overexpressing the exogenous polynucleotides of some embodiments of the invention (using the cloned or synthetic genes listed in Table 23 above) under the regulation of a constitutive promoter (35S) when grown under nitrogen deficient conditions (1.5 mM $KNO_3$, 1 mM $KH_2PO_4$, 1 mM $MgSO_4$, 3.6 mM $K_2SO_4$, 2 mM $CaCl_2$ and microelements) as compared to control plants.

The genes presented in Tables 36 and 37, hereinbelow, have improved plant NUE since they produced higher seed yield, harvest index, seed weight (expressed as 1000-seed weight) and plant biomass [(as expressed as plant dry weight (DW)] when grown under standard nitrogen growth conditions, compared to control plants indicating the high ability of the plant to better metabolize the nitrogen present in the medium.

Tables 36 and 37 depict analyses of dry weight, seed yield, harvest index, seed size (expressed as 1000-seed weight) when grown under standard nitrogen conditions (6 mM $KNO_3$, 1 mM $KH_2PO_4$, 1 mM $MgSO_4$, 2 mM $CaCl_2$ and microelements) in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 36

Transgenic plants exogenously expressing the polynucleotides of some embodiments of the invention exhibit improved plant biomass (dry weight) and seed yield under standard nitrogen conditions

| | | Dry Weight | | | | | Seed Yield | | |
|---|---|---|---|---|---|---|---|---|---|
| Gene Name | Event # | Ave. | P-Value | % incr. | Gene Name | Event # | Ave. | P-Value | % incr. |
| NUE255 | 9431.4 | 1.394 | 5.6E−01 | 14.344 | NUE234 | 9162.5 | 0.523 | 1.0E−01 | 16.207 |
| NUE255 | 9432.1 | 1.499 | 5.9E−02 | 22.894 | Control | | 0.450 | | |
| NUE255 | 9433.1 | 1.409 | 1.0E−01 | 15.530 | NUE241 | 9631.4 | 0.364 | 3.0E−01 | −12.185 |
| Control | | 1.219 | | | Control | | 0.414 | | |
| NUE525 | 9531.1 | 1.635 | 6.1E−03 | 34.085 | NUE255 | 9431.4 | 0.436 | 7.4E−01 | 5.346 |
| Control | | 1.219 | | | NUE255 | 9432.1 | 0.483 | 3.5E−01 | 16.593 |
| NUE545 | 9484.2 | 1.246 | 7.0E−01 | 2.204 | NUE255 | 9433.1 | 0.444 | 1.0E−01 | 7.100 |
| NUE545 | 9481.3 | 1.631 | 3.4E−04 | 33.726 | Control | | 0.414 | | |
| Control | | 1.219 | | | NUE525 | 9534.1 | 0.486 | 2.6E−03 | 17.328 |
| NUE549 | 9341.1 | 1.381 | 6.7E−02 | 13.275 | NUE525 | 9531.1 | 0.504 | 4.0E−01 | 21.719 |
| NUE549 | 9342.3 | 1.310 | 2.7E−01 | 7.432 | Control | | 0.414 | | |

TABLE 36-continued

Transgenic plants exogenously expressing the polynucleotides of
some embodiments of the invention exhibit improved plant biomass
(dry weight) and seed yield under standard nitrogen conditions

| | | Dry Weight | | | | | Seed Yield | | |
|---|---|---|---|---|---|---|---|---|---|
| Gene Name | Event # | Ave. | P-Value | % incr. | Gene Name | Event # | Ave. | P-Value | % incr. |
| Control | | 1.219 | | | NUE549 | 9341.1 | 0.447 | 6.4E−01 | 8.031 |
| NUE563 | 9451.1 | 1.303 | 5.6E−01 | 6.868 | Control | | 0.414 | | |
| NUE563 | 9452.3 | 1.473 | 1.6E−02 | 20.788 | NUE563 | 9451.1 | 0.419 | 8.6E−01 | 1.237 |
| Control | | 1.219 | | | NUE563 | 9452.3 | 0.454 | 6.5E−01 | 9.572 |
| NUE565 | 9443.2 | 1.348 | 9.3E−02 | 10.507 | Control | | 0.414 | | |
| NUE565 | 9444.3 | 1.376 | 4.7E−01 | 12.814 | NUE566 | 9512.4 | 0.458 | 1.8E−01 | 10.657 |
| Control | | 1.219 | | | Control | | 0.414 | | |
| NUE566 | 9512.4 | 1.471 | 5.8E−03 | 20.605 | NUE568 | 9464.2 | 0.429 | 8.6E−01 | 3.674 |
| Control | | 1.219 | | | NUE568 | 9462.3 | 0.423 | 7.7E−01 | 2.233 |
| NUE568 | 9461.2 | 1.571 | 8.6E−04 | 28.806 | Control | | 0.414 | | |
| NUE568 | 9464.2 | 1.366 | 4.9E−01 | 11.994 | NUE573 | 9491.4 | 0.455 | 5.1E−01 | 9.769 |
| NUE568 | 9462.3 | 1.288 | 3.8E−01 | 5.638 | NUE573 | 9492.1 | 0.486 | 4.5E−01 | 17.465 |
| Control | | 1.219 | | | NUE573 | 9493.4 | 0.449 | 7.5E−01 | 8.482 |
| NUE573 | 9491.4 | 1.249 | 8.9E−01 | 2.460 | Control | | 0.414 | | |
| NUE573 | 9492.1 | 1.668 | 1.3E−01 | 36.802 | NUE582 | 9561.2 | 0.452 | 4.7E−01 | 9.239 |
| NUE573 | 9493.4 | 1.478 | 7.2E−02 | 21.213 | Control | | 0.414 | | |
| NUE573 | 9491.2 | 1.407 | 1.0E−01 | 15.377 | | | | | |
| Control | | 1.219 | | | | | | | |

Table 36: Analyses of plant biomass (dry weight) and see yield of transgenic plants overexpressing the exogenous polynucleotides of some embodiments of the invention (using the cloned or synthetic genes listed in Table 23 above) under the regulation of a constitutive promoter (35S) when grown under standard nitrogen conditions (6 mM KNO$_3$, 1 mM KH$_2$PO$_4$, 1 mM MgSO$_4$, 2 mM CaCl$_2$ and microelements) as compared to control plants.
"Incr." = increment; "RGR" = relative growth rate; "Ave." = average.

TABLE 37

Transgenic plants exogenously expressing the polynucleotides of some embodiments of the invention
exhibit improved harvest index and seed weight under standard nitrogen conditions

| | | Harvest Index | | | | | Seed Weight | | |
|---|---|---|---|---|---|---|---|---|---|
| Gene Name | Event # | Ave. | P-Value | % incr. | Gene Name | Event # | Ave. | P-Value | % incr. |
| NUE234 | 9162.5 | 0.368 | 3.7E−02 | 15.734 | NUE241 | 9631.4 | 0.022 | 3.3E−02 | 6.274 |
| Control | | 0.318 | | | Control | | 0.021 | | |
| NUE525 | 9534.1 | 0.477 | 4.5E−01 | 38.546 | NUE255 | 9432.1 | 0.023 | 2.5E−02 | 11.793 |
| Control | | 0.344 | | | NUE255 | 9433.1 | 0.021 | 6.6E−02 | 4.087 |
| NUE573 | 9491.4 | 0.366 | 3.7E−01 | 6.179 | Control | | 0.021 | | |
| Control | | 0.344 | | | NUE525 | 9534.1 | 0.021 | 1.0E+00 | 0.008 |
| NUE582 | 9561.2 | 0.466 | 2.2E−01 | 35.384 | NUE525 | 9531.1 | 0.025 | 3.6E−01 | 22.277 |
| Control | | 0.344 | | | Control | | 0.021 | | |
| | | | | | NUE545 | 9481.3 | 0.024 | 3.0E−01 | 17.664 |
| | | | | | Control | | 0.021 | | |
| | | | | | NUE549 | 9341.1 | 0.022 | 5.8E−01 | 9.152 |
| | | | | | NUE549 | 9342.3 | 0.023 | 5.6E−01 | 11.416 |
| | | | | | Control | | 0.021 | | |
| | | | | | NUE563 | 9451.1 | 0.023 | 1.1E−01 | 10.668 |
| | | | | | NUE563 | 9452.3 | 0.022 | 3.5E−01 | 5.095 |
| | | | | | Control | | 0.021 | | |
| | | | | | NUE565 | 9443.2 | 0.024 | 2.0E−01 | 15.540 |
| | | | | | NUE565 | 9444.3 | 0.021 | 9.1E−01 | 1.159 |
| | | | | | Control | | 0.021 | | |
| | | | | | NUE566 | 9512.4 | 0.022 | 8.6E−02 | 5.164 |
| | | | | | Control | | 0.021 | | |
| | | | | | NUE568 | 9461.2 | 0.024 | 3.0E−01 | 19.048 |
| | | | | | NUE568 | 9464.2 | 0.022 | 6.1E−01 | 8.243 |
| | | | | | NUE568 | 9462.3 | 0.023 | 6.1E−04 | 10.961 |
| | | | | | Control | | 0.021 | | |
| | | | | | NUE573 | 9491.4 | 0.021 | 7.1E−01 | 1.229 |
| | | | | | NUE573 | 9492.1 | 0.021 | 1.8E−01 | 3.164 |

TABLE 37-continued

Transgenic plants exogenously expressing the polynucleotides of some embodiments of the invention exhibit improved harvest index and seed weight under standard nitrogen conditions

| | | Harvest Index | | | | | Seed Weight | | |
|---|---|---|---|---|---|---|---|---|---|
| Gene Name | Event # | Ave. | P-Value | % incr. | Gene Name | Event # | Ave. | P-Value | % incr. |
| | | | | | NUE573 | 9493.4 | 0.022 | 1.9E−01 | 8.883 |
| | | | | | NUE573 | 9491.2 | 0.023 | 4.0E−01 | 14.335 |
| | | | | | Control | | 0.021 | | |
| | | | | | NUE582 | 9561.2 | 0.024 | 1.6E−03 | 15.172 |
| | | | | | Control | | 0.021 | | |

Table 37: Analyses of harvest index and seed weight of transgenic plants overexpressing the exogenous polynucleotides of some embodiments of the invention (using the cloned or synthetic genes listed in Table 23 above) under the regulation of a constitutive promoter (35S) when grown under standard nitrogen conditions (6 mM $KNO_3$, 1 mM $KH_2PO_4$, 1 mM $MgSO_4$, 2 mM $CaCl_2$ and microelements) as compared to control plants.
"Incr." = increment; "RGR" = relative growth rate; "Ave." = average.

Improvement of rosette area as well as rosette growth rate supports the fact that plants can produce larger plant biomass by better exploiting the nitrogen available in the soil. In addition a production of a larger number of leaves as well as a higher plot coverage when grown at low nitrogen conditions indicate a larger photosynthetic capacity of the plant when grown at different nitrogen growth conditions The genes presented in Tables 38 and 39, hereinbelow, have improved plant NUE and produced larger plant biomass when grown under limiting nitrogen growth conditions, compared to control plants. In addition a production of a larger number of leaves as well as a higher plot coverage when grown at low nitrogen conditions indicate a larger photosynthetic capacity of the plant when grown at low nitrogen growth conditions Tables 38 and 39 depict analyses of rosette area and leaf number (rosette diameter, rosette area, leaf number, leaf blade area and plot coverage) when grown under limiting nitrogen conditions (1.5 mM $KNO_3$, 1 mM $KH_2PO_4$, 1 mM $MgSO_4$, 3.6 mM $K_2SO_4$, 2 mM $CaCl_2$ and microelements) in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 38

Transgenic plants exogenously expressing the polynucleotides of some embodiments of the invention exhibit improved rosette growth performance (rosette diameter and area and plot coverage) under nitrogen deficient conditions

| | | Rosette Diameter [cm] | | | Rosette Area [cm²] | | | Plot Coverage [%] | | |
|---|---|---|---|---|---|---|---|---|---|---|
| Gene Name | Event # | Ave. | p-value | % incr. | Ave. | p-value | % incr. | Ave. | p-value | % incr. |
| NUE234 | 9163.4 | 2.26 | 1.6E−01 | 8.49 | 1.634 | 2.7E−01 | 7.24 | 13.07 | 2.7E−01 | 7.24 |
| Control | | 2.08 | | | 1.523 | | | 12.19 | | |
| NUE241 | 9632.3 | 1.72 | 4.1E−01 | 20.77 | 1.008 | 5.3E−01 | 42.18 | 8.06 | 5.3E−01 | 42.18 |
| NUE241 | 9631.4 | 1.57 | 6.4E−02 | 10.20 | 0.886 | 1.7E−03 | 24.97 | 7.09 | 1.7E−03 | 24.97 |
| Control | | 1.42 | | | 0.709 | | | 5.67 | | |
| NUE249 | 9122.2 | 2.20 | 2.3E−01 | 5.86 | 1.696 | 2.6E−01 | 11.33 | 13.57 | 2.6E−01 | 11.33 |
| Control | | 2.08 | | | 1.523 | | | 12.19 | | |
| NUE525 | 9534.1 | 1.84 | 9.3E−02 | 29.75 | 1.255 | 6.6E−02 | 77.06 | 9.45 | 1.9E−01 | 66.71 |
| NUE525 | 9531.2 | 1.83 | 2.1E−02 | 29.02 | 1.191 | 8.3E−02 | 68.09 | 8.98 | 2.2E−01 | 58.33 |
| NUE525 | 9533.1 | 1.74 | 7.1E−02 | 22.38 | 1.060 | 1.4E−01 | 49.54 | 8.48 | 1.4E−01 | 49.54 |
| NUE525 | 9531.3 | 1.58 | 4.3E−01 | 11.39 | 0.884 | 5.3E−01 | 24.70 | 7.07 | 5.3E−01 | 24.70 |
| NUE525 | 9533.4 | 1.71 | 1.5E−03 | 20.13 | 1.048 | 1.5E−04 | 47.84 | 8.38 | 1.5E−04 | 47.84 |
| NUE525 | 9531.1 | 1.62 | 8.0E−02 | 13.70 | 1.025 | 2.8E−02 | 44.64 | 8.20 | 2.8E−02 | 44.64 |
| Control | | 1.42 | | | 0.709 | | | 5.67 | | |
| NUE536 | 9234.1 | 2.29 | 2.1E−02 | 9.74 | 1.734 | 3.2E−01 | 13.79 | 13.87 | 3.2E−01 | 13.79 |
| Control | | 2.08 | | | 1.523 | | | 12.19 | | |
| NUE545 | 9484.2 | 1.97 | 1.5E−07 | 38.83 | 1.311 | 4.1E−08 | 84.91 | 10.49 | 4.1E−08 | 84.91 |
| NUE545 | 9482.4 | 1.71 | 2.1E−01 | 19.99 | 0.999 | 2.1E−01 | 40.87 | 7.99 | 2.1E−01 | 40.87 |
| NUE545 | 9481.3 | 1.79 | 4.6E−01 | 26.22 | 1.025 | 4.9E−01 | 44.66 | 8.20 | 4.9E−01 | 44.66 |
| NUE545 | 9484.4 | 2.01 | 1.6E−07 | 41.45 | 1.265 | 2.1E−05 | 78.42 | 10.12 | 2.1E−05 | 78.42 |
| Control | | 1.42 | | | 0.709 | | | 5.67 | | |
| NUE549 | 9341.1 | 1.61 | | 13.18 | 0.956 | 2.2E−01 | 34.91 | 7.65 | 2.2E−01 | 34.91 |
| Control | | 1.42 | | | 0.709 | | | 5.67 | | |
| NUE563 | 9454.1 | 1.61 | 1.6E−01 | 13.12 | 0.930 | 1.0E−01 | 31.25 | 7.44 | 1.0E−01 | 31.25 |
| NUE563 | 9452.3 | 1.56 | 4.6E−01 | 10.02 | 0.828 | 5.7E−01 | 16.76 | 6.62 | 5.7E−01 | 16.76 |

TABLE 38-continued

Transgenic plants exogenously expressing the polynucleotides of some embodiments of the invention exhibit improved rosette growth performance (rosette diameter and area and plot coverage) under nitrogen deficient conditions

| Gene Name | Event # | Rosette Diameter [cm] | | | Rosette Area [cm$^2$] | | | Plot Coverage [%] | | |
|---|---|---|---|---|---|---|---|---|---|---|
| | | Ave. | p-value | % incr. | Ave. | p-value | % incr. | Ave. | p-value | % incr. |
| NUE563 | 9453.4 | 1.72 | 1.7E−01 | 21.08 | 1.077 | 1.9E−01 | 51.96 | 8.62 | 1.9E−01 | 51.96 |
| NUE563 | 9452.1 | 1.48 | 7.5E−02 | 4.31 | 0.720 | 8.4E−01 | 1.64 | 5.76 | 8.4E−01 | 1.64 |
| Control | | 1.42 | | | 0.709 | | | 5.67 | | |
| NUE565 | 9444.1 | 1.72 | 3.1E−01 | 20.73 | 0.889 | 2.7E−01 | 25.43 | 7.11 | 2.7E−01 | 25.43 |
| NUE565 | 9442.4 | 1.63 | 8.5E−04 | 14.54 | 0.839 | 9.5E−02 | 18.42 | 6.72 | 9.5E−02 | 18.42 |
| Control | | 1.42 | | | 0.709 | | | 5.67 | | |
| NUE566 | 9514.3 | 1.75 | 2.1E−01 | 22.85 | 1.113 | 2.3E−01 | 56.97 | 8.27 | 1.2E−01 | 45.76 |
| NUE566 | 9513.1 | 1.63 | 3.0E−01 | 14.74 | 0.915 | 2.3E−01 | 29.04 | 7.32 | 2.3E−01 | 29.04 |
| NUE566 | 9512.4 | 1.58 | 5.0E−01 | 11.26 | 0.927 | 4.3E−01 | 30.79 | 7.42 | 4.3E−01 | 30.79 |
| NUE566 | 9514.1 | 1.72 | 6.9E−02 | 21.08 | 1.061 | 2.3E−01 | 49.66 | 8.02 | 3.7E−01 | 41.52 |
| Control | | 1.42 | | | 0.709 | | | 5.67 | | |
| NUE568 | 9474.4 | 1.66 | 2.3E−01 | 16.75 | 0.937 | 2.9E−02 | 32.20 | 7.50 | 2.9E−02 | 32.20 |
| NUE568 | 9461.2 | 1.79 | 2.1E−01 | 26.22 | 1.216 | 1.6E−01 | 71.50 | 9.72 | 1.6E−01 | 71.50 |
| NUE568 | 9462.4 | 1.76 | 3.3E−01 | 23.46 | 1.072 | 2.7E−01 | 51.17 | 8.57 | 2.7E−01 | 51.17 |
| NUE568 | 9462.3 | 1.69 | 5.8E−02 | 19.20 | 1.005 | 1.8E−01 | 41.72 | 8.04 | 1.8E−01 | 41.72 |
| NUE568 | 9463.4 | 1.78 | 2.3E−01 | 25.46 | 1.018 | 3.6E−01 | 43.57 | 8.14 | 3.6E−01 | 43.57 |
| NUE568 | 9473.3 | 1.52 | 3.4E−01 | 6.95 | 0.826 | 1.9E−01 | 16.55 | 6.61 | 1.9E−01 | 16.55 |
| Control | | 1.42 | | | 0.709 | | | 5.67 | | |
| NUE573 | 9491.4 | 1.72 | 2.1E−01 | 21.02 | 1.007 | 2.4E−01 | 42.03 | 8.05 | 2.4E−01 | 42.03 |
| NUE573 | 9492.1 | 2.01 | 1.1E−05 | 41.63 | 1.404 | 4.1E−03 | 98.05 | 11.23 | 4.1E−03 | 98.05 |
| NUE573 | 9493.4 | 1.77 | 4.9E−06 | 24.30 | 1.106 | 3.3E−04 | 56.00 | 8.31 | 1.5E−01 | 46.46 |
| NUE573 | 9494.3 | 1.82 | 1.4E−06 | 27.69 | 1.177 | 6.2E−03 | 66.10 | 9.42 | 6.2E−03 | 66.10 |
| NUE573 | 9491.2 | 1.79 | 1.2E−01 | 26.17 | 1.115 | 1.8E−01 | 57.32 | 8.92 | 1.8E−01 | 57.32 |
| NUE573 | 9492.2 | 1.75 | 1.2E−01 | 22.83 | 1.016 | 1.5E−01 | 43.40 | 8.13 | 1.5E−01 | 43.40 |
| Control | | 1.42 | | | 0.709 | | | 5.67 | | |
| NUE575 | 9501.4 | 2.04 | 1.4E−02 | 43.55 | 1.338 | 8.7E−08 | 88.73 | 10.70 | 8.7E−08 | 88.73 |
| NUE575 | 9504.1 | 1.93 | 1.8E−01 | 35.73 | 1.259 | 2.5E−01 | 77.60 | 10.07 | 2.5E−01 | 77.60 |
| NUE575 | 9503.1 | 1.84 | 2.2E−01 | 29.22 | 1.282 | 2.0E−01 | 80.88 | 10.26 | 2.0E−01 | 80.88 |
| NUE575 | 9502.1 | 1.73 | 2.7E−01 | 21.38 | 1.097 | 2.1E−01 | 54.82 | 8.78 | 2.1E−01 | 54.82 |
| Control | | 1.42 | | | 0.709 | | | 5.67 | | |
| NUE578 | 9524.3 | 1.92 | 6.1E−02 | 34.78 | 1.274 | 4.5E−02 | 79.68 | 10.19 | 4.5E−02 | 79.68 |
| NUE578 | 9524.1 | 2.13 | 1.5E−01 | 49.88 | 1.602 | 1.4E−01 | 126.00 | 12.12 | 2.2E−01 | #### |
| NUE578 | 9523.3 | 1.97 | 1.9E−02 | 38.35 | 1.400 | 4.0E−02 | 97.45 | 11.20 | 4.0E−02 | 97.45 |
| NUE578 | 9522.3 | 1.75 | 4.8E−04 | 22.83 | 1.095 | 6.4E−05 | 54.54 | 8.76 | 6.4E−05 | 54.54 |
| Control | | 1.42 | | | 0.709 | | | 5.67 | | |
| NUE580 | 9552.3 | 1.52 | 1.2E−01 | 6.68 | 0.783 | 3.5E−02 | 10.46 | 6.26 | 3.5E−02 | 10.46 |
| NUE580 | 9551.3 | 1.71 | 1.7E−01 | 19.93 | 1.049 | 2.0E−01 | 48.02 | 8.39 | 2.0E−01 | 48.02 |
| NUE580 | 9553.4 | 1.73 | 1.1E−05 | 21.63 | 1.058 | 5.1E−06 | 49.24 | 8.46 | 5.1E−06 | 49.24 |
| NUE580 | 9551.4 | 1.85 | 6.7E−02 | 30.17 | 1.284 | 6.8E−02 | 81.21 | 10.28 | 6.8E−02 | 81.21 |
| NUE580 | 9554.4 | 1.70 | 2.7E−01 | 19.55 | 1.084 | 2.8E−01 | 52.96 | 8.67 | 2.8E−01 | 52.96 |
| Control | | 1.42 | | | 0.709 | | | 5.67 | | |
| NUE582 | 9561.1 | 1.73 | 3.0E−01 | 21.81 | 1.026 | 3.3E−01 | 44.69 | 7.60 | 2.5E−01 | 34.04 |
| NUE582 | 9562.1 | 1.60 | 3.4E−01 | 12.36 | 0.985 | 2.2E−01 | 38.99 | 7.88 | 2.2E−01 | 38.99 |
| NUE582 | 9562.4 | 1.58 | 4.7E−01 | 11.39 | 0.920 | 4.7E−01 | 29.79 | 7.00 | 6.1E−01 | 23.36 |
| NUE582 | 9563.3 | 1.76 | 2.1E−01 | 23.73 | 1.071 | 1.4E−01 | 51.05 | 8.57 | 1.4E−01 | 51.05 |
| NUE582 | 9561.2 | 1.92 | 6.2E−02 | 34.91 | 1.328 | 9.8E−02 | 87.34 | 10.02 | 2.1E−01 | 76.63 |
| Control | | 1.42 | | | 0.709 | | | 5.67 | | |

Table 38: Analyses of rosette diameter and area and plot coverage of transgenic plants overexpressing the exogenous polynucleotides of some embodiments of the invention (using the cloned or synthetic genes listed in Table 23 above) under the regulation of a constitutive promoter (35S) when grown under nitrogen deficient conditions (1.5 mM KNO$_3$, 1 mM KH$_2$PO$_4$, 1 mM MgSO$_4$, 3.6 mM K$_2$SO$_4$, 2 mM CaCl$_2$ and microelements) as compared to control plants.
"Incr." = increment; "Ave." = average.

TABLE 39

Transgenic plants exogenously expressing the polynucleotides of some embodiments of the invention exhibit improved rosette growth performance (leaf number and leaf blade) under nitrogen deficient conditions

| Gene Name | Event # | Leaf Number Ave. | p-value | % incr. | Leaf Blade Area [cm²] Ave. | p-value | % incr. |
|---|---|---|---|---|---|---|---|
| NUE241 | 9632.3 | 8.0 | 6.4E-01 | 7.34 | 0.174 | 5.3E-01 | 30.98 |
| NUE241 | 9631.4 | 8.3 | 1.6E-01 | 10.69 | 0.156 | 2.8E-02 | 17.43 |
| Control | | 7.5 | | | 0.133 | | |
| NUE249 | 9122.2 | 9.8 | 1.1E-01 | 4.20 | 0.266 | 4.7E-02 | 12.23 |
| Control | | 9.4 | | | 0.237 | | |
| NUE525 | 9534.1 | 8.8 | 5.9E-02 | 17.88 | 0.199 | 1.6E-01 | 49.90 |
| NUE525 | 9531.2 | 8.9 | 3.6E-05 | 19.80 | 0.181 | 4.1E-02 | 36.68 |
| NUE525 | 9533.1 | 7.8 | 1.9E-01 | 4.82 | 0.175 | 3.3E-01 | 31.80 |
| NUE525 | 9531.3 | 7.6 | 8.6E-01 | 2.31 | 0.149 | 6.4E-01 | 12.26 |
| NUE525 | 9533.4 | 8.3 | 8.0E-02 | 11.53 | 0.176 | 2.0E-02 | 32.40 |
| NUE525 | 9531.1 | 8.4 | 3.0E-05 | 12.37 | 0.161 | 3.4E-03 | 21.39 |
| Control | | 7.5 | | | 0.133 | | |
| NUE536 | 9234.1 | 9.4 | 9.7E-01 | 0.19 | 0.266 | 3.0E-01 | 12.00 |
| Control | | 9.4 | | | 0.237 | | |
| NUE545 | 9484.2 | 8.7 | 4.6E-02 | 16.56 | 0.216 | 2.8E-03 | 62.69 |
| NUE545 | 9482.4 | 8.0 | 4.7E-01 | 7.34 | 0.174 | 1.6E-01 | 31.20 |
| NUE545 | 9481.3 | 7.8 | 7.2E-01 | 3.98 | 0.188 | 4.7E-01 | 41.85 |
| NUE545 | 9484.4 | 8.3 | 1.6E-01 | 10.69 | 0.207 | 2.6E-07 | 56.09 |
| Control | | 7.5 | | | 0.133 | | |
| NUE549 | 9341.1 | 7.9 | 6.7E-01 | 5.66 | 0.160 | 8.3E-02 | 20.34 |
| Control | | 7.5 | | | 0.133 | | |
| NUE563 | 9454.1 | 8.3 | 1.6E-01 | 10.69 | 0.154 | 1.7E-01 | 16.19 |
| NUE563 | 9452.3 | 7.4 | 9.8E-01 | -0.21 | 0.150 | 6.1E-01 | 13.28 |
| NUE563 | 9453.4 | 8.1 | 1.9E-01 | 9.01 | 0.181 | 2.2E-01 | 36.86 |
| NUE563 | 9452.1 | | | | 0.141 | 4.4E-01 | 6.33 |
| Control | | 7.5 | | | 0.133 | | |
| NUE565 | 9444.1 | 7.7 | 8.6E-02 | 3.14 | 0.162 | 2.2E-01 | 21.85 |
| NUE565 | 9442.4 | 7.8 | 1.9E-02 | 4.82 | 0.148 | 1.4E-01 | 11.60 |
| Control | | 7.5 | | | 0.133 | | |
| NUE566 | 9514.3 | 7.8 | 4.5E-01 | 4.94 | 0.188 | 5.6E-02 | 41.70 |
| NUE566 | 9513.1 | 7.8 | 1.8E-01 | 3.98 | 0.162 | 3.2E-01 | 22.40 |
| NUE566 | 9512.4 | 8.1 | 5.4E-01 | 8.18 | 0.170 | 3.9E-01 | 28.31 |
| NUE566 | 9514.1 | 8.0 | 4.2E-01 | 7.82 | 0.180 | 1.9E-01 | 35.77 |
| Control | | 7.5 | | | 0.133 | | |
| NUE568 | 9474.4 | 7.9 | 3.1E-01 | 5.66 | 0.175 | 4.2E-02 | 31.80 |
| NUE568 | 9461.2 | 8.6 | 9.9E-03 | 15.72 | 0.195 | 9.6E-02 | 47.20 |
| NUE568 | 9462.4 | 8.1 | 1.3E-01 | 8.18 | 0.193 | 3.2E-01 | 45.51 |
| NUE568 | 9462.3 | 7.8 | 5.7E-01 | 3.98 | 0.176 | 5.3E-02 | 32.52 |
| NUE568 | 9463.4 | 7.6 | 6.1E-01 | 2.31 | 0.185 | 3.7E-01 | 39.91 |
| NUE568 | 9473.3 | 7.9 | 4.6E-01 | 6.50 | 0.148 | 1.8E-01 | 11.71 |
| Control | | 7.5 | | | 0.133 | | |
| NUE573 | 9491.4 | 7.9 | 6.7E-01 | 5.66 | 0.168 | 2.6E-01 | 27.07 |
| NUE573 | 9492.1 | 9.1 | 6.1E-02 | 22.43 | 0.234 | 3.8E-02 | 76.54 |
| NUE573 | 9493.4 | 8.0 | 3.1E-01 | 7.94 | 0.193 | 9.4E-07 | 45.94 |
| NUE573 | 9494.3 | 8.1 | 3.6E-02 | 9.01 | 0.193 | 1.3E-05 | 45.95 |
| NUE573 | 9491.2 | 8.7 | 2.0E-01 | 16.56 | 0.181 | 2.2E-01 | 36.33 |
| NUE573 | 9492.2 | 7.6 | 6.7E-01 | 1.47 | 0.183 | 5.8E-02 | 38.25 |
| Control | | 7.5 | | | 0.133 | | |
| NUE575 | 9501.4 | 8.5 | 1.1E-01 | 14.05 | 0.216 | 1.9E-02 | 62.82 |
| NUE575 | 9504.1 | 8.5 | 2.0E-01 | 14.05 | 0.214 | 2.2E-01 | 61.54 |
| NUE575 | 9503.1 | 8.4 | 3.8E-01 | 13.21 | 0.207 | 2.1E-01 | 55.92 |
| NUE575 | 9502.1 | 8.4 | 2.5E-01 | 13.21 | 0.182 | 2.6E-01 | 37.35 |
| Control | | 7.5 | | | 0.133 | | |
| NUE578 | 9524.3 | 8.4 | 2.3E-01 | 12.37 | 0.208 | 1.5E-07 | 57.07 |
| NUE578 | 9524.1 | 9.1 | 1.3E-01 | 22.19 | 0.242 | 1.6E-01 | 82.58 |
| NUE578 | 9523.3 | 8.8 | 3.1E-06 | 17.40 | 0.223 | 7.2E-02 | 68.19 |
| NUE578 | 9522.3 | 8.4 | 2.3E-01 | 12.37 | 0.178 | 2.4E-04 | 34.51 |
| Control | | 7.5 | | | 0.133 | | |
| NUE580 | 9552.3 | 8.1 | 1.6E-03 | 8.18 | 0.135 | 6.4E-01 | 1.85 |
| NUE580 | 9551.3 | 8.5 | 1.3E-05 | 14.05 | 0.175 | 2.4E-01 | 31.72 |
| NUE580 | 9553.4 | 7.9 | 1.8E-01 | 6.50 | 0.185 | 1.4E-01 | 39.73 |
| NUE580 | 9551.4 | 8.5 | 2.0E-01 | 14.05 | 0.202 | 2.0E-05 | 52.26 |
| NUE580 | 9554.4 | 7.9 | 9.4E-02 | 5.66 | 0.183 | 3.4E-01 | 38.26 |
| Control | | 7.5 | | | 0.133 | | |
| NUE582 | 9561.1 | 8.3 | 2.8E-01 | 11.29 | 0.171 | 3.9E-01 | 28.94 |
| NUE582 | 9562.1 | 8.1 | 1.9E-01 | 9.01 | 0.168 | 3.4E-01 | 26.84 |
| NUE582 | 9562.4 | 7.7 | 5.3E-01 | 2.67 | 0.164 | 5.0E-01 | 24.06 |
| NUE582 | 9563.3 | 8.4 | 1.0E-04 | 13.21 | 0.186 | 1.5E-01 | 40.09 |
| NUE582 | 9561.2 | 8.7 | 7.5E-02 | 16.08 | 0.217 | 1.5E-01 | 63.53 |
| Control | | 7.5 | | | 0.133 | | |

Table 39: Analyses of leaf number and leaf blade of transgenic plants overexpressing the exogenous polynucleotides of some embodiments of the invention (using the cloned or synthetic genes listed in Table 23 above) under the regulation of a constitutive promoter (35S) when grown under nitrogen deficient conditions (1.5 mM KNO₃, 1 mM KH₂PO₄, 1 mM MgSO₄, 3.6 mM K₂SO₄, 2 mM CaCl₂ and microelements) as compared to control plants.
"Incr." = increment; "Ave." = average.

The genes presented in Tables 40 and 41, hereinbelow, have improved plant growth rate when grown at limiting nitrogen fertilization levels. These genes improved the growth rate of the rosette and faster covered the soil when grown at limiting nitrogen growth conditions.

Tables 40 and 41 depict analyses of the growth rate of the rosette diameter, rosette area, leaf blade area, leaf number and plot coverage when grown under limiting nitrogen conditions (1.5 mM KNO₃, 1 mM KH₂PO₄, 1 mM MgSO₄, 3.6 mM K₂SO₄, 2 mM CaCl₂ and microelements) in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 40

Transgenic plants exogenously expressing the polynucleotides of some embodiments of the invention exhibit improved growth rate (RGR of leaf blade area and RGR of leaf number) under nitrogen deficient conditions

| Gene Name | Event # | RGR Of Leaf Blade Area Average | p-value | % increment | RGR Of Leaf Number Average | p-value | % increment |
|---|---|---|---|---|---|---|---|
| NUE241 | 9633.4 | 0.016 | 8.8E-01 | 1.45 | 0.567 | 0.330 | 13.34 |
| NUE241 | 9632.3 | 0.021 | 4.2E-02 | 30.38 | 0.548 | 0.538 | 9.72 |
| NUE241 | 9631.4 | 0.019 | 6.1E-02 | 17.16 | 0.536 | 0.579 | 7.27 |
| Control | | 0.016 | | | 0.500 | | |
| NUE525 | 9534.1 | 0.023 | 6.7E-05 | 43.97 | 0.612 | 0.105 | 22.43 |
| NUE525 | 9531.2 | 0.020 | 6.2E-03 | 25.68 | 0.661 | 0.016 | 32.14 |
| NUE525 | 9533.1 | 0.020 | 2.0E-02 | 25.03 | 0.503 | 0.954 | 0.71 |
| NUE525 | 9531.3 | 0.017 | 7.1E-01 | 3.98 | 0.508 | 0.918 | 1.54 |

TABLE 40-continued

Transgenic plants exogenously expressing the polynucleotides of some embodiments of the invention exhibit improved growth rate (RGR of leaf blade area and RGR of leaf number) under nitrogen deficient conditions

| Gene Name | Event # | RGR Of Leaf Blade Area | | | RGR Of Leaf Number | | |
|---|---|---|---|---|---|---|---|
| | | Average | p-value | % increment | Average | p-value | % increment |
| NUE525 | 9533.4 | 0.020 | 1.4E−02 | 22.12 | 0.560 | 0.372 | 11.94 |
| NUE525 | 9531.1 | 0.018 | 1.3E−01 | 13.01 | 0.557 | 0.392 | 11.36 |
| Control | | 0.016 | | | 0.500 | | |
| NUE545 | 9484.2 | 0.026 | 1.1E−07 | 60.54 | | | |
| NUE545 | 9482.4 | 0.021 | 6.0E−03 | 28.52 | | | |
| NUE545 | 9482.2 | 0.018 | | 9.81 | | | |
| NUE545 | 9481.3 | 0.022 | 2.1E−02 | 39.32 | | | |
| NUE545 | 9484.4 | 0.025 | 1.3E−06 | 54.25 | | | |
| Control | | 0.016 | | | | | |
| NUE549 | 9341.1 | 0.018 | 1.6E−01 | 12.49 | | | |
| Control | | 0.016 | | | | | |
| NUE563 | 9454.1 | 0.018 | 1.4E−01 | 13.13 | 0.544 | 0.509 | 8.79 |
| NUE563 | 9452.3 | 0.018 | 3.7E−01 | 9.76 | | | |
| NUE563 | 9453.4 | 0.021 | 2.7E−03 | 30.97 | 0.580 | 0.223 | 16.07 |
| Control | | 0.016 | | | 0.500 | | |
| NUE565 | 9444.1 | 0.020 | 3.2E−02 | 21.06 | | | |
| Control | | 0.016 | | | | | |
| NUE566 | 9514.3 | 0.022 | 3.5E−03 | 34.09 | 0.558 | 0.384 | 11.55 |
| NUE566 | 9513.1 | 0.020 | 3.2E−02 | 22.23 | 0.551 | 0.432 | 10.19 |
| NUE566 | 9512.4 | 0.021 | 1.2E−02 | 31.16 | 0.575 | 0.285 | 14.98 |
| NUE566 | 9514.1 | 0.021 | 5.5E−03 | 29.97 | 0.515 | | 3.05 |
| Control | | 0.016 | | | 0.500 | | |
| NUE568 | 9474.4 | 0.022 | 6.2E−04 | 34.41 | | | |
| NUE568 | 9461.2 | 0.024 | 1.2E−04 | 46.02 | 0.567 | 0.327 | 13.35 |
| NUE568 | 9462.4 | 0.024 | 5.3E−04 | 48.85 | 0.527 | 0.687 | 5.52 |
| NUE568 | 9462.3 | 0.022 | 1.2E−03 | 35.77 | | | |
| NUE568 | 9463.4 | 0.022 | 2.5E−03 | 38.12 | | | |
| Control | | 0.016 | | | 0.500 | | |
| NUE573 | 9491.4 | 0.018 | 1.4E−01 | 14.16 | | | |
| NUE573 | 9492.1 | 0.029 | 7.4E−09 | 77.15 | 0.606 | 0.122 | 21.29 |
| NUE573 | 9493.4 | 0.023 | 9.0E−05 | 42.33 | 0.539 | 0.549 | 7.79 |
| NUE573 | 9494.3 | 0.023 | 1.3E−04 | 40.79 | 0.573 | 0.271 | 14.63 |
| NUE573 | 9491.2 | 0.020 | 9.4E−03 | 26.53 | 0.565 | 0.383 | 13.00 |
| NUE573 | 9492.2 | 0.022 | 4.2E−04 | 39.19 | | | |
| Control | | 0.016 | | | 0.500 | | |
| NUE575 | 9501.4 | 0.026 | 2.8E−07 | 59.00 | 0.554 | 0.441 | 10.78 |
| NUE575 | 9504.3 | 0.016 | 8.9E−01 | −1.86 | 0.517 | 0.813 | 3.41 |
| NUE575 | 9504.1 | 0.025 | 1.3E−04 | 55.64 | 0.560 | 0.398 | 12.06 |
| NUE575 | 9503.1 | 0.024 | 1.4E−04 | 51.12 | 0.615 | 0.126 | 23.04 |
| NUE575 | 9502.1 | 0.021 | 1.5E−02 | 28.36 | 0.513 | 0.852 | 2.58 |
| Control | | 0.016 | | | 0.500 | | |
| NUE578 | 9524.3 | 0.025 | 4.9E−06 | 56.63 | 0.575 | 0.268 | 14.98 |
| NUE578 | 9524.1 | 0.029 | 3.0E−07 | 77.86 | 0.630 | 0.050 | 25.93 |
| NUE578 | 9523.3 | 0.027 | 6.9E−08 | 65.64 | 0.561 | 0.372 | 12.29 |
| NUE578 | 9522.3 | 0.021 | 1.6E−03 | 32.66 | 0.606 | 0.119 | 21.29 |
| Control | | 0.016 | | | 0.500 | | |
| NUE580 | 9551.3 | 0.021 | 6.5E−03 | 28.15 | 0.538 | 0.545 | 7.62 |
| NUE580 | 9554.2 | | | | 0.564 | 0.339 | 12.76 |
| NUE580 | 9553.4 | 0.023 | 1.5E−04 | 40.79 | 0.526 | 0.686 | 5.28 |
| NUE580 | 9551.4 | 0.024 | 1.3E−05 | 47.33 | 0.524 | 0.734 | 4.82 |
| NUE580 | 9554.4 | 0.022 | 4.0E−03 | 37.25 | | | |
| Control | | 0.016 | | | 0.500 | | |
| NUE582 | 9561.1 | 0.021 | 1.3E−02 | 29.36 | 0.585 | 0.225 | 16.94 |
| NUE582 | 9562.1 | 0.020 | 1.8E−02 | 26.50 | 0.560 | 0.379 | 11.94 |
| NUE582 | 9562.4 | 0.020 | 3.7E−02 | 26.29 | 0.556 | 0.464 | 11.24 |
| NUE582 | 9563.3 | 0.023 | 1.7E−04 | 44.35 | 0.615 | 0.113 | 23.04 |
| NUE582 | 9561.2 | 0.026 | 1.4E−06 | 61.66 | 0.605 | 0.124 | 21.11 |
| Control | | 0.016 | | | 0.500 | | |

Table 40: Analyses of growth rate (RGR of leaf blade area and RGR of leaf number) of transgenic plants overexpressing the exogenous polynucleotides of some embodiments of the invention (using the cloned or synthetic genes listed in Table 23 above) under the regulation of a constitutive promoter (35S) when grown under nitrogen deficient conditions (1.5 mM $KNO_3$, 1 mM $KH_2PO_4$, 1 mM $MgSO_4$, 3.6 mM $K_2SO_4$, 2 mM $CaCl_2$ and microelements) as compared to control plants.

TABLE 41

Transgenic plants exogenously expressing the polynucleotides of some embodiments of the invention exhibit improved growth rate (RGR of rosette area and diameter and RGR of plot coverage) under nitrogen deficient conditions

| Gene Name | Event # | RGR Of Rosette Area | | | RGR Of Rosette Diameter | | | RGR Of Plot Coverage | | |
|---|---|---|---|---|---|---|---|---|---|---|
| | | Ave. | p-value | % incr. | Ave. | p-value | % incr. | Ave. | p-value | % incr. |
| NUE241 | 9633.4 | 0.102 | 2.9E−01 | 13.04 | 0.130 | 6.4E−01 | −3.23 | 0.82 | 2.9E−01 | 13.04 |
| NUE241 | 9632.3 | 0.131 | 2.2E−02 | 44.18 | 0.163 | 5.3E−02 | 21.41 | 1.05 | 2.2E−02 | 44.18 |
| NUE241 | 9631.4 | 0.114 | 2.6E−02 | 25.68 | 0.151 | 8.4E−02 | 12.12 | 0.91 | 2.6E−02 | 25.68 |
| Control | | 0.091 | | | 0.135 | | | 0.72 | | |
| NUE525 | 9534.1 | 0.160 | 3.4E−07 | 76.36 | 0.164 | 3.4E−03 | 21.78 | 1.20 | 2.3E−05 | 66.06 |
| NUE525 | 9531.2 | 0.150 | 3.9E−06 | 65.52 | 0.161 | 7.7E−03 | 19.52 | 1.13 | 2.0E−04 | 55.87 |
| NUE525 | 9533.1 | 0.135 | 3.4E−04 | 48.53 | 0.153 | 5.1E−02 | 13.37 | 1.08 | 3.4E−04 | 48.53 |
| NUE525 | 9531.3 | 0.111 | 1.1E−01 | 22.62 | 0.135 | 9.8E−01 | 0.21 | 0.89 | 1.1E−01 | 22.62 |
| NUE525 | 9533.4 | 0.130 | 3.6E−04 | 43.83 | 0.149 | 1.1E−01 | 11.07 | 1.04 | 3.6E−04 | 43.83 |
| NUE525 | 9531.1 | 0.129 | 6.5E−04 | 42.14 | 0.140 | 5.5E−01 | 4.10 | 1.03 | 6.5E−04 | 42.14 |
| Control | | 0.091 | | | 0.135 | | | 0.72 | | |
| NUE545 | 9484.2 | 0.168 | 4.4E−08 | 85.85 | 0.184 | 4.2E−06 | 36.37 | 1.35 | 4.4E−08 | 85.85 |
| NUE545 | 9482.4 | 0.127 | 3.1E−03 | 40.34 | 0.154 | 6.9E−02 | 14.35 | 1.02 | 3.1E−03 | 40.34 |
| NUE545 | 9482.2 | 0.098 | | 8.66 | 0.135 | 9.6E−01 | 0.34 | 0.79 | 4.4E−01 | 8.66 |
| NUE545 | 9481.3 | 0.130 | 2.3E−02 | 43.77 | 0.173 | 3.3E−02 | 28.42 | 1.04 | 2.3E−02 | 43.77 |
| NUE545 | 9484.4 | 0.163 | 2.7E−07 | 79.91 | 0.194 | 4.6E−07 | 43.83 | 1.30 | 2.7E−07 | 79.91 |
| Control | | 0.091 | | | 0.135 | | | 0.72 | | |
| NUE549 | 9341.1 | 0.118 | 1.4E−02 | 30.70 | 0.140 | 6.0E−01 | 3.79 | 0.95 | 1.4E−02 | 30.70 |
| Control | | 0.091 | | | 0.135 | | | 0.72 | | |
| NUE563 | 9454.1 | 0.119 | 9.5E−03 | 31.19 | 0.148 | 1.5E−01 | 9.88 | 0.95 | 9.5E−03 | 31.19 |
| NUE563 | 9452.3 | 0.104 | 2.4E−01 | 15.20 | 0.140 | 6.0E−01 | 4.00 | 0.84 | 2.4E−01 | 15.20 |
| NUE563 | 9453.4 | 0.137 | 2.1E−04 | 51.54 | 0.155 | 3.6E−02 | 15.50 | 1.10 | 2.1E−04 | 51.54 |
| Control | | 0.091 | | | 0.135 | | | 0.72 | | |
| NUE565 | 9444.1 | 0.111 | 6.2E−02 | 22.99 | 0.157 | 6.4E−02 | 16.45 | 0.89 | 6.2E−02 | 22.99 |
| Control | | 0.091 | | | 0.135 | | | 0.72 | | |
| NUE566 | 9514.3 | 0.143 | 3.0E−04 | 58.15 | 0.162 | 4.2E−02 | 20.44 | 1.07 | 6.9E−04 | 47.03 |
| NUE566 | 9513.1 | 0.118 | 1.7E−02 | 30.34 | 0.155 | 4.8E−02 | 14.92 | 0.94 | 1.7E−02 | 30.34 |
| NUE566 | 9512.4 | 0.121 | 2.4E−02 | 33.06 | 0.156 | 7.6E−02 | 15.84 | 0.96 | 2.4E−02 | 33.06 |
| NUE566 | 9514.1 | 0.134 | 1.1E−03 | 48.17 | 0.160 | 1.1E−02 | 18.57 | 1.02 | 1.0E−02 | 40.14 |
| Control | | 0.091 | | | 0.135 | | | 0.72 | | |
| NUE568 | 9474.4 | 0.121 | 7.0E−03 | 33.08 | 0.160 | 1.2E−02 | 19.19 | 0.96 | 7.0E−03 | 33.08 |
| NUE568 | 9461.2 | 0.157 | 7.6E−06 | 73.36 | 0.170 | 4.1E−03 | 26.24 | 1.26 | 7.6E−06 | 73.36 |
| NUE568 | 9462.4 | 0.139 | 5.3E−04 | 53.79 | 0.172 | 5.8E−03 | 27.76 | 1.11 | 5.3E−04 | 53.79 |
| NUE568 | 9462.3 | 0.131 | 1.4E−03 | 44.88 | 0.167 | 1.3E−03 | 23.84 | 1.05 | 1.4E−03 | 44.88 |
| NUE568 | 9463.4 | 0.129 | 3.7E−03 | 42.01 | 0.159 | 2.5E−02 | 18.33 | 1.03 | 3.7E−03 | 42.01 |
| Control | | 0.091 | | | 0.135 | | | 0.72 | | |
| NUE573 | 9491.4 | 0.123 | 6.0E−03 | 35.42 | 0.149 | 1.7E−01 | 10.44 | 0.98 | 6.0E−03 | 35.42 |
| NUE573 | 9492.1 | 0.182 | 5.7E−09 | 100.76 | 0.190 | 1.2E−06 | 41.04 | 1.46 | 5.7E−09 | 100.76 |
| NUE573 | 9493.4 | 0.141 | 5.6E−05 | 55.36 | 0.166 | 2.1E−03 | 23.03 | 1.06 | 6.8E−04 | 45.86 |
| NUE573 | 9494.3 | 0.151 | 5.3E−06 | 66.87 | 0.171 | 6.6E−04 | 26.79 | 1.21 | 5.3E−06 | 66.87 |
| NUE573 | 9491.2 | 0.139 | 1.3E−04 | 53.69 | 0.164 | 1.1E−02 | 21.53 | 1.11 | 1.3E−04 | 53.69 |
| NUE573 | 9492.2 | 0.130 | 1.5E−03 | 43.69 | 0.165 | 4.8E−03 | 22.63 | 1.04 | 1.5E−03 | 43.69 |
| Control | | 0.091 | | | 0.135 | | | 0.72 | | |
| NUE575 | 9501.4 | 0.172 | 9.2E−09 | 89.99 | 0.198 | 1.1E−07 | 47.36 | 1.38 | 9.2E−09 | 89.99 |
| NUE575 | 9504.3 | 0.095 | 7.7E−01 | 4.69 | 0.135 | 1.0E+00 | −0.04 | 0.76 | 7.7E−01 | 4.69 |
| NUE575 | 9504.1 | 0.160 | 4.5E−05 | 76.22 | 0.178 | 3.5E−03 | 32.48 | 1.28 | 4.5E−05 | 76.22 |
| NUE575 | 9503.1 | 0.165 | 4.1E−06 | 82.22 | 0.168 | 1.2E−02 | 24.58 | 1.32 | 4.1E−06 | 82.22 |
| NUE575 | 9502.1 | 0.136 | 9.0E−04 | 50.03 | 0.151 | 1.3E−01 | 12.57 | 1.09 | 9.0E−04 | 50.03 |
| Control | | 0.091 | | | 0.135 | | | 0.72 | | |
| NUE578 | 9524.3 | 0.165 | 6.9E−07 | 81.99 | 0.185 | 2.5E−04 | 37.68 | 1.32 | 6.9E−07 | 81.99 |
| NUE578 | 9524.1 | 0.206 | 3.9E−09 | 127.63 | 0.202 | 1.1E−06 | 49.79 | 1.56 | 4.4E−07 | 115.41 |
| NUE578 | 9523.3 | 0.181 | 4.2E−09 | 99.40 | 0.179 | 1.9E−05 | 33.16 | 1.45 | 4.2E−09 | 99.40 |
| NUE578 | 9522.3 | 0.141 | 6.5E−05 | 55.95 | 0.167 | 1.6E−03 | 24.01 | 1.13 | 6.5E−05 | 55.95 |
| Control | | 0.091 | | | 0.135 | | | 0.72 | | |
| NUE580 | 9551.3 | 0.135 | 3.5E−04 | 48.50 | 0.157 | 2.7E−02 | 16.48 | 1.08 | 3.5E−04 | 48.50 |
| NUE580 | 9554.2 | 0.093 | 8.5E−01 | | 0.130 | 7.1E−01 | | 0.74 | 8.5E−01 | |
| NUE580 | 9553.4 | 0.137 | 1.5E−04 | 51.17 | 0.169 | 8.0E−04 | 25.59 | 1.10 | 1.5E−04 | 51.17 |
| NUE580 | 9551.4 | 0.165 | 2.1E−07 | 82.42 | 0.170 | 1.3E−03 | 26.33 | 1.32 | 2.1E−07 | 82.42 |
| NUE580 | 9554.4 | 0.138 | 1.0E−03 | 52.73 | 0.152 | 9.4E−02 | 12.99 | 1.11 | 1.0E−03 | 52.73 |
| Control | | 0.091 | | | 0.135 | | | 0.72 | | |
| NUE582 | 9561.1 | 0.133 | 2.5E−03 | 47.08 | 0.167 | 6.9E−03 | 24.32 | 0.99 | 7.7E−03 | 36.09 |
| NUE582 | 9562.1 | 0.127 | 3.4E−03 | 40.44 | 0.152 | 7.7E−02 | 13.15 | 1.02 | 3.4E−03 | 40.44 |

TABLE 41-continued

Transgenic plants exogenously expressing the polynucleotides of some embodiments of the invention exhibit improved growth rate (RGR of rosette area and diameter and RGR of plot coverage) under nitrogen deficient conditions

| Gene Name | Event # | RGR Of Rosette Area | | | RGR Of Rosette Diameter | | | RGR Of Plot Coverage | | |
|---|---|---|---|---|---|---|---|---|---|---|
| | | Ave. | p-value | % incr. | Ave. | p-value | % incr. | Ave. | p-value | % incr. |
| NUE582 | 9562.4 | 0.120 | 2.8E−02 | 32.82 | 0.153 | 1.1E−01 | 13.90 | 0.91 | 1.0E−01 | 26.19 |
| NUE582 | 9563.3 | 0.141 | 2.1E−04 | 55.33 | 0.178 | 4.6E−04 | 32.62 | 1.13 | 2.1E−04 | 55.33 |
| NUE582 | 9561.2 | 0.172 | 9.3E−08 | 89.88 | 0.186 | 1.1E−05 | 37.84 | 1.30 | 4.6E−06 | 79.08 |
| Control | | 0.091 | | | 0.135 | | | 0.72 | | |

Table 41: Analyses of growth rate (RGR of rosette area and diameter and RGR of plot coverage) of transgenic plants overexpressing the exogenous polynucleotides of some embodiments of the invention (using the cloned or synthetic genes listed in Table 23 above) under the regulation of a constitutive promoter (35S) when grown under nitrogen deficient conditions (1.5 mM $KNO_3$, 1 mM $KH_2PO_4$, 1 mM $MgSO_4$, 3.6 mM $K_2SO_4$, 2 mM $CaCl_2$ and microelements) as compared to control plants.

The genes presented in Tables 42 and 43, hereinbelow, have improved plant NUE and produced larger plant biomass when grown under standard nitrogen fertilization conditions, compared to control plants. In addition a production of a larger number of leaves as well as a higher plot coverage when grown at low nitrogen conditions indicate a larger photosynthetic capacity of the plant when grown at high nitrogen growth conditions. Table 42 and 43 depict analyses of rosette area and leaf number (rosette diameter, rosette area, leaf number, leaf blade area and plot coverage) when grown under standard nitrogen fertilization conditions (6 mM $KNO_3$, 1 mM $KH_2PO_4$, 1 mM $MgSO_4$, 2 mM $CaCl_2$ and microelements) in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 42

Transgenic plants exogenously expressing the polynucleotides of some embodiments of the invention exhibit improved rosette growth performance (rosette diameter and area and plot coverage) under standard nitrogen conditions

| Gene Name | Event # | Rosette Diameter [cm] | | | Rosette Area [cm²] | | | Plot Coverage [%] | | |
|---|---|---|---|---|---|---|---|---|---|---|
| | | Ave. | P-Value | % incr. | Ave. | P-Value | % incr. | Ave. | P-Value | % incr. |
| NUE230 | 9154.2 | 2.16 | 1.1E−02 | 6.87 | 1.57 | 4.6E−03 | 17.45 | 12.56 | 4.6E−03 | 17.45 |
| Control | | 2.02 | | | 1.34 | | | 10.69 | | |
| NUE234 | 9163.4 | 2.40 | 2.7E−02 | 18.64 | 1.72 | 1.7E−02 | 28.84 | 13.78 | 1.7E−02 | 28.84 |
| NUE234 | 9162.5 | 2.14 | 2.1E−02 | 5.87 | 1.52 | 1.6E−02 | 13.45 | 12.13 | 1.6E−02 | 13.45 |
| Control | | 2.02 | | | 1.34 | | | 10.69 | | |
| NUE248 | 8983.1 | 2.21 | 2.2E−03 | 9.45 | 1.58 | 3.5E−03 | 18.29 | 12.65 | 3.5E−03 | 18.29 |
| Control | | 2.02 | | | 1.34 | | | 10.69 | | |
| NUE249 | 9122.2 | 2.27 | 8.3E−02 | 12.44 | 1.62 | 1.8E−03 | 20.83 | 12.92 | 1.8E−03 | 20.83 |
| Control | | 2.02 | | | 1.34 | | | 10.69 | | |
| NUE268 | 8996.3 | 2.17 | 1.2E−02 | 7.34 | 1.64 | 2.2E−03 | 23.05 | 13.16 | 2.2E−03 | 23.05 |
| Control | | 2.02 | | | 1.34 | | | 10.69 | | |
| NUE525 | 9534.1 | 1.96 | 1.0E−01 | 12.33 | 1.37 | 4.5E−02 | 27.78 | 10.97 | 4.5E−02 | 27.78 |
| NUE525 | 9531.2 | 2.17 | 8.8E−02 | 24.47 | 1.65 | 7.2E−02 | 53.32 | 13.17 | 7.2E−02 | 53.32 |
| NUE525 | 9533.1 | 2.11 | 3.4E−01 | 21.09 | 1.57 | 3.5E−01 | 46.56 | 12.59 | 3.5E−01 | 46.56 |
| NUE525 | 9531.3 | 2.00 | 2.9E−02 | 14.68 | 1.47 | 1.9E−02 | 37.33 | 11.79 | 1.9E−02 | 37.33 |
| NUE525 | 9533.4 | 2.08 | 3.2E−01 | 19.24 | 1.47 | 3.6E−01 | 36.69 | 11.74 | 3.6E−01 | 36.69 |
| Control | | 1.75 | | | 1.07 | | | 8.59 | | |
| NUE536 | 9233.3 | 2.28 | 2.2E−01 | 12.83 | 1.71 | 1.7E−01 | 27.70 | 13.66 | 1.7E−01 | 27.70 |
| NUE536 | 9234.1 | 2.43 | 6.8E−02 | 20.35 | 1.92 | 2.6E−02 | 43.88 | 15.39 | 2.6E−02 | 43.88 |
| Control | | 2.02 | | | 1.34 | | | 10.69 | | |
| NUE545 | 9484.2 | 2.37 | 1.2E−03 | 35.50 | 1.74 | 8.5E−03 | 62.13 | 13.92 | 8.5E−03 | 62.13 |
| NUE545 | 9482.4 | 1.93 | 6.8E−02 | 10.29 | 1.37 | 5.9E−01 | 27.95 | 10.99 | 5.9E−01 | 27.95 |
| NUE545 | 9481.3 | 2.09 | 8.6E−03 | 19.87 | 1.51 | 7.8E−03 | 40.62 | 12.08 | 7.8E−03 | 40.62 |
| NUE545 | 9484.4 | 2.15 | 8.4E−02 | 22.97 | 1.55 | 1.7E−01 | 43.98 | 12.37 | 1.7E−01 | 43.98 |
| Control | | 1.75 | | | 1.07 | | | 8.59 | | |
| NUE549 | 9343.6 | 1.93 | 4.9E−01 | 10.73 | 1.22 | 6.2E−01 | 13.86 | 9.78 | 6.2E−01 | 13.86 |
| NUE549 | 9341.1 | 1.94 | 5.1E−01 | 11.16 | 1.33 | 4.3E−01 | 23.54 | 10.61 | 4.3E−01 | 23.54 |
| NUE549 | 9342.3 | 2.01 | 2.7E−02 | 15.03 | 1.38 | 4.3E−02 | 28.53 | 11.04 | 4.3E−02 | 28.53 |
| Control | | 1.75 | | | 1.07 | | | 8.59 | | |
| NUE560 | 9423.4 | 2.23 | 4.7E−01 | 10.17 | 1.66 | 4.2E−01 | 24.21 | 13.28 | 4.2E−01 | 24.21 |
| Control | | 2.02 | | | 1.34 | | | 10.69 | | |
| NUE568 | 9461.2 | 2.35 | 2.3E−03 | 34.72 | 2.01 | 1.3E−02 | 87.26 | 16.08 | 1.3E−02 | 87.26 |
| NUE568 | 9461.3 | 2.05 | 9.9E−02 | 17.54 | 1.48 | 7.0E−02 | 38.17 | 11.87 | 7.0E−02 | 38.17 |

TABLE 42-continued

Transgenic plants exogenously expressing the polynucleotides of some embodiments of the invention exhibit improved rosette growth performance (rosette diameter and area and plot coverage) under standard nitrogen conditions

| Gene Name | Event # | Rosette Diameter [cm] | | | Rosette Area [cm$^2$] | | | Plot Coverage [%] | | |
|---|---|---|---|---|---|---|---|---|---|---|
| | | Ave. | P-Value | % incr. | Ave. | P-Value | % incr. | Ave. | P-Value | % incr. |
| NUE568 | 9462.4 | 1.92 | 2.1E−01 | 9.87 | 1.25 | 3.4E−01 | 16.76 | 9.46 | 6.7E−01 | 10.14 |
| NUE568 | 9463.4 | 2.01 | 7.4E−02 | 14.90 | 1.41 | 7.7E−02 | 31.41 | 11.29 | 7.7E−02 | 31.41 |
| Control | | 1.75 | | | 1.07 | | | 8.59 | | |
| NUE573 | 9491.4 | 2.10 | 9.7E−03 | 20.13 | 1.48 | 1.4E−02 | 37.74 | 11.83 | 1.4E−02 | 37.74 |
| NUE573 | 9492.1 | 2.01 | 1.0E−01 | 15.05 | 1.36 | 7.2E−02 | 26.45 | 8.02 | 8.5E−01 | −6.67 |
| NUE573 | 9493.4 | 1.99 | 1.3E−01 | 14.08 | 1.38 | 7.7E−02 | 28.86 | 10.42 | 3.7E−01 | 21.28 |
| NUE573 | 9491.2 | 2.18 | 1.1E−01 | 25.09 | 1.59 | 1.3E−01 | 48.09 | 12.72 | 1.3E−01 | 48.09 |
| NUE573 | 9494.3 | 1.98 | 7.0E−02 | 13.52 | 1.45 | 1.0E−01 | 34.78 | 11.57 | 1.0E−01 | 34.78 |
| NUE573 | 9492.2 | 1.94 | 4.4E−01 | 11.14 | 1.46 | 5.2E−01 | 35.94 | 9.79 | 5.7E−01 | 14.02 |
| Control | | 1.75 | | | 1.07 | | | 8.59 | | |
| NUE575 | 9501.4 | 1.96 | 2.8E−01 | 12.36 | 1.31 | 2.7E−01 | 22.00 | 10.48 | 2.7E−01 | 22.00 |
| NUE575 | 9504.1 | 2.13 | 4.8E−02 | 21.96 | 1.58 | 7.9E−02 | 47.31 | 12.65 | 7.9E−02 | 47.31 |
| NUE575 | 9503.1 | 1.95 | 9.7E−02 | 11.94 | 1.24 | 3.4E−01 | 15.70 | 9.94 | 3.4E−01 | 15.70 |
| NUE575 | 9502.1 | 1.99 | 4.1E−01 | 14.24 | 1.44 | 3.8E−01 | 34.12 | 10.35 | 6.9E−01 | 20.49 |
| Control | | 1.75 | | | 1.07 | | | 8.59 | | |
| NUE578 | 9524.1 | 2.15 | 3.4E−03 | 23.14 | 1.64 | 1.9E−03 | 52.74 | 13.12 | 1.9E−03 | 52.74 |
| NUE578 | 9524.3 | 2.08 | 6.0E−01 | 18.89 | 1.58 | 5.2E−01 | 47.61 | 12.68 | 5.2E−01 | 47.61 |
| NUE578 | 9523.3 | 2.37 | 8.6E−02 | 35.89 | 1.79 | 2.9E−02 | 66.79 | 13.36 | 1.4E−03 | 55.59 |
| NUE578 | 9522.3 | 2.07 | 1.3E−01 | 18.61 | 1.63 | 1.2E−01 | 51.78 | 13.03 | 1.2E−01 | 51.78 |
| Control | | 1.75 | | | 1.07 | | | 8.59 | | |
| NUE580 | 9552.3 | 1.92 | 1.1E−01 | 10.01 | 1.24 | 2.4E−01 | 15.83 | 9.95 | 2.4E−01 | 15.83 |
| NUE580 | 9551.3 | 1.98 | 4.3E−02 | 13.26 | 1.47 | 1.4E−02 | 37.05 | 11.77 | 1.4E−02 | 37.05 |
| NUE580 | 9554.4 | 2.03 | 3.7E−01 | 16.34 | 1.52 | 2.0E−01 | 41.78 | 12.18 | 2.0E−01 | 41.78 |
| Control | | 1.75 | | | 1.07 | | | 8.59 | | |
| NUE582 | 9561.1 | 2.25 | 9.2E−02 | 28.98 | 1.73 | 1.6E−01 | 61.52 | 13.87 | 1.6E−01 | 61.52 |
| NUE582 | 9561.2 | 2.10 | 7.1E−03 | 20.11 | 1.56 | 4.6E−03 | 45.40 | 12.49 | 4.6E−03 | 45.40 |
| Control | | 1.75 | | | 1.07 | | | 8.59 | | |
| NUE585 | 9661.1 | 2.46 | 4.9E−02 | 21.69 | 2.02 | 1.2E−05 | 50.77 | 16.12 | 1.2E−05 | 50.77 |
| Control | | 2.02 | | | 1.34 | | | 10.69 | | |
| NUE588 | 9591.3 | 2.14 | 1.3E−01 | 5.91 | 1.50 | 5.3E−02 | 12.38 | 12.02 | 5.3E−02 | 12.38 |
| Control | | 2.02 | | | 1.34 | | | 10.69 | | |

Table 42: Analyses of rosette growth performance (rosette diameter and area and plot coverage) of transgenic plants overexpressing the exogenous polynucleotides of some embodiments of the invention (using the cloned or synthetic genes listed in Table 23 above) under the regulation of a constitutive promoter (35S) when grown under standard nitrogen (6 mM KNO$_3$, 1 mM KH$_2$PO$_4$, 1 mM MgSO$_4$, 2 mM CaCl$_2$ and microelements) as compared to control plants.

TABLE 43

Transgenic plants exogenously expressing the polynucleotides of some embodiments of the invention exhibit improved rosette growth performance (leaf number and leaf blade area) under standard nitrogen conditions

| Gene Name | Event # | Leaf Number | | | Leaf Blade Area [cm$^2$] | | |
|---|---|---|---|---|---|---|---|
| | | Ave. | P-Value | % incr. | Ave. | P-Value | % incr. |
| NUE230 | 9154.2 | 8.75 | 1.4E−01 | 4.03 | 0.26 | 7.3E−03 | 16.16 |
| Control | | 8.41 | | | 0.23 | | |
| NUE234 | 9163.4 | 8.88 | 4.2E−01 | 5.52 | 0.28 | 2.9E−02 | 23.30 |
| NUE234 | 9162.5 | 8.06 | 5.7E−01 | −4.14 | 0.26 | 9.0E−02 | 12.41 |
| Control | | 8.41 | | | 0.23 | | |
| NUE248 | 8983.1 | 8.75 | 1.4E−01 | 4.03 | 0.25 | 1.0E−02 | 11.97 |
| Control | | 8.41 | | | 0.23 | | |
| NUE249 | 9122.2 | 9.25 | 2.2E−02 | 9.98 | 0.27 | 3.5E−03 | 17.48 |
| Control | | 8.41 | | | 0.23 | | |
| NUE268 | 8996.3 | 8.81 | 1.4E−02 | 4.78 | 0.28 | 6.2E−04 | 21.22 |
| Control | | 8.41 | | | 0.23 | | |
| NUE525 | 9534.1 | 8.88 | 3.4E−02 | 9.44 | 0.23 | 6.6E−02 | 20.64 |
| NUE525 | 9531.2 | 9.06 | 9.5E−03 | 11.75 | 0.26 | 1.3E−01 | 39.24 |
| NUE525 | 9533.1 | 8.63 | 5.6E−01 | 6.36 | 0.24 | 3.4E−01 | 29.39 |
| NUE525 | 9531.3 | 8.69 | 4.8E−01 | 7.13 | 0.23 | 2.3E−02 | 23.65 |
| NUE525 | 9533.4 | 8.88 | 4.8E−01 | 9.44 | 0.23 | 3.5E−01 | 24.51 |
| Control | | 8.11 | | | 0.19 | | |
| NUE536 | 9233.3 | 9.50 | 1.2E−02 | 12.95 | 0.27 | 2.8E−01 | 18.94 |
| NUE536 | 9234.1 | 9.44 | 6.1E−02 | 12.21 | 0.29 | 7.6E−02 | 28.74 |
| Control | | 8.41 | | | 0.23 | | |
| NUE545 | 9484.2 | 9.31 | 1.5E−01 | 14.84 | 0.28 | 2.1E−03 | 47.68 |
| NUE545 | 9482.4 | 8.56 | 6.3E−01 | 5.59 | 0.22 | 6.6E−01 | 18.07 |
| NUE545 | 9481.3 | 8.06 | 8.7E−01 | −0.58 | 0.27 | 1.2E−03 | 41.88 |
| NUE545 | 9484.4 | 8.88 | 1.1E−01 | 9.44 | 0.25 | 8.3E−02 | 31.54 |
| Control | | 8.11 | | | 0.19 | | |
| NUE549 | 9343.6 | 8.81 | 7.7E−02 | 8.67 | 0.20 | 6.6E−01 | 8.33 |
| NUE549 | 9341.1 | 8.44 | 6.7E−01 | 4.05 | 0.21 | 6.0E−01 | 14.37 |
| NUE549 | 9342.3 | 9.06 | 1.1E−01 | 11.75 | 0.21 | 1.3E−01 | 13.98 |
| Control | | 8.11 | | | 0.19 | | |
| NUE560 | 9423.4 | 8.75 | 1.3E−02 | 4.03 | 0.28 | 4.4E−01 | 21.95 |
| Control | | 8.41 | | | 0.23 | | |
| NUE568 | 9461.2 | 9.63 | 1.5E−02 | 18.69 | 0.30 | 2.1E−02 | 59.80 |
| NUE568 | 9461.3 | 8.94 | 2.6E−01 | 10.21 | 0.23 | 3.2E−02 | 25.07 |
| NUE568 | 9462.4 | 8.48 | 3.5E−01 | 4.60 | 0.21 | 4.6E−01 | 13.21 |
| NUE568 | 9463.4 | 8.69 | 7.2E−02 | 7.13 | 0.24 | 7.0E−02 | 28.16 |
| Control | | 8.11 | | | 0.19 | | |
| NUE573 | 9491.4 | 8.63 | 2.3E−01 | 6.36 | 0.23 | 6.2E−02 | 22.82 |
| NUE573 | 9492.1 | 8.81 | 7.7E−02 | 8.67 | 0.23 | 3.9E−02 | 20.79 |
| NUE573 | 9493.4 | 8.86 | 4.2E−02 | 9.22 | 0.22 | 8.1E−02 | 17.66 |
| NUE573 | 9491.2 | 8.63 | 1.2E−01 | 6.36 | 0.25 | 1.2E−01 | 33.61 |
| NUE573 | 9494.3 | 9.13 | 1.5E−02 | 12.52 | 0.23 | 9.9E−02 | 20.47 |
| NUE573 | 9492.2 | 8.46 | 7.1E−01 | 4.30 | 0.23 | 5.5E−01 | 25.07 |

TABLE 43-continued

Transgenic plants exogenously expressing the polynucleotides of some embodiments of the invention exhibit improved rosette growth performance (leaf number and leaf blade area) under standard nitrogen conditions

| Gene Name | Event # | Leaf Number Ave. | P-Value | % incr. | Leaf Blade Area [cm²] Ave. | P-Value | % incr. |
|---|---|---|---|---|---|---|---|
| Control |  | 8.11 |  |  | 0.19 |  |  |
| NUE575 | 9501.4 | 8.38 | 3.6E-01 | 3.28 | 0.21 | 3.9E-01 | 14.56 |
| NUE575 | 9504.1 | 9.06 | 9.5E-03 | 11.75 | 0.25 | 1.1E-01 | 33.06 |
| NUE575 | 9503.1 | 8.06 | 9.2E-01 | -0.58 | 0.22 | 3.3E-01 | 16.13 |
| NUE575 | 9502.1 | 8.98 | 3.9E-01 | 10.73 | 0.22 | 3.0E-01 | 18.72 |
| Control |  | 8.11 |  |  | 0.19 |  |  |
| NUE578 | 9524.1 | 8.50 | 1.9E-01 | 4.82 | 0.26 | 7.3E-03 | 40.77 |
| NUE578 | 9524.3 | 8.31 | 8.7E-01 | 2.50 | 0.25 | 5.4E-03 | 32.70 |
| NUE578 | 9523.3 | 9.48 | 1.5E-02 | 16.93 | 0.28 | 4.2E-03 | 51.09 |
| NUE578 | 9522.3 | 9.06 | 1.1E-01 | 11.75 | 0.24 | 1.9E-01 | 27.90 |
| Control |  | 8.11 |  |  | 0.19 |  |  |
| NUE580 | 9552.3 | 8.56 | 1.4E-01 | 5.59 | 0.20 | 4.9E-01 | 7.20 |
| NUE580 | 9551.3 | 8.69 | 7.2E-02 | 7.13 | 0.23 | 1.6E-02 | 25.62 |
| NUE580 | 9554.4 | 8.63 | 4.8E-01 | 6.36 | 0.23 | 3.5E-01 | 24.90 |
| Control |  | 8.11 |  |  | 0.19 |  |  |
| NUE582 | 9561.1 | 9.44 | 2.7E-01 | 16.38 | 0.27 | 1.6E-01 | 43.32 |
| NUE582 | 9561.2 | 8.94 | 1.8E-01 | 10.21 | 0.25 | 5.5E-03 | 33.79 |
| Control |  | 8.11 |  |  | 0.19 |  |  |
| NUE585 | 9661.1 | 8.94 | 4.0E-03 | 6.26 | 0.33 | 1.8E-02 | 43.63 |
| Control |  | 8.41 |  |  | 0.23 |  |  |
| NUE588 | 9591.3 | 9.19 | 5.6E-04 | 9.24 | 0.25 | 2.6E-02 | 9.62 |
| Control |  | 8.41 |  |  | 0.23 |  |  |

Table 43: Analyses of rosette growth performance (leaf number and leaf blade area) of transgenic plants overexpressing the exogenous polynucleotides of some embodiments of the invention (using the cloned or synthetic genes listed in Table 23 above) under the regulation of a constitutive promoter (35S) when grown under standard nitrogen (6 mM KNO₃, 1 mM KH₂PO₄, 1 mM MgSO₄, 2 mM CaCl₂ and microelements) as compared to control plants.

The genes presented in Tables 44 and 45, hereinbelow, have improved plant growth rate when grown at limiting nitrogen fertilization levels. These genes improved the growth rate of the rosette and faster covered the soil when grown at standard nitrogen fertilization levels. These genes produced faster growing plants showing a better utilization of the nitrogen present.

Tables 44 and 45 depict analyses of the growth rate of the rosette diameter, rosette area, leaf blade area, leaf number and plot coverage when grown under standard nitrogen conditions (6 mM KNO₃, 1 mM KH₂PO₄, 1 mM MgSO₄, 2 mM CaCl₂ and microelements) in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 44

Transgenic plants exogenously expressing the polynucleotides of some embodiments of the invention exhibit improved growth rate (RGR of leaf blade area, leaf number and rosette area) under standard nitrogen conditions

| Gene Name | Event # | RGR Of Leaf Blade Area Ave. | P-Value | % incr. | RGR Of Leaf Number Ave. | P-Value | % incr. | RGR Of Rosette Area Ave. | P-Value | % incr. |
|---|---|---|---|---|---|---|---|---|---|---|
| NUE230 | 9154.2 | 0.032 | 2.5E-01 | 18.08 | 0.561 | 0.862 | -1.88 | 0.20 | 2.8E-01 | 18.63 |
| NUE230 | 9153.3 | 0.034 | 1.5E-01 | 25.07 | 0.629 | 0.404 | 9.96 | 0.22 | 9.2E-02 | 32.65 |
| Control |  | 0.027 |  |  | 0.572 |  |  | 0.16 |  |  |
| NUE525 | 9534.1 | 0.027 | 3.4E-01 | 17.00 | 0.577 | 0.820 | 3.62 | 0.18 | 2.5E-01 | 25.20 |
| NUE525 | 9531.2 | 0.032 | 4.9E-02 | 37.26 | 0.619 | 0.479 | 11.17 | 0.21 | 2.0E-02 | 53.67 |
| NUE525 | 9533.1 | 0.029 | 2.1E-01 | 23.87 | 0.570 | 0.889 | 2.25 | 0.20 | 6.0E-02 | 45.89 |
| NUE525 | 9531.3 | 0.028 | 2.3E-01 | 21.75 | 0.618 | 0.485 | 10.96 | 0.19 | 9.2E-02 | 37.52 |
| NUE525 | 9533.4 | 0.028 | 2.4E-01 | 22.32 | 0.581 | 0.783 | 4.35 | 0.19 | 1.2E-01 | 36.12 |
| Control |  | 0.023 |  |  | 0.557 |  |  | 0.14 |  |  |
| NUE536 | 9233.3 | 0.032 | 2.0E-01 | 21.11 | 0.696 | 0.053 | 21.70 | 0.21 | 9.8E-02 | 30.44 |
| NUE536 | 9234.1 | 0.035 | 6.2E-02 | 31.13 | 0.719 | 0.025 | 25.69 | 0.24 | 1.6E-02 | 46.81 |
| Control |  | 0.027 |  |  | 0.572 |  |  | 0.16 |  |  |
| NUE545 | 9484.2 | 0.034 | 1.4E-02 | 47.61 | 0.666 | 0.224 | 19.56 | 0.23 | 7.1E-03 | 63.45 |
| NUE545 | 9482.4 | 0.026 | 5.0E-01 | 13.65 | 0.617 | 0.523 | 10.85 | 0.18 | 2.8E-01 | 26.57 |
| NUE545 | 9481.3 | 0.032 | 3.8E-02 | 39.71 | 0.478 |  |  | 0.19 | 7.9E-02 | 38.94 |
| NUE545 | 9484.4 | 0.030 | 1.3E-01 | 27.62 | 0.542 |  |  | 0.20 | 6.8E-02 | 41.88 |
| Control |  | 0.023 |  |  | 0.557 |  |  | 0.14 |  |  |
| NUE568 | 9474.3 | 0.025 | 7.0E-01 | 7.00 | 0.535 |  |  | 0.15 | 6.4E-01 | 10.17 |
| NUE568 | 9471.3 | 0.024 | 7.5E-01 | 5.65 | 0.627 | 0.423 | 12.49 | 0.17 | 3.4E-01 | 20.52 |
| NUE568 | 9461.2 | 0.037 | 3.1E-03 | 58.77 | 0.665 | 0.208 | 19.45 | 0.26 | 3.9E-04 | 88.65 |
| NUE568 | 9474.4 | 0.026 | 5.5E-01 | 10.89 | 0.526 | 0.726 | -5.61 | 0.15 | 6.2E-01 | 10.72 |
| NUE568 | 9461.3 | 0.029 | 1.9E-01 | 23.81 | 0.643 | 0.342 | 15.47 | 0.20 | 8.0E-02 | 39.53 |
| Control |  | 0.023 |  |  | 0.557 |  |  | 0.14 |  |  |
| NUE573 | 9491.4 | 0.026 | 4.3E-01 | 14.05 | 0.543 | 0.872 | -2.57 | 0.19 | 1.2E-01 | 34.11 |
| NUE573 | 9493.4 | 0.026 | 4.9E-01 | 12.34 | 0.653 | 0.270 | 17.18 | 0.18 | 2.0E-01 | 28.04 |

TABLE 44-continued

Transgenic plants exogenously expressing the polynucleotides of some embodiments of the invention exhibit improved growth rate (RGR of leaf blade area, leaf number and rosette area) under standard nitrogen conditions

| Gene Name | Event # | RGR Of Leaf Blade Area Ave. | P-Value | % incr. | RGR Of Leaf Number Ave. | P-Value | % incr. | RGR Of Rosette Area Ave. | P-Value | % incr. |
|---|---|---|---|---|---|---|---|---|---|---|
| NUE573 | 9491.2 | 0.030 | 1.0E-01 | 30.33 | 0.519 | 0.657 | -6.87 | 0.21 | 4.2E-02 | 46.75 |
| NUE573 | 9492.2 | 0.029 | 2.3E-01 | 24.31 | 0.531 | 0.791 | -4.60 | 0.19 | 1.6E-01 | 35.61 |
| Control |  | 0.023 |  |  | 0.557 |  |  | 0.14 |  |  |
| NUE575 | 9504.1 | 0.030 | 1.1E-01 | 30.22 | 0.624 | 0.428 | 12.01 | 0.21 | 4.0E-02 | 47.00 |
| NUE575 | 9503.1 | 0.027 | 4.0E-01 | 15.42 | 0.516 | 0.651 | -7.29 | 0.16 | 4.7E-01 | 15.58 |
| NUE575 | 9502.1 | 0.026 | 4.7E-01 | 13.38 | 0.609 | 0.566 | 9.32 | 0.19 | 1.7E-01 | 32.29 |
| Control |  | 0.023 |  |  | 0.557 |  |  | 0.14 |  |  |
| NUE578 | 9524.1 | 0.033 | 3.3E-02 | 41.00 | 0.613 | 0.511 | 10.12 | 0.22 | 1.8E-02 | 54.74 |
| NUE578 | 9524.3 | 0.031 | 1.5E-01 | 31.93 | 0.608 | 0.642 | 9.18 | 0.21 | 7.3E-02 | 49.17 |
| NUE578 | 9523.3 | 0.034 | 1.6E-02 | 46.45 | 0.665 | 0.213 | 19.44 | 0.23 | 5.4E-03 | 65.74 |
| NUE578 | 9522.3 | 0.029 | 2.1E-01 | 23.38 | 0.685 | 0.143 | 23.02 | 0.21 | 2.4E-02 | 52.52 |
| Control |  | 0.023 |  |  | 0.557 |  |  | 0.14 |  |  |
| NUE580 | 9551.3 | 0.029 | 1.4E-01 | 26.91 | 0.602 | 0.608 | 8.02 | 0.19 | 8.4E-02 | 38.45 |
| NUE580 | 9554.4 | 0.027 | 3.8E-01 | 16.77 | 0.543 | 0.875 | -2.57 | 0.19 | 9.4E-02 | 38.64 |
| Control |  | 0.023 |  |  | 0.557 |  |  | 0.14 |  |  |
| NUE582 | 9561.1 | 0.032 | 4.1E-02 | 39.34 | 0.666 | 0.252 | 19.56 | 0.22 | 1.2E-02 | 60.37 |
| NUE582 | 9562.1 | 0.027 | 3.5E-01 | 17.41 | 0.577 | 0.833 | 3.51 | 0.17 | 3.0E-01 | 23.28 |
| NUE582 | 9562.4 | 0.027 | 3.8E-01 | 15.92 | 0.568 | 0.902 | 1.94 | 0.16 | 4.4E-01 | 16.65 |
| NUE582 | 9561.2 | 0.032 | 7.0E-02 | 37.29 | 0.665 | 0.255 | 19.42 | 0.22 | 3.1E-02 | 54.06 |
| Control |  | 0.023 |  |  | 0.557 |  |  | 0.14 |  |  |
| NUE585 | 9661.3 | 0.030 | 4.5E-01 | 11.39 | 0.684 | 0.145 | 19.49 | 0.18 | 5.3E-01 | 10.62 |
| NUE585 | 9661.1 | 0.039 | 1.2E-02 | 43.80 | 0.658 | 0.178 | 14.96 | 0.25 | 7.0E-03 | 52.30 |
| Control |  | 0.027 |  |  | 0.572 |  |  | 0.16 |  |  |
| NUE588 | 9591.3 | 0.031 | 2.6E-01 | 17.23 | 0.713 | 0.052 | 24.56 | 0.19 | 3.2E-01 | 17.29 |
| Control |  | 0.027 |  |  | 0.572 |  |  | 0.16 |  |  |

Table 44: Analyses of growth rate (RGR of leaf blade area, leaf number and rosette area) of transgenic plants overexpressing the exogenous polynucleotides of some embodiments of the invention (using the cloned or synthetic genes listed in Table 23 above) under the regulation of a constitutive promoter (35S) when grown under standard nitrogen (6 mM KNO$_3$, 1 mM KH$_2$PO$_4$, 1 mM MgSO$_4$, 2 mM CaCl$_2$ and microelements) as compared to control plants.

TABLE 45

Transgenic plants exogenously expressing the polynucleotides of some embodiments of the invention exhibit improved growth rate (RGR of rosette diameter and plot coverage) under standard nitrogen conditions

| Gene Name | Event # | RGR Of Rosette Diameter Ave. | P-Value | % incr. | RGR Of Plot Coverage Ave. | P-Value | % incr. |
|---|---|---|---|---|---|---|---|
| NUE230 | 9154.2 | 0.20 | 0.612 | 5.67 | 1.56 | 0.283 | 18.63 |
| NUE230 | 9153.3 | 0.21 | 0.382 | 10.99 | 1.75 | 0.092 | 32.65 |
| Control |  | 0.19 |  |  | 1.32 |  |  |
| NUE525 | 9534.1 | 0.18 | 0.672 | 6.16 | 1.40 | 0.249 | 25.20 |
| NUE525 | 9531.2 | 0.21 | 0.188 | 19.78 | 1.72 | 0.020 | 53.67 |
| NUE525 | 9533.1 | 0.21 | 0.239 | 18.66 | 1.63 | 0.060 | 45.89 |
| NUE525 | 9531.3 | 0.20 | 0.407 | 12.27 | 1.54 | 0.092 | 37.52 |
| NUE525 | 9533.4 | 0.20 | 0.308 | 16.23 | 1.52 | 0.125 | 36.12 |
| Control |  | 0.17 |  |  | 1.12 |  |  |
| NUE536 | 9233.3 | 0.22 | 0.250 | 13.45 | 1.72 | 0.098 | 30.44 |
| NUE536 | 9234.1 | 0.23 | 0.068 | 21.81 | 1.93 | 0.016 | 46.81 |
| Control |  | 0.19 |  |  | 1.32 |  |  |
| NUE545 | 9484.2 | 0.23 | 0.024 | 34.81 | 1.83 | 0.007 | 63.45 |
| NUE545 | 9482.4 | 0.18 | 0.741 | 5.45 | 1.42 | 0.281 | 26.57 |
| NUE545 | 9481.3 | 0.20 | 0.304 | 15.24 | 1.55 | 0.079 | 38.94 |
| NUE545 | 9484.4 | 0.21 | 0.215 | 18.52 | 1.59 | 0.068 | 41.88 |
| Control |  | 0.17 |  |  | 1.12 |  |  |
| NUE568 | 9474.3 | 0.18 | 0.868 | 2.45 | 1.23 | 0.641 | 10.17 |
| NUE568 | 9471.3 | 0.17 | 0.853 | -2.69 | 1.35 | 0.345 | 20.52 |
| NUE568 | 9461.2 | 0.23 | 0.039 | 31.20 | 2.11 | 0.000 | 88.65 |
| NUE568 | 9474.4 | 0.18 | 0.947 | 0.98 | 1.24 | 0.624 | 10.72 |
| NUE568 | 9461.3 | 0.21 | 0.218 | 18.40 | 1.56 | 0.080 | 39.53 |
| Control |  | 0.17 |  |  | 1.12 |  |  |
| NUE573 | 9491.4 | 0.19 | 0.582 | 8.00 | 1.50 | 0.121 | 34.11 |
| NUE573 | 9493.4 | 0.19 | 0.589 | 7.89 | 1.35 | 0.349 | 20.66 |
| NUE573 | 9491.2 | 0.21 | 0.222 | 18.90 | 1.64 | 0.042 | 46.75 |
| NUE573 | 9492.2 | 0.18 | 0.821 | 3.40 | 1.27 | 0.542 | 13.46 |
| Control |  | 0.17 |  |  | 1.12 |  |  |
| NUE575 | 9504.1 | 0.21 | 0.196 | 19.39 | 1.64 | 0.040 | 47.00 |
| NUE575 | 9503.1 | 0.19 | 0.644 | 6.72 | 1.29 | 0.472 | 15.58 |
| NUE575 | 9502.1 | 0.19 | 0.637 | 7.16 | 1.33 | 0.439 | 19.10 |
| Control |  | 0.17 |  |  | 1.12 |  |  |
| NUE578 | 9524.1 | 0.21 | 0.154 | 21.31 | 1.73 | 0.018 | 54.74 |
| NUE578 | 9524.3 | 0.21 | 0.302 | 19.94 | 1.67 | 0.073 | 49.17 |
| NUE578 | 9523.3 | 0.23 | 0.036 | 33.14 | 1.73 | 0.017 | 54.56 |
| NUE578 | 9522.3 | 0.19 | 0.472 | 10.54 | 1.71 | 0.024 | 52.52 |
| Control |  | 0.17 |  |  | 1.12 |  |  |
| NUE580 | 9551.3 | 0.20 | 0.319 | 14.57 | 1.55 | 0.084 | 38.45 |
| NUE580 | 9554.4 | 0.18 | 0.764 | 4.75 | 1.55 | 0.094 | 38.64 |
| Control |  | 0.17 |  |  | 1.12 |  |  |
| NUE582 | 9561.1 | 0.22 | 0.112 | 24.58 | 1.79 | 0.012 | 60.37 |
| NUE582 | 9562.1 | 0.19 | 0.548 | 9.10 | 1.38 | 0.300 | 23.28 |
| NUE582 | 9562.4 | 0.19 | 0.469 | 10.79 | 1.31 | 0.438 | 16.65 |
| NUE582 | 9561.2 | 0.20 | 0.325 | 16.03 | 1.72 | 0.031 | 54.06 |
| Control |  | 0.17 |  |  | 1.12 |  |  |
| NUE585 | 9661.3 | 0.20 | 0.518 | 7.29 | 1.46 | 0.528 | 10.62 |
| NUE585 | 9661.1 | 0.22 | 0.142 | 17.93 | 2.00 | 0.007 | 52.30 |
| Control |  | 0.19 |  |  | 1.32 |  |  |

TABLE 45-continued

Transgenic plants exogenously expressing the polynucleotides of some embodiments of the invention exhibit improved growth rate (RGR of rosette diameter and plot coverage) under standard nitrogen conditions

| Gene Name | Event # | RGR Of Rosette Diameter | | | RGR Of Plot Coverage | | |
|---|---|---|---|---|---|---|---|
| | | Ave. | P-Value | % incr. | Ave. | P-Value | % incr. |
| NUE588 | 9591.3 | 0.21 | 0.413 | 9.34 | 1.54 | 0.317 | 17.29 |
| Control | | 0.19 | | | 1.32 | | |

Table 45: Analyses of growth rate (RGR of rosette diameter and plot coverage) of transgenic plants overexpressing the exogenous polynucleotides of some embodiments of the invention (using the cloned or synthetic genes listed in Table 23 above) under the regulation of a constitutive promoter (35S) when grown under standard nitrogen (6 mM $KNO_3$, 1 mM $KH_2PO_4$, 1 mM $MgSO_4$, 2 mM $CaCl_2$ and microelements) as compared to control plants.

Example 7

Assay 3: Nitrogen Use Efficiency Measured Until Bolting Stage: Plant Biomass and Plant Growth Rate at Limited and Standard Nitrogen Concentration Under Greenhouse Conditions This assay follows seed yield production, the biomass formation and the rosette area growth of plants grown in the greenhouse at limiting and non-limiting nitrogen growth conditions. Transgenic *Arabidopsis* seeds were sown in agar media supplemented with ½ MS medium and a selection agent (Kanamycin). The $T_2$ transgenic seedlings were then transplanted to 1.7 trays filled with peat and perlite in a 1:1 ratio. The trays were irrigated with a solution containing nitrogen limiting conditions, which were achieved by irrigating the plants with a solution containing 1.5 mM inorganic nitrogen in the form of $KNO_3$, supplemented with 1 mM $KH_2PO_4$, 1 mM $MgSO_4$, 3.6 mM KCl, 2 mM $CaCl_2$ and microelements, while normal nitrogen levels were achieved by applying a solution of 6 mM inorganic nitrogen also in the form of $KNO_3$ with 1 mM $KH_2PO_4$, 1 mM $MgSO_4$, 2 mM $CaCl_2$ and microelements. All plants were grown in the greenhouse until mature seeds. Plant biomass (the above ground tissue) was weight immediately after harvesting the rosette (plant fresh weight [FW]). Following, plants were dried in an oven at 50° C. for 48 hours and weighted (plant dry weight [DW]).

Each construct was validated at its $T_2$ generation. Transgenic plants transformed with a construct conformed by an empty vector carrying the 35S promoter and the selectable marker was used as control.

The plants were analyzed for their overall size, growth rate, fresh weight and dry matter. Transgenic plants performance was compared to control plants grown in parallel under the same conditions.

The experiment was planned in nested randomized plot distribution. For each gene of the invention three to five independent transformation events were analyzed from each construct.

Digital Imaging

A laboratory image acquisition system, which consists of a digital reflex camera (Canon EOS 300D) attached with a 55 mm focal length lens (Canon EF-S series), mounted on a reproduction device (Kaiser RS), which includes 4 light units (4×150 Watts light bulb) was used for capturing images of plant samples.

The image capturing process was repeated every 2 days starting from day 1 after transplanting till day 15. Same camera, placed in a custom made iron mount, was used for capturing images of larger plants sawn in white tubs in an environmental controlled greenhouse. During the capture process, the tubes were placed beneath the iron mount, while avoiding direct sun light and casting of shadows.

An image analysis system was used, which consists of a personal desktop computer (Intel P4 3.0 GHz processor) and a public domain program—ImageJ 1.39 [Java based image processing program which was developed at the U.S. National Institutes of Health and freely available on the internet at Hypertext Transfer Protocol://rsbweb (dot) nih (dot) gov/]. Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Leaf Analysis

Using the digital analysis leaves data was calculated, including leaf number, rosette area, rosette diameter, leaf blade area, plot coverage and leaf petiole area.

Vegetative growth rate: is the rate of growth of the plant as defined by formula VIII, IX, X and XI as described above:

Relative growth rate of leaf blade area=Regression coefficient of leaf area along time course.   Formula VIII:

Relative growth rate of rosette area=Regression coefficient of rosette area along time course.   Formula IX:

Relative growth rate of rosette diameter=Regression coefficient of rosette diameter along time course.   Formula X:

Relative growth rate of plot coverage=Regression coefficient of plot coverage along time course.   Formula XI:

Plant Fresh and Dry Weight

On about day 40 from sowing, the plants were harvested and directly weight for the determination of the plant fresh weight (FW) and left to dry at 50° C. in a drying chamber for about 48 hours before weighting to determine plant dry weight (DW).

Statistical Analyses

To identify genes conferring significantly improved NUE, the results obtained from the transgenic plants were compared to those obtained from control plants. To identify outperforming genes and constructs, results from the independent transformation events tested are analyzed separately. Data was analyzed using Student's t-test and results were considered significant if the p value was less than 0.1. The JMP statistics software package was used (Version 5.2.1, SAS Institute Inc., Cary, N.C., USA).

Experimental Results:

The genes presented in Tables 46 and 47, hereinbelow, have improved plant NUE when grown under limiting nitrogen growth conditions, compared to control plants. These genes produced larger plants with a larger photosynthetic capacity when grown under limiting nitrogen conditions.

Tables 46 and 47 depict analyses of plant biomass and photosynthetic area (fresh weight, dry weight, rosette diameter, rosette area and plot coverage) when grown under limiting nitrogen conditions (1.5 mM $KNO_3$, 1 mM $KH_2PO_4$, 1 mM $MgSO_4$, 3.6 mM KCl, 2 mM $CaCl_2$ and microelements) in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 46

Transgenic plants exogenously expressing the polynucleotides of some embodiments of the invention exhibit improved plant biomass (dry weight and fresh weight) under limiting nitrogen conditions

| Gene Name | Event # | Dry Weight [g] | | | Fresh Weight [g] | | |
|---|---|---|---|---|---|---|---|
| | | Average | P-Value | % increment | Average | P-Value | % increment |
| NUE227 | 9851.4 | 0.076 | 0.014 | 44.26 | 0.725 | 0.002 | 79.65 |
| NUE227 | 9854.2 | 0.059 | 0.202 | 12.33 | 0.569 | 0.000 | 40.93 |
| NUE227 | 9853.1 | 0.069 | 0.025 | 31.25 | 0.581 | 0.092 | 44.03 |
| NUE227 | 9851.1 | 0.063 | 0.052 | 19.43 | 0.581 | 0.205 | 44.03 |
| NUE227 | 9852.3 | 0.063 | 0.063 | 18.24 | 0.519 | 0.469 | 28.54 |
| Control | | 0.053 | | | 0.404 | | |
| NUE233 | 10173.5 | 0.035 | 0.055 | 34.48 | 0.243 | 0.838 | −1.89 |
| Control | | 0.026 | | | 0.248 | | |
| NUE256 | 10061.4 | 0.034 | 0.031 | 32.08 | | | |
| NUE256 | 10061.1 | 0.044 | 0.126 | 70.50 | 0.325 | 0.250 | 31.29 |
| Control | | 0.026 | | | 0.248 | | |
| NUE512 | 9284.2 | 0.044 | 0.417 | −17.23 | 0.419 | 0.794 | 3.76 |
| NUE512 | 9283.1 | 0.066 | 0.033 | 25.34 | 0.488 | 0.088 | 20.80 |
| NUE512 | 9284.3 | 0.052 | 0.900 | −1.86 | 0.469 | 0.566 | 16.15 |
| NUE512 | 9282.3 | 0.064 | 0.066 | 20.61 | 0.506 | 0.005 | 25.44 |
| NUE512 | 9283.3 | 0.063 | 0.247 | 18.24 | 0.538 | 0.002 | 33.19 |
| NUE512 | 9281.3 | 0.079 | 0.066 | 49.32 | 0.538 | 0.023 | 33.41 |
| Control | | 0.053 | | | 0.404 | | |
| NUE514 | 9403.5 | 0.050 | 0.581 | −5.41 | 0.388 | 0.807 | −3.98 |
| NUE514 | 9404.4 | 0.054 | 0.964 | 2.20 | 0.439 | 0.759 | 8.85 |
| NUE514 | 9402.2 | 0.056 | 0.468 | 6.42 | 0.594 | 0.000 | 47.12 |
| NUE514 | 9402.5 | 0.057 | 0.553 | 7.60 | 0.488 | 0.088 | 20.80 |
| Control | | 0.053 | | | 0.404 | | |
| NUE531 | 10082.2 | 0.042 | 0.001 | 62.84 | 0.235 | 0.976 | −5.26 |
| NUE531 | 10081.5 | 0.029 | 0.810 | 10.46 | 0.219 | 0.334 | −11.63 |
| Control | | 0.026 | | | 0.248 | | |
| NUE532 | 9222.4 | 0.069 | 0.066 | 31.25 | 0.606 | 0.296 | 50.22 |
| NUE532 | 9222.3 | 0.061 | 0.773 | 15.88 | 0.444 | 0.148 | 9.96 |
| NUE532 | 9222.1 | 0.064 | 0.570 | 20.61 | 0.525 | 0.117 | 30.09 |
| NUE532 | 9223.3 | 0.062 | 0.093 | 17.06 | 0.475 | 0.603 | 17.70 |
| NUE532 | 9224.4 | 0.035 | 0.007 | −32.94 | 0.467 | 0.037 | 15.71 |
| NUE532 | 9223.5 | 0.057 | 0.746 | 7.60 | 0.556 | 0.242 | 37.83 |
| Control | | 0.053 | | | 0.404 | | |
| NUE535 | 9086.2 | 0.056 | 0.915 | 5.24 | 0.550 | 0.477 | 36.28 |
| Control | | 0.053 | | | 0.404 | | |
| NUE537 | 9392.2 | 0.053 | 0.988 | 0.51 | 0.550 | 0.021 | 36.28 |
| NUE537 | 9393.2 | 0.055 | 0.847 | 3.72 | 0.589 | 0.065 | 46.02 |
| NUE537 | 9393.1 | 0.060 | 0.274 | 13.51 | 0.444 | 0.148 | 9.96 |
| NUE537 | 9393.3 | 0.068 | 0.033 | 28.89 | 0.575 | 0.014 | 42.48 |
| Control | | 0.053 | | | 0.404 | | |
| NUE576 | 9794.1 | 0.039 | 0.090 | 48.89 | 0.294 | 0.028 | 18.67 |
| Control | | 0.026 | | | 0.248 | | |
| NUE576 | 9791.3 | | | | 0.431 | 0.838 | 6.86 |
| NUE576 | 9792.4 | | | | 0.500 | 0.007 | 23.89 |
| NUE576 | 9792.3 | | | | 0.550 | 0.159 | 36.28 |
| Control | | | | | 0.404 | | |

Table 46: Analyses of plant biomass (dry and fresh weight) of transgenic plants overexpressing the exogenous polynucleotides of some embodiments of the invention (using the cloned or synthetic genes listed in Table 23 above) under the regulation of a constitutive promoter (35S) when grown under limiting nitrogen (1.5 mM KNO$_3$, 1 mM KH$_2$PO$_4$, 1 mM MgSO$_4$, 3.6 mM KCl, 2 mM CaCl$_2$ and microelements) as compared to control plants.

TABLE 47

Transgenic plants exogenously expressing the polynucleotides of some embodiments of the invention exhibit improved plant biomass (rosette diameter and area and plot coverage) under limiting nitrogen conditions

| Gene Name | Event # | Rosette Diameter [cm] | | | Rosette Area [cm$^2$] | | | Plot Coverage [%] | | |
|---|---|---|---|---|---|---|---|---|---|---|
| | | Ave. | P-Value | % incr. | Ave. | P-Value | % incr. | Ave. | P-Value | % incr. |
| NUE227 | 9851.4 | 2.040 | 2.4E−02 | 48.28 | 1.477 | 7.6E−02 | 115.90 | 11.819 | 7.6E−02 | 115.90 |
| NUE227 | 9854.2 | 1.778 | 5.9E−02 | 29.24 | 1.070 | 7.0E−03 | 56.44 | 8.564 | 7.0E−03 | 56.44 |
| NUE227 | 9853.1 | 1.679 | 9.5E−02 | 22.03 | 0.979 | 1.1E−01 | 43.09 | 7.833 | 1.1E−01 | 43.09 |

TABLE 47-continued

Transgenic plants exogenously expressing the polynucleotides of some embodiments of the invention exhibit improved plant biomass (rosette diameter and area and plot coverage) under limiting nitrogen conditions

| Gene Name | Event # | Rosette Diameter [cm] | | | Rosette Area [cm²] | | | Plot Coverage [%] | | |
|---|---|---|---|---|---|---|---|---|---|---|
| | | Ave. | P-Value | % incr. | Ave. | P-Value | % incr. | Ave. | P-Value | % incr. |
| NUE227 | 9851.1 | 1.555 | 2.8E−01 | 13.03 | 0.915 | 2.8E−01 | 33.71 | 7.320 | 2.8E−01 | 33.71 |
| NUE227 | 9852.3 | 1.889 | 1.7E−01 | 37.33 | 1.298 | 1.8E−01 | 89.71 | 10.386 | 1.8E−01 | 89.71 |
| Control | | 1.376 | | | 0.684 | | | 5.474 | | |
| NUE233 | 10173.5 | 1.778 | 1.9E−01 | 7.66 | 1.080 | 3.2E−01 | 16.76 | 7.559 | 7.1E−01 | 5.15 |
| Control | | 1.651 | | | 0.925 | | | 7.189 | | |
| NUE256 | 10061.1 | 1.991 | 2.6E−03 | 20.56 | 1.333 | 2.7E−02 | 44.13 | 10.664 | 2.0E−02 | 48.34 |
| Control | | 1.651 | | | 0.925 | | | 7.189 | | |
| NUE512 | 9284.2 | 1.475 | 7.1E−01 | 7.21 | 0.794 | 7.0E−01 | 15.97 | 6.349 | 7.0E−01 | 15.97 |
| NUE512 | 9283.1 | 1.581 | 1.8E−01 | 14.91 | 0.916 | 2.6E−02 | 33.86 | 7.328 | 2.6E−02 | 33.86 |
| NUE512 | 9284.3 | 1.395 | 9.0E−01 | 1.41 | 0.719 | 8.2E−01 | 5.14 | 5.755 | 8.2E−01 | 5.14 |
| NUE512 | 9282.3 | 1.588 | 2.6E−01 | 15.43 | 0.928 | 6.3E−02 | 35.67 | 7.427 | 6.3E−02 | 35.67 |
| NUE512 | 9283.3 | 1.410 | 8.2E−01 | 2.50 | 0.789 | 3.9E−01 | 15.37 | 6.315 | 3.9E−01 | 15.37 |
| NUE512 | 9281.3 | 1.526 | 3.8E−01 | 10.94 | 0.824 | 4.1E−01 | 20.42 | 6.236 | 6.5E−01 | 13.91 |
| Control | | 1.376 | | | 0.684 | | | 5.474 | | |
| NUE514 | 9403.5 | 1.581 | 5.6E−01 | 14.93 | 0.901 | 5.4E−01 | 31.69 | 7.209 | 5.4E−01 | 31.69 |
| NUE514 | 9404.4 | 1.608 | 2.3E−01 | 16.92 | 0.930 | 2.0E−01 | 35.86 | 6.923 | 2.2E−02 | 26.47 |
| NUE514 | 9402.2 | 1.996 | 1.8E−01 | 45.07 | 1.395 | 1.5E−01 | 103.85 | 11.159 | 1.5E−01 | 103.85 |
| NUE514 | 9402.5 | 1.860 | 3.2E−01 | 35.21 | 1.160 | 3.2E−01 | 69.52 | 9.280 | 3.2E−01 | 69.52 |
| NUE514 | 9404.5 | 1.689 | 2.2E−01 | 22.77 | 1.006 | 4.7E−02 | 47.02 | 8.048 | 4.7E−02 | 47.02 |
| Control | | 1.376 | | | 0.684 | | | 5.474 | | |
| NUE527 | 9201.1 | 1.773 | 1.4E−02 | 28.89 | 1.109 | 9.3E−02 | 62.12 | 8.875 | 9.3E−02 | 62.12 |
| Control | | 1.376 | | | 0.684 | | | 5.474 | | |
| NUE531 | 10081.5 | 1.758 | 4.5E−01 | 6.49 | 1.043 | 5.1E−01 | 12.74 | 8.342 | 4.3E−01 | 16.04 |
| Control | | 1.651 | | | 0.925 | | | 7.189 | | |
| NUE532 | 9222.4 | 1.752 | 3.9E−01 | 27.34 | 1.056 | 4.4E−01 | 54.32 | 8.448 | 4.4E−01 | 54.32 |
| NUE532 | 9222.3 | 1.668 | 4.6E−04 | 21.24 | 1.034 | 8.3E−05 | 51.08 | 8.270 | 8.3E−05 | 51.08 |
| NUE532 | 9222.1 | 1.623 | 3.8E−01 | 17.95 | 1.016 | 2.8E−01 | 48.52 | 8.130 | 2.8E−01 | 48.52 |
| NUE532 | 9223.3 | 1.585 | 5.5E−03 | 15.23 | 0.902 | 6.2E−03 | 31.88 | 7.219 | 6.2E−03 | 31.88 |
| NUE532 | 9224.4 | 1.732 | 1.4E−04 | 25.88 | 1.060 | 6.5E−05 | 54.91 | 7.941 | 2.3E−02 | 45.06 |
| NUE532 | 9223.5 | 1.899 | 7.1E−02 | 38.02 | 1.294 | 3.2E−02 | 89.11 | 10.353 | 3.2E−02 | 89.11 |
| Control | | 1.376 | | | 0.684 | | | 5.474 | | |
| NUE535 | 9086.2 | 1.696 | 2.2E−01 | 23.27 | 0.938 | 2.2E−01 | 37.03 | 7.502 | 2.2E−01 | 37.03 |
| NUE535 | 9084.2 | 1.463 | 6.4E−01 | 6.35 | 0.827 | 4.3E−01 | 20.92 | 6.620 | 4.3E−01 | 20.92 |
| NUE535 | 9081.1 | 1.521 | 3.3E−01 | 10.57 | 0.823 | 3.0E−01 | 20.21 | 6.581 | 3.0E−01 | 20.21 |
| NUE535 | 9082.1 | 1.432 | 5.6E−01 | 4.10 | 0.742 | 3.8E−01 | 8.46 | 5.938 | 3.8E−01 | 8.46 |
| Control | | 1.376 | | | 0.684 | | | 5.474 | | |
| NUE537 | 9391.1 | 1.503 | 5.2E−01 | 9.24 | 0.807 | 3.8E−01 | 17.86 | 6.452 | 3.8E−01 | 17.86 |
| NUE537 | 9392.2 | 1.475 | 4.9E−01 | 7.21 | 0.851 | 3.4E−01 | 24.32 | 6.806 | 3.4E−01 | 24.32 |
| NUE537 | 9393.2 | 1.532 | 8.5E−03 | 11.34 | 0.955 | 4.1E−04 | 39.59 | 7.157 | 4.5E−02 | 30.73 |
| NUE537 | 9393.1 | 1.856 | 1.7E−03 | 34.95 | 1.225 | 7.0E−05 | 78.96 | 9.797 | 7.0E−05 | 78.96 |
| NUE537 | 9392.3 | 1.429 | 8.3E−01 | 3.89 | 0.784 | 7.3E−01 | 14.54 | 6.270 | 7.3E−01 | 14.54 |
| NUE537 | 9393.3 | 1.739 | 5.3E−02 | 26.42 | 1.092 | 1.5E−02 | 59.52 | 8.733 | 1.5E−02 | 59.52 |
| Control | | 1.376 | | | 0.684 | | | 5.474 | | |
| NUE576 | 9794.1 | 1.963 | 1.5E−01 | 18.86 | 1.350 | 2.3E−01 | 45.96 | 10.800 | 2.1E−01 | 50.23 |
| Control | | 1.651 | | | 0.925 | | | 7.189 | | |
| NUE576 | 9791.3 | 1.416 | 8.6E−01 | 2.94 | 0.753 | 7.4E−01 | 10.01 | 6.022 | 7.4E−01 | 10.01 |
| NUE576 | 9792.4 | 1.826 | 2.1E−05 | 32.75 | 1.204 | 2.4E−04 | 75.90 | 9.629 | 2.4E−04 | 75.90 |
| NUE576 | 9792.3 | 1.912 | 5.4E−06 | 39.03 | 1.208 | 1.1E−05 | 76.46 | 9.660 | 1.1E−05 | 76.46 |
| Control | | 1.376 | | | 0.684 | | | 5.474 | | |

Table 47: Analyses of plant biomass (rosette diameter and area and plot coverage) of transgenic plants overexpressing the exogenous polynucleotides of some embodiments of the invention (using the cloned or synthetic genes listed in Table 23 above) under the regulation of a constitutive promoter (35S) when grown under limiting nitrogen (1.5 mM KNO$_3$, 1 mM KH$_2$PO$_4$, 1 mM MgSO$_4$, 3.6 mM KCl, 2 mM CaCl$_2$ and microelements) as compared to control plants.

The genes presented in Table 48, hereinbelow, have improved plant NUE when grown under limiting nitrogen growth conditions, compared to control plants. These genes produced larger photosynthetic areas as it can be observed by their larger leaf number, leaf blade area and petiole area.

Table 48 depicts analyses of plant photosynthetic area (leaf number, leaf blade area and petiole area) when grown under limiting nitrogen conditions (1.5 mM $KNO_3$, 1 mM $KH_2PO_4$, 1 mM $MgSO_4$, 3.6 mM KCl, 2 mM $CaCl_2$ and microelements) in plants overexpressing the polynucleotides of some embodiments of the invention under the regulation of a constitutive promoter (35S)). Evaluation of each gene was performed by testing the performance of several events. Some of the genes were evaluated in more than one tissue culture assay and the results obtained were repeated. Event with p-value <0.1 was considered statistically significant.

TABLE 48

Transgenic plants exogenously expressing the polynucleotides of some embodiments of the invention exhibit improved photosynthetic area (leaf number, leaf blade area and petiole area) under limiting nitrogen conditions

| Gene Name | Event # | Leaf Number Ave. | P-Value | % incr. | Leaf Blade Area [cm$^2$] Ave. | P-Value | % incr. | Leaf Petiole Length [cm] Ave. | P-Value | % incr. |
|---|---|---|---|---|---|---|---|---|---|---|
| NUE227 | 9851.4 | 8.56 | 1.9E−02 | 16.38 | 0.24 | 4.6E−02 | 108.44 | 0.38 | 6.5E−02 | 69.59 |
| NUE227 | 9854.2 | 7.63 | 1.5E−01 | 3.64 | 0.19 | 5.8E−03 | 67.63 | 0.32 | 1.2E−04 | 41.44 |
| NUE227 | 9853.1 | 7.81 | 3.5E−02 | 6.19 | 0.17 | 2.2E−01 | 49.04 | 0.26 | 3.8E−02 | 14.04 |
| NUE227 | 9851.1 | 7.69 | 2.8E−01 | 4.49 | 0.16 | 2.9E−01 | 35.75 | 0.24 | 4.7E−01 | 5.61 |
| NUE227 | 9852.3 | 8.50 | 2.4E−01 | 15.53 | 0.21 | 1.1E−01 | 82.96 | 0.32 | 4.4E−01 | 41.85 |
| Control |  | 7.36 |  |  | 0.11 |  |  | 0.22 |  |  |
| NUE233 | 10173.5 | 7.79 | 6.0E−01 | 2.05 | 0.19 | 4.0E−01 | 15.50 | 0.26 | 5.8E−01 | 8.27 |
| Control |  | 7.63 |  |  | 0.17 |  |  | 0.24 |  |  |
| NUE256 | 10061.1 | 8.13 | 2.5E−01 | 6.50 | 0.23 | 8.4E−02 | 39.00 | 0.31 | 2.0E−01 | 30.30 |
| Control |  | 7.63 |  |  | 0.17 |  |  | 0.24 |  |  |
| NUE512 | 9283.1 | 7.63 | 2.5E−01 | 3.64 | 0.16 | 7.0E−02 | 42.74 | 0.24 | 1.2E−01 | 8.56 |
| NUE512 | 9284.3 | 6.88 | 5.0E−01 | −6.55 | 0.13 | 4.9E−01 | 15.53 | 0.21 | 8.3E−01 | −5.04 |
| NUE512 | 9282.3 | 7.38 | 9.8E−01 | 0.24 | 0.16 | 3.9E−02 | 41.04 | 0.26 | 5.5E−01 | 14.40 |
| NUE512 | 9283.3 | 7.56 | 6.3E−01 | 2.79 | 0.13 | 6.1E−01 | 12.00 | 0.25 | 6.2E−02 | 11.05 |
| NUE512 | 9281.3 | 7.08 | 7.9E−01 | −3.76 | 0.15 | 3.8E−02 | 31.49 | 0.23 | 9.9E−01 | 0.30 |
| Control |  | 7.36 |  |  | 0.11 |  |  | 0.22 |  |  |
| NUE514 | 9403.5 | 7.31 | 8.7E−01 | −0.61 | 0.16 | 5.0E−01 | 35.23 | 0.28 | 4.7E−01 | 25.62 |
| NUE514 | 9404.4 | 8.04 | 4.1E−01 | 9.22 | 0.14 | 1.2E−01 | 25.05 | 0.26 | 1.1E−02 | 17.01 |
| NUE514 | 9402.2 | 8.75 | 2.5E−01 | 18.93 | 0.22 | 1.4E−01 | 89.22 | 0.35 | 3.1E−01 | 55.03 |
| NUE514 | 9402.5 | 8.38 | 2.7E−01 | 13.83 | 0.19 | 3.3E−01 | 63.94 | 0.32 | 3.1E−01 | 42.26 |
| NUE514 | 9404.5 | 8.56 | 1.0E−01 | 16.38 | 0.16 | 3.9E−02 | 37.00 | 0.30 | 3.7E−01 | 31.67 |
| Control |  | 7.36 |  |  | 0.11 |  |  | 0.22 |  |  |
| NUE527 | 9201.1 | 8.19 | 2.0E−03 | 11.29 | 0.17 | 1.3E−01 | 49.68 | 0.33 | 1.7E−03 | 45.43 |
| NUE527 | 9201.2 | 6.94 | 6.5E−01 | −5.70 | 0.12 | 5.8E−01 | 7.58 | 0.22 | 9.3E−01 | −1.31 |
| Control |  | 7.36 |  |  | 0.11 |  |  | 0.22 |  |  |
| NUE531 | 10082.2 | 8.24 | 7.1E−02 | 7.98 | 0.15 | 2.3E−01 | −12.84 | 0.27 | 3.9E−01 | 13.71 |
| NUE531 | 10081.5 | 8.31 | 4.4E−02 | 8.95 | 0.17 | 9.4E−01 | 1.15 | 0.27 | 3.2E−02 | 15.99 |
| Control |  | 7.63 |  |  | 0.17 |  |  | 0.24 |  |  |
| NUE532 | 9222.4 | 7.56 | 8.4E−01 | 2.79 | 0.17 | 4.2E−01 | 51.79 | 0.30 | 4.1E−01 | 32.08 |
| NUE532 | 9222.3 | 8.31 | 3.5E−02 | 12.99 | 0.16 | 2.5E−05 | 41.75 | 0.29 | 1.5E−03 | 30.67 |
| NUE532 | 9222.1 | 7.94 | 1.1E−01 | 7.89 | 0.16 | 2.6E−01 | 40.64 | 0.27 | 5.0E−01 | 21.12 |
| NUE532 | 9223.3 | 7.31 | 9.4E−01 | −0.61 | 0.15 | 2.6E−01 | 32.70 | 0.28 | 1.5E−03 | 26.20 |
| NUE532 | 9224.4 | 8.27 | 1.3E−03 | 12.38 | 0.16 | 3.4E−02 | 41.63 | 0.32 | 6.8E−02 | 43.77 |
| NUE532 | 9223.5 | 8.25 | 9.8E−02 | 12.14 | 0.20 | 1.5E−02 | 72.88 | 0.35 | 1.5E−02 | 58.06 |
| Control |  | 7.36 |  |  | 0.11 |  |  | 0.22 |  |  |
| NUE535 | 9086.2 | 7.75 | 5.7E−01 | 5.34 | 0.16 | 2.0E−01 | 37.02 | 0.34 | 2.1E−01 | 52.44 |
| NUE535 | 9084.2 | 6.88 | 4.0E−01 | −6.55 | 0.15 | 2.4E−01 | 28.20 | 0.23 | 8.7E−01 | 2.43 |
| NUE535 | 9081.1 | 8.31 | 1.4E−01 | 12.99 | 0.13 | 4.7E−01 | 12.91 | 0.28 | 2.6E−03 | 25.65 |
| NUE535 | 9082.1 | 7.25 | 6.2E−01 | −1.46 | 0.13 | 2.5E−02 | 12.04 | 0.26 | 4.5E−01 | 14.26 |
| Control |  | 7.36 |  |  | 0.11 |  |  | 0.22 |  |  |
| NUE537 | 9391.1 | 7.81 | 4.8E−01 | 6.19 | 0.14 | 2.6E−01 | 23.28 | 0.25 | 5.7E−01 | 11.88 |
| NUE537 | 9392.2 | 7.31 | 9.4E−01 | −0.61 | 0.14 | 2.9E−01 | 25.68 | 0.26 | 4.1E−01 | 14.53 |
| NUE537 | 9393.2 | 7.56 | 7.2E−01 | 2.79 | 0.15 | 2.2E−02 | 33.42 | 0.24 | 5.1E−01 | 4.72 |
| NUE537 | 9393.1 | 8.63 | 1.7E−03 | 17.23 | 0.19 | 4.6E−02 | 69.46 | 0.34 | 4.7E−04 | 52.73 |
| NUE537 | 9392.3 | 7.19 | 8.5E−01 | −2.31 | 0.13 | 7.3E−01 | 10.02 | 0.25 | 7.4E−01 | 11.68 |
| NUE537 | 9393.3 | 8.00 | 4.8E−01 | 8.74 | 0.18 | 2.6E−02 | 56.70 | 0.30 | 3.1E−04 | 33.39 |
| Control |  | 7.36 |  |  | 0.11 |  |  | 0.22 |  |  |
| NUE576 | 9794.1 | 8.13 | 5.7E−01 | 6.50 | 0.24 | 1.4E−01 | 42.20 | 0.30 | 5.0E−01 | 28.80 |
| Control |  | 7.63 |  |  | 0.17 |  |  | 0.24 |  |  |
| NUE576 | 9791.3 | 7.00 | 6.7E−01 | −4.85 | 0.13 | 6.3E−01 | 15.21 | 0.24 | 8.0E−01 | 7.24 |
| NUE576 | 9792.4 | 8.75 | 1.1E−03 | 18.93 | 0.18 | 1.4E−04 | 55.06 | 0.35 | 2.8E−02 | 56.82 |
| NUE576 | 9792.3 | 8.06 | 2.1E−01 | 9.59 | 0.20 | 2.9E−05 | 71.82 | 0.34 | 9.6E−04 | 52.50 |
| Control |  | 7.36 |  |  | 0.11 |  |  | 0.22 |  |  |

Table 48: Analyses of photosynthetic area (leaf number, leaf blade area and petiole area) of transgenic plants overexpressing the exogenous polynucleotides of some embodiments of the invention (using the cloned or synthetic genes listed in Table 23 above) under the regulation of a constitutive promoter (35S) when grown under limiting nitrogen (1.5 mM $KNO_3$, 1 mM $KH_2PO_4$, 1 mM $MgSO_4$, 3.6 mM KCl, 2 mM $CaCl_2$ and microelements) as compared to control plants.

The genes presented in Table 49, hereinbelow, have improved plant growth rate when grown at limiting nitrogen fertilization levels. These genes improved the growth rate of the rosette and faster covered the soil when grown under limiting nitrogen growth conditions, compared to control plants. These genes produced faster growing plants showing a better utilization of the nitrogen present.

Table 49 depicts analyses of the growth rate of the rosette diameter, rosette area, leaf blade area, leaf number and plot coverage when grown under standard nitrogen conditions when grown under limiting nitrogen conditions (1.5 mM $KNO_3$, 1 mM $KH_2PO_4$, 1 mM $MgSO_4$, 3.6 mM KCl, 2 mM $CaCl_2$ and microelements) in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 49

Transgenic plants exogenously expressing the polynucleotides of some embodiments of the invention exhibit improved rosette growth performance (RGR of rosette area and diameter and plot coverage) under limiting nitrogen conditions

| Gene Name | Event # | RGR Of Rosette Area | | | RGR Of Rosette Diameter | | | RGR Of Plot Coverage | | |
|---|---|---|---|---|---|---|---|---|---|---|
| | | Ave. | P-Value | % incr. | Ave. | P-Value | % incr. | Ave. | P-Value | % incr. |
| NUE227 | 9851.4 | 0.183 | 2.6E−05 | 118.89 | 0.189 | 2.0E−03 | 44.11 | 1.462 | 2.6E−05 | 118.89 |
| NUE227 | 9854.2 | 0.133 | 7.4E−03 | 59.50 | 0.172 | 2.0E−02 | 31.13 | 1.066 | 7.4E−03 | 59.50 |
| NUE227 | 9853.1 | 0.120 | 4.6E−02 | 43.12 | 0.157 | 1.2E−01 | 19.92 | 0.956 | 4.6E−02 | 43.12 |
| NUE227 | 9851.1 | 0.112 | 1.2E−01 | 33.76 | 0.152 | 2.5E−01 | 15.45 | 0.894 | 1.2E−01 | 33.76 |
| NUE227 | 9852.3 | 0.161 | 5.4E−04 | 93.37 | 0.174 | 2.5E−02 | 32.77 | 1.292 | 5.4E−04 | 93.37 |
| Control | | 0.084 | | | 0.131 | | | 0.668 | | |
| NUE256 | 10063.4 | 0.132 | 5.2E−01 | 11.42 | 0.132 | 7.1E−01 | −6.29 | 0.923 | 9.8E−01 | 0.41 |
| NUE256 | 10061.1 | 0.167 | 1.2E−02 | 40.75 | 0.160 | 4.0E−01 | 13.13 | 1.332 | 1.2E−02 | 44.97 |
| Control | | 0.118 | | | 0.141 | | | 0.919 | | |
| NUE512 | 9284.2 | 0.100 | 3.9E−01 | 19.99 | 0.142 | 5.7E−01 | 8.06 | 0.802 | 3.9E−01 | 19.99 |
| NUE512 | 9283.1 | 0.115 | 7.3E−02 | 37.78 | 0.150 | 2.7E−01 | 14.31 | 0.920 | 7.3E−02 | 37.78 |
| NUE512 | 9284.3 | 0.091 | 6.8E−01 | 8.61 | 0.136 | 7.8E−01 | 3.59 | 0.726 | 6.8E−01 | 8.61 |
| NUE512 | 9282.3 | 0.116 | 6.6E−02 | 38.73 | 0.151 | 2.8E−01 | 14.64 | 0.927 | 6.6E−02 | 38.73 |
| NUE512 | 9283.3 | 0.098 | 4.0E−01 | 17.73 | 0.125 | 6.8E−01 | −5.14 | 0.787 | 4.0E−01 | 17.73 |
| NUE512 | 9281.3 | 0.103 | 2.5E−01 | 23.92 | 0.140 | 6.0E−01 | 6.87 | 0.783 | 4.2E−01 | 17.24 |
| Control | | 0.084 | | | 0.131 | | | 0.668 | | |
| NUE514 | 9403.5 | 0.108 | 2.4E−01 | 28.84 | 0.137 | 7.8E−01 | 4.40 | 0.861 | 2.4E−01 | 28.84 |
| NUE514 | 9404.4 | 0.117 | 6.4E−02 | 39.59 | 0.155 | 1.6E−01 | 17.67 | 0.869 | 1.4E−01 | 30.04 |
| NUE514 | 9402.2 | 0.177 | 8.9E−05 | 111.43 | 0.195 | 1.5E−03 | 48.26 | 1.412 | 8.9E−05 | 111.43 |
| NUE514 | 9403.2 | 0.105 | 3.4E−01 | 26.02 | 0.140 | 7.1E−01 | 6.57 | 0.842 | 3.4E−01 | 26.02 |
| NUE514 | 9402.5 | 0.144 | 8.3E−03 | 72.44 | 0.180 | 2.7E−02 | 37.10 | 1.152 | 8.3E−03 | 72.44 |
| NUE514 | 9404.5 | 0.126 | 1.8E−02 | 50.85 | 0.164 | 6.6E−02 | 24.82 | 1.008 | 1.8E−02 | 50.85 |
| Control | | 0.084 | | | 0.131 | | | 0.668 | | |
| NUE527 | 9201.1 | 0.131 | 1.5E−02 | 56.83 | 0.146 | 3.8E−01 | 11.45 | 1.048 | 1.5E−02 | 56.83 |
| Control | | 0.084 | | | 0.131 | | | 0.668 | | |
| NUE532 | 9222.4 | 0.132 | 3.4E−02 | 58.62 | 0.177 | 4.2E−02 | 34.79 | 1.060 | 3.4E−02 | 58.62 |
| NUE532 | 9222.3 | 0.124 | 2.7E−02 | 48.99 | 0.148 | 3.2E−01 | 12.66 | 0.995 | 2.7E−02 | 48.99 |
| NUE532 | 9222.1 | 0.124 | 3.9E−02 | 48.48 | 0.153 | 2.5E−01 | 16.37 | 0.992 | 3.9E−02 | 48.48 |
| NUE532 | 9223.3 | 0.106 | 2.0E−01 | 26.75 | 0.135 | 8.3E−01 | 2.62 | 0.847 | 2.0E−01 | 26.75 |
| NUE532 | 9224.4 | 0.132 | 9.5E−03 | 58.37 | 0.159 | 1.0E−01 | 21.08 | 0.991 | 2.7E−02 | 48.37 |
| NUE532 | 9223.5 | 0.162 | 1.4E−04 | 94.31 | 0.169 | 3.4E−02 | 28.67 | 1.298 | 1.4E−04 | 94.31 |
| Control | | 0.084 | | | 0.131 | | | 0.668 | | |
| NUE535 | 9086.2 | 0.118 | 6.7E−02 | 40.98 | 0.169 | 3.7E−02 | 28.72 | 0.942 | 6.7E−02 | 40.98 |
| NUE535 | 9084.2 | 0.103 | 2.6E−01 | 23.65 | 0.138 | 7.0E−01 | 4.93 | 0.826 | 2.6E−01 | 23.65 |
| NUE535 | 9081.1 | 0.101 | 3.1E−01 | 20.62 | 0.137 | 7.2E−01 | 4.66 | 0.806 | 3.1E−01 | 20.62 |
| Control | | 0.084 | | | 0.131 | | | 0.668 | | |
| NUE537 | 9391.1 | 0.101 | 3.0E−01 | 20.89 | 0.143 | 5.1E−01 | 8.62 | 0.808 | 3.0E−01 | 20.89 |
| NUE537 | 9392.2 | 0.107 | 1.9E−01 | 27.77 | 0.142 | 5.0E−01 | 8.29 | 0.854 | 1.9E−01 | 27.77 |
| NUE537 | 9393.2 | 0.120 | 4.4E−02 | 43.18 | 0.135 | 8.3E−01 | 2.61 | 0.894 | 1.1E−01 | 33.89 |
| NUE537 | 9393.1 | 0.156 | 5.1E−04 | 86.73 | 0.198 | 2.4E−04 | 50.58 | 1.247 | 5.1E−04 | 86.73 |
| NUE537 | 9392.3 | 0.101 | 3.8E−01 | 20.36 | 0.140 | 6.6E−01 | 6.28 | 0.804 | 3.8E−01 | 20.36 |
| NUE537 | 9393.3 | 0.133 | 1.0E−02 | 59.56 | 0.162 | 7.9E−02 | 23.54 | 1.066 | 1.0E−02 | 59.56 |
| Control | | 0.084 | | | 0.131 | | | 0.668 | | |
| NUE576 | 9793.4 | 0.163 | 1.1E−01 | 37.49 | 0.157 | 5.5E−01 | 11.44 | 1.139 | 3.0E−01 | 23.91 |
| NUE576 | 9792.4 | 0.139 | 2.6E−01 | 17.71 | 0.167 | 2.7E−01 | 18.29 | 1.047 | 4.2E−01 | 13.98 |
| NUE576 | 9794.1 | 0.168 | 1.7E−02 | 41.95 | 0.161 | 4.0E−01 | 14.09 | 1.343 | 1.6E−02 | 46.20 |
| Control | | 0.118 | | | 0.141 | | | 0.919 | | |
| NUE576 | 9792.4 | 0.150 | 8.5E−04 | 79.96 | 0.162 | 6.5E−02 | 23.36 | 1.202 | 8.5E−04 | 79.96 |
| NUE576 | 9792.3 | 0.149 | 1.2E−03 | 78.96 | 0.177 | 1.3E−02 | 34.59 | 1.196 | 1.2E−03 | 78.96 |
| NUE576 | 9794.1 | 0.095 | 5.1E−01 | 14.23 | 0.145 | 4.7E−01 | 10.57 | 0.763 | 5.1E−01 | 14.23 |
| NUE576 | 9793.3 | 0.104 | 2.4E−01 | 24.59 | 0.140 | 6.4E−01 | 6.33 | 0.771 | 4.4E−01 | 15.45 |
| Control | | 0.084 | | | 0.131 | | | 0.668 | | |

Table 49: Analyses of rosette growth performance (RGR of rosette area and diameter and plot coverage) of transgenic plants overexpressing the exogenous polynucleotides of some embodiments of the invention (using the cloned or synthetic genes listed in Table 23 above) under the regulation of a constitutive promoter (35S) when grown under limiting nitrogen (1.5 mM $KNO_3$, 1 mM $KH_2PO_4$, 1 mM $MgSO_4$, 3.6 mM KCl, 2 mM $CaCl_2$ and microelements) as compared to control plants.

The genes presented in Tables 50 and 51, hereinbelow, have improved plant NUE when grown under standard nitrogen growth conditions, compared to control plants. These genes produced larger plants with a larger photosynthetic area when grown under standard nitrogen growth conditions, compared to control plants.

Tables 50 and 51 depicts analyses of plant biomass (fresh weight, dry weight, rosette diameter, rosette area and plot coverage) when grown under standard nitrogen conditions (6 mM $KNO_3$, 1 mM $KH_2PO_4$, 1 mM $MgSO_4$, 2 mM $CaCl_2$ and microelements) in plants overexpressing the polynucleotides of some embodiments of the invention under the regulation of a constitutive promoter (35S)). Evaluation of each gene was performed by testing the performance of several events. Some of the genes were evaluated in more than one tissue culture assay and the results obtained were repeated. Event with p-value <0.1 was considered statistically significant.

TABLE 50

Transgenic plants exogenously expressing the polynucleotides of some embodiments of the invention exhibit improved plant biomass (dry weight and fresh weight) under standard nitrogen conditions

| Gene Name | Event # | Dry Weight Ave. | P-Value | % increment | Fresh Weight Ave. | P-Value | % increment |
|---|---|---|---|---|---|---|---|
| NUE227 | 9851.4 | 0.170 | 1.8E−01 | 18.41 | 1.631 | 2.1E−01 | 12.64 |
| NUE227 | 9854.2 | 0.163 | 1.7E−01 | 13.18 | 1.744 | 2.1E−02 | 20.41 |
| NUE227 | 9853.1 | 0.202 | 2.1E−01 | 40.61 | 2.019 | 1.9E−02 | 39.40 |
| NUE227 | 9852.3 | 0.199 | 2.6E−01 | 38.87 | 1.794 | 3.7E−01 | 23.86 |
| Control | | 0.144 | | | 1.448 | | |
| NUE233 | 10174.3 | 0.128 | 1.3E−01 | 21.58 | 1.206 | 1.0E−01 | 19.80 |
| NUE233 | 10173.7 | 0.143 | 1.4E−02 | 36.31 | 1.210 | 3.8E−01 | 20.15 |
| Control | | 0.105 | | | 1.007 | | |
| NUE256 | 10063.4 | 0.139 | 4.0E−01 | 32.65 | 1.363 | 1.6E−01 | 35.31 |
| NUE256 | 10061.3 | 0.118 | 5.8E−01 | 12.64 | 1.025 | 9.2E−01 | 1.80 |
| Control | | 0.105 | | | 1.007 | | |
| NUE512 | 9282.3 | 0.177 | 2.0E−01 | 23.20 | 1.881 | 2.8E−03 | 29.90 |
| Control | | 0.144 | | | 1.448 | | |
| NUE514 | 9403.5 | 0.168 | 2.3E−02 | 17.10 | 1.556 | 5.9E−01 | 7.46 |
| NUE514 | 9402.2 | 0.161 | 2.2E−01 | 11.88 | 1.769 | 3.7E−02 | 22.13 |
| NUE514 | 9404.5 | 0.153 | 5.0E−01 | 6.65 | 1.531 | 3.9E−01 | 5.73 |
| NUE514 | 9402.5 | 0.171 | 1.7E−01 | 19.28 | 1.488 | 7.3E−01 | 2.71 |
| Control | | 0.144 | | | 1.448 | | |
| NUE531 | 10081.5 | 0.115 | 5.2E−01 | 10.00 | 1.086 | 5.9E−01 | 7.83 |
| Control | | 0.105 | | | 1.007 | | |
| NUE532 | 9222.4 | 0.175 | 4.9E−01 | 21.89 | 1.750 | 3.4E−01 | 20.84 |
| NUE532 | 9223.3 | 0.156 | 2.3E−01 | 8.83 | 1.556 | 2.8E−01 | 7.46 |
| NUE532 | 9223.5 | 0.164 | 4.4E−01 | 14.05 | 1.669 | 5.3E−02 | 15.23 |
| Control | | 0.144 | | | 1.448 | | |
| NUE537 | 9391.1 | 0.178 | 1.3E−01 | 24.07 | 1.669 | 4.8E−02 | 15.23 |
| NUE537 | 9393.1 | 0.168 | 2.4E−01 | 16.92 | 1.743 | 3.2E−02 | 20.35 |
| Control | | 0.144 | | | 1.448 | | |

Table 50: Analyses of plant biomass (dry weight and fresh weight) of transgenic plants overexpressing the exogenous polynucleotides of some embodiments of the invention (using the cloned or synthetic genes listed in Table 23 above) under the regulation of a constitutive promoter (35S) when grown under standard nitrogen (6 mM $KNO_3$, 1 mM $KH_2PO_4$, 1 mM $MgSO_4$, 2 mM $CaCl_2$ and microelements) as compared to control plants.
"Ave." = average.

TABLE 51

Transgenic plants exogenously expressing the polynucleotides of some embodiments of the invention exhibit improved plant biomass (rosette diameter and area and plot coverage) under standard nitrogen conditions

| Gene Name | Event # | Rosette Diameter Ave. | P-Value | % incr. | Rosette Area Ave. | P-Value | % incr. | Plot Coverage Ave. | P-Value | % incr. |
|---|---|---|---|---|---|---|---|---|---|---|
| NUE227 | 9851.4 | 1.82 | 8.6E−01 | −1.70 | 1.29 | 3.5E−01 | 9.98 | 10.30 | 3.5E−01 | 9.98 |
| NUE227 | 9854.2 | 2.13 | 7.6E−02 | 14.82 | 1.40 | 2.1E−01 | 19.82 | 11.22 | 2.1E−01 | 19.82 |
| NUE227 | 9853.1 | 1.96 | 6.1E−01 | 5.70 | 1.45 | 1.8E−01 | 23.64 | 11.58 | 1.8E−01 | 23.64 |
| NUE227 | 9852.3 | 1.94 | 5.9E−01 | 4.72 | 1.40 | 5.8E−01 | 19.24 | 11.17 | 5.8E−01 | 19.24 |
| Control | | 1.85 | | | 1.17 | | | 9.37 | | |
| NUE233 | 10174.3 | 2.69 | 2.8E−01 | 12.27 | 2.54 | 3.0E−01 | 24.73 | 20.36 | 2.7E−01 | 27.64 |
| NUE233 | 10173.7 | 2.61 | 4.7E−01 | 9.02 | 2.49 | 4.0E−01 | 22.00 | 18.84 | 5.9E−01 | 18.14 |
| Control | | 2.40 | | | 2.04 | | | 15.95 | | |
| NUE256 | 10063.4 | 3.37 | 1.5E−03 | 40.59 | 3.25 | 1.4E−01 | 59.40 | 24.17 | 2.9E−02 | 51.58 |
| NUE256 | 10061.3 | 2.89 | 3.3E−01 | 20.50 | 2.38 | 5.8E−01 | 16.48 | 19.01 | 5.3E−01 | 19.20 |
| Control | | 2.40 | | | 2.04 | | | 15.95 | | |
| NUE512 | 9282.3 | 2.08 | 3.8E−02 | 12.43 | 1.38 | 1.3E−01 | 18.07 | 11.06 | 1.3E−01 | 18.07 |
| Control | | 1.85 | | | 1.17 | | | 9.37 | | |

TABLE 51-continued

Transgenic plants exogenously expressing the polynucleotides of some embodiments of the invention exhibit improved plant biomass (rosette diameter and area and plot coverage) under standard nitrogen conditions

| Gene Name | Event # | Rosette Diameter | | | Rosette Area | | | Plot Coverage | | |
|---|---|---|---|---|---|---|---|---|---|---|
| | | Ave. | P-Value | % incr. | Ave. | P-Value | % incr. | Ave. | P-Value | % incr. |
| NUE514 | 9403.5 | 2.14 | 1.9E−02 | 15.56 | 1.44 | 6.0E−02 | 23.37 | 11.56 | 6.0E−02 | 23.37 |
| NUE514 | 9402.2 | 2.03 | 9.8E−02 | 9.60 | 1.46 | 5.4E−02 | 24.90 | 11.70 | 5.4E−02 | 24.90 |
| NUE514 | 9404.5 | 2.13 | 2.1E−02 | 14.76 | 1.56 | 1.6E−02 | 32.88 | 12.45 | 1.6E−02 | 32.88 |
| NUE514 | 9402.5 | 2.15 | 3.9E−02 | 16.09 | 1.45 | 5.6E−02 | 23.83 | 11.60 | 5.6E−02 | 23.83 |
| Control | | 1.85 | | | 1.17 | | | 9.37 | | |
| NUE531 | 10081.5 | 2.78 | 1.5E−01 | 16.08 | 2.50 | 2.5E−01 | 22.65 | 18.66 | 3.0E−01 | 17.01 |
| NUE531 | 10083.2 | 2.99 | 6.6E−02 | 24.72 | 3.18 | 2.0E−01 | 56.02 | 24.12 | 3.4E−01 | 51.24 |
| Control | | 2.40 | | | 2.04 | | | 15.95 | | |
| NUE532 | 9222.4 | 2.04 | 2.8E−01 | 10.29 | 1.43 | 2.2E−01 | 22.08 | 11.44 | 2.2E−01 | 22.08 |
| NUE532 | 9223.3 | 2.04 | 9.0E−02 | 10.28 | 1.38 | 1.3E−01 | 18.26 | 11.08 | 1.3E−01 | 18.26 |
| NUE532 | 9223.5 | 2.23 | 5.3E−03 | 20.20 | 1.64 | 6.4E−03 | 40.20 | 13.13 | 6.4E−03 | 40.20 |
| Control | | 1.85 | | | 1.17 | | | 9.37 | | |
| NUE537 | 9391.1 | 1.87 | 8.6E−01 | 0.96 | 1.22 | 6.7E−01 | 4.43 | 9.78 | 6.7E−01 | 4.43 |
| NUE537 | 9393.1 | 1.90 | 7.6E−01 | 2.36 | 1.34 | 4.7E−01 | 14.85 | 10.17 | 7.5E−01 | 8.55 |
| Control | | 1.85 | | | 1.17 | | | 9.37 | | |

Table 51: Analyses of plant biomass (rosette diameter and area and plot coverage) of transgenic plants overexpressing the exogenous polynucleotides of some embodiments of the invention (using the cloned or synthetic genes listed in Table 23 above) under the regulation of a constitutive promoter (35S) when grown under standard nitrogen (6 mM $KNO_3$, 1 mM $KH_2PO_4$, 1 mM $MgSO_4$, 2 mM $CaCl_2$ and microelements) as compared to control plants. "Incr." = increment; "Ave." = average.

The genes presented in Table 52, hereinbelow, have improved plant NUE when grown under standard nitrogen growth conditions, compared to control plants. These genes produced larger photosynthetic areas as it can be observed by their larger leaf number, leaf blade area and petiole area as compared to control plants.

Table 52 depicts analyses of plant photosynthetic area (leaf number and petiole area) when grown under standard nitrogen conditions (6 mM $KNO_3$, 1 mM $KH_2PO_4$, 1 mM $MgSO_4$, 2 mM $CaCl_2$ and microelements) in plants overexpressing the polynucleotides of some embodiments of the invention under the regulation of a constitutive promoter (35S)). Evaluation of each gene was performed by testing the performance of several events. Some of the genes were evaluated in more than one tissue culture assay and the results obtained were repeated. Event with p-value <0.1 was considered statistically significant.

TABLE 52

Transgenic plants exogenously expressing the polynucleotides of some embodiments of the invention exhibit improved photosynthetic areas (leaf blade area and leaf petiole length) under standard nitrogen growth conditions

| Gene Name | Event # | Leaf Blade Area [$cm^2$] | | | Leaf Petiole Length | | |
|---|---|---|---|---|---|---|---|
| | | Ave. | P-Value | % increment | Ave. | P-Value | % increment |
| NUE227 | 9851.4 | 0.219 | 1.6E−01 | 15.14 | 0.305 | 7.2E−02 | −14.52 |
| NUE227 | 9854.2 | 0.249 | 2.6E−02 | 30.94 | 0.373 | 4.6E−01 | 4.52 |
| NUE227 | 9853.1 | 0.248 | 6.6E−02 | 30.68 | 0.364 | 7.9E−01 | 2.16 |
| NUE227 | 9852.3 | 0.232 | 4.4E−01 | 22.31 | 0.331 | 4.7E−01 | −7.20 |
| Control | | 0.190 | | | 0.357 | | |
| NUE233 | 10174 | 0.437 | 1.8E−01 | 28.66 | 0.424 | 3.3E−01 | 15.67 |
| NUE233 | 10174 | 0.440 | 1.8E−01 | 29.28 | 0.440 | 2.3E−01 | 20.06 |
| Control | | 0.340 | | | 0.366 | | |
| NUE256 | 10063 | 0.518 | 2.3E−01 | 52.46 | 0.491 | 1.9E−01 | 34.00 |
| NUE256 | 10061 | 0.384 | 4.9E−01 | 13.04 | 0.426 | 4.3E−01 | 16.39 |
| Control | | 0.340 | | | 0.366 | | |
| NUE512 | 9282.3 | 0.244 | 2.3E−02 | 28.51 | 0.370 | 4.7E−01 | 3.82 |
| Control | | 0.190 | | | 0.357 | | |
| NUE514 | 9403.5 | 0.245 | 1.2E−01 | 28.88 | 0.380 | 2.4E−01 | 6.47 |
| NUE514 | 9402.2 | 0.225 | 1.3E−01 | 18.56 | 0.373 | 4.4E−01 | 4.60 |
| NUE514 | 9404.5 | 0.246 | 5.1E−02 | 29.57 | 0.358 | 9.5E−01 | 0.42 |
| NUE514 | 9402.5 | 0.235 | 4.4E−02 | 23.86 | 0.414 | 3.7E−02 | 16.10 |
| Control | | 0.190 | | | 0.357 | | |
| NUE531 | 10082 | 0.393 | 2.5E−01 | 15.61 | 0.445 | 5.6E−02 | 21.67 |
| NUE531 | 10083 | 0.526 | 4.9E−02 | 54.72 | 0.503 | 4.4E−02 | 37.48 |
| Control | | 0.340 | | | 0.366 | | |
| NUE532 | 9222.4 | 0.238 | 1.8E−01 | 25.41 | 0.380 | 4.4E−01 | 6.51 |
| NUE532 | 9223.3 | 0.217 | 3.5E−01 | 13.98 | 0.418 | 3.3E−02 | 17.17 |
| NUE532 | 9223.5 | 0.261 | 1.1E−02 | 37.44 | 0.404 | 9.7E−02 | 13.18 |
| Control | | 0.190 | | | 0.357 | | |

TABLE 52-continued

Transgenic plants exogenously expressing the polynucleotides of some embodiments of the invention exhibit improved photosynthetic areas (leaf blade area and leaf petiole length) under standard nitrogen growth conditions

| Gene Name | Event # | Leaf Blade Area [cm$^2$] | | | Leaf Petiole Length | | |
|---|---|---|---|---|---|---|---|
| | | Ave. | P-Value | % increment | Ave. | P-Value | % increment |
| NUE537 | 9391.1 | 0.206 | 4.1E−01 | 8.34 | 0.340 | 4.9E−01 | −4.82 |
| NUE537 | 9393.1 | 0.204 | 6.9E−01 | 7.22 | 0.369 | 5.6E−01 | 3.52 |
| Control | | 0.190 | | | 0.357 | | |

Table 52: Analyses of photosynthetic areas (leaf blade area and leaf petiole length) of transgenic plants overexpressing the exogenous polynucleotides of some embodiments of the invention (using the cloned or synthetic genes listed in Table 23 above) under the regulation of a constitutive promoter (35S) when grown under standard nitrogen (6 mM KNO$_3$, 1 mM KH$_2$PO$_4$, 1 mM MgSO$_4$, 2 mM CaCl$_2$ and microelements) as compared to control plants.
"Ave." = average.

Example 8

Evaluating Trasngenic Plant Growth Under Abiotic Stress Conditions

One of the consequences of drought is the induction of osmotic stress in the area surrounding the roots; therefore, in many scientific studies, PEG (e.g., 1.5% PEG8000) is used to simulate the osmotic stress conditions resembling the high osmolarity found during drought stress.

Assay 1: Abiotic Stress Tolerance Assay Under Tissue Culture Conditions

Plant growth was evaluated under salinity (150 mM NaCl) or osmotic stress [poly (ethylene glycol) (PEG)] in tissue culture conditions.

Surface sterilized seeds were sown in basal media [50% Murashige-Skoog medium (MS) supplemented with 0.8% plant agar as solidifying agent] in the presence of Kanamycin (for selecting only transgenic plants). After sowing, plates were transferred for 2-3 days for stratification at 4° C. and then grown at 25° C. under 12-hour light 12-hour dark daily cycles for 7 to 10 days. At this time point, seedlings randomly chosen were carefully transferred to plates containing 150 mM or 1.5% PEG: 0.5 MS media or Normal growth conditions (0.5 MS media). Each plate contained 5 seedlings of the same transgenic event, and 3-4 different plates (replicates) for each event. For each polynucleotide of the invention at least four independent transformation events were analyzed from each construct. Plants expressing the polynucleotides of the invention were compared to the average measurement of the control plants (empty vector or GUS reporter gene under the same promoter) used in the same experiment.

Digital Imaging

A laboratory image acquisition system, which consists of a digital reflex camera (Canon EOS 300D) attached with a 55 mm focal length lens (Canon EF-S series), mounted on a reproduction device (Kaiser RS), which included 4 light units (4×150 Watts light bulb) and located in a darkroom, was used for capturing images of plantlets sawn in agar plates.

An image analysis system was used, which consists of a personal desktop computer (Intel P4 3.0 GHz processor) and a public domain program—ImageJ 1.39 (Java based image processing program which was developed at the U.S. National Institutes of Health and freely available on the internet at Hypertext Transfer Protocol://rsbweb (dot) nih (dot) gov/). Images were captured in resolution of 10 Mega Pixels (3888×2592 pixels) and stored in a low compression JPEG (Joint Photographic Experts Group standard) format. Next, analyzed data was saved to text files and processed using the JMP statistical analysis software (SAS institute).

Seedling Analysis

Using the digital analysis seedling data was calculated, including leaf area, root coverage and root length.

The relative growth rate for the various seedling parameters was calculated according to the following formulas V, VI and VII as described above.

Formula V: Relative growth rate of leaf area=Regression coefficient of leaf area along time course.

Formula VI: Relative growth rate of root coverage=Regression coefficient of root coverage along time course.

Formula VII: Relative growth rate of root length=Regression coefficient of root coverage along time course.

At the end of the experiment, plantlets were removed from the media and weighed for the determination of plant fresh weight. Plantlets were then dried for 24 hours at 60° C., and weighed again to measure plant dry weight for later statistical analysis. Growth rate was determined by comparing the leaf area coverage, root coverage and root length, between each couple of sequential photographs, and results were used to resolve the effect of the gene introduced on plant vigor, under osmotic stress, as well as under optimal conditions. Similarly, the effect of the gene introduced on biomass accumulation, under osmotic stress as well as under optimal conditions, was determined by comparing the plants' fresh and dry weight to that of control plants (containing the GUS reporter gene under the same promoter). From every construct created, 3-5 independent transformation events were examined in replicates.

Statistical Analyses

To identify genes conferring significantly improved tolerance to abiotic stresses or enlarged root architecture, the results obtained from the transgenic plants were compared to those obtained from control plants. To identify outperforming genes and constructs, results from the independent transformation events tested were analyzed separately. To evaluate the effect of a gene event over a control the data was analyzed by Student's t-test and the p value was calculated. Results were considered significant if p≤0.1. The JMP statistics software package was used (Version 5.2.1, SAS Institute Inc., Cary, N.C., USA).

Experimental Results:

The genes presented in Tables 53, 54 and 55, hereinbelow, have improved plant ABST (abiotic stress tolerance) when grown under high salinity concentration levels, compared to control plants. Results showed that the genes also improved plant performance under non-salinity conditions.

Tables 53, 54 and 55 depict analyses of plant performance (leaves and roots area) under normal (0 mM NaCl) or high salinity (150 mM NaCl) conditions in plants overexpressing the polynucleotides of some embodiments of the invention under the regulation of a constitutive promoter (35S). Evaluation of each gene was performed by testing the performance of several events. Some of the genes were evaluated in more than one tissue culture assay and the results obtained were repeated. Event with p-value <0.1 was considered statistically significant.

TABLE 53

Transgenic plants exogenously expressing the polynucleotides of some embodiments of the invention exhibit improved plant performance (leaves and roots area) under normal (standard) conditions

| | | | Leaves Area [cm$^2$] | | | Roots Area [cm$^2$] | | |
|---|---|---|---|---|---|---|---|---|
| Treatment | Gene name | Event | Average | Statistics | % increment | Average | Statistics | % increment |
| 0 mM NaCl | CT81 | 4995.1 | 0.60 | A | 23.04 | 0.25 | A | 57.13 |
| 0 mM NaCl | CT81 | 4991.1 | 0.53 | AB | 7.91 | 0.16 | B | 0.18 |
| 0 mM NaCl | Control | 4543.3 | 0.49 | B | | 0.16 | B | |

Table 53: Analyses of plant performance (leaves area and root area) of transgenic plants overexpressing the exogenous polynucleotides of some embodiments of the invention (using the cloned or synthetic genes listed in Table 23 above) under the regulation of a constitutive promoter (35S) when grown under standard conditions (0 mM NaCl) compared to control plants.

TABLE 54

Transgenic plants exogenously expressing the polynucleotides of some embodiments of the invention exhibit improved plant performance (leaves area) under salinity stress

| | Gene | | Leaves Area [cm$^2$] | | |
|---|---|---|---|---|---|
| Treatment | name | Event | Average | Statistics | % increment |
| 150 mM NaCl | CT81 | 4991.1 | 0.25 | A | 27.57 |
| 150 mM NaCl | CT81 | 4995.1 | 0.21 | B | 3.74 |
| 150 mM NaCl | CT81 | 4993.1 | 0.20 | B | 2.09 |
| 150 mM NaCl | Control | 4543.3 | 0.20 | B | |

Table 54: Analyses of plant performance (leaves area) of transgenic plants overexpressing the exogenous polynucleotides of some embodiments of the invention (using the cloned or synthetic genes listed in Table 23 above) under the regulation of a constitutive promoter (35S) when grown under salinity conditions (150 mM NaCl) compared to control plants.

TABLE 55

Transgenic plants exogenously expressing the polynucleotides of some embodiments of the invention exhibit improved plant performance (roots area) under salinity conditions

| | Gene | | Roots Area [cm$^2$] | | |
|---|---|---|---|---|---|
| Treatment | name | Event | Average | Statistics | % increment |
| 150 mM NaCl | CT81 | 4995.1 | 0.24 | A | 44.30 |
| 150 mM NaCl | CT81 | 4991.1 | 0.22 | A | 30.09 |
| 150 mM NaCl | Control | 4543.3 | 0.17 | B | 0.00 |

Table 55: Analyses of plant performance (roots area) of transgenic plants overexpressing the exogenous polynucleotides of some embodiments of the invention (using the cloned or synthetic genes listed in Table 23 above) under the regulation of a constitutive promoter (35S) when grown under salinity conditions (150 mM NaCl) compared to control plants.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10208316B2). An electronic copy of the "Sequence Listing" will also be available from the USPTO upon request and payment of the fee set forth in 37 CFR 1.19(b)(3).

What is claimed is:

1. A method of increasing nitrogen use efficiency, and/or tolerance to nitrogen deficiency of a plant as compared to a native plant of the same species, which is grown under the same growth conditions, the method comprising:
   (a) over-expressing within the plant a polypeptide comprising the amino acid sequence selected from the group consisting of SEQ ID NOs: 236, 2296-2302 and 2304-2312, and
   (b) selecting a plant over-expressing said polypeptide for an increased nitrogen use efficiency, and/or an increased tolerance to nitrogen deficiency as compared to the native plant of the same species, which is grown under the same growth conditions,
thereby increasing the nitrogen use efficiency and/or tolerance to nitrogen deficiency of the plant as compared to the native plant of the same species, which is grown under the same growth conditions.

2. The method of claim 1, further comprising:
   (a) isolating a regenerable portion from plants selected according to the method of claim 1, to thereby obtain an isolated regenerable portion, and;
   (b) regenerating plants from said isolated regenerable portion.

3. The method of claim 1, wherein said polypeptide is set forth by SEQ ID NO: 236.

4. The method of claim 1, wherein said polypeptide is expressed from a nucleic acid sequence selected from the group consisting of SEQ ID NOs: 2494, 99, and 1232-1248.

5. The method of claim 4, wherein said nucleic acid is sequence selected from the group consisting of SEQ ID NOs: 2494 and 99.

6. The method of claim 1, further comprising growing the plant over-expressing said polypeptide under nitrogen deficiency.

7. A method of growing a crop comprising growing a crop plant over-expressing a polypeptide comprising an amino acid sequence selected from the group consisting of SEQ ID NOs: 236, 2296-2302 and 2304-2312 as compared to a native plant of the same species, which is grown under the same growth conditions, wherein said crop plant is derived from parent plants that over-express said polypeptide and that have been selected for an increased nitrogen use efficiency, and/or an increased tolerance to nitrogen deficiency as compared to the native plant of the same species, which is grown under the same growth conditions, and said crop plant over-expressing said polypeptide having said increased nitrogen use efficiency, and/or said increased tolerance to nitrogen deficiency, thereby growing the crop.

8. The method of claim 7, wherein said polypeptide is set forth by SEQ ID NO: 236.

9. The method of claim 7, wherein said polypeptide is expressed from a nucleic acid sequence selected from the group consisting of SEQ ID NOs: 2494 and 99.

10. A method of increasing nitrogen use efficiency, growth rate of leaf area, growth rate of root coverage, dry weight and/or fresh weight under nitrogen deficient conditions, the method comprising:
    (a) over-expressing within the plant a polypeptide comprising the amino acid sequence selected from the group consisting of SEQ ID NOs: 236, 2296-2302 and 2304-2312, and
    (b) selecting a plant over-expressing said polypeptide for an increased nitrogen use efficiency, growth rate of leaf area, growth rate of root coverage, dry weight and/or fresh weight under nitrogen deficient conditions as compared to the native plant of the same species, which is grown under the same growth conditions,
thereby increasing the nitrogen use efficiency, growth rate of leaf area, growth rate of root coverage, dry weight and/or fresh weight under nitrogen deficient conditions.

11. The method of claim 10, further comprising:
    (a) isolating a regenerable portion from plants selected according to the method of claim 10, to thereby obtain an isolated regenerable portion, and;
    (b) regenerating plants from said isolated regenerable portion.

12. The method of claim 10, wherein said polypeptide is set forth by SEQ ID NO: 236.

13. The method of claim 10, wherein said polypeptide is expressed from a nucleic acid sequence selected from the group consisting of SEQ ID NOs: 2494, 99, and 1232-1248.

14. The method of claim 10, wherein said polypeptide is expressed from a nucleic acid sequence selected from the group consisting of SEQ ID NOs: 2494 and 99.

15. A method of growing a crop comprising growing a crop plant over-expressing a polypeptide comprising an amino acid sequence selected from the group consisting of SEQ ID NOs: 236, 2296-2302 and 2304-2312 as compared to a native plant of the same species, which is grown under the same growth conditions, wherein said crop plant is derived from parent plants that over-express said polypeptide and that have been selected for an increased nitrogen use efficiency, an increased growth rate of leaf area under nitrogen deficient conditions, an increased growth rate of root coverage under nitrogen deficient conditions, an increased dry weight under nitrogen deficient conditions and/or an increased fresh weight under nitrogen deficient conditions tolerance as compared to the native plant of the same species, which is grown under the same growth conditions, and said crop plant over-expressing said polypeptide having said increased nitrogen use efficiency, said increased growth rate of leaf area under nitrogen deficient conditions, said increased growth rate of root coverage under nitrogen deficient conditions, said increased dry weight under nitrogen deficient conditions and/or said increased fresh weight under nitrogen deficient conditions, thereby growing the crop.

16. The method of claim 15, wherein said polypeptide is set forth by SEQ ID NO: 236.

17. The method of claim 15, wherein said polypeptide is expressed from a nucleic acid sequence selected from the group consisting of SEQ ID NOs: 2494, 99, and 1232-1248.

18. The method of claim 15, wherein said nucleic acid is sequence selected from the group consisting of SEQ ID NOs: 2494 and 99.

* * * * *